ized Amino

(12) United States Patent
Vendeville et al.

(10) Patent No.: US 11,820,773 B2
(45) Date of Patent: *Nov. 21, 2023

(54) TRICYCLIC COMPOUNDS

(71) Applicant: ALIGOS THERAPEUTICS, INC., South San Francisco, CA (US)

(72) Inventors: Sandrine Vendeville, Brussels (BE); Yannick Debing, Bilzen (BE); Pierre Jean-Marie Bernard Raboisson, Wavre (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 17/456,106

(22) Filed: Nov. 22, 2021

(65) Prior Publication Data

US 2022/0169650 A1 Jun. 2, 2022

Related U.S. Application Data

(60) Provisional application No. 63/261,713, filed on Sep. 27, 2021, provisional application No. 63/117,935, filed on Nov. 24, 2020.

(51) Int. Cl.
| | |
|---|---|
| *C07D 471/16* | (2006.01) |
| *A61K 45/06* | (2006.01) |
| *A61P 31/14* | (2006.01) |
| *A61K 31/675* | (2006.01) |
| *A61K 31/519* | (2006.01) |

(52) U.S. Cl.
CPC .......... *C07D 471/16* (2013.01); *A61K 31/519* (2013.01); *A61K 31/675* (2013.01); *A61K 45/06* (2013.01); *A61P 31/14* (2018.01)

(58) Field of Classification Search
None
See application file for complete search history.

(56) References Cited

U.S. PATENT DOCUMENTS

| | | |
|---|---|---|
| 11,136,321 B2 | 10/2021 | Vendeville |
| 2020/0147124 A1 | 5/2020 | Beigelman et al. |
| 2020/0407361 A1 | 12/2020 | Vendeville |
| 2022/0000874 A1 | 1/2022 | Vendeville |

FOREIGN PATENT DOCUMENTS

| | | |
|---|---|---|
| WO | WO 2008/090379 | 7/2008 |
| WO | WO 2008/157273 | 12/2008 |
| WO | WO 2015/065338 | 5/2015 |
| WO | WO 2017/156255 | 9/2017 |
| WO | WO 2018/219356 | 12/2018 |
| WO | WO 2020/097342 A1 | 5/2020 |
| WO | WO 2020/243199 A1 | 12/2020 |

OTHER PUBLICATIONS

International Search Report and Written Opinion dated Feb. 16, 2022 for PCT Application No. PCT/US2021/060366, filed Nov. 22, 2021.
7.Liang, "Hepatitis B: The Virus and Disease" Hepatology (2009) 49(S5):S13-S21.
U.S. Appl. No. 17/446,651, Tricyclic Compounds, filed Sep. 1, 2021.
Fang, Z., et al., "Discovery of pyrazolo [1, 5-a] pyrimidine-3-carbonitrile derivatives as a new class of histone lysine demethylase 4D (KDM4D) inhibitors" Bioorganic & Medicinal Chemistry Letters (2017) 27(14):3201-3204.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
International Preliminary Report on Patentability dated May 30, 2023 for PCT Application No. PCT/US2021/060366, filed Nov. 22, 2021.

*Primary Examiner* — Zinna Northington Davis
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

21 Claims, No Drawings

Specification includes a Sequence Listing.

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: HBV forward primer

<400> SEQUENCE: 1
gtgtctgcgg cgttttatca                                        20

<210> SEQ ID NO 2
<211> LENGTH: 21
<212> TYPE: DNA
<213> ORGANISM: Artificial Sequence
<220> FEATURE:
<223> OTHER INFORMATION: HBV reverse primer

<400> SEQUENCE: 2
gacaaacggg caacatacct t                                      21

<210> SEQ ID NO 3
<211> LENGTH: 28
<212> TYPE: DNA
<213> ORGANISM: Artificial Sequence
<220> FEATURE:
<223> OTHER INFORMATION: HBV probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 9
<223> OTHER INFORMATION: N=T-ZEN

```
<220> FEATURE:
<221> NAME/KEY: modified_base
<222> LOCATION: 28
<223> OTHER INFORMATION: N=C-3IABkFQ

<400> SEQUENCE: 3
nctctkcanc ctgctgctat gcctcatn                                              28
```

TRICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 63/117,935, filed Nov. 24, 2020 and 63/261,713, filed Sep. 27, 2021.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

REFERENCE TO SEQUENCE LISTING

The present application is filed with a Sequence Listing in Electronic format. The Sequence Listing is provided as a file entitled ALIG062.txt, created Nov. 22, 2021, which is approximately 4 kb in size. The information in the electronic format of the sequence listing is incorporated herein by reference in its entirety.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine group and a di-substituted amine group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$, $(CH_3)_2CHCH_2-$ and $(CH_3)_3C-$. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, benzoisothiazole, isothiazole, 1,2,3-triazole, 1,2,4-triazole, benzotriazole, thiadiazole, tetrazole, pyridine, pyridazine, pyrimidine, pyrazine, purine, pteridine, quinoline, isoquinoline, quinazoline, quinoxaline, cinnoline, triazine and [1,2,4]triazolo[4,3-a]pyridine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, isoindolin-1-one and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "optionally substituted" and/or by substituting both hydrogens on the same carbon with a cycloalkyl group (e.g.,

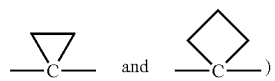

or a monocyclic heterocyclyl (such as

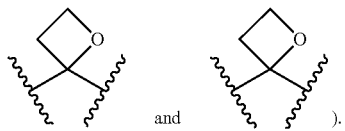 [SMILES: *C1(*)CCO1 ; *C1(*)CCO1]

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR, wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by a alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). In some instances, a haloalkoxy can be —OR, wherein R is a $C_{1-4}$ alkyl substituted by 1, 2 or 3 halogens. Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$^A$)—" group wherein each X is a halogen, and R$^A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a —C(=O)— group.

An "S-sulfonamido" group refers to a "—SO$_2$N(R$^A$R$^B$)" group in which R$^A$ and R$^B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$^A$)—" group in which R and R$^A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$^A$R$^B$)" group in which R$^A$ and R$^B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$^A$)—" group in which R and R$^A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$^A$R$^B$)" group in which R$^A$ and R$^B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$^A$)—" group in which R and R$^A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$^A$R$^B$)" group in which R$^A$ and R$^B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$^A$)—" group in which R and R$^A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—NHR$^A$" in which R$^A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NHR$^A$, wherein R$^A$ can be an unsubstituted C$_{1-6}$ alkyl or an unsubstituted or a substituted benzyl.

A "di-substituted amine" refers to a "—NR$^A$R$^B$" in which R$^A$ and R$^B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NR$^A$R$^B$, wherein R$^A$ and R$^B$ can be independently an unsubstituted C$_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

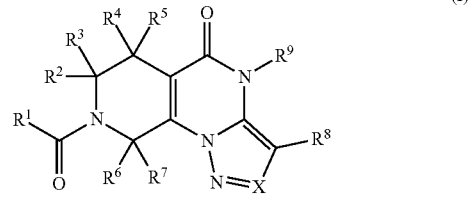

wherein: X can be CH, CD, CF, C(CH$_3$) or N (nitrogen); $R^1$ can be a 3,4-substituted phenyl substituted with two moieties independently selected from —Cl (chloro), —Br (bromo), —CHF$_2$, —CF$_3$, —CH$_3$ and —CN (cyano); $R^2$ and $R^3$ can be independently selected from hydrogen, an unsubstituted $C_{1-4}$ alkyl, an unsubstituted $C_{1-4}$ haloalkyl, an optionally substituted $C_{3-4}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be —CHR$^{8a}$R$^{8b}$; R$^{8a}$ can be hydrogen or —CH$_3$; R$^{8b}$ can be selected from an unsubstituted $C_{1-4}$ alkyl, an unsubstituted $C_{2-4}$ alkenyl, an unsubstituted $C_{2-4}$ alkynyl, an optionally substituted monocyclic $C_{3-6}$ cycloalkyl, an optionally substituted phenyl, an optionally substituted monocyclic heteroaryl and an optionally substituted monocyclic heterocyclyl; and $R^9$ can be a substituted aryl, an optionally substituted heteroaryl or an optionally substituted heterocyclyl.

As described herein, $R^1$ can be a 3,4-substituted phenyl substituted with two moieties independently selected from —Cl (chloro), —Br (bromo), —CHF$_2$, —CF$_3$, —CH$_3$ and —CN (cyano). The two moieties attached to $R^1$ can be different from each other. In some embodiments, $R^1$ can be a 3,4-substituted phenyl, wherein the 4-substitution is —Br. Examples of substitution patterns on the 3,4-substituted phenyl can be where the 3-substitution can be —Cl, —Br, —CHF$_2$, —CF$_3$, —CH$_3$ and —CN; and the 4-substitution can be —Br. Examples of $R^1$ moieties include the following:

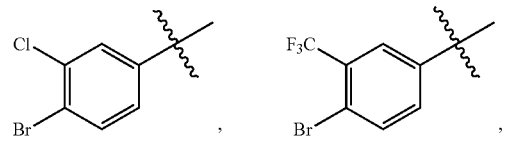

-continued

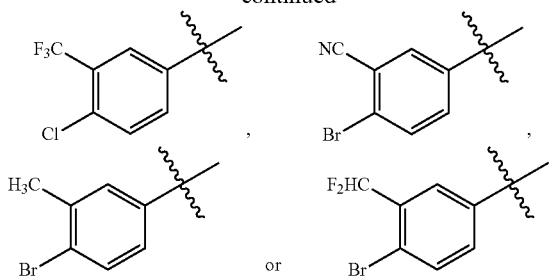

As provided herein, both hydrogen and non-hydrogen moieties can be present on the piperidine ring of a compound of Formula (I), or a pharmaceutically acceptable salt thereof. In some embodiments, $R^2$ can be hydrogen. In other embodiments, $R^2$ can be an unsubstituted $C_{1-4}$ alkyl. In still other embodiments, $R^2$ can be an unsubstituted $C_{1-4}$ haloalkyl. For example, $R^2$ can be methyl, ethyl, n-propyl, iso-propyl, n-butyl, iso-butyl, sec-butyl, tert-butyl, —CHF$_2$, —CH$_2$F, —CF$_3$, —CH$_2$Cl, —CHCl$_2$ and —CCl$_3$. In yet still other embodiments, $R^2$ can be an optionally substituted $C_{3-4}$ cycloalkyl, an optionally substituted aryl, an optionally substituted heteroaryl or an optionally substituted heterocyclyl. In some embodiments, $R^2$ can be an optionally substituted aryl($C_{1-4}$ alkyl), an optionally substituted heteroaryl ($C_{1-4}$ alkyl) or an optionally substituted heterocyclyl($C_{1-4}$ alkyl). Exemplary $R^2$ groups include, but are not limited to, an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

As with $R^2$, $R^3$ can be hydrogen or non-hydrogen moieties as described herein. In some embodiments, $R^3$ can be hydrogen. In other embodiments, $R^3$ can be an unsubstituted $C_{1-4}$ alkyl, such as those described herein. In still other embodiments, $R^3$ can be an unsubstituted $C_{1-4}$ haloalkyl, for example, —CHF$_2$, —CH$_2$F, —CF$_3$, —CH$_2$Cl, —CHCl$_2$ and —CCl$_3$. In yet still other embodiments, $R^3$ can be an optionally substituted $C_{3-4}$ cycloalkyl, an optionally substituted aryl, an optionally substituted heteroaryl or an optionally substituted heterocyclyl. In some embodiments, $R^3$ can be an optionally substituted aryl($C_{1-4}$ alkyl), an optionally substituted heteroaryl($C_{1-4}$ alkyl) or an optionally substituted heterocyclyl($C_{1-4}$ alkyl). In other embodiments, $R^3$ can be an optionally substituted phenyl, an optionally substituted monocyclic heteroaryl or an optionally substituted monocyclic heterocyclyl.

Each of $R^4$ and $R^5$ can be independently hydrogen or selected from the non-hydrogen moieties described herein. In some embodiments, $R^4$ can be hydrogen. In other embodiments, $R^4$ can be an unsubstituted $C_{1-4}$ alkyl, such as methyl, ethyl, n-propyl, iso-propyl, n-butyl, iso-butyl, sec-butyl and tert-butyl. In still other embodiments, $R^4$ can be an unsubstituted $C_{1-4}$ haloalkyl. Exemplary unsubstituted $C_{1-4}$ haloalkyls are described herein, and include —CHF$_2$, —CH$_2$F, —CF$_3$, —CH$_2$Cl, —CHCl$_2$ and —CCl$_3$. In yet still other embodiments, $R^4$ can be an optionally substituted aryl, an optionally substituted heteroaryl or an optionally substituted heterocyclyl. In some embodiments, $R^4$ can be an optionally substituted aryl($C_{1-4}$ alkyl), an optionally substituted heteroaryl($C_{1-4}$ alkyl) or an optionally substituted heterocyclyl ($C_{1-4}$ alkyl). For example, $R^4$ can be an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

In some embodiments, $R^5$ can be hydrogen. In other embodiments, $R^5$ can be an unsubstituted $C_{1-4}$ alkyl. In still other embodiments, $R^5$ can be an unsubstituted $C_{1-4}$ haloalkyl. Exemplary unsubstituted $C_{1-4}$ alkyls and unsubstituted $C_{1-4}$ haloalkyls are described herein and include those described with respect to $R^4$. In yet still other embodiments, $R^5$ can be an optionally substituted aryl (such as an optionally phenyl), an optionally substituted heteroaryl (such as an optionally substituted monocyclic heteroaryl) or an optionally substituted heterocyclyl (for example, an optionally substituted monocyclic heterocyclyl). In some embodiments, $R^5$ can be an optionally substituted aryl($C_{1-4}$ alkyl), an optionally substituted heteroaryl($C_{1-4}$ alkyl) or an optionally substituted heterocyclyl($C_{1-4}$ alkyl). For example, $R^5$ can be an unsubstituted or a substituted benzyl, an unsubstituted or a substituted 5-membered monocyclic heteroaryl, an unsubstituted or a substituted 6-membered monocyclic heteroaryl, an unsubstituted or a substituted 5-membered monocyclic heterocyclyl or an unsubstituted or a substituted 6-membered monocyclic heterocyclyl.

The heteroaryl and heterocyclyl for $R^2$, $R^3$, $R^4$ and $R^5$ and included in the heteroaryl($C_{1-4}$ alkyl) and heterocyclyl($C_{1-4}$ alkyl) for $R^2$, $R^3$, $R^4$ and $R^5$ can include 3, 4, 5 or 6 ring(s) atoms and include 1, 2 or 3 heteroatoms such as N (nitrogen), O (oxygen) and S (sulfur). For example, the heteroaryl for $R^2$, $R^3$, $R^4$ and $R^5$ and included in the heteroaryl($C_{1-4}$ alkyl) for $R^2$, $R^3$, $R^4$ and $R^5$ can be an optionally substituted 5- or 6-membered monocyclic heteroaryl that includes 1 heteroatom selected from N, O and S; and the heterocyclyl for $R^2$, $R^3$, $R^4$ and $R^5$ and included in the heterocyclyl($C_{1-4}$ alkyl) for $R^2$, $R^3$, $R^4$ and $R^5$ can be an optionally substituted 5- or 6-membered monocyclic heterocyclyl that includes 1 heteroatom selected from N, O and S.

In some embodiments, $R^6$ can be hydrogen. In other embodiments, $R^6$ can be an unsubstituted $C_{1-4}$ alkyl. In still other embodiments, $R^6$ can be an unsubstituted $C_{1-4}$ haloalkyl. Suitable unsubstituted $C_{1-4}$ alkyls and unsubstituted $C_{1-4}$ haloalkyls include methyl, ethyl, n-propyl, iso-propyl, n-butyl, iso-butyl, sec-butyl, tert-butyl, —CHF$_2$, —CH$_2$F, —CF$_3$, —CH$_2$Cl, —CHCl$_2$ and —CCl$_3$.

In some embodiments, $R^7$ can be hydrogen. In other embodiments, $R^7$ can be an unsubstituted $C_{1-4}$ alkyl, such as methyl, ethyl, n-propyl, iso-propyl, n-butyl, iso-butyl, sec-butyl or tert-butyl. In still other embodiments, $R^7$ can be an unsubstituted $C_{1-4}$ haloalkyl, for example, —CHF$_2$, —CH$_2$F, —CF$_3$, —CH$_2$Cl, —CHCl$_2$ and —CCl$_3$.

In some embodiments, $R^2$, $R^3$, $R^4$, $R^5$, $R^6$ and $R^7$ can be each hydrogen. In other embodiments, at least one of $R^2$, $R^3$, $R^4$, $R^5$, $R^6$ and $R^7$ can be a non-hydrogen group, such as those described herein in the previous paragraphs. In some embodiments, $R^2$ can be a non-hydrogen moiety; and $R^3$, $R^4$, $R^5$, $R^6$ and $R^7$ can be each hydrogen. For example, $R^2$ can be an unsubstituted $C_{1-4}$ alkyl (such as methyl); and $R^3$, $R^4$, $R^5$, $R^6$ and $R^7$ can be each hydrogen. As another example, $R^2$ can be an unsubstituted $C_{3-4}$ cycloalkyl (such as cyclopropyl or cyclobutyl); and $R^3$, $R^4$, $R^5$, $R^6$ and $R^7$ can be each hydrogen.

The 5-membered ring of Formula (I) shown herein can include 2 or 3 nitrogens. In some embodiments, when X is N (nitrogen), the 5-membered ring of Formula (I) can be a 1,2,3-triazole and have the structure of Formula (Ia). In other embodiments, when X is CH, the 5-membered ring of Formula (I) can be a pyrazole and have the structure of Formula (Ib). In still other embodiments, when X is CD, the 5-membered ring of Formula (I) can be a deuterium-substituted pyrazole and have the structure of Formula (Ic). In yet still other embodiments, when X is CF, the 5-membered ring of Formula (I) can be a fluoro-substituted pyrazole and have the structure of Formula (Id). In some embodiments, when X is C(CH$_3$), the 5-membered ring of Formula (I) can be a methyl-substituted pyrazole and have the structure of Formula (Ie).

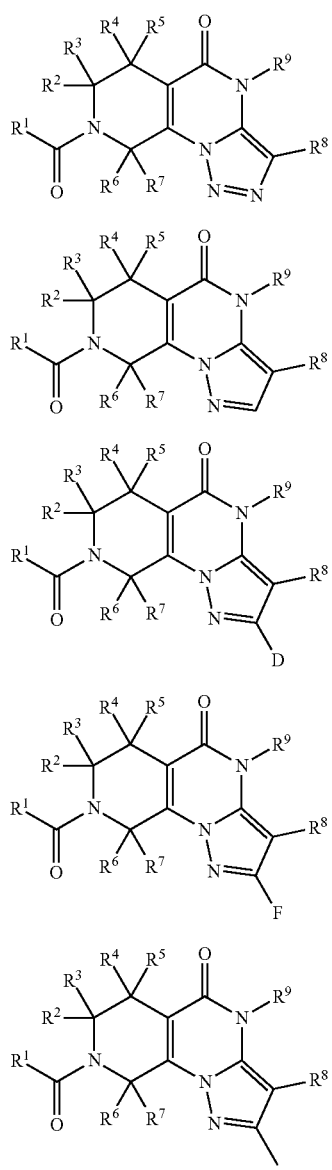

The R$^9$ substituent of Formula (I) can be a variety of cyclic moieties such as those described herein. In some embodiments, R$^9$ can be a substituted aryl. As an example, R$^9$ can be a substituted phenyl. The phenyl for R$^9$ can be substituted with one or more substituents, such as those described herein (including those listed in the definition of "optionally substituted" and/or those provided in this paragraph). In some embodiments, R$^9$ can be a substituted phenyl, wherein the phenyl can be substituted with one or more substituents independently selected from —C(=O) NHCH$_3$, halogen, an unsubstituted 5- or 6-membered monocyclic heteroaryl, a 5- or 6-membered monocyclic heteroaryl substituted with a moiety selected from an unsubstituted C$_{1-4}$ alkyl and a C$_{1-4}$ haloalkyl, an unsubstituted 5- or 6-membered monocyclic heterocyclyl, a 5- or 6-membered monocyclic heterocyclyl substituted with a moiety selected from the group consisting of an unsubstituted C$_{1-4}$ alkyl and a C$_{1-4}$ haloalkyl, —C(=O)—NR$^{12}$—CH$_2$—R$^{13}$, (wherein R$^{12}$ can be hydrogen or an unsubstituted C$_{1-4}$ alkyl; R$^{13}$ can be selected from hydroxy, α-amino acid and —O—P(=O) (OR$^{14}$)$_2$; and each R$^{14}$ can be independently hydrogen or an unsubstituted C$_{1-4}$ alkyl; and wherein the α-amino acid can be connected via its hydroxy that is part of its main-chain carboxylic acid).

The substituent(s) described herein can be on various positions of the phenyl ring. For example, a substituent can be present at the ortho-, meta- or para-position. In some embodiments, R$^9$ can be substituted at the ortho-position. In some embodiments, R$^9$ can be substituted at the meta-position. In some embodiments, R$^9$ can be substituted at the para-position. The number of substituents on the phenyl of R$^9$ can also vary. There can be 1, 2, 3 or more than 3 substituents present on the phenyl of R$^9$. In some embodiments, one substituent can be present on the phenyl of R$^9$. In other embodiments, two substituents can be present on the phenyl of R$^9$. In still other embodiments, three substituents or more than three substituents can be present on the phenyl of R$^9$. In some embodiments, one substituent can be present on the phenyl of R$^9$ at the para-position. In other embodiments, one substituent can be present on the phenyl of R$^9$ at the para-position and a second substituent can be present on the phenyl of R$^9$ at the meta-position. In still other embodiments, one substituent can be present on the phenyl of R$^9$ at the para-position and a second substituent can be present on the phenyl of R$^9$ at the ortho-position.

The possible substituents that can be present on the substituted phenyl for R$^9$ include those listed in the definition of "optionally substituted" and/or those provided in this paragraph, such as —C(=O)NHCH$_3$, —C(=O)N(an unsubstituted C$_{1-4}$ alkyl)-CH$_2$-(α-amino acid), wherein the α-amino acid is linked to the —CH$_2$— via its main-chain oxygen that is part of its carboxylic acid group (such as —C(=O)N(an unsubstituted C$_{1-4}$ alkyl)-CH$_2$—O—C (=O)—C(an unsubstituted C$_{1-4}$ alkyl)NH$_2$), halogen, an unsubstituted 5- or 6-membered monocyclic heteroaryl, a 5- or 6-membered monocyclic heteroaryl substituted with a moiety selected from an unsubstituted C$_{1-4}$ alkyl and a C$_{1-4}$ haloalkyl, an unsubstituted 5- or 6-membered monocyclic heterocyclyl, a 5- or 6-membered monocyclic heterocyclyl substituted with a moiety selected from the group consisting of an unsubstituted C$_{1-4}$ alkyl and a C$_{1-4}$ haloalkyl, —C(=O)—N(an unsubstituted C$_{1-4}$ alkyl)-CH$_2$—OH, —C(=O)—N(an unsubstituted C$_{1-4}$ alkyl)-CH$_2$—O—P (=O)(OH)$_2$, —C(=O)—N(an unsubstituted C$_{1-4}$ alkyl)-CH$_2$—O—P(=O)(OH)(an unsubstituted C$_{1-4}$ alkyl) and —C(=O)—N(an unsubstituted C$_{1-4}$ alkyl)-CH$_2$—O—P (=O)(an unsubstituted C$_{1-4}$ alkyl)$_2$. When substituent that is present on the substituted phenyl for R$^9$ includes an α-amino acid, the α-amino acid can be an L-α-amino acid or D-α-amino acid, including glycine, alanine, valine, leucine and isoleucine. In some embodiments, R$^9$ can be a substituted phenyl, substituted with —CONHCH$_3$, for example R$^9$ can be

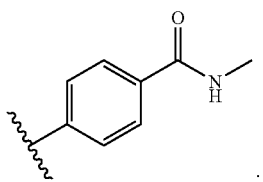 [SMILES: *c1ccc(C(=O)NC)cc1]

The phenyl can be substituted with a 5- or 6-membered monocyclic heteroaryl, such as pyrazole, imidazole, 1,2,3-triazole, 1,2,4-triazole and tetrazole. The 5- or 6-membered monocyclic heteroaryl present on the substituted phenyl of $R^9$ can be unsubstituted or substituted. When the 5- or 6-membered monocyclic heteroaryl is substituted, the monocyclic heteroaryl can be substituted with one or more moieties selected from an unsubstituted $C_{1-4}$ alkyl (including methyl) and an unsubstituted $C_{1-4}$ haloalkyl (including $CF_3$). In some embodiments, $R^9$ can be substituted with an unsubstituted or a substituted pyrazole, an unsubstituted or a substituted imidazole, an unsubstituted or a substituted 1,2,3-triazole, an unsubstituted or a substituted 1,2,4-triazole or an unsubstituted or a substituted tetrazole. Examples of 5- or 6-membered monocyclic heteroaryls that can be present on the substituted phenyl of $R^9$ include the following:

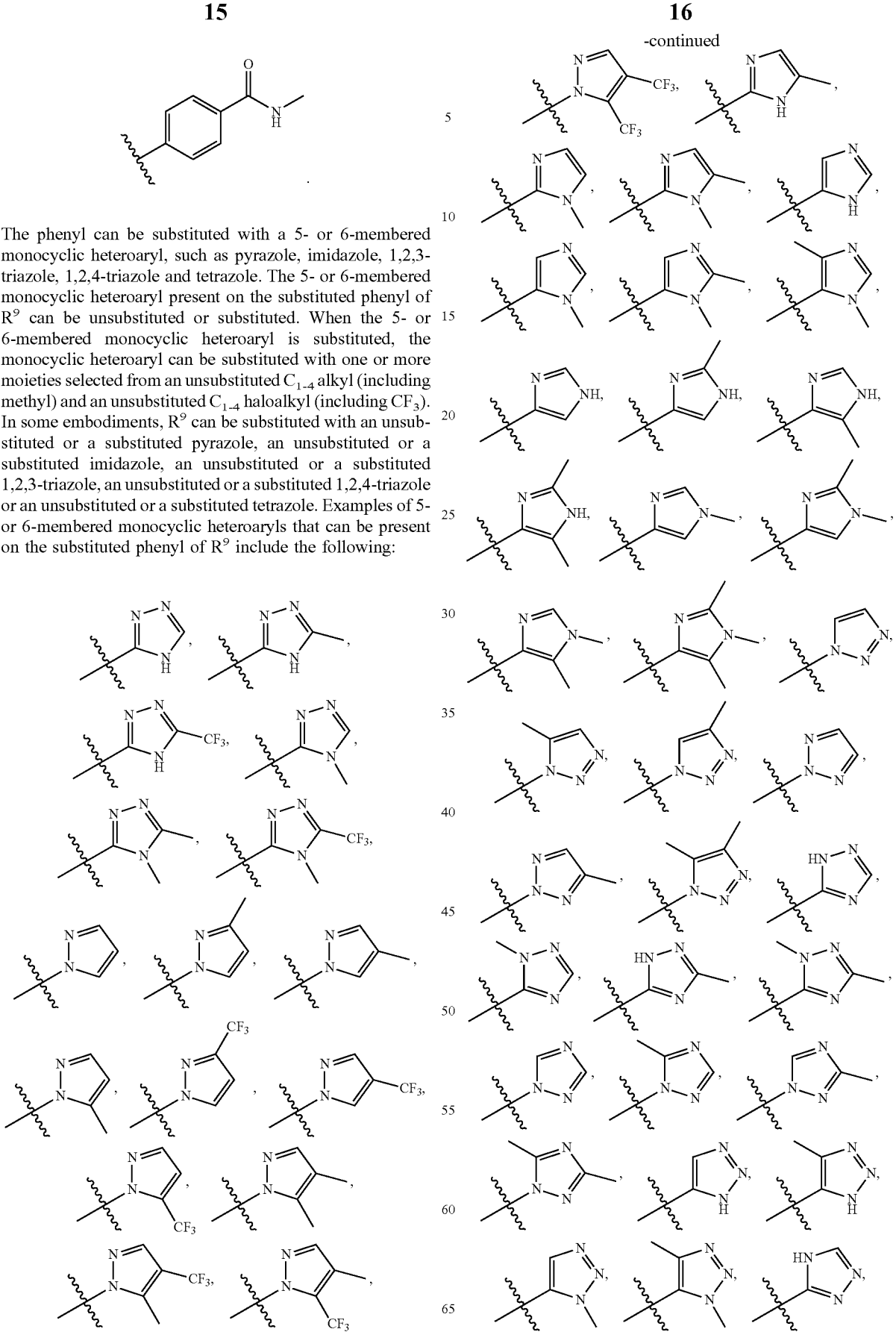

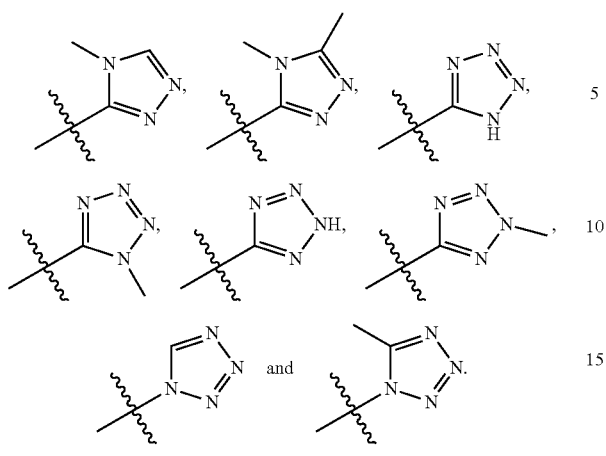
In some embodiments, the 5- or 6-membered monocyclic heteroaryls that can be present on the substituted phenyl of $R^9$ include the following:
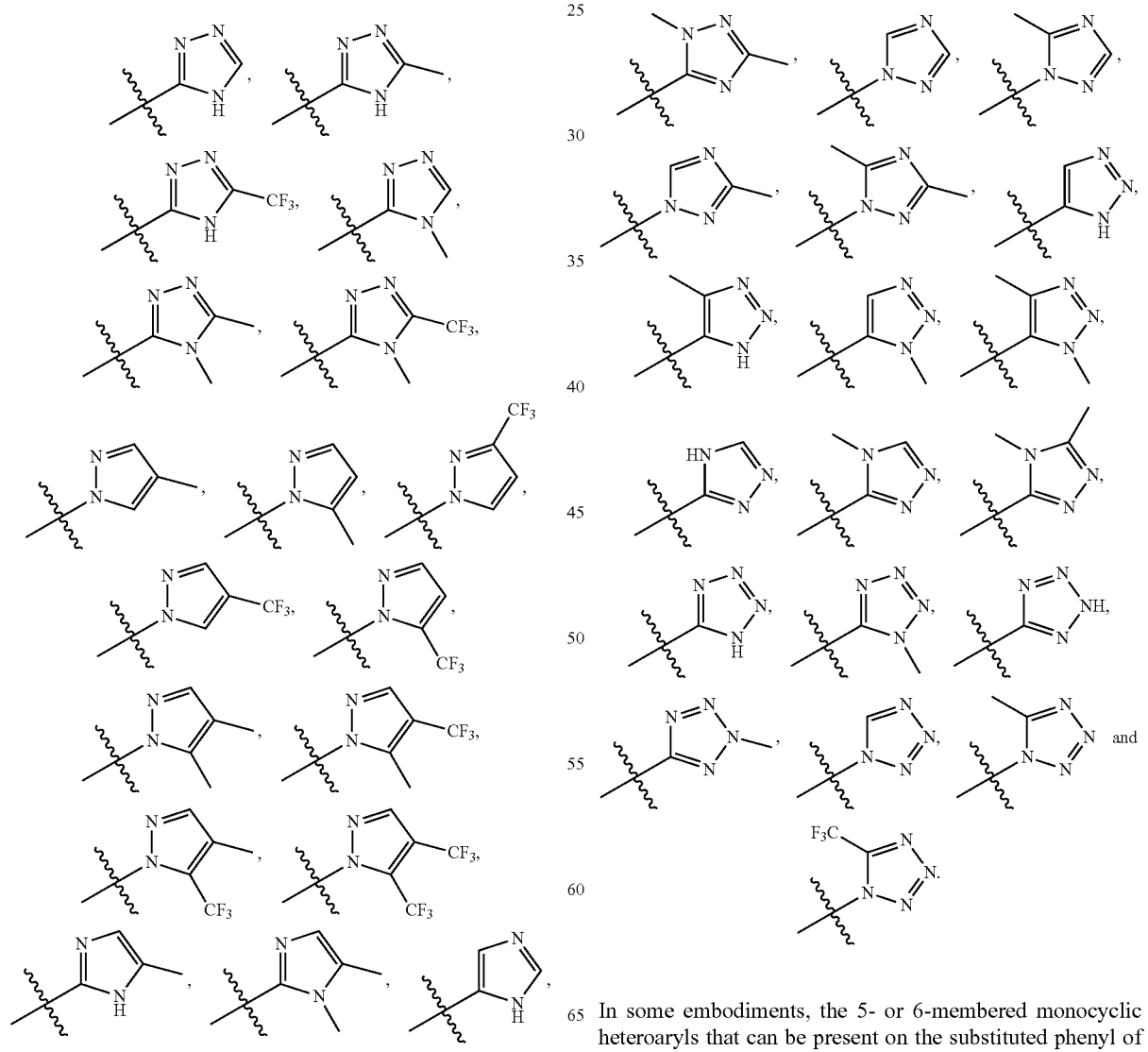
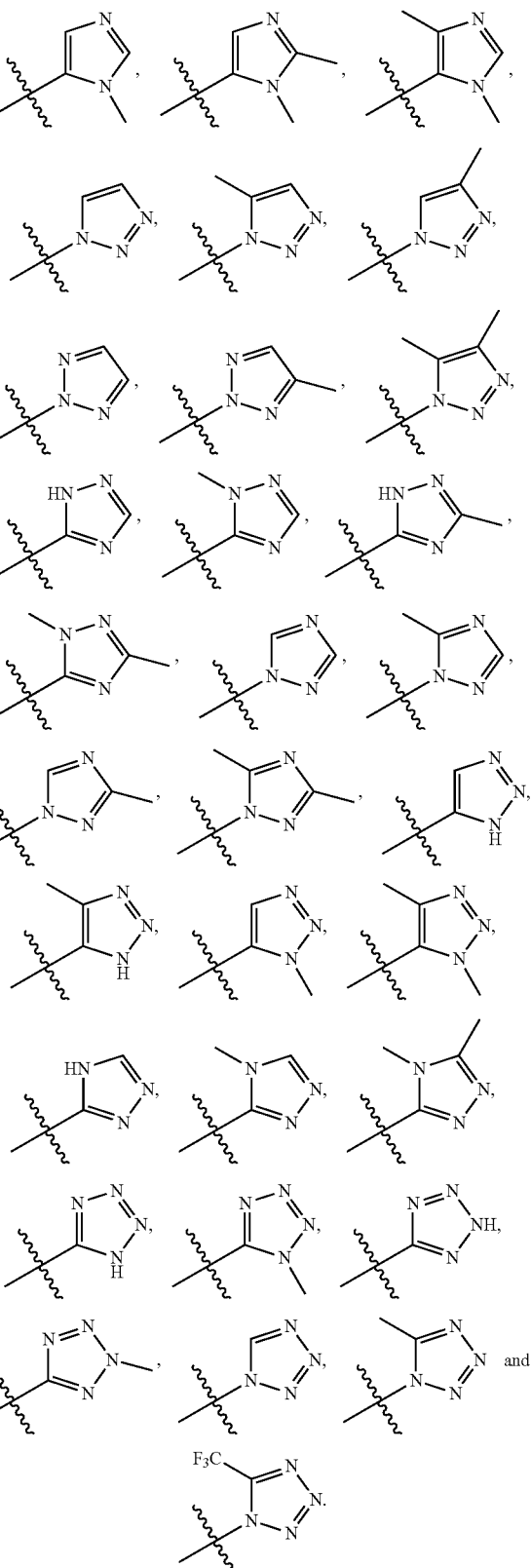
In some embodiments, the 5- or 6-membered monocyclic heteroaryls that can be present on the substituted phenyl of $R^9$ include the following:

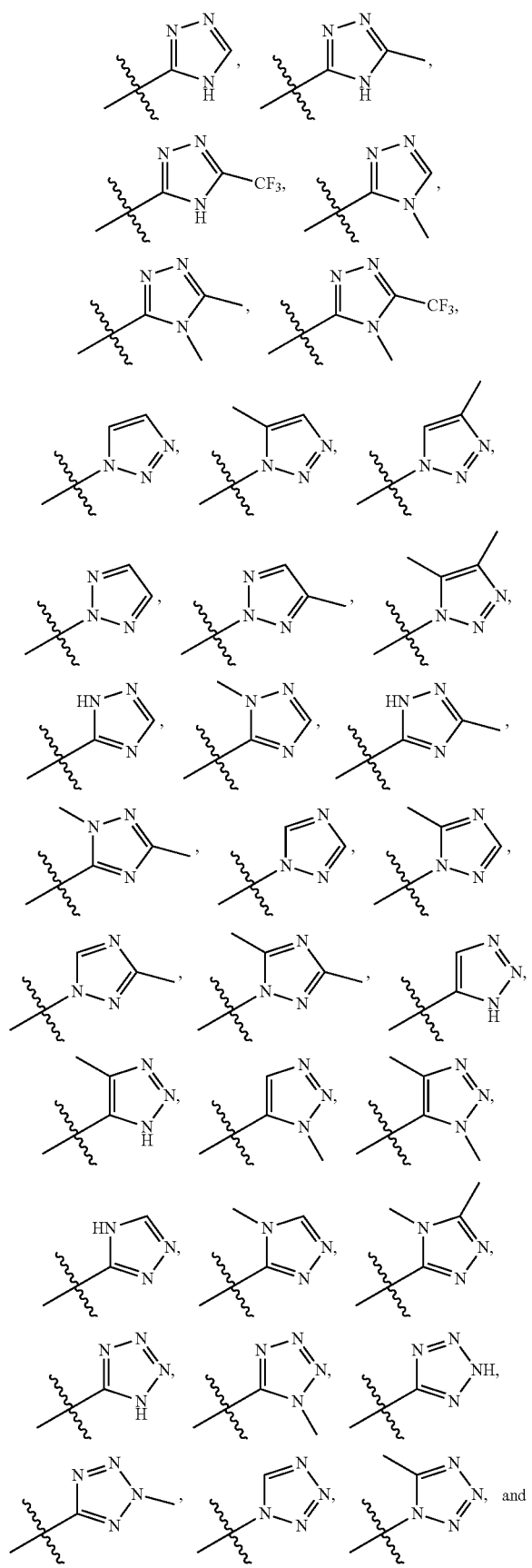

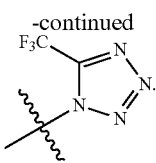

-continued

The phenyl can be substituted with a 5- or 6-membered monocyclic heterocyclyl, such as oxo-triazole (e.g. oxo-1,2,4-triazole) or oxo-oxadiazole (e.g. oxo-1,2,4-oxadiazole). The 5- or 6-membered monocyclic heteroaryl present on the substituted phenyl of $R^9$ can be unsubstituted or substituted. When the 5- or 6-membered monocyclic heterocyclyl is substituted, the monocyclic heterocyclyl can be substituted with one or more moieties selected from an unsubstituted $C_{1-4}$ alkyl (including methyl) and an unsubstituted $C_{1-4}$ haloalkyl (including $CF_3$). Examples of 5- or 6-membered monocyclic heterocyclyls that can be present on the substituted phenyl of $R^9$ include the following:

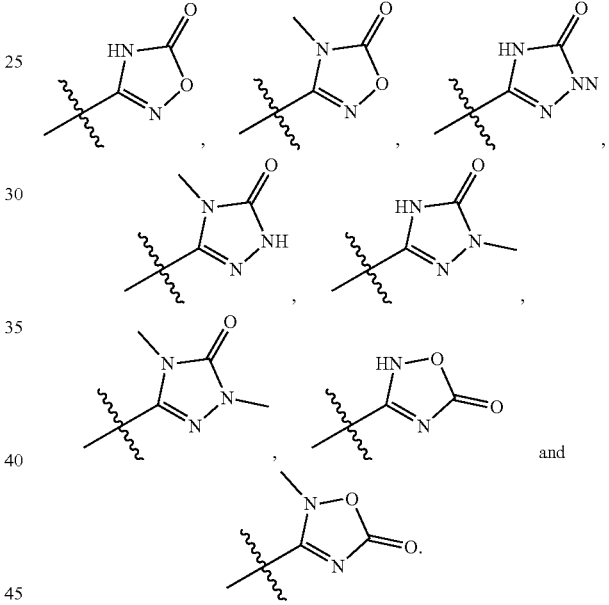

In some embodiments, $R^9$ can be an optionally substituted heteroaryl. The optionally substituted heteroaryl can be a monocyclic or a bicyclic heteroaryl. In some embodiments, $R^9$ can be an optionally substituted monocyclic heteroaryl, such as a 5- or 6-membered, nitrogen-containing monocyclic heteroaryl. As an example, $R^9$ can be an unsubstituted or a substituted pyrazole, an unsubstituted or a substituted pyrazine, an unsubstituted or a substituted pyrimidine, an unsubstituted or a substituted pyridazine and an unsubstituted or a substituted pyridine. When the monocyclic heteroaryl is substituted, the monocyclic heteroaryl can be substituted with one or more moieties selected from an unsubstituted $C_{1-4}$ alkyl (including methyl), an unsubstituted $C_{1-4}$ haloalkyl (including $CF_3$), an unsubstituted C-amido (such as —C(=O)NHCH$_3$), a mono-substituted amino group (such as —NHCH$_3$) and an optionally substituted monocyclic heteroaryl. In some embodiments, when the $R^9$ monocyclic heteroaryl is substituted with a monocyclic heteroaryl, the substituent monocyclic heteroaryl is optionally substituted with one or more moieties selected from an unsubstituted $C_{1-4}$ alkyl (including methyl) and an unsubstituted $C_{1-4}$ haloalkyl (including $CF_3$), for example

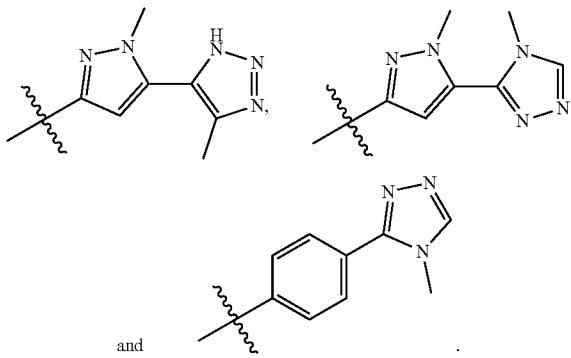

and

Exemplary optionally substituted monocyclic heteroaryls for $R^9$ include, but are not limited to, the following:

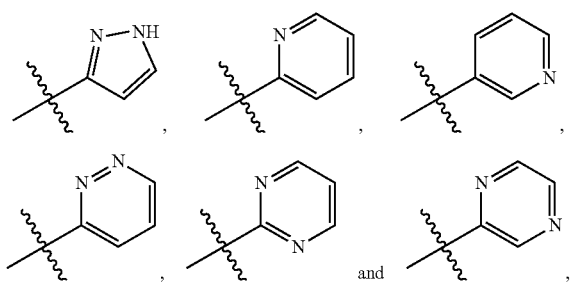 [SMILES: *c1cc[nH]n1 ; *c1ccccn1 ; *c1cccnc1 ; *c1cccnn1 ; *c1ncccn1 ; *c1cnccn1]

including, for example, substituted pyrazole such as

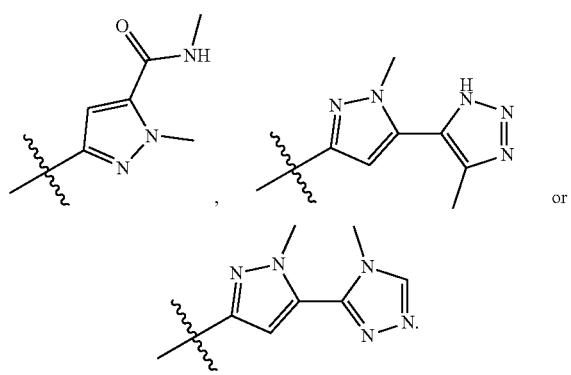 [SMILES: *c1cc(C(=O)NC)n(C)n1 ; *c1cc(-c2[nH]nnc2C)n(C)n1 ; *c1cc(-c2nncn2C)n(C)n1]

In some embodiments optionally substituted monocyclic heteroaryls for $R^9$ include, but are not limited to, the following:

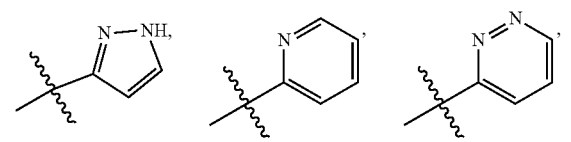

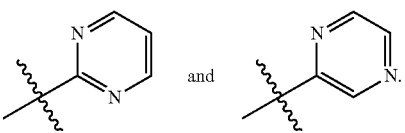

In some embodiments, $R^9$ can be an optionally substituted bicyclic heteroaryl, such as a 9- or 10-membered, nitrogen-containing bicyclic heteroaryl. Non-limiting examples of bicyclic heteroaryls for $R^9$ include an unsubstituted or a substituted indazole, an unsubstituted or a substituted benzimidazole, an unsubstituted or a substituted benzo[d]isothiazole, an unsubstituted or a substituted benzo[c]isoxazole, an unsubstituted or a substituted benzo[d]isoxazole, an unsubstituted or a substituted [1,2,4]triazolo[4,3-a]pyridine, an unsubstituted or a substituted benzimidazole, an unsubstituted or a substituted benzotriazole and 3H-imidazo[4,5-c]pyridine. When the bicyclic heteroaryl is substituted, the bicyclic heteroaryl can be substituted with one or more moieties selected from an unsubstituted $C_{1-4}$ alkyl (including methyl), an unsubstituted $C_{1-4}$ haloalkyl (including $CF_3$), an unsubstituted $C_{1-4}$ hydroxyalkyl (such as $-CH_2-OH$, $-CH_2CH_2-OH$, $-CH_2CH_2CH_2-OH$ and $-CH_2CH_2CH_2CH_2-OH$), an unsubstituted C-amido (such as $-C(=O)NHCH_3$), and a mono-substituted amino group (such as $-NHCH_3$). In some embodiments, $R^9$ can be selected from

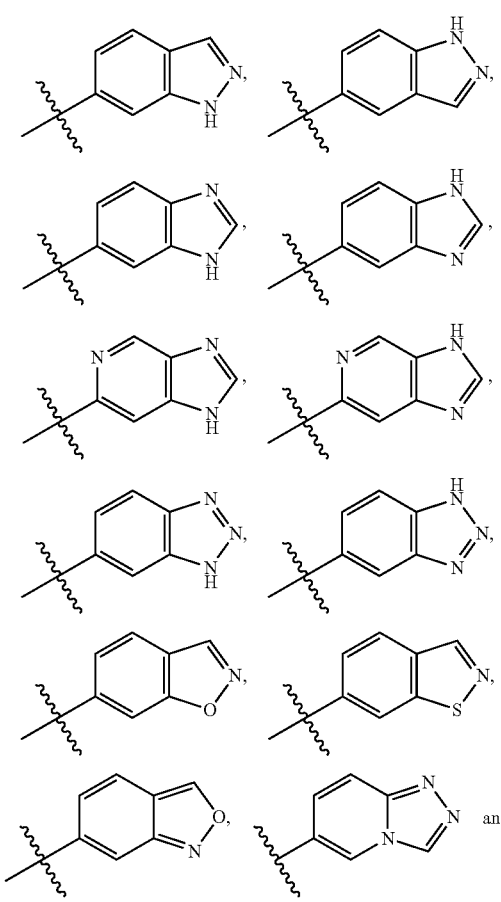

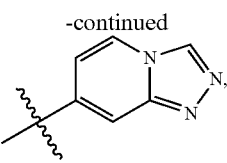

wherein each moiety can be unsubstituted or substituted. In some embodiments, R$^9$ can be selected from

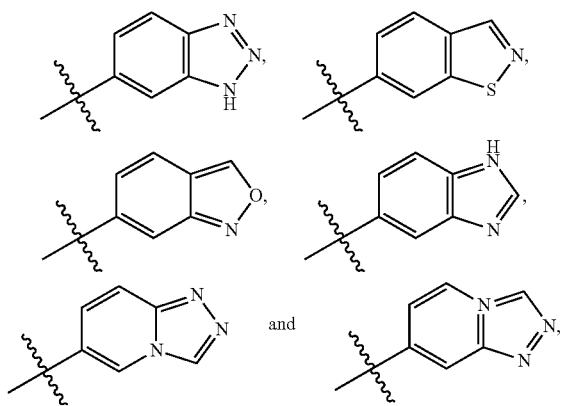

wherein each moiety can be unsubstituted or substituted.

In some embodiments, R$^9$ can be an optionally substituted heterocyclyl. The heterocyclyl can be an optionally substituted monocyclic heterocyclyl or an optionally substituted bicyclic heterocyclyl. The monocyclic heterocyclyl can be a 5- or 6-membered, nitrogen-containing monocyclic heterocyclyl; and the bicyclic heterocyclyl can be a 9- or 10-membered, nitrogen-containing bicyclic heterocyclyl. An example of a suitable heterocyclyl for R$^9$ is an unsubstituted or a substituted isoindolin-1-one, such as

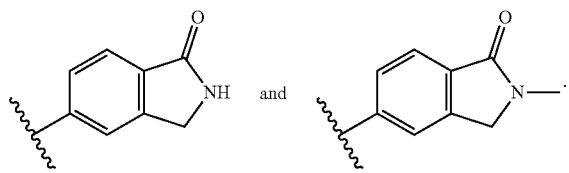 [SMILES: *c1ccc2c(c1)CNC2=O ; *c1ccc2c(c1)CN(C)C2=O]

As described herein, in some embodiments, R$^9$ can be an unsubstituted heteroaryl or an unsubstituted heterocyclyl. In other embodiments, R$^9$ can be a substituted heteroaryl or a substituted heterocyclyl, wherein the heteroaryl and/or the heterocyclyl can be substituted with one or more substituents independently selected from —C(=O)NHCH$_3$, NHCH$_3$, —NHCH$_2$CH$_3$, —N(CH$_3$)$_2$, —N(CH$_2$CH$_3$)$_2$, methyl, ethyl and —CF$_3$.

As shown for Formula (I), R$^8$ can be —CHR$^{8a}$R$^{8b}$. In some embodiments, R$^{8a}$ can be hydrogen. In other embodiments, R$^{8a}$ can be —CH$_3$.

Various moieties are suitable for R$^{8b}$. In some embodiments, R$^{8b}$ can be an unsubstituted C$_{1-4}$ alkyl, such as methyl, ethyl, n-propyl, isopropyl, n-butyl, iso-butyl, sec-butyl and tert-butyl. As provided herein, R$^{8b}$ can be unsaturated hydrocarbon moieties. In some embodiments, R$^{8b}$ can be an unsubstituted C$_{2-4}$ alkenyl. In other embodiments, R$^{8b}$ can be an unsubstituted C$_{2-4}$ alkynyl. Examples of C$_{2-4}$ alkenyls and C$_{2-4}$ alkynyls include, but are not limited to, ethenyl, propenyl (straight-chained and branched), butenyl (straight-chained and branched), ethynyl, propynyl (straight-chained and branched) and butynyl (straight-chained and branched). Cyclic moieties can also be present for R$^{8b}$. In some embodiments, R$^{8b}$ can be an unsubstituted or a substituted monocyclic C$_{3-6}$ cycloalkyl. Exemplary monocyclic C$_{3-6}$ cycloalkyls include cyclopropyl, cyclobutyl, cyclopentyl and cyclohexyl. In other embodiments, R$^{8b}$ can be an unsubstituted or a substituted phenyl. In still other embodiments, R$^{8b}$ can be an unsubstituted or a substituted monocyclic heteroaryl. In yet still other embodiments, R$^{8b}$ can be an unsubstituted or a substituted monocyclic heterocyclyl. The monocyclic heteroaryl and monocyclic heterocyclyl can be 5- or 6-membered, and can include one or more heteroatoms (such as 1, 2 or 3 heteroatoms) selected from N (nitrogen), O (oxygen) and S (sulfur). Additional examples of R$^{8b}$ cyclic groups include, but are not limited to, tetrahydrofuran, tetrahydrothiophene, furan, thiophene and pyridine.

In some embodiments, the phenyl, the monocyclic heteroaryl and the monocyclic heterocyclyl for R$^{8b}$ can be unsubstituted. In other embodiments, the phenyl, the monocyclic heteroaryl and the monocyclic heterocyclyl for R$^{8b}$ can be substituted. When the phenyl, the monocyclic heteroaryl and the monocyclic heterocyclyl for R$^{8b}$ are substituted, one or more halogens (such as fluoro, chloro and bromo) can be present.

In some embodiments, a compound of Formula (I), or a pharmaceutically acceptable salt thereof, can be a compound of Formula (Ic), or a pharmaceutically acceptable salt thereof, having the structure:

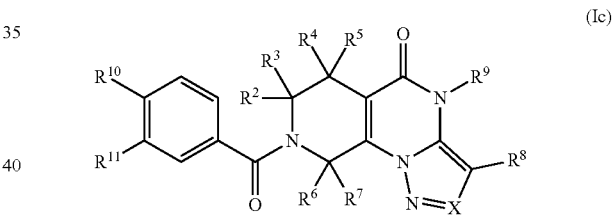

wherein: X, R$^2$, R$^3$, R$^4$, R$^5$, R$^6$, R$^7$, R$^8$ and R$^9$ can be as defined in Formula (I), R$^{10}$ can be selected from —Cl, —Br, —CHF$_2$, —CF$_3$, —CH$_3$ and —CN; and R$^{11}$ can be selected from —CHF$_2$, —CF$_3$, and —CH$_3$. In some embodiments for Formula (Ic), R$^{11}$ can be —CF$_3$. In some embodiments for Formula (Ic), R$^{11}$ can be —CF$_3$ and R$^{10}$ can be —Cl or —Br. In some embodiments for Formula (Ic), R$^{11}$ can be —CF$_3$ and R$^{10}$ can be —Br.

In some embodiments, a compound of Formula (I), or a pharmaceutically acceptable salt thereof, can be where X can be CH or N; R$^1$ can be a 3,4-substituted phenyl substituted with two moieties independently selected from the group consisting of —Cl, —Br, —CHF$_2$, —CF$_3$, —CH$_3$ and —CN; R$^2$ and R$^3$ can be independently selected from the group consisting of hydrogen, an unsubstituted C$_{1-4}$ alkyl, an unsubstituted C$_{1-4}$ haloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^4$ and R$^5$ can be independently selected from the group consisting of hydrogen, an unsubstituted C$_{1-4}$ alkyl, an unsubstituted C$_{1-4}$ haloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^6$ and R$^7$ can be independently selected from the group consisting of hydrogen, an unsubstituted C$_{1-4}$ alkyl and an unsubstituted C$_{1-4}$ haloalkyl; R$^8$ can be —CHR$^{8a}$R$^{8b}$; R$^{8a}$ can be hydrogen or —CH$_3$; R$^{8b}$ can be selected from the group consisting of an unsubstituted C$_{1-4}$ alkyl, an optionally substituted monocyclic C$_{3-6}$ cycloalkyl, an optionally substituted phenyl, an optionally substituted monocyclic heteroaryl and an optionally substituted monocyclic heterocyclyl; and R$^9$ can be a substituted aryl, an optionally substituted heteroaryl or an optionally substituted heterocyclyl.

In some embodiments, a compound of Formula (I), or a pharmaceutically acceptable salt thereof, can be where X can be CH or N; R$^1$ can be a 3,4-substituted phenyl substituted with two moieties independently selected from the group consisting of —Cl, —Br, —CHF$_2$, —CF$_3$, —CH$_3$ and —CN; R$^2$ and R$^3$ can be independently selected from hydrogen, an unsubstituted C$_{1-4}$ alkyl, an unsubstituted C$_{1-4}$ haloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^4$ and R$^5$ can be independently selected from hydrogen, an unsubstituted C$_{1-4}$ alkyl, an unsubstituted C$_{1-4}$ haloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl); R$^6$ and R$^7$ can be independently selected from hydrogen, an unsubstituted C$_{1-4}$ alkyl and an unsubstituted C$_{1-4}$ haloalkyl; R$^8$ can be —CHR$^{8a}$R$^{8b}$; R$^{8a}$ can be hydrogen or —CH$_3$; R$^{8b}$ can be selected from an unsubstituted C$_{1-4}$ alkyl, an unsubstituted C$_{2-4}$ alkenyl, an unsubstituted C$_{2-4}$ alkynyl, an optionally substituted monocyclic C$_{3-6}$ cycloalkyl, an optionally substituted phenyl, an optionally substituted monocyclic heteroaryl and an optionally substituted monocyclic heterocyclyl; and R$^9$ can be a substituted aryl, an optionally substituted heteroaryl or an optionally substituted heterocyclyl.

Examples of compounds of Formula (I) include the following:

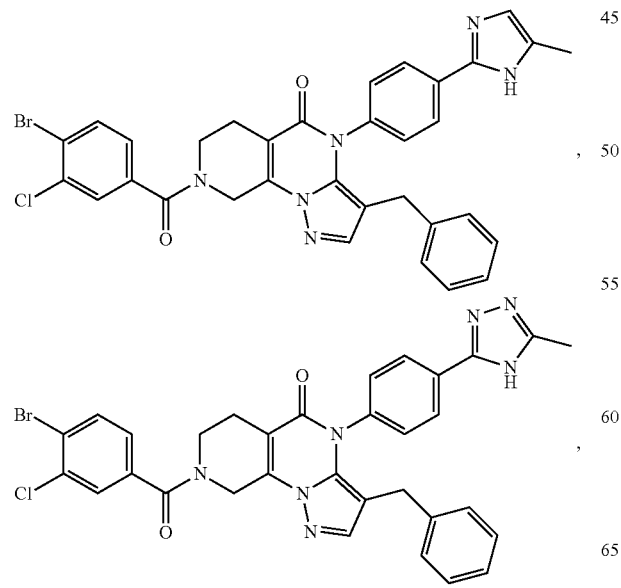

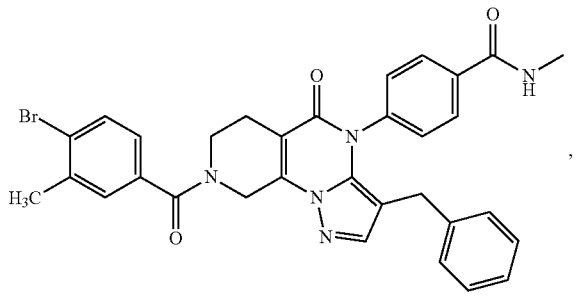

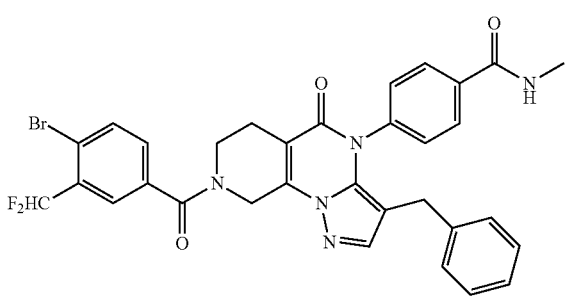

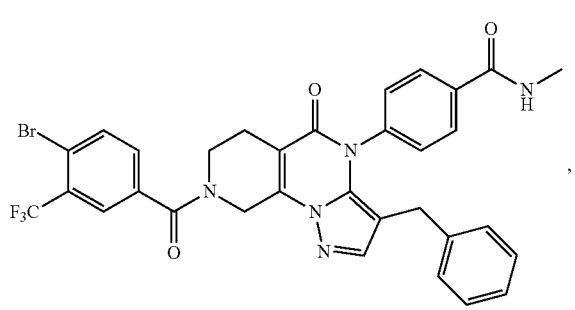

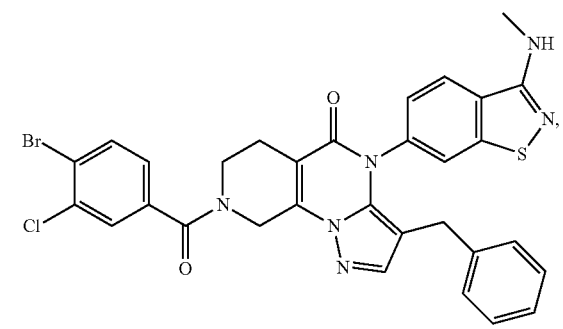

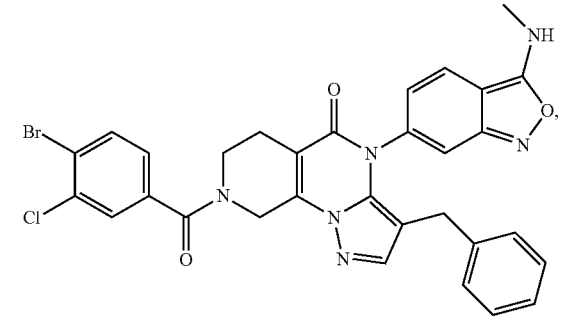

27
-continued
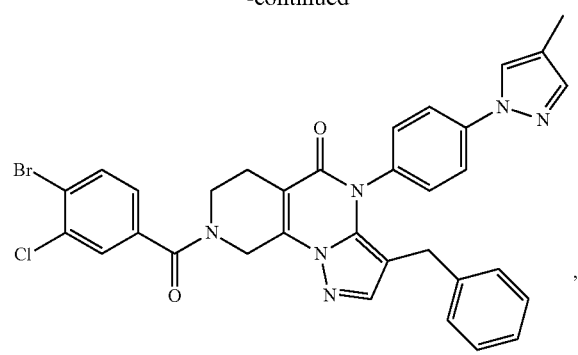
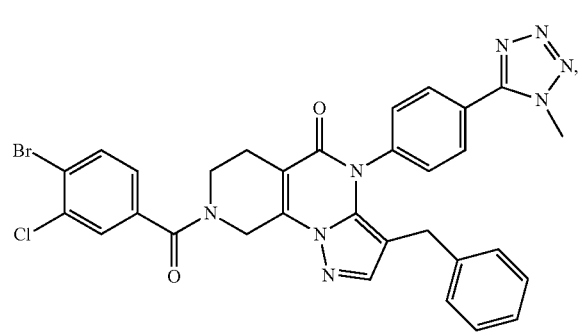
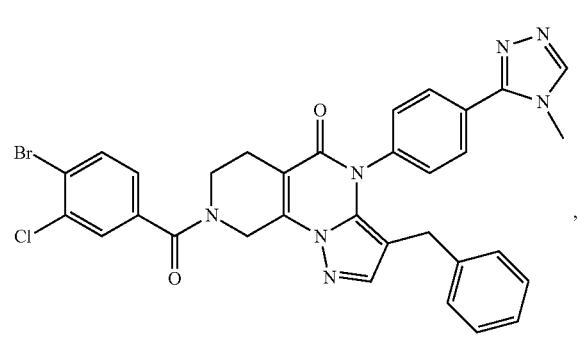
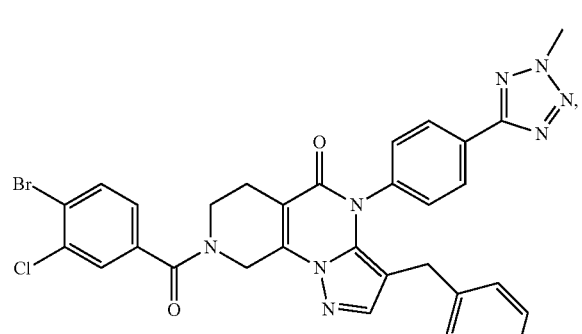
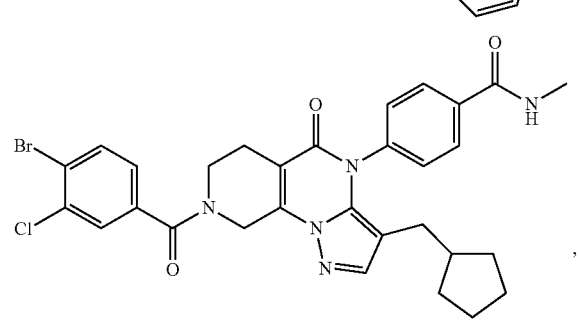
28
-continued
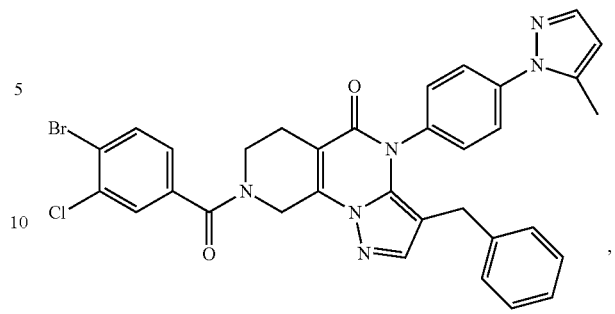
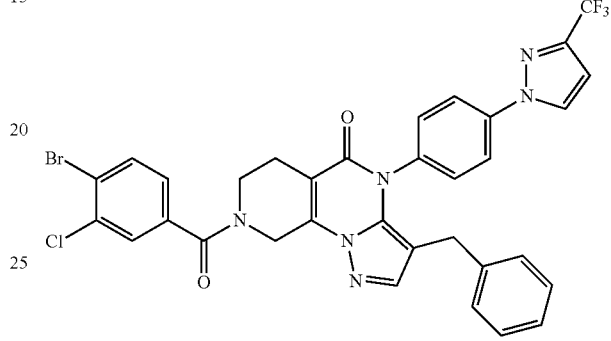
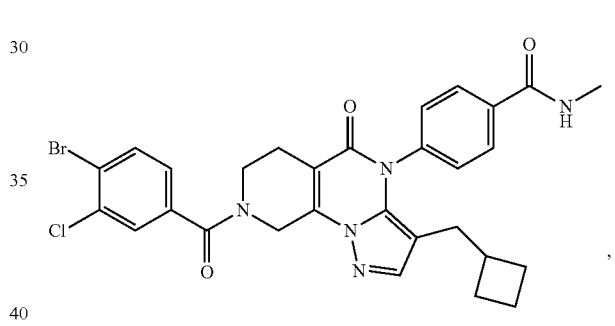
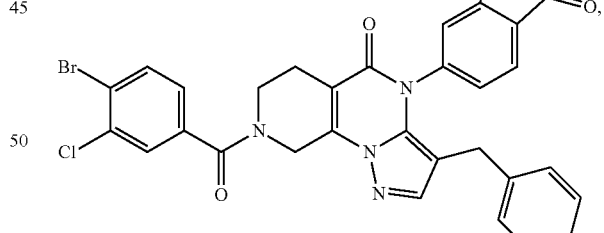
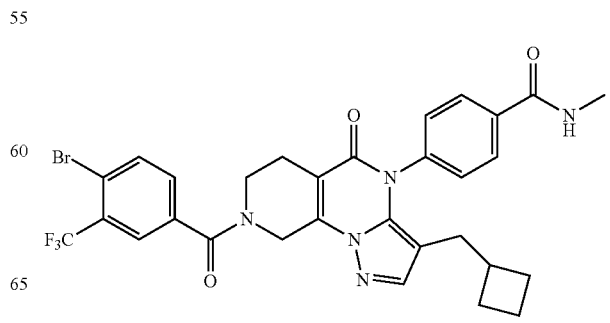

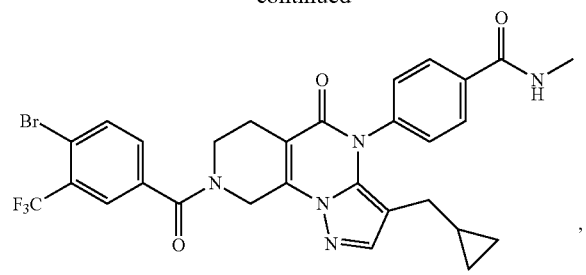,
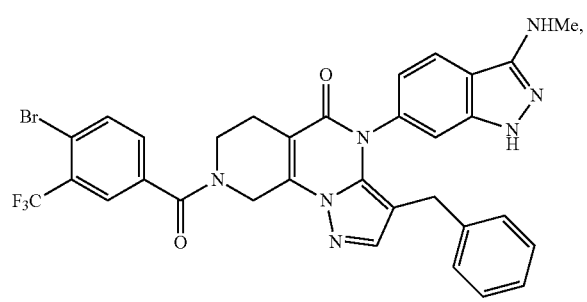,
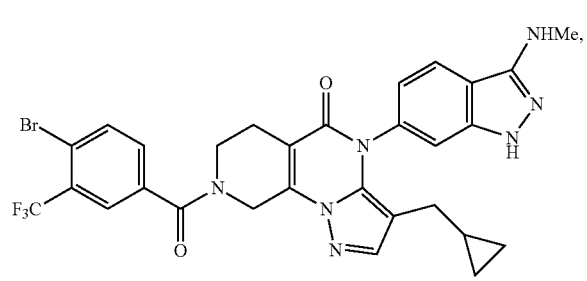,
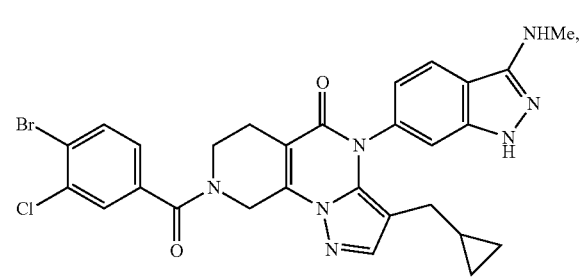,
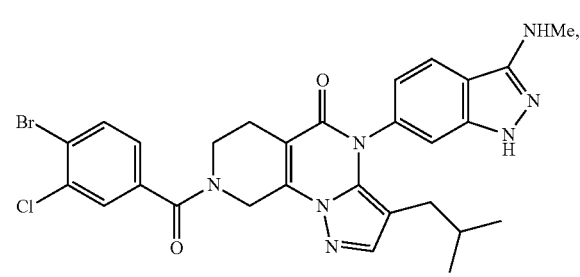,
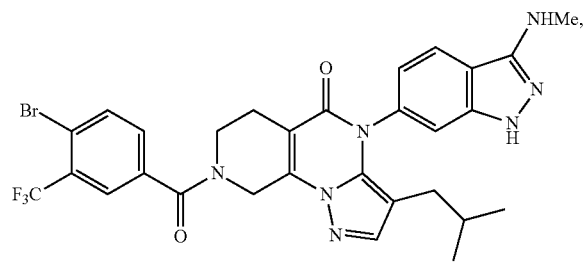,
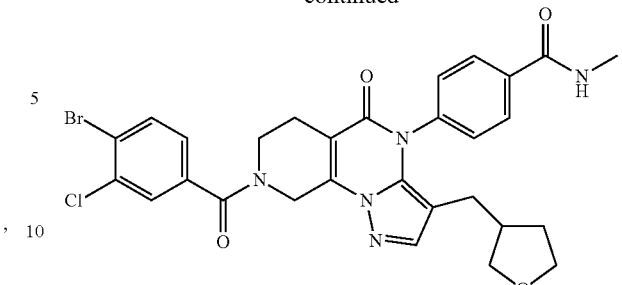,
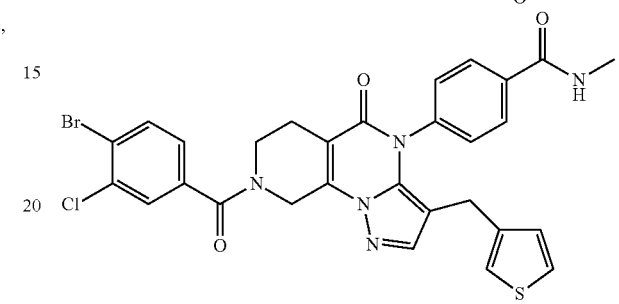,
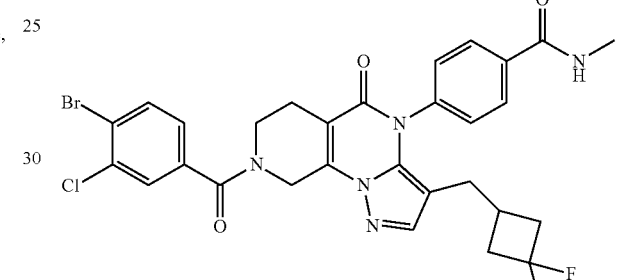,
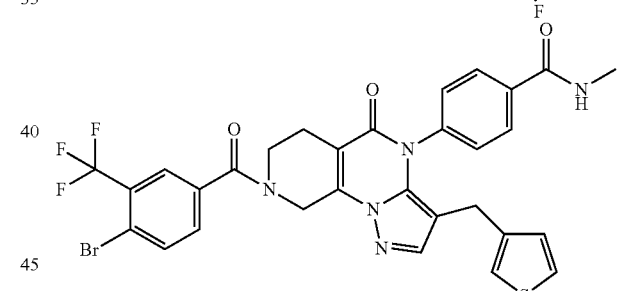,
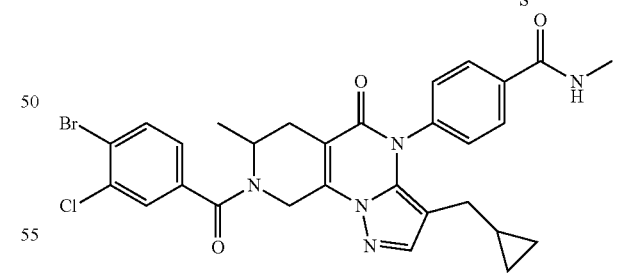,
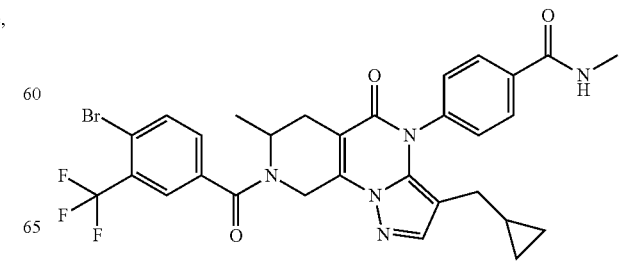,

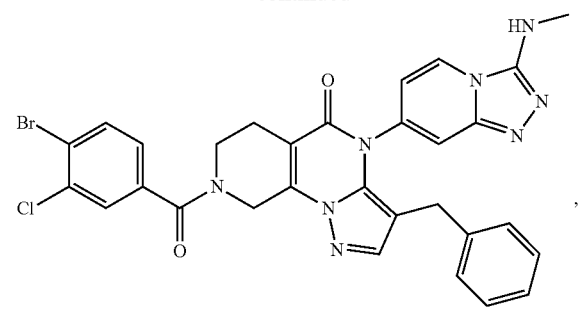
,
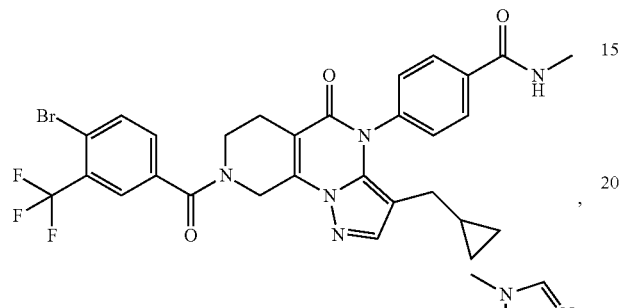
,
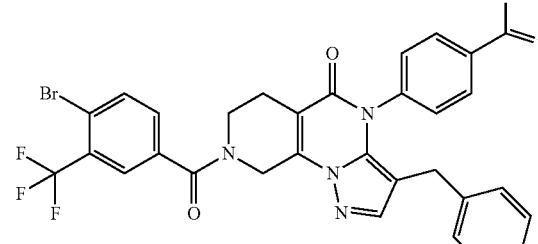
,
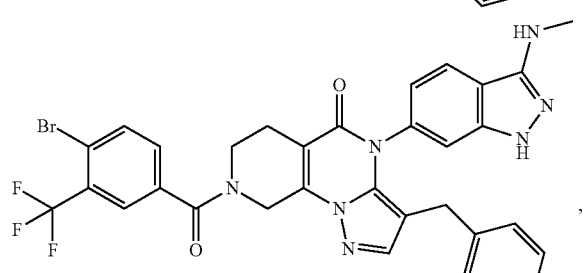
,
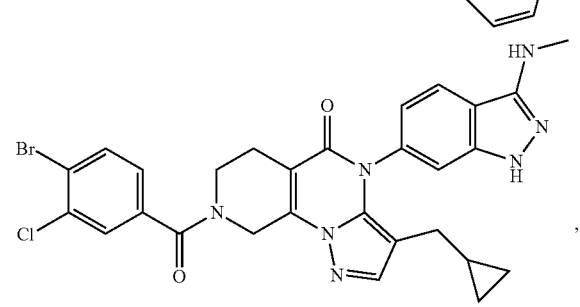
,
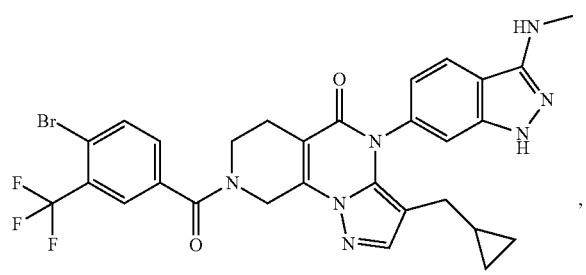
,
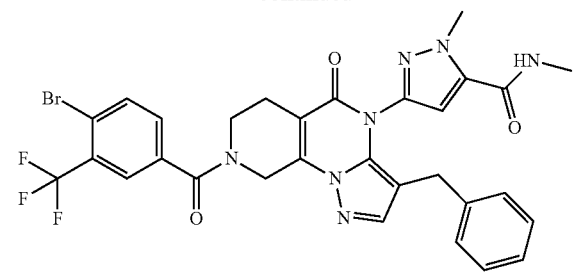
,
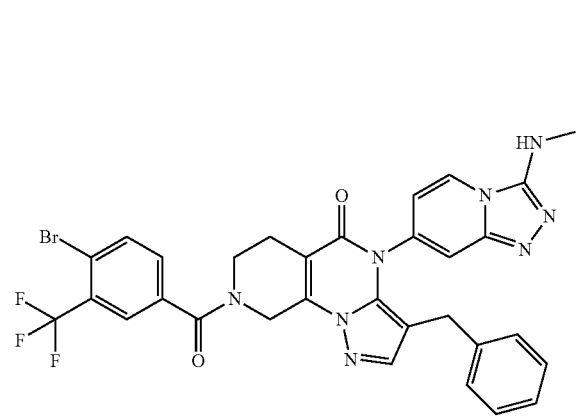
,
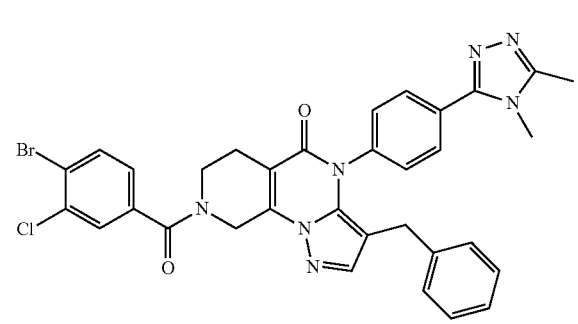
,
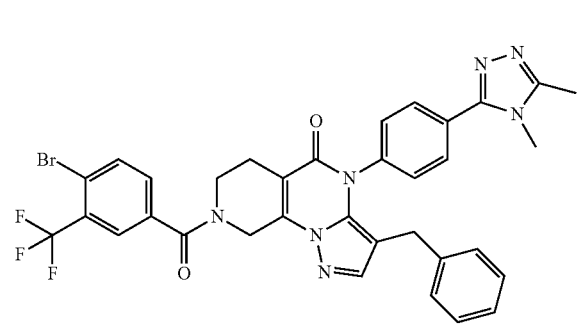
,
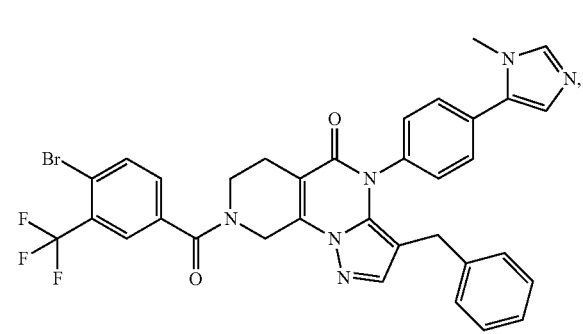
, 33
-continued
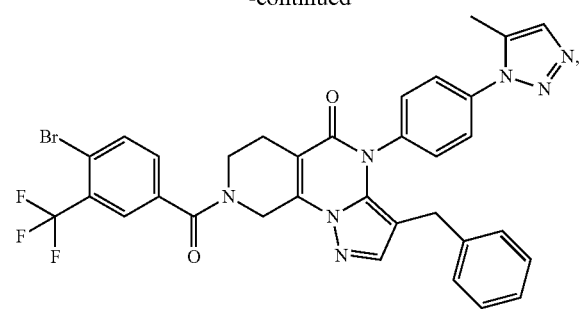
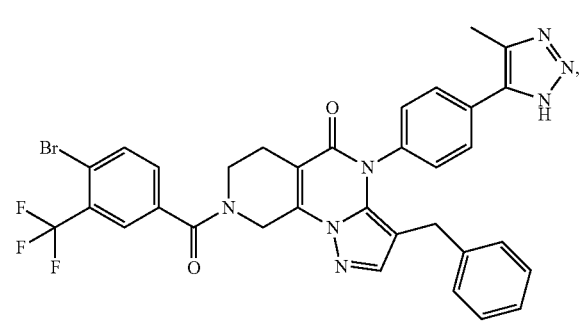
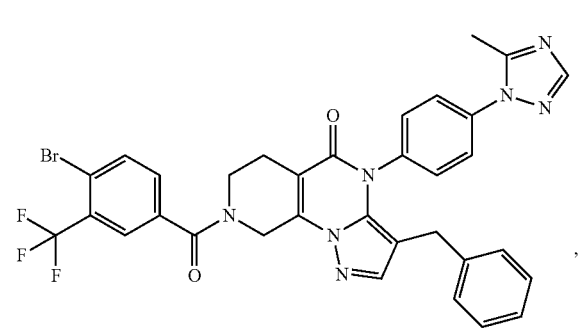
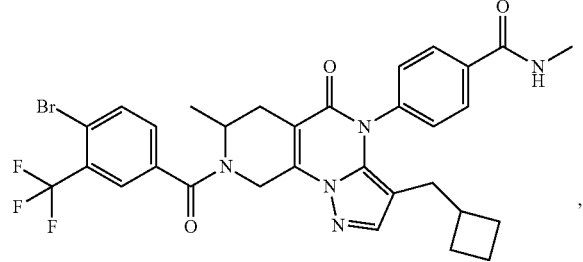
,
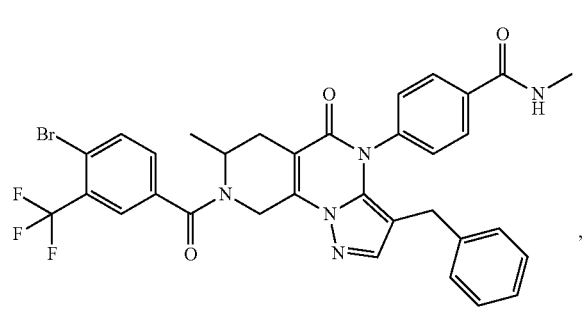
,
34
-continued
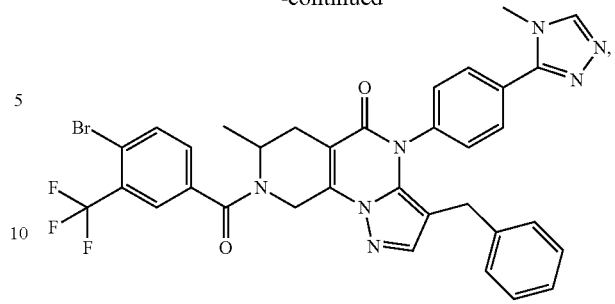
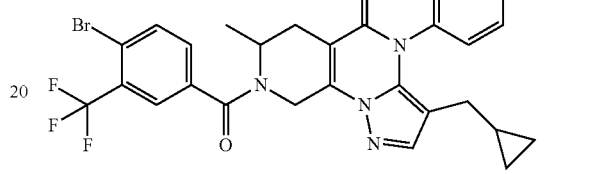
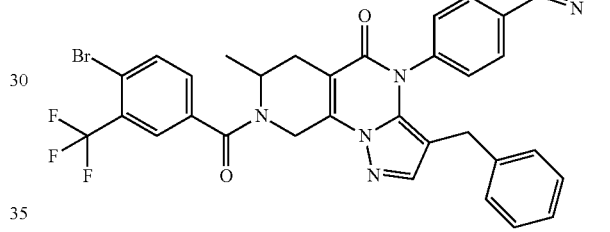
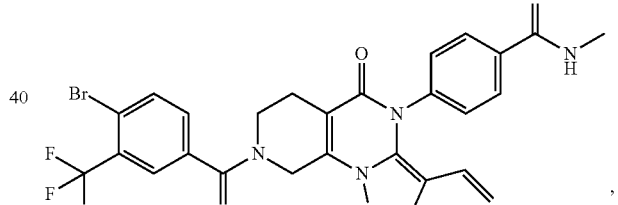
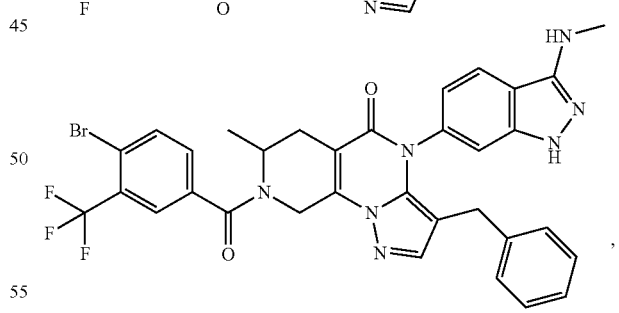
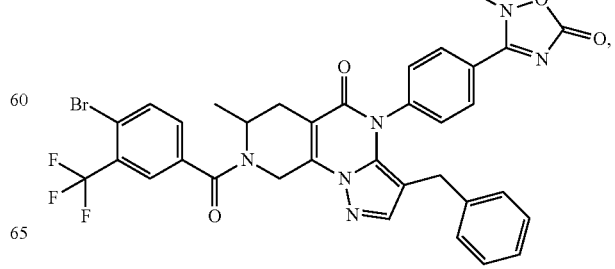
,

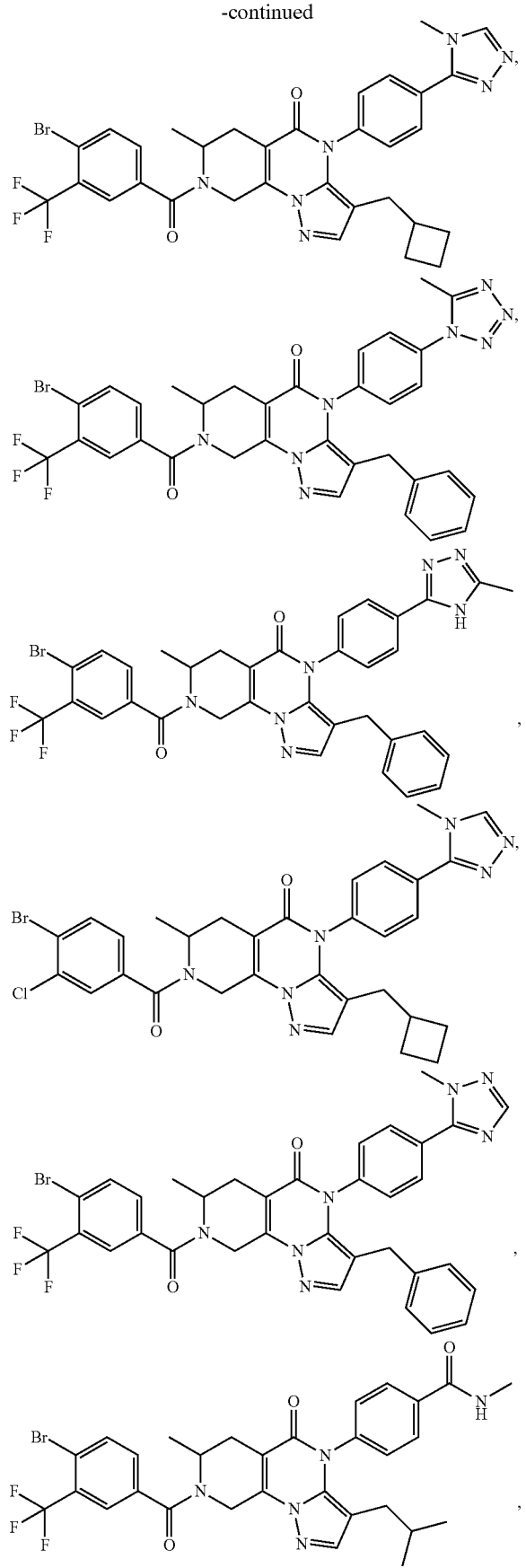
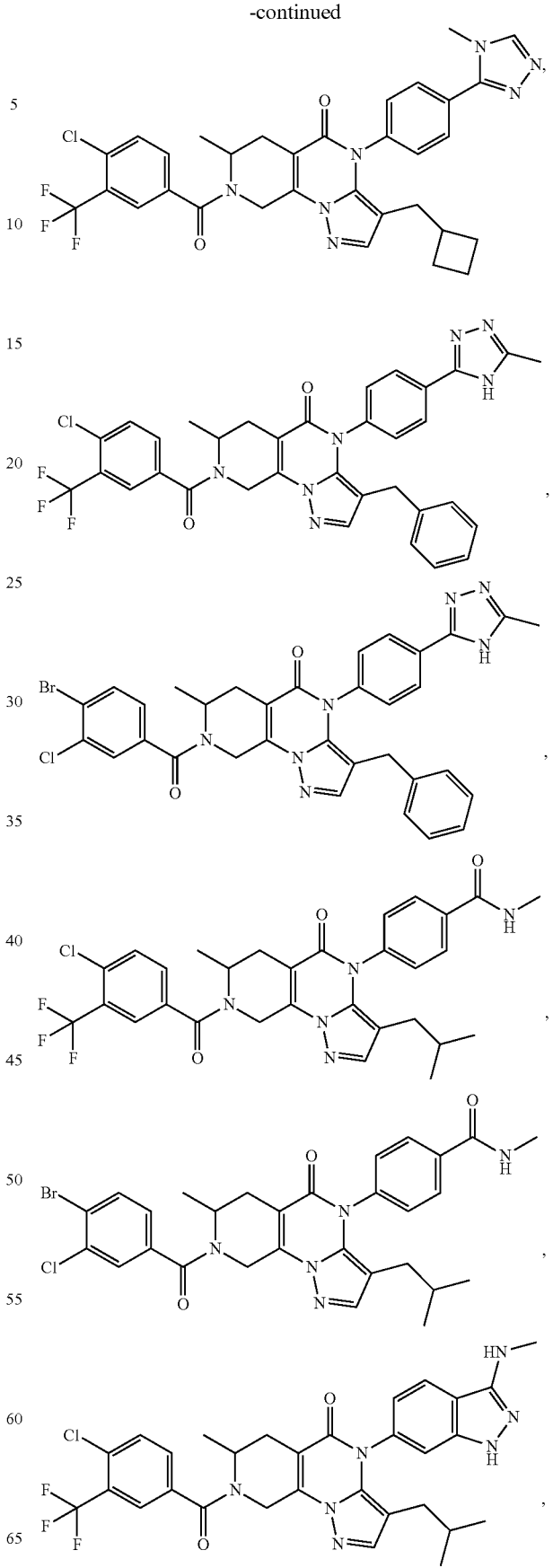

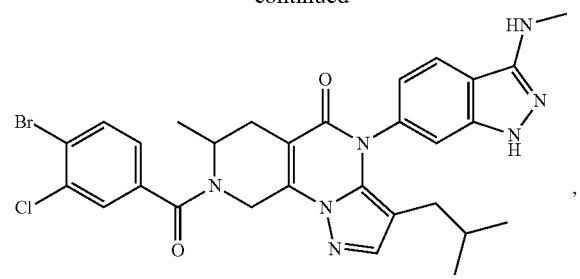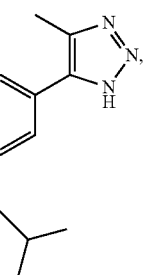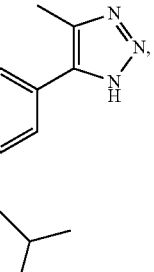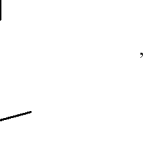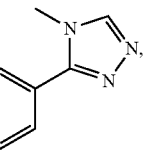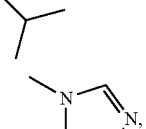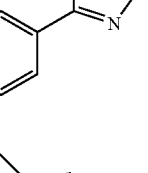

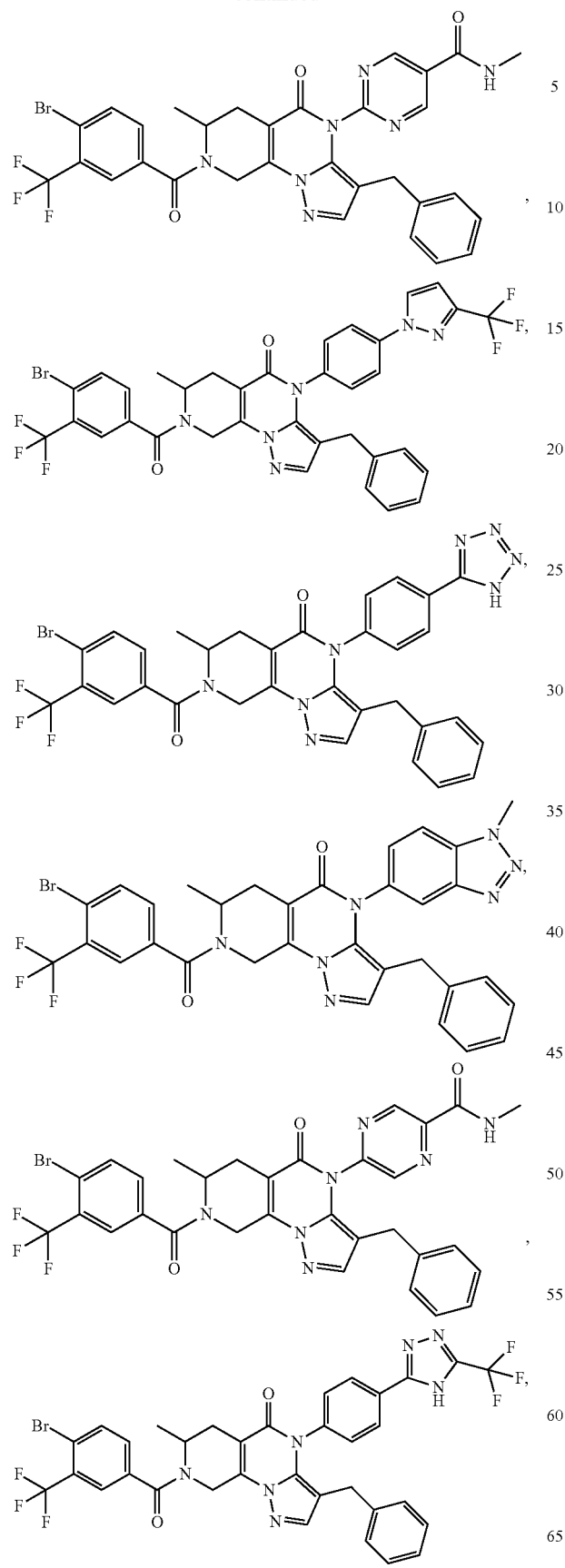
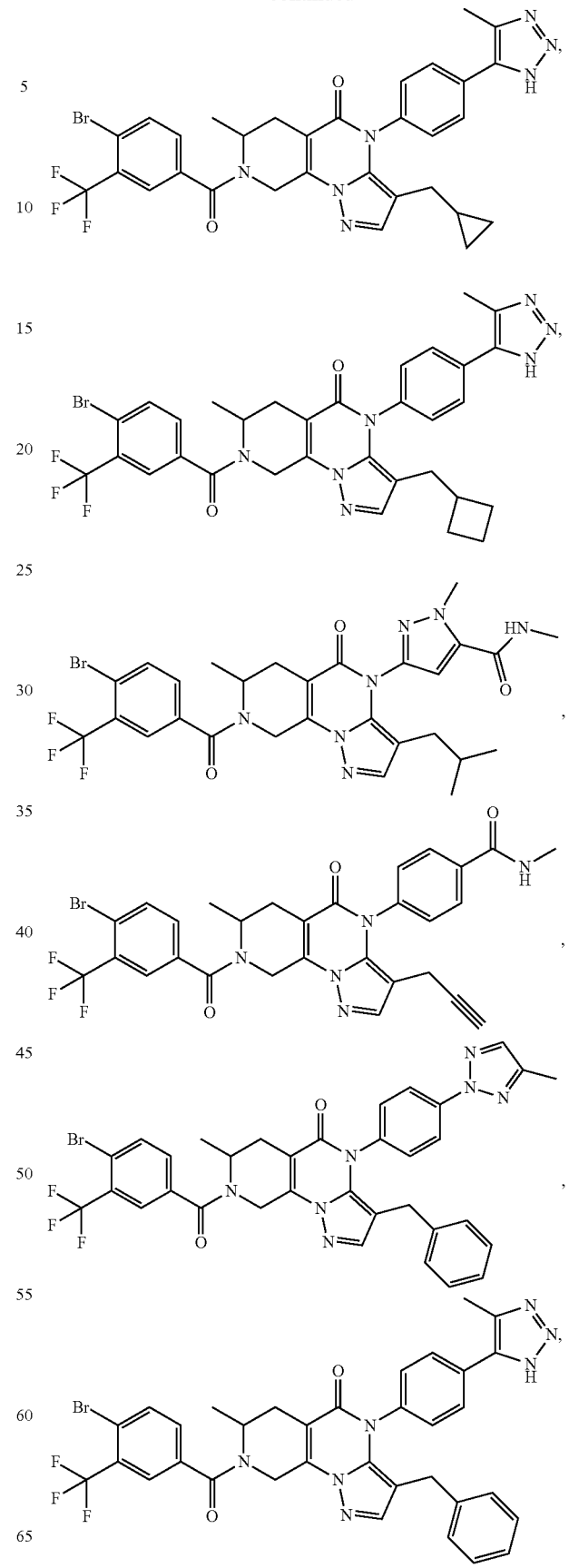

41
-continued
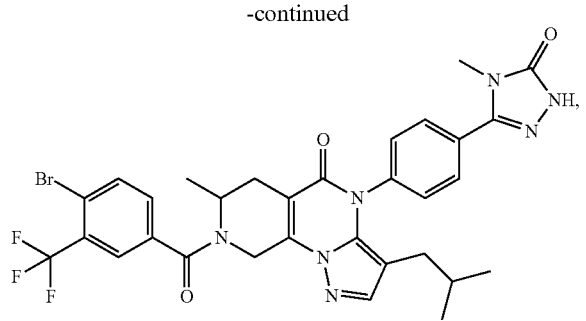
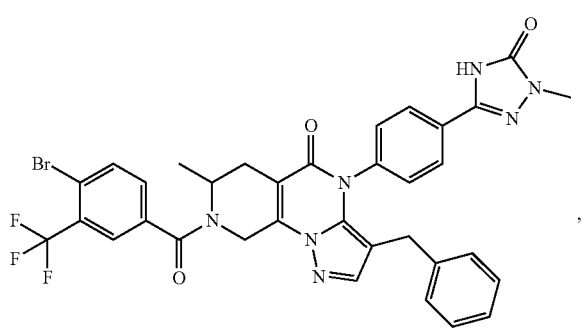
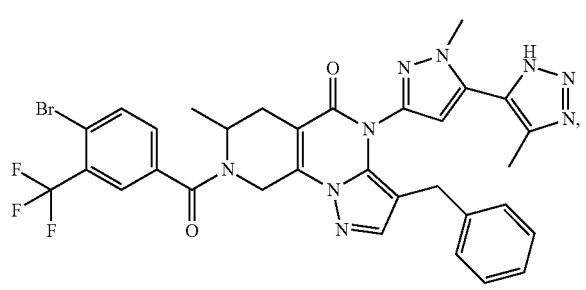
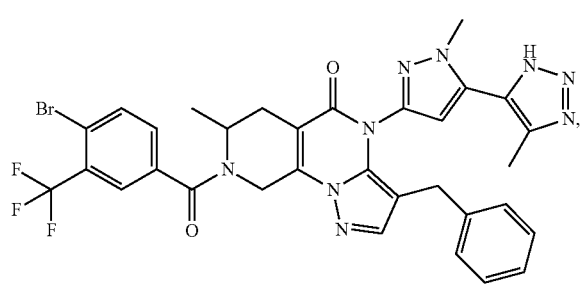
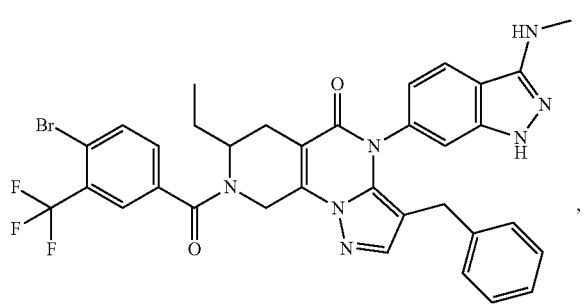
42
-continued
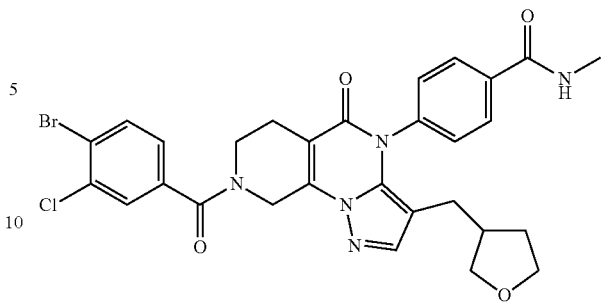
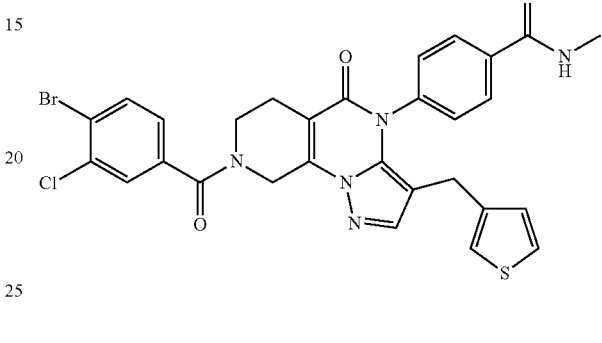
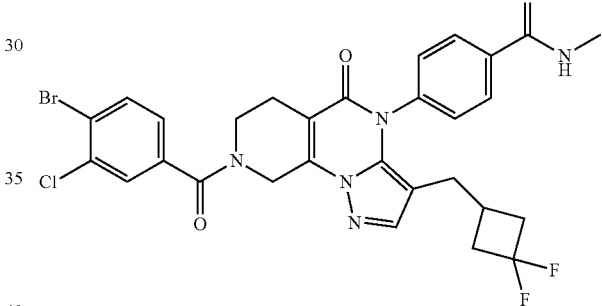
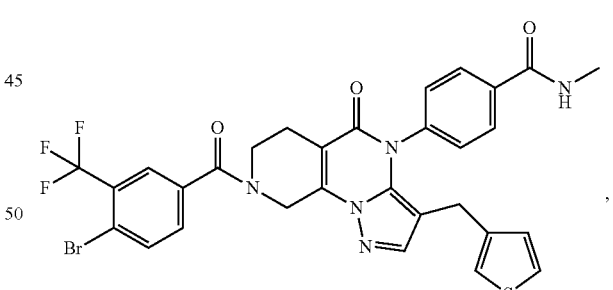
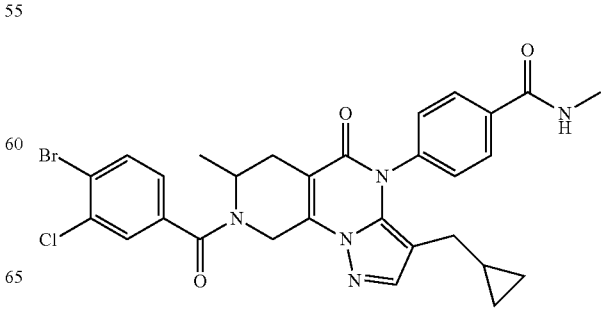

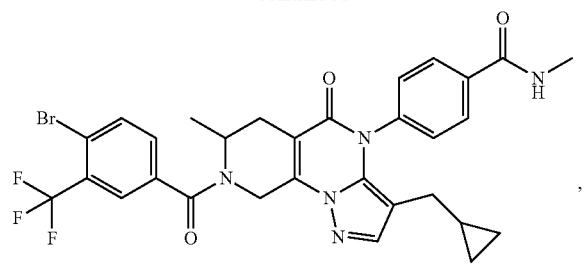
,
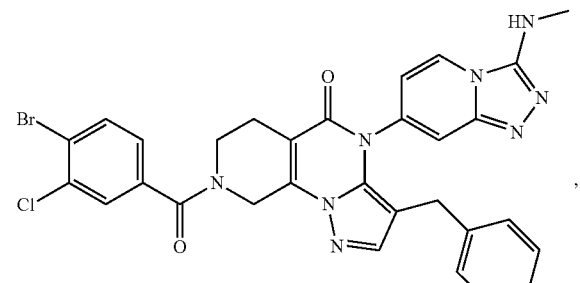
,
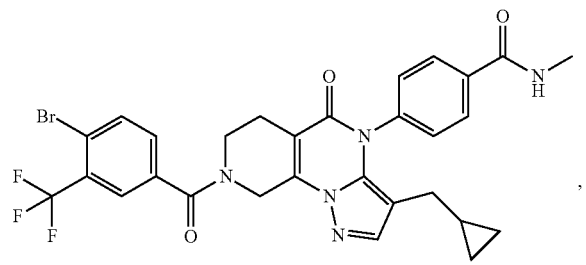
,
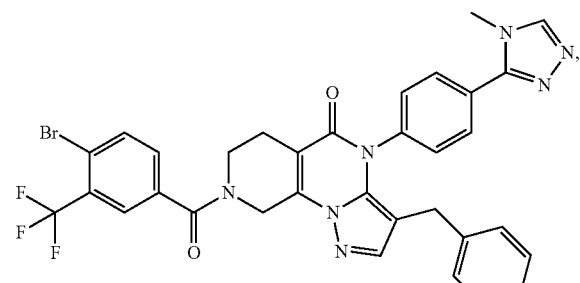
,
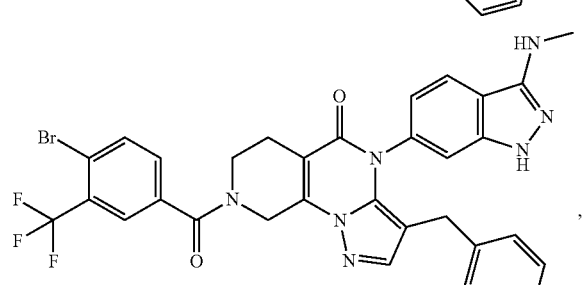
,
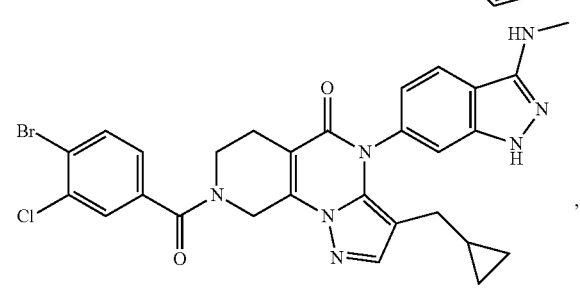
,
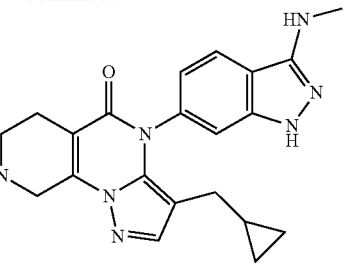
,
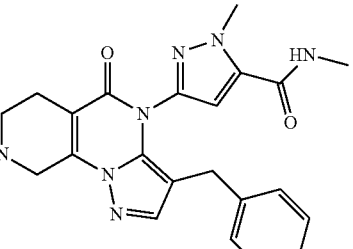
,
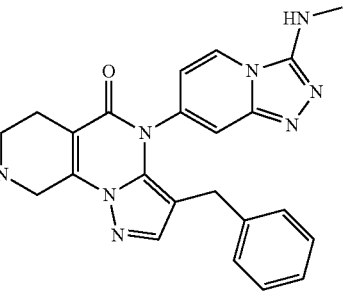
,
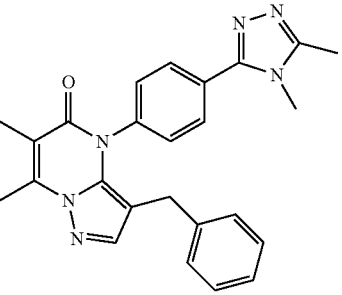
,
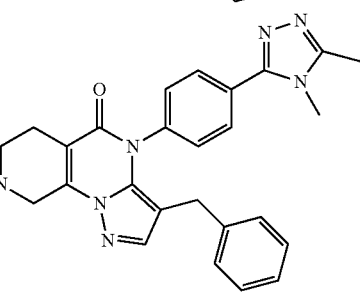
,
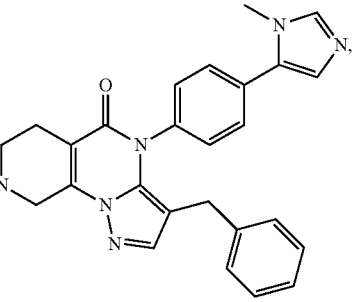

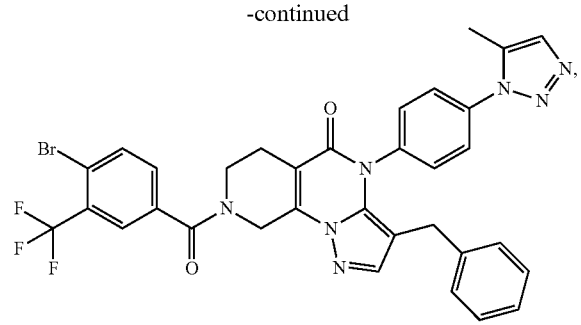
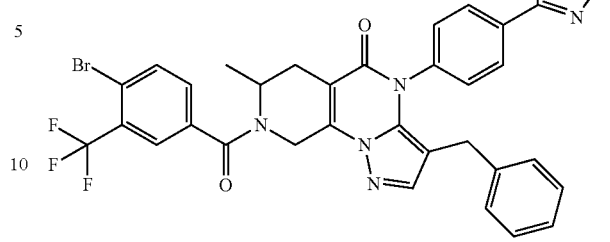
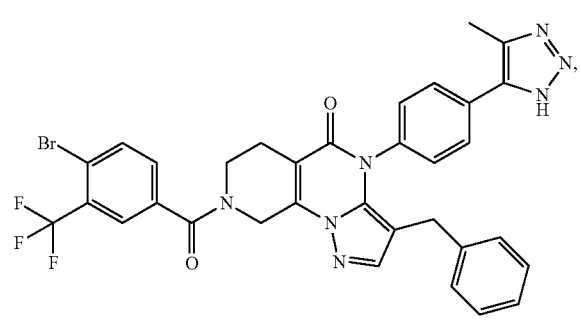
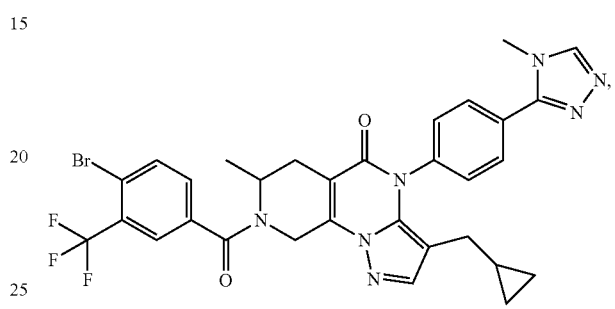
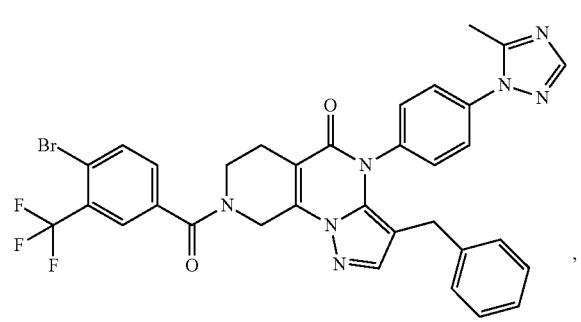
,
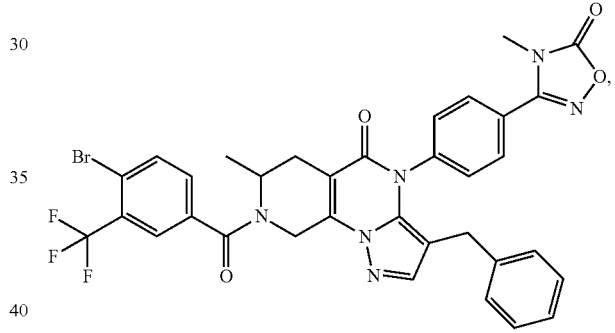
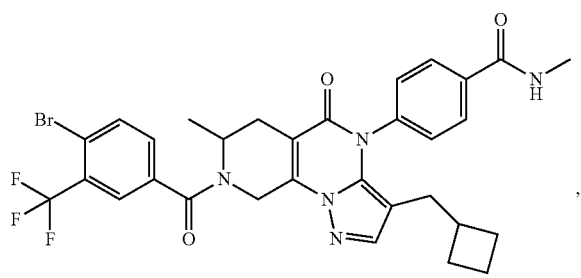
,
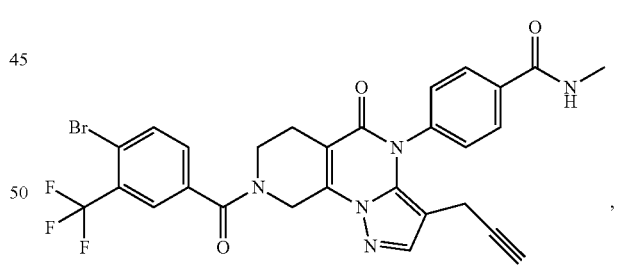
,
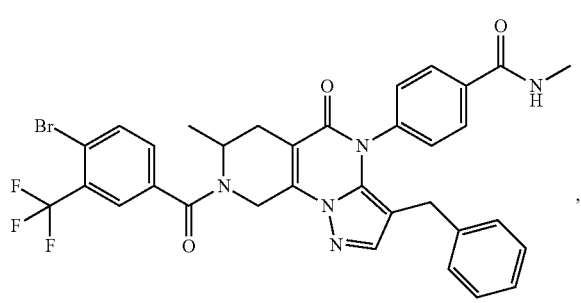
,
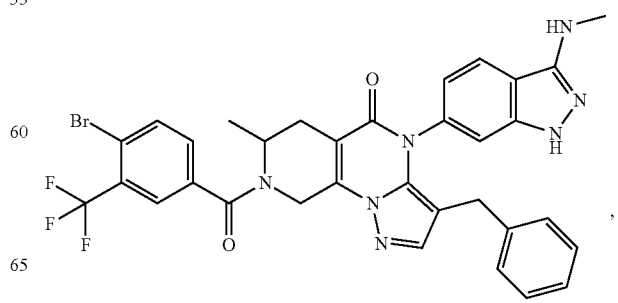
,

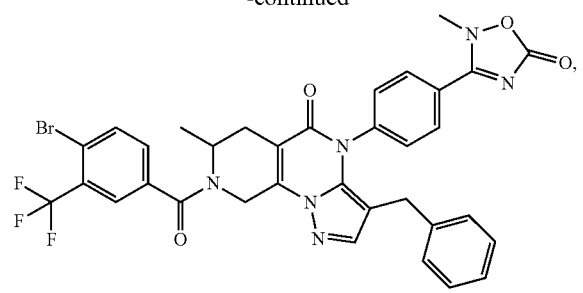
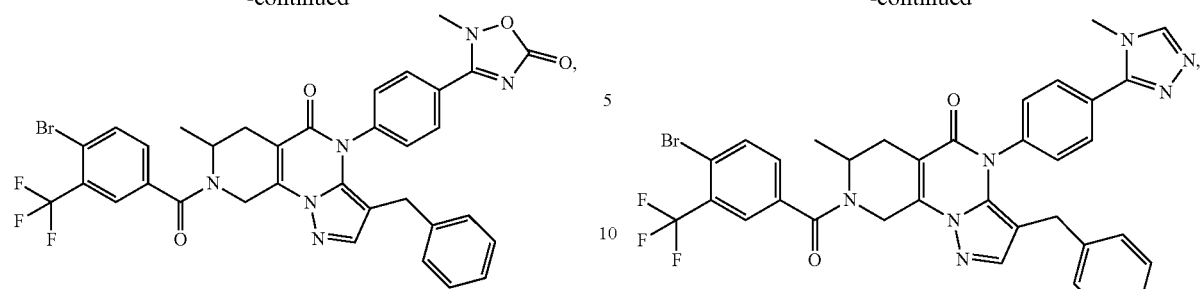

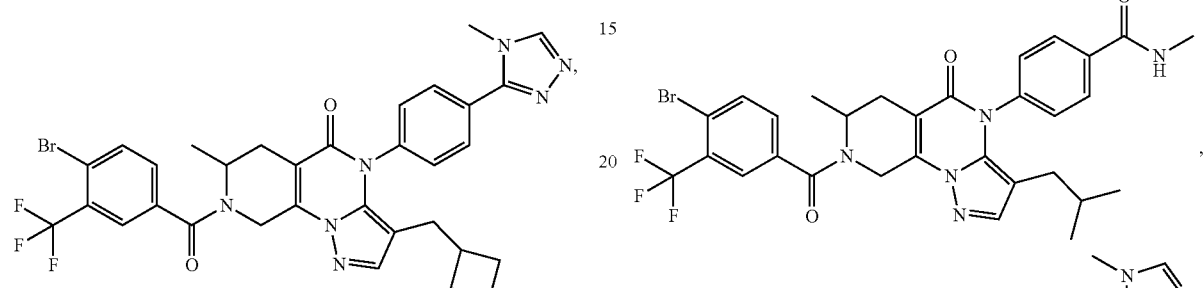

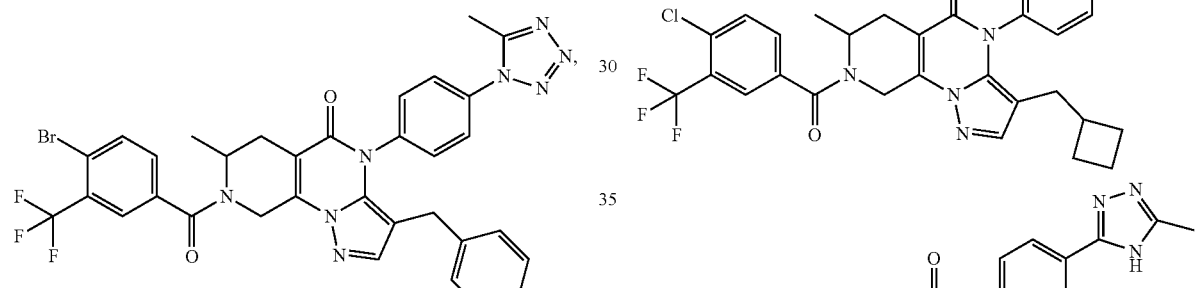
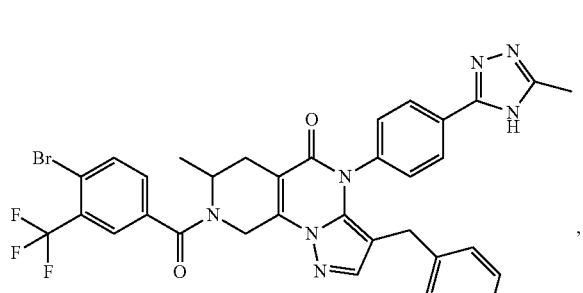
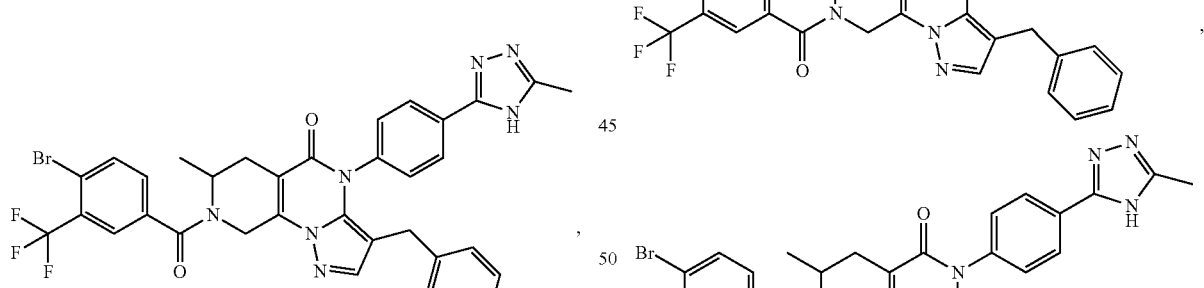
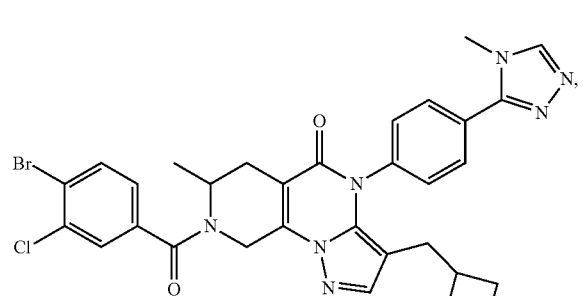
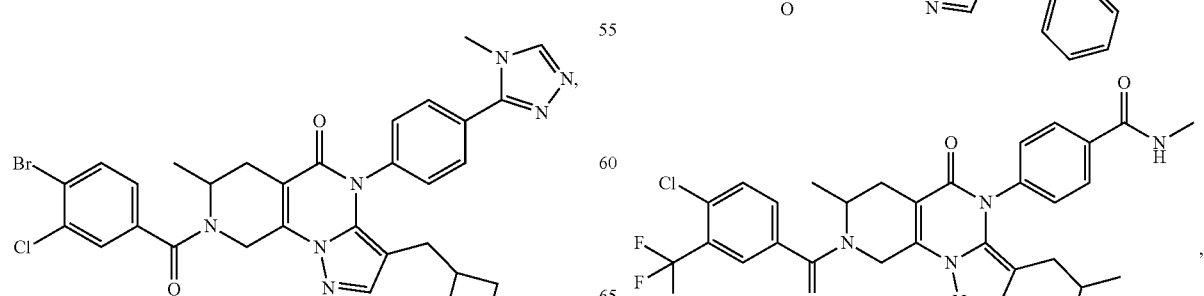

49
-continued
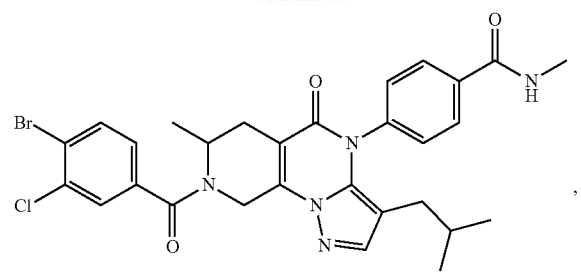
,
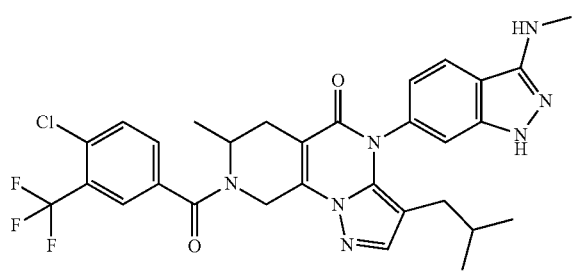
,
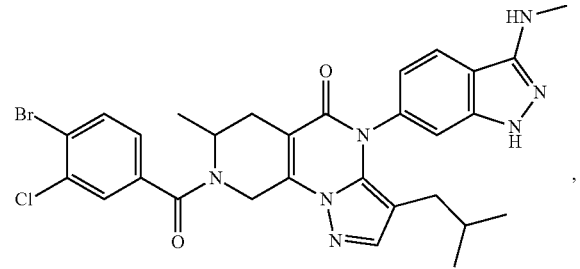
,
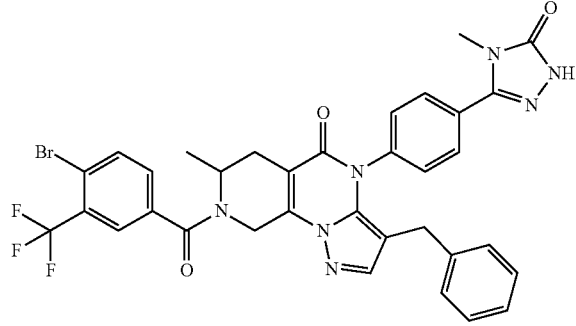
,
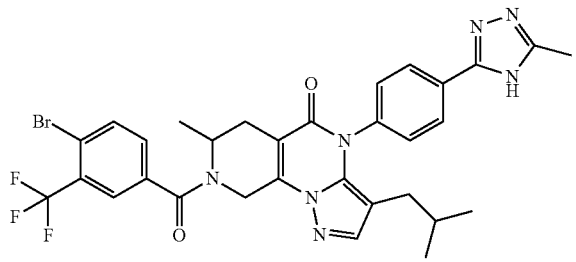
,
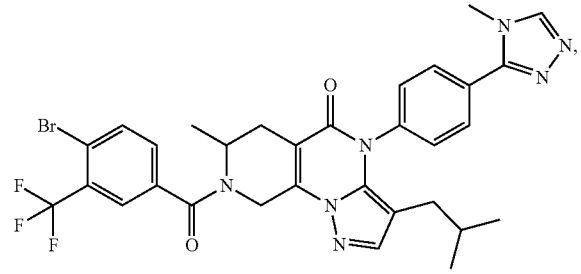
50
-continued
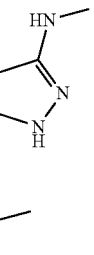
,
,
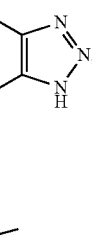
,
,
,
, 51
-continued
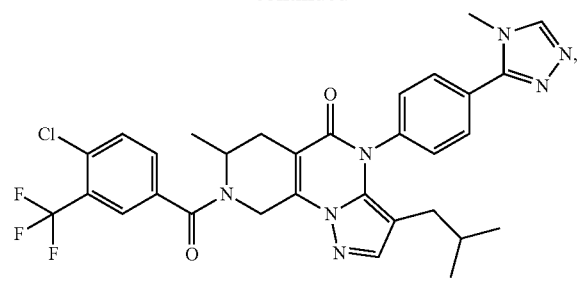
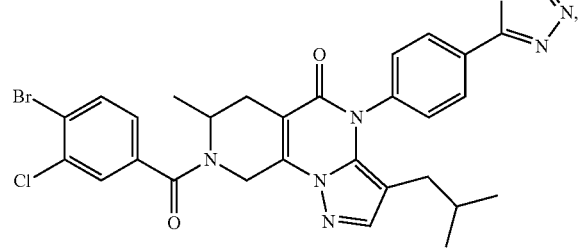
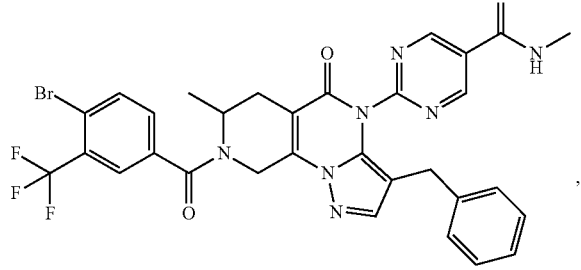
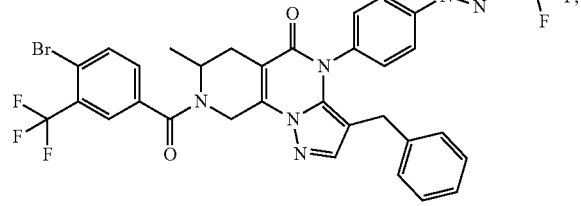
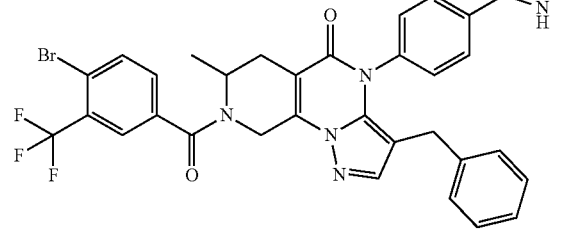
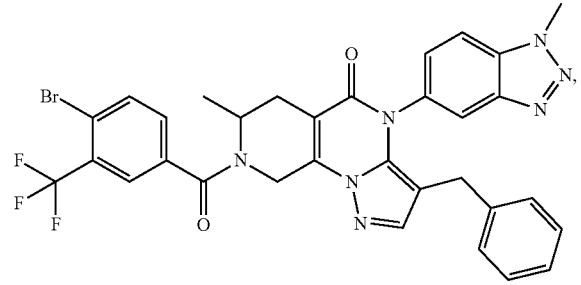
52
-continued
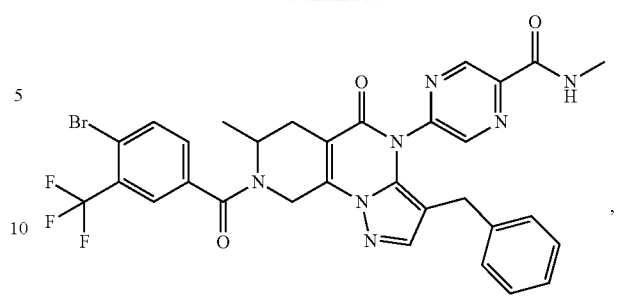
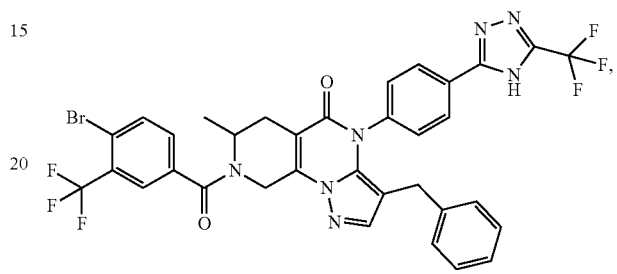
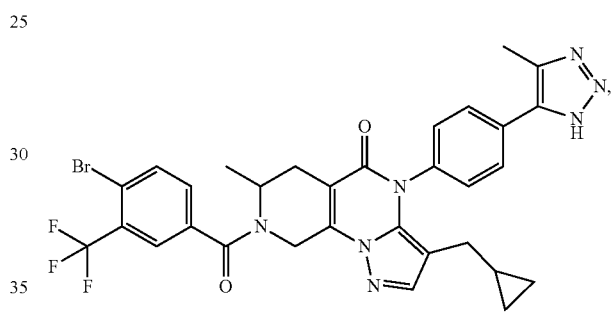
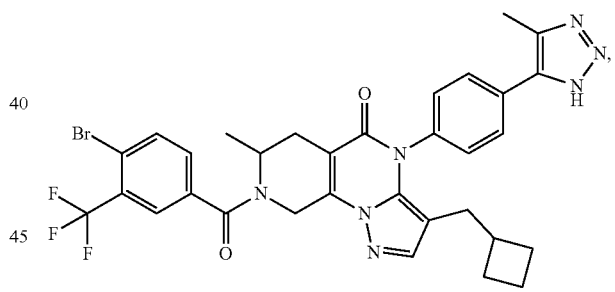
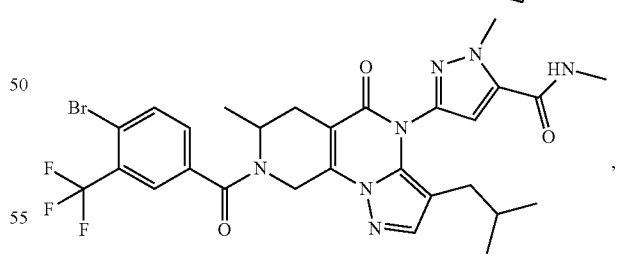
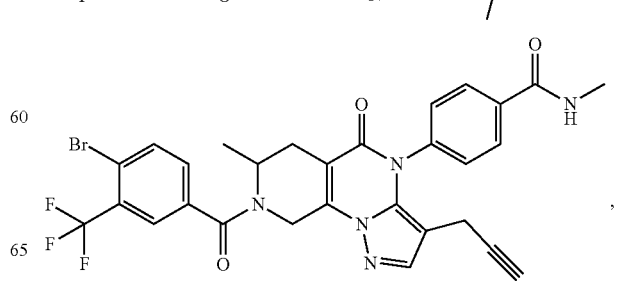

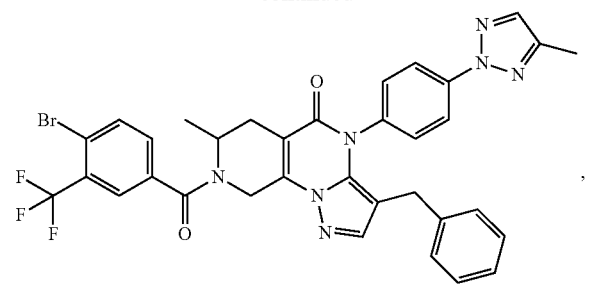
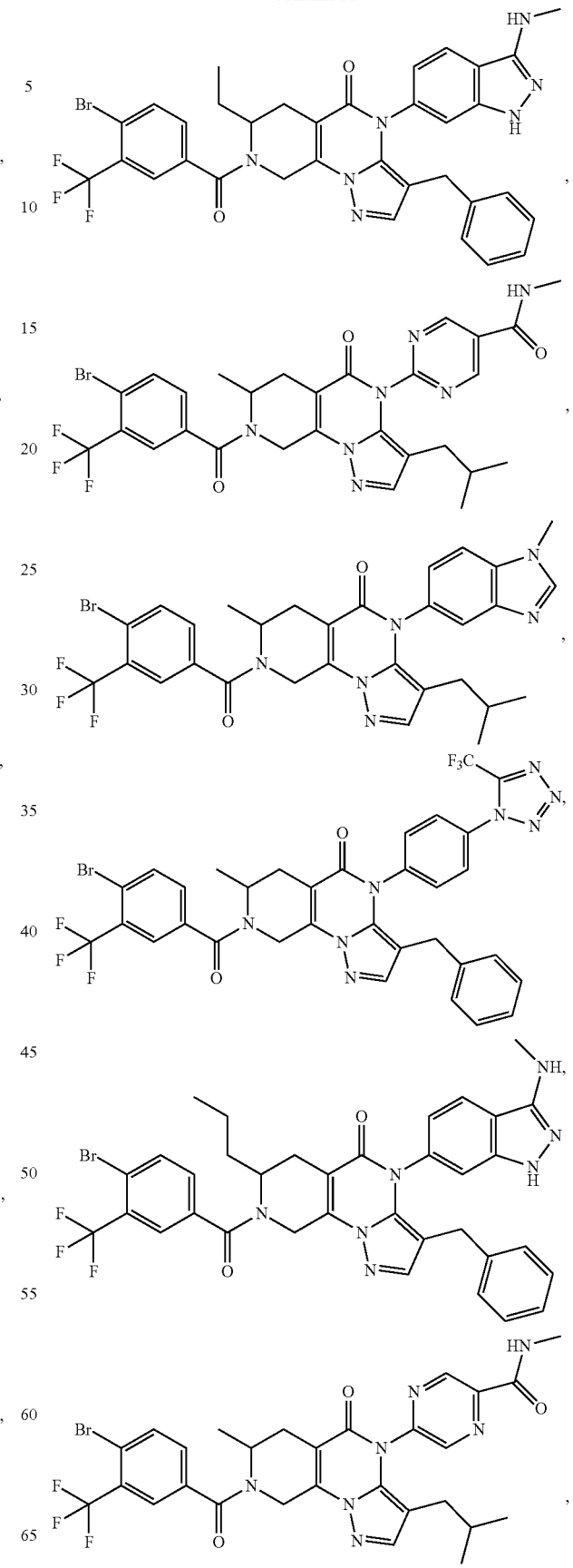

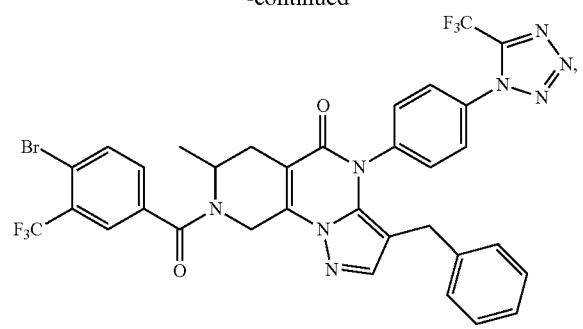
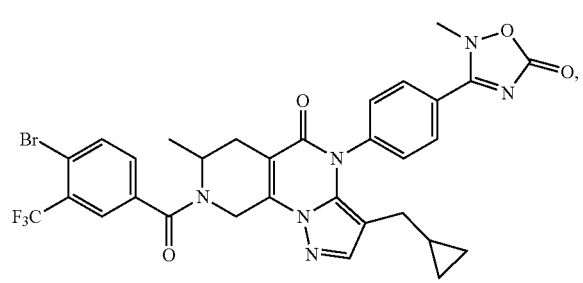
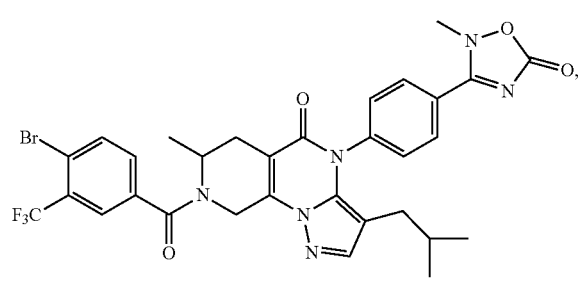
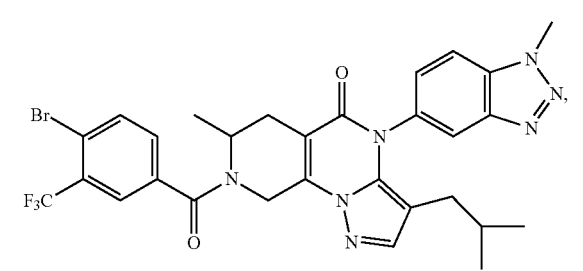
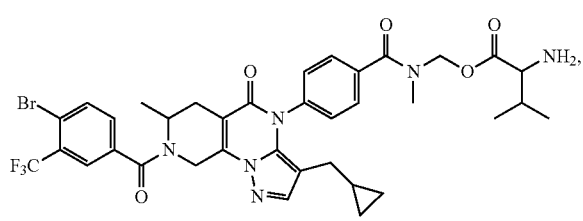
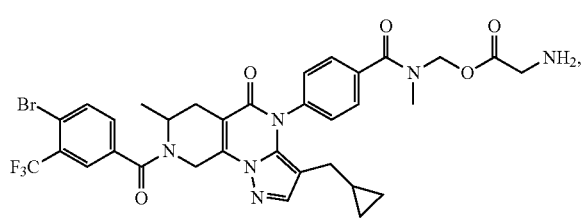
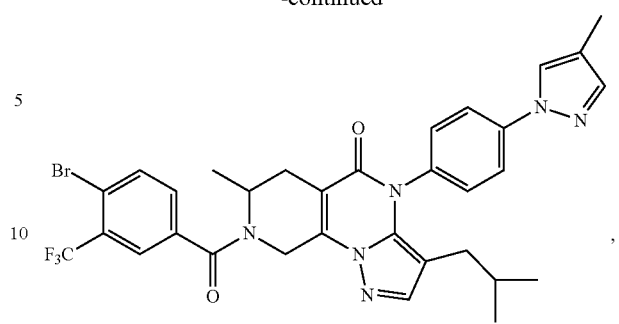
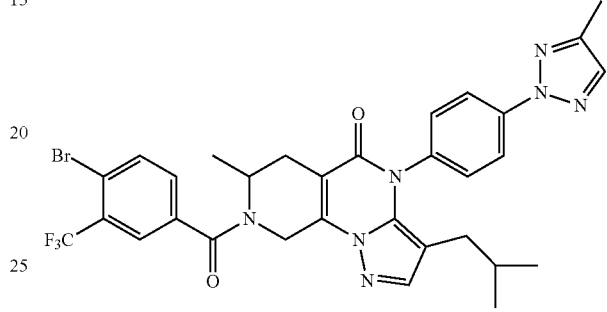
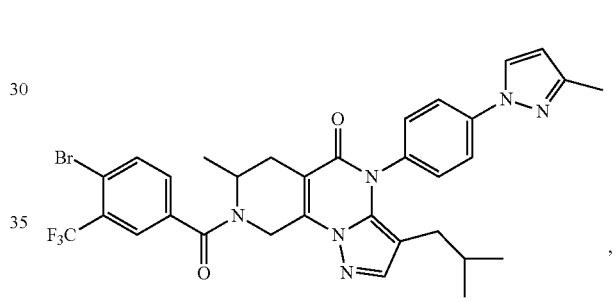
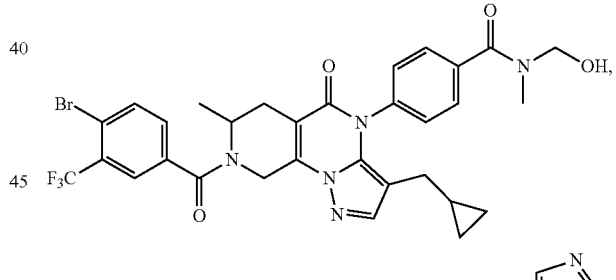
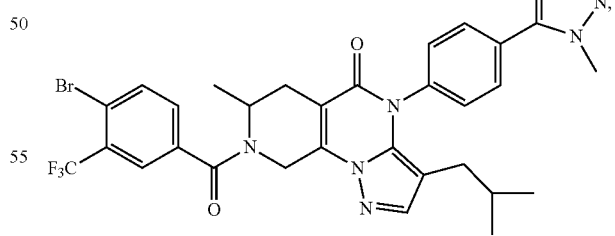
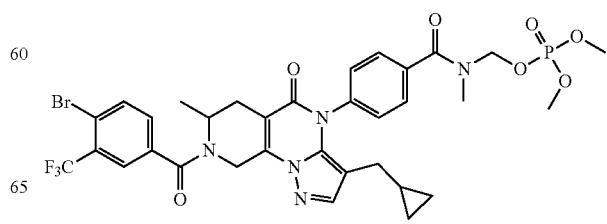

57
-continued
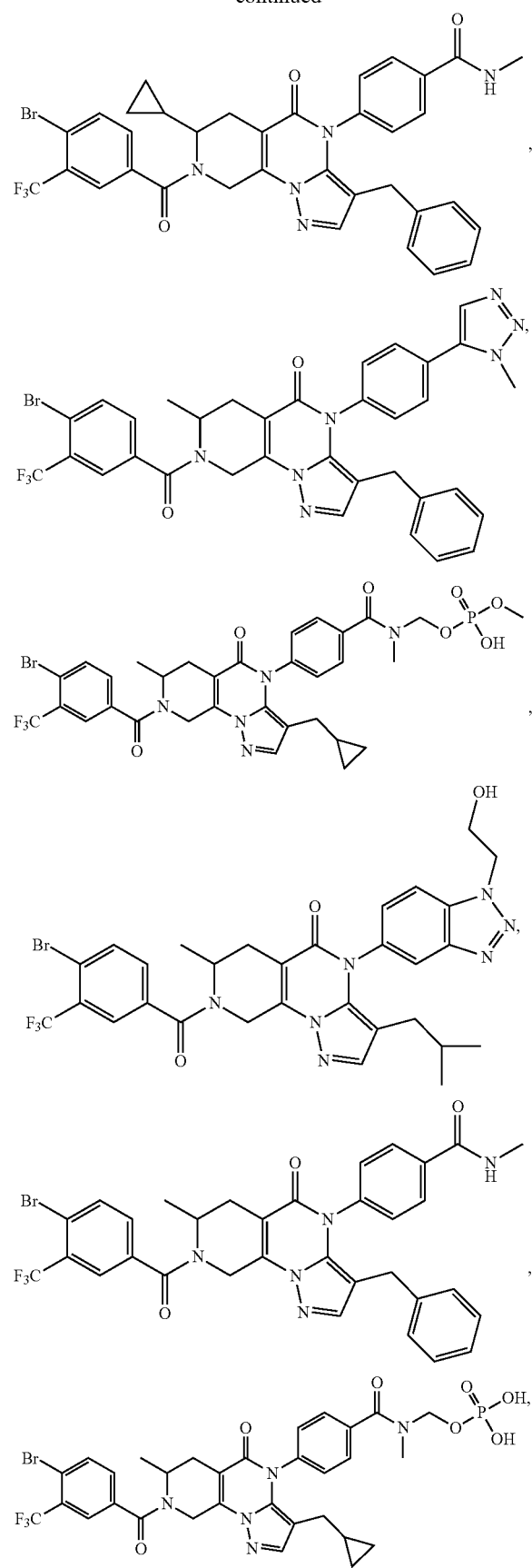
58
-continued
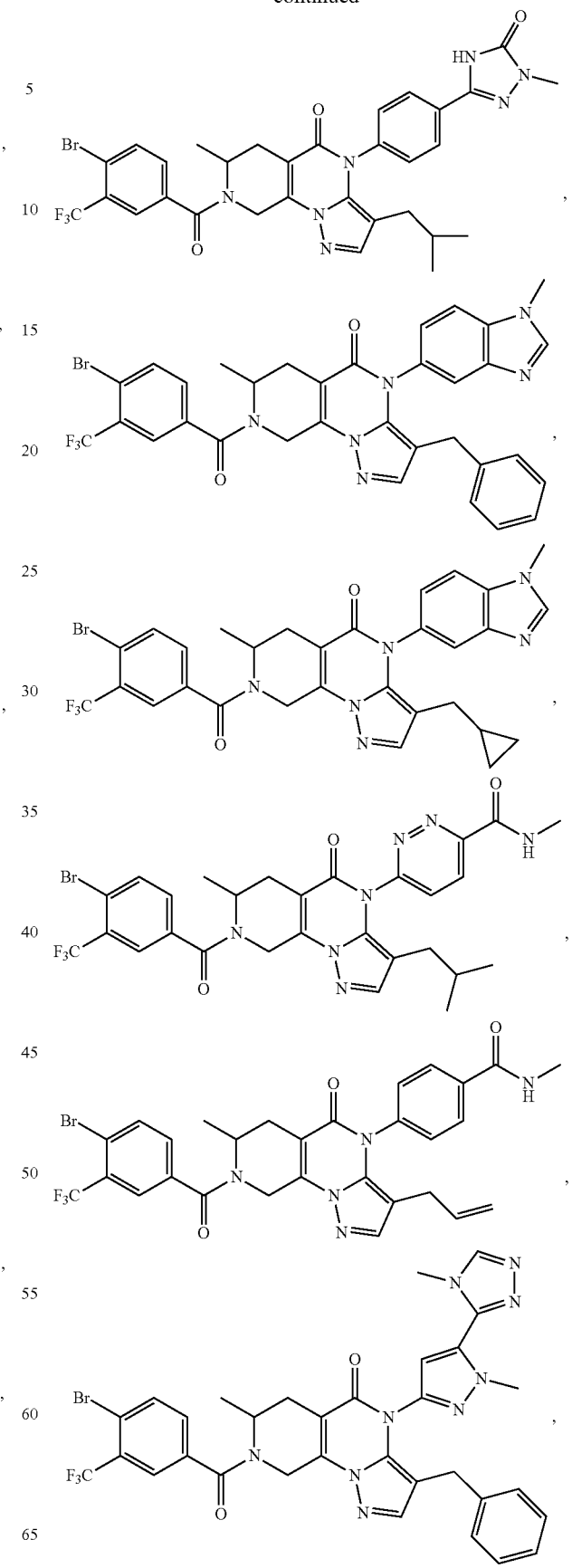

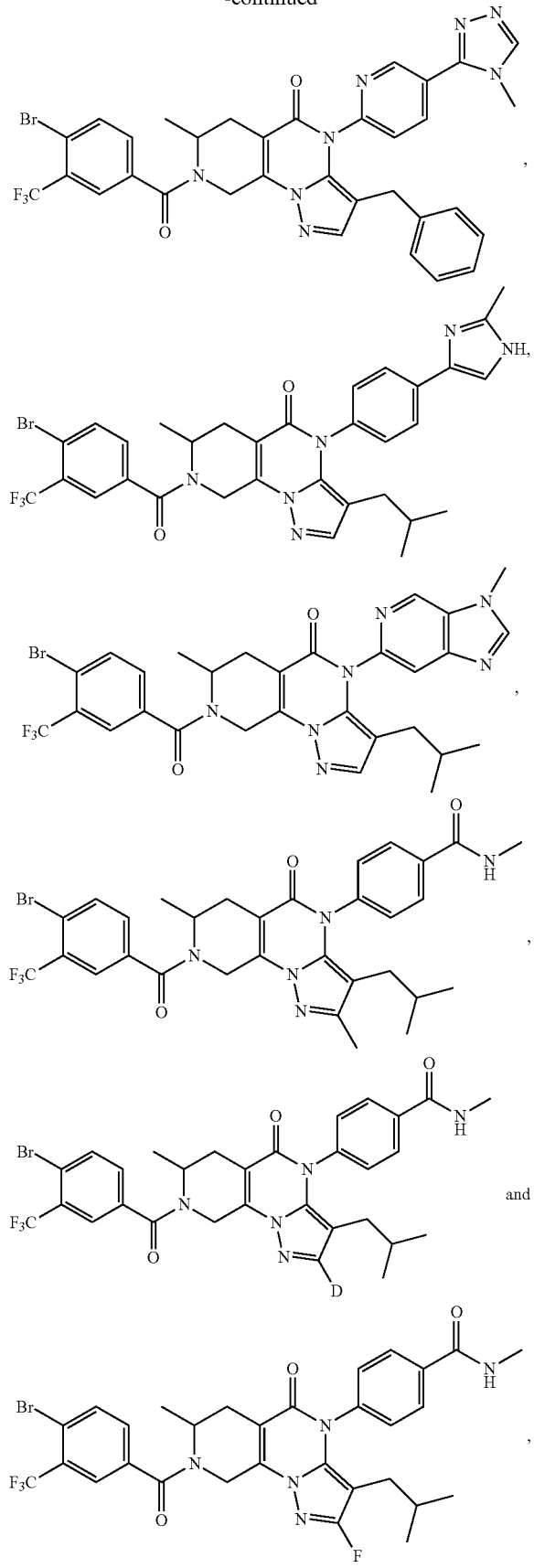
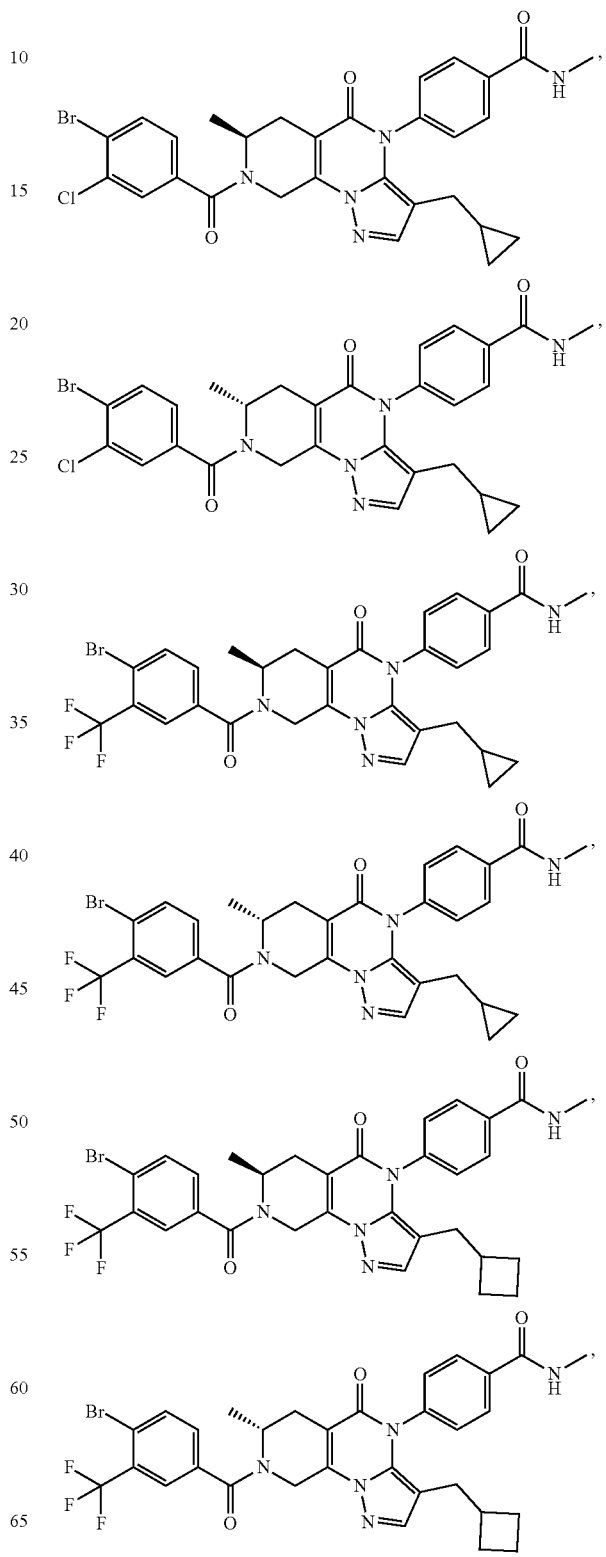
or a pharmaceutically acceptable salt of any of the foregoing.
Additional examples of a compound of Formula (I), or a pharmaceutically acceptable salt thereof, include the following:

61
-continued
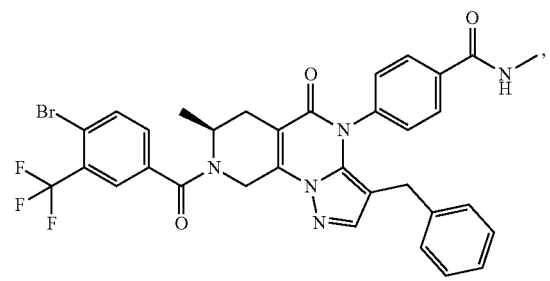
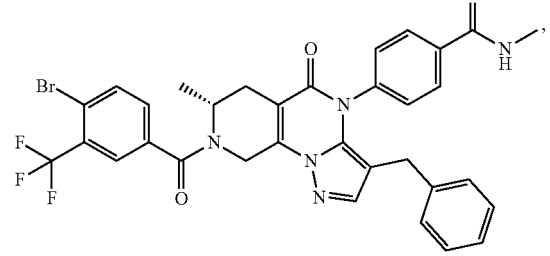
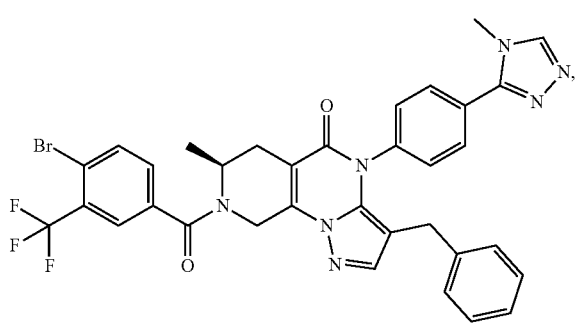
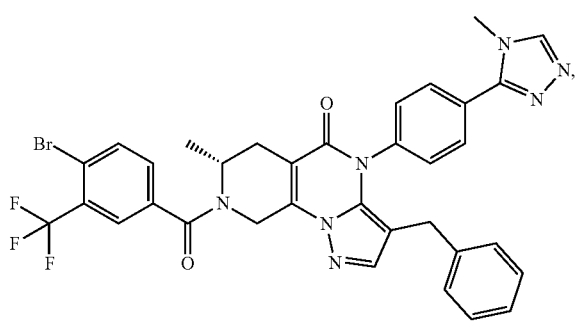
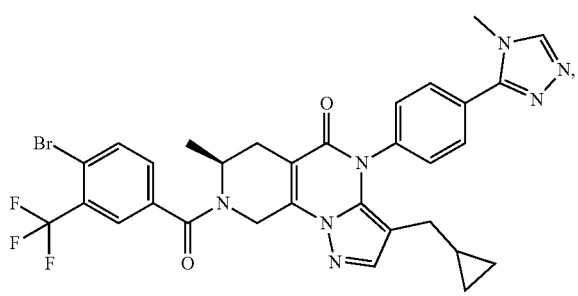
62
-continued
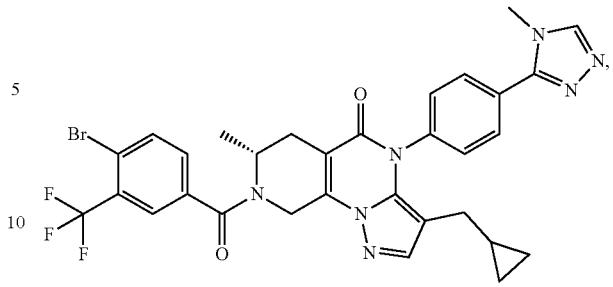
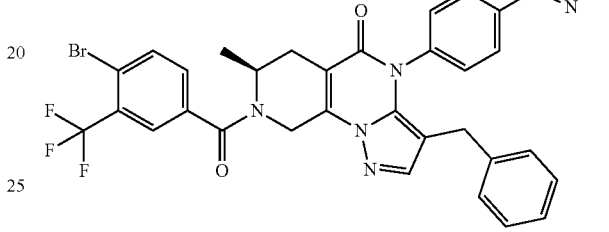
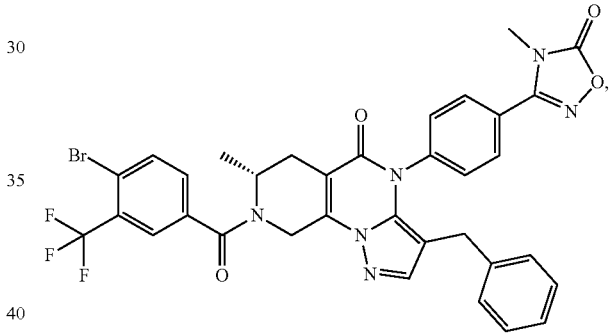
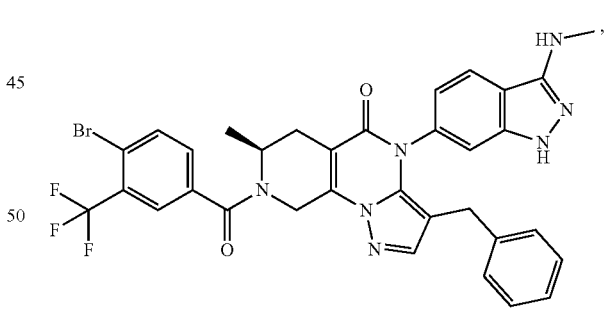
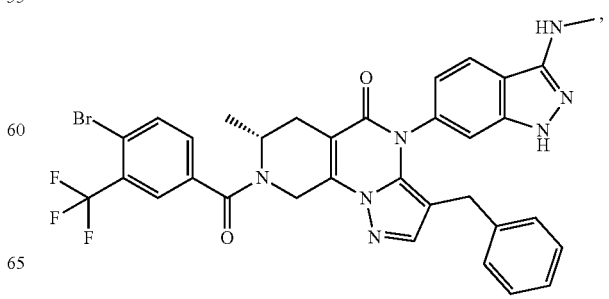

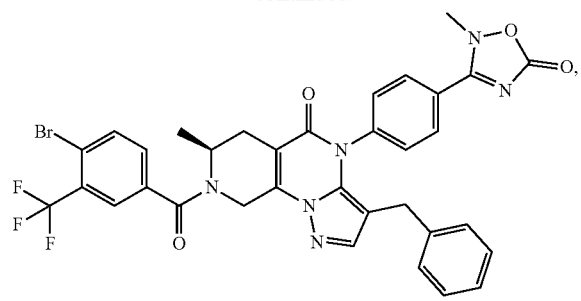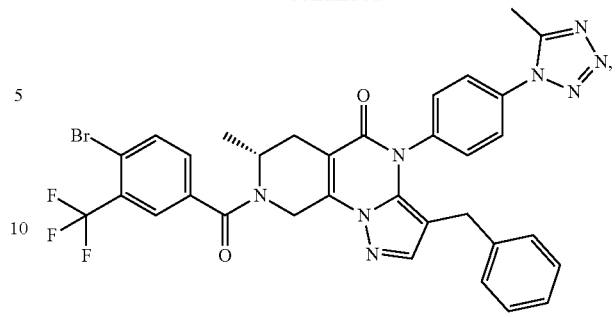

65
-continued
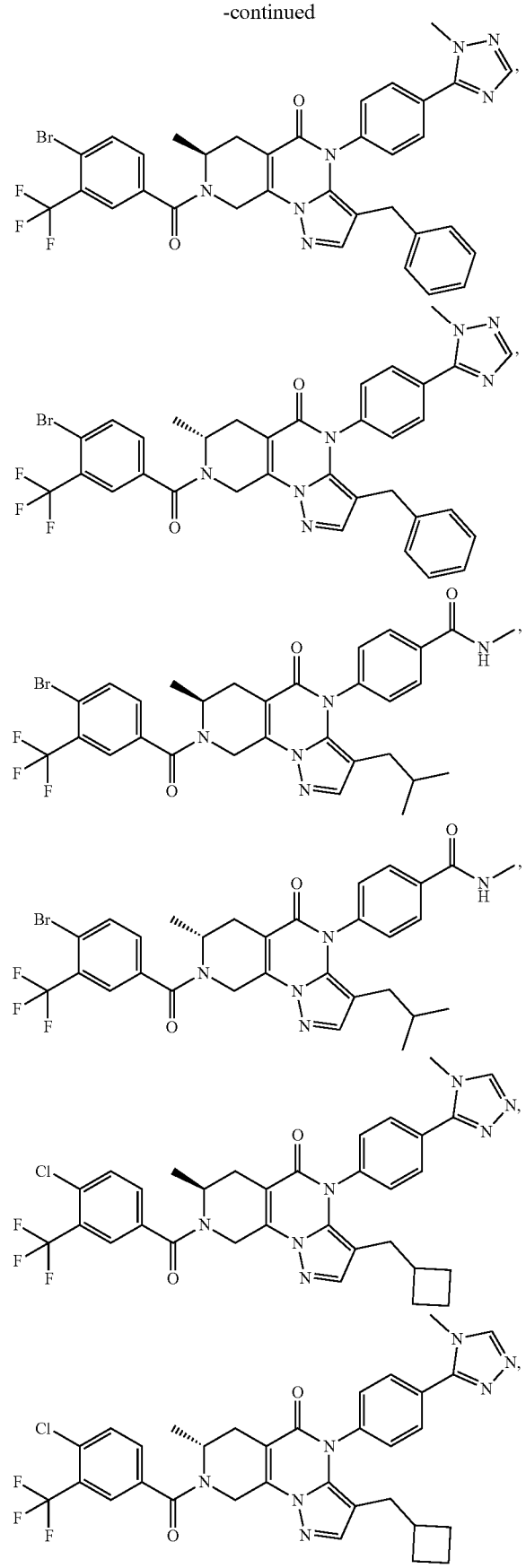
66
-continued
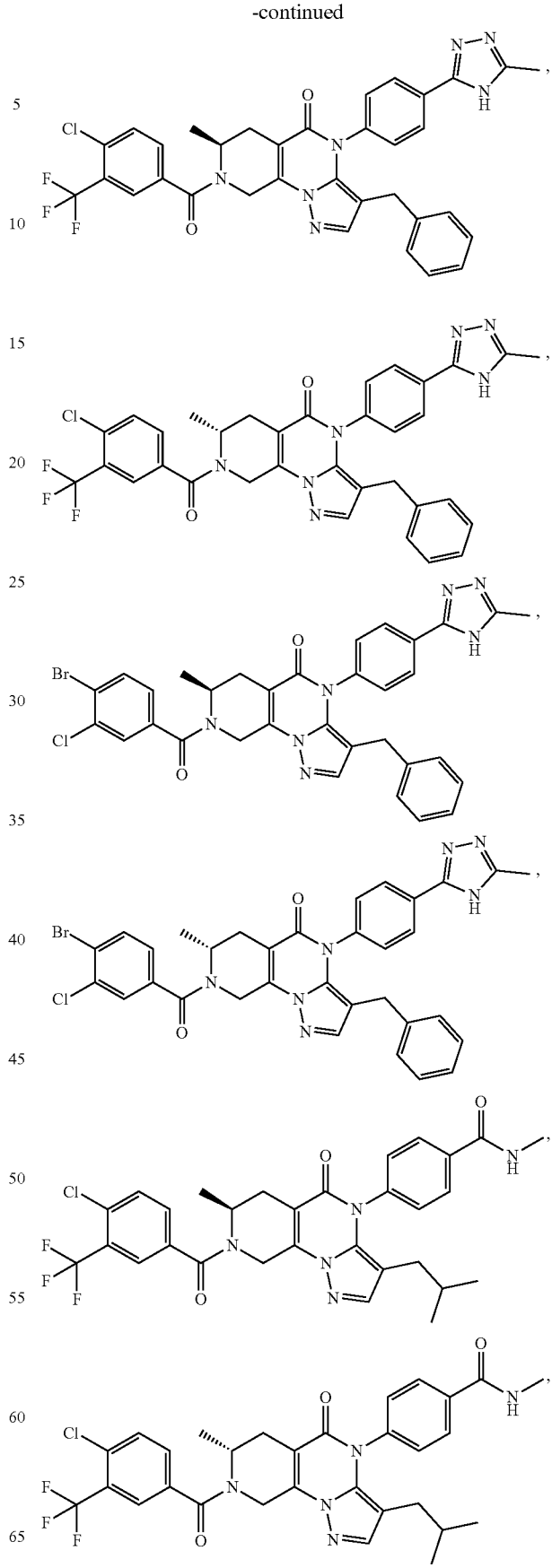

67
-continued
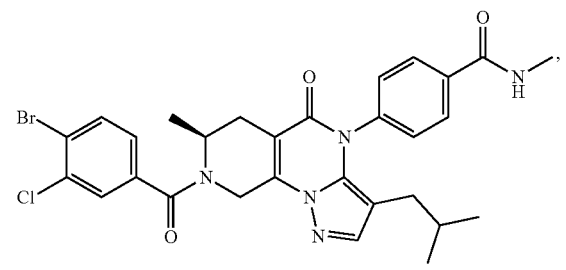
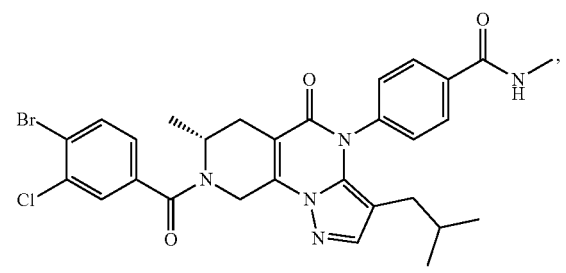
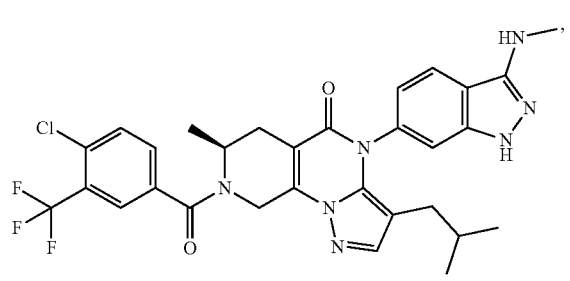
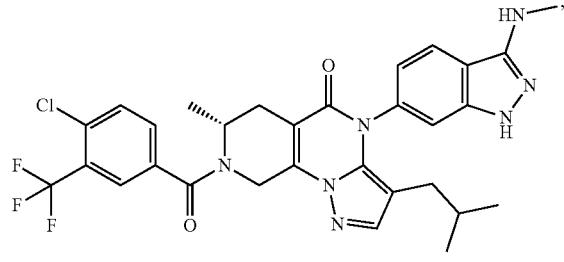
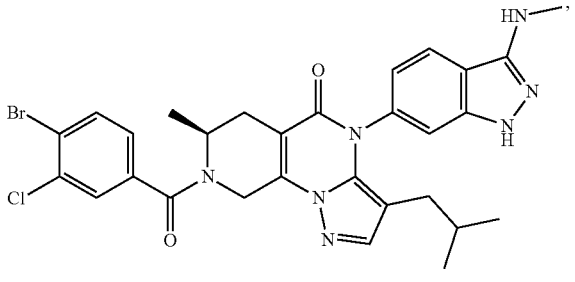
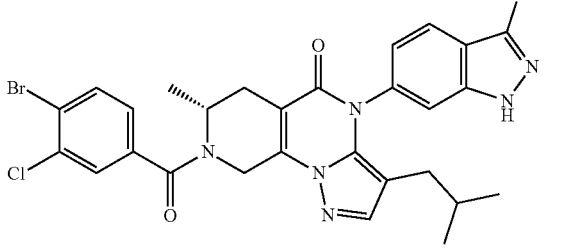
68
-continued
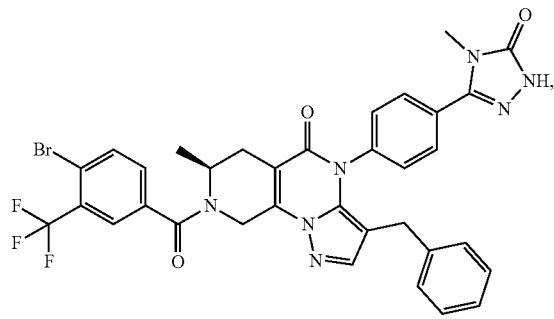
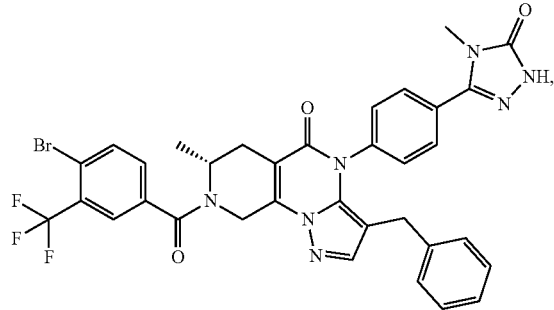
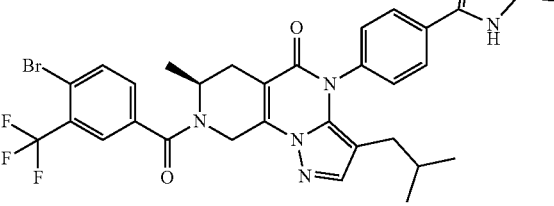
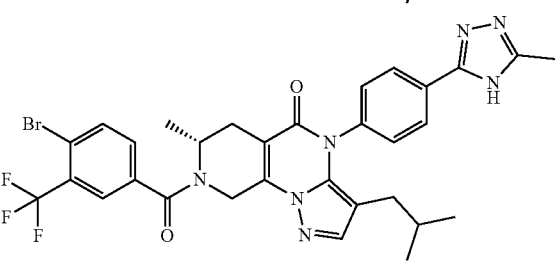
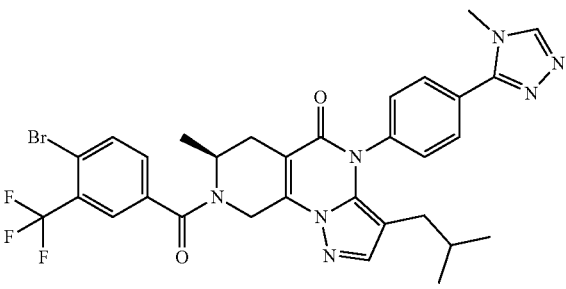
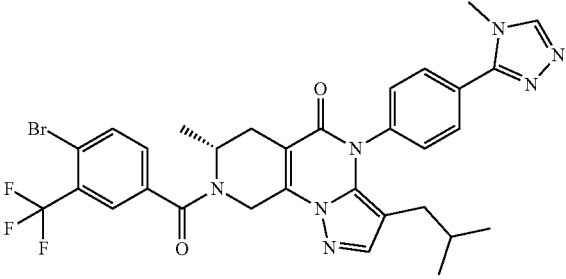

69
-continued
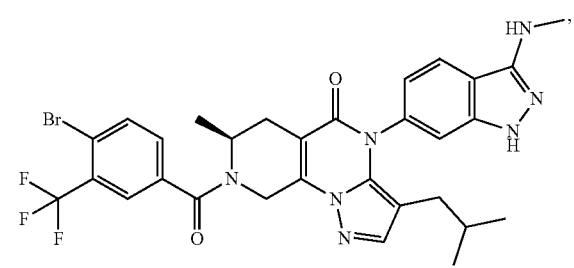
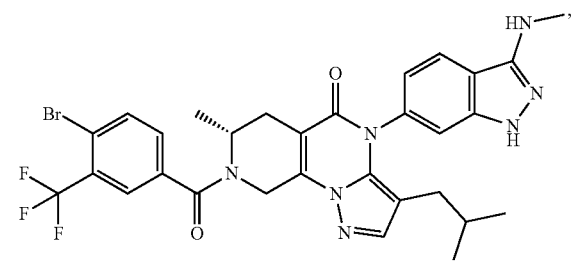
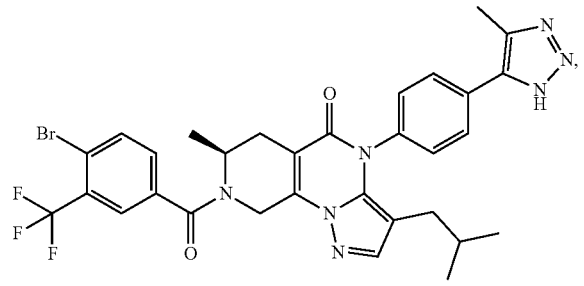
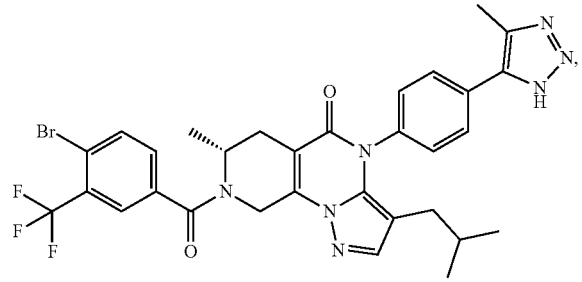
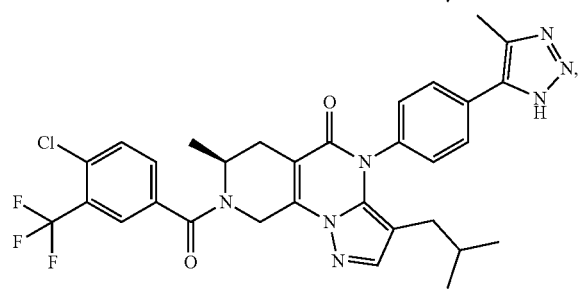
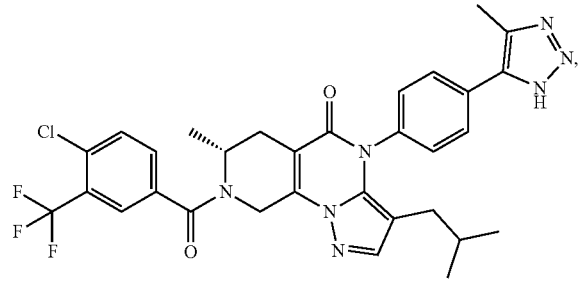
70
-continued
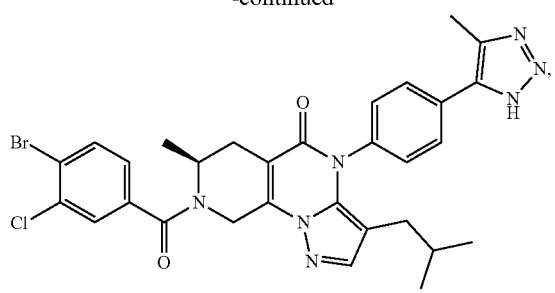
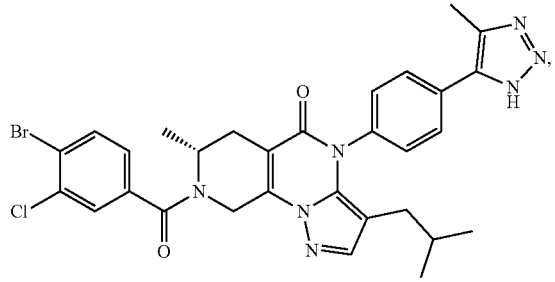
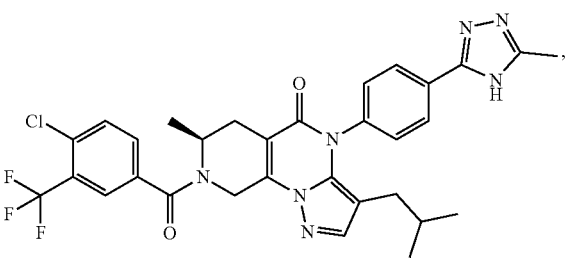
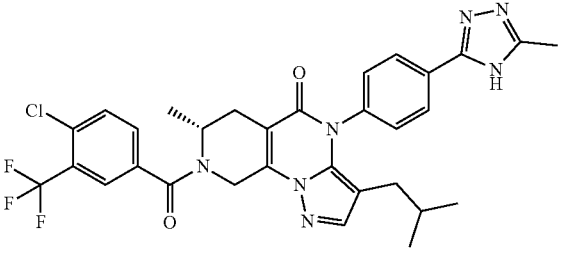
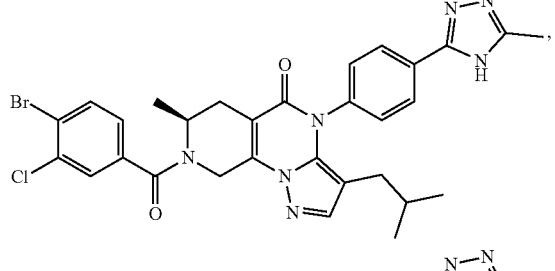
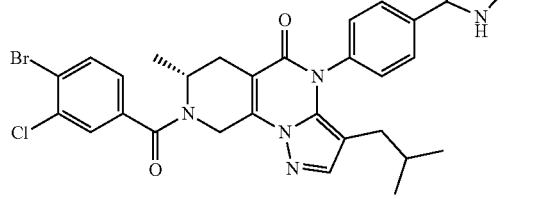

71
-continued
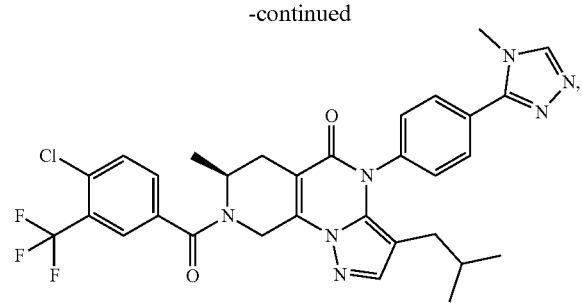
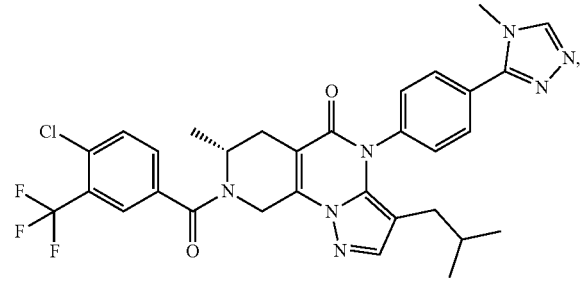
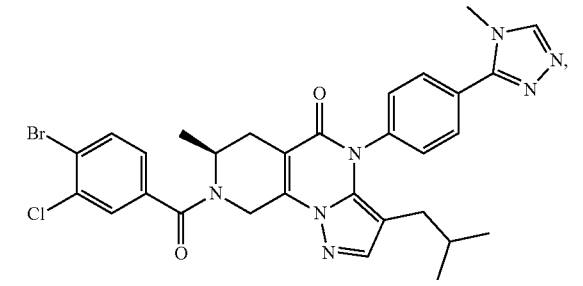
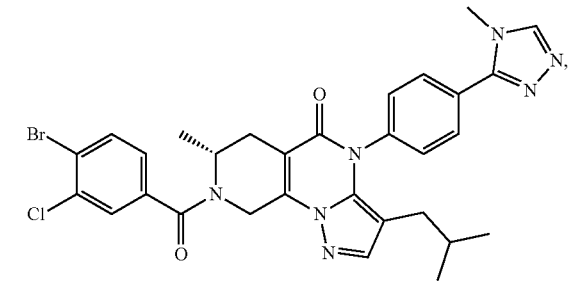
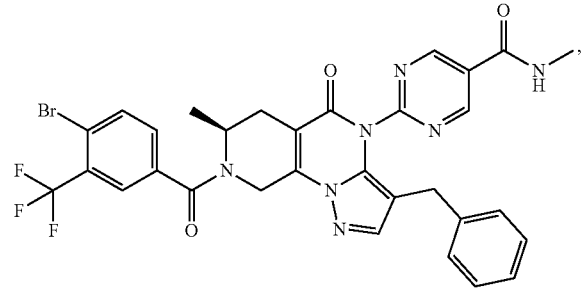
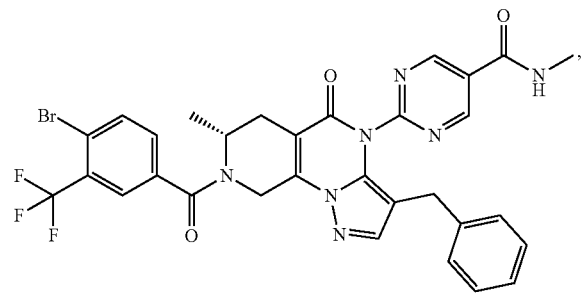
72
-continued
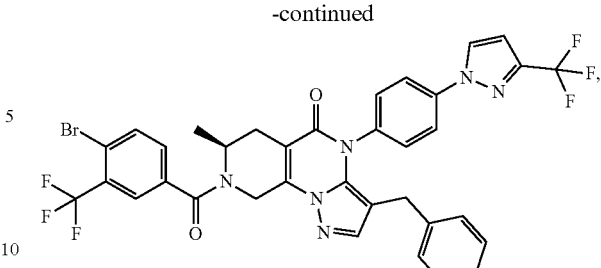
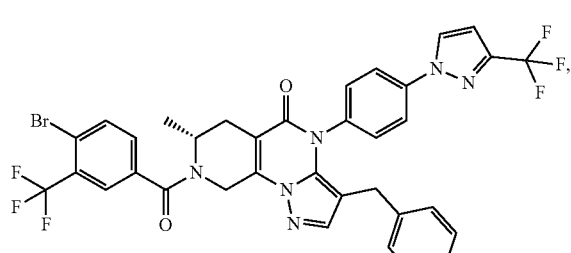
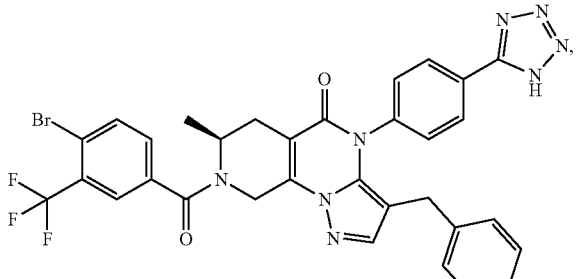
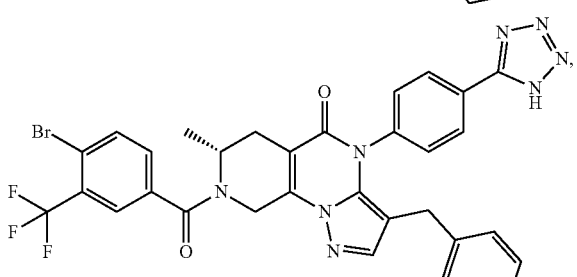
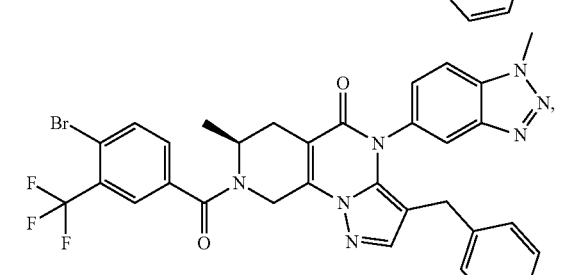
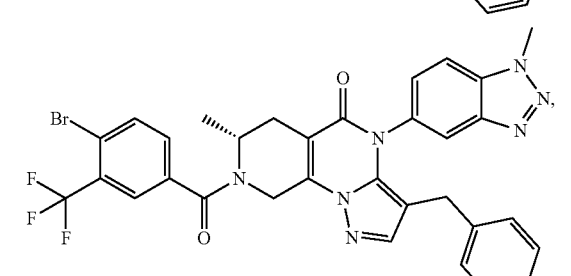

73
-continued
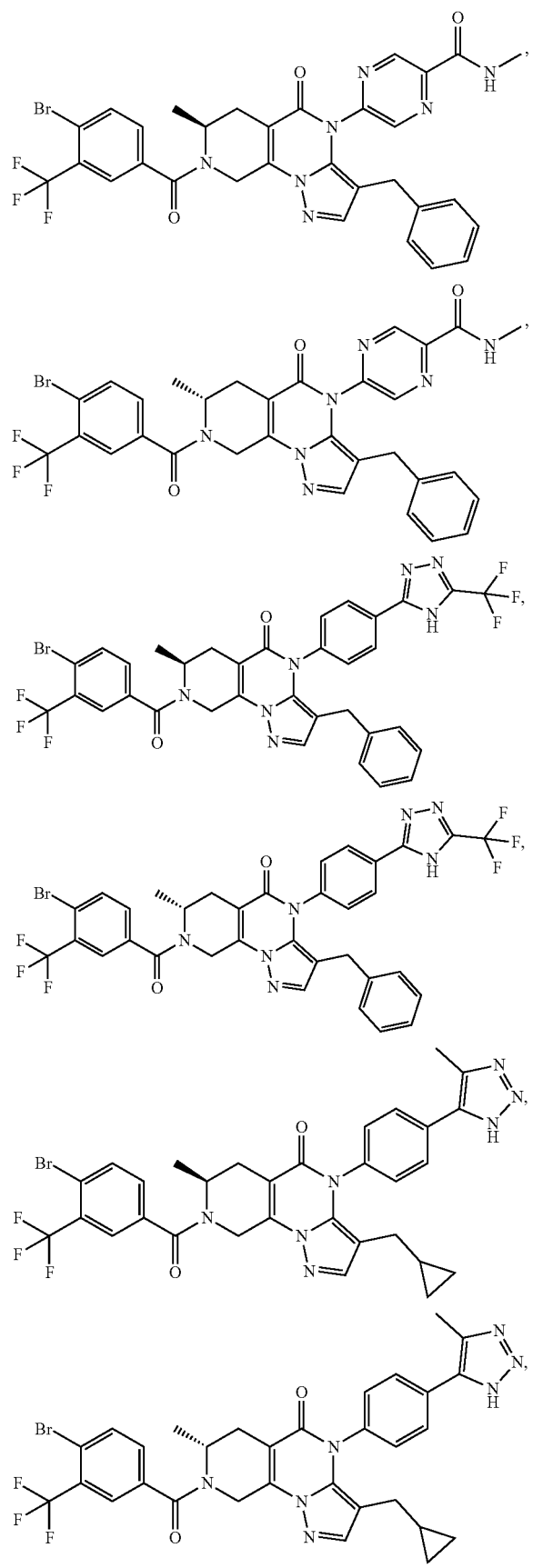
74
-continued
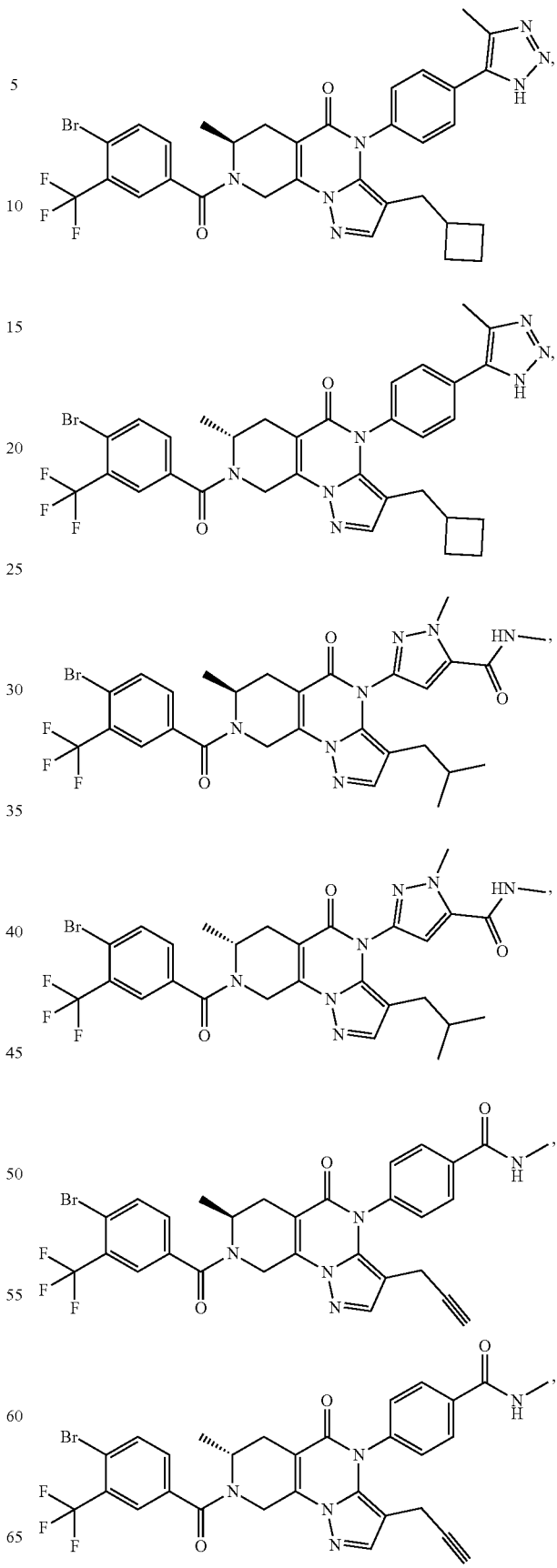

75
-continued
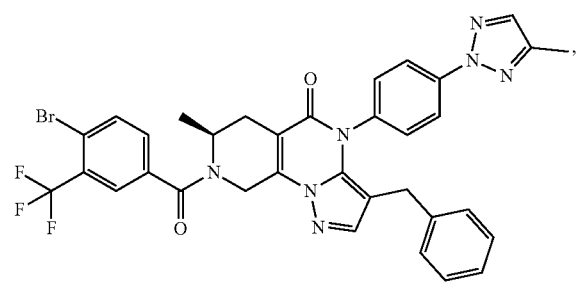
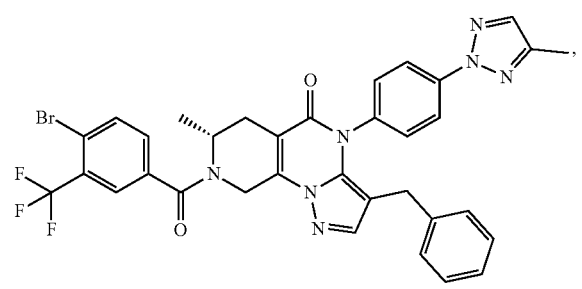
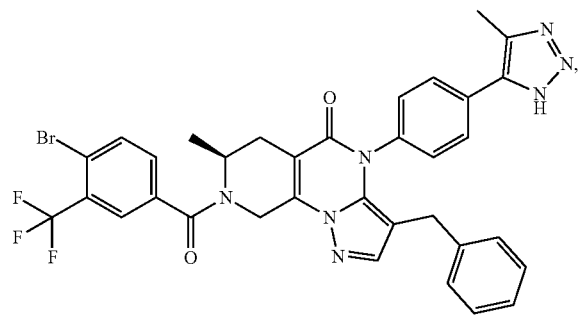
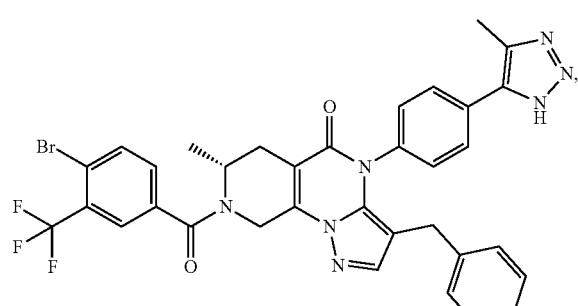
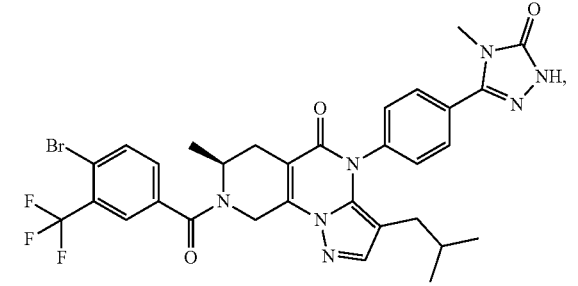
76
-continued
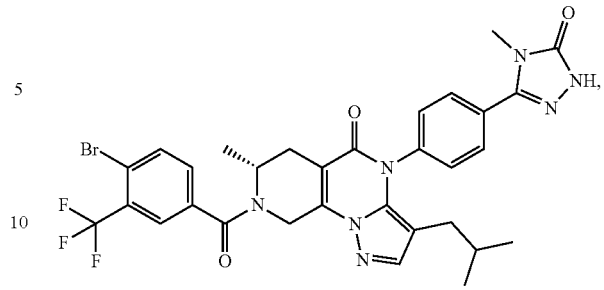
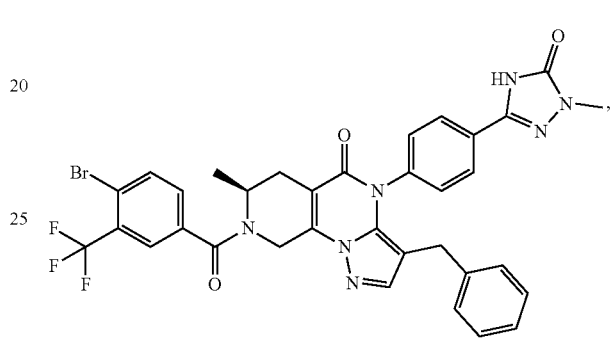
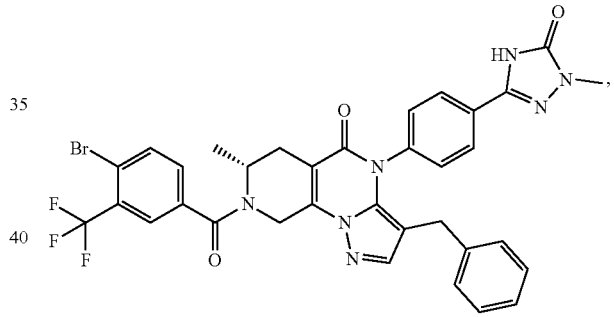
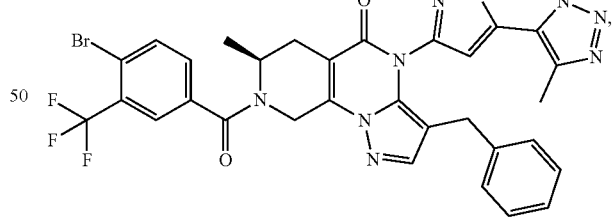
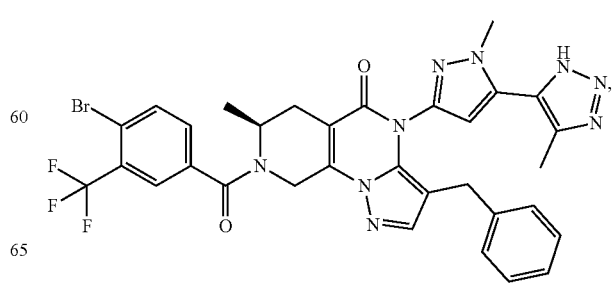

77
-continued
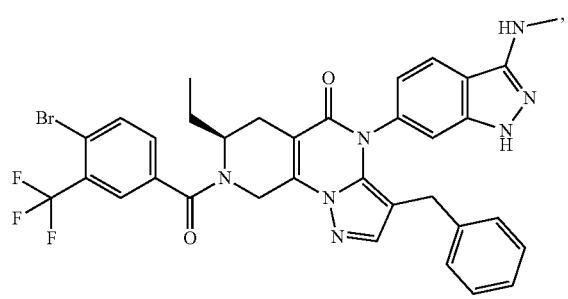
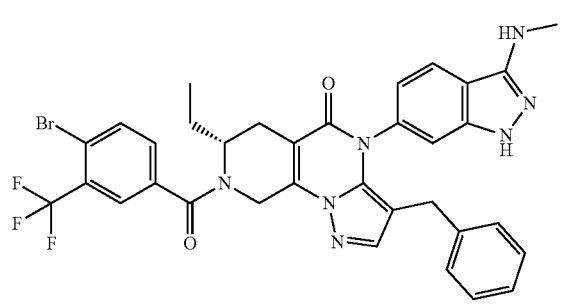
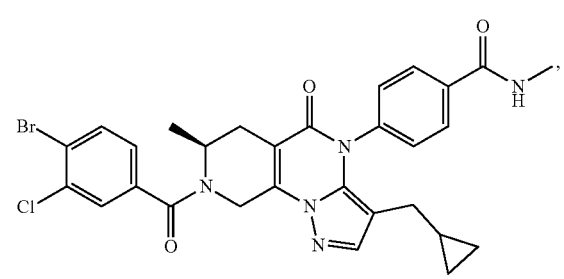
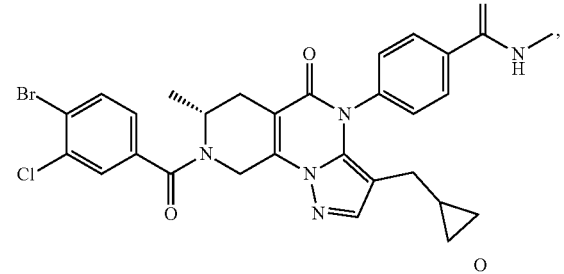
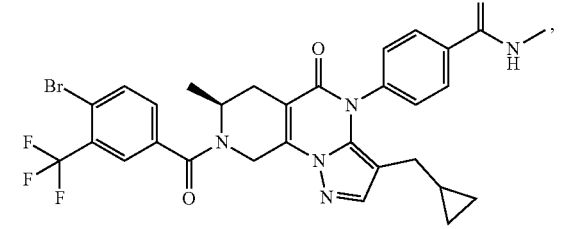
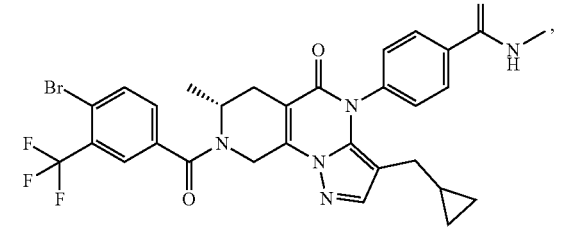
78
-continued
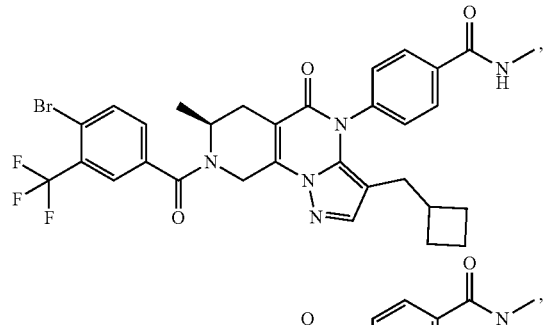
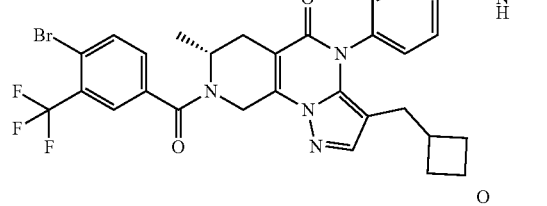
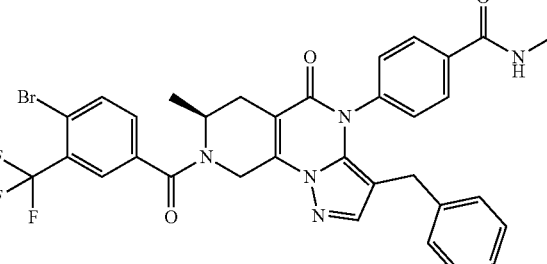
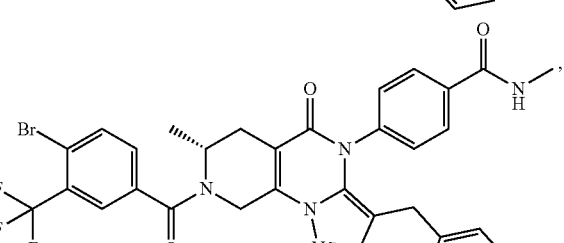
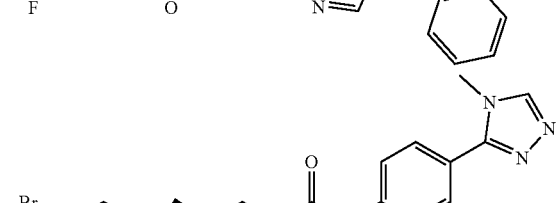
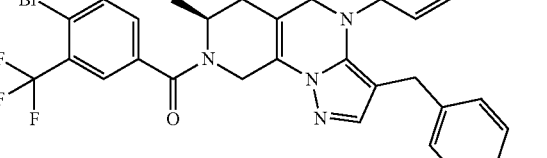
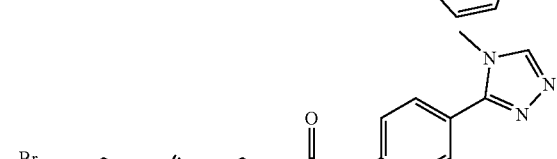
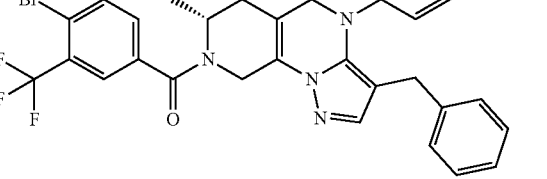

79
-continued
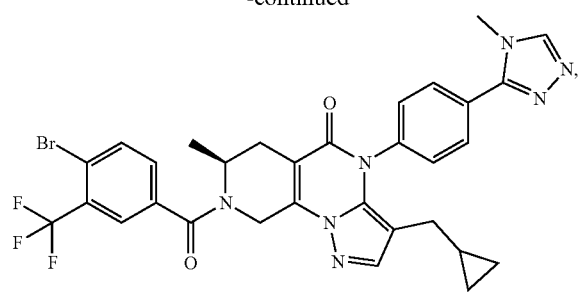
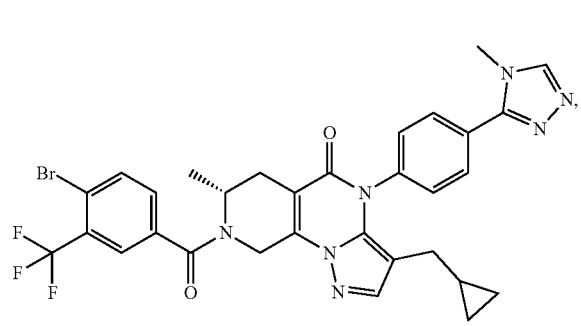
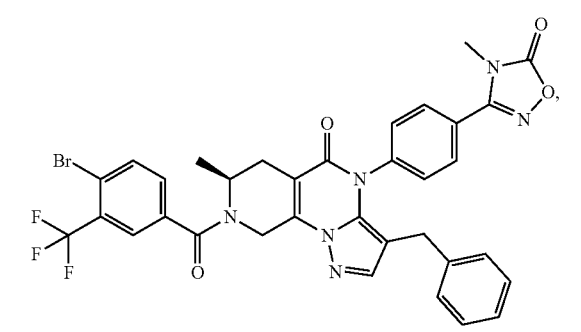
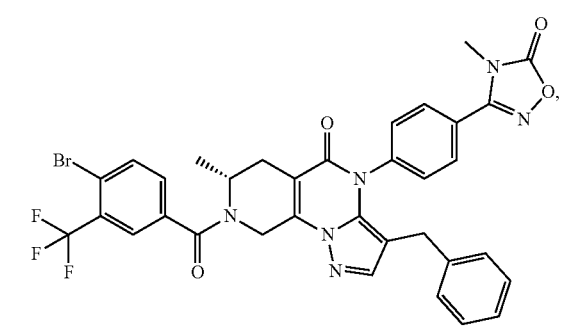
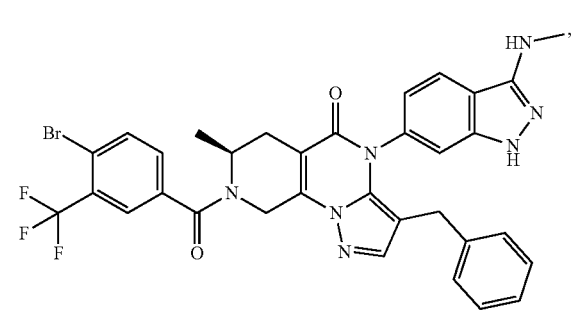
80
-continued
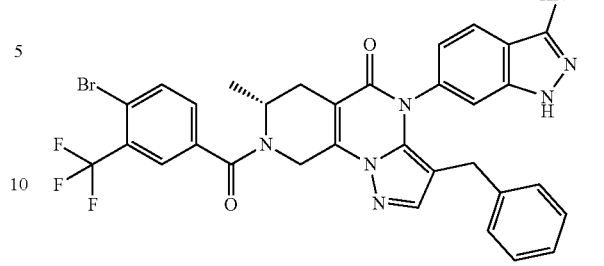
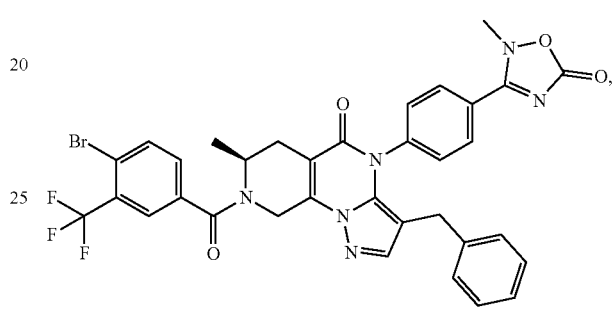
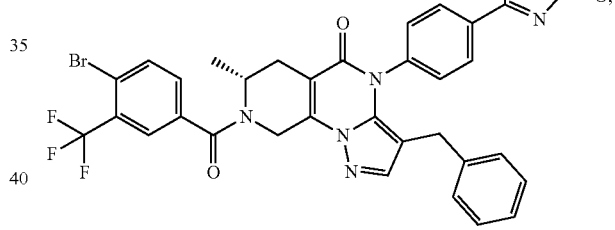
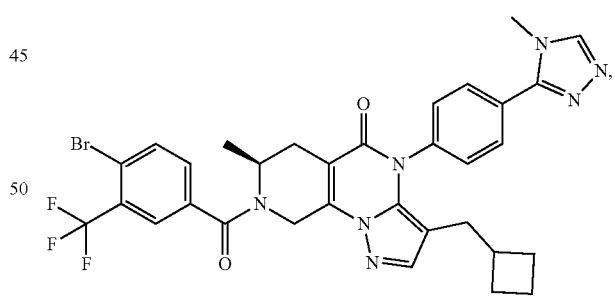
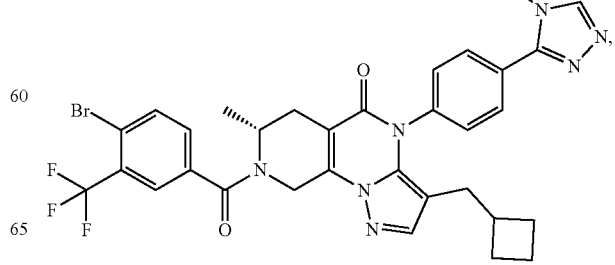

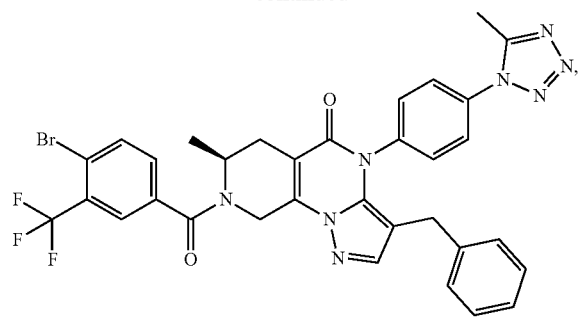
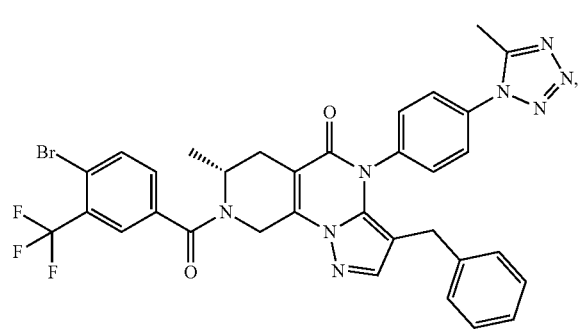
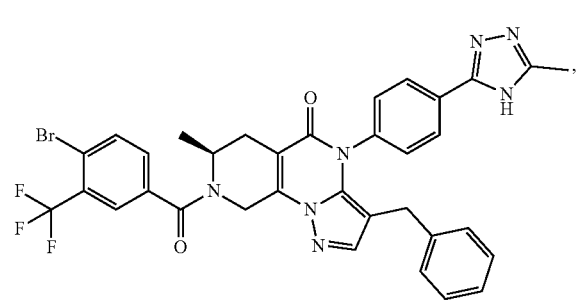
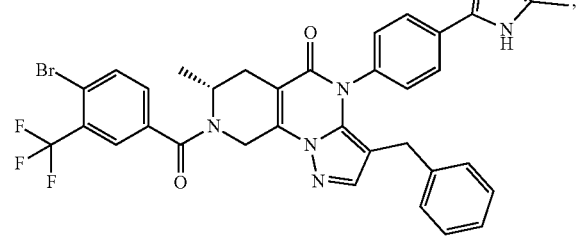
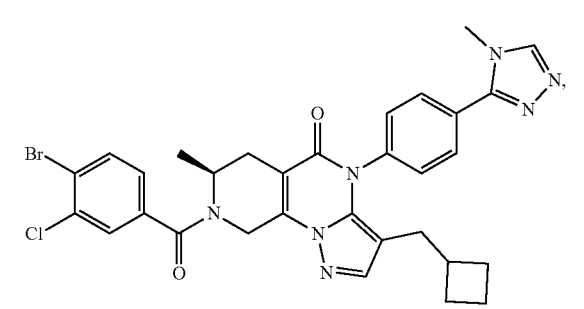
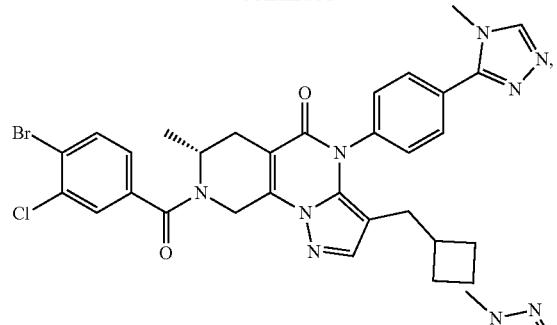
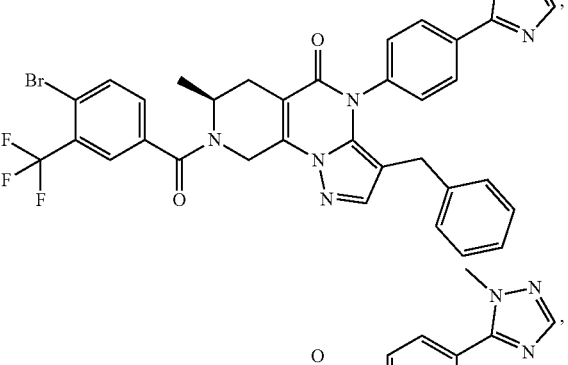

83
-continued
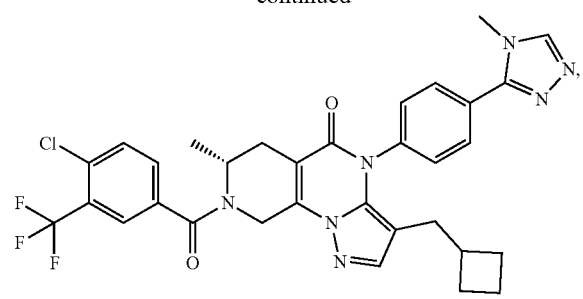
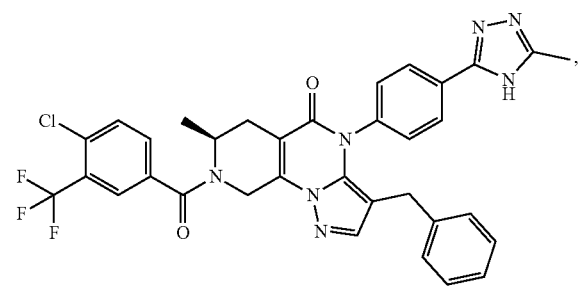
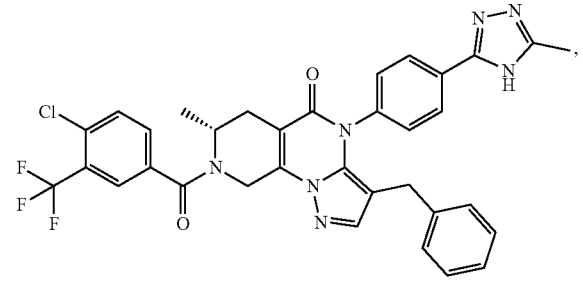
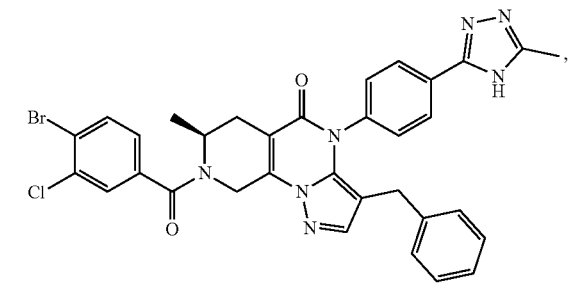
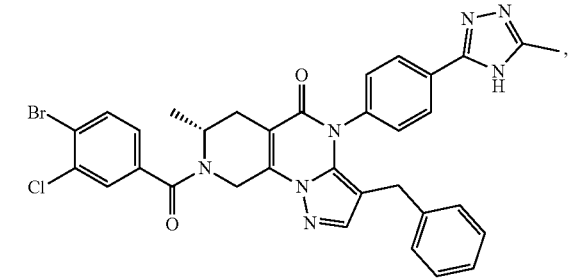
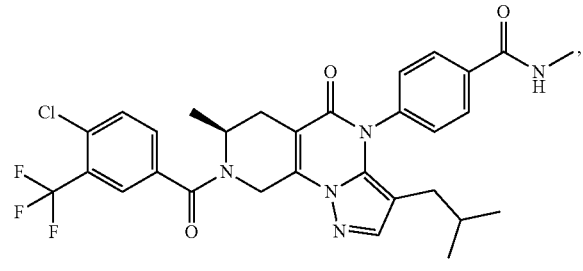
84
-continued
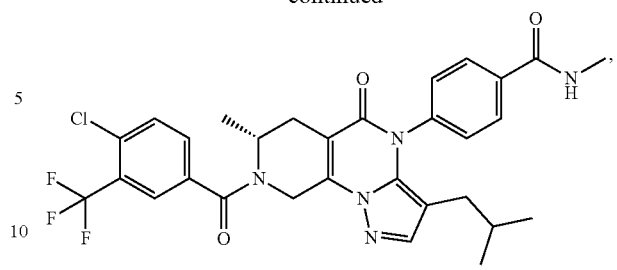
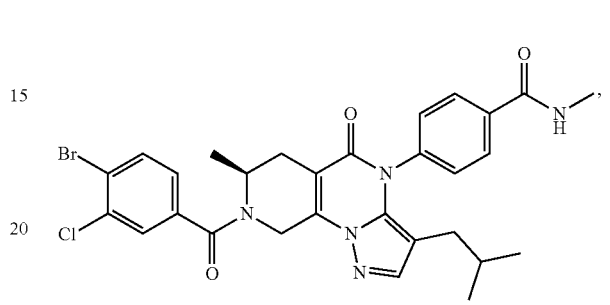
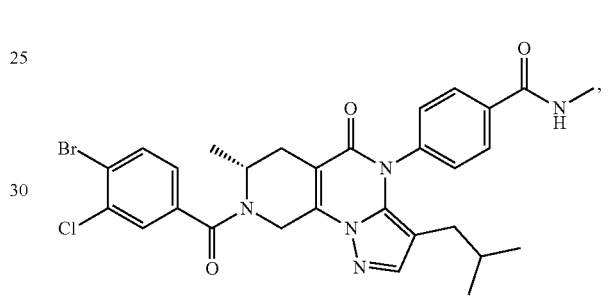
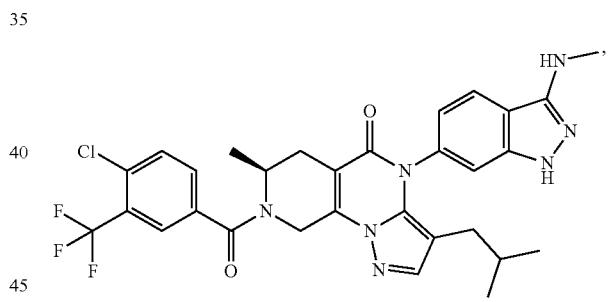
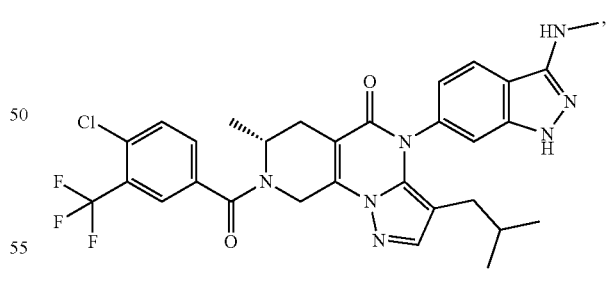
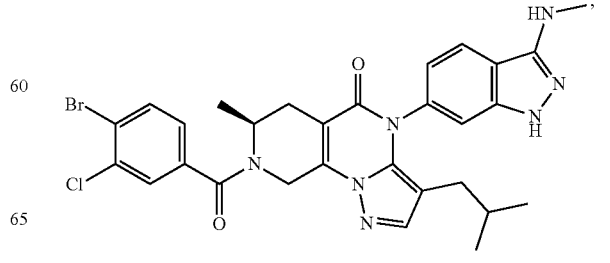

85
-continued
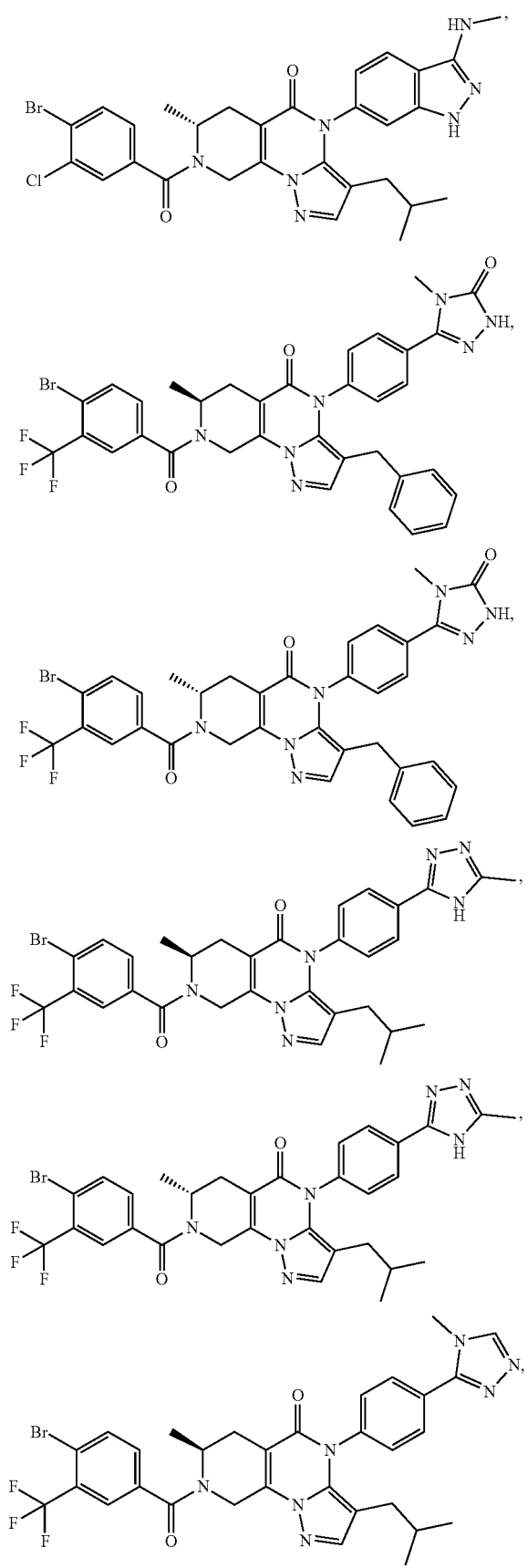
86
-continued
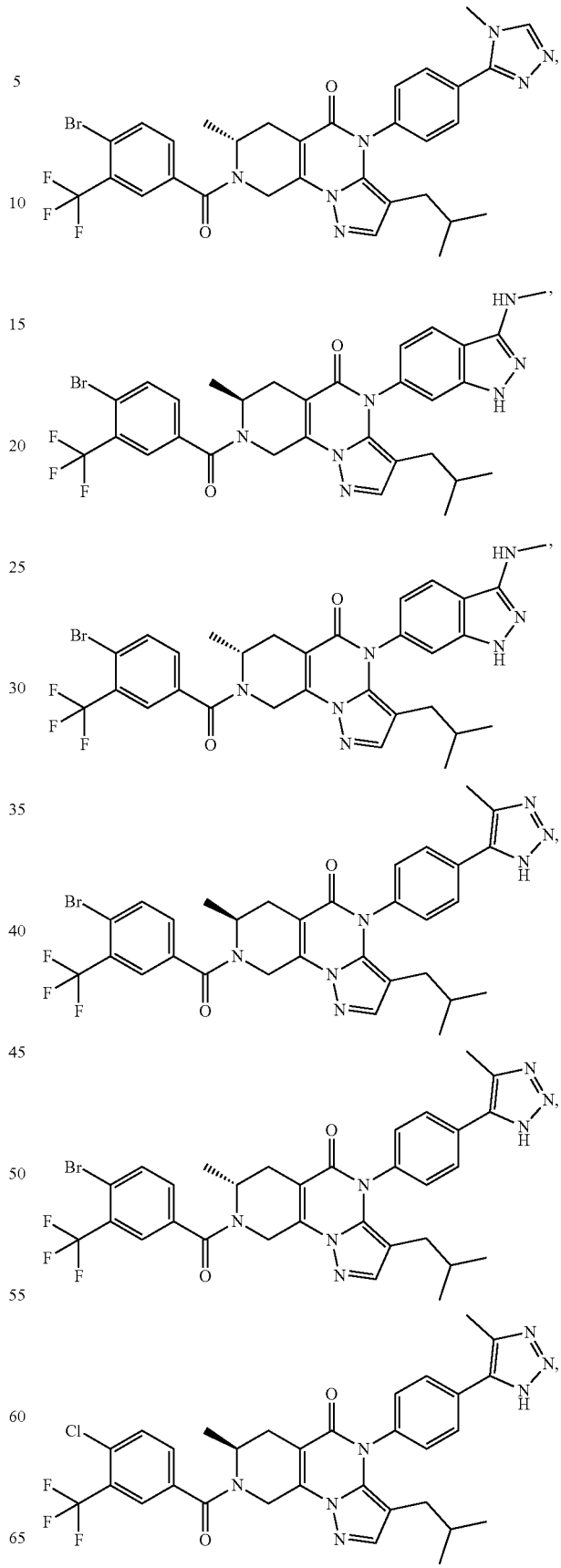

87
-continued
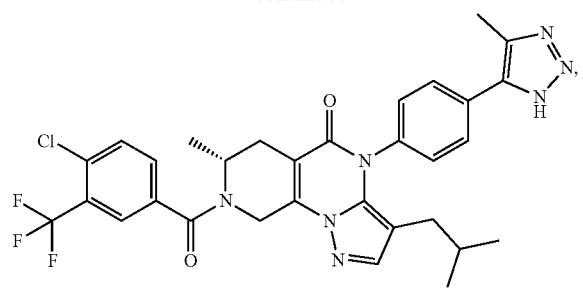
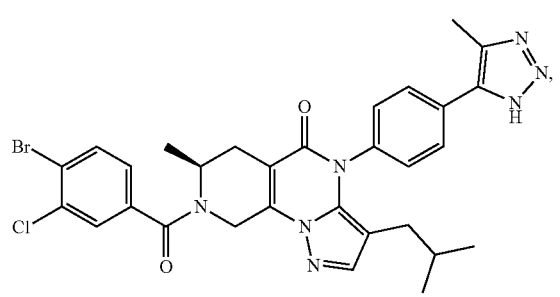
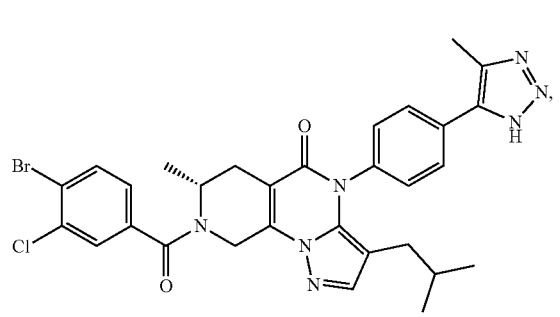
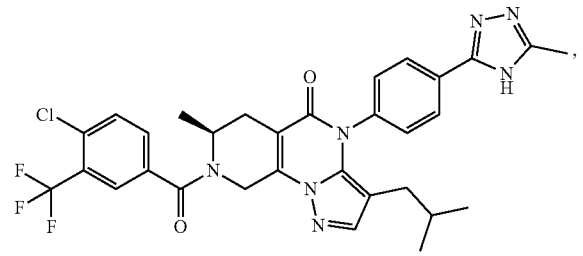
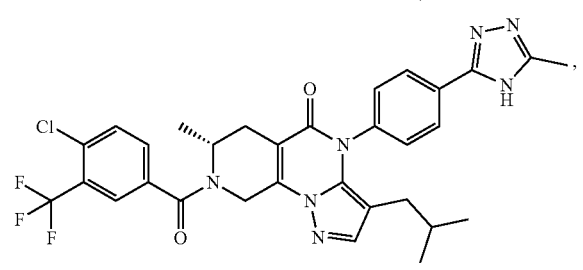
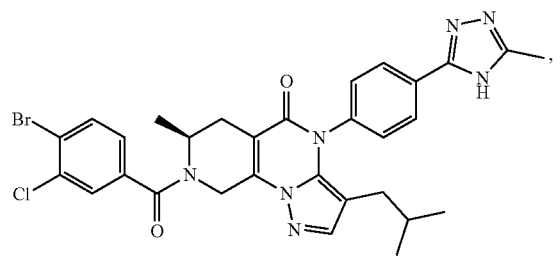
88
-continued
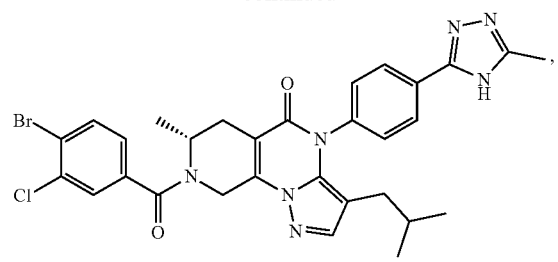
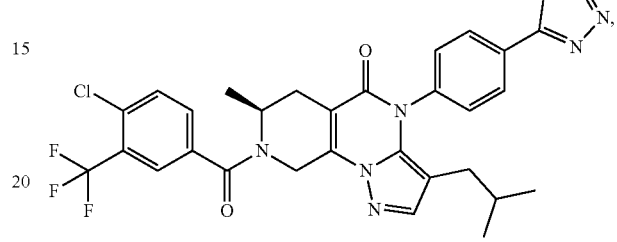
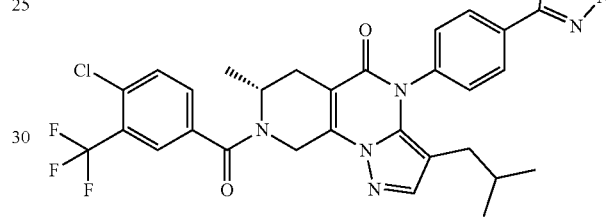
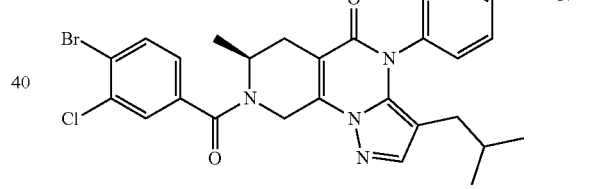
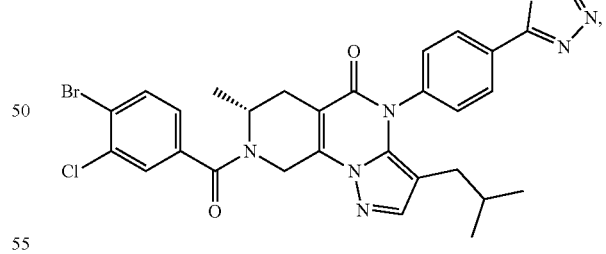
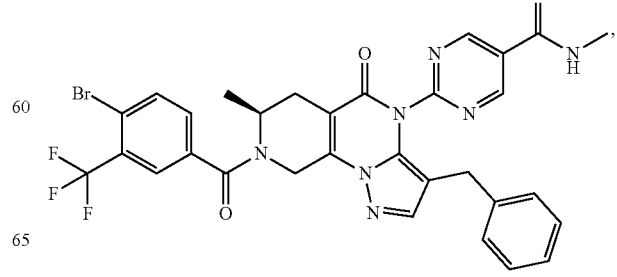

89
-continued
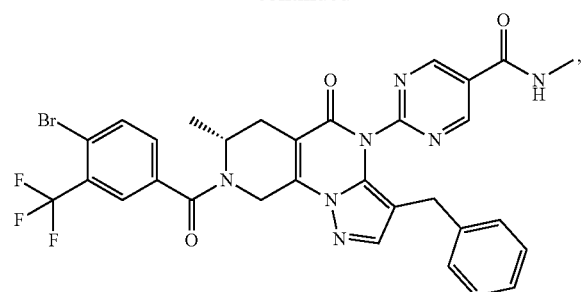
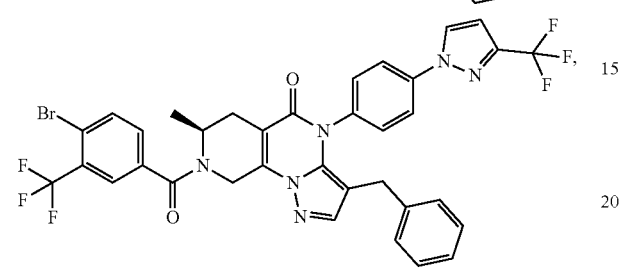
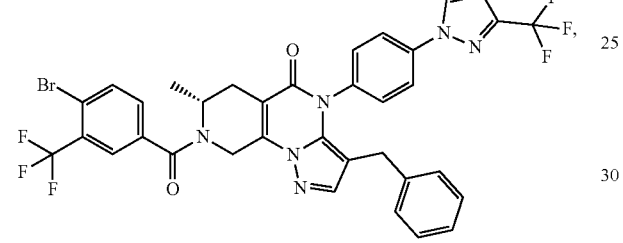
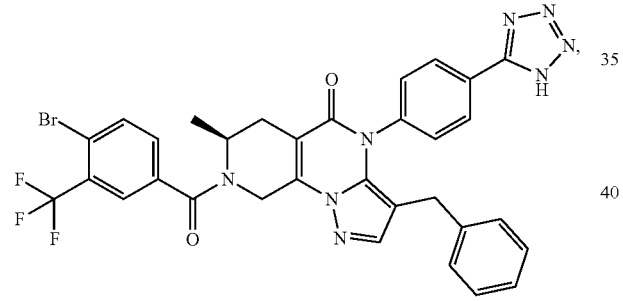
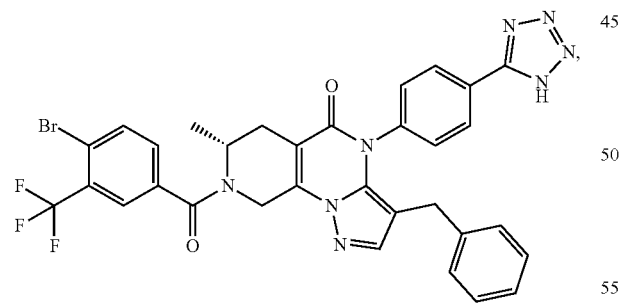
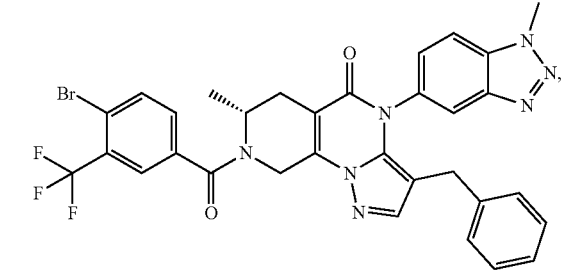
90
-continued
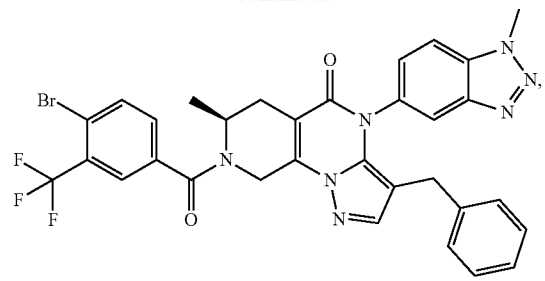
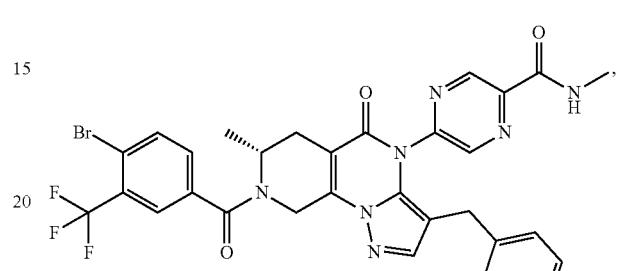
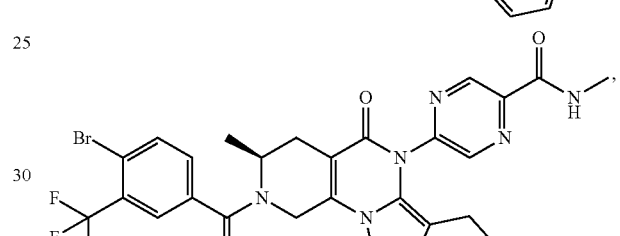
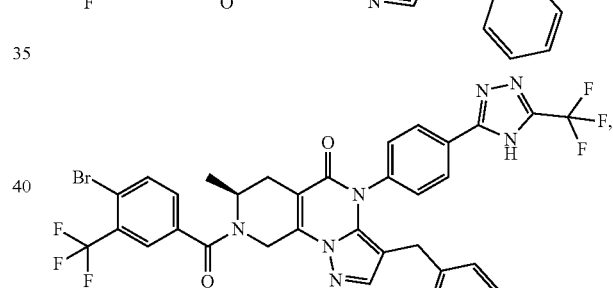
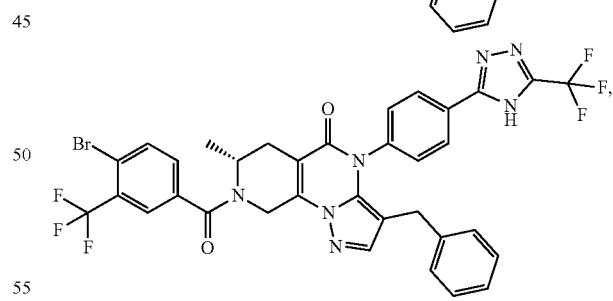
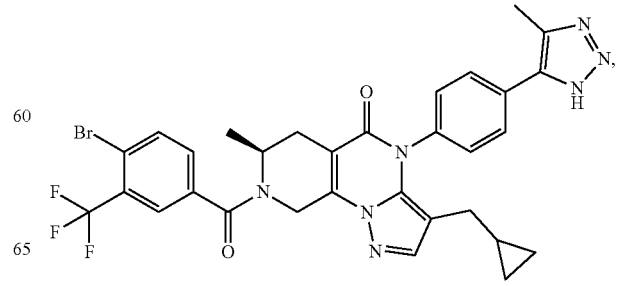

91
-continued
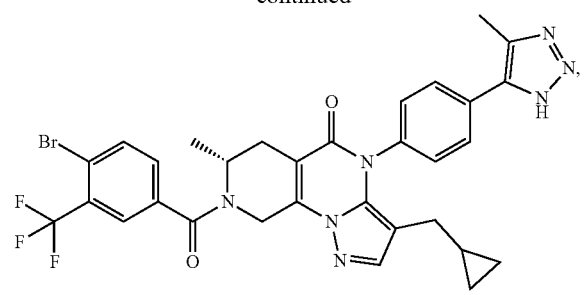
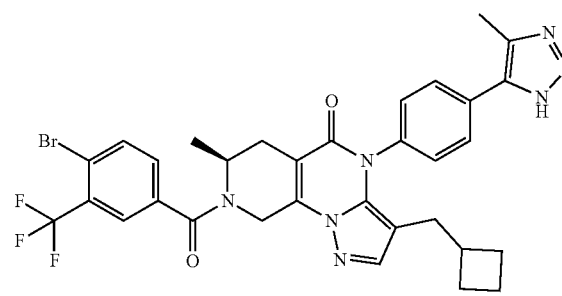
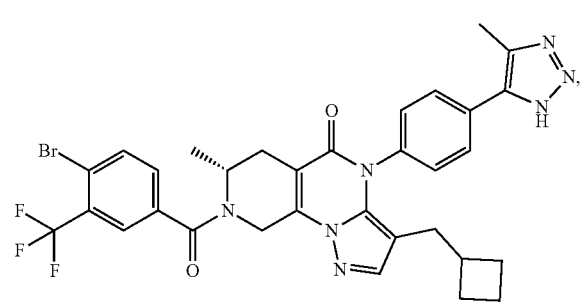
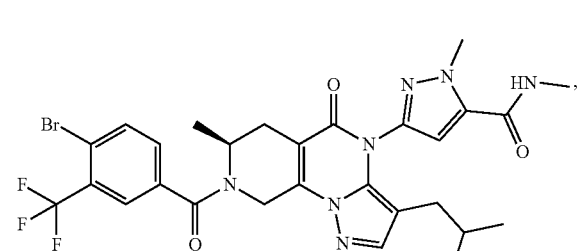
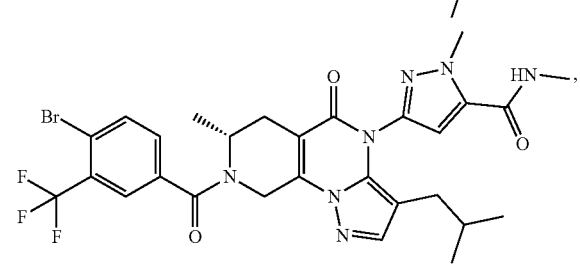
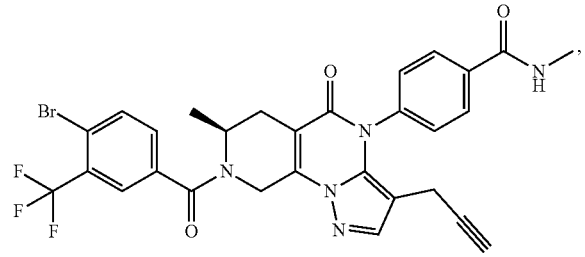
92
-continued
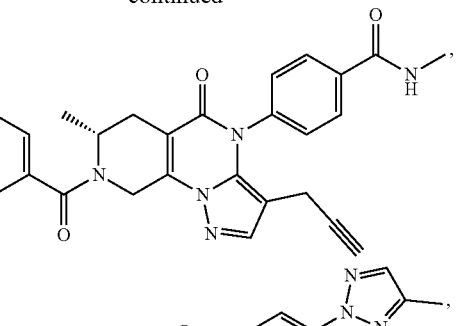
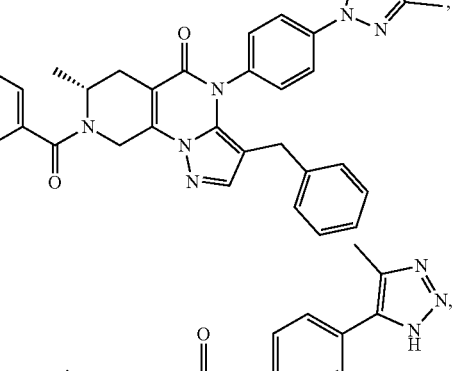
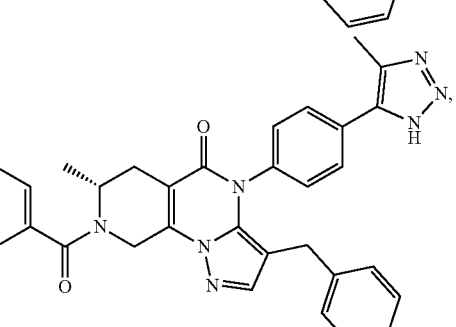
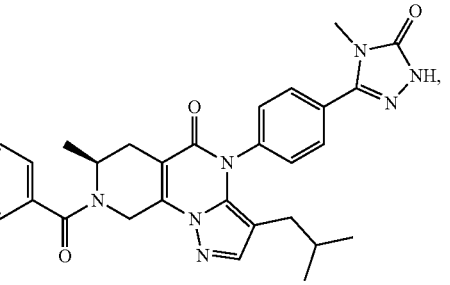

93
-continued
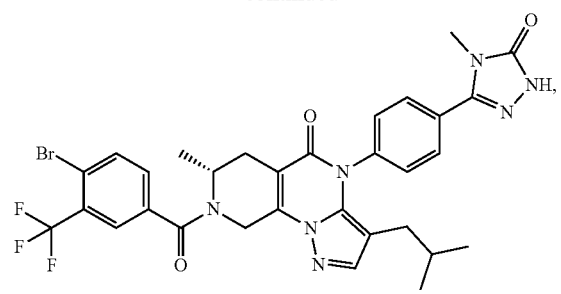
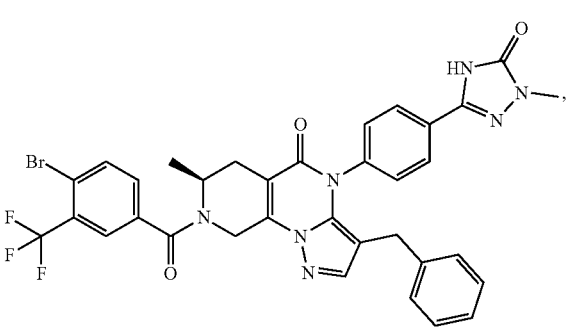
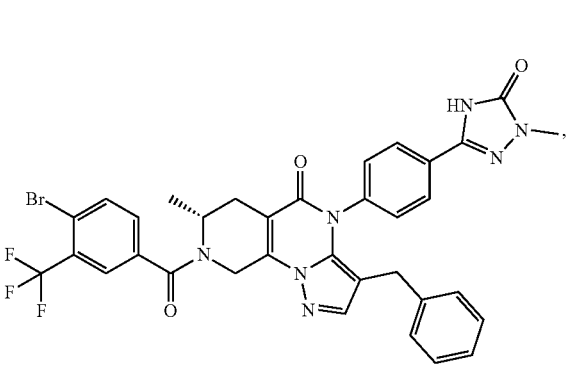
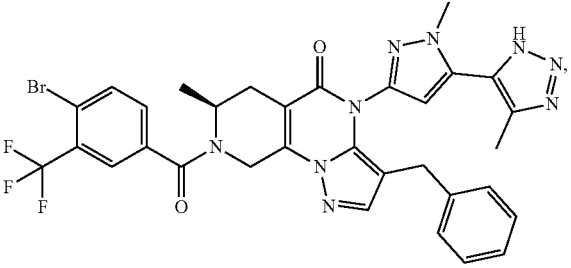
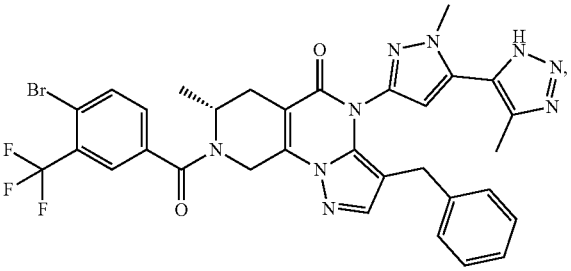
94
-continued
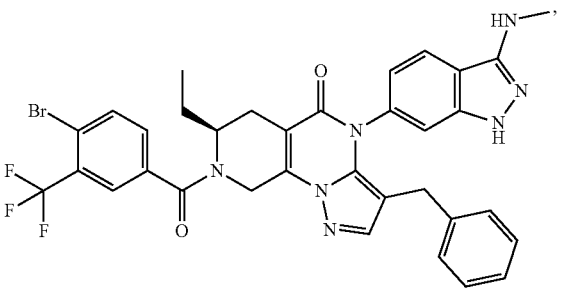
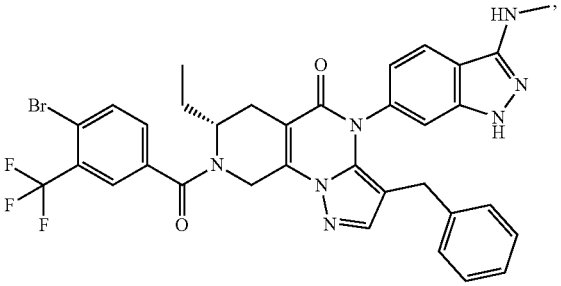
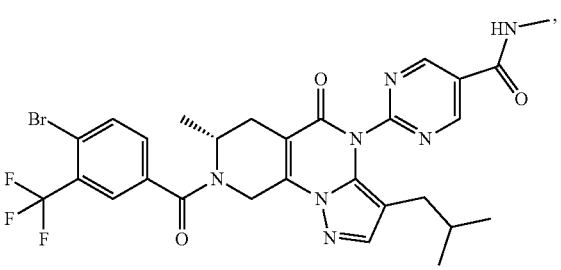
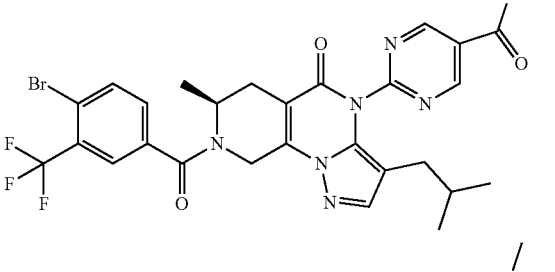
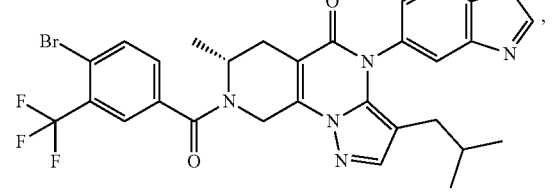
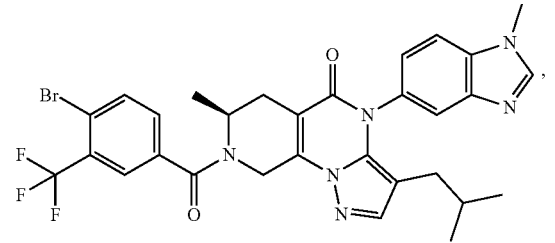

95
-continued
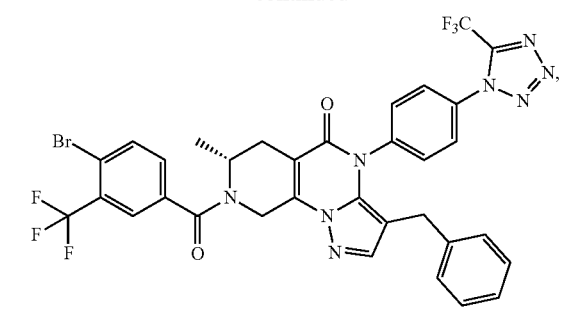
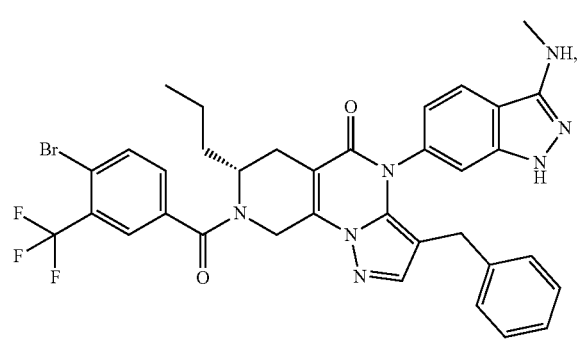
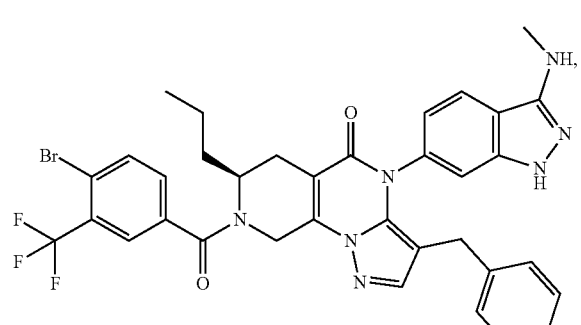
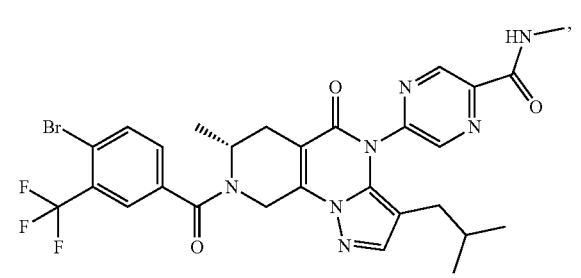
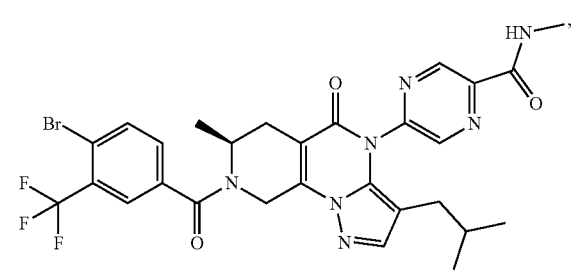
96
-continued
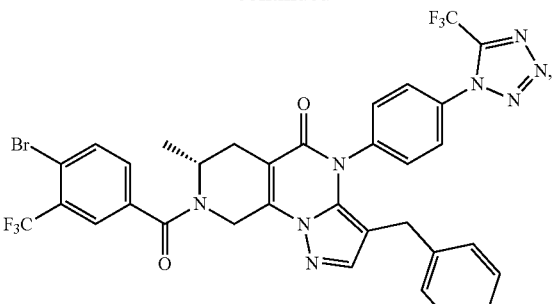
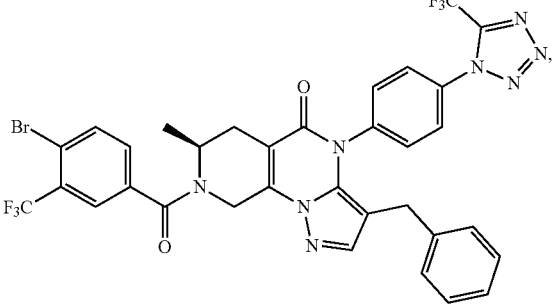
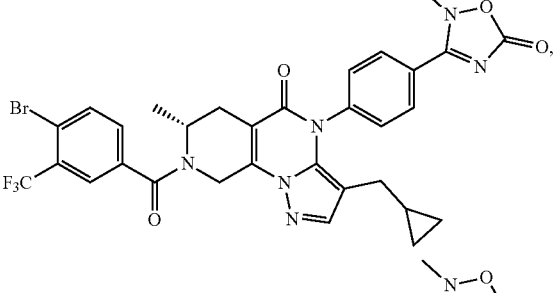
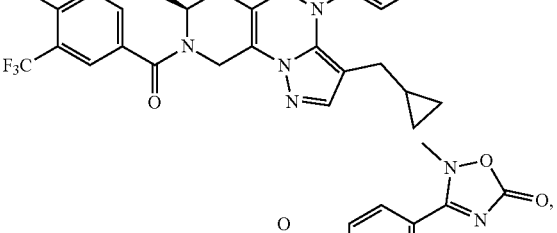
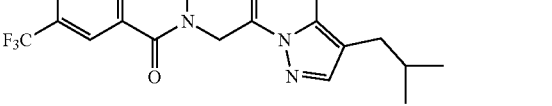
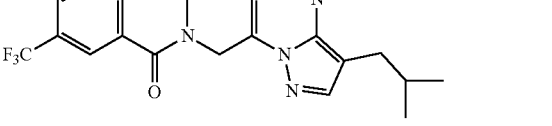

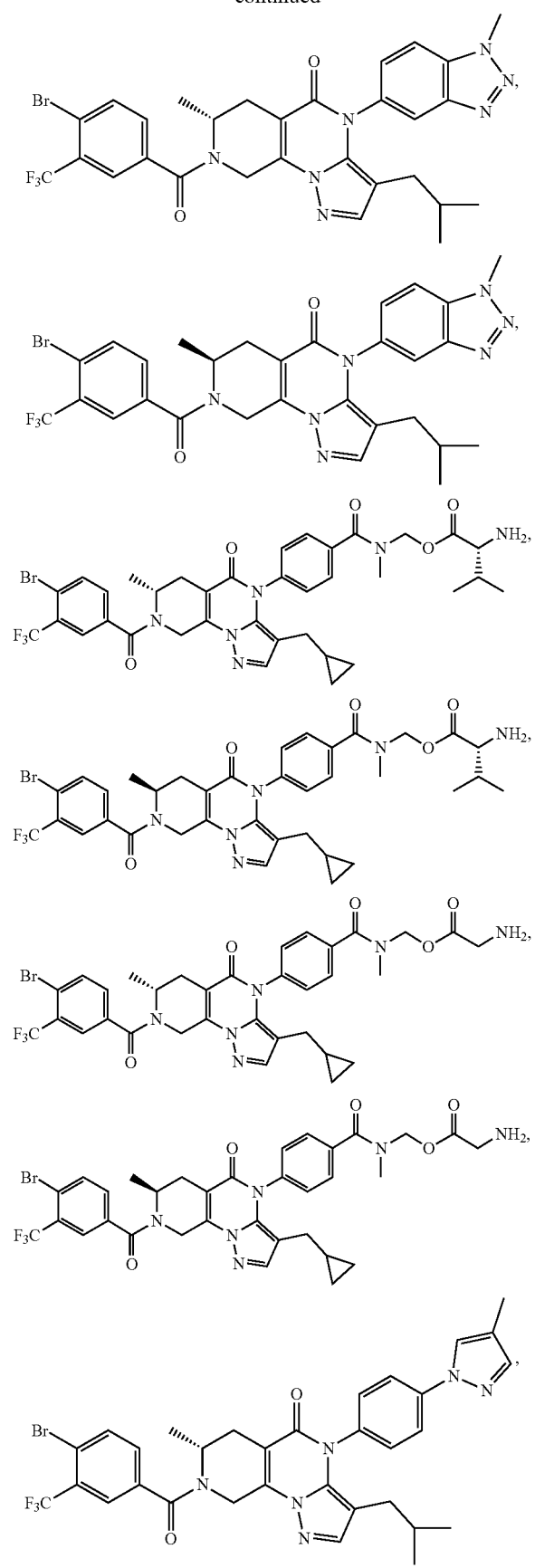
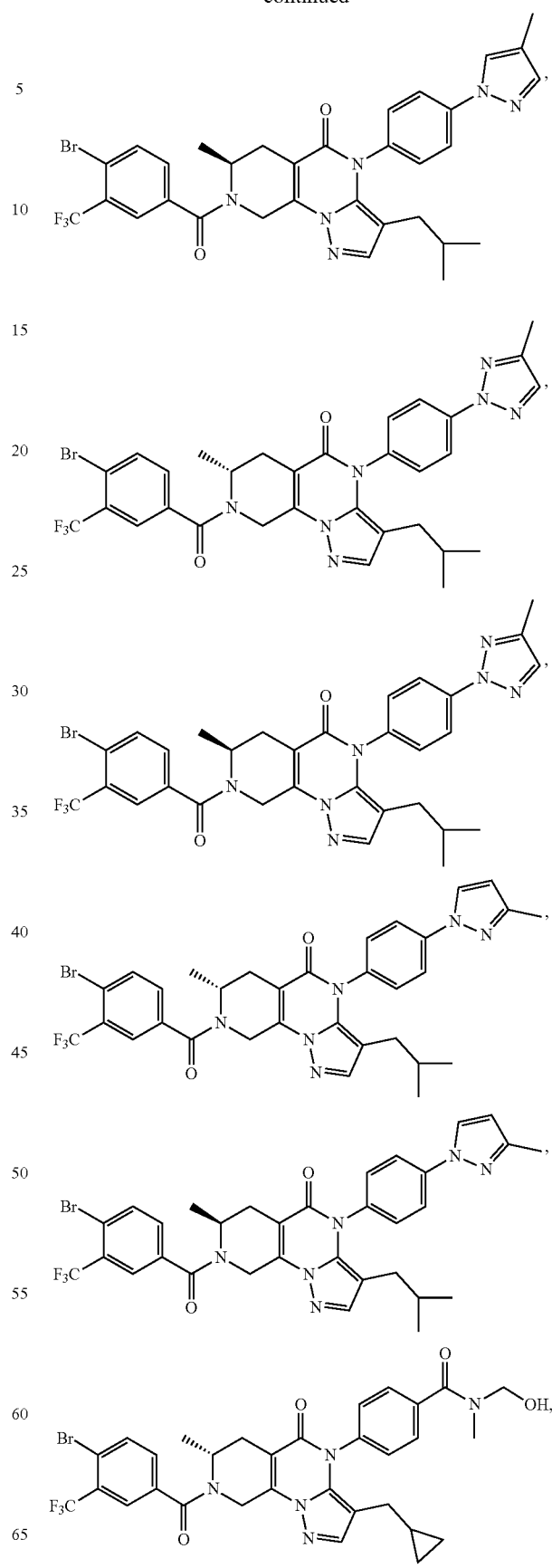

99
-continued
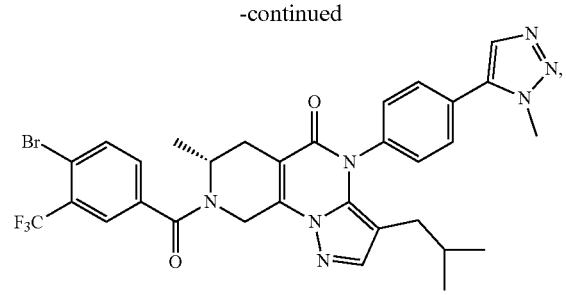
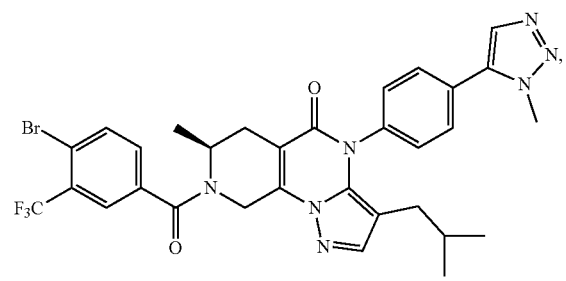
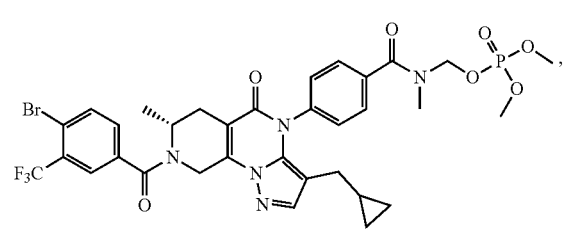
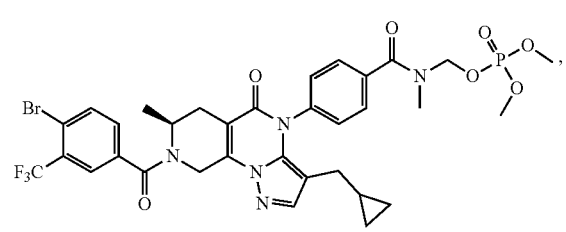
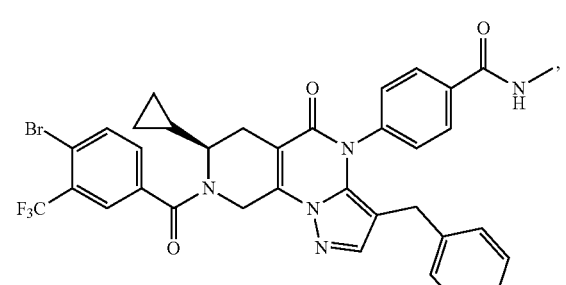
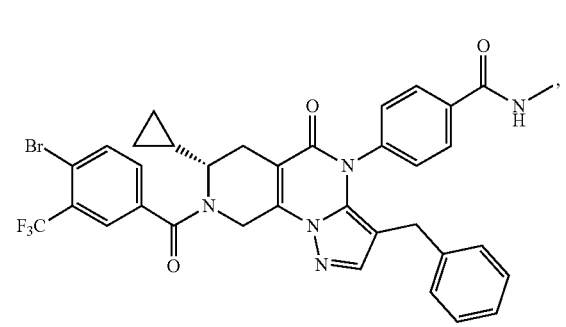
100
-continued
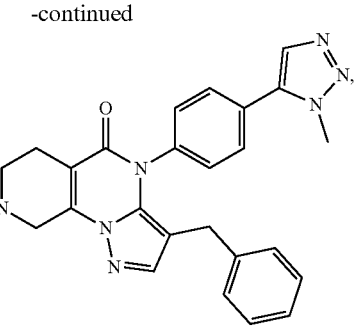
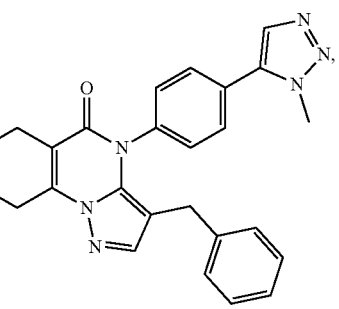
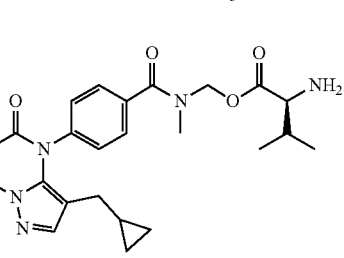
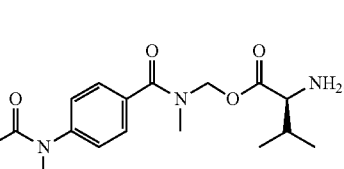
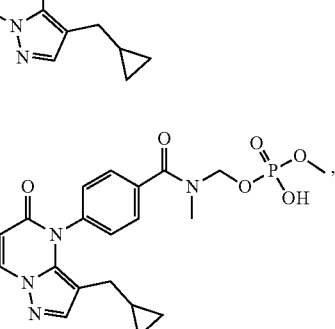
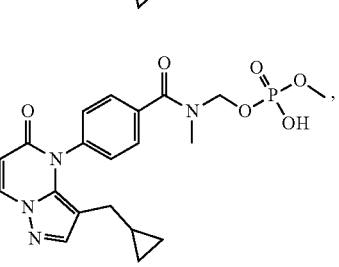

101
-continued
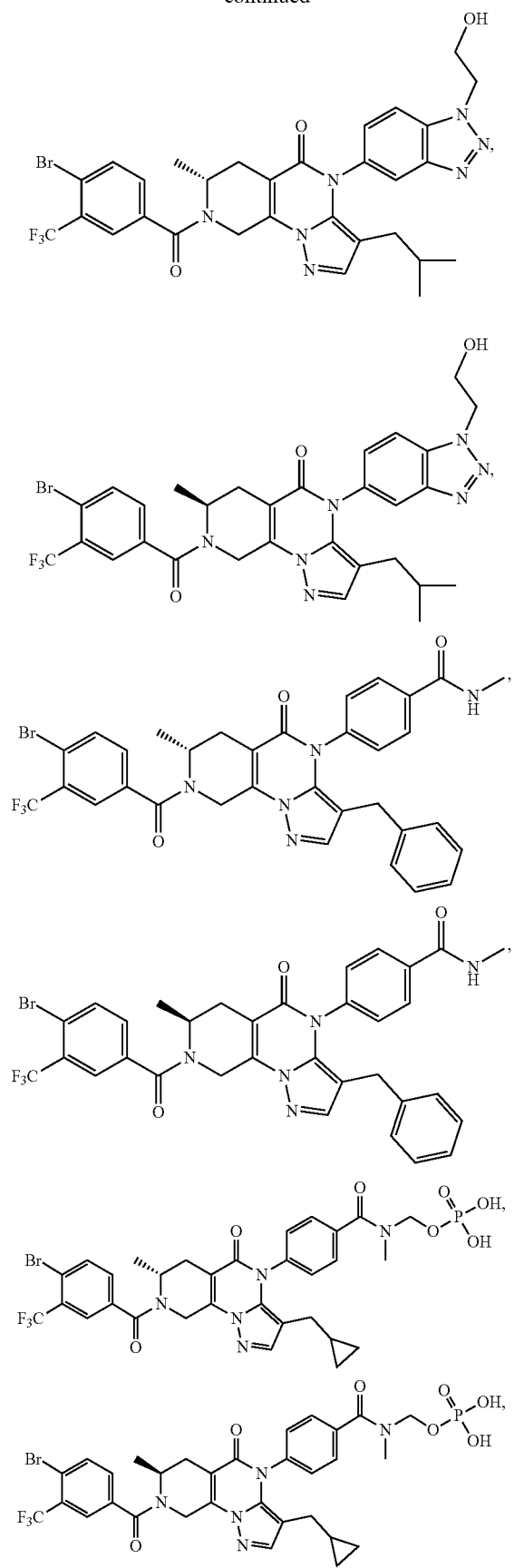
102
-continued
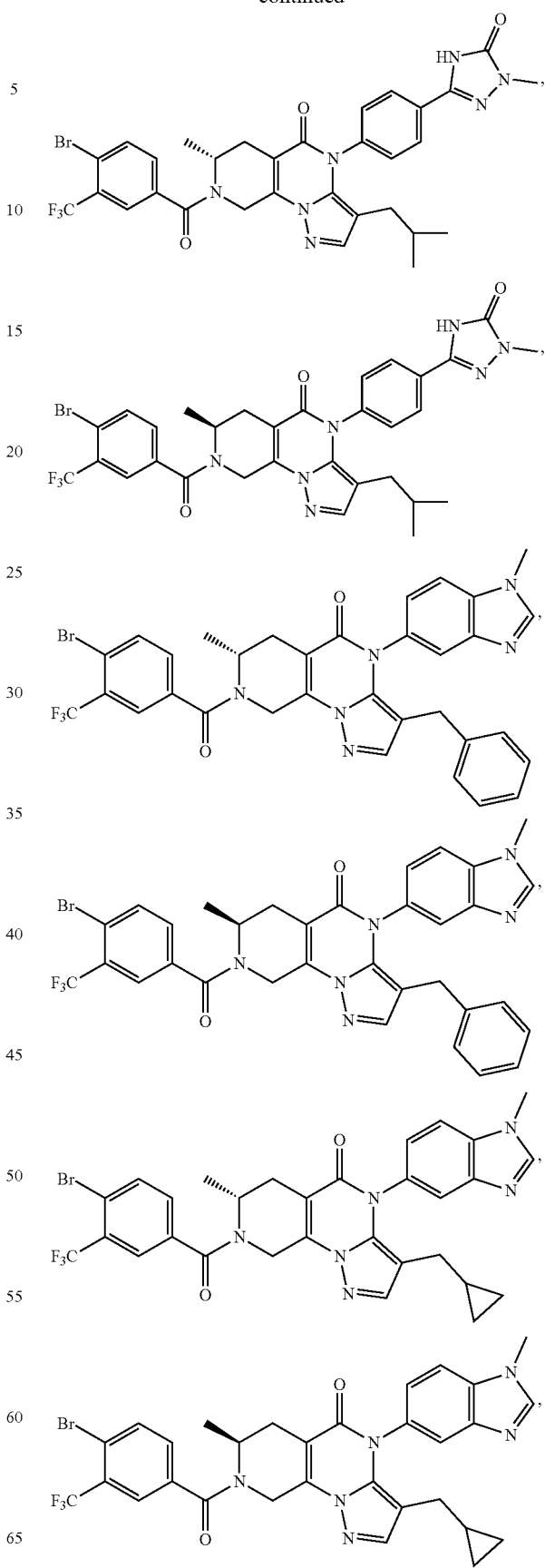

103
-continued
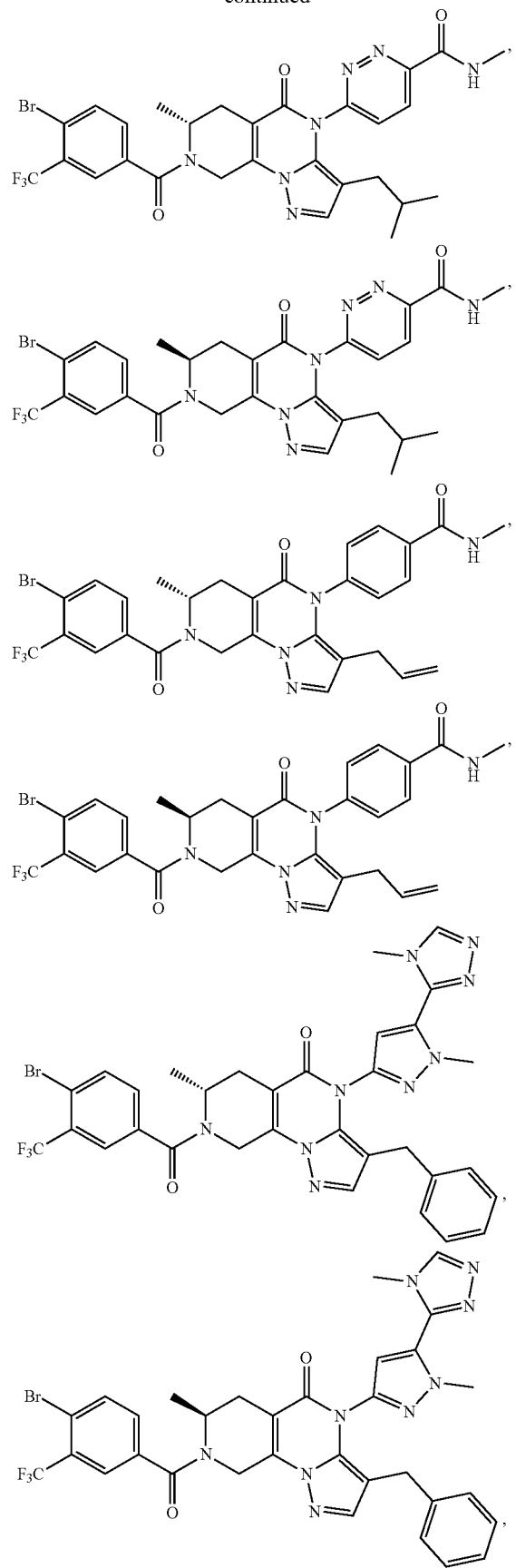
104
-continued
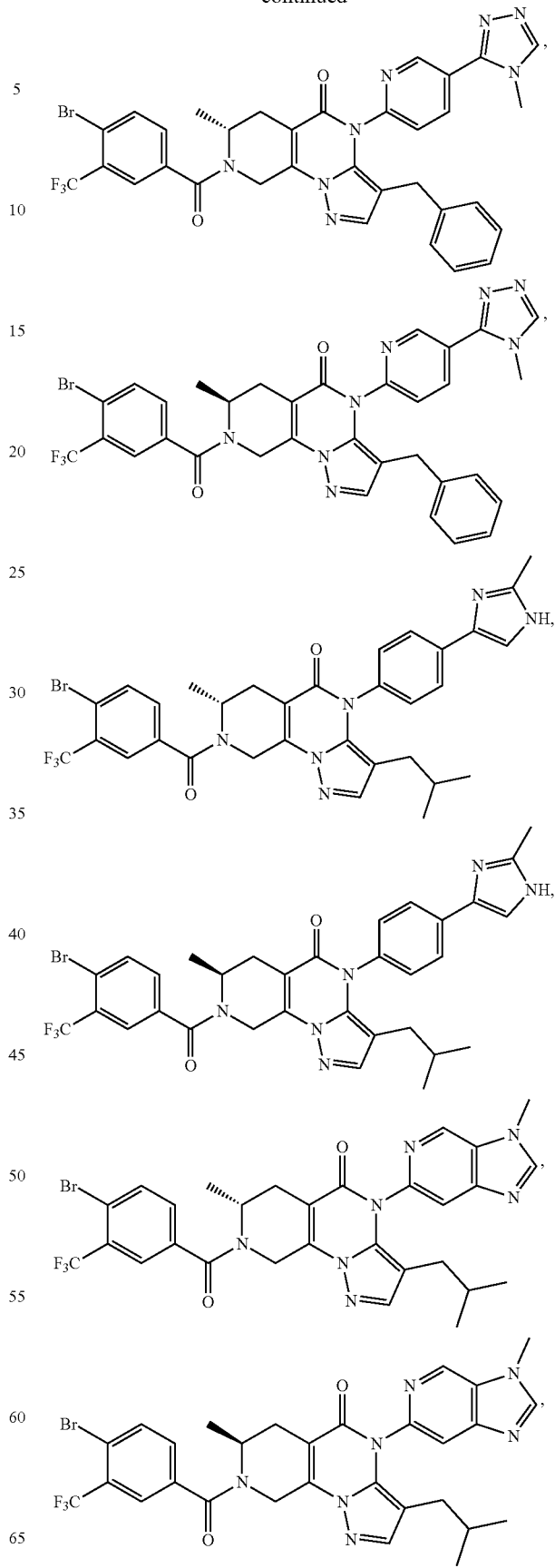

-continued

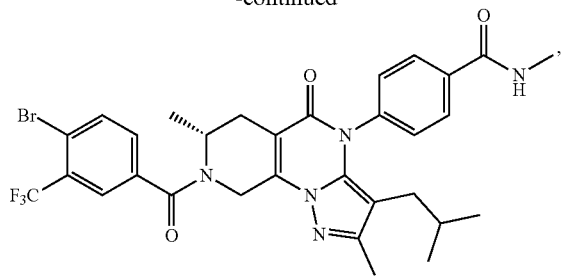

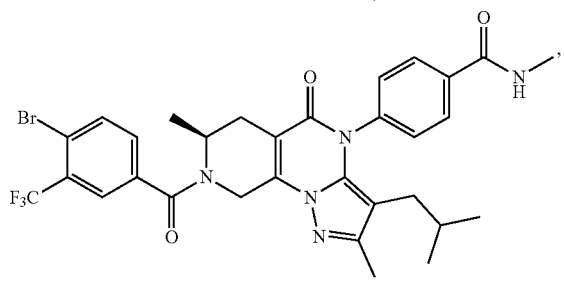

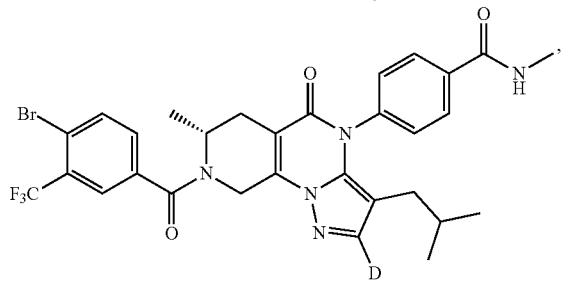

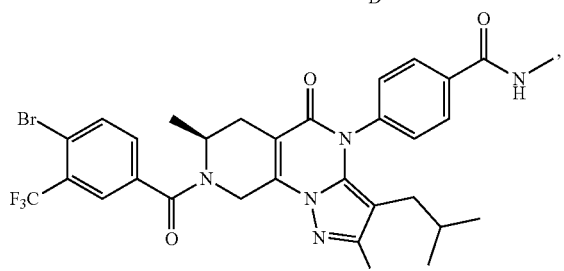

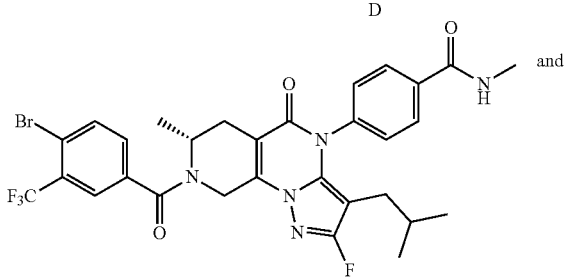

and

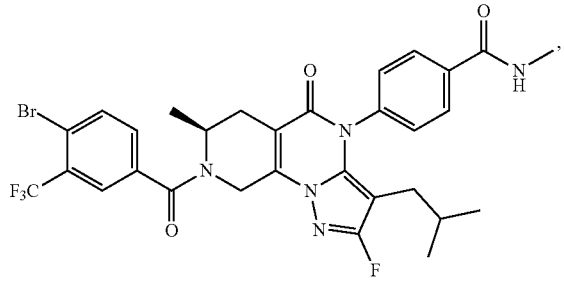

or a pharmaceutically acceptable salt of any of the foregoing.

In some embodiments, when $R^2$, $R^3$, $R^4$, $R^5$, $R^6$ and $R^7$ are each H; $R^1$ is

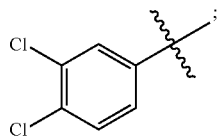 [SMILES: *c1ccc(Cl)c(Cl)c1]

$R^{8a}$ is H; and $R^{8b}$ is unsubstituted phenyl, then $R^9$ is not phenyl substituted at the 4-position with an unsubstituted $C_{1-4}$ alkoxy (such as —$OCH_3$) or an unsubstituted C-amido (for example, —C(=O)$NHCH_3$). In some embodiments, when $R^2$, $R^3$, $R^4$, $R^5$, $R^6$ and $R^7$ are each H; $R^1$ is

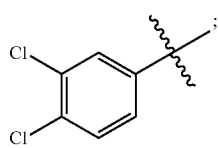 [SMILES: *c1ccc(Cl)c(Cl)c1]

$R^{8a}$ is H; and $R^{8b}$ is unsubstituted phenyl, then $R^9$ cannot be a phenyl substituted at the 4-position with an unsubstituted $C_{1-4}$ alkoxy (such as —$OCH_3$) or an unsubstituted C-amido (for example, —C(=O)$NHCH_3$). In some embodiments, when $R^2$ is H or $CH_3$; $R^3$, $R^4$, $R^5$, $R^6$ and $R^7$ are each H; $R^{8a}$ is H or $CH_3$; $R^{8b}$ is an unsubstituted phenyl; and $R^9$ is a phenyl substituted at the 4-position with an unsubstituted C-amido (such as —C(=O)$NHCH_3$), then $R^1$ cannot be

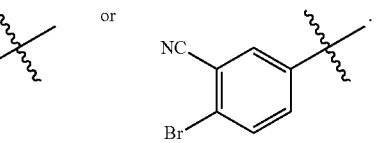

In some embodiments, when $R^2$, $R^3$, $R^4$, $R^5$, $R^6$ and $R^7$ are each H; $R^1$ is

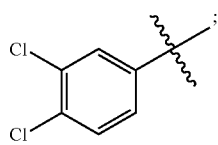 [SMILES: *c1ccc(Cl)c(Cl)c1]

$R^9$ is a phenyl substituted at the 4-position with an unsubstituted C-amido (such as —C(=O)$NHCH_3$); and $R^{8a}$ is H, then $R^{8b}$ cannot be a phenyl substituted at the 4-position with an unsubstituted $C_{1-6}$ haloalkoxy (for example, —$OCF_3$) or —CN. In some embodiments, when $R^2$, $R^3$, $R^4$, $R^5$, $R^6$ and $R^7$ are each H; $R^1$ is

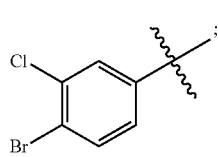

$R^9$ is a phenyl substituted at the 4-position with an unsubstituted C-amido (such as —C(=O)NHCH₃); and $R^{8a}$ is H, then $R^{8b}$ cannot be an unsubstituted $C_{2-4}$ alkynyl (such as —C≡CH), an unsubstituted monocyclic $C_{3-6}$ cycloalkyl (including cyclopropyl), an unsubstituted $C_{1-4}$ alkyl (including isopropyl), an unsubstituted pyridinyl (such as pyridin-2-yl, pyridin-3-yl and pyridin-4-yl), a phenyl substituted at the 3-position with a halogen (for example, fluoro), a phenyl substituted at the 4-position with a halogen (such as fluoro), an unsubstituted $C_{1-4}$ alkoxy (such as —OCH₃), —CN or an unsubstituted $C_{1-6}$ haloalkoxy (for example, —OCF₃), and a phenyl substituted at the 2-position with a halogen (such as fluoro) and the 4-position with an unsubstituted $C_{1-4}$ alkoxy (such as —OCH₃) or —CN. In some embodiments, when $R^2$, $R^3$, $R^4$, $R^5$, $R^6$ and $R^7$ are each H; $R^1$ is

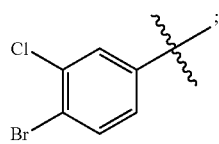

$R^{8a}$ is H; and $R^{8b}$ is an unsubstituted phenyl, then $R^9$ cannot be a bicyclic heteroaryl or a bicyclic heterocyclyl (examples of bicyclic heteroaryls and bicyclic heterocyclyls include the following: 3-aminobenzo[d]isoxazol-6-yl, 3-(methylamino)benzo[d]isoxazol-6-yl, 3-amino-1H-indazol-6-yl, 3-(methylamino)-1H-indazol-6-yl and 1-oxoisoindolin-5-yl), a monocyclic heteroaryl (such as pyridin-5-yl substituted at the 2-position with —C(=O)NHCH₃), a monocyclic $C_{3-6}$ cycloalkyl (for example, cyclohexyl substituted at the 4-position with —C(=O)NHCH₃), a phenyl substituted at the 4-position with a —C-amido (for example, a —C-amido selected from —C(=O)NH₂, —C(=O)NHCH₂CH₃, —C(=O)NHCH(CH₃)₂ and —C(=O)NH-cyclopropyl), a phenyl substituted at the 4-position with a monocyclic heteroaryl (for example, an unsubstituted pyrazol-1-yl, unsubstituted imidazol-2-yl, 2-methyl-imidazol-5-yl, 3-methyl-pyrazol-1-yl and 1-methyl-imidazol-2-yl), a phenyl substituted at the 3-position with —C-amido (such as —C(=O)NHCH₃) or a phenyl substituted at the 3-position with halogen (such as chloro) and the 4-position with —C-amido (for example, —C(=O)NHCH₃). In some embodiments, when $R^2$, $R^3$, $R^4$, $R^5$, $R^6$ and $R^7$ are each H; $R^1$ is

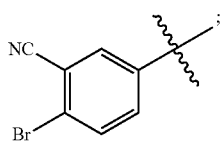 [SMILES: *c1ccc(Br)c(C#N)c1]

$R^9$ is a phenyl substituted with —C(=O)NHCH₃; and $R^{8a}$ is H, then $R^{8b}$ cannot be a phenyl substituted at the 2-position with a halogen (such as fluoro), a phenyl substituted at the 2-position with a halogen (such as fluoro) and the 4-position with —CN or an unsubstituted $C_{1-4}$ alkoxy (for example, —OCH₃), or a phenyl substituted at the 4-position with a halogen (such as fluoro) or an unsubstituted $C_{1-4}$ alkoxy (for example, —OCH₃). In some embodiments, when $R^2$, $R^3$, $R^4$, $R^5$, $R^6$ and $R^7$ are each H; $R^1$ is

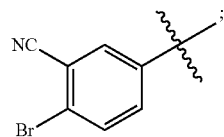 [SMILES: *c1ccc(Br)c(C#N)c1]

$R^{8a}$ is H; and $R^{8b}$ is an unsubstituted phenyl, and then $R^9$ cannot be a phenyl substituted at the 4-position with an unsubstituted C-amido (for example, —C(=O)NH₂, —C(=O)NHCH₂CH₃, —C(=O)NHCH(CH₃)₂, —C(=O)NHcyclopropyl), an unsubstituted pyrazol-1-yl or an unsubstituted imidazol-2-yl. In some embodiments, a compound of Formula (I), or a pharmaceutically acceptable salt thereof, cannot be a compound, or a pharmaceutically acceptable salt thereof, provided in WO 2020/243199. In some embodiments, a compound of Formula (I), or a pharmaceutically acceptable salt thereof, cannot be a compound, or a pharmaceutically acceptable salt thereof, selected from

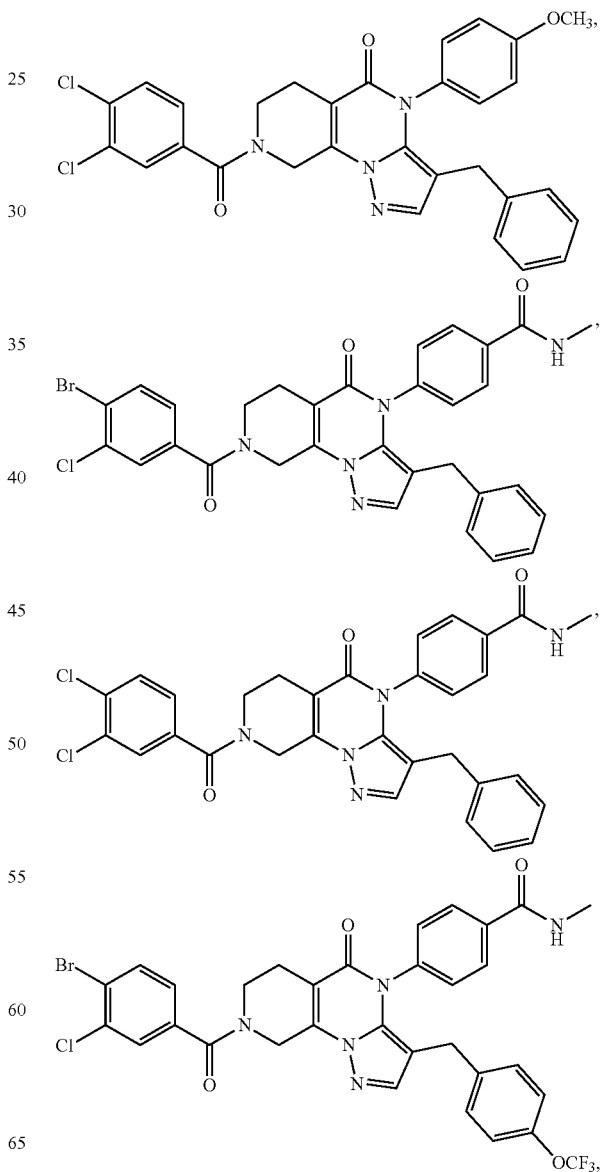

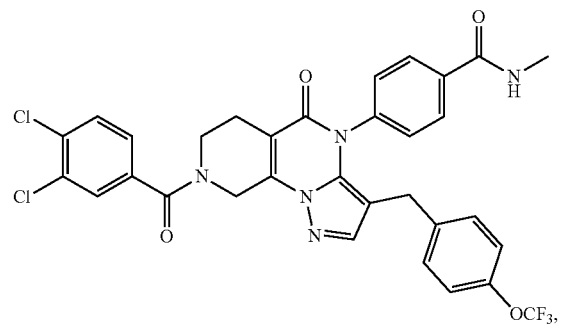
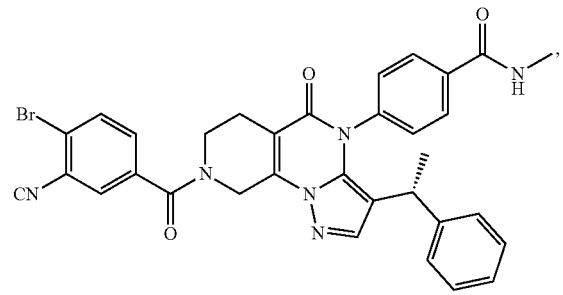
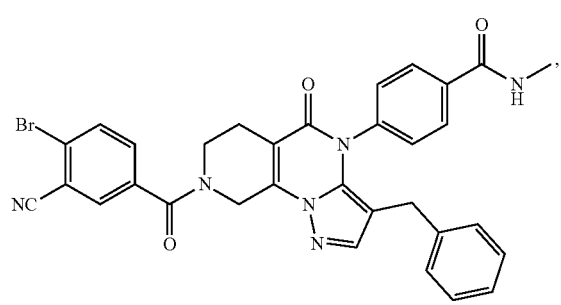
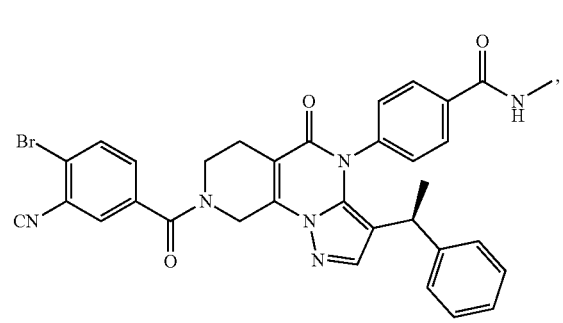
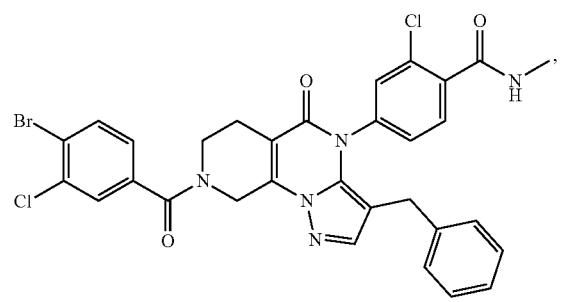
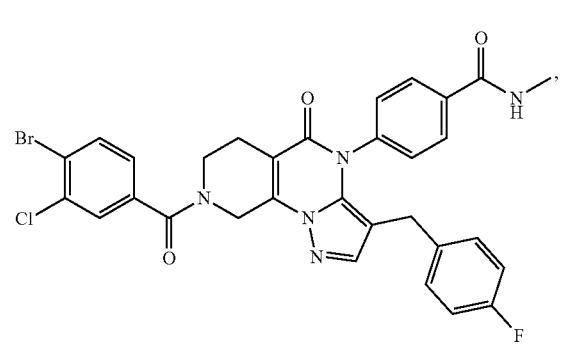
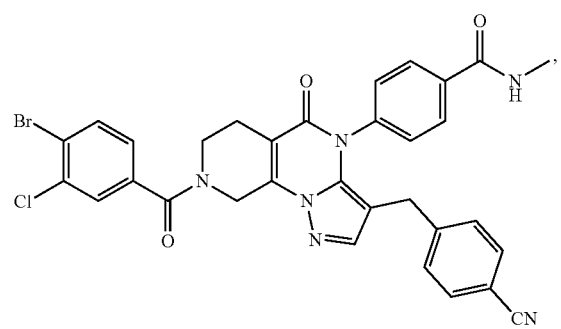
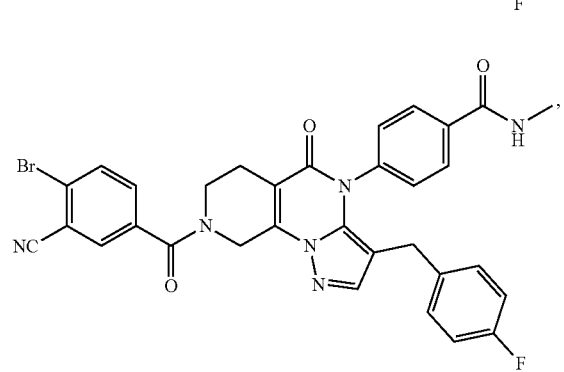
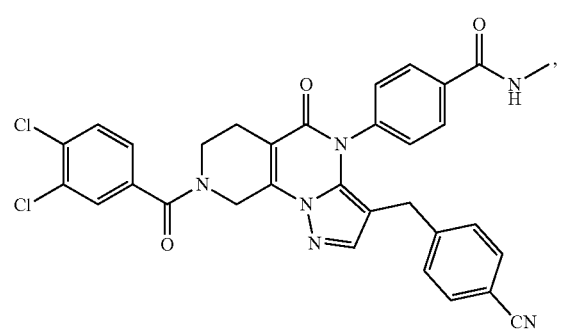
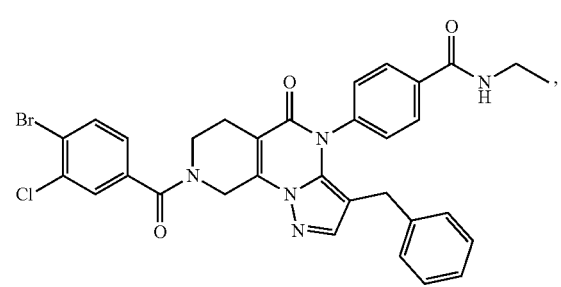

111
-continued
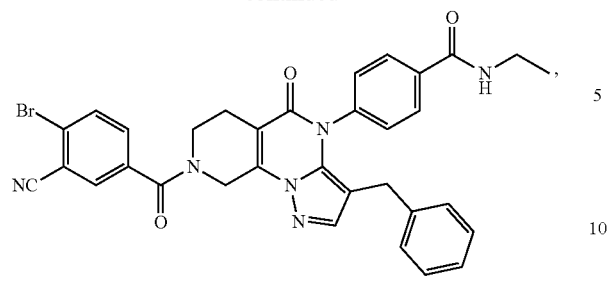
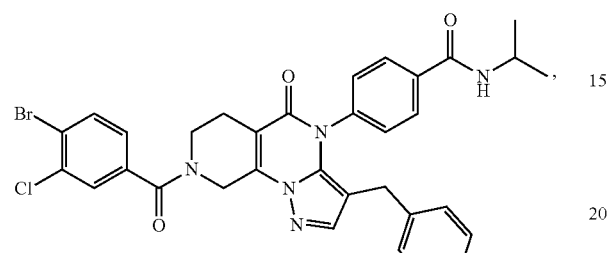
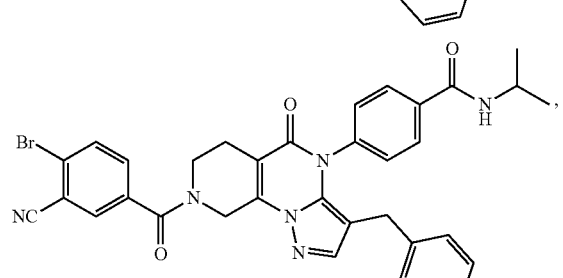
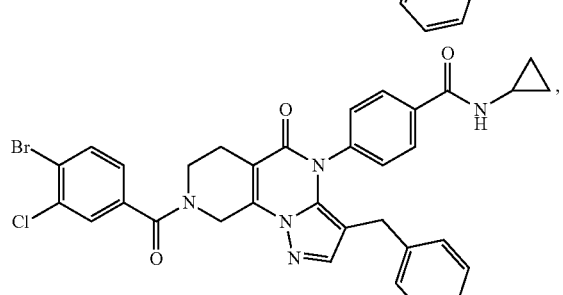
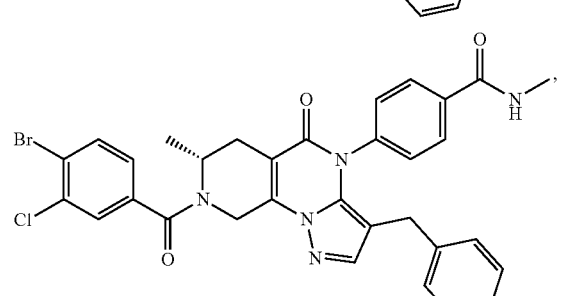
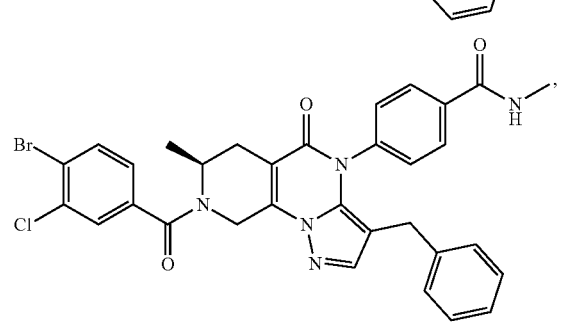
112
-continued
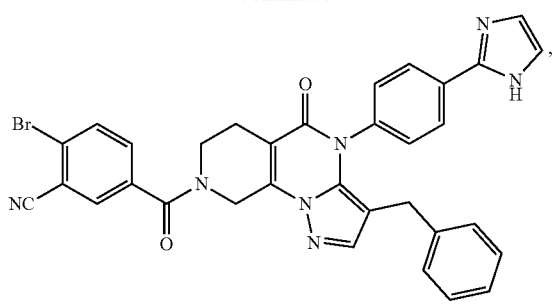
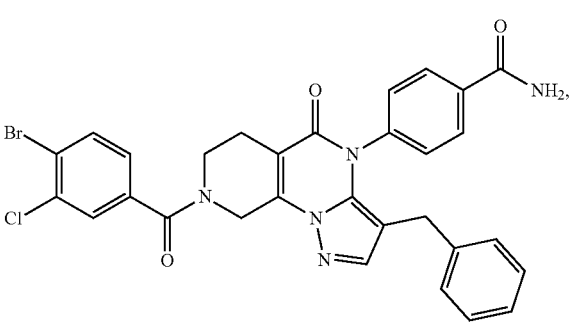
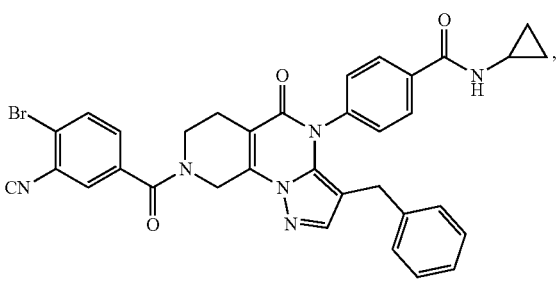
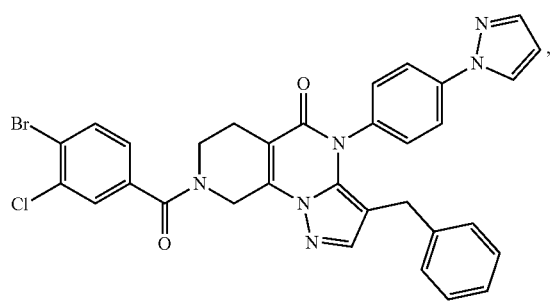
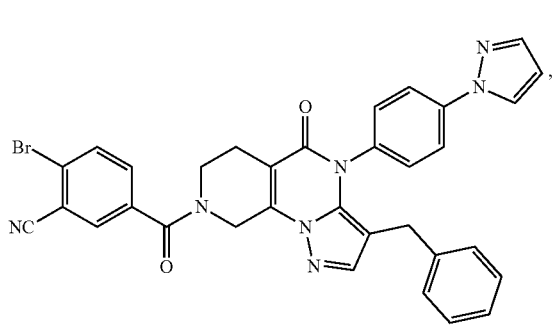

113
-continued
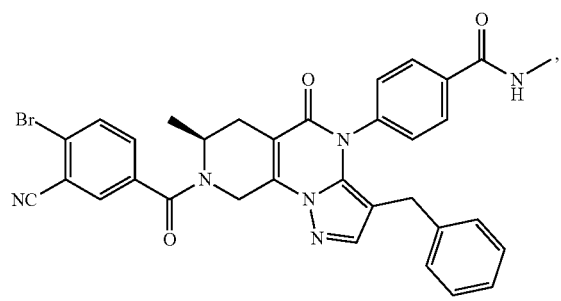
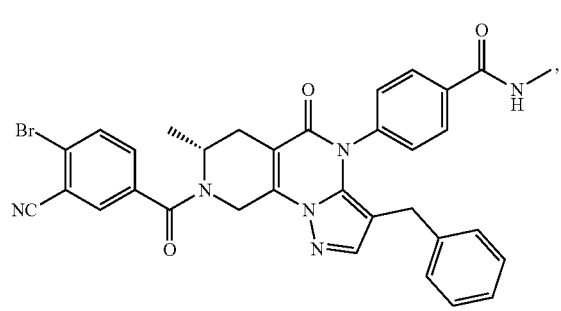
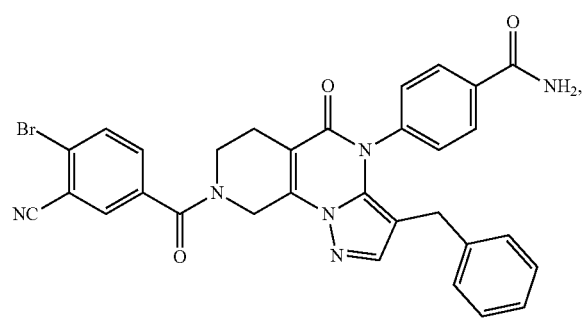
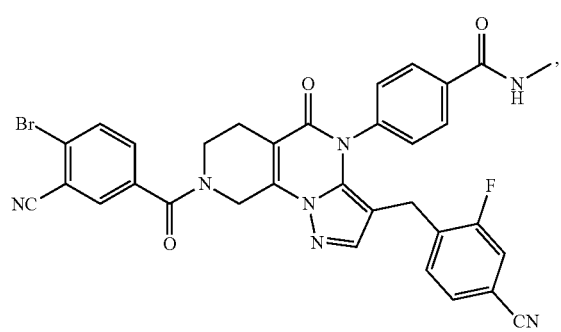
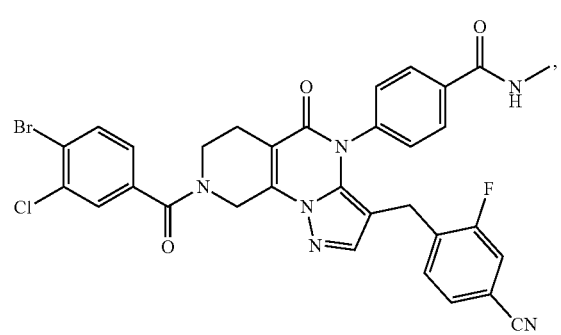
114
-continued
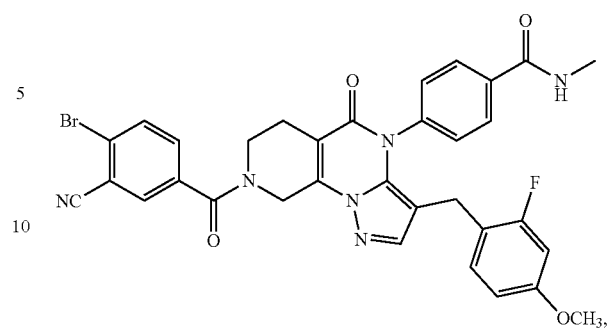
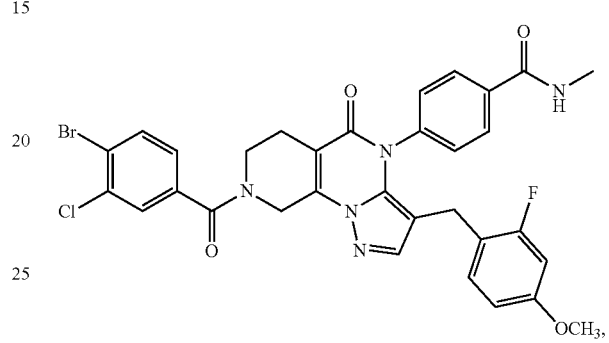
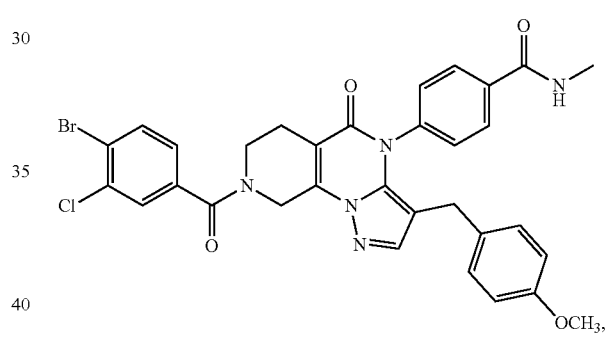
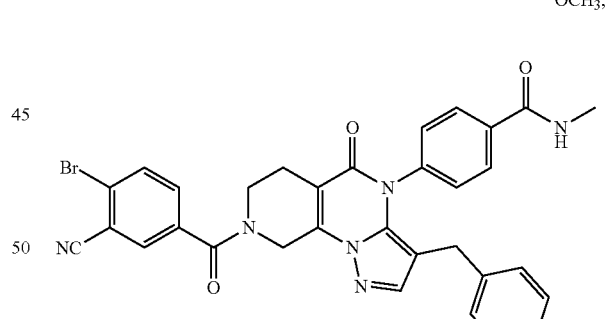
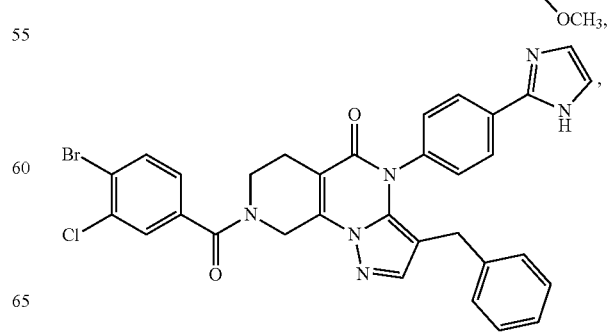

115
-continued
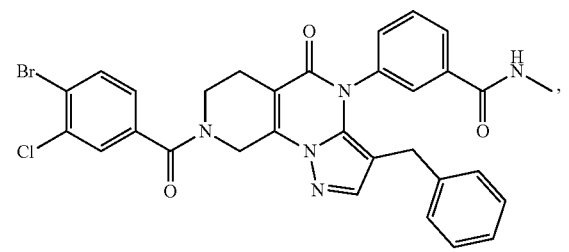
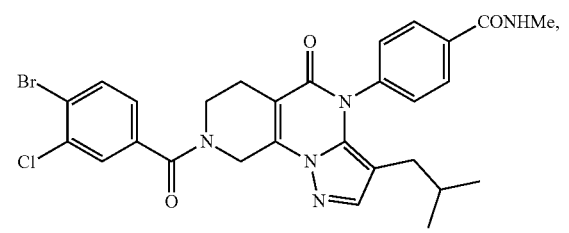
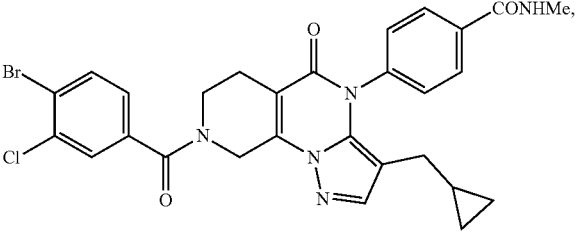
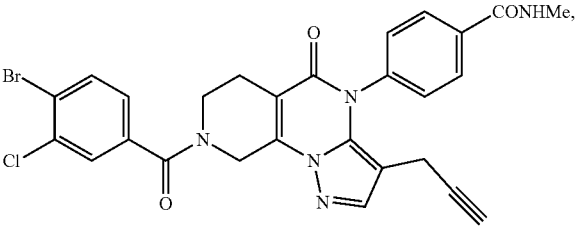
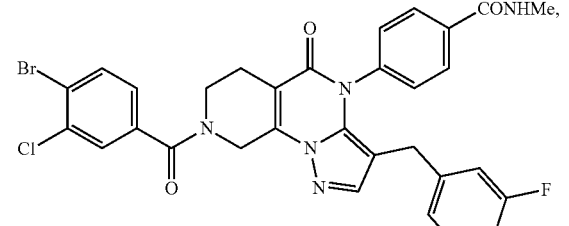
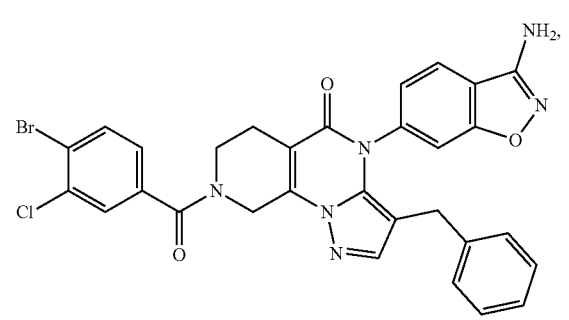
116
-continued
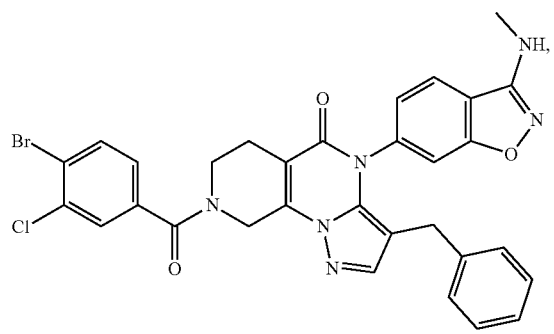
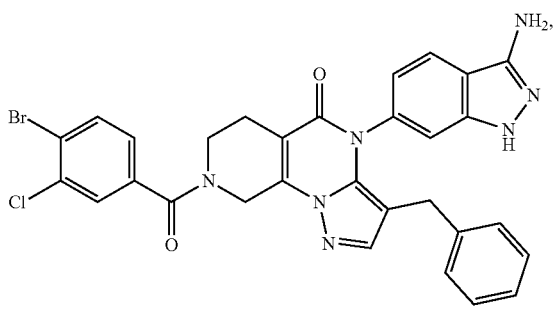
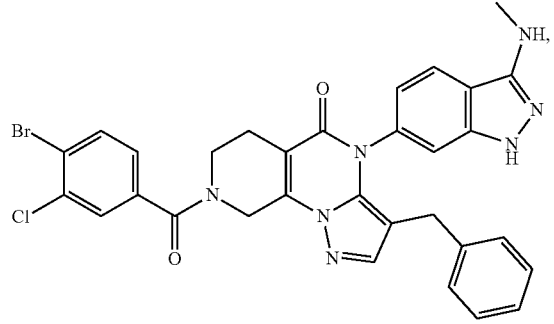
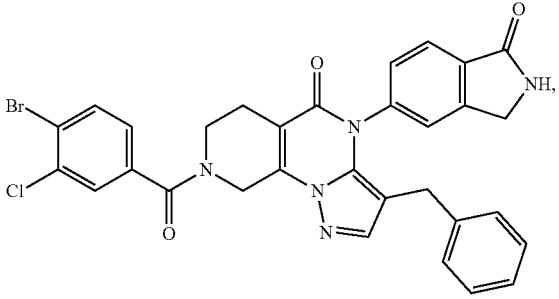
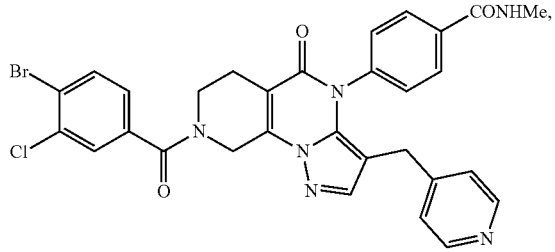

-continued

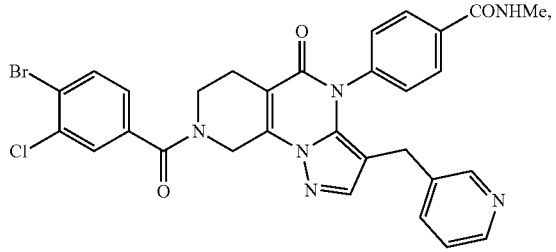

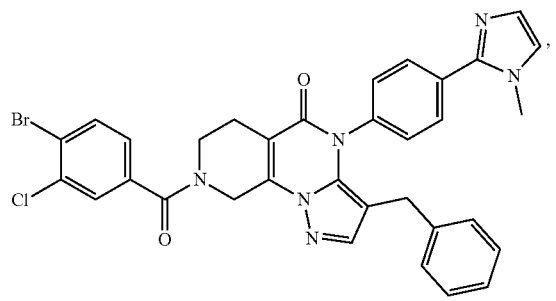

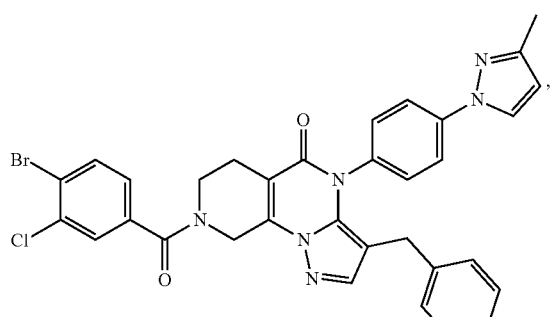

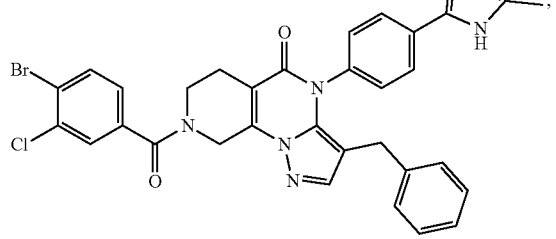

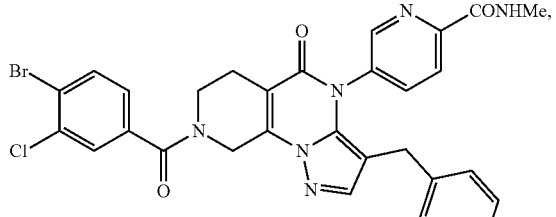

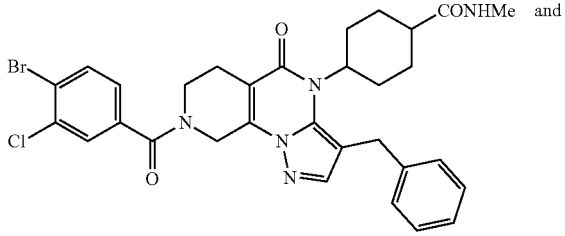 and

-continued

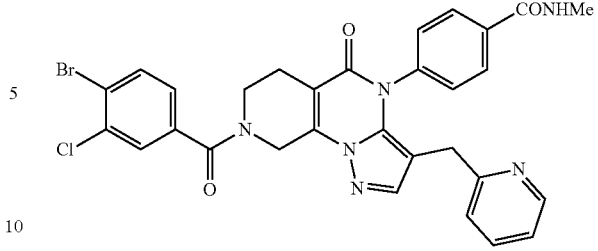

(including pharmaceutically acceptable salts of any of the foregoing).

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme I

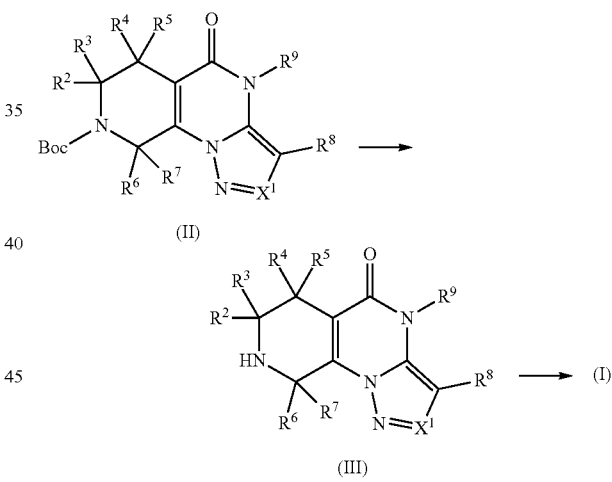

Compounds of Formula (I) can be prepared from a Boc intermediate of Formula (II). The Boc group can be cleaved using acidic conditions, for example, in presence of HCl in a suitable solvent (such as 1,4-dioxane) or in presence of cupper triflate. The coupling of an intermediate of Formula (III) with a suitable agent can afford a compound of Formula (I), including pharmaceutically acceptable salts thereof. As an example, compounds of Formula (I), along with pharmaceutically acceptable salts thereof, can be obtained by reacting a compound of Formula (III) with an acyl chloride of general formula $R^1$—C(═O)—Cl in the presence of a base in a suitable solvent. Other compounds of Formula (I), including pharmaceutically acceptable salts thereof, can be obtained by reacting a compound of Formula (III) with a carboxylic acid of formula $R^1$—C(═O)—OH in presence of an amide coupling agent (such as HATU or EDCI/HOBt) in a suitable solvent and in the presence of a suitable base.

Other compounds of Formula (I) together with pharmaceutically acceptable salts thereof can be prepared from a compound of Formula (III) using methods known in the art.

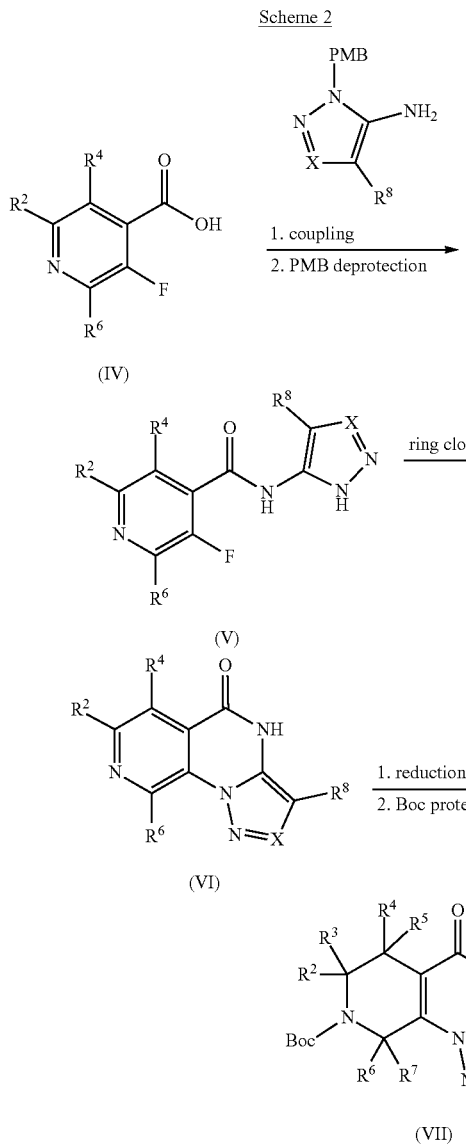

A compound of Formula (I), in which $R^2$, $R^4$ and $R^6$ are hydrogen, can be prepared from an intermediate of formula (VII) whose synthesis is depicted in Scheme 2. A carboxylic acid derivative of Formula (IV) can be coupled with a protected pyrazol-5-amine substituted with a $R^8$ group, using coupling procedures known in the art for the formation of amide bond to provide a compound of Formula (V). Examples of coupling procedures can use suitable coupling reagents (such as HATU), in the presence of a suitable base (for example, DIEA) in a suitable solvent (such as DMF), followed by the deprotection of the protecting PMB group under acidic conditions (such as TFA). Treatment of a compound of Formula (V) with a base (such as cesium carbonate) in a suitable solvent (such as DMF) can provide a cyclized compound of Formula (VI). Subsequently, a compound of Formula (VII) in which $R^2$, $R^4$ and $R^6$ are hydrogen, can be obtained by reduction of a compound of Formula (VI) using, for example, catalytic hydrogenation with Pd/C in EtOH, followed by the introduction of a Boc protecting group, using conditions known in the art (such as reaction with Boc$_2$O in presence of TEA in DCM). Alternatively, the reduction of the pyridyl moiety of a compound of Formula (VI) can be achieved in several steps. For example, a compound of Formula (VI) can be alkylated with 3,4-dimethoxy benzylbromide in a suitable solvent (such as acetonitrile) to afford a pyridinium intermediate that can be isolated, and then reduced with sodium triacetoxyborohydride in a suitable solvent (such as 1,2-dichloroethane). The dimethoxybenzyl group can be cleaved using procedures known to those skilled in the art. Exemplary procedures include using chloroethylchloroformate in a suitable solvent (such as 1,2-dichloroethane) followed by the treatment with methanol.

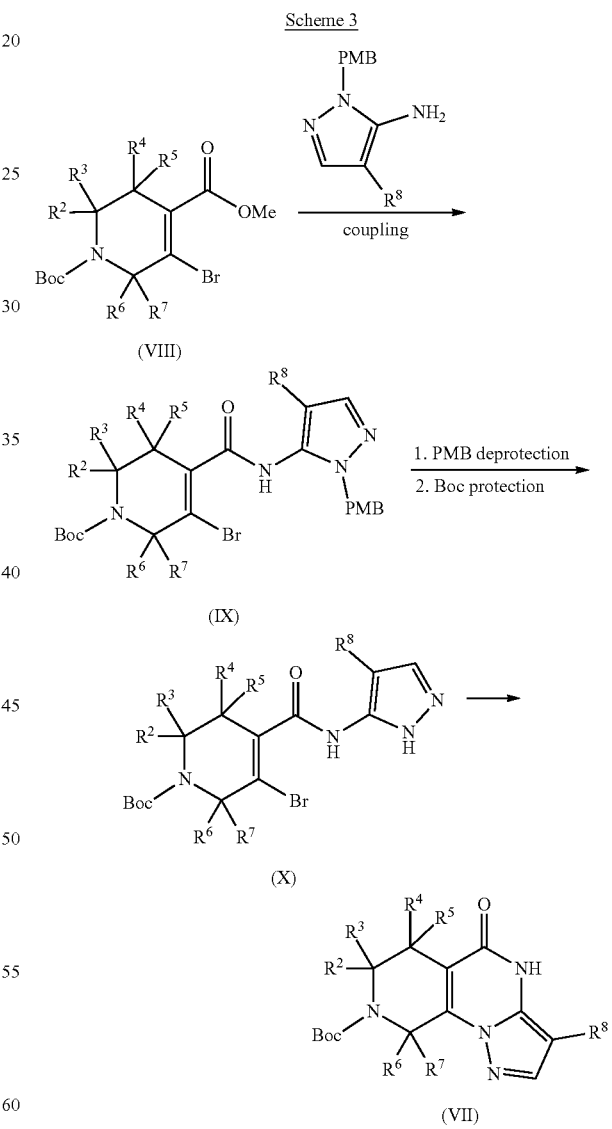

An intermediate of Formula (VII) can alternatively be prepared as depicted in Scheme 3. An ester of a compound of Formula (VIII) can be reacted with a protected pyrazol-5-amine substituted with a $R^8$ group in the presence of a base (such as LiHMDS) in a suitable solvent (such as THF) to obtain an amide of Formula (IX). Subsequent deprotection of the PMB group in acidic conditions (such as TFA) followed by treatment with Boc₂O in presence of a base (for example, Et₃N) in a solvent (for example, MeOH) can give a compound of Formula (X).

Cyclization of a compound of Formula (X) can be achieved by using methods known in the art. For example, a compound of Formula (X) can be reacted with a base (such as potassium carbonate) in presence of cupper in a suitable solvent (such as DMF) to afford a compound of Formula (VII).

Scheme 4

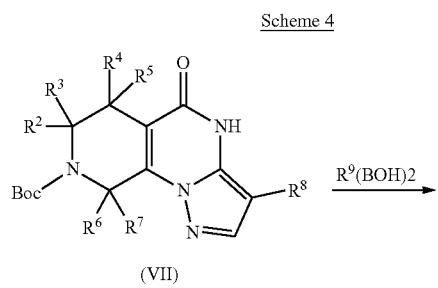

(VII)

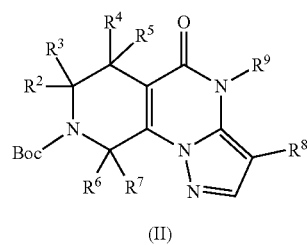

(II)

A compound of Formula (II) can be obtained from a compound of Formula (VII) as depicted in Scheme 4. Reaction of a compound of Formula (VII) with a compound of Formula R⁹B(OH)₂ in the presence of a copper-based agent, such as Cu(OTf)₂ or Cu(OAc)₂, and a base (such as pyridine or trimethylamine) in a solvent (for example, DMF or DCM) can provide a compound of Formula (II). Other conditions to substitute a lactam known in the art can also be used to introduce a R⁹ moiety. For example, a compound of Formula R⁹Br or R⁹Cl can react with a compound of Formula (VII), in the presence of a palladium catalyst (such as Pd₂(dba)₃), a ligand (such as XantPhos) and a base (for example, K₃PO₄) in a suitable solvent (such as dioxane).

Scheme 5

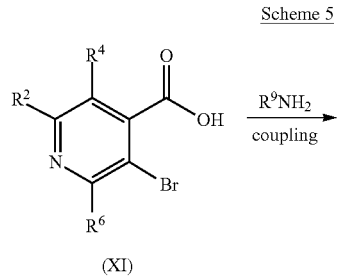

(XI)

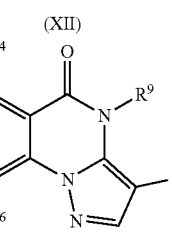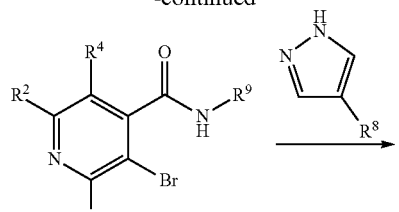

(XII)

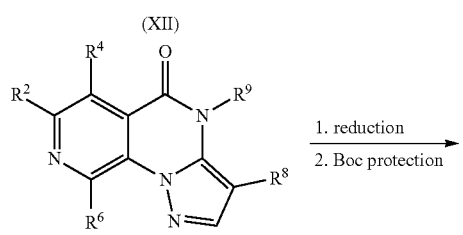

(XIII)

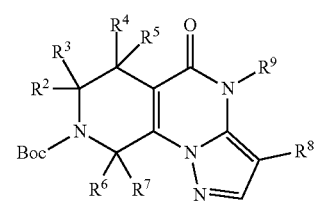

(II)

A compound of Formula (II) in which R², R⁴ and R⁶ are each H can be prepared from a pyridine-4-carboxylic acid derivative of Formula (XI) as shown in Scheme 5. An amine of general formula R⁹—NH₂, can be introduced on the acid of a compound of Formula (XI) using amide coupling reactions known to those skilled in the art. For example, EDC/HOBt in the presence of a base (such as diisopropylethylamine) in a suitable solvent (for example, DMF) to afford a compound of Formula (XII). The reaction of a compound of Formula (XII) with a pyrazole substituted by a R⁸ group, in presence of 1,10-phenanthroline, CuI and a base (such as sodium ethoxide) in a suitable solvent (such as DMF) in the presence of oxygen can give a compound of Formula (XIII). The reduction of the pyridyl moiety in a compound of Formula (XIII) by hydrogenation in the presence of a suitable catalyst, such as Pd/C, in a suitable solvent (such as methanol) followed by the introduction of a Boc protecting group, using conditions known in the art (for example, reaction with Boc₂O in presence of TEA in DCM) can provide a compound of Formula (II) in which R², R⁴ and R⁶ are each hydrogen.

Alternatively, the reduction of the pyridyl moiety of a compound of Formula (XIII) can be achieved in several steps. For example, a compound of Formula (XIII) can be alkylated with 3,4-dimethoxy benzylbromide in a suitable solvent (such as acetonitrile) to afford a pyridinium intermediate that can be isolated, and then reduced with sodium triacetoxyborohydride in a suitable solvent (such as 1,2-dichloroethane). The dimethoxybenzyl group can be cleaved using procedures known to those skilled in the art. Exemplary procedures include using chloroethylchloroformate in a suitable solvent (such as 1,2-dichloroethane) followed by a treatment with methanol.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction <$10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels including STOPS™ compounds), an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139, REP 2165 and those described in WO 2020/097342 and US 2020/0147124, which is hereby incorporated by reference for the purpose of the STOPS™ compounds provided therein, such as modified oligonucleotides identified as Nos. 1-392.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1

4-[5-benzyl-12-[4-bromo-3-(trifluoromethyl)benzoyl]-8-oxo-2,3,7,12-tetrazacyclo[7.4.0.0^2,6]trideca-1(9),3,5-trien-7-yl]-N-methyl-benzamide (4)

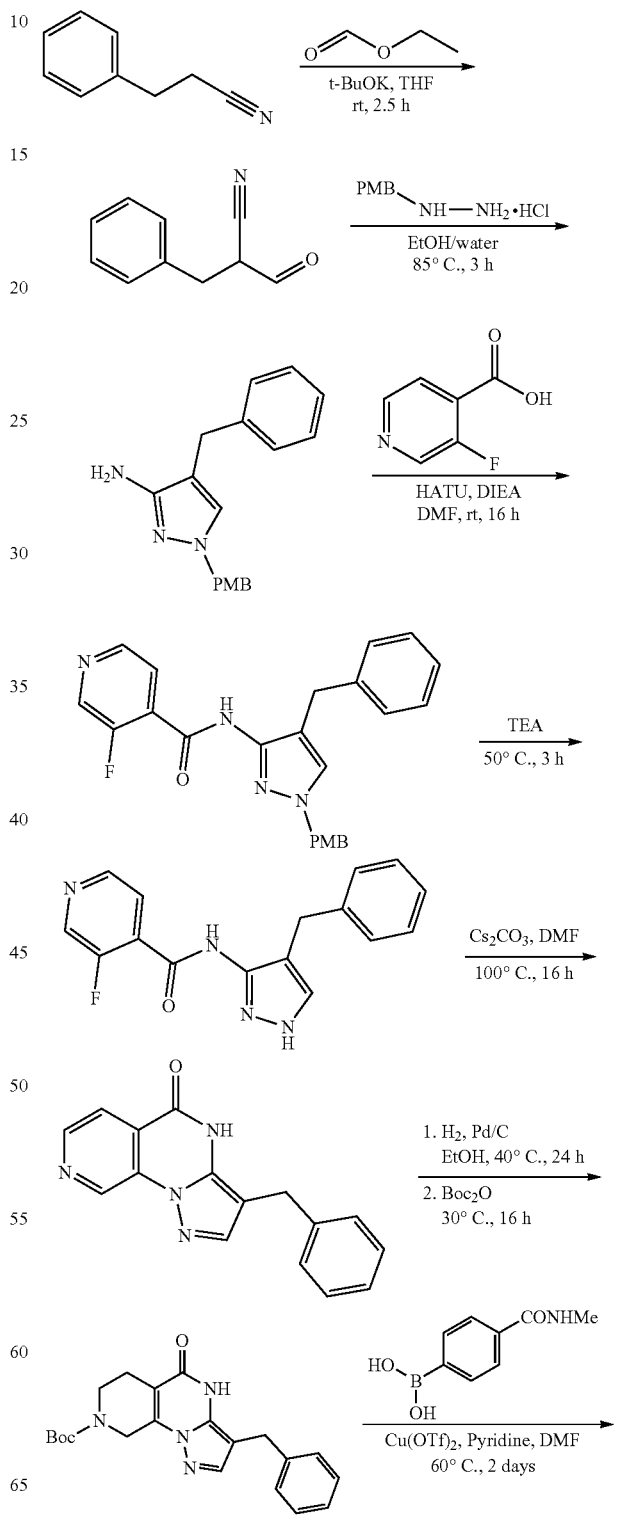

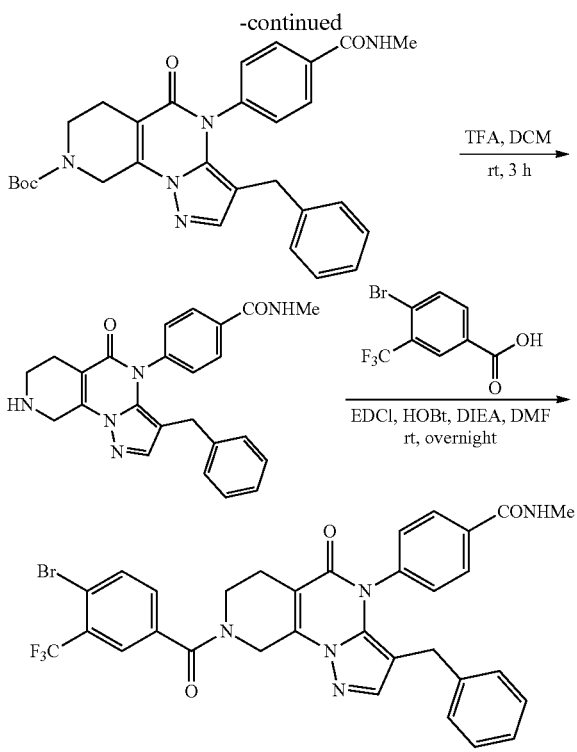

To a solution of 3-phenylpropanitrile (12.0 g, 91.5 mmol, 1.00 eq.) in anhydrous tetrahydrofuran (300 mL) was added potassium tert-butoxide (30.8 g, 274 mmol, 2.99 eq.) at 0° C. under N$_2$ atmosphere. The mixture was stirred for 15 mins at room temperature (rt). Ethyl formate (33.9 g, 457 mmol, 5.00 eq.) was added dropwise to above mixture at rt, and the mixture was stirred for 2.5 h at rt. The reaction was quenched with 1.0 M HCl (1200 mL) and extracted with ethyl acetate (3×1200 mL). The combined organic layers were washed with water (2×500 mL), dried over anhydrous sodium sulfate, filtered and concentrated under reduced pressure. The residue was purified by silica gel column chromatography and eluted with 0-20% ethyl acetate in petroleum ether to afford 2-benzyl-3-oxopropanenitrile (13.4 g, 92% yield) as yellow oil. LCMS (ESI, m/z): 158 [M−1]$^−$.

A mixture of 2-benzyl-3-oxopropanenitrile (3.20 g, 20.1 mmol, 1.00 eq.) and (4-methoxybenzyl)hydrazine hydrochloride (5.32 g, 28.2 mmol, 1.40 eq.) in ethanol (60 mL) and water (10 mL) was stirred for 3 h at 85° C. The mixture was concentrated under reduced pressure. The residue was purified by silica gel column chromatography and eluted with 0-100% ethyl acetate in petroleum ether to afford 4-benzyl-1-(4-methoxybenzyl)-1H-pyrazol-3-amine (2.80 g, 48% yield) as a yellow solid. LCMS (ESI, m/z): 294 [M+H]$^+$.

A mixture of 4-benzyl-1-(4-methoxybenzyl)-1H-pyrazol-3-amine (8.80 g, 30.0 mmol, 1.00 eq.), 3-fluoroisonicotinic acid (12.7 g, 90.0 mmol, 3.00 eq.), 2-(7-azabenzotriazol-1-yl)-N,N,N',N'-tetramethyluronium hexafluorophosphate (28.5 g, 75.0 mmol, 2.50 eq.) and N,N-diisopropylethylamine (19.4 g, 150 mmol, 5.00 eq.) in anhydrous N,N-dimethylformamide (100 mL) was stirred for 16 h at rt. The mixture was concentrated under reduced pressure. The residue was purified by silica gel column chromatography and eluted with 0 20% methanol in dichloromethane to afford N-(4-benzyl-1-(4-methoxybenzyl)-1H-pyrazol-3-yl)-3-fluoroisonicotinamide (11.3 g, 90% yield) as a light brown solid. LCMS (ESI, m/z): 417 [M+H]$^+$.

A suspension of N-(4-benzyl-1-(4-methoxybenzyl)-1H-pyrazol-3-yl)-3-fluoroisonicotinamide (11.3 g, 27.1 mmol, 1.00 eq.) in trifluoroacetic acid (140 mL) was stirred for 3 h at 50° C. The mixture was cooled to ambient temperature and concentrated under reduced pressure. The residue was triturated with diethyl ether and ethyl acetate (400 mL, v:v=3:1). The solids were collected by filtration, washed with hexane (100 mL) and dried to afford N-(4-benzyl-1H-pyrazol-3-yl)-3-fluoroisonicotinamide (7.10 g, 88% yield) as a yellow solid. LCMS (ESI, m/z): 297 [M+H]$^+$.

A mixture of N-(4-benzyl-1H-pyrazol-3-yl)-3-fluoroisonicotinamide (7.10 g, 24.0 mmol, 1.00 eq.) and cesium carbonate (28.2 g, 86.5 mmol, 3.60 eq.) in anhydrous N,N-dimethylformamide (150 mL) was stirred for 16 h at 100° C. The mixture was cooled to ambient temperature, and the solids were filtered off. The filter cake was washed with ethyl acetate (2×50 mL). The combined filtrate was concentrated under reduced pressure. The residue was purified by silica gel column chromatography and eluted with 0-20% methanol in dichloromethane to afford 3-benzylpyrazolo[1,5-a]pyrido[4,3-e]pyrimidin-5(4H)-one (5.99 g, 90% yield) as a light orange solid. LCMS (ESI, m/z): 277 [M+H]$^+$.

To a suspension of 3-benzylpyrazolo[1,5-a]pyrido[4,3-e]pyrimidin-5(4H)-one (5.99 g, 21.7 mmol, 1.00 eq.) in ethanol (500 mL) was added 10% palladium carbon (6.00 g). The mixture was stirred for 24 h at 40° C. under H$_2$ (3 atm). Di-tert butyl dicarbonate (9.47 g, 43.4 mmol, 2.00 eq.) was added to the mixture. The mixture was stirred for 16 h at 30° C. The solids were filtered off, and the filter cake was washed with methanol (3×100 mL). The combined filtrate was concentrated under reduced pressure. The residue was purified by silica gel column chromatography and eluted with 0-100% ethyl acetate in petroleum ether to afford tert-butyl 3-benzyl-5-oxo-5,6,7,9-tetrahydropyrazolo[1,5-a]pyrido[4,3-e]pyrimidine-8(4H)-carboxylate (2.55 g, 31% yield) as a light yellow solid. LCMS (ESI, m/z): 381 [M+H]$^+$.

A mixture of tert-butyl 5-benzyl-8-oxo-2,3,7,12-tetraazatricyclo[7.4.0.0^[2,6]]trideca-1(9),3,5-triene-12-carboxylate (600 mg, 1.58 mmol, 1.00 eq.), 4-(methylcarbamoyl)phenylboronic acid (423 mg, 2.37 mmol, 1.50 eq.), copper(II) trifluoromethanesulfonate (570 mg, 1.58 mmol, 1.00 eq.), pyridine (374 mg, 4.73 mmol, 3.00 eq.) and N,N-dimethylformamide (10 mL) was stirred for 2 days at 60° C. under oxygen atmosphere. The reaction was quenched with water (50 mL). The mixture was extracted with ethyl acetate (3×40 mL). The organic layers were combined, washed with brine (3×10 mL), dried over anhydrous sodium sulfate, filtered and concentrated under reduced pressure. The residue was purified by Prep-TLC (silica, petroleum ether:ethyl acetate=1:1) to afford tert-butyl 5-benzyl-7-[4-(methylcarbamoyl)phenyl]-8-oxo-2,3,7,12-tetraazatricyclo[7.4.0.0^[2,6]]trideca-1(9),3,5-triene-12-carboxylate (408 mg, 50% yield) as a light brown solid. LCMS (ESI, m/z): 514[M+H]$^+$.

A 100 mL round-bottom flask were charged with tert-butyl 5-benzyl-7-[4-(methylcarbamoyl)phenyl]-8-oxo-2,3,7,12-tetraazatricyclo[7.4.0.0^[2,6]]trideca-1 (9),3,5-triene-12-carboxylate (400 mg, 0.779 mmol, 1.00 eq.), trifluoroacetic acid (2 mL) and dichloromethane (10 mL) at rt. The mixture was stirred for 3 h at rt and then concentrated under reduced pressure to afford 4-[5-benzyl-8-oxo-2,3,7,12-tetraazatricyclo[7.4.0.0^[2,6]]trideca-1(9),3,5-trien-7-yl]-N-methylbenzamide (420 mg, crude) as a red oil. LCMS (ESI, m/z): 414 [M+H]$^+$.

A 40 mL round-bottom flask were charged with 4-[5-benzyl-8-oxo-2,3,7,12-tetraazatricyclo[7.4.0.0^[2,6]]trideca-1 (9),3,5-trien-7-yl]-N-methylbenzamide trifluoroacetic acid salt (140 mg, 0.339 mmol, 1.00 eq.), 4-bromo-3-(trifluoromethyl)benzoic acid (109 mg, 0.407 mmol, 1.20 eq.), N-(3-dimethylaminopropyl)-N'-ethylcarbodiimide (97.4 mg, 0.509 mmol, 1.50 eq.), 1-hydroxybenzotriazole (68.6 mg, 0.509 mmol, 1.50 eq.), N,N-diisopropylethylamine (131 mg, 1.02 mmol, 3.00 eq.) and N,N-dimethylformamide (2.00 mL) at rt. The mixture was stirred for overnight at rt. The reaction was quenched with water (10 mL), and the mixture was extracted with ethyl acetate (3×30 mL). The organic layers were combined, washed with brine (3×30 mL), dried over anhydrous sodium sulfate, filtered and concentrated under reduced pressure. The crude product was purified by Prep-HPLC with the following conditions: Column: XBridge Shield RP18 OBD Column, 30×150 mm, 5 μm; Mobile Phase A: water (10 mmol/L $NH_4HCO_3$+0.1% $NH_3 \cdot H_2O$), Mobile Phase B: ACN; Flow rate: 60 mL/min; Gradient: 39% B to 59% B in 7 min to afford 4-[5-benzyl-12-[4-bromo-3-(trifluoromethyl)benzoyl]-8-oxo-2,3,7,12-tetraazatricyclo[7.4.0.0^[2,6]]trideca-1(9),3,5-trien-7-yl]-N-methylbenzamide (83.8 mg, 37% yield) as a white solid. LCMS (ESI, m/z): 664 $[M+H]^+$. $^1H$ NMR (400 MHz, $CDCl_3$) δ 7.85-7.82 (m, 2H), 7.75-7.73 (m, 2H), 7.53-7.33 (m, 2H), 7.22 (d, J=4.2 Hz, 2H), 7.21-7.12 (m, 3H), 6.68 (s, 2H), 6.17 (d, J=2.4 Hz, 1H), 5.17-4.87 (m, 2H), 4.05-3.72 (m, 2H), 3.07-3.03 (m, 5H), 2.74 (s, 2H).

Example 2

5-benzyl-12-(4-bromo-3-chloro-benzoyl)-7-[4-(4-methyl-1,2,4-triazol-3-yl)phenyl]-2,3,7,12-tetrazatricyclo[7.4.0.0^2,6]trideca-1(9),3,5-trien-8-one (9)

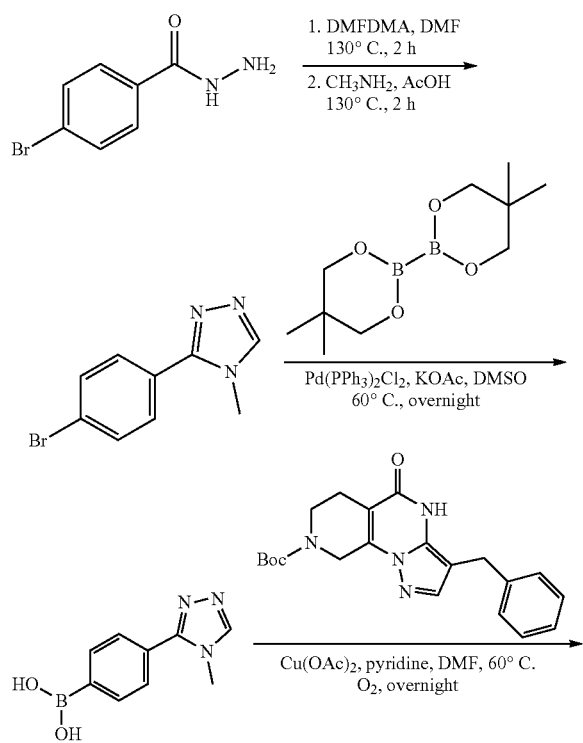

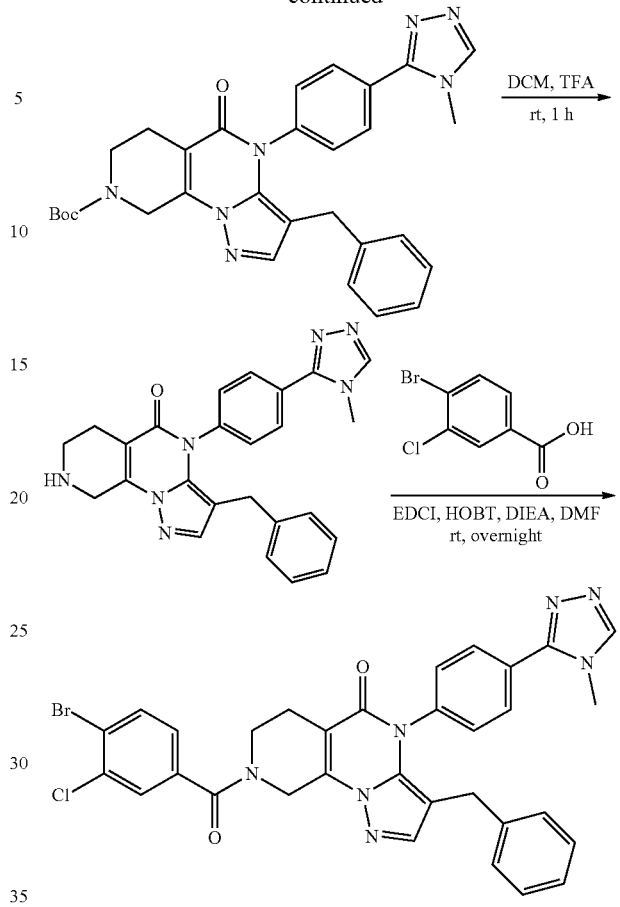

A mixture of 4-bromobenzohydrazide (2.00 g, 9.30 mmol, 1.00 eq.) and N,N-dimethylformamide dimethyl acetal (1.33 g, 11.2 mmol, 1.20 eq.) and N,N-dimethylformamide (2 mL) was heated in a microwave reactor at 130° C. for 2 h. The mixture was cooled to rt, methylamine (3.50 g, 37.2 mmol, 4.00 eq., 33% in water) was added followed by the addition of acetic acid (3.35 g, 55.8 mmol, 6.00 eq.). The mixture was heated in a microwave reactor at 130° C. for 2 h and diluted with water (50 mL). The pH value of the mixture was adjusted to >7 with NaOH (2 M aq.). The mixture was extracted with ethyl acetate (3×200 mL). The combined water layers were extracted with dichloromethane:methanol (10:1) (3×200 mL), dried over anhydrous sodium sulfate, filtered and concentrated under reduced pressure to afford 3-(4-bromophenyl)-4-methyl-1,2,4-triazole (2.42 g, crude) as a yellow solid. LCMS (ESI, m/z): 238 $[M+H]^+$.

A 100 mL round-bottom flask were charged with 3-(4-bromophenyl)-4-methyl-1,2,4-triazole (2.30 g, 9.66 mmol, 1.00 eq.), 2-(5,5-dimethyl-1,3,2-dioxaborinan-2-yl)-5,5-dimethyl-1,3,2-dioxaborinane (4.36 g, 19.3 mmol, 2.00 eq.), dichlorobis(triphenylphosphine)palladium (0.680 g, 0.966 mmol, 0.10 eq.), potassium acetate (2.84 g, 28.9 mmol, 3.00 eq.) and dimethyl sulfoxide (10 mL) at rt. The mixture was stirred for overnight at 60° C. under $N_2$ atmosphere, and the reaction quenched with water (50 mL). The mixture was extracted with ethyl acetate (3×300 mL). The organic layers were combined, washed with brine (3×100 mL), dried over anhydrous sodium sulfate, filtered and concentrated under reduced pressure. The residue was purified by silica gel column chromatography and eluted with dichloromethane:

methanol (10:1) to afford the crude product. The crude product was purified by Prep-HPLC with the following conditions: Column: XSelect CSH Fluoro Phenyl, 30 mm×150 mm, 5 μm; Mobile Phase A: Water (50 mmol/L TFA), Mobile Phase B: ACN; Flow rate: 60 mL/min; Gradient: 3% B to 15% B in 10 min to afford 4-(4-methyl-1,2,4-triazol-3-yl)phenylboronic acid (180 mg, 9% yield) as brown oil. LCMS (ESI, m/z): 204 [M+H]$^+$.

A 100 mL round-bottom flask were charged with tert-butyl 5-benzyl-8-oxo-2,3,7,12-tetraazatricyclo[7.4.0.0^{2,6}]trideca-1(9),3,5-triene-12-carboxylate (220 mg, 0.578 mmol, 1.00 eq.), 4-(4-methyl-1,2,4-triazol-3-yl)phenylboronic acid (176 mg, 0.867 mmol, 1.50 eq.), cupric acetate (105 mg, 0.578 mmol, 1.00 eq.), pyridine (137 mg, 1.73 mmol, 3.00 eq.) and N,N-dimethylformamide (10 mL) at rt. The mixture was stirred for overnight at 60° C. under oxygen atmosphere, and the reaction was quenched with water (50 mL). The mixture was extracted with ethyl acetate (3×100 mL). The organic layers were combined, washed with brine (3×100 mL), dried over anhydrous sodium sulfate, filtered and concentrated under reduced pressure. The residue was purified by Prep-TLC (silica, dichloromethane:methanol=10:1) to afford the crude product. The crude product was purified by Prep-HPLC with the following conditions: Column: XBridge Prep OBD C$_{18}$ Column, 30 mm×150 mm, 5 μm; Mobile Phase A: Water (50 mmol/L NH$_4$HCO$_3$), Mobile Phase B: ACN; Flow rate: 25 mL/min; Gradient: 40% B to 60% B in 9 min to afford tert-butyl 5-benzyl-7-[4-(4-methyl-1,2,4-triazol-3-yl)phenyl]-8-oxo-2,3,7,12-tetraazatricyclo[7.4.0.0^{2,6}]trideca-1(9),3,5-triene-12-carboxylate (30 mg, 10% yield) as an off-white solid. LCMS (ESI, m/z): 538 [M+H]$^+$.

A 20 mL vial were charged with tert-butyl 5-benzyl-7-[4-(4-methyl-1,2,4-triazol-3-yl)phenyl]-8-oxo-2,3,7,12-tetraazatricyclo[7.4.0.0^{2,6}]trideca-1(9),3,5-triene-12-carboxylate (30.0 mg, 0.0560 mmol, 1.00 eq.), trifluoroacetic acid (1 mL) and dichloromethane (5 mL) at rt. The mixture was stirred for 1 h at rt and concentrated under reduced pressure to afford 5-benzyl-7-[4-(4-methyl-1,2,4-triazol-3-yl)phenyl]-2,3,7,12-tetraazatricyclo[7.4.0.0^{2,6}]trideca-1(9),3,5-trien-8-one (24.0 mg, crude) as a light yellow solid. LCMS (ESI, m/z): 438 [M+H]$^+$.

A 40 mL vial were charged with 5-benzyl-7-[4-(4-methyl-1,2,4-triazol-3-yl)phenyl]-2,3,7,12-tetraazatricyclo[7.4.0.0^{2,6}]trideca-1(9),3,5-trien-8-one (24.0 mg, 0.0550 mmol, 1.00 eq.), 4-bromo-3-chlorobenzoic acid (16.8 mg, 0.0720 mmol, 1.30 eq.), 3-(3-dimethylaminopropyl)-1-ethylcarbodiimide hydrochloride (13.7 mg, 0.0720 mmol, 1.30 eq.), 1-hydroxybenzotriazole (9.64 mg, 0.0720 mmol, 1.30 eq.), N,N-diisopropylethylamine (42.5 mg, 0.330 mmol, 6.00 eq.) and N,N-dimethylformamide (5 mL) at rt. The mixture was stirred for overnight at rt and diluted with ethyl acetate (200 mL). The mixture was washed with water (3×20 mL), dried over anhydrous sodium sulfate, filtered and concentrated under reduced pressure. The residue was purified by Prep-TLC (silica, dichloromethane:methanol=10:1) to afford the crude product. The crude product was purified by Prep-HPLC with the following conditions: Column: Kinetex EVO prep C$_{18}$, 30×150 mm, 5 μm; Mobile Phase A: Water (50 mmol/L NH$_4$HCO$_3$), Mobile Phase B: ACN; Flow rate: 60 mL/min; Gradient: 34% B to 54% B in 7 min, to afford 5-benzyl-12-(4-bromo-3-chlorobenzoyl)-7-[4-(4-methyl-1,2,4-triazol-3-yl)phenyl]-2,3,7,12-tetraazatricyclo[7.4.0.0^{2,6}]trideca-1(9),3,5-trien-8-one (9.40 mg, 26% yield) as an off-white solid. LCMS (ESI, m/z): 654 [M+H]$^+$. $^1$H NMR (400 MHz, DMSO-d$_6$) δ 8.62 (s, 1H), 7.92 (d, J=7.4 Hz 1H), 7.78 (d, J=8.3 Hz 3H), 7.68 (s, 1H), 7.46 (s, 3H), 7.11 (s, 3H), 7.75 (s, 2H), 5.01 (s, 1H), 4.80 (s, 1H), 3.90 (s, 1H), 3.76 (s, 3H), 3.63 (s, 1H), 3.10 (s, 2H), 2.60-2.50 (s, 2H).

Example 3

4-[12-(4-bromo-3-chloro-benzoyl)-5-(cyclopentylmethyl)-8-oxo-2,3,7,12-tetrazatricyclo[7.4.0.0^2,6] trideca-1(9),3,5-trien-7-yl]-N-methyl-benzamide (11)

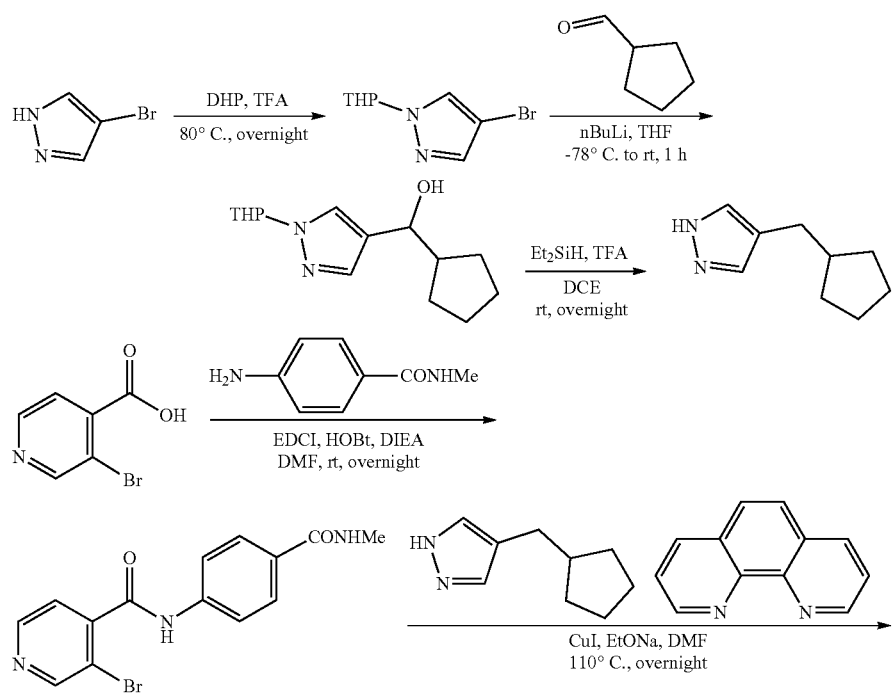

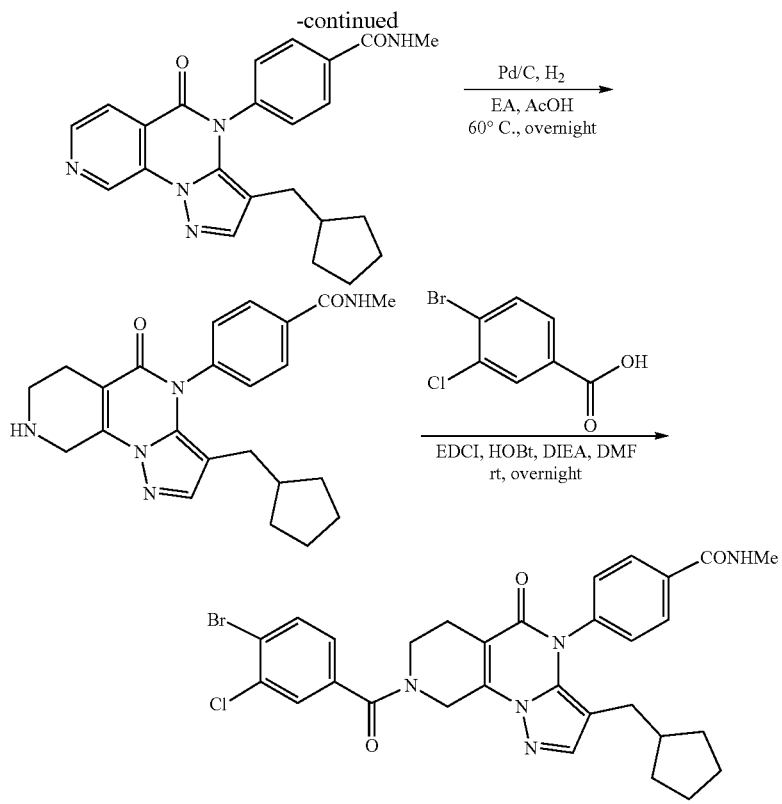

A mixture of 4-bromopyrazole (7.00 g, 47.6 mmol, 1.00 eq.), dihydropyran (6.01 g, 71.4 mmol, 1.50 eq.) and 2,2,2-trifluoroacetic acid (0.271 g, 2.38 mmol, 0.05 eq.) was stirred for overnight at 80° C. The mixture was diluted with ethyl acetate (200 mL), washed with sat. sodium bicarbonate (3×20 mL) and sat. sodium chloride (1×20 mL), dried over anhydrous sodium sulfate, filtered and concentrated under reduced pressure. The residue was purified by silica gel column chromatography and eluted with dichloromethane:petroleum ether (9:1) to afford 4-bromo-1-(oxan-2-yl)pyrazole (9.30 g, 84% yield) as light yellow oil. LCMS (ESI, m/z): 231 [M+H]+.

A mixture of 4-bromo-1-(oxan-2-yl) pyrazole (2.30 g, 9.95 mmol, 1.00 eq.) and tetrahydrofuran (30 mL) under $N_2$ was added n-butyllithium (7.96 mL, 19.9 mmol, 2.00 eq., 2.5 M in hexane) at −78° C. The mixture was stirred for 0.5 h at −78° C. and cyclopentane carboxaldehyde (1.95 g, 19.9 mmol, 2.00 eq.) in tetrahydrofuran (2 mL) was added at −78° C. The mixture was allowed to warm to rt and then stirred for 1 h at rt. The reaction was quenched with sat. ammonium chloride (100 mL aq.) at 0° C. and then extracted with ethyl acetate (3×100 mL). The combined organic layers were dried over anhydrous sodium sulfate, filtered and concentrated under reduced pressure. The residue was purified by silica gel column chromatography and eluted with petroleum ether:ethyl acetate (1:5) to afford cyclopentyl[1-(oxan-2-yl)pyrazol-4-yl]methanol (1.05 g, 42% yield) as yellow oil. LCMS (ESI, m/z): 251 [M+H]+.

A mixture of cyclopentyl[1-(oxan-2-yl) pyrazol-4-yl] methanol (1.00 g, 3.99 mmol, 1.00 eq.), triethylsilane (6.97 g, 59.9 mmol, 15.00 eq.), trifluoroacetic acid (13.6 g, 119 mmol, 30.00 eq.) and 1,2-dichloroethane (15 mL) was stirred overnight at rt under $N_2$ atmosphere. The mixture was diluted with ethyl acetate (80 mL) and washed with water (3×30 mL). The combined organic layers were dried over anhydrous sodium sulfate, filtered and concentrated under reduced pressure. The residue was purified by silica gel column chromatography and eluted with ethyl acetate:petroleum ether (5:1) to afford 4-(cyclopentylmethyl)-1H-pyrazole (0.809 g, crude) as an off-white solid. LCMS (ESI, m/z): 151 [M+H]+.

To a stirred mixture of 3-bromopyridine-4-carboxylic acid (20.0 g, 99.0 mmol, 1.00 eq.), N-(3-dimethylaminopropyl)-N'-ethylcarbodiimide hydrochloride (22.7 g, 118 mmol, 1.20 eq.) and 1-hydroxybenzotriazole (16.0 g, 118 mmol, 1.20 eq.) in N,N-dimethylformamide (300 mL) was added N,N-diisopropylethylamine (38.3 g, 297 mmol, 3.00 eq.) and 4-amino-N-methylbenzamide (14.8 g, 99.0 mmol, 1.00 eq.) in portions. The mixture was stirred for overnight at rt, and the reaction was quenched with water (1 L). The mixture was extracted with ethyl acetate (3×500 mL). The organic layers were combined, washed with brine (3×500 mL), dried over anhydrous sodium sulfate, filtered and concentrated under reduced pressure. The residue was triturated with ethyl acetate (20 mL). The solids were collected by filtration, washed with hexane (100 mL) and dried to afford 3-bromo-N-[4-(methylcarbamoyl)phenyl]pyridine-4-carboxamide (6.30 g, 19% yield) as an off-white solid. LCMS (ESI, m/z): 334 [M+H]+.

A mixture of 3-bromo-n-[4-(methylcarbamoyl)phenyl] pyridine-4-carboxamide (1.20 g, 3.59 mmol, 1.00 eq.), 4-(cyclopentylmethyl)-1H-pyrazole (593 mg, 3.95 mmol, 1.10 eq.), 1,10-phenanthroline (194 mg, 1.07 mmol, 0.30 eq.), cuprous iodide (205 mg, 1.07 mmol, 0.30 eq.), sodium ethoxide (1.22 g, 17.9 mmol, 5.00 eq.) and N,N-dimethylformamide (60 mL) was stirred for overnight at 110° C. under oxygen atmosphere. The mixture was diluted with ethyl acetate (120 mL) and washed with water (3×60 mL).

The organic layer was dried over anhydrous sodium sulfate, filtered and concentrated under reduced pressure. The residue was purified by silica gel column chromatography and eluted with petroleum ether:ethyl acetate (1:3) to afford 4-[5-(cyclopentylmethyl)-8-oxo-2,3,7,12-tetraazatricyclo[7.4.0.0^{2,6}]trideca-1(9),3,5,10,12-pentaen-7-yl]-N-methylbenzamide (525 mg, 36% yield) as a light yellow solid. LCMS (ESI, m/z): 402 [M+H]$^+$.

A mixture of 4-[5-(cyclopentylmethyl)-8-oxo-2,3,7,12-tetraazatricyclo[7.4.0.0^{2,6}]trideca-1(9),3,5,10,12-pentaen-7-yl]-N-methylbenzamide (475 mg, 1.18 mmol, 1.00 eq.), 10% Pd/C (100 mg), acetic acid (2 mL) and ethyl acetate (10 mL) was stirred for overnight at 60° C. under H$_2$ atmosphere (3 atm). The solids were filtered off, and the filtrate was diluted with water (20 mL). The pH value of the mixture was adjusted to 8-9 with sat. sodium carbonate (aq.). The mixture was extracted with ethyl acetate (3×50 mL). The combined organic layers were dried over anhydrous sodium sulfate, filtered and concentrated under reduced pressure to afford 4-[5-(cyclopentylmethyl)-8-oxo-2,3,7,12-tetraazatricyclo[7.4.0.0^{2,6}]trideca-1(9),3,5-trien-7-yl]-N-methylbenzamide (413 mg, crude) as a light yellow solid. LCMS (ESI, m/z): 406 [M+H]$^+$.

To a stirred mixture of 4-bromo-3-chlorobenzoic acid (104 mg, 0.444 mmol, 1.20 eq.), N-(3-dimethylaminopropyl)-N'-ethylcarbodiimide hydrochloride (85.1 mg, 0.444 mmol, 1.20 eq.) and 1-hydroxybenzotriazole (59.9 mg, 0.444 mmol, 1.20 eq.) in N,N-dimethylformamide (3 mL) was added 4-[5-(cyclopentylmethyl)-8-oxo-2,3,7,12-tetraazatricyclo[7.4.0.0^{2,6}]trideca-1(9),3,5-trien-7-yl]-N-methylbenzamide (150 mg, 0.370 mmol, 1.00 eq.) and N,N-diisopropylethylamine (143 mg, 1.11 mmol, 3.00 eq.). The mixture was stirred overnight at rt and purified by Prep-HPLC with the following conditions: Column: YMC-Actus Triart C$_{18}$, 30×150 mm, 5 μm; Mobile Phase A: Water (10 mmol/L NH$_4$HCO$_3$+0.1% NH$_3$·H$_2$O), Mobile Phase B: ACN; Flow rate: 60 mL/min; Gradient: 46% B to 76% B in 7 min) to afford 4-[12-(4-bromo-3-chlorobenzoyl)-5-(cyclopentylmethyl)-8-oxo-2,3,7,12-tetraazatricyclo[7.4.0.0^{2,6}]trideca-1(9),3,5-trien-7-yl]-N-methylbenzamide (101 mg, 43% yield) as a white solid. LCMS (ESI, m/z): 622 [M+H]$^+$. $^1$H NMR (300 MHz, DMSO-d$_6$) δ 7.94 (d, J=4.0 Hz, 2H), 7.73 (d, J=4.0 Hz, 1H), 7.53 (d, J=4.0 Hz, 2H), 7.41 (d, J=4.0 Hz, 2H), 7.25 (d, J=4.0 Hz, 1H), 6.23 (d, J=2.0 Hz, 1H), 5.13-4.84 (m, 2H), 4.01-3.72 (m, 2H), 3.07 (d, J=2.0 Hz, 3H), 2.73 (s, 2H), 1.58 (d, J=6.0 Hz, 3H), 1.41 (d, J=2.0 Hz, 6H), 0.80 (d, J=4.0 Hz, 2H).

Example 4

4-[5-(cyclopropylmethyl)-8-oxo-2,3,7,12-tetraazatricyclo[7.4.0.0^[2,6]]trideca-1 (9),3,5-trien-7-yl]-N-methylbenzamide

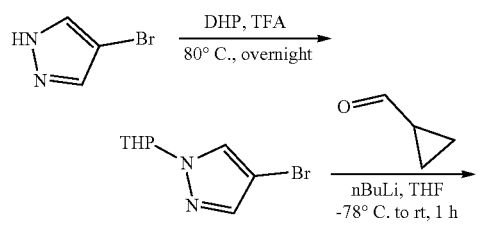

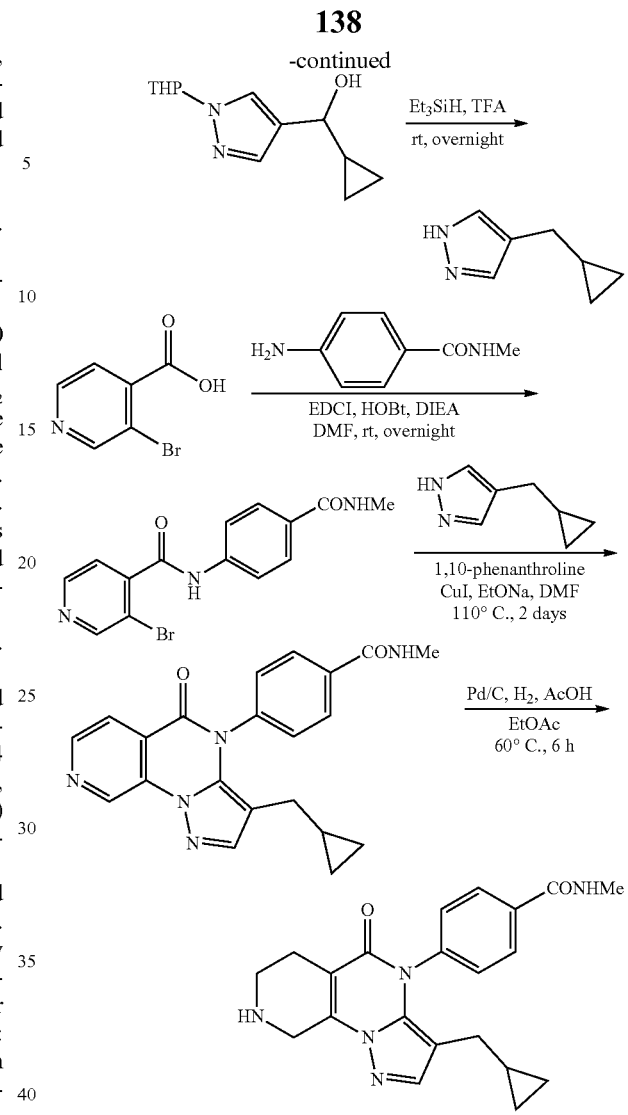

A mixture of 4-bromopyrazole (7.00 g, 47.6 mmol, 1.00 eq.), dihydropyran (6.01 g, 71.4 mmol, 1.50 eq.) and 2,2,2-trifluoroacetic acid (0.271 g, 2.38 mmol, 0.05 eq.) was stirred for overnight at 80° C. The mixture was diluted with ethyl acetate (200 mL) and washed with sat. sodium bicarbonate (3×20 mL) and sat. sodium chloride (1×20 mL), dried over anhydrous sodium sulfate, filtered and concentrated under reduced pressure. The residue was purified by silica gel column chromatography and eluted with dichloromethane:petroleum ether (9:1) to afford 4-bromo-1-(oxan-2-yl)pyrazole (9.30 g, 84% yield) as light yellow oil. LCMS (ESI, m/z): 231 [M+H]$^+$.

A mixture of 4-bromo-1-(oxan-2-yl)pyrazole (1.00 g, 4.33 mmol, 1.00 eq.) and tetrahydrofuran (5 mL) under N$_2$ was added n-butyllithium (3.46 mL, 8.66 mmol, 2.00 eq., 2.5 M in hexane) at −78° C. The mixture was stirred for 30 min at −78° C. under N$_2$ atmosphere. Cyclopropanecarbaldehyde (0.606 g, 8.66 mmol, 2.00 eq.) in tetrahydrofuran (0.5 mL) was added at −78° C. The mixture was allowed to warm to rt, and the mixture was stirred for 1 h at rt under N$_2$ atmosphere. The reaction was quenched with sat. ammonium chloride (30 mL aq.) at 0° C. and then extracted with ethyl acetate (3×100 mL). The combined organic layers were dried over anhydrous sodium sulfate, filtered and concentrated under reduced pressure. The residue was purified by silica gel column chromatography and eluted with petroleum ether:ethyl acetate (1:1) to afford cyclopropyl[1-(oxan-2-yl)pyrazol-4-yl]methanol (670 mg, 70% yield) as colorless oil. LCMS (ESI, m/z): 223 [M+H]$^+$.

A mixture of cyclopropyl[1-(oxan-2-yl)pyrazol-4-yl] methanol (400 mg, 1.80 mmol, 1.00 eq.), 1,2-dichloroethane (50 mL), triethylsilane (314 mg, 27.0 mmol, 15.0 eq.) and 2,2,2-trifluoroacetic acid (6.15 g, 54.0 mmol, 30.0 eq.) was stirred overnight at rt. The mixture was concentrated under reduced pressure, and the pH value of the mixture was adjusted to 8-9 with sat. sodium bicarbonate (aq.). The mixture was extracted with dichloromethane (3×80 mL). The combined organic layers were dried over anhydrous sodium sulfate, filtered and concentrated under reduced pressure. The residue was purified by silica gel column chromatography and eluted with petroleum ether:ethyl acetate (1:1) to afford 4-(cyclopropylmethyl)-1H-pyrazole (150 mg, 68% yield) as colorless oil. LCMS (ESI, m/z): 123 [M+H]$^+$.

To a stirred mixture of 3-bromopyridine-4-carboxylic acid (20.0 g, 99.0 mmol, 1.00 eq.), N-(3-dimethylaminopropyl)-N'-ethylcarbodiimide hydrochloride (22.7 g, 118 mmol, 1.20 eq.) and 1-hydroxybenzotriazole (16.0 g, 118 mmol, 1.20 eq.) in N,N-dimethylformamide (300 mL) was added N,N-diisopropylethylamine (38.3 g, 297 mmol, 3.00 eq.) and 4-amino-n-methylbenzamide (14.8 g, 99.0 mmol, 1.00 eq.) in portions. The mixture was stirred for overnight at rt, and the reaction was quenched with water (1 L). The mixture was extracted with ethyl acetate (3×500 mL). The organic layers were combined, washed with brine (3×500 mL), dried over anhydrous sodium sulfate, filtered and concentrated under reduced pressure. The residue was triturated with ethyl acetate (20 mL) and the solids were collected by filtration, washed with hexane (100 mL) and dried to afford 3-bromo-N-[4-(methylcarbamoyl)phenyl]pyridine-4-carboxamide (6.30 g, 19% yield) as an off-white solid. LCMS (ESI, m/z): 334 [M+H]$^+$.

A mixture of 3-bromo-N-[4-(methylcarbamoyl)phenyl] pyridine-4-carboxamide (300 mg, 0.898 mmol, 1.00 eq.), 4-(cyclopropylmethyl)-1H-pyrazole (142 mg, 1.17 mmol, 1.30 eq.), cuprous iodide (51.3 mg, 0.269 mmol, 0.30 eq.), 1,10-phenanthroline (48.5 mg, 0.269 mmol, 0.30 eq.), sodium ethoxide (183 mg, 2.69 mmol, 3.00 eq.) and N,N-dimethylformamide (5 mL) was stirred for 2 days at 110° C. under oxygen atmosphere. The mixture was diluted with ethyl acetate (200 mL), washed with water (3×20 mL) and sat. sodium chloride (1×20 mL), dried over anhydrous sodium sulfate, filtered and concentrated under reduced pressure. The residue was purified by silica gel column chromatography and eluted with petroleum ether:ethyl acetate (1:3) to afford 4-[5-(cyclopropylmethyl)-8-oxo-2,3,7,12-tetraazatricyclo[7.4.0.0ˆ[2,6]]trideca-1 (9),3,5,10,12-pentaen-7-yl]-N-methylbenzamide (50.0 mg, 15% yield) as a grey solid. LCMS (ESI, m/z): 374 [M+H]$^+$.

A mixture of 4-[5-(cyclopropylmethyl)-8-oxo-2,3,7,12-tetraazatricyclo[7.4.0.0ˆ[2,6]]trideca-1(9),3,5,10,12-pentaen-7-yl]-N-methylbenzamide (40.0 mg, 0.107 mmol, 1.00 eq.), ethyl acetate (5 mL), acetic acid (0.6 mL) and 10% Pd/C (5.00 mg) was stirred for 6 h at 60° C. under H$_2$ atmosphere (3 atm). The solids were filtered off, and the filtrate was diluted with water (20 mL). The pH value of the mixture was adjusted to 8-9 with sat. sodium carbonate (aq.). The mixture was extracted with ethyl acetate (3×50 mL). The combined organic layers were dried over anhydrous sodium sulfate, filtered and concentrated under reduced pressure to afford 4-[5-(cyclopropylmethyl)-8-oxo-2,3,7,12-tetraazatricyclo[7.4.0.0ˆ[2,6]]trideca-1(9),3,5-trien-7-yl]-N-methylbenzamide (40 mg, crude) as a light yellow solid. LCMS (ESI, m/z): 378 [M+H]$^+$.

Example 5 tert-butyl 5-oxo-3-(pyridin-3-ylmethyl)-5,6,7,9-tetrahydropyrazolo[1,5-a]pyrido[4,3-e]pyrimidine-8 (4H)-carboxylate

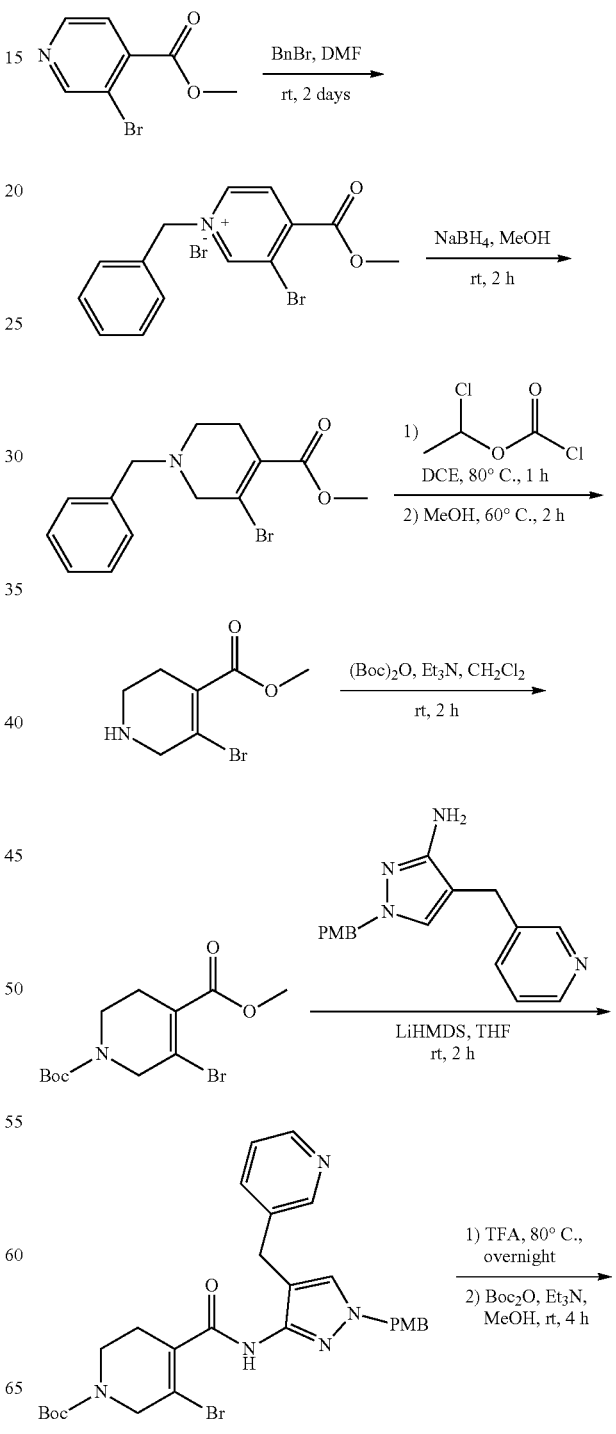

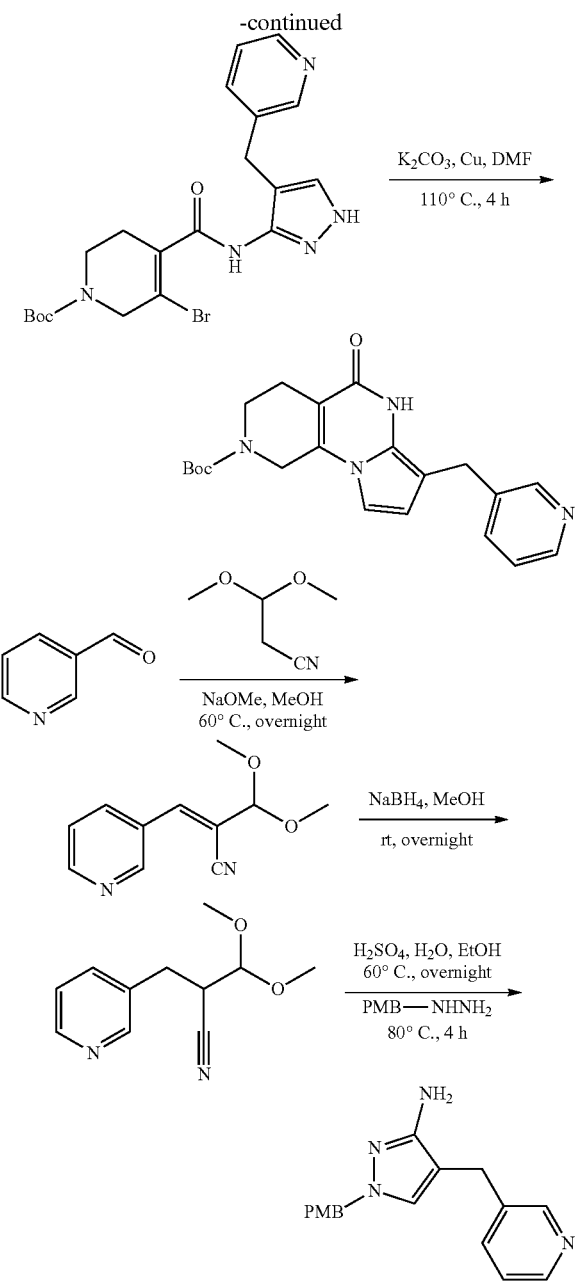

A mixture of methyl 3-bromopyridine-4-carboxylate (7.00 g, 32.4 mmol, 1.00 eq.), benzyl bromide (5.54 g, 32.4 mmol, 1.00 eq.) and N,N-dimethylformamide (100 mL) was stirred for 2 days at rt. The mixture was diluted with ethyl acetate (100 mL) and washed with water (3×200 mL). The combined organic layers were dried over anhydrous sodium sulfate, filtered and concentrated under reduced pressure to provide 1-benzyl-3-bromo-4-(methoxycarbonyl)pyridin-1-ium bromide (13.0 g, crude) as light yellow oil. LCMS (ESI, m/z): 306 [M−Br]$^+$. The product was used in the next step directly without further purification.

A mixture of 7-tert-butyl 1-benzyl-3-bromo-4-(methoxycarbonyl)pyridin-1-ium bromide (9.00 g, 23.2 mmol, 1.00 eq.), sodium borohydride (4.43 g, 117 mmol, 5.04 eq.) and methanol (150 mL) was stirred for 2 h at rt, and then concentrated under reduced pressure. The mixture was diluted with ethyl acetate (100 mL) and washed with water (3×100 mL). The combined organic layers were dried over anhydrous sodium sulfate, filtered and concentrated under reduced pressure. The residue was purified by silica gel column chromatography and eluted with ethyl acetate:petroleum ether (4:1) to afford methyl 1-benzyl-3-bromo-5,6-dihydro-2H-pyridine-4-carboxylate (5.80 g, 80% yield) as light yellow oil. LCMS (ESI, m/z): 310 [M+H]$^+$.

A mixture of methyl 1-benzyl-3-bromo-5,6-dihydro-2H-pyridine-4-carboxylate (5.80 g, 18.7 mmol, 1.00 eq.), 1-chloroethyl carbonochloridate (2.67 g, 18.7 mmol, 1.00 eq.) and 1,2-dichloroethane (200 mL) was stirred for 1 h at 80° C. and then concentrated under reduced pressure. Methanol (100 mL) was added. The resulting solution was stirred for an additional 1 h at 60° C. and concentrated under reduced pressure. The residue was purified by silica gel column chromatography and eluted with dichloromethane:methanol (10:1) to afford methyl 3-bromo-1,2,5,6-tetrahydropyridine-4-carboxylate (4.90 g, crude) as light yellow oil. LCMS (ESI, m/z): 220 [M+H]$^+$.

A mixture of methyl 3-bromo-1,2,5,6-tetrahydropyridine-4-carboxylate (4.90 g, 22.2 mmol, 1.00 eq.), di-tert-butyl dicarbonate (7.29 g, 33.4 mmol, 1.50 eq.), triethylamine (9.01 g, 89.1 mmol, 4.00 eq.), dichloromethane (100 mL) was stirred for 2 h at rt, and then concentrated under reduced pressure. The residue was diluted with ethyl acetate (100 mL) and washed with water (3×100 mL). The combined organic layers were dried over anhydrous sodium sulfate, filtered and concentrated under reduced pressure. The residue was purified by silica gel column chromatography and eluted with ethyl acetate:petroleum ether (1:5) to afford 1-tert-butyl 4-methyl 3-bromo-5,6-dihydro-2H-pyridine-1,4-dicarboxylate (3.70 g, 52% yield) as light yellow oil. LCMS (ESI, m/z): 320 [M+H]$^+$.

A mixture of 3-pyridinecarboxaldehyde (5.00 g, 46.7 mmol, 1.00 eq.), 3,3-dimethoxypropanenitrile (5.37 g, 46.6 mmol, 1.00 eq.), sodium methanolate (5.04 g, 93.4 mmol, 2.00 eq.) and methanol (150 mL) was stirred overnight at 60° C., and then concentrated under reduced pressure. The residue was diluted with ethyl acetate (100 mL) and washed with water (3×100 mL). The combined organic layers were dried over anhydrous sodium sulfate, filtered and concentrated under reduced pressure. The residue was purified by silica gel column chromatography and eluted with ethyl acetate:petroleum ether (4:1) to afford (2E)-2-(dimethoxymethyl)-3-(pyridin-3-yl)prop-2-enenitrile (4.00 g, 42% yield) as light yellow oil. LCMS (ESI, m/z): 205 [M+H]$^+$.

A mixture of (2E)-2-(dimethoxymethyl)-3-(pyridin-3-yl)prop-2-enenitrile (4.00 g, 19.6 mmol, 1.00 eq.), sodium borohydride (7.41 g, 196 mmol, 10.00 eq.) and methanol (200 mL) was stirred overnight at rt, and then concentrated under reduced pressure. The residue was diluted with ethyl acetate (100 mL) and washed with water (3×100 mL). The combined organic layers were dried over anhydrous sodium sulfate, filtered and concentrated under reduced pressure. The residue was purified by silica gel column chromatography and eluted with ethyl acetate:petroleum ether (4:1) to afford 2-(dimethoxymethyl)-3-(pyridin-3-yl)propanenitrile (2.40 g, 59% yield) as light yellow oil. LCMS (ESI, m/z): 207 [M+H]$^+$.

A mixture of 2-(dimethoxymethyl)-3-(pyridin-3-yl)propanenitrile (2.00 g, 9.70 mmol, 1.00 eq.), ethanol (8 mL), water (8 mL) and sulfuric acid (1.90 g, 19.4 mmol, 2.00 eq.) was stirred overnight at 60° C. [(4-methoxyphenyl)methyl] hydrazine (1.48 g, 9.69 mmol, 1.00 eq.) was added. The resulting solution was stirred for an additional 4 h at 80° C., and the reaction quenched with water (50 mL). The pH value of the mixture was adjusted to 6-7 with sat. sodium bicarbonate. The mixture was extracted with ethyl acetate (3×100 mL). The combined organic layers were washed with water (2×50 mL), dried over anhydrous sodium sulfate, filtered and concentrated under reduced pressure. The crude product was purified by reverse flash chromatography with the following gradient conditions: column, $C_{18}$; mobile phase, ACN in water, 5% to 20% gradient in 20 min; detector, 254 nm to afford 1-[(4-methoxyphenyl)methyl]-4-(pyridin-3-ylmethyl)pyrazol-3-amine (1.10 g, 38% yield) as light yellow oil. LCMS (ESI, m/z): 295 [M+H]$^+$.

A mixture 1-tert-butyl 4-methyl 3-bromo-5,6-dihydro-2H-pyridine-1,4-dicarboxylate (543 mg, 1.69 mmol, 1.00 eq.), 1-[(4-methoxyphenyl)methyl]-4-(pyridin-3-ylmethyl)pyrazol-3-amine (500 mg, 1.69 mmol, 1.00 eq.), tetrahydrofuran (10 mL) and lithium bis(trimethylsilyl)amide (2.0 mL, 2.00 mmol, 1.18 eq., 1 M in tetrahydrofuran) was stirred for 2 h at rt, and the reaction quenched by water (20 mL). The solution was extracted with ethyl acetate (100 mL). The organic layers were combined, washed with water (3×100 mL), dried over anhydrous sodium sulfate, filtered and concentrated under reduced pressure. The residue was purified by silica gel column chromatography and eluted with ethyl acetate to afford tert-butyl 3-bromo-4-({1-[(4-methoxyphenyl)methyl]-4-(pyridin-3-ylmethyl)pyrazol-3-yl}carbamoyl)-5,6-dihydro-2H-pyridine-1-carboxylate (200 mg, 20% yield) as a light yellow solid. LCMS (ESI, m/z): 582 [M+H]$^+$.

A mixture tert-butyl 3-bromo-4-({1-[(4-methoxyphenyl)methyl]-4-(pyridin-3-ylmethyl)pyrazol-3-yl}carbamoyl)-5,6-dihydro-2H-pyridine-1-carboxylate (200 mg, 0.343 mmol, 1.00 eq.) and trifluoroacetic acid (3 mL) was stirred for overnight at 80° C., and then concentrated under reduced pressure. Triethylamine (174 mg, 1.72 mmol, 5.00 eq.), methanol (10 mL) and di-tert-butyl dicarbonate (150 mg, 0.687 mmol, 2.00 eq.) was added. The resulting solution was stirred for an additional 4 h at rt and then concentrated under reduced pressure. The residue was purified by silica gel column chromatography and eluted with ethyl acetate to afford tert-butyl 3-bromo-4-{[4-(pyridin-3-ylmethyl)-1H-pyrazol-3-yl]carbamoyl}-5,6-dihydro-2H-pyridine-1-carboxylate (120 mg, 75% yield) as a light yellow solid. LCMS (ESI, m/z): 462 [M+H]$^+$.

A mixture tert-butyl 3-bromo-4-{[4-(pyridin-3-ylmethyl)-1H-pyrazol-3-yl]carbamoyl}-5,6-dihydro-2H-pyridine-1-carboxylate (120 mg, 0.260 mmol, 1.00 eq.), copper powder (82.5 mg, 1.30 mmol, 5.00 eq.), potassium carbonate (108 mg, 0.779 mmol, 3.00 eq.) and N,N-dimethylformamide (8 mL) was stirred for 4 h at 110° C. The solution was diluted with ethyl acetate (100 mL) and washed with water (3×100 mL). The combined organic layers were dried over anhydrous sodium sulfate, filtered and concentrated under reduced pressure. The residue was purified by silica gel column chromatography and eluted with ethyl acetate to afford tert-butyl 5-oxo-3-(pyridin-3-ylmethyl)-5,6,7,9-tetrahydropyrazolo[1,5-a]pyrido[4,3-e]pyrimidine-8(4H)-carboxylate (5.0 mg, 5% yield) as a light yellow solid. LCMS (ESI, m/z): 382 [M+H]$^+$.

Example 6

5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1)

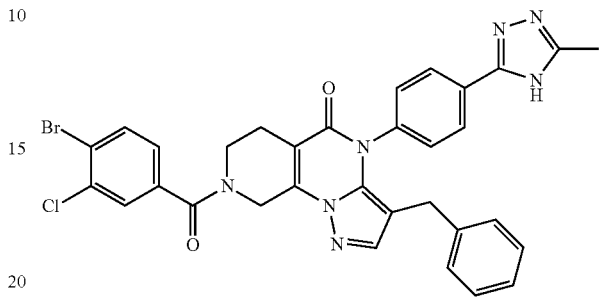

The title compound was obtained following a similar procedure reported for the synthesis of 4-[5-benzyl-12-[4-bromo-3-(trifluoromethyl)benzoyl]-8-oxo-2,3,7,12-tetrazatricyclo[7.4.0.0^2,6]trideca-1(9),3,5-trien-7-yl]-N-methyl-benzamide (4), using (4-(4-(4-methoxybenzyl)-5-methyl-4H-1,2,4-triazol-3-yl)phenyl)boronic acid in place of 4-(methylcarbamoyl)phenylboronic acid in step 7, and 4-bromo-3-chlorobenzoic acid in place of 4-bromo-3-(trifluoromethyl)benzoic acid in the last step. LCMS (ESI, m/z): 656.05 [M+H]$^+$ Br pattern. $^1$H NMR (300 MHz, CDCl$_3$) δ 11.5 (br, 1H), 8.04 (d, J=8.4 Hz, 2H), 7.75 (d, J=8.2 Hz, 1H), 7.69-7.62 (m, 1H), 7.46 (s, 1H), 7.31 (s, 1H), 7.28-7.21 (m, 2H), 7.17-7.06 (m, 3H), 6.72 (s, 2H), 5.42-4.69 (m, 2H), 4.32-3.45 (m, 2H), 3.10 (s, 2H), 2.79 (s, 2H), 2.47 (s, 3H).

Example 7

4-[5-benzyl-12-(4-bromo-3-methyl-benzoyl)-8-oxo-2,3,7,12-tetrazatricyclo[7.4.0.0"2,6]trideca-1(9),3,5-trien-7-yl]-N-methyl-benzamide (2)

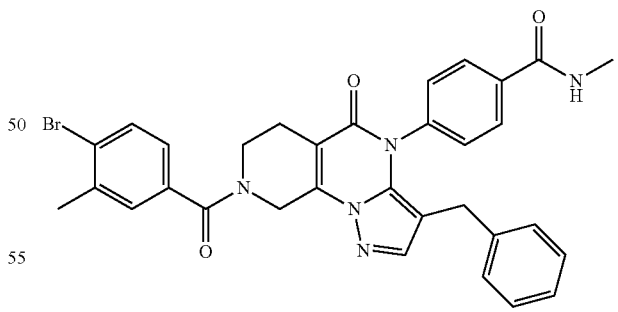

The title compound was obtained following a similar procedure reported for the synthesis of 4-[5-benzyl-12-[4-bromo-3-(trifluoromethyl)benzoyl]-8-oxo-2,3,7,12-tetrazatricyclo[7.4.0.0^2,6]trideca-1(9),3,5-trien-7-yl]-N-methyl-benzamide (4), using 4-bromo-3-methylbenzoic acid in place of 4-bromo-3-(trifluoromethyl)benzoic acid in the last step. LCMS (ESI, m/z): 612.1 [M+H]$^+$ Br pattern. $^1$H NMR (400 MHz, CDCl$_3$) δ 7.75-7.73 (m, 2H), 7.62 (d, J=8.12 Hz, 1H), 7.52-7.38 (m, 2H), 7.25 (d, J=12.56 Hz, 2H), 7.21-7.12

(m, 4H), 6.68 (s, 2H), 6.17 (d, J=2.4 Hz, 1H), 5.15-4.90 (m, 2H), 4.08-3.73 (m, 2H), 3.07-3.03 (m, 5H) 2.71 (s, 2H), 2.44 (s, 3H).

Example 8

4-[5-benzyl-12-[4-bromo-3-(difluoromethyl)benzoyl]-8-oxo-2,3,7,12-tetrazatricyclo[7.4.0.0^2,6]trideca-1(9),3,5-trien-7-yl]-N-methyl-benzamide (3)

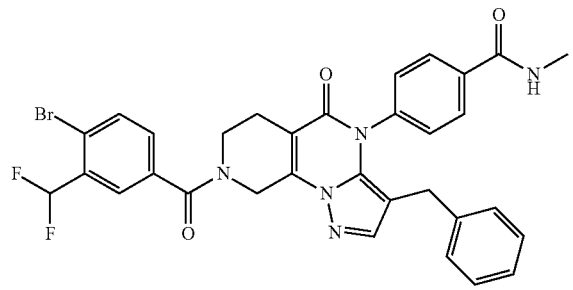 [SMILES: CNC(=O)c1ccc(-n2c(=O)c3c(n4ncc(Cc5ccccc5)c24)CN(C(=O)c2ccc(Br)c(C(F)F)c2)CC3)cc1]

The title compound was obtained following a similar procedure reported for the synthesis of 4-[5-benzyl-12-[4-bromo-3-(trifluoromethyl)benzoyl]-8-oxo-2,3,7,12-tetrazatricyclo[7.4.0.0^2,6]trideca-1(9),3,5-trien-7-yl]-N-methyl-benzamide (4), using 4-bromo-3-difluoromethylbenzoic acid in place of 4-bromo-3-(trifluoromethyl)benzoic acid in the last step. LCMS (ESI, m/z): 648.05 [M+H]$^+$ Br pattern. $^1$H NMR (400 MHz, CDCl$_3$) δ 7.81 (s, 1H), 7.75-7.72 (m, 3H), 7.55-7.47 (m, 2H), 7.37-7.21 (m, 2H), 7.21-7.12 (m, 3H), 7.06-6.79 (m, 1H), 6.68 (s, 2H), 6.18 (d, J=2.44 Hz, 1H), 5.17-4.85 (m, 2H), 4.04-3.72 (m, 2H), 3.19-3.02 (m, 5H), 2.73 (s, 2H).

Example 9

5-benzyl-12-(4-bromo-3-chloro-benzoyl)-7-[3-(methylamino)-1,2-benzothiazol-6-yl]-2,3,7,12-tetrazatricyclo[7.4.0.0^2,6]trideca-1(9),3,5-trien-8-one (5)

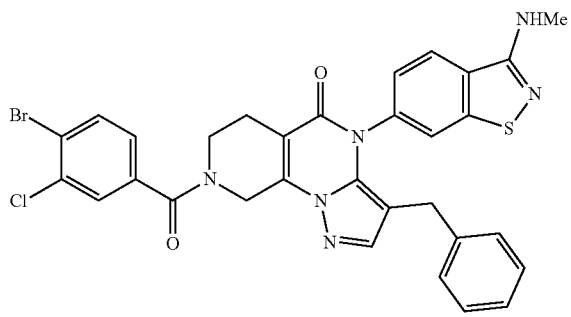 [SMILES: CNc1nsc2cc(-n3c(=O)c4c(n5ncc(Cc6ccccc6)c35)CN(C(=O)c3ccc(Br)c(Cl)c3)CC4)ccc12]

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (3-((tert-butoxycarbonyl)(methyl)amino)benzo[d]isothiazol-5-yl)boronic acid in place of (4-(4-(4-methoxybenzyl)-5-methyl-4H-1,2,4-triazol-3-yl)phenyl)boronic acid. LCMS (ESI, m/z): 660.95 [M+H]$^+$ Br pattern. $^1$H NMR (400 MHz, CDCl$_3$) δ 7.74-7.72 (m, 1H), 7.61-7.49 (m, 4H), 7.26 (s, 1H), 7.12-7.08 (m, 4H), 6.58 (d, J=2 Hz, 2H), 5.16-4.89 (m, 3H), 4.05-3.69 (m, 2H), 3.21 (d, J=4 Hz, 3H), 3.09-2.96 (m, 2H), 2.73 (s, 2H).

Example 10

5-benzyl-12-(4-bromo-3-chloro-benzoyl)-7-[3-(methylamino)-2,1-benzoxazol-6-yl]-2,3,7,12-tetrazatricyclo[7.4.0.0^2,6]trideca-1(9),3,5-trien-8-one (6)

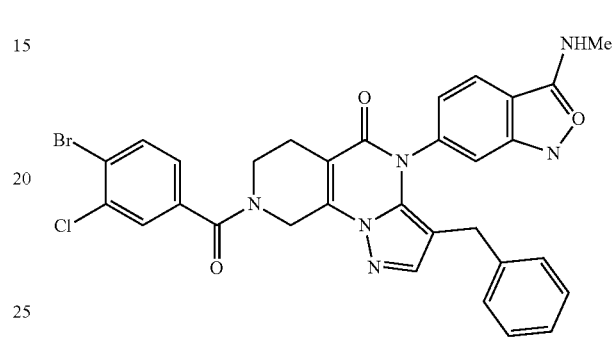

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (3-((tert-butoxycarbonyl)(methyl)amino)benzo[c]isoxazol-5-yl)boronic acid in place of (4-(4-(4-methoxybenzyl)-5-methyl-4H-1,2,4-triazol-3-yl)phenyl)boronic acid. LCMS (ESI, m/z): 645.0 [M+H]$^+$ Br pattern. $^1$H NMR (300 MHz, CDCl$_3$) δ 7.75 (d, J=8.1 Hz, 1H), 7.64 (s, 1H), 7.45 (d, J=8.4 Hz, 2H), 7.29-7.20 (m, 2H), 7.18-7.07 (m, 3H), 7.03 (d, J=8.2 Hz, 1H), 6.64 (s, 2H), 5.14 (s, 2H), 4.35 (d, J=5.5 Hz, 1H), 3.79 (s, 2H), 3.32-2.94 (m, 5H), 2.76 (s, 2H).

Example 11

5-benzyl-12-(4-bromo-3-chloro-benzoyl)-7-[4-(4-methylpyrazol-1-yl)phenyl]-2,3,7,12-tetrazatricyclo[7.4.0.0^2,6]trideca-1(9),3,5-trien-8-one (7)

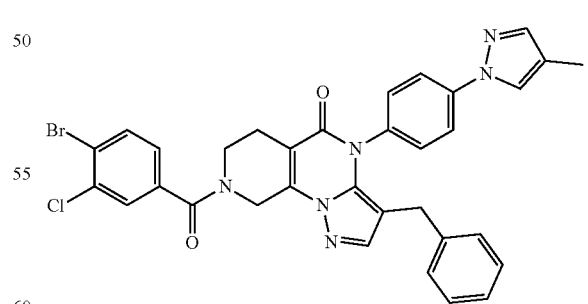

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (4-(4-methyl-1H-pyrazol-1-yl)phenyl)boronic acid in place of (4-(4-(4-methoxybenzyl)-5- methyl-4H-1,2,4-triazol-3-yl)phenyl)boronic acid. LCMS (ESI, m/z): 655.15 [M+H]⁺ Br pattern. ¹H NMR (300 MHz, DMSO-d₆) δ 8.33 (s, 1H), 7.92 (d, J=8.2 Hz, 1H), 7.81 (d, J=8.7 Hz, 3H), 7.62 (s, 2H), 7.55-7.32 (m, 3H), 7.11 (s, 3H), 6.76 (s, 2H), 5.19-4.63 (m, 2H), 3.93 (s, 1H), 3.63 (s, 1H), 3.16-2.98 (m, 2H), 2.66-2.54 (m, 2H), 2.12 (s, 3H).

Example 12

5-benzyl-12-(4-bromo-3-chloro-benzoyl)-7-[4-(1-methyltetrazol-5-yl)phenyl]-2,3,7,12-tetrazatricyclo[7.4.0.0^2,6]trideca-1(9),3,5-trien-8-one (8)

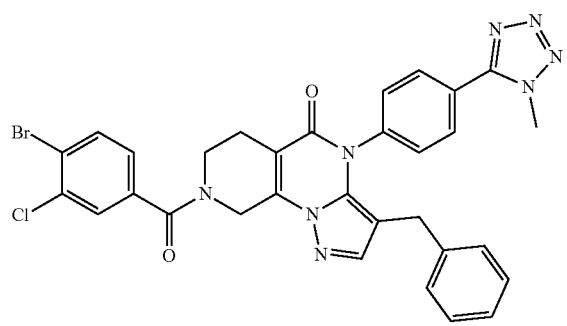 [SMILES: Cn1nnnc1-c1ccc(-n2c(=O)c3c(n4ncc(Cc5ccccc5)c24)CN(C(=O)c2ccc(Br)c(Cl)c2)CC3)cc1]

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (4-(1-methyl-1H-tetrazol-5-yl)phenyl)boronic acid in place of (4-(4-(4-methoxybenzyl)-5-methyl-4H-1,2,4-triazol-3-yl)phenyl)boronic acid. LCMS (ESI, m/z): 657.0 [M+H]⁺ Br pattern. ¹H NMR (300 MHz, CDCl₃) δ 7.80-7.71 (m, 3H), 7.64 (s, 1H), 7.55 (s, 1H), 7.41-7.34 (m, 2H), 7.33-7.29 (m, 1H), 7.14 (d, J=6.4 Hz, 3H), 6.70 (s, 2H), 5.17 (s, 2H), 4.21 (s, 3H), 3.88 (m, 2H), 3.22 (s, 2H), 2.77 (s, 2H).

Example 13

5-benzyl-12-(4-bromo-3-chloro-benzoyl)-7-[4-(2-methyltetrazol-5-yl)phenyl]-2,3,7,12-tetrazatricyclo[7.4.0.0^2,6]trideca-1(9),3,5-trien-8-one (10)

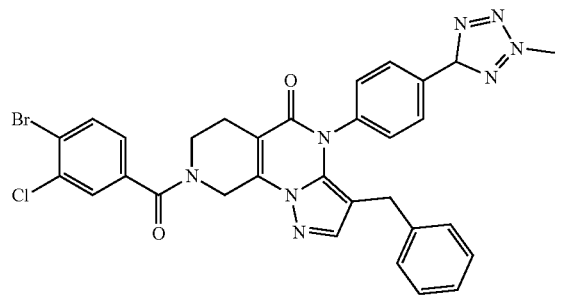

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (4-(2-methyl-2H-tetrazol-5-yl) phenyl)boronic acid in place of (4-(4-(4-methoxybenzyl)-5-methyl-4H-1,2,4-triazol-3-yl)phenyl)boronic acid. LCMS (ESI, m/z): 656.95 [M+H]⁺ Br pattern. ¹H NMR (400 MHz, CDCl₃) δ 8.22-8.15 (m, 2H), 7.75 (d, J=8.2 Hz, 1H), 7.57 (d, J=59.4 Hz, 2H), 7.35-7.29 (m, 3H), 7.18-7.09 (m, 3H), 6.71 (d, J=6.5 Hz, 2H), 5.3-4.8 (m, 2H), 4.46 (s, 3H), 4.1-3.7 (m, 2H), 3.15 (s, 2H), 2.77 (s, 2H).

Example 14

5-benzyl-12-(4-bromo-3-chloro-benzoyl)-7-[4-(5-methylpyrazol-1-yl)phenyl]-2,3,7,12-tetrazatricyclo[7.4.0.0^2,6]trideca-1(9),3,5-trien-8-one (12)

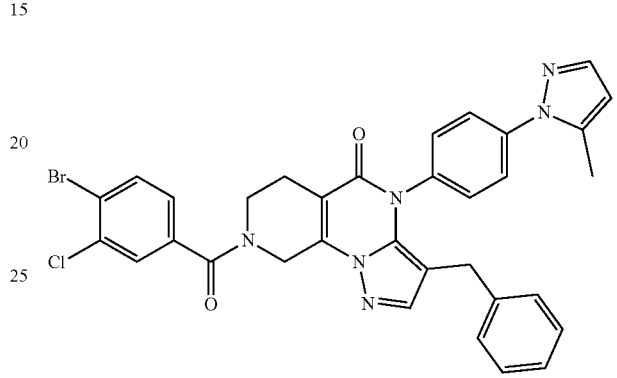

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (4-(5-methyl-1H-pyrazol-1-yl)phenyl)boronic acid in place of (4-(4-(4-methoxybenzyl)-5-methyl-4H-1,2,4-triazol-3-yl)phenyl)boronic acid. LCMS (ESI, m/z): 655.10 [M+H]⁺ Br pattern. ¹H NMR (300 MHz, DMSO-d₆) δ 7.91 (d, J=8.2 Hz, 1H), 7.84-7.73 (m, 1H), 7.67 (s, 1H), 7.59 (d, J=1.7 Hz, 1H), 7.57 (s, 1H), 7.54 (s, 1H), 7.42 (s, 3H), 7.22-6.99 (m, 3H), 6.86-6.63 (m, 2H), 6.30 (d, J=1.6 Hz, 1H), 4.99 (s, 1H), 4.78 (s, 1H), 3.91 (s, 1H), 3.62 (s, 1H), 3.16-3.01 (m, 2H), 2.71-2.56 (m, 2H), 2.34 (s, 3H).

Example 15

5-benzyl-12-(4-bromo-3-chloro-benzoyl)-7-[4-[3-(trifluoromethyl)pyrazol-1-yl]phenyl]-2,3,7,12-tetrazatricyclo[7.4.0.0^2,6]trideca-1(9),3,5-trien-8-one (13)

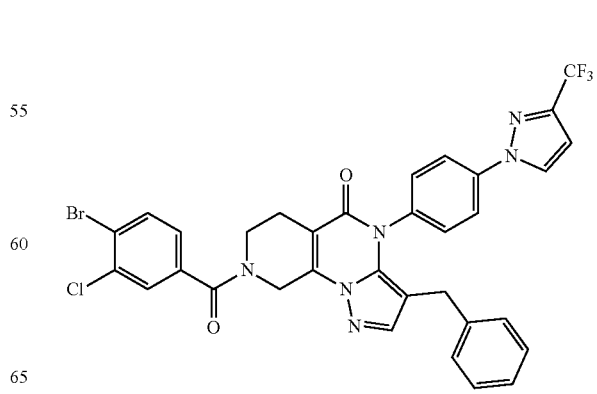

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (4-(3-(trifluoromethyl)-1H-pyrazol-1-yl)phenyl)boronic acid in place of (4-(4-(4-methoxybenzyl)-5-methyl-4H-1,2,4-triazol-3-yl)phenyl)boronic acid. LCMS (ESI, m/z): 709.15 [M+H]+ Br pattern. ¹H NMR (300 MHz, CDCl₃) δ 7.99 (d, J=2.6 Hz, 1H), 7.82-7.68 (m, 3H), 7.68-7.59 (m, 1H), 7.50 (s, 1H), 7.35-7.24 (m, 3H), 7.21-7.05 (m, 3H), 6.84-6.63 (m, 3H), 5.16 (br m, 1H), 4.93 (br m, 1H), 3.91 (br m, 1H), 3.77 (br m, 1H), 3.19 (s, 2H), 2.76 (s, 2H).

Example 16

4-[12-(4-bromo-3-chloro-benzoyl)-5-(cyclobutylmethyl)-8-oxo-2,3,7,12-tetrazatricyclo[7.4.0.0^2,6]trideca-1(9),3,5-trien-7-yl]-N-methyl-benzamide (14)

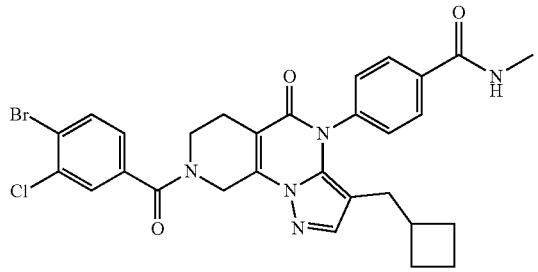 [SMILES: CNC(=O)c1ccc(-n2c(=O)c3c(n4ncc(CC5CCC5)c24)CN(C(=O)c2ccc(Br)c(Cl)c2)CC3)cc1]

The title compound was obtained following a similar procedure reported for the synthesis of 4-[12-(4-bromo-3-chlorobenzoyl)-5-(cyclopentylmethyl)-8-oxo-2,3,7,12-tetraazatricyclo[7.4.0.0^{2,6}]trideca-1(9),3,5-trien-7-yl]-N-methylbenzamide (11), using cyclobutanecarbaldehyde in place of cyclopentanecarbaldehyde in the second step. LCMS (ESI, m/z): 610.15 [M+H]+ Br pattern. ¹H NMR (300 MHz, CDCl₃) δ 8.06-7.83 (m, 2H), 7.72 (d, J=8.2 Hz, 1H), 7.65-7.56 (m, 1H), 7.48 (s, 1H), 7.40 (d, J=8.3 Hz, 2H), 7.23 (s, 1H), 6.33 (d, J=5.0 Hz, 1H), 5.11 (br m, 1H), 4.90 (br m, 1H), 3.96 (br m, 1H), 3.73 (br m, 1H), 3.04 (d, J=4.8 Hz, 3H), 2.72 (s, 2H), 2.26-1.94 (m, 1H), 1.79 (dd, J=13.9, 6.6 Hz, 2H), 1.62 (d, J=7.5 Hz, 4H), 1.46-1.19 (m, 2H).

Example 17

5-benzyl-12-(4-bromo-3-chloro-benzoyl)-7-(2-methyl-1-oxo-isoindolin-5-yl)-2,3,7,12-tetrazatricyclo[7.4.0.0^2,6]trideca-1(9),3,5-trien-8-one (15)

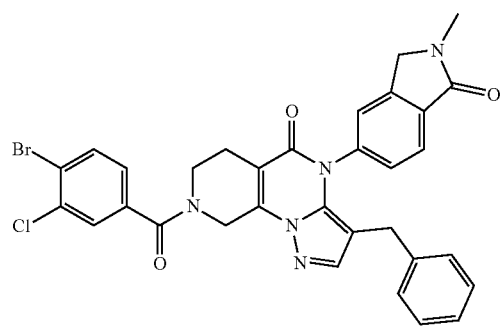 [SMILES: CN1Cc2cc(-n3c(=O)c4c(n5ncc(Cc6ccccc6)c35)CN(C(=O)c3ccc(Br)c(Cl)c3)CC4)ccc2C1=O]

The title compound was obtained following a similar procedure reported for the synthesis of 5-benzyl-12-(4-bromo-3-chloro-benzoyl)-7-[4-(5-methyl-4H-1,2,4-triazol-3-yl)phenyl]-2,3,7,12-tetrazatricyclo[7.4.0.0^2,6]trideca-1(9),3,5-trien-8-one (1), using (2-methyl-1-oxoisoindolin-5-yl)boronic acid in place of (4-(4-(4-methoxybenzyl)-5-methyl-4H-1,2,4-triazol-3-yl)phenyl)boronic acid. LCMS (ESI, m/z): 644.0 [M+H]+ Br pattern. ¹H NMR (300 MHz, CDCl₃) δ 7.92 (d, J=8.0 Hz, 1H), 7.76 (d, J=8.2 Hz, 1H), 7.60 (m, 2H), 7.38-7.31 (m, 2H), 7.18-7.03 (m, 4H), 6.62 (d, J=5.9 Hz, 2H), 5.07 (br m, 2H), 4.40-3.62 (m, 4H), 3.22 (m, 4H), 2.95 (d, J=17.0 Hz, 1H), 2.70 (br s, 2H).

Example 18

4-[12-[4-bromo-3-(trifluoromethyl)benzoyl]-5-(cyclobutylmethyl)-8-oxo-2,3,7,12-tetrazatricyclo[7.4.0.0^2,6]trideca-1(9),3,5-trien-7-yl]-N-methyl-benzamide (16)

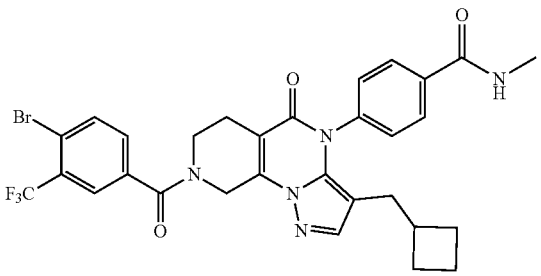 [SMILES: CNC(=O)c1ccc(-n2c(=O)c3c(n4ncc(CC5CCC5)c24)CN(C(=O)c2ccc(Br)c(C(F)(F)F)c2)CC3)cc1]

The title compound was obtained following a similar procedure reported for the synthesis of 4-[12-(4-bromo-3-chloro-benzoyl)-5-(cyclobutylmethyl)-8-oxo-2,3,7,12-tetrazatricyclo[7.4.0.0^2,6]trideca-1(9),3,5-trien-7-yl]-N-methyl-benzamide (14), using 4-bromo-3-trifluoromethylbenzoic acid in place of 4-bromo-3-chlorobenzoic acid in the last step. LCMS (ESI, m/z): 644.15 [M+H]+ Br pattern. ¹H NMR (300 MHz, CDCl₃) δ 8.05-7.91 (m, 2H), 7.89-7.76 (m, 2H), 7.63-7.46 (m, 2H), 7.41 (d, J=8.2 Hz, 2H), 6.47 (d, J=5.0 Hz, 1H), 5.14 (br m, 1H), 4.89 (br m, 1H), 4.03 (br m, 1H), 3.74 (br m, 1H), 3.04 (d, J=4.8 Hz, 3H), 2.75 (br s, 2H), 2.26-1.96 (m, 1H), 1.93-1.75 (m, 2H), 1.64 (m, 4H), 1.36 (q, J=8.7 Hz, 2H).

Example 19

4-[12-(4-bromo-3-chloro-benzoyl)-8-oxo-5-(tetrahydrofuran-3-ylmethyl)-2,3,7,12-tetrazatricyclo[7.4.0.0^2,6]trideca-1(9),3,5-trien-7-yl]-N-methyl-benzamide (17)

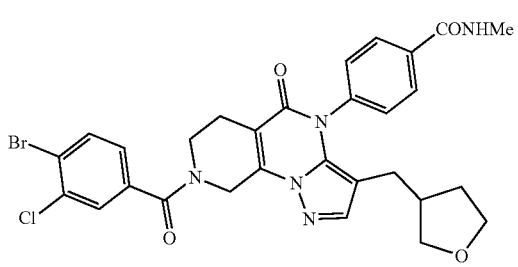

The title compound was obtained following a similar procedure reported in Example 3, using 4-((tetrahydrofuran-3-yl)methyl)-1H-pyrazol-5-amine instead of 4-(cyclopentyl-methyl)-1H-pyrazole. LCMS (ESI, m/z): 624.05 [M+H]+ Br pattern. $^1$H NMR (300 MHz, CDCl$_3$) δ 7.96 (m, 2H), 7.80-7.65 (m, 1H), 7.56 (m, 2H), 7.42 (m, 2H), 7.24 (s, 1H), 6.42-6.20 (m, 1H), 5.28-4.68 (m, 2H), 3.95-3.50 (m, 5H), 3.18-3.00 (m, 4H), 2.74 (br s, 2H), 2.04-1.80 (m, 1H), 1.75-1.65 (m, 3H), 1.30-1.10 (m, 1H).

Example 20

4-[12-(4-bromo-3-chloro-benzoyl)-8-oxo-5-(3-thienylmethyl)-2,3,7,12-tetrazatricyclo[7.4.0.0^2,6]trideca-1(9),3,5-trien-7-yl]-N-methyl-benzamide (18)

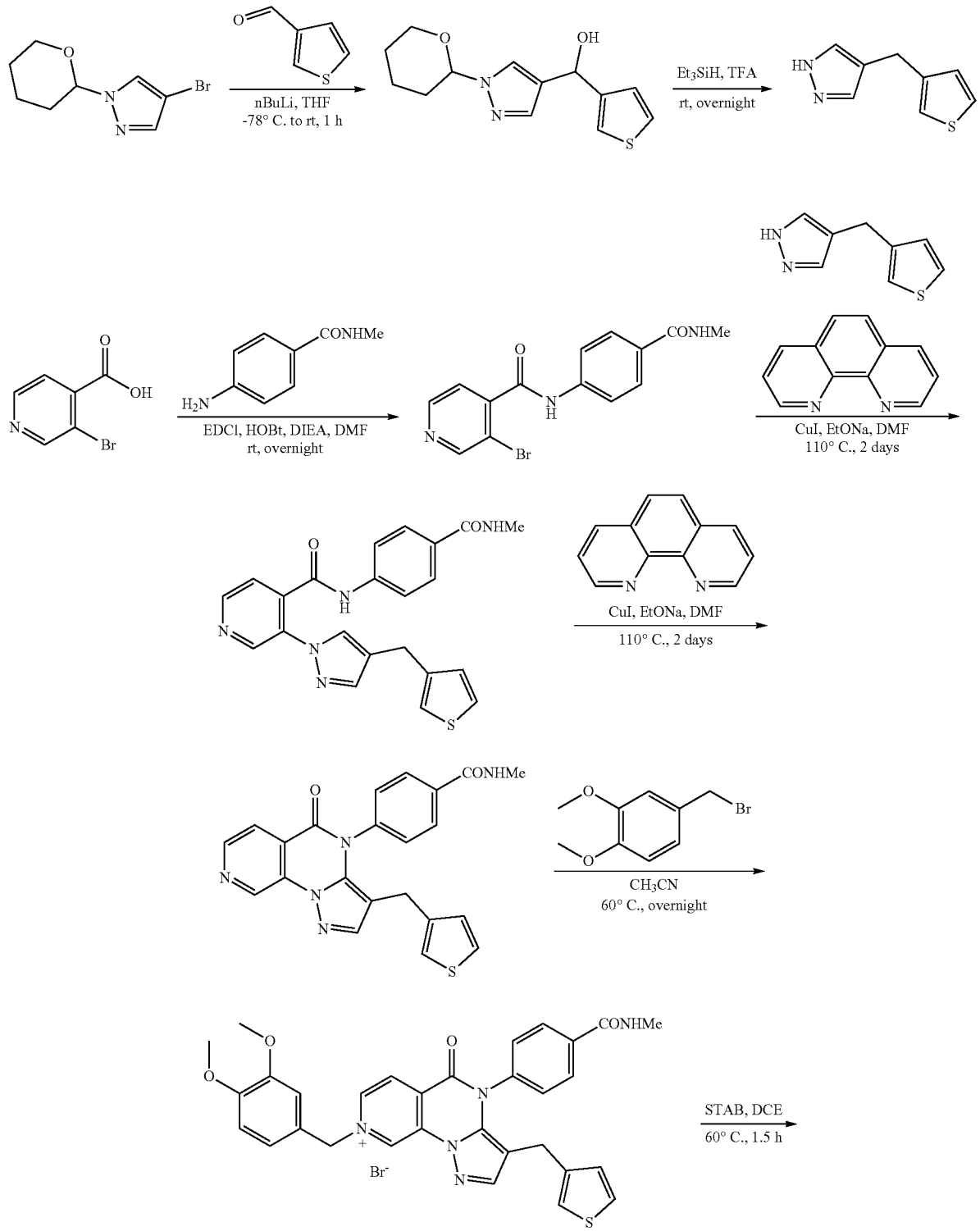

-continued

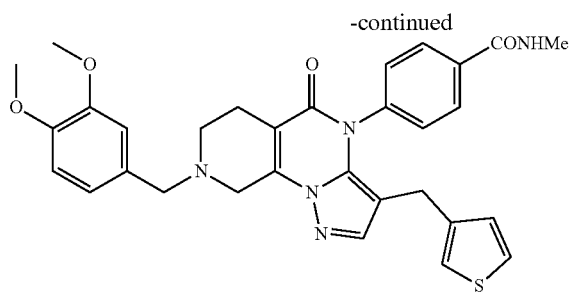

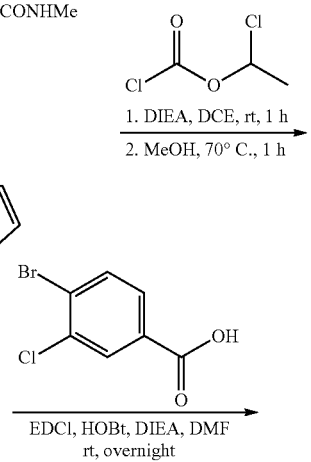

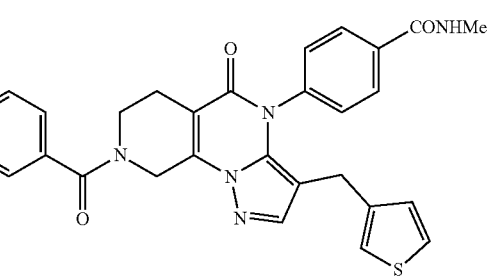

(18)

A 250 mL round-bottom flask was charged with 4-bromo-1-(oxan-2-yl)pyrazole (3.00 g, 13.0 mmol, 1.00 eq.) and THF (30 mL) under nitrogen. n-BuLi (7.79 mL, 19.5 mmol, 2.5 eq., 2.5 M in hexane) was added at −78° C. The mixture was stirred for 30 min at −78° C. 3-thiophenecarboxaldehyde (2.18 g, 19.5 mmol, 1.50 eq.) in THF (10 mL) was added at −78° C. The mixture was warmed to rt and then stirred for 1 h at rt. The reaction was quenched with sat. NH$_4$Cl (30 mL aq.) at 0° C. The mixture was extracted with ethyl acetate (3×50 mL). The organic layers were combined, washed with water (3×20 mL), dried over anhydrous sodium sulfate, filtered and concentrated under reduced pressure. The residue was purified by silica gel column chromatography, eluted with ethyl acetate:petroleum ether (1:1) to afford [1-(oxan-2-yl)pyrazol-4-yl](thiophen-3-yl)methanol (1.90 g, 55% yield) as a colorless oil. LCMS (ESI, m/z): 265 [M+H]$^+$.

A 100 mL round-bottom flask was charged with [1-(oxan-2-yl)pyrazol-4-yl](thiophen-3-yl)methanol (1.80 g, 6.81 mmol, 1.00 eq.), trifluoroacetic acid (23.3 g, 204 mmol, 30.0 eq.), Et$_3$SiH (11.9 g, 102 mmol, 15.0 eq.) and DCE (5 mL) at rt. The mixture was stirred for overnight at rt and then concentrated under reduced pressure. The residue was basified to pH 8-9 with sat. NaHCO$_3$ (aq.). The mixture was extracted with dichloromethane (3×80 mL). The organic layers were combined, washed with water (3×50 mL), dried over anhydrous sodium sulfate, filtered and concentrated under reduced pressure. The residue was purified by silica gel column chromatography, eluted with ethyl acetate:petroleum ether (1:1) to afford 4-(thiophen-3-ylmethyl)-1H-pyrazole (850 mg, 74% yield) as a colorless oil. LCMS (ESI, m/z): 165 [M+H]$^+$.

A 250 mL round bottom flask was charged with 3-bromopyridine-4-carboxylic acid (14.8 g, 73.3 mmol, 1.10 eq.), 4-amino-N-methylbenzamide (10.0 g, 66.7 mmol, 1.00 eq.), EDCI (15.3 g, 79.8 mmol, 1.20 eq.), HOBt (10.8 g, 79.8 mmol, 1.20 eq.), DIEA (26.0 g, 202 mmol, 3.00 eq.) and DMF (50 mL). The solution was stirred for overnight at rt. The reaction was quenched by water (200 mL). The mixture was extracted with ethyl acetate (3×200 mL). The organic layers were combined, washed with water (3×100 mL), dried over anhydrous sodium sulfate, filtered and concentrated under reduced pressure. The residue was purified by silica gel column chromatography, eluted with ethyl acetate: petroleum ether (9:1) to afford 3-bromo-N-[4-(methylcarbamoyl)phenyl]pyridine-4-carboxamide (6.50 g, 29% yield) as a white solid. LCMS (ESI, m/z): 334 [M+H]$^+$.

A 100 mL round-bottom flask was charged with 3-bromo-N-[4-(methylcarbamoyl)phenyl]pyridine-4-carboxamide (1.55 g, 4.63 mmol, 1.00 eq.), 4-(thiophen-3-ylmethyl)-1H-pyrazole (799 mg, 4.87 mmol, 1.05 eq.), 1,10-phenanthroline (0.167 g, 0.928 mmol, 0.20 eq.), CuI (0.180 g, 0.928 mmol, 0.20 eq.), EtONa (1.58 g, 23.2 mmol, 5.00 eq.) and DMF (20 mL) at rt. The mixture was stirred for 2 days at 110° C. under an oxygen atmosphere. The reaction was quenched with water (100 mL). The mixture was extracted with ethyl acetate (3×50 mL). The organic layers were combined, washed with water (3×20 mL), dried over anhydrous sodium sulfate, filtered and concentrated under reduced pressure to afford N-(4-(methylcarbamoyl)phenyl)-3-(4-(thiophen-3-ylmethyl)-1H-pyrazol-1-yl)isonicotinamide (1.94 g, crude) as a yellow oil. LCMS (ESI, m/z): 418 [M+H]$^+$.

A 100 mL round-bottom flask was charged with N-(4-(methylcarbamoyl)phenyl)-3-(4-(thiophen-3-ylmethyl)-1H-pyrazol-1-yl)isonicotinamide (1.94 g, 4.63 mmol, 1.00 eq.), 1,10-phenanthroline (0.167 g, 0.928 mmol, 0.20 eq.), CuI (0.180 g, 0.928 mmol, 0.20 eq.), EtONa (1.58 g, 23.2 mmol, 5.00 eq.) and DMF (20 mL) at rt. The mixture was stirred for 2 days at 110° C. under an oxygen atmosphere. The reaction was quenched with water (100 mL). The mixture was extracted with ethyl acetate (3×50 mL). The organic layers were combined, washed with water (3×20 mL), dried over anhydrous sodium sulfate, filtered and concentrated under reduced pressure. The residue was purified by silica gel column chromatography, eluted with ethyl acetate:tetrahydrofuran (4:1) to afford N-[4-(methylcarbamoyl)phenyl]-3-[4-(thiophen-3-ylmethyl)pyrazol-1-yl]pyridine-4-carboxamide (385 mg, 20% yield) as a light yellow oil. LCMS (ESI, m/z): 416 [M+H]$^+$.

A 100 mL round-bottom flask was charged with N-methyl-4-[8-oxo-5-(thiophen-3-ylmethyl)-2,3,7,12-tetraazatricyclo[7.4.0.0^{2,6}]trideca-1(9),3,5,10,12-pentaen-7-yl]benzamide (700 mg, 1.68 mmol, 1.00 eq.), 4-(bromomethyl)-1,2-dimethoxybenzene (584 mg, 2.52 mmol, 1.50 eq.) and acetonitrile (10 mL). The mixture was stirred for overnight at 60° C. and then concentrated under reduced pressure to afford 8-(3,4-dimethoxybenzyl)-4-(4-(methylcarbamoyl)phenyl)-5-oxo-3-(thiophen-3-ylmethyl)-4,5-dihydropyrazolo[1,5-a]pyrido[4,3-e]pyrimidin-8-ium bromide (1.25 g, crude) as a yellow oil. LCMS (ESI, m/z): 566 [M–Br]$^+$.

A 100 mL round-bottom flask was charged with 8-(3,4-dimethoxybenzyl)-4-(4-(methylcarbamoyl)phenyl)-5-oxo-3-(thiophen-3-ylmethyl)-4,5-dihydropyrazolo[1,5-a]pyrido[4,3-e]pyrimidin-8-ium bromide (450 mg, 0.696 mmol, 1.00 eq.), STAB (841 mg, 3.97 mmol, 5.70 eq.) and DCE (10 mL) at rt. The mixture was stirred for 1.5 h at 60° C. The reaction was quenched with water (100 mL). The mixture was extracted with dichloromethane (3×100 mL). The organic layers were combined, washed with water (3×50 mL), dried over anhydrous sodium sulfate, filtered and concentrated under reduced pressure. The residue was purified by silica gel column chromatography, eluted with dichloromethane:methanol (10:1) to afford 4-{12-[(3,4-dimethoxyphenyl)methyl]-8-oxo-5-(thiophen-3-ylmethyl)-2,3,7,12-tetraazatricyclo[7.4.0.0^{2,6}]trideca-1(9),3,5-trien-7-yl}-N-methylbenzamide (238 mg, 60% yield) as a yellow solid. LCMS (ESI, m/z): 570 [M+H]$^+$.

A 40 mL vial was charged with 4-{12-[(3,4-dimethoxyphenyl)methyl]-8-oxo-5-(thiophen-3-ylmethyl)-2,3,7,12-tetraazatricyclo[7.4.0.0^{2,6}]trideca-1(9),3,5-trien-7-yl}-N-methylbenzamide (190 mg, 0.334 mmol, 1.00 eq.), chloroethyl chloroformate (52.45 mg, 0.367 mmol, 1.10 eq.), DIEA (64.6 mg, 0.501 mmol, 1.50 eq.) and DCE (5 mL) at rt. The mixture was stirred for 1 h at rt and then concentrated under reduced pressure. MeOH (3.0 mL) was added. The mixture was stirred for 1 h at 70° C. and then concentrated under reduced pressure. The residue was purified by prep-TLC with dichloromethane:methanol (5:1) to afford N-methyl-4-[8-oxo-5-(thiophen-3-ylmethyl)-2,3,7,12-tetraazatricyclo[7.4.0.0^{2,6}]trideca-1(9),3,5-trien-7-yl]benzamide (120 mg, 86% yield) as a yellow solid. LCMS (ESI, m/z): 420 [M+H]$^+$.

A 40 mL vial was charged with N-methyl-4-[8-oxo-5-(thiophen-3-ylmethyl)-2,3,7,12-tetraazatricyclo[7.4.0.0^{2,6}]trideca-1(9),3,5-trien-7-yl]benzamide (60.0 mg, 0.143 mmol, 1.00 eq.), 4-bromo-3-chlorobenzoic acid (50.5 mg, 0.214 mmol, 1.50 eq.), EDCI (32.9 mg, 0.172 mmol, 1.20 eq.), HOBT (23.1 mg, 0.172 mmol, 1.20 eq.), DIEA (92.4 mg, 0.715 mmol, 5.00 eq.) and DMF (10 mL) at rt. The mixture was stirred for overnight at rt. The reaction was quenched with water (50 mL). The mixture was extracted with ethyl acetate (3×50 mL). The organic layers were combined, washed with water (3×20 mL), dried over anhydrous sodium sulfate, filtered and concentrated under reduced pressure. The crude product was purified by prep-HPLC with the following conditions: Column: Xselect CSH OBD Column 30×150 mm 5 um; Mobile Phase A: Water (50 mmol/L NH$_4$HCO$_3$), Mobile Phase B: ACN; Flow rate: 60 mL/min; Gradient: 33% B to 63% B in 9 min to afford 4-[12-(4-bromo-3-chlorobenzoyl)-8-oxo-5-(thiophen-3-ylmethyl)-2,3,7,12-tetraazatricyclo[7.4.0.0^{2,6}]trideca-1(9),3,5-trien-7-yl]-N-methylbenzamide (12.3 mg, 13% yield) as a white solid. LCMS (ESI, m/z): 636 [M+H]$^+$, 637.95 [M+H]$^+$ Br pattern. $^1$H NMR (400 MHz, CDCl$_3$) 6.79-7.72 (m, 3H), 7.61 (s, 1H), 7.55 (m, 1H), 7.24 (d, J=4.0 Hz, 2H), 7.13 (m, 1H), 6.44 (m, 2H), 6.20 (br s, 1H), 5.23-4.85 (m, 2H), 4.02-3.73 (m, 2H), 3.04 (m, 5H), 2.73 (br s, 2H).

Example 21

4-[12-(4-bromo-3-chloro-benzoyl)-5-[(3,3-difluorocyclobutyl)methyl]-8-oxo-2,3,7,12-tetrazatricyclo[7.4.0.0^2,6]trideca-1(9),3,5-trien-7-yl]-N-methylbenzamide (19)

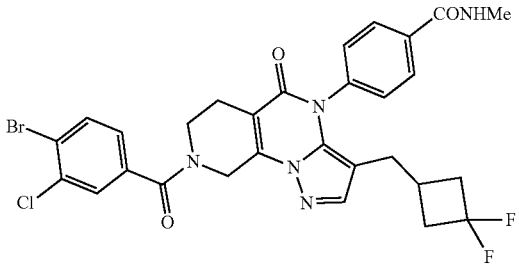

The title compound was obtained following a similar procedure reported in Example 3, using 4-((3,3-difluorocyclobutyl)methyl)-1H-pyrazole in place of 4-(cyclopentylmethyl)-1H-pyrazole. LCMS (ESI, m/z): 644.05 [M+H]$^+$ Br pattern. $^1$H NMR (400 MHz, CDCl$_3$) δ 8.01-7.94 (m, 2H), 7.75 (d, J=8.2 Hz, 1H), 7.68-7.58 (m, 1H), 7.57-7.33 (m, 3H), 7.26 (m, 1H), 6.28 (d, J=5.0 Hz, 1H), 5.25-4.78 (m, 2H), 4.13-3.64 (m, 2H), 3.08 (d, J=4.8 Hz, 3H), 2.86-2.65 (m, 2H), 2.59-2.32 (m, 2H), 2.02-1.82 (m, 3H), 1.79 (d, J=7.0 Hz, 2H).

Example 22

4-[12-[4-bromo-3-(trifluoromethyl)benzoyl]-8-oxo-5-(3-thienylmethyl)-2,3,7,12-tetrazatricyclo[7.4.0.0^2,6]trideca-1(9),3,5-trien-7-yl]-N-methylbenzamide (20)

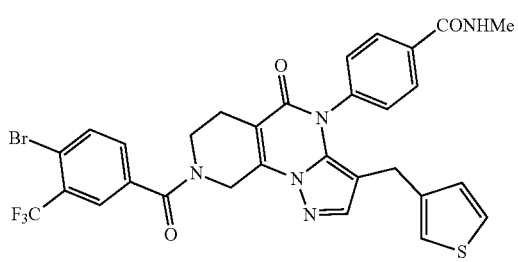

The title compound was obtained following a similar procedure reported in Example 20, using 4-bromo-3-(trifluoromethyl)benzoic acid in place of 4-bromo-3-chlorobenzoic acid in the last step. LCMS (ESI, m/z): 672.1 [M+H]$^+$ Br pattern. $^1$H NMR (400 MHz, CDCl$_3$) δ 7.86-7.83 (m, 2H), 7.78 (d, J=4.0 Hz, 2H), 7.53-7.46 (m, 2H), 7.24 (d, J=4.0 Hz, 2H), 7.14-7.12 (m, 1H), 6.45 (s, 2H), 6.16 (d, J=2.0 Hz, 1H), 5.34-4.68 (m, 2H), 4.19-3.58 (m, 2H), 3.05 (d, J=2.0 Hz, 5H), 2.74 (br s, 2H).

Example 23

N-methyl-4-[rac-(11R)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzamide (21a) and N-methyl-4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzamide (21b)

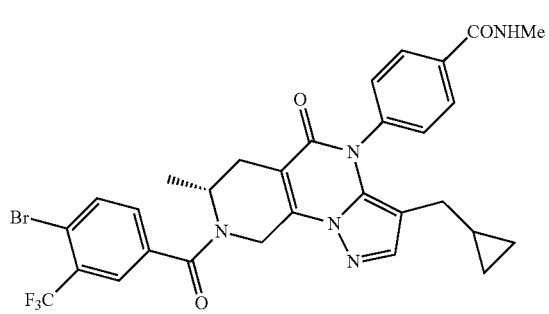

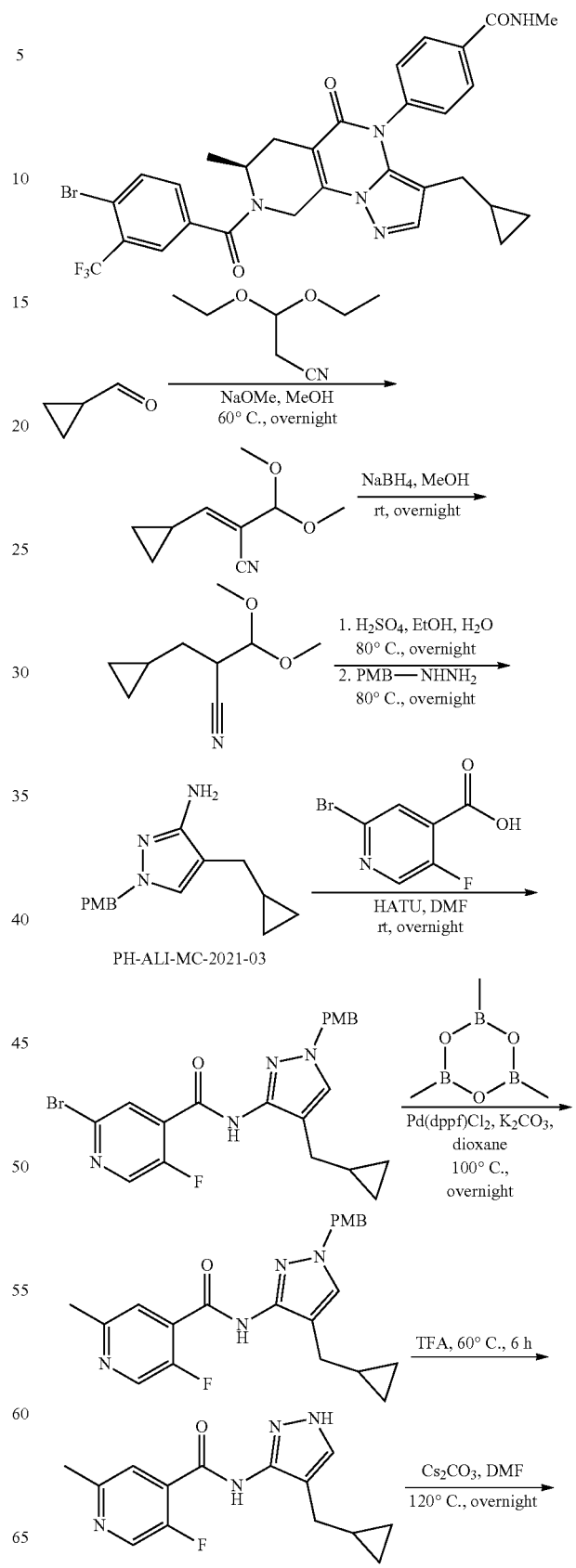

-continued

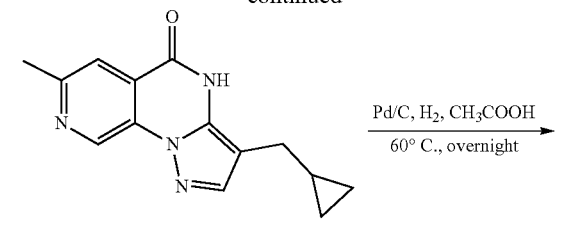

Pd/C, H₂, CH₃COOH
60° C., overnight

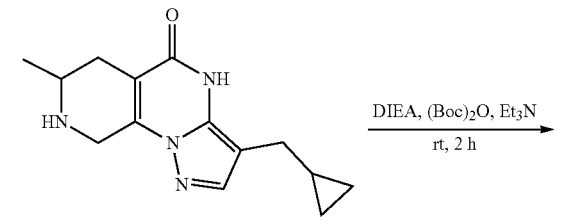

DIEA, (Boc)₂O, Et₃N
rt, 2 h

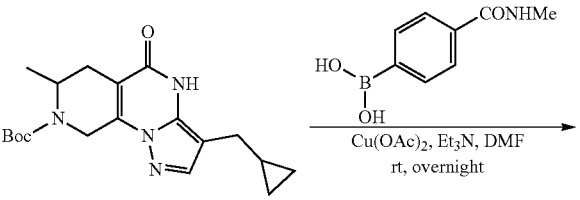

Cu(OAc)₂, Et₃N, DMF
rt, overnight

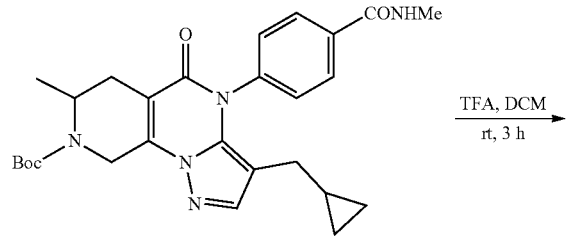

TFA, DCM
rt, 3 h

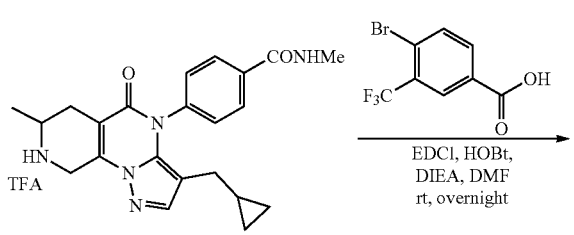

EDCl, HOBt,
DIEA, DMF
rt, overnight

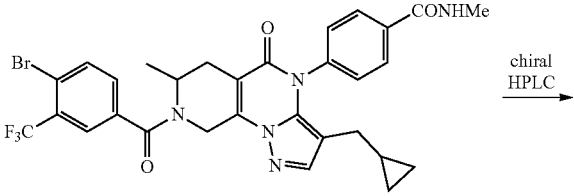

(21)

chiral HPLC

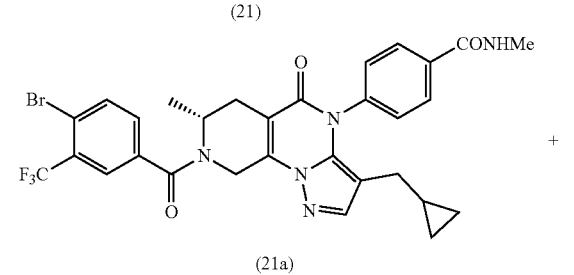

(21a)

-continued

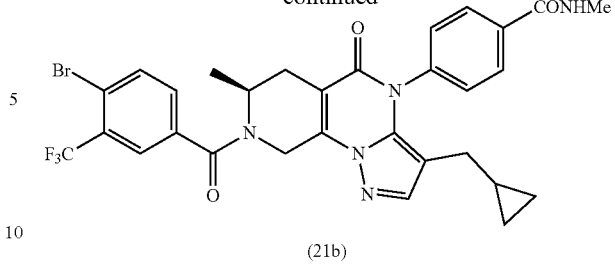

(21b)

To a stirred solution of cyclopropanecarbaldehyde (200 g, 2.85 mol, 1.00 eq.) and 3,3-diethoxypropanenitrile (408 g, 2.85 mol, 1.00 eq.) in MeOH (4000 mL) was added NaOMe (308 g, 5.71 mol, 2.00 eq.) at rt. The mixture was stirred for overnight at 60° C. under a nitrogen atmosphere and then concentrated under reduced pressure. The reaction was quenched with water (2000 mL) and then extracted with ethyl acetate (3×1500 mL). The combined organic layers were dried over anhydrous sodium sulfate. After filtration, the filtrate was concentrated under reduced pressure. The residue was purified by silica gel column chromatography with ethyl acetate:petroleum ether (4:1) to afford (2E)-3-cyclopropyl-2-(dimethoxymethyl)prop-2-enenitrile (273 g, 57% yield) as a colorless oil.

To a stirred solution of (2E)-3-cyclopropyl-2-(dimethoxymethyl)prop-2-enenitrile (273 g, 1.63 mol, 1.00 eq.) in MeOH (7 L) was added NaBH₄ (308 g, 8.16 mol, 5.00 eq.) in portions at 0° C. The mixture was stirred for overnight at rt. The reaction was quenched with water (2 L) and then concentrated under reduced pressure. The mixture was extracted with ethyl acetate (3×2 L). The combined organic layers were dried over anhydrous sodium sulfate. After filtration, the filtrate was concentrated under reduced pressure to afford 3-cyclopropyl-2-(dimethoxymethyl)propanenitrile (260 g, crude) as a colorless oil.

To a stirred solution of 3-cyclopropyl-2-(dimethoxymethyl)propanenitrile (260 g, 1.54 mol, 1.00 eq.) in EtOH (5 L) was added H₂SO₄ (753 g, 7.68 mol, 5.0 eq.) in water (2.5 L) at rt under a nitrogen atmosphere. The mixture was stirred for overnight at 80° C. [(4-Methoxyphenyl)methyl]hydrazine (350 g, 2.30 mol, 1.50 eq.) was added and stirred for 6 hours at 80° C. under a nitrogen atmosphere. The mixture was concentrated under reduced pressure. The residue was basified to pH=8 with saturated sodium bicarbonate solution and then extracted with ethyl acetate (3×2 L). The combined organic layers were dried over anhydrous sodium sulfate. After filtration, the filtrate was concentrated under reduced pressure. The residue was purified by silica gel column chromatography, eluted with ethyl acetate:petroleum ether (3:1) to afford 4-(cyclopropylmethyl)-1-[(4-methoxyphenyl)methyl]pyrazol-3-amine (100.6 g, 26% yield) as an off-white solid. LCMS (ESI, m/z): 258 [M+H]⁺, ¹HNMR (300 MHz, CDCl₃) δ 7.27 (s, 1H), 7.17-7.08 (m, 2H), 6.91-6.82 (m, 2H), 5.14 (s, 2H), 3.78 (s, 3H), 3.30 (s, 2H), 2.26 (d, J=6.4 Hz, 2H), 1.07-0.78 (m, 1H), 0.59-0.34 (m, 2H), 0.25-0.07 (m, 2H).

A 1 L round bottom flask was charged with 4-(cyclopropylmethyl)-1-[(4-methoxyphenyl)methyl]pyrazol-3-amine (30.0 g, 116 mmol, 1.00 eq.), 2-bromo-5-fluoropyridine-4-carboxylic acid (28.0 g, 128 mmol, 1.10 eq.), HATU (62.1 g, 163 mmol, 1.4 eq.), DIEA (45.2 g, 350 mmol, 3 eq.) and DMF (500 mL). The solution was stirred for overnight at rt. The reaction was quenched by water (2 L). The mixture was stirred for 30 min. The solid was collected by filtration, washed with water (3×200 mL), dried under reduced pressure to provide 2-bromo-N-[4-(cyclopropylmethyl)-1-[(4-methoxyphenyl)methyl]pyrazol-3-yl]-5-fluoropyridine-4-carboxamide (51.0 g, 95% yield) as a light yellow solid. LCMS (ESI, m/z): 459 [M+H]$^+$.

A 2 L round bottom flask was charged with 2-bromo-N-[4-(cyclopropylmethyl)-1-[(4-methoxyphenyl)methyl]pyrazol-3-yl]-5-fluoropyridine-4-carboxamide (51.0 g, 111 mmol, 1.00 eq.), trimethyl-1,3,5,2,4,6-trioxatriborinane (60.0 g, 238 mmol, 2.14 eq., 50% in THF), Pd(dppf)Cl$_2$ (4.06 g, 5.55 mmol, 0.05 eq.), K$_2$CO$_3$ (46.0 g, 333 mmol, 3.00 eq.) and 1,4-dioxane (1.0 L). The solution was stirred for overnight at 100° C. under N$_2$ atmosphere. The reaction was quenched by water (1.0 L). The mixture was extracted with ethyl acetate (3×1 L). The organic layers were combined, washed with water (3×500 mL), dried over anhydrous sodium sulfate, filtered and concentrated under reduced pressure. The residue was purified by silica gel column chromatography, eluted with ethyl acetate:petroleum ether (1:3) to afford N-[4-(cyclopropylmethyl)-1-[(4-methoxyphenyl)methyl]pyrazol-3-yl]-5-fluoro-2-methylpyridine-4-carboxamide (40.0 g, 91% yield) as a light yellow solid. LCMS (ESI, m/z): 395 [M+H]$^+$.

A 500 mL round bottom flask was charged with N-[4-(cyclopropylmethyl)-1-[(4-methoxyphenyl)methyl]pyrazol-3-yl]-5-fluoro-2-methylpyridine-4-carboxamide (30.0 g, 76.1 mmol, 1.00 eq.) and TFA (200 mL). The solution was stirred for 6 h at 60° C. and then concentrated under reduced pressure to provide N-[4-(cyclopropylmethyl)-1H-pyrazol-3-yl]-5-fluoro-2-methylpyridine-4-carboxamide (30.6 g, crude) as a brown solid. LCMS (ESI, m/z): 275 [M+H]$^+$.

A 500 mL round bottom flask was charged with N-[4-(cyclopropylmethyl)-1H-pyrazol-3-yl]-5-fluoro-2-methylpyridine-4-carboxamide (30.6 g, 112 mmol, 1.00 eq.), Cs$_2$CO$_3$ (71.3 g, 218 mmol, 1.95 eq.) and DMF (200 mL). The solution was stirred for overnight at 120° C. The reaction was quenched by water (1 L). The mixture was extracted with ethyl acetated (3×1 L). The organic layers were combined, washed with water (3×500 mL), dried over anhydrous sodium sulfate, filtered and concentrated under reduced pressure to provide 5-(cyclopropylmethyl)-11-methyl-2,3,7,12-tetraazatricyclo[7.4.0.0ˆ{2,6}]trideca-1(13),3,5,9,11-pentaen-8-one (15.5 g, 55% yield) as a white solid. LCMS (ESI, m/z): 255 [M+H]$^+$.

A 500 mL round bottom flask was charged with 5-(cyclopropylmethyl)-11-methyl-2,3,7,12-tetraazatricyclo[7.4.0.0ˆ{2,6}]trideca-1(9),3,5,10,12-pentaen-8-one (15.5 g, 60.9 mmol, 1.00 eq.), Pd/C (1.50 g) and AcOH (200 mL). The solution was stirred for overnight at 60° C. under H$_2$ atmosphere. The solid was filtered off and washed with AcOH (50 mL). The filtrate was concentrated under reduced pressure to provide 5-(cyclopropylmethyl)-11-methyl-2,3,7,12-tetraazatricyclo[7.4.0.0ˆ{2,6}]trideca-1(9),3,5-trien-8-one (15.0 g, 95% yield) as a white solid. LCMS (ESI, m/z): 259 [M+H]$^+$.

A 500 mL round bottom was charged with 5-(cyclopropylmethyl)-11-methyl-2,3,7,12-tetraazatricyclo[7.4.0.0ˆ{2,6}]trideca-1 (9),3,5-trien-8-one (15.0 g, 58.1 mmol, 1.00 eq.), Et$_3$N (17.6 g, 174 mmol, 3.00 eq.) and DCM (250 mL). (Boc)$_2$O (19.0 g, 87.1 mmol, 1.50 eq.) was added at rt. The solution was stirred for 2 h at rt. The reaction was quenched with water (300 mL). The mixture was extracted with DCM (3×500 mL). The organic layers were combined, washed with water (3×300 mL), dried over anhydrous sodium sulfate, filtered and concentrated under reduced pressure. The residue was purified by silica gel column chromatography, eluted with ethyl acetate:petroleum ether (1:4) to afford tert-butyl 5-(cyclopropylmethyl)-11-methyl-8-oxo-2,3,7,12-tetraazatricyclo[7.4.0.0ˆ{2,6}]trideca-1(9),3,5-triene-12-carboxylate (14.5 g, 69% yield) as a white solid. LCMS (ESI, m/z): 359 [M+H]$^+$.

A 500 mL round bottom flask was charged with tert-butyl 5-(cyclopropylmethyl)-11-methyl-8-oxo-2,3,7,12-tetraazatricyclo[7.4.0.0ˆ{2,6}]trideca-1(9),3,5-triene-12-carboxylate (14.5 g, 40.4 mmol, 1.00 eq.), 4-(methylcarbamoyl)phenylboronic acid (14.5 g, 80.9 mmol, 2.00 eq.), Cu(OAc)$_2$ (7.35 g, 40.5 mmol, 1.00 eq.), Et$_3$N (12.3 g, 121 mmol, 3.00 eq.) and DCM (250 mL). The solution was stirred for overnight at rt under 02 atmosphere. The reaction was quenched by water (500 mL). The mixture was extracted with DCM (3×500 mL). The organic layers were combined, washed with water (3×200 mL), dried over anhydrous sodium sulfate, filtered and concentrated under reduced pressure. The residue was purified by silica gel column chromatography, eluted with ethyl acetate:petroleum ether (10:1) to afford tert-butyl 5-(cyclopropylmethyl)-11-methyl-7-[4-(methylcarbamoyl)phenyl]-8-oxo-2,3,7,12-tetraazatricyclo[7.4.0.0ˆ{2,6}]trideca-1(9),3,5-triene-12-carboxylate (7.00 g, 35% yield) as a white solid. LCMS (ESI, m/z): 492 [M+H]$^+$.

A 500 mL round bottom flask was charged with tert-butyl 5-(cyclopropylmethyl)-11-methyl-7-[4-(methylcarbamoyl)phenyl]-8-oxo-2,3,7,12-tetraazatricyclo[7.4.0.0ˆ{2,6}]trideca-1(9),3,5-triene-12-carboxylate (7.00 g, 14.2 mmol, 1.00 eq.), TFA (40 mL) and DCM (200 mL). The solution was stirred for 3 h at rt. The mixture was concentrated under reduced pressure to provide 4-[5-(cyclopropylmethyl)-11-methyl-8-oxo-2,3,7,12-tetraazatricyclo[7.4.0.0ˆ{2,6}]trideca-1(9),3,5-trien-7-yl]-N-methylbenzamide trifluoroacetic acid salt (7.00 g, crude) as a light brown solid. LCMS (ESI, m/z): 392 [M-TFA+H]$^+$.

A 500 ml round bottom flask was charged with 4-[5-(cyclopropylmethyl)-11-methyl-8-oxo-2,3,7,12-tetraazatricyclo[7.4.0.0ˆ{2,6}]trideca-1(9),3,5-trien-7-yl]-N-methylbenzamide trifluoroacetic acid salt (7.00 g, 13.9 mmol, 1.00 eq.), 4-bromo-3-(trifluoromethyl)benzoic acid (4.62 g, 17.2 mmol, 1.24 eq.), EDCI (4.11 g, 21.5 mmol, 1.55 eq.), DMF (200 mL), DIEA (7.39 g, 57.2 mmol, 4.12 eq.) and HOBT (2.90 g, 21.5 mmol, 1.55 eq.). The solution was stirred for overnight at rt. The reaction was quenched by water (500 mL). The mixture was extracted with ethyl acetate (3×500 mL). The organic layers were combined, washed with water (3×500 mL), dried over anhydrous sodium sulfate, filtered and concentrated under reduced pressure. The residue was purified by silica gel column chromatography, eluted with acetate:petroleum ether (10:1) to afford the crude product. The crude product (6.8 g) was purified by SFC with the following conditions (Column: CHIRAL ART Amylose-SA, 5*25 cm, 5 μm; Mobile Phase A: CO$_2$, Mobile Phase B: MEOH (0.1% 2M NH$_3$-MEOH); Flow rate: 200 mL/min; Gradient: isocratic 50% B; Column Temperature (° C.): 35; Back Pressure (bar): 100; Wave Length: 220 nm; RT1 (min): 5.42; RT2 (min): 10.37; Sample Solvent: MeOH:DCM=1:1; Injection Volume: 12 mL; Number Of Runs: 15) to afford 4-[(11R)-12-[4-bromo-3-(trifluoromethyl)benzoyl]-5-(cyclopropylmethyl)-11-methyl-8-oxo-2,3,7,12-tetraazatricyclo[7.4.0.0ˆ{2,6}]trideca-1(9),3,5-trien-7-yl]-N-methylbenzamide 21a (the first peak, 2.501 g, 27% yield) as a white solid, and 4-[(11S)-12-[4-bromo-3-(trifluoromethyl)benzoyl]-5-(cyclopropylmethyl)-11-methyl-8-oxo-2,3,7,12-tetraazatricyclo[7.4.0.0ˆ{2,6}]trideca-1(9),3,5-trien-7-yl]-N-methylbenzamide 21b (the second peak, 2.5 g, 27% yield) as a white solid. LCMS (ESI, m/z): 642 [M+H]$^+$, 644.2 [M+H]$^+$ Br pattern. $^1$H NMR (400 MHz, CDCl$_3$) δ 7.94 (t, J=8.8 Hz, 2H), 7.88-7.79 (m, 2H), 7.74 (s, 1H), 7.52-7.34 (m, 3H), 6.45 (d, J=5.5 Hz, 1H), 6.06-5.19 (br, 1H), 5.06-4.17 (br, 2H), 3.05 (d, J=4.5 Hz, 3H), 2.82 (d, J=15.6 Hz, 1H), 2.67 (d, J=17.2 Hz, 1H), 1.49 (d, J=6.8 Hz, 2H), 1.35 (d, J=6.8 Hz, 3H), 0.60 (q, J=6.2 Hz, 1H), 0.46-0.33 (m, 2H), −0.13 (m, 2H).

Example 24

N-methyl-4-[rac-(11R)-12-[4-bromo-3-chlorobenzoyl]-5-(cyclopropylmethyl)-11-methyl-8-oxo-2,3,7,12-tetrazatricyclo[7.4.0.0^2,6]trideca-1(9),3,5-trien-7-yl]benzamide (22a) and N-methyl-4-[rac-(11S)-12-[4-bromo-3-chlorobenzoyl]-5-(cyclopropylmethyl)-11-methyl-8-oxo-2,3,7,12-tetrazatricyclo[7.4.0.0^2,6]trideca-1(9),3,5-trien-7-yl]benzamide (22b)

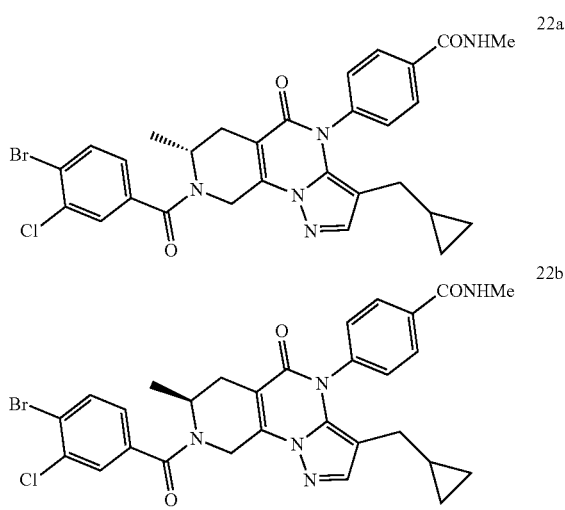

The title compounds were obtained following a similar procedure reported in Example 23, using 4-bromo-3-chlorobenzoic acid in place of 4-bromo-3-(trifluoromethyl)benzoic acid in the last step. Chiral HPLC purification (chiralpak IA-3 4.6*50 mm 3 μm, MtBE (0.1% DEA):EtOH 60:40) provided (22a) as the first eluting enantiomer (Rt=1.29 min) and (22b) as the second eluting enantiomer (Rt=3.53 min). LCMS (ESI, m/z): 610.05 [M+H]+ Br pattern. 1H NMR (300 MHz, CDCl3) δ 7.93 (t, J=6.8 Hz, 2H), 7.80-7.62 (m, 2H), 7.56 (d, J=1.9 Hz, 1H), 7.48-7.32 (m, 2H), 7.20 (dd, J=8.2, 2.0 Hz, 1H), 6.29 (d, J=5.3 Hz, 1H), 5.72 (m, 1H), 4.44 (m, 2H), 3.05 (d, J=4.8 Hz, 3H), 2.91-2.50 (m, 2H), 1.48 (d, J=6.9 Hz, 2H), 1.32 (d, J=6.8 Hz, 3H), 0.59 (m, 1H), 0.39 (t, J=6.5 Hz, 2H), −0.12 (m, 2H).

Example 25

5-benzyl-12-(4-bromo-3-chloro-benzoyl)-7-[3-(methylamino)-[1,2,4]triazolo[4,3-a]pyridin-7-yl]-2,3,7,12-tetrazatricyclo[7.4.0.0^2,6]trideca-1(9),3,5-trien-8-one (23)

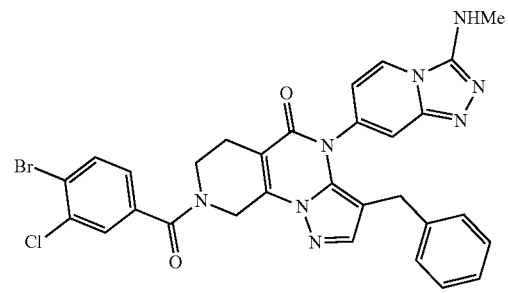 [SMILES: CNc1nnc2cc(-n3c(=O)c4c(n5ncc(Cc6ccccc6)c35)CN(C(=O)c3ccc(Br)c(Cl)c3)CC4)ccn12]

The title compound was obtained following a similar procedure reported in Example 2, using 7-bromo-N-[(4-methoxyphenyl)methyl]-N-methyl-[1,2,4]triazolo[4,3-a]pyridin-3-amine in place of (4-(4-methyl-4H-1,2,4-triazol-3-yl)phenyl)boronic acid, and replacing the Chan-Lam coupling conditions by Buchwald coupling conditions (XantPhos, Pd2(dba)3, K3PO4, dioxane, 100 deg, 16 h). LCMS (ESI, m/z): 645.05 [M+H]+ Br pattern. 1H NMR (300 MHz, CDCl3) δ 7.74 (d, J=8.1 Hz 1H), 7.60 (m, 2H), 7.41 (s, 1H), 7.26 (s, 1H), 7.24 (s, 1H), 7.10-6.98 (m, 3H), 6.50 (d, J=7.5 Hz 2H), 6.13 (d, J=7.2 Hz 1H), 5.40-4.70 (m, 2H), 4.22 (br s, 1H), 3.95-3.58 (m, 3H), 3.40-3.20 (m, 4H), 2.72 (s, 2H).

Example 26

4-[12-[4-bromo-3-(trifluoromethyl)benzoyl]-5-(cyclopropylmethyl)-8-oxo-2,3,7,12-tetrazatricyclo[7.4.0.0^2,6]trideca-1(9),3,5-trien-7-yl]-N-methyl-benzamide (24)

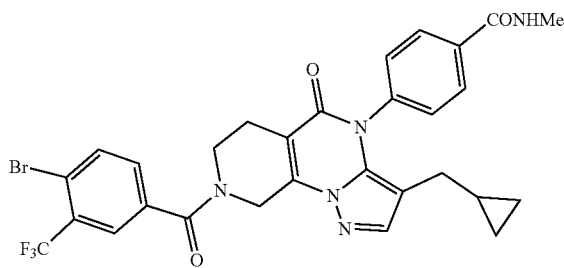

Coupling of 4-[5-(cyclopropylmethyl)-8-oxo-2,3,7,12-tetraazatricyclo[7.4.0.0^[2,6]]trideca-1(9),3,5-trien-7-yl]-N-methylbenzamide with 4-bromo-3-(trifluoromethyl)benzoic acid, following the conditions reported in Example 1, afforded compound (24). LCMS (ESI, m/z): 628.10 [M+H]+ Br pattern. 1H NMR (400 MHz, CDCl3) δ 8.00-7.90 (m, 2H), 7.90-7.80 (m, 2H), 7.80-7.59 (m, 1H), 7.59-7.49 (m, 1H), 7.39 (d, J=7.2 Hz, 2H), 6.49-6.11 (m, 1H), 5.35-4.71 (m, 2H), 4.20-3.55 (m, 2H), 3.03 (d, J=4.4 Hz, 3H), 2.74 (br s, 2H), 1.47 (d, J=6.8 Hz, 2H), 0.70-0.50 (m, 1H), 0.45-0.27 (m, 2H), −0.05--0.21 (m, 2H).

Example 27

5-benzyl-12-[4-bromo-3-(trifluoromethyl)benzoyl]-7-[4-(4-methyl-1,2,4-triazol-3-yl)phenyl]-2,3,7,12-tetrazatricyclo[7.4.0.0^2,6]trideca-1(9),3,5-trien-8-one (25)

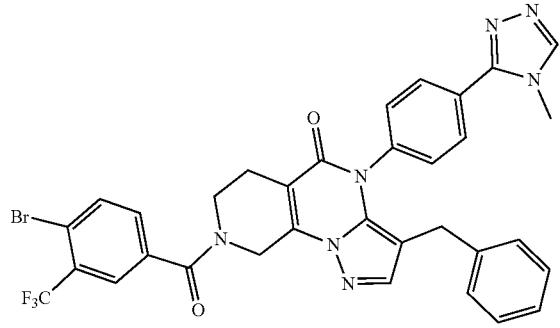 [SMILES: Cn1cnnc1-c1ccc(-n2c(=O)c3c(n4ncc(Cc5ccccc5)c24)CN(C(=O)c2ccc(Br)c(C(F)(F)F)c2)CC3)cc1]

The title compound was obtained following a similar procedure reported in Example 2, using 4-bromo-3-(trifluoromethyl)benzoic acid in place of 4-bromo-3-chlorobenzoic acid in the last step. LCMS (ESI, m/z): 690.05 [M+H]+ Br pattern. $^1$H NMR (300 MHz, CDCl$_3$) δ 8.35 (br s, 1H), 7.84 (d, J=8.4 Hz 2H), 7.71 (d, J=7.5 Hz 2H), 7.54 (d, J=8.1 Hz 2H), 7.32 (d, J=7.2 Hz 2H), 7.20-7.00 (m, 3H), 6.70 (d, J=3.3 Hz 2H), 5.30-4.90 (m, 2H), 3.80 (s, 5H), 3.17 (s, 2H), 2.76 (br s, 2H).

Example 28

5-benzyl-12-[4-bromo-3-(trifluoromethyl)benzoyl]-7-[3-(methylamino)-1H-indazol-6-yl]-2,3,7,12-tetrazatricyclo[7.4.0.0^2,6]trideca-1(9),3,5-trien-8-one (26)

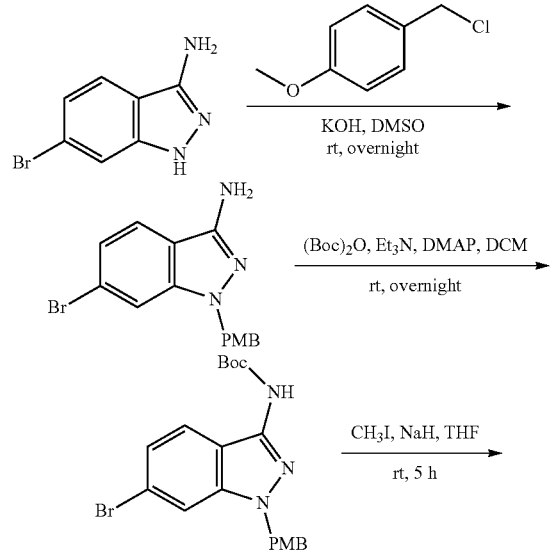

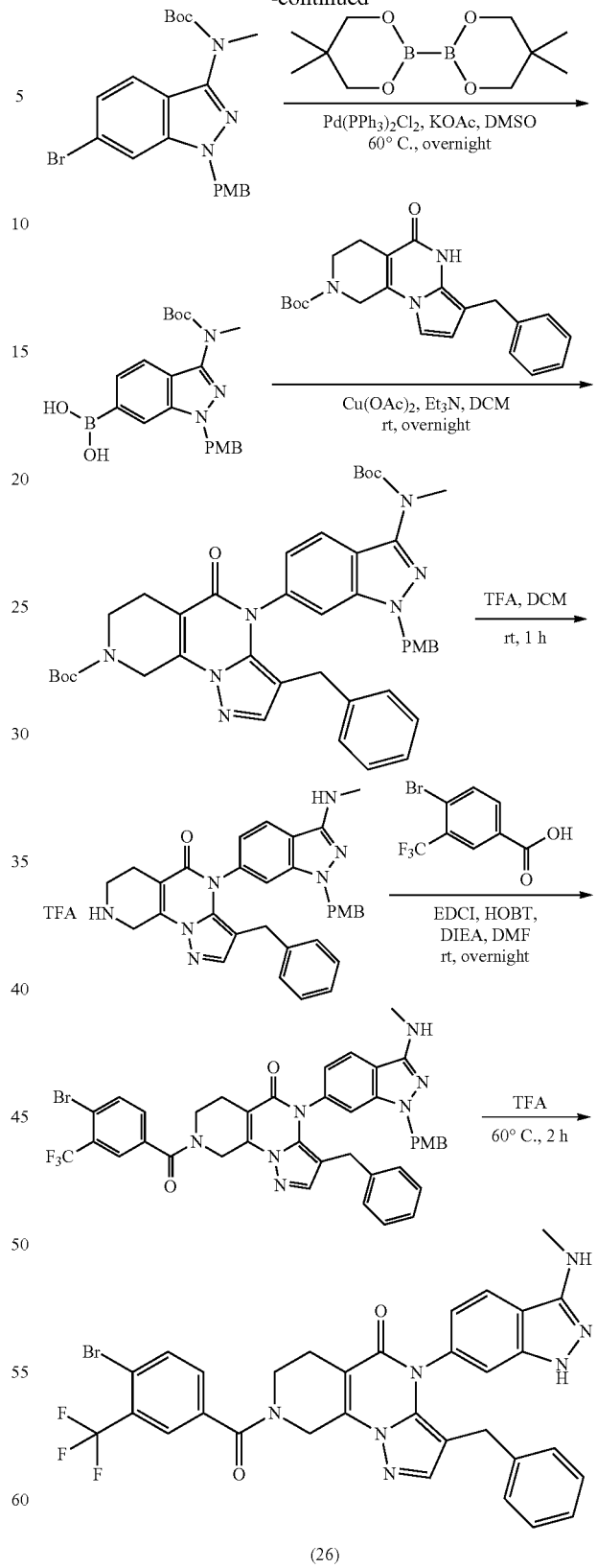

A mixture of 6-bromo-1H-indazol-3-amine (3.00 g, 14.1 mmol, 1.00 eq.), 4-methoxybenzyl chloride (2.88 g, 18.4 mmol, 1.30 eq.), KOH (1.98 g, 35.3 mmol, 2.49 eq.) and DMSO (100 mL) was stirred for overnight at rt. The mixture was diluted with ethyl acetate (100 mL) and washed with water (3×100 mL). The organic layer was dried over anhydrous sodium sulfate. After filtration, the filtrate was concentrated under reduced pressure. The residue was purified by silica gel column chromatography, eluted with ethyl acetate:petroleum ether (1:2) to afford 6-bromo-1-[(4-methoxyphenyl)methyl]indazol-3-amine (4.10 g, 91% yield) as a light yellow solid. LCMS (ESI, m/z): 332 $[M+H]^+$.

A mixture of 6-bromo-1-[(4-methoxyphenyl)methyl]indazol-3-amine (4.10 g, 12.3 mmol, 1.00 eq.), $Boc_2O$ (3.23 g, 14.8 mmol, 1.20 eq.), triethylamine (2.50 g, 24.7 mmol, 2.00 eq.), DMAP (0.302 g, 2.47 mmol, 0.20 eq.) and dichloromethane (100 mL) was stirred for overnight at rt. The reaction was quenched with water (100 mL). The mixture was extracted with dichloromethane (3×100 mL). The organic layers were combined, washed with water (3×50 mL), dried over anhydrous sodium sulfate, filtered and concentrated under reduced pressure. The residue was purified by silica gel column chromatography, eluted with ethyl acetate:petroleum ether (1:3) to afford tert-butyl N-{6-bromo-1-[(4-methoxyphenyl)methyl]indazol-3-yl}carbamate (3.28 g, 78% yield) as a yellow solid. LCMS (ESI, m/z): 432 $[M+H]^+$.

Sodium hydride (0.910 g, 22.8 mmol, 3.00 eq., 60% dispersion in mineral oil) was added to a mixture of tert-butyl N-{6-bromo-1-[(4-methoxyphenyl)methyl]indazol-3-yl}carbamate (3.28 g, 7.59 mmol, 1.00 eq.) and tetrahydrofuran (100 mL) at 0° C. The mixture was stirred for 30 min at rt. Iodomethane (1.29 g, 9.10 mmol, 1.20 eq.) was added, the mixture was stirred for 4 h at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:2) to afford tert-butyl N-{6-bromo-1-[(4-methoxyphenyl)methyl]indazol-3-yl}-N-methylcarbamate (2.70 g, 79% yield) as a yellow solid. LCMS (ESI, m/z): 446 $[M+H]^+$.

A mixture of tert-butyl N-{6-bromo-1-[(4-methoxyphenyl)methyl]indazol-3-yl}-N-methylcarbamate (1.00 g, 2.24 mmol, 1.00 eq.), 2-(5,5-dimethyl-1,3,2-dioxaborinan-2-yl)-5,5-dimethyl-1,3,2-dioxaborinane (1.52 g, 6.72 mmol, 3.00 eq.), bis(triphenylphosphine)palladium chloride (0.157 g, 0.224 mmol, 0.100 eq.), KOAc (0.660 g, 6.72 mmol, 3.00 eq.) and DMSO (10 mL) was stirred overnight at 60° C. under a nitrogen atmosphere. The reaction was quenched with water (50 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:2) to afford the crude product. The residue was purified by reverse flash chromatography with the following conditions: column, $C_{18}$ column; mobile phase, acetonitrile in water (0.05% TFA), 10% to 50% gradient in 20 min to afford 3-[(tert-butoxycarbonyl)(methyl)amino]-1-[(4-methoxyphenyl)methyl]indazol-6-ylboronic acid (740 mg, 84% yield) as a white solid. LCMS (ESI, m/z): 412 $[M+H]^+$.

A mixture of 3-[(tert-butoxycarbonyl)(methyl)amino]-1-[(4-methoxyphenyl)methyl]indazol-6-ylboronic acid (324 mg, 0.788 mmol, 1.20 eq.), tert-butyl 5-benzyl-8-oxo-2,3,7,12-tetraazatricyclo[7.4.0.0^{2,6}]trideca-1(9),3,5-triene-12-carboxylate (250 mg, 0.657 mmol, 1.00 eq.), cupric acetate (119 mg, 0.657 mmol, 1.00 eq.), triethylamine (199 mg, 1.97 mmol, 3.00 eq.) and dichloromethane (30 mL) was stirred for overnight at rt under an oxygen atmosphere. The reaction was quenched with water (50 mL). The mixture was extracted with dichloromethane (3×50 mL). The organic layers were combined, washed with water (3×50 mL), dried over anhydrous sodium sulfate, filtered and concentrated under reduced pressure. The residue was purified by silica gel column chromatography, eluted with ethyl acetate:petroleum ether (1:2) to afford the crude product. The crude product was purified by prep-HPLC with the following conditions: Column: XBridge Shield RP18 OBD Column, 19×150 mm, 5 um; Mobile Phase A: Water (10 mmol/L $NH_4HCO_3$+0.1% $NH_3·H_2O$), Mobile Phase B: ACN; Flow rate: 25 mL/min; Gradient: 70% B to 92% B in 9 min to afford tert-butyl 5-benzyl-7-{13-[(tert-butoxycarbonyl)(methyl)amino]-1-[(4-methoxyphenyl)methyl]indazol-6-yl}-8-oxo-2,3,7,12-tetraazatricyclo[7.4.0.0^{2,6}]trideca-1(9),3,5-triene-12-carboxylate (180 mg, 37% yield) as a white solid. LCMS (ESI, m/z): 746 $[M+H]^+$.

A mixture of tert-butyl 5-benzyl-7-{13-[(tert-butoxycarbonyl)(methyl)amino]-1-[(4-methoxyphenyl)methyl]indazol-6-yl}-8-oxo-2,3,7,12-tetraazatricyclo[7.4.0.0^{2,6}]trideca-1(9),3,5-triene-12-carboxylate (180 mg, 0.241 mmol, 1.00 eq.), trifluoroacetic acid (3 mL) and dichloromethane (15 mL) was stirred for 1 h at rt. The mixture was concentrated under reduced pressure to afford 5-benzyl-7-{11-[(4-methoxyphenyl)methyl]-3-(methylamino)indazol-6-yl}-2,3,7,12-tetraazatricyclo[7.4.0.0^{2,6}]trideca-1(9),3,5-trien-8-one trifluoroacetic acid salt (150 mg, crude) as a light yellow oil. LCMS (ESI, m/z): 546 $[M+H-TFA]^+$.

A mixture of 5-benzyl-7-{1-[(4-methoxyphenyl)methyl]-3-(methylamino)indazol-6-yl}-2,3,7,12-tetraazatricyclo[7.4.0.0^{2,6}]trideca-1(9),3,5-trien-8-one trifluoroacetic acid salt (150 mg, 0.227 mmol, 1.00 eq.), 4-bromo-3-(trifluoromethyl)benzoic acid (69.0 mg, 0.256 mmol, 1.12 eq.), EDCI (67.0 mg, 0.350 mmol, 1.54 eq.), HOBt (47.2 mg, 0.350 mmol, 1.54 eq.), N,N-diisopropylethylamine (90.4 mg, 0.699 mmol, 3.08 eq.) and DMF (20 mL) was stirred for overnight at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (4:1) to afford 5-benzyl-12-[4-bromo-3-(trifluoromethyl)benzoyl]-7-{1-[(4-methoxyphenyl)methyl]-3-(methylamino)indazol-6-yl}-2,3,7,12-tetraazatricyclo[7.4.0.0^{2,6}]trideca-1(9),3,5-trien-8-one (170 mg, 94% yield) as a light yellow solid. LCMS (ESI, m/z): 796 $[M+H]^+$.

A mixture of 5-benzyl-12-[4-bromo-3-(trifluoromethyl)benzoyl]-7-{11-[(4-methoxyphenyl)methyl]-3-(methylamino)indazol-6-yl}-2,3,7,12-tetraazatricyclo[7.4.0.0^{2,6}]trideca-1(9),3,5-trien-8-one (160 mg, 0.201 mmol, 1.00 eq.) and trifluoroacetic acid (20 mL) was stirred for 2 h at 60° C. and then concentrated under reduced pressure. The residue was purified by prep-HPLC with the following conditions: Column: XBridge Shield $RP_{18}$ OBD Column, 30×150 mm, 5 um; Mobile Phase A: Water (10 mmol/L $NH_4HCO_3$+0.1% $NH_3·H_2O$), Mobile Phase B: ACN; Flow rate: 60 mL/min; Gradient: 46% B to 66% B in 7 min to afford 5-benzyl-12-[4-bromo-3-(trifluoromethyl)benzoyl]-7-[3-(methylamino)-1H-indazol-6-yl]-2,3,7,12-tetraazatricyclo[7.4.0.0^{2,6}]trideca-1(9),3,5-trien-8-one (26) (68.8 mg, 51% yield) as a white solid. LCMS (ESI, m/z): 676

[M+H]⁺. ¹H NMR (400 MHz, CDCl₃) δ 7.96-7.79 (m, 2H), 7.63-7.35 (m, 3H), 7.16-7.03 (m, 3H), 6.89 (m, 2H), 6.61 (s, 2H), 5.35-4.72 (m, 2H), 4.30-3.63 (m, 3H), 3.08 (m, 4H), 2.85 (m, 3H).

Example 29

12-(4-bromo-3-chloro-benzoyl)-5-(cyclopropylmethyl)-7-[3-(methylamino)-1H-indazol-6-yl]-2,3,7,12-tetrazatricyclo[7.4.0.0^2,6]trideca-1(9),3,5-trien-8-one (27)

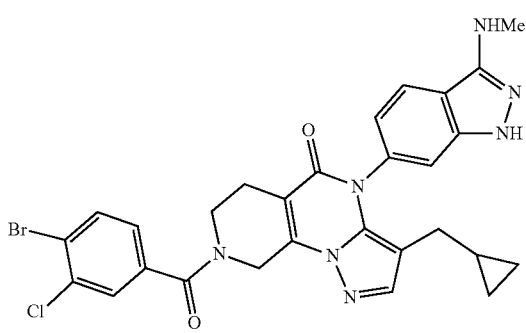

The title compound was obtained following a similar route reported in Example 28, using tert-butyl 3-(cyclopropylmethyl)-5-oxo-5,6,7,9-tetrahydropyrazolo[1,5-a]pyrido[4,3-e]pyrimidine-8(4H)-carboxylate in place of tert-butyl 3-benzyl-5-oxo-5,6,7,9-tetrahydropyrazolo[1,5-a]pyrido[4,3-e]pyrimidine-8(4H)-carboxylate, and 4-bromo-3-chlorobenzoic acid instead of 4-bromo-3-(trifluoromethyl)benzoic acid. LCMS (ESI, m/z): 608.10 [M+H]⁺ Br pattern. ¹H NMR (400 MHz, DMSO-d₆) δ 11.69 (s, 1H), 8.01-7.61 (m, 4H), 7.44 (m, 1H), 7.33 (s, 1H), 6.88 (d, J=8.6 Hz, 1H), 6.14 (q, J=5.0 Hz, 1H), 5.08-4.70 (m, 2H), 4.00-3.55 (m, 2H), 2.90 (d, J=5.0 Hz, 3H), 2.62-2.54 (m, 2H), 1.39 (m, 2H), 0.64-0.45 (m, 1H), 0.32-0.14 (m, 2H), −0.12-−0.28 (m, 2H).

Example 30

12-[4-bromo-3-(trifluoromethyl)benzoyl]-5-(cyclopropylmethyl)-7-[3-(methylamino)-1H-indazol-6-yl]-2,3,7,12-tetrazatricyclo[7.4.0.0^2,6]trideca-1(9),3,5-trien-8-one (28)

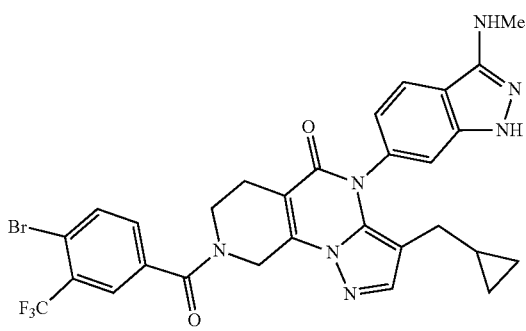

The title compound was obtained following a similar route reported in Example 28, using tert-butyl 3-(cyclopropylmethyl)-5-oxo-5,6,7,9-tetrahydropyrazolo[1,5-a]pyrido[4,3-e]pyrimidine-8(4H)-carboxylate in place of tert-butyl 3-benzyl-5-oxo-5,6,7,9-tetrahydropyrazolo[1,5-a]pyrido[4,3-e]pyrimidine-8(4H)-carboxylate. LCMS (ESI, m/z): 640.15 [M+H]⁺ Br pattern. ¹H NMR (400 MHz, CDCl₃) δ 7.93-7.83 (m, 2H), 7.79-7.50 (m, 3H), 7.22 (s, 1H), 6.88 (br s, 1H), 5.40-4.67 (m, 2H), 4.22-3.62 (m, 2H), 3.10 (s, 3H), 2.81 (br s, 2H), 1.42 (d, J=6.9 Hz, 2H), 0.67-0.49 (m, 1H), 0.40-0.25 (m, 2H), −0.10-−0.26 (m, 2H).

Example 31

5-[5-benzyl-12-[4-bromo-3-(trifluoromethyl)benzoyl]-8-oxo-2,3,7,12-tetrazatricyclo[7.4.0.0^2,6]trideca-1(9),3,5-trien-7-yl]-N,2-dimethyl-pyrazole-3-carboxamide (29)

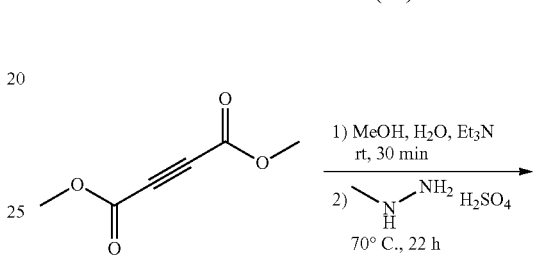

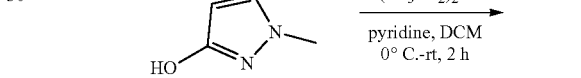

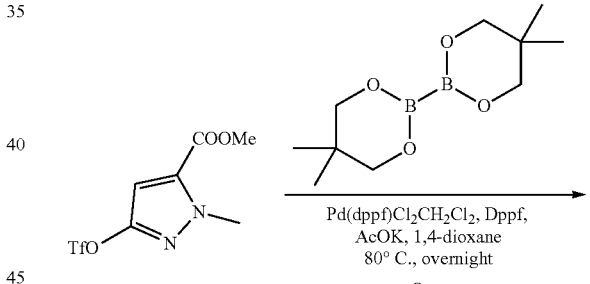

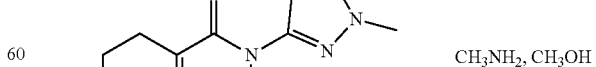

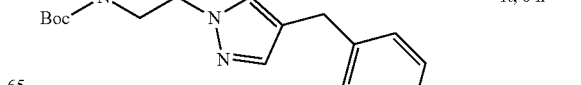

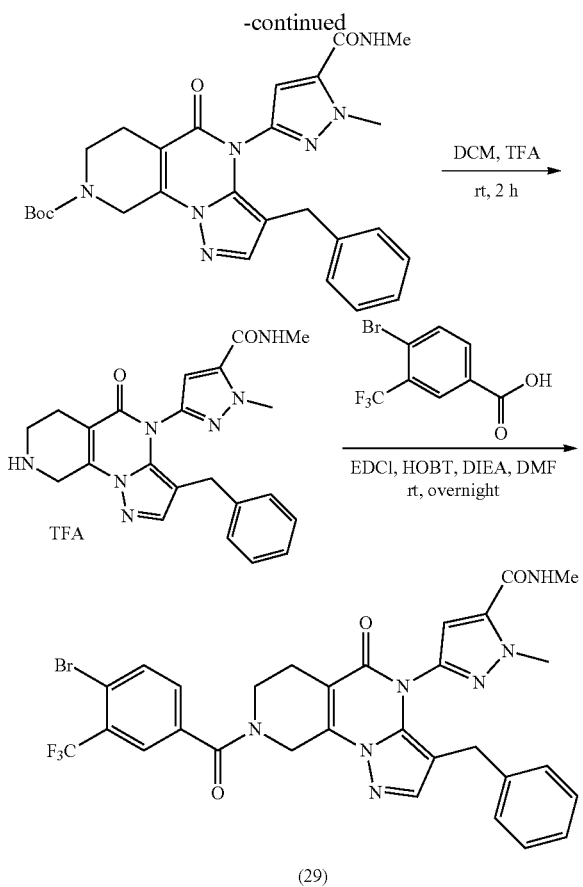

(29)

A 250 mL round-bottom flask was charged with dimethyl acetylenedicarboxylate (4.00 g, 28.1 mmol, 1.00 eq.), MeOH (50 mL) and water (50 mL). Et₃N (5.70 g, 56.3 mmol, 2.00 eq.) was added slowly at rt. The solution was stirred 30 min at rt. Methylhydrazine sulfuric acid salt (6.09 g, 42.2 mmol, 1.50 eq.) was added, and the mixture was stirred for 22 h at 70° C. The mixture was diluted with water (200 mL), and then acidified to pH 6 with HCl (aq. 1.00 mol/L). The mixture was extracted with ethyl acetate (3×100 mL). The organic layers were combined, washed with water (3×50 mL), dried over anhydrous sodium sulfate, filtered and concentrated under reduced pressure. The residue was purified by silica gel column chromatography, eluted with ethyl acetate:petroleum ether (4:1) to afford methyl 5-hydroxy-2-methylpyrazole-3-carboxylate (1.82 g, 41% yield) as a brown crude solid. LCMS (ESI, m/z): 157 [M+H]⁺.

A 250 mL round-bottom flask was charged with methyl 5-hydroxy-2-methylpyrazole-3-carboxylate (1.20 g, 7.69 mmol, 1.00 eq.), pyridine (0.910 g, 11.5 mmol, 1.50 eq.) and dichloromethane (60 mL) at 0° C. Triflic anhydride (3.25 g, 11.5 mmol, 1.50 eq.) was added dropwise at 0° C. The solution was stirred for 2 h at rt. The reaction was quenched with water (100 mL). The mixture was extracted with dichloromethane (3×100 mL). The organic layers were combined, dried over anhydrous sodium sulfate, filtered and concentrated under reduced pressure. The residue was purified by silica gel column chromatography, eluted with ethyl acetate:petroleum ether (5:4) to afford methyl 2-methyl-5-(trifluoromethanesulfonyloxy)pyrazole-3-carboxylate (0.650 g, 29% yield) as a yellow oil. LCMS (ESI, m/z): 289 [M+H]⁺.

A 100 mL round-bottom flask was charged with methyl 2-methyl-5-(trifluoromethanesulfonyloxy)pyrazole-3-carboxylate (500 mg, 1.74 mmol, 1.00 eq.), 2-(5,5-dimethyl-1,3,2-dioxaborinan-2-yl)-5,5-dimethyl-1,3,2-dioxaborinane (784 mg, 3.47 mmol, 2.00 eq.), Pd(dppf)Cl₂·CH₂Cl₂ (70.7 mg, 0.087 mmol, 0.05 eq.), potassium acetate (511 mg, 5.21 mmol, 3.00 eq.), dppf (47.9 mg, 0.09 mmol, 0.05 eq.) and 1,4-dioxane (50 mL). The solution was stirred overnight at 80° C. and then concentrated under reduced pressure. The mixture was diluted with water (100 mL) and extracted with ethyl acetate (3×100 mL). The organic layers were combined, washed with water (3×50 mL), dried over anhydrous sodium sulfate, filtered and concentrated under reduced pressure. The crude product was purified by prep-HPLC with the following conditions: Column: XBridge Prep OBD C₁₈ Column, 30×150 mm 5 um; Mobile Phase A: Water (0.05% TFA), Mobile Phase B: ACN; Flow rate: 60 mL/min; Gradient: 32% B to 65% B in 10 min to afford 5-(methoxycarbonyl)-1-methylpyrazol-3-ylboronic acid (106 mg, 33% yield) as a yellow solid. LCMS (ESI, m/z): 185 [M+H]⁺.

A 100 mL round-bottom flask was charged with tert-butyl 5-benzyl-8-oxo-2,3,7,12-tetraazatricyclo[7.4.0.0ˆ{2,6}]trideca-1(9),3,5-triene-12-carboxylate (300 mg, 0.789 mmol, 1.00 eq.), 5-(methoxycarbonyl)-1-methylpyrazol-3-ylboronic acid (216 mg, 1.183 mmol, 1.50 eq.), Cu(OAc)₂ (286 mg, 1.58 mmol, 2.00 eq.), trimethylamine (239 mg, 2.37 mmol, 3.00 eq.) and dichloromethane (50 mL). The mixture was stirred for 2 days at rt under an oxygen atmosphere. The reaction was quenched with water (100 mL). The mixture was extracted with dichloromethane (3×100 mL). The combined organic layers were dried over anhydrous sodium sulfate, filtered and concentrated under reduced pressure. The residue was purified by silica gel column chromatography, eluted with ethyl acetate:petroleum ether (2:1) to afford tert-butyl 5-benzyl-7-[5-(methoxycarbonyl)-1-methylpyrazol-3-yl]-8-oxo-2,3,7,12-tetraazatricyclo[7.4.0.0ˆ{2,6}]trideca-1(9),3,5-triene-12-carboxylate (32.7 mg, 8% yield) as a yellow solid. LCMS (ESI, m/z): 519 [M+H]⁺.

A 100 mL round-bottom flask was charged with tert-butyl 5-benzyl-7-[5-(methoxycarbonyl)-1-methylpyrazol-3-yl]-8-oxo-2,3,7,12-tetraazatricyclo[7.4.0.0ˆ{2,6}]trideca-1(9),3,5-triene-12-carboxylate (50.0 mg, 0.096 mmol, 1.00 eq.) and methanol (30 mL). Methylamine (30-33 wt % in absolute ethanol, 1.00 mL) was added dropwise. The solution was stirred for 6 h at rt and then concentrated under reduced pressure to afford tert-butyl 3-benzyl-4-(1-methyl-5-(methylcarbamoyl)-1H-pyrazol-3-yl)-5-oxo-5,6,7,9-tetrahydropyrazolo[1,5-a]pyrido[4,3-e]pyrimidine-8(4H)-carboxylate (27.0 mg, crude) as a yellow oil. LCMS (ESI, m/z): 518 [M+H]⁺.

A 100 mL round bottom flask was charged with tert-butyl 5-benzyl-7-[1-methyl-5-(methylcarbamoyl)pyrazol-3-yl]-8-oxo-2,3,7,12-tetraazatricyclo[7.4.0.0ˆ{2,6}]trideca-1(9),3,5-triene-12-carboxylate (100 mg, 0.193 mmol, 1.00 eq.), dichloromethane (30 mL) and trifluoroacetic acid (6 mL). The solution was stirred for 2 h at rt and then concentrated under reduced pressure to afford 3-(3-benzyl-5-oxo-6,7,8,9-tetrahydropyrazolo[1,5-a]pyrido[4,3-e]pyrimidin-4(5H)-yl)-N,1-dimethyl-1H-pyrazole-5-carboxamide trifluoroacetic acid salt (100 mg, crude) as a yellow oil. LCMS (ESI, m/z): 418 [M+H-TFA]⁺.

A 100 mL round bottom flask was charged with 5-{15-benzyl-8-oxo-2,3,7,12-tetraazatricyclo[7.4.0.0ˆ{2,6}]trideca-1(9),3,5-trien-7-yl}-N,2-dimethylpyrazole-3-carboxamide (100 mg, 0.188 mmol, 1.00 eq.), 4-bromo-3-(trifluoromethyl)benzoic acid (96.7 mg, 0.360 mmol, 1.91 eq.), EDCI (68.9 mg, 0.360 mmol, 1.91 eq.), HOBt (48.6 mg, 0.360 mmol, 1.91 eq.), DIEA (121 mg, 0.940 mmol, 5.00 eq.) and DMF (5 mL) at rt. The mixture was stirred for overnight at rt. The reaction was quenched with water (50 mL). The mixture was extracted with ethyl acetate (3×100 mL). The organic layers were combined, washed with water (3×100 mL), dried over anhydrous sodium sulfate, filtered and concentrated under reduced pressure. The mixture was concentrated under reduced pressure. The residue was purified by silica gel column chromatography, eluted with ethyl acetate:petroleum (9:1) to afford the crude product. Then the product was separated by prep-HPLC: Column: XBridge Shield $RP_{18}$ OBD Column, 19×150 mm, 5 um; Mobile Phase A: Water (10 mmol/L $NH_4HCO_3$+0.1% $NH_3 \cdot H_2O$), Mobile Phase B: ACN; Flow rate: 25 mL/min; Gradient: 45% B to 65% B in 9 min to afford 5-{15-benzyl-12-[4-bromo-3-(trifluoromethyl)benzoyl]-8-oxo-2,3,7,12-tetraazatricyclo[7.4.0.0^{2,6}]trideca-1 (9),3,5-trien-7-yl}-N,2-dimethylpyrazole-3-carboxamide (29) (12.8 mg, 10% yield). $^1$H NMR (300 MHz, $CDCl_3$) δ 7.83 (d, J=8.8 Hz, 2H), 7.52 (d, J=8.1 Hz, 2H), 7.17 (m, 3H), 6.83 (d, J=7.2 Hz, 2H), 6.17 (s, 1H), 5.84 (s, 1H), 5.14 (s, 2H), 4.09 (s, 3H), 3.73 (s, 2H), 3.30 (s, 2H), 2.87 (d, J=4.8 Hz, 3H), 2.73 (s, 2H). LCMS (ESI, m/z): 668 [M+H]$^+$.

Example 32

5-benzyl-12-[4-bromo-3-(trifluoromethyl)benzoyl]-7-[3-(methylamino)-[1,2,4]triazolo[4,3-a]pyridin-7-yl]-2,3,7,12-tetrazatricyclo[7.4.0.0^2,6]trideca-1(9),3,5-trien-8-one (30)

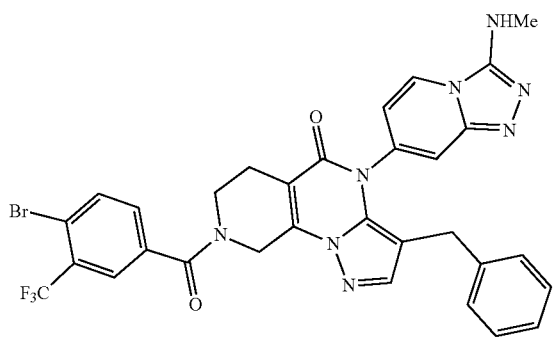

The title compound was obtained following a similar procedure reported in Example 25, using 4-bromo-3-(trifluoromethyl)benzoic acid in place of 4-bromo-3-chlorobenzoic acid in the last step. LCMS (ESI, m/z): 679.10 [M+H]$^+$ Br pattern. $^1$H NMR (300 MHz, $CDCl_3$) δ 7.84 (d, J=8.1 Hz 2H), 7.60-7.50 (m, 2H), 7.41 (s, 1H), 7.31 (d, J=7.2 1H), 7.12-6.90 (m, 4H), 6.51 (d, J=7.2 Hz 2H), 6.25-6.00 (m, 1H), 5.42-4.70 (m, 2H), 4.46-4.22 (m, 1H), 3.80-3.60 (m, 2H), 3.35 (d, J=16.5 Hz 1H), 3.25 (s, 3H), 2.73 (br s, 2H).

Example 33

5-benzyl-12-(4-bromo-3-chloro-benzoyl)-7-[4-(4,5-dimethyl-1,2,4-triazol-3-yl)phenyl]-2,3,7,12-tetrazatricyclo[7.4.0.0^2,6]trideca-1(9),3,5-trien-8-one (31)

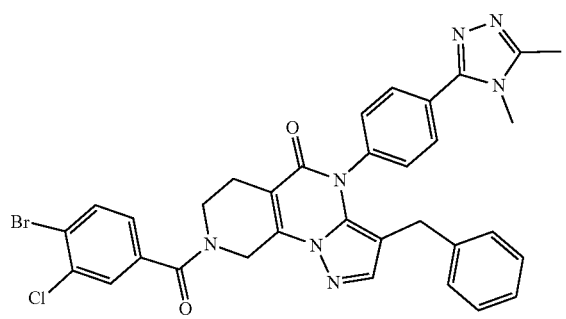

The title compound was obtained following a similar procedure reported in Example 2, using (4-(4,5-dimethyl-4H-1,2,4-triazol-3-yl)phenyl)boronic acid in place of (4-(4-methyl-4H-1,2,4-triazol-3-yl)phenyl)boronic acid. LCMS (ESI, m/z): 670.10 [M+H]$^+$ Br pattern. $^1$H NMR (300 MHz, $CDCl_3$) δ 7.73 (d, J=8.2 Hz, 1H), 7.67-7.62 (m, 3H), 7.48 (br s, 1H), 7.32-7.27 (m, 3H), 7.17-7.05 (m, 3H), 6.71 (d, J=6.5 Hz, 2H), 5.20-4.75 (m, 2H), 3.79 (m, 2H), 3.60 (s, 3H), 3.15 (s, 2H), 2.74 (br s, 2H), 2.54 (s, 3H).

Example 34

5-benzyl-12-[4-bromo-3-(trifluoromethyl)benzoyl]-7-[4-(4,5-dimethyl-1,2,4-triazol-3-yl)phenyl]-2,3,7,12-tetrazatricyclo[7.4.0.0^2,6]trideca-1(9),3,5-trien-8-one (32)

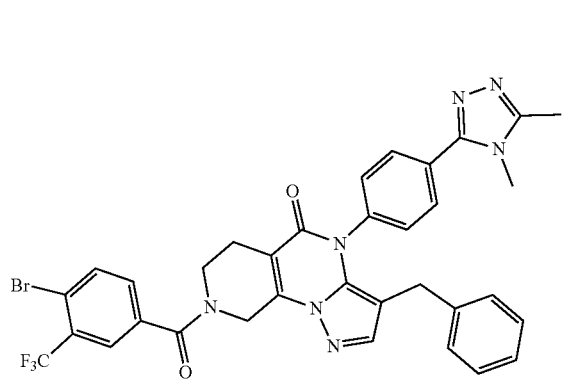

The title compound was obtained following a similar procedure reported in Example 1, using (4-(4,5-dimethyl-4H-1,2,4-triazol-3-yl)phenyl)boronic acid in place of 4-(methylcarbamoyl)phenylboronic acid. LCMS (ESI, m/z): 704.15 [M+H]$^+$ Br pattern. $^1$H NMR (300 MHz, $CDCl_3$) δ 7.84 (d, J=8.4 Hz, 2H), 7.66 (d, J=8.1 Hz, 2H), 7.57-7.44 (m, 2H), 7.31 (d, J=8.1 Hz, 2H), 7.18-7.06 (m, 3H), 6.70 (d, J=6.5 Hz, 2H), 5.23-4.75 (m, 2H), 3.81 (m, 2H), 3.61 (s, 3H), 3.16 (s, 2H), 2.75 (br s, 2H), 2.55 (s, 3H).

Example 35

5-benzyl-12-[4-bromo-3-(trifluoromethyl)benzoyl]-7-[4-(3-methylimidazol-4-yl)phenyl]-2,3,7,12-tetrazatricyclo[7.4.0.0^2,6]trideca-1(9),3,5-trien-8-one (33)

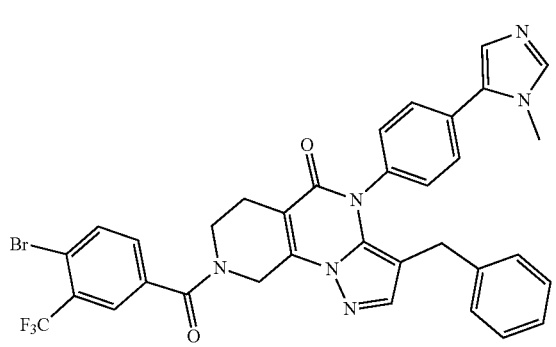

The title compound was obtained following a similar procedure reported in Example 1, using (4-(1-methyl-1H-imidazol-5-yl)phenyl)boronic acid in place of 4-(methylcarbamoyl)phenylboronic acid. LCMS (ESI, m/z): 689.10 [M+H]$^+$ Br pattern. $^1$H NMR (300 MHz, CDCl$_3$) δ 7.91-7.78 (m, 2H), 7.61 (s, 1H), 7.53 (d, J=8.9 Hz, 2H), 7.42-7.32 (m, 2H), 7.25-7.16 (m, 3H), 7.16-7.07 (m, 3H), 6.75-6.63 (m, 2H), 5.25-4.75 (m, 2H), 3.84 (m, 2H), 3.69 (s, 3H), 3.18 (s, 2H), 2.76 (br s, 2H).

Example 36

5-benzyl-12-[4-bromo-3-(trifluoromethyl)benzoyl]-7-[4-(5-methyltriazol-1-yl)phenyl]-2,3,7,12-tetrazatricyclo[7.4.0.0^2,6]trideca-1(9),3,5-trien-8-one (34)

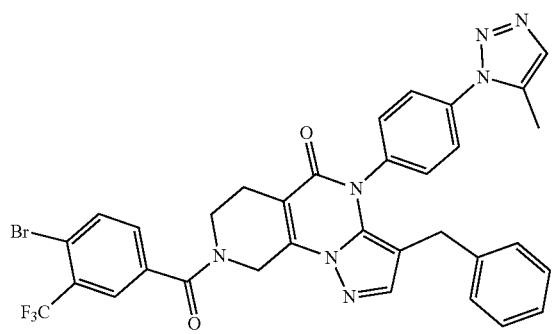

The title compound was obtained following a similar procedure reported in Example 1, using (4-(5-methyl-1H-1,2,3-triazol-1-yl)phenyl)boronic acid in place of 4-(methylcarbamoyl)phenylboronic acid. LCMS (ESI, m/z): 688.20 [M+H]$^+$ Br pattern. $^1$H NMR (300 MHz, CDCl$_3$) δ 7.84 (d, J=8.7 Hz, 2H), 7.61 (d, J=1.0 Hz, 1H), 7.54 (d, J=7.2 Hz, 2H), 7.50-7.43 (m, 2H), 7.35-7.27 (m, 2H), 7.20-6.99 (m, 3H), 6.80-6.57 (m, 2H), 5.25-4.75 (m, 2H), 4.1-3.65 (m, 2H), 3.23 (s, 2H), 2.76 (br s, 2H), 2.39 (s, 3H).

Example 37

5-benzyl-12-[4-bromo-3-(trifluoromethyl)benzoyl]-7-[4-(4-methyl-1H-triazol-5-yl)phenyl]-2,3,7,12-tetrazatricyclo[7.4.0.0^2,6]trideca-1(9),3,5-trien-8-one (35)

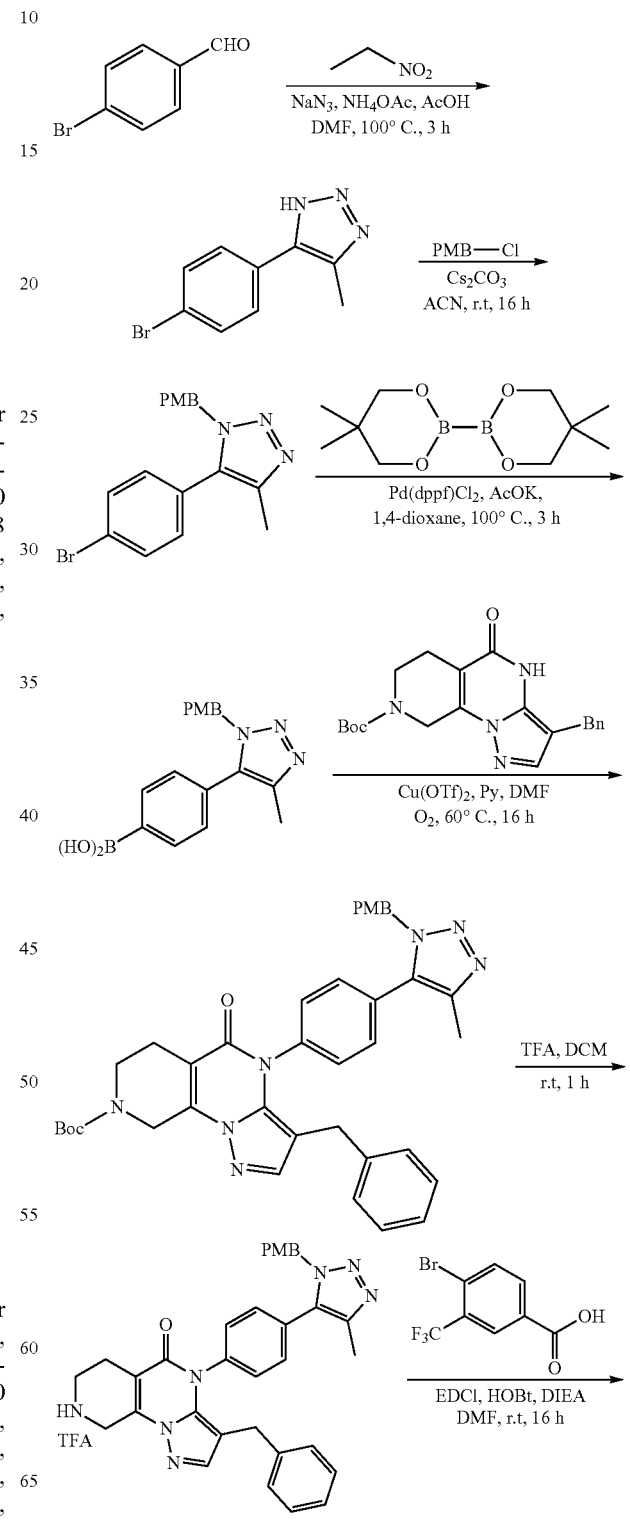

-continued

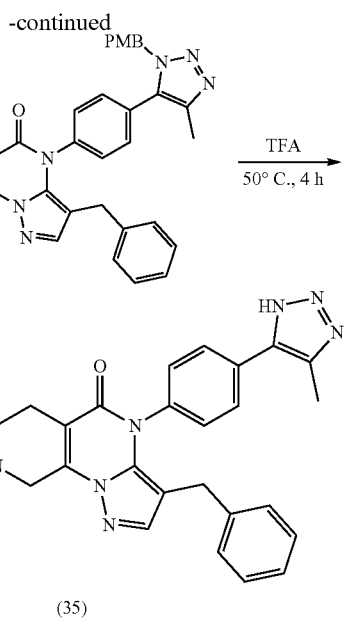

(35)

To a mixture of 4-bromobenzaldehyde (19.0 g, 103 mmol, 1.00 eq.), nitroethane (22.0 mL, 308 mmol, 3.00 eq.), NH₄OAc (8.01 g, 103 mmol, 1.00 eq.) and sodium azide (8.37 g, 128 mmol, 1.25 eq.) in DMF (1 L) was added dropwise acetic acid (1.50 mL, 25.7 mmol, 0.25 eq.) carefully under nitrogen. The mixture was stirred for 3 h at 100° C. under nitrogen. The reaction was quenched with water (2 L). The mixture was extracted with ethyl acetate (3×1 L). The organic layers were combined, washed with water (3×1 L), dried over anhydrous sodium sulfate, filtered and concentrated under reduced pressure. The residue was purified by silica gel column chromatography, eluted with 0-53% ethyl acetate in petroleum ether to afford 5-(4-bromophenyl)-4-methyl-1H-1,2,3-triazole (20.9 g, 86% yield) as a yellow solid. LCMS (ESI, m/z): 238 [M+H]⁺.

To a mixture of 5-(4-bromophenyl)-4-methyl-1H-1,2,3-triazole (20.9 g, 87.8 mmol, 1.00 eq.) and Cs₂CO₃ (114 g, 351 mmol, 4.00 eq.) in acetonitrile (1 L) was added dropwise 1-(chloromethyl)-4-methoxybenzene (41.4 g, 263 mmol, 3.00 eq.) at 0° C. The mixture was stirred for 16 h at rt. The reaction was quenched with water (2 L). The mixture was extracted with ethyl acetate (3×1 L). The organic layers were combined, washed with water (3×1 L), dried over anhydrous sodium sulfate, filtered and concentrated under reduced pressure. The residue was purified by silica gel column chromatography, eluted with 0-20% ethyl acetate in petroleum ether to afford 5-(4-bromophenyl)-1-(4-methoxybenzyl)-4-methyl-1H-1,2,3-triazole (18.2 g, 58% yield) as a yellow solid. LCMS (ESI, m/z): 358 [M+H]⁺.

To a mixture of 5-(4-bromophenyl)-1-(4-methoxybenzyl)-4-methyl-1H-1,2,3-triazole (7.16 g, 20.0 mmol, 1.00 eq.), 5,5,5',5'-tetramethyl-2,2'-bi(1,3,2-dioxaborinane) (9.04 g, 40.00 mmol, 2.00 eq.) and potassium acetate (9.82 g, 100 mmol, 5.00 eq.) in 1,4-dioxane (140 mL) was added Pd(dppf)Cl₂·CH₂Cl₂ (1.63 g, 2.00 mmol, 0.10 eq.). The mixture was stirred for 3 h at 100° C. The solids were filtered off. The filtrate was concentrated under reduced pressure. The residue was purified by silica gel column chromatography, eluted with 0-32% ethyl acetate in petroleum ether to afford the corresponding boronic ester. The corresponding boronic ester was purified by reverse phase chromatography with following condition: Column: Agela C₁₈ Column, 330 g; Mobile Phase A: Water (0.05% TFA), Mobile Phase B: ACN; Flow rate: 60 mL/min; Gradient: 0% B to 72% B in 40 min to afford (4-(1-(4-methoxybenzyl)-4-methyl-1H-1,2,3-triazol-5-yl)phenyl)boronic acid (5.01 g, 78% yield) as a gray white solid. LCMS (ESI, m/z): 324 [M+H]⁺.

To a mixture of tert-butyl 3-benzyl-5-oxo-5,6,7,9-tetrahydropyrazolo[1,5-a]pyrido[4,3-e]pyrimidine-8(4H)-carboxylate (5.16 g, 13.6 mmol, 1.00 eq.) and (4-(1-(4-methoxybenzyl)-4-methyl-1H-1,2,3-triazol-5-yl)phenyl) boronic acid (4.82 g, 14.9 mmol, 1.10 eq.) in DMF (100 mL) were added copper (II) trifluoromethanesulfonate (9.82 g, 27.1 mmol, 2.00 eq.) and pyridine (5.5 mL, 67.8 mmol, 5.00 eq.) at rt. The mixture was stirred for 16 h at 60° C. under oxygen and then concentrated under reduced pressure. The residue was purified by silica gel column chromatography, eluted with 0-68% ethyl acetate in petroleum ether. The product was re-purified by reverse phase chromatography with following condition: Column: Agela C₁₈ Column, 330 g; Mobile Phase A: Water (10 mM NH₄HCO₃), Mobile Phase B: ACN; Flow rate: 60 mL/min; Gradient: 0% B to 89% B in 40 min to afford tert-butyl 3-benzyl-4-(4-(1-(4-methoxybenzyl)-4-methyl-1H-1,2,3-triazol-5-yl)phenyl)-5-oxo-5,6,7,9-tetrahydropyrazolo[1,5-a]pyrido[4,3-e]pyrimidine-8(4H)-carboxylate (3.10 g, 35% yield) as a light yellow solid. LCMS (ESI, m/z): 658 [M+H]⁺.

To a solution of tert-butyl 3-benzyl-4-(4-(1-(4-methoxybenzyl)-4-methyl-1H-1,2,3-triazol-5-yl)phenyl)-5-oxo-5,6,7,9-tetrahydropyrazolo[1,5-a]pyrido[4,3-e]pyrimidine-8(4H)-carboxylate (3.10 g, 4.72 mmol, 1.00 eq.) in DCM (135 mL) was added TFA (27 mL) dropwise at 0° C. The mixture was stirred for 1 h at rt, and then concentrated under reduced pressure to afford 3-benzyl-4-(4-(1-(4-methoxybenzyl)-4-methyl-1H-1,2,3-triazol-5-yl)phenyl)-6,7,8,9-tetrahydropyrazolo[1,5-a]pyrido[4,3-e]pyrimidin-5(4H)-one trifluoroacetic acid salt (3.20 g, crude) as a light brown oil, which was used in the next step without any further purification. LCMS (ESI, m/z): 558 [M+H-TFA]±.

To a solution of 3-benzyl-4-(4-(1-(4-methoxybenzyl)-4-methyl-1H-1,2,3-triazol-5-yl)phenyl)-6,7,8,9-tetrahydropyrazolo[1,5-a]pyrido[4,3-e]pyrimidin-5(4H)-one trifluoroacetic acid salt (3.20 g, 4.76 mmol assumed, 1.00 eq.) and 4-bromo-3-(trifluoromethyl)benzoic acid (1.52 g, 5.66 mmol, 1.19 eq.) in DMF (90 mL) were added EDCI (2.26 g, 11.8 mmol, 2.48 eq.), HOBt (1.91 g, 14.2 mmol, 2.98 eq.) and DIEA (6.14 g, 47.6 mmol, 10.0 eq.) at 0° C. The mixture was stirred for 16 h at rt. The reaction was quenched with water (400 mL). The mixture was extracted with ethyl acetate (3×1 L). The organic layers were combined, washed with water (3×1 L), dried over anhydrous sodium sulfate, filtered and concentrated under reduced pressure. The residue was purified by silica gel column chromatography, eluted with 0-74% ethyl acetate in petroleum ether to afford 3-benzyl-8-(4-bromo-3-(trifluoromethyl)benzoyl)-4-(4-(1-(4-methoxybenzyl)-4-methyl-1H-1,2,3-triazol-5-yl)phenyl)-6,7,8,9-tetrahydropyrazolo[1,5-a]pyrido[4,3-e]pyrimidin-5(4H)-one (3.15 g, 82% yield) as a light yellow solid. LCMS (ESI, m/z): 808 [M+H]⁺.

A suspension of 3-benzyl-8-(4-bromo-3-(trifluoromethyl)benzoyl)-4-(4-(1-(4-methoxybenzyl)-4-methyl-1H-1,2,3-triazol-5-yl)phenyl)-6,7,8,9-tetrahydropyrazolo[1,5-a]pyrido[4,3-e]pyrimidin-5(4H)-one (3.15 g, 3.90 mmol, 1.0 eq.) in TFA (100 mL) was stirred for 4 h at 50° C. and then concentrated under reduced pressure. The residue was purified by reverse phase chromatography with following condition: Column: Agela C₁₈ Column, 330 g; Mobile Phase A: Water (10 mmol/L NH₄HCO₃), Mobile Phase B: ACN; Flow rate: 60 mL/min; Gradient: 0% B to 80% B in 50 min to afford 3-benzyl-8-(4-bromo-3-(trifluoromethyl)benzoyl)-4-(4-(4-methyl-1H-1,2,3-triazol-5-yl)phenyl)-6,7,8,9-tetrahydropyrazolo[1,5-a]pyrido[4,3-e]pyrimidin-5(4H)-one (35) (2.0390 g, 76% yield) as an off-white solid. LCMS (ESI, m/z): 688 [M+H]$^+$. $^1$H NMR (400 MHz, CDCl$_3$) δ 7.88-7.83 (m, 2H), 7.64 (d, J=8.8 Hz, 2H), 7.56-7.49 (m, 2H), 7.21 (d, J=8.0 Hz, 2H), 7.15-7.10 (m, 3H), 6.71 (s, 2H), 5.40-4.80 (m, 2H), 4.30-3.50 (m, 2H), 3.13 (s, 2H), 2.68-2.58 (m, 2H), 2.42 (s, 3H).

Example 38

5-benzyl-12-[4-bromo-3-(trifluoromethyl)benzoyl]-7-[4-(5-methyl-1,2,4-triazol-1-yl)phenyl]-2,3,7,12-tetrazatricyclo[7.4.0.0^2,6]trideca-1(9),3,5-trien-8-one (36)

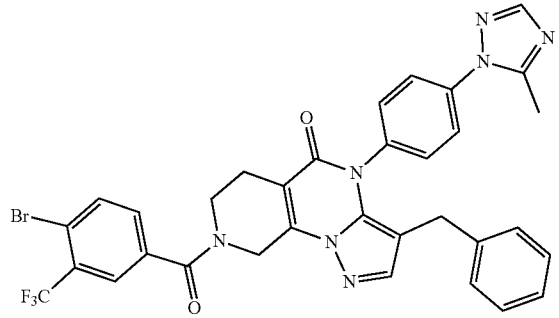

The title compound was obtained following a similar procedure reported in Example 1, using (4-(5-methyl-1H-1,2,4-triazol-1-yl)phenyl)boronic acid in place of 4-(methylcarbamoyl)phenylboronic acid. LCMS (ESI, m/z): 688.10 [M+H]$^+$ Br pattern. $^1$H NMR (300 MHz, CDCl$_3$) δ 8.02 (s, 1H), 7.89-7.83 (m, 2H), 7.56 (d, J=8.2 Hz, 2H), 7.50 (d, J=8.2 Hz, 2H), 7.34-7.25 (m, 2H), 7.20-7.12 (m, 3H), 6.74 (m, 2H), 5.30-4.75 (m, 2H), 4.20-3.65 (m, 2H), 3.23 (s, 2H), 2.78 (br s, 2H), 2.61 (s, 3H).

Example 39

N-methyl-4-[rac-(11R)-12-[4-bromo-3-(trifluoromethyl)benzoyl]-5-(cyclobutylmethyl)-11-methyl-8-oxo-2,3,7,12-tetrazatricyclo[7.4.0.0^2,6]trideca-1(9),3,5-trien-7-yl]benzamide (37a) and N-methyl-4-[rac-(11S)-12-[4-bromo-3-(trifluoromethyl)benzoyl]-5-(cyclobutylmethyl)-11-methyl-8-oxo-2,3,7,12-tetrazatricyclo[7.4.0.0^2,6]trideca-1(9),3,5-trien-7-yl]benzamide (37b)

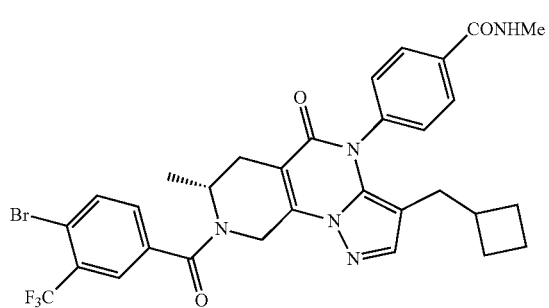

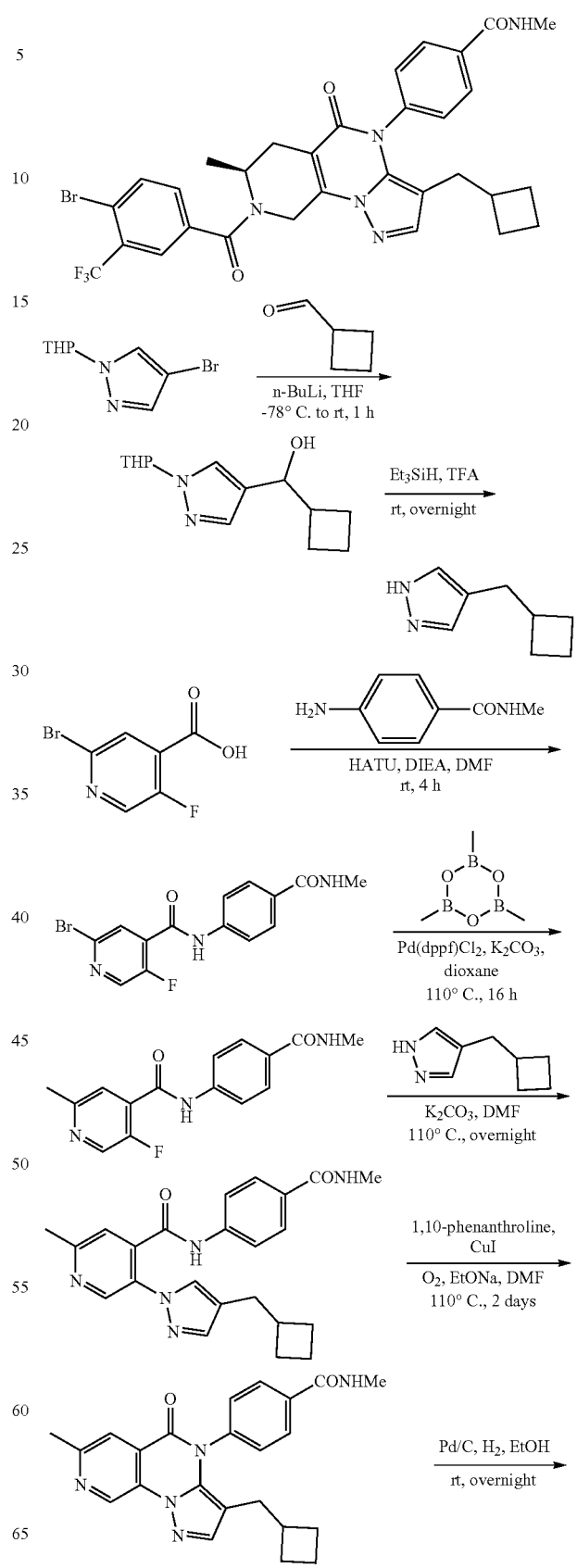

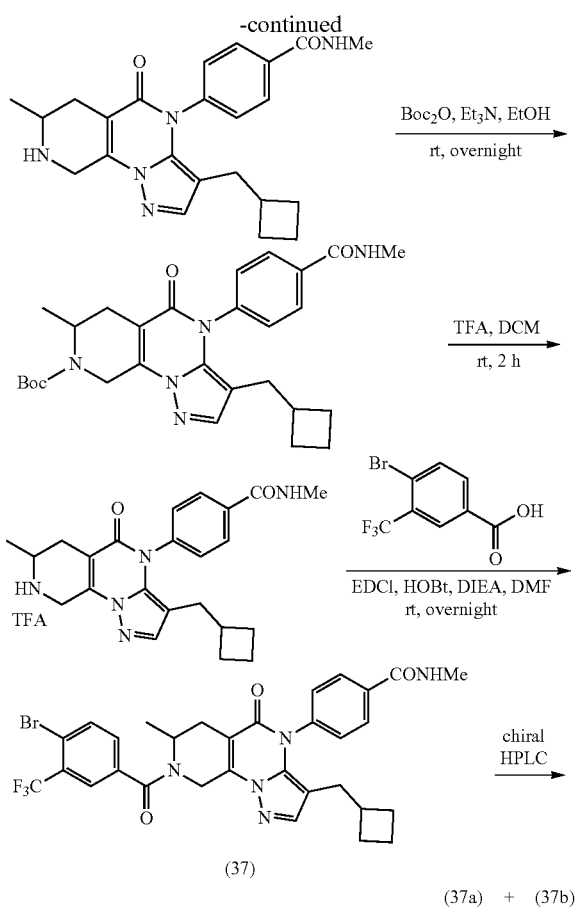

A 250 mL round-bottom flask was charged with 4-bromo-1-(oxan-2-yl)pyrazole (2.50 g, 10.8 mmol, 1.00 eq.) and THF (40 mL) at −78° C. n-BuLi (4.76 mL, 11.9 mmol, 1.10 eq., 2.5 M in hexane) was added at −78° C. The mixture was stirred for 0.5 h at −78° C. under a nitrogen atmosphere. Cyclobutyral (1.00 g, 11.9 mmol, 1.10 eq.) was added at −78° C. The mixture was stirred for 1 h at −78° C. The reaction was quenched with methanol (10 mL) at rt. The mixture was concentrated under reduced pressure. The residue was purified by silica gel column chromatography, eluted with dichloromethane:methanol (10:1) to afford cyclobutyl[1-(oxan-2-yl)pyrazol-4-yl]methanol (2.20 g, 86% yield) as a yellow solid. LCMS (ESI, m/z): 237 [M+H]⁺.

A 250 mL round-bottom flask was charged with cyclobutyl[1-(oxan-2-yl)pyrazol-4-yl]methanol (2.50 g, 10.6 mmol, 1.00 eq.), trifluoroacetic acid (10 mL) and triethylsilane (10 mL) at rt. The mixture was stirred for overnight at rt and then concentrated under reduced pressure. The reaction was quenched with water (40 mL) and extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with ethyl acetate to afford 4-(cyclobutylmethyl)-1H-pyrazole (1.20 g, 83% yield) as a yellow solid. LCMS (ESI, m/z): 137 [M+H]⁺.

A 250 mL round-bottom flask was charged with 2-bromo-5-fluoropyridine-4-carboxylic acid (4.00 g, 18.2 mmol, 1.00 eq.), 4-amino-N-methylbenzamide (3.00 g, 20.0 mmol, 1.1 eq.), HATU (7.60 g, 20.0 mmol, 1.10 eq.), N,N-diisopropylethylamine (4.68 g, 36.2 mmol, 1.99 eq.) and DMF (50 mL) at rt. The mixture was stirred for 4 h at rt. The reaction was quenched with water (60 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with dichloromethane:methanol (10:1) to afford 2-bromo-5-fluoro-N-[4-(methylcarbamoyl)phenyl]pyridine-4-carboxamide (4.20 g, 66% yield) as a yellow solid. LCMS (ESI, m/z): 352 [M+H]⁺.

A 100 mL round-bottom flask was charged with 2-bromo-5-fluoro-N-[4-(methylcarbamoyl)phenyl]pyridine-4-carboxamide (3.00 g, 8.52 mmol, 1.00 eq.), trimethyl-1,3,5,2,4,6-trioxatriborinane (10.7 g, 42.6 mmol, 5.00 eq., 50% wt in THF), K₂CO₃ (3.53 g, 25.6 mmol, 3.00 eq.), 1, 1'-bis(diphenylphosphino)ferrocene palladium(II)dichloride (623 mg, 0.852 mmol, 0.10 eq.) and 1,4-dioxane (50 mL). The mixture was stirred for 16 h at 110° C. under a nitrogen atmosphere. The reaction was quenched with water (200 mL). The mixture was extracted with ethyl acetate (3×200 mL). The organic layers were combined, washed with water (3×100 mL), dried over anhydrous sodium sulfate, filtered and concentrated under reduced pressure. The residue was purified by silica gel column chromatography, eluted with dichloromethane:methanol (12:1) to afford 5-fluoro-2-methyl-N-[4-(methylcarbamoyl)phenyl]pyridine-4-carboxamide (2.20 g, 80% yield) as a yellow solid. LCMS (ESI, m/z): 288 [M+H]⁺.

A 100 mL round-bottom flask was charged with 5-fluoro-2-methyl-N-[4-(methylcarbamoyl)phenyl]pyridine-4-carboxamide (2.20 g, 7.66 mmol, 1.00 eq.), potassium carbonate (3.17 g, 23.0 mmol, 3.00 eq.), 4-(cyclobutylmethyl)-1H-pyrazole (1.20 g, 8.76 mmol, 1.14 eq.) and DMF (20 mL) at rt. The mixture was stirred for overnight at 110° C. under an oxygen atmosphere. The reaction was quenched with water (100 mL). The mixture was stirred for 4 h at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate to afford 5-[4-(cyclobutylmethyl)pyrazol-1-yl]-2-methyl-N-[4-(methylcarbamoyl)phenyl]pyridine-4-carboxamide (2.10 g, 68% yield) as a yellow solid. LCMS (ESI, m/z): 404 [M+H]⁺.

A 250 mL round-bottom flask was charged with 5-[4-(cyclobutylmethyl)pyrazol-1-yl]-2-methyl-N-[4-(methylcarbamoyl)phenyl]pyridine-4-carboxamide (2.00 g, 4.96 mmol, 1.00 eq.), copper(I) iodide (0.280 g, 1.49 mmol, 0.30 eq.), 1,10-phenanthroline (0.268 g, 1.49 mmol, 0.30 eq.), sodium ethylate (1.01 g, 14.9 mmol, 3.00 eq.) and DMF (20 mL) at rt. The mixture was stirred for 2 days at 110° C. under an oxygen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with dichloromethane:methanol (10:1) to afford 4-(3-(cyclobutylmethyl)-7-methyl-5-oxopyrazolo[1,5-a]pyrido[4,3-e]pyrimidin-4(5H)-yl)-N-methylbenzamide (780 mg, 39% yield) as a yellow solid. LCMS (ESI, m/z): 402 [M+H]⁺.

A 100 mL round-bottom flask was charged with 4-(3-(cyclobutylmethyl)-7-methyl-5-oxopyrazolo[1,5-a]pyrido

[4,3-e]pyrimidin-4(5H)-yl)-N-methylbenzamide (760 mg, 1.89 mmol, 1.00 eq.), ethanol (100 mL) and 10% Pd/C (200 mg) at rt. The mixture was stirred for overnight at rt under a hydrogen atmosphere (2-3 atm). The solids were filtered off, and the filter cake was washed with dichloromethane (2×50 mL). The filtrate was concentrated under reduced pressure. The residue was purified by reverse flash chromatography with the following conditions: column, Agela $C_{18}$ Column; mobile phase, Mobile Phase A: Water, Mobile Phase B: ACN; Flow rate: 60 mL/min; Gradient: 0% B to 72% B in 40 min to afford 4-(3-(cyclobutylmethyl)-7-methyl-5-oxo-6,7,8,9-tetrahydropyrazolo[1,5-a]pyrido[4,3-e]pyrimidin-4(5H)-yl)-N-methylbenzamide (630 mg, 82% yield) as a yellow solid. LCMS (ESI, m/z): 406 [M+H]$^+$.

A 100 mL round-bottom flask were charged with 4-(3-(cyclobutylmethyl)-7-methyl-5-oxo-6,7,8,9-tetrahydropyrazolo[1,5-a]pyrido[4,3-e]pyrimidin-4(5H)-yl)-N-methylbenzamide (600 mg, 1.48 mmol, 1.00 eq.), triethylamine (449 mg, 4.44 mmol, 3.00 eq.) and ethanol (30 mL) at rt. The mixture was stirred overnight at rt and then concentrated under reduced pressure. The residue was purified by prep-TLC with ethyl acetate to afford tert-butyl 3-(cyclobutylmethyl)-7-methyl-4-(4-(methylcarbamoyl)phenyl)-5-oxo-5,6,7,9-tetrahydropyrazolo[1,5-a]pyrido[4,3-e]pyrimidine-8(4H)-carboxylate (530 mg, 71% yield) as a yellow solid. LCMS (ESI, m/z): 506 [M+H]$^+$.

A 100 mL round-bottom flask were added tert-butyl 3-(cyclobutylmethyl)-7-methyl-4-(4-(methylcarbamoyl)phenyl)-5-oxo-5,6,7,9-tetrahydropyrazolo[1,5-a]pyrido[4,3-e]pyrimidine-8(4H)-carboxylate (530 mg, 1.05 mmol, 1.00 eq.), trifluoroacetic acid (2 mL) and dichloromethane (5 mL) at rt. The mixture was stirred for 2 h at rt and then concentrated under reduced pressure to afford 4-(3-(cyclobutylmethyl)-7-methyl-5-oxo-6,7,8,9-tetrahydropyrazolo[1,5-a]pyrido[4,3-e]pyrimidin-4(5H)-yl)-N-methylbenzamide trifluoroacetic acid salt (528 mg, crude) as a yellow oil. LCMS (ESI, m/z): 406 [M+H-TFA]$^+$.

A 40 mL vial were added 4-bromo-3-(trifluoromethyl)benzoic acid (343 mg, 1.28 mmol, 1.30 eq.), 4-(3-(cyclobutylmethyl)-7-methyl-5-oxo-6,7,8,9-tetrahydropyrazolo[1,5-a]pyrido[4,3-e]pyrimidin-4(5H)-yl)-N-methylbenzamide trifluoroacetic acid salt (510 mg, 0.981 mmol, 1.00 eq.), N-(3-dimethylaminopropyl)-N'-ethylcarbodiimide hydrochloride (245 mg, 1.28 mmol, 1.30 eq.), 1-hydroxybenzotrizole (172 mg, 1.28 mmol, 1.30 eq.), DIEA (634 mg, 4.91 mmol, 5.00 eq.) and DMF (8 mL) at rt. The mixture was stirred overnight at rt. The reaction was quenched with water (50 mL). The mixture was extracted with ethyl acetate (3×100 mL). The organic layers were combined, washed with water (3×100 mL), dried over anhydrous sodium sulfate, filtered and concentrated under reduced pressure. The residue was purified by prep-TLC with ethyl acetate to afford the crude product. The crude product was purified by prep-Chiral-HPLC with the following conditions: Column: CHIRAL ART Amylose-SA, 2×25 cm, 5 μm; Mobile Phase A: MtBE (0.5% 2M NH$_3$-MeOH)-HPLC, Mobile Phase B: EtOH-HPLC; Flow rate: 20 mL/min; Gradient: 30% B to 30% B in 16 min to afford (R)-4-(8-(4-bromo-3-(trifluoromethyl)benzoyl)-3-(cyclobutylmethyl)-7-methyl-5-oxo-6,7,8,9-tetrahydropyrazolo[1,5-a]pyrido[4,3-e]pyrimidin-4(5H)-yl)-N-methylbenzamide (37a) (the first eluting enantiomer, 92.0 mg, 14% yield) as a light yellow solid, and (37b) (the second eluting enantiomer, 92.0 mg, 14% yield). LCMS (ESI, m/z): 656 [M+H]$^+$. $^1$H NMR (300 MHz, CDCl$_3$) δ 7.98 (m, 2H), 7.90-7.78 (m, 2H), 7.59-7.35 (m, 4H), 6.29 (d, J=5.2 Hz, 1H), 4.47 (m, 2H), 3.08 (d, J=4.7 Hz, 3H), 2.91-2.61 (m, 2H), 2.20-2.07 (m, 1H), 1.98-1.53 (m, 7H), 1.43-1.27 (m, 5H).

Example 40

N-methyl-4-[rac-(11R)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]benzamide (38a) and N-methyl-4-[rac-(11S)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]benzamide (38b)

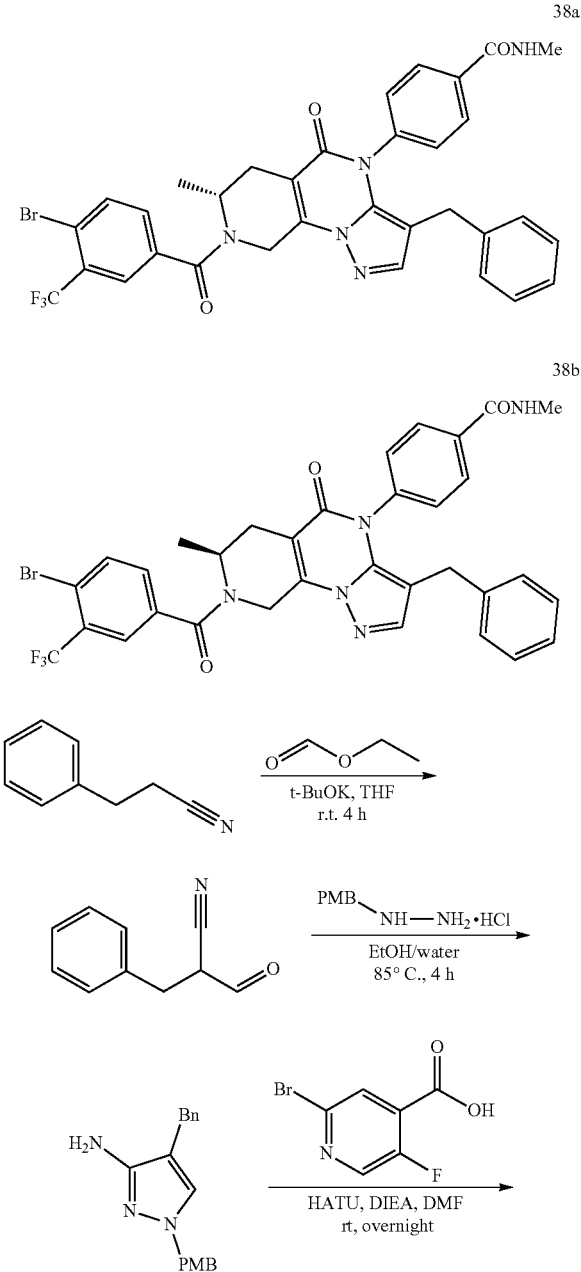

-continued

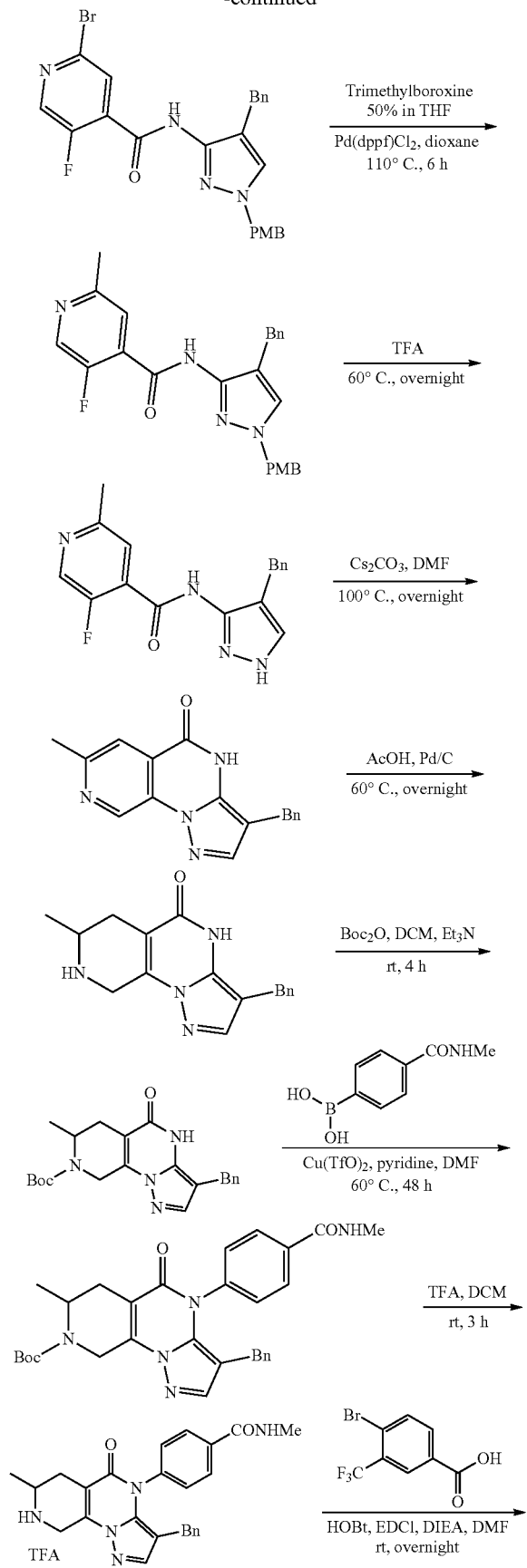

-continued

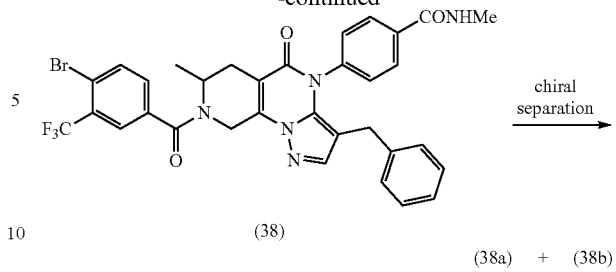

(38)

(38a) + (38b)

A 1 L round bottom flask was charged with benzylacetonitrile (25.0 g, 0.190 mol, 1.00 eq.) and anhydrous tetrahydrofuran (500 mL). The t-BuOK (64.1 g, 0.571 mol, 3.00 eq.) was added at 0° C. The mixture was stirred for 10 mins at rt. Ethyl formate (70.6 g, 0.954 mol, 5.00 eq.) was added dropwise at 0° C. The solution was stirred for 4 h at rt. The reaction was quenched with water (1 L). The mixture was extracted with ethyl acetate (3×500 mL). The combined organic layers were washed with brine (2×500 mL) and water (500 mL), dried over anhydrous sodium sulfate, filtered and concentrated under reduced pressure to afford 2-formyl-3-phenylpropanenitrile (30.0 g, crude) as a brown yellow oil.

A 1 L round bottom flask was charged with 2-formyl-3-phenylpropanenitrile (30.0 g, 188 mmol, 1.00 eq.), [(4-methoxyphenyl)methyl]hydrazine hydrochloride (35.5 g, 188 mmol, 1.00 eq.), EtOH (300 mL) and water (100 mL). The solution was stirred for 4 h at 80° C. and then concentrated under reduced pressure. The residue was diluted with ethyl acetate (1 L), washed with water (3×300 mL), dried over anhydrous sodium, filtered and concentrated under reduced pressure. The residue was purified by trituration with ethyl acetate (80 mL). The light yellow solid was collected by filtration and dried under reduced pressure to afford 4-benzyl-1-[(4-methoxyphenyl)methyl]pyrazol-3-amine (21.0 g, 38% yield) as a light yellow solid. LCMS (ESI, m/z): 294 [M+H]$^+$.

A 250 mL round bottom flask was charged with 4-benzyl-1-[(4-methoxyphenyl)methyl]pyrazol-3-amine (10.0 g, 34.1 mmol, 1.00 eq.), 2-bromo-5-fluoroisonicotinic acid (9.00 g, 40.9 mmol, 1.20 eq.), HATU (19.4 g, 51.1 mmol, 1.50 eq.), DIEA (13.2 g, 102 mmol, 3.00 eq.) and DMF (100 mL). The mixture was stirred for overnight at rt. The reaction was quenched with water (500 mL). The solids were collected by filtration and dried under reduced pressure to afford N-{4-benzyl-1-[(4-methoxyphenyl)methyl]pyrazol-3-yl}-2-bromo-5-fluoropyridine-4-carboxamide (14.5 g, 85% yield) as a light yellow solid. LCMS (ESI, m/z): 495 [M+H]$^+$.

A 500 mL three neck round bottom flask was charged with N-{4-benzyl-1-[(4-methoxyphenyl)methyl]pyrazol-3-yl}-2-bromo-5-fluoropyridine-4-carboxamide (14.3 g, 28.8 mmol, 1.00 eq.), trimethyl-1,3,5,2,4,6-trioxatriborinane (14.5 g, 57.7 mmol, 2.00 eq., 50% wt in THF), Pd(dppf)Cl$_2$ (1.06 g, 1.44 mmol, 0.05 eq.), K$_2$CO$_3$ (7.98 g, 57.7 mmol, 2.00 eq.) and 1,4-dioxane (200 mL). The solution was stirred for 6 h at 110° C. under nitrogen. The reaction was quenched with water (200 mL). The mixture was extracted with ethyl acetate (3×200 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford N-{4-benzyl-1-[(4-methoxyphenyl)methyl]

pyrazol-3-yl}-5-fluoro-2-methylpyridine-4-carboxamide (11.0 g, 88% yield) as a white solid. LCMS (ESI, m/z): 431 [M+H]$^+$.

A 100 mL round bottom flask was charged with N-{4-benzyl-1-[(4-methoxyphenyl)methyl]pyrazol-3-yl}-5-fluoro-2-methylpyridine-4-carboxamide (4.00 g, 9.29 mmol, 1.00 eq.) and trifluoroacetic acid (50 mL). The solution was stirred for overnight at 60° C. and then concentrated under reduced pressure to afford N-(4-benzyl-1H-pyrazol-3-yl)-5-fluoro-2-methylpyridine-4-carboxamide (3.50 g, crude) as a brown solid. LCMS (ESI, m/z): 311 [M+H]$^+$.

A 500 mL round bottom flask was charged with N-(4-benzyl-1H-pyrazol-3-yl)-5-fluoro-2-methylpyridine-4-carboxamide (3.50 g, 11.2 mmol, 1.00 eq.), Cs$_2$CO$_3$ (7.35 g, 22.5 mmol, 2.00 eq.) and DMF (50 mL). The solution was stirred for overnight at 100° C. The reaction was quenched with water (100 mL). The mixture was extracted with dichloromethane (3×100 mL). The organic layers were combined, washed with water (3×100 mL), dried over anhydrous sodium sulfate, filtered and concentrated under reduced pressure to afford 5-benzyl-11-methyl-2,3,7,12-tetraazatricyclo[7.4.0.0ˆ{2,6}]trideca-1(9),3,5,10,12-pentaen-8-one (2.50 g, 76% yield) as a light yellow solid. LCMS (ESI, m/z): 291 [M+H]$^+$.

A 250 mL round bottom flask was charged with 5-benzyl-11-methyl-2,3,7,12-tetraazatricyclo[7.4.0.0ˆ{2,6}]trideca-1(9),3,5,10,12-pentaen-8-one (1.00 g, 3.44 mmol, 1.00 eq.), 10% Pd/C (100 mg) and AcOH (50 mL). The solution was stirred for overnight at 60° C. under hydrogen atmosphere (2-3 atm). The solids were filtered off, and the mixture was washed with methanol (3×20 mL). The filtrate was concentrated under reduced pressure to afford 5-benzyl-11-methyl-2,3,7,12-tetraazatricyclo[7.4.0.0ˆ{2,6}]trideca-1(9),3,5-trien-8-one (1.00 g, 98% yield) as a colorless oil. LCMS (ESI, m/z): 295 [M+H]$^+$.

A 100 mL vial was charged with 5-benzyl-11-methyl-2,3,7,12-tetraazatricyclo[7.4.0.0ˆ{2,6}]trideca-1 (9),3,5-trien-8-one (1.00 g, 3.40 mmol, 1.00 eq.), Boc$_2$O (0.890 g, 4.07 mmol, 1.20 eq.), Et$_3$N (1.03 g, 10.2 mmol, 3.00 eq.) and dichloromethane (30 mL). The solution was stirred for 4 h at rt. The reaction was quenched with water (100 mL). The mixture was extracted with dichloromethane (3×100 mL). The organic layers were combined, dried over anhydrous sodium sulfate, filtered and concentrated under reduced pressure. The residue was purified by silica gel column chromatography, eluted with ethyl acetate:petroleum ether (1:1) to afford tert-butyl 5-benzyl-11-methyl-8-oxo-2,3,7,12-tetraazatricyclo[7.4.0.0ˆ{2,6}]trideca-1(9),3,5-triene-12-carboxylate (1.10 g, 82% yield) as a white solid. LCMS (ESI, m/z): 395 [M+H]$^+$.

A 100 mL round bottom flask was charged with tert-butyl 5-benzyl-11-methyl-8-oxo-2,3,7,12-tetraazatricyclo[7.4.0.0ˆ{2,6}]trideca-1(9),3,5-triene-12-carboxylate (500 mg, 1.26 mmol, 1.00 eq.), 4-(methylcarbamoyl)phenylboronic acid (453 mg, 2.54 mmol, 2.00 eq.), Cu(OTf)$_2$ (458 mg, 1.26 mmol, 1.00 eq.), pyridine (200 mg, 2.53 mmol, 2.00 eq.) and DMF (20 mL). The solution was stirred for 48 h at 60° C. under an oxygen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford tert-butyl 5-benzyl-11-methyl-7-[4-(methylcarbamoyl)phenyl]-8-oxo-2,3,7,12-tetraazatricyclo[7.4.0.0ˆ{2,6}]trideca-1(9),3,5-triene-12-carboxylate (260 mg, 39% yield) as a white solid. LCMS (ESI, m/z): 528 [M+H]$^+$.

A 100 mL round bottom flask was charged with tert-butyl 5-benzyl-11-methyl-7-[4-(methylcarbamoyl)phenyl]-8-oxo-2,3,7,12-tetraazatricyclo[7.4.0.0ˆ{2,6}]trideca-1(9),3,5-triene-12-carboxylate (260 mg, 0.492 mmol, 1.00 eq.), TFA (5 mL) and DCM (20 mL). The solution was stirred for 3 h at rt and then concentrated under reduced pressure to afford 4-{15-benzyl-11-methyl-8-oxo-2,3,7,12-tetraazatricyclo[7.4.0.0ˆ{2,6}]trideca-1(9),3,5-trien-7-yl}-N-methylbenzamide trifluoroacetic acid salt (261 mg, crude) as a brown solid. LCMS (ESI, m/z): 428 [M+H-TFA]$^+$.

A 40 mL vial were charged with 4-{15-benzyl-11-methyl-8-oxo-2,3,7,12-tetraazatricyclo[7.4.0.0ˆ{2,6}]trideca-1(9),3,5-trien-7-yl}-N-methylbenzamide trifluoroacetic acid salt (261 mg, 0.481 mmol, 1.00 eq.), 4-bromo-3-(trifluoromethyl)benzoic acid (196 mg, 0.730 mmol, 1.50 eq.), HOBt (123 mg, 0.912 mmol, 1.90 eq.), EDCI (174 mg, 0.912 mmol, 1.90 eq.), DIEA (314 mg, 2.43 mmol, 5.00 eq.) and DMF (10 mL). The solution was stirred for overnight at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (10:1) to afford the crude product. The crude product was purified by prep-Chiral-HPLC with the following conditions: Column: CHIRALPAK IA-3, 2×25 cm, 5 μm; Mobile Phase A: MtBE (0.5% 2M NH$_3$-MeOH)-HPLC, Mobile Phase B: EtOH-HPLC; Flow rate: 20 mL/min; Gradient: 30% B to 30% B in 20 min to afford 4-[(11R)-5-benzyl-12-[4-bromo-3-(trifluoromethyl)benzoyl]-11-methyl-8-oxo-2,3,7,12-tetraazatricyclo[7.4.0.0ˆ{2,6}]trideca-1(9),3,5-trien-7-yl]-N-methylbenzamide (38a) (the first eluting enantiomer, 69.2 mg, 21% yield) as a white solid, and (38b) (the second eluting enantiomer, 103 mg, 31% yield) as a white solid. $^1$H NMR (400 MHz, CDCl$_3$) δ 7.92-7.67 (m, 4H), 7.57-7.41 (m, 2H), 7.30-7.27 (m, 1H), 7.25-7.12 (m, 4H), 6.79-6.65 (m, 2H), 6.25 (m, 1H), 5.89 (s, 1H), 4.69-3.95 (m, 2H), 3.17-2.96 (m, 5H), 2.82 (d, J=17.3 Hz, 1H), 2.68 (d, J=17.2 Hz, 1H), 1.37 (d, J=6.9 Hz, 3H). LCMS (ESI, m/z): 678 [M+H]$^+$.

Example 41
4-[12-[4-bromo-3-(trifluoromethyl)benzoyl]-8-oxo-5-prop-2-ynyl-2,3,7,12-tetrazatricyclo[7.4.0.0^2,6]trideca-1(9),3,5-trien-7-yl]-N-methyl-benzamide (42)
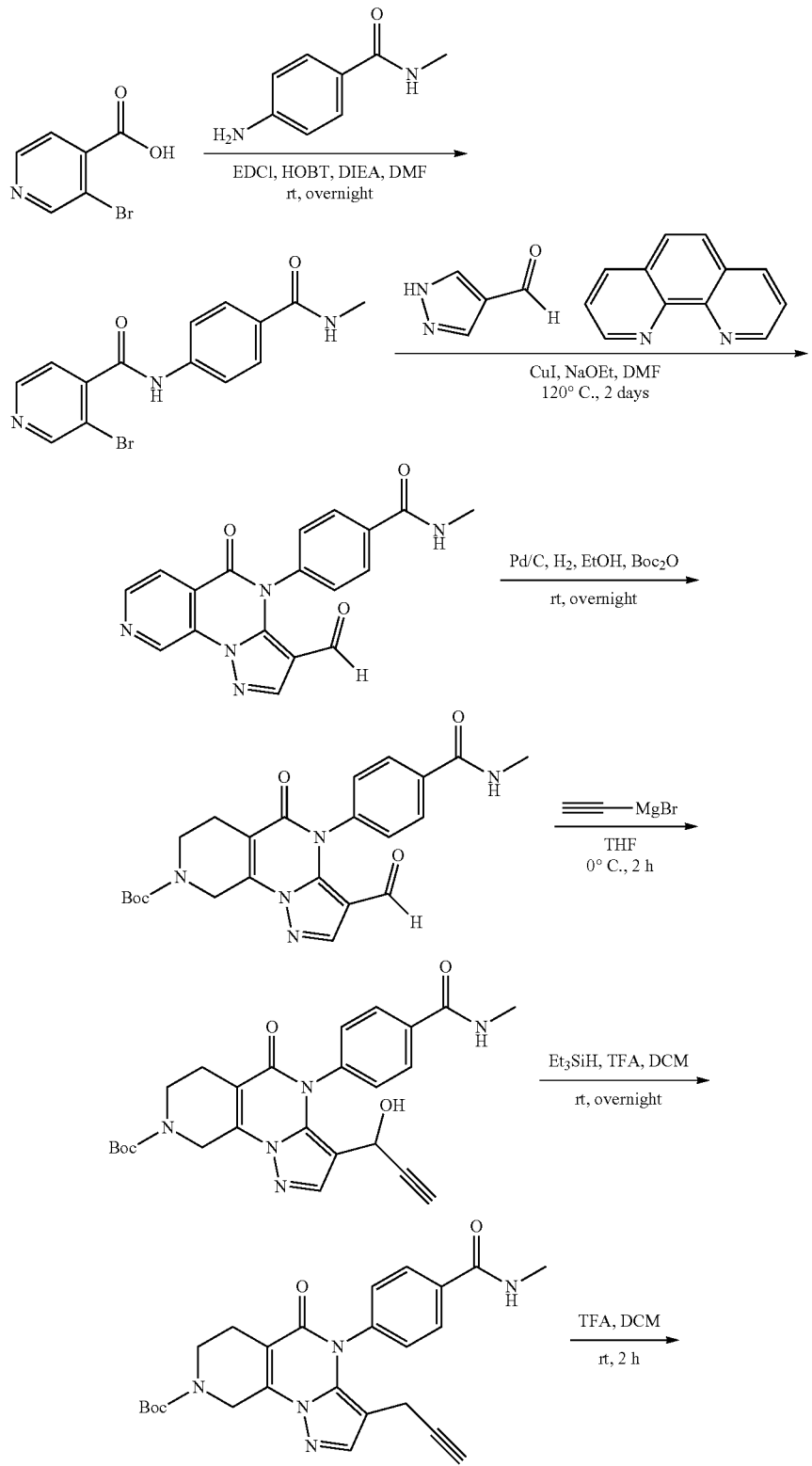

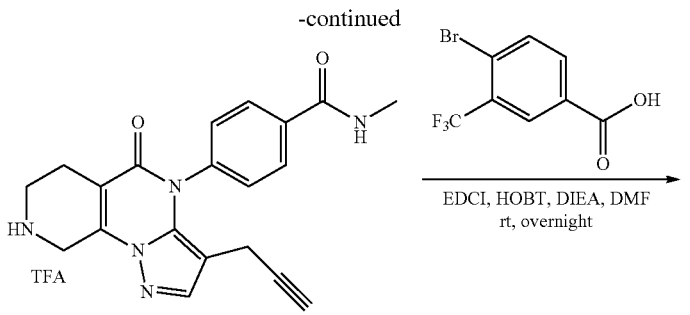

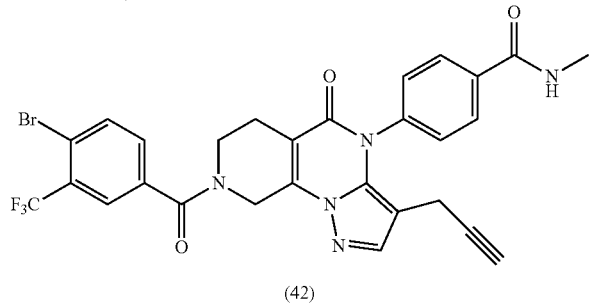

(42)

A 250 mL round bottom flask was charged with 3-bromopyridine-4-carboxylic acid (14.8 g, 73.3 mmol, 1.10 eq.), 4-amino-N-methylbenzamide (10.0 g, 66.7 mmol, 1.00 eq.), EDCI (15.3 g, 80.0 mmol, 1.20 eq.), HOBt (10.8 g, 80.0 mmol, 1.20 eq.), DIEA (26.0 g, 202 mmol, 3.00 eq.) and DMF (100 mL). The solution was stirred for overnight at rt. The reaction was quenched with water (200 mL). The mixture was extracted with ethyl acetate (3×200 mL). The organic layers were combined, washed with water (3×200 mL), dried over anhydrous sodium sulfate, filtered and concentrated under reduced pressure. The residue was purified by silica gel column chromatography, eluted with ethyl acetate:petroleum ether (9:1) to afford 3-bromo-N-[4-(methylcarbamoyl)phenyl]pyridine-4-carboxamide (6.50 g, 29% yield) as a white solid. LCMS (ESI, m/z): 334 [M+H]⁺.

A 250 mL round-bottom flask was charged with 3-bromo-N-[4-(methylcarbamoyl)phenyl]pyridine-4-carboxamide (5.00 g, 15.0 mmol, 1.00 eq.), 1H-pyrazole-4-carbaldehyde (1.44 g, 15.0 mmol, 1.00 eq.), 1,10-phenanthroline (0.540 g, 2.99 mmol, 0.20 eq.), copper(I) iodide (0.570 g, 2.99 mmol, 0.20 eq.), sodium ethylate (3.05 g, 44.9 mmol, 3.00 eq.) and DMF (100 mL) at rt. The mixture was stirred for 2 days at 120° C. under an oxygen atmosphere. The reaction was quenched with water (150 mL) at rt. The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate to afford 4-(3-formyl-5-oxopyrazolo[1,5-a]pyrido[4,3-e]pyrimidin-4(5H)-yl)-N-methylbenzamide (2.80 g, 54% yield) as a yellow solid. LCMS (ESI, m/z): 348 [M+H]⁺.

A 250 mL round-bottom flask was charged with 4-(3-formyl-5-oxopyrazolo[1,5-a]pyrido[4,3-e]pyrimidin-4(5H)-yl)-N-methylbenzamide (2.80 g, 8.06 mmol, 1.00 eq.), ethanol (100 mL), 10% Pd/C (1.72 g) and di-tert-butyl dicarbonate (3.52 g, 16.1 mmol, 2.00 eq.) at rt. The mixture was stirred for overnight at rt under a hydrogen atmosphere (2-3 atm). The solids were filtered off, and the filter cake was washed with dichloromethane (3×50 mL). The filtrate was concentrated under reduced pressure. The residue was purified by silica gel column chromatography, eluted with dichloromethane:methanol (10:1) to afford tert-butyl 3-formyl-4-(4-(methylcarbamoyl)phenyl)-5-oxo-5,6,7,9-tetrahydropyrazolo[1,5-a]pyrido[4,3-e]pyrimidine-8(4H)-carboxylate (700 mg, 19% yield) as a yellow solid. LCMS (ESI, m/z): 452 [M+H]⁺.

A solution of tert-butyl 3-formyl-4-(4-(methylcarbamoyl)phenyl)-5-oxo-5,6,7,9-tetrahydropyrazolo[1,5-a]pyrido[4,3-e]pyrimidine-8(4H)-carboxylate (500 mg, 1.11 mmol, 1.00 eq.) in tetrahydrofuran (20 mL) was added bromo(ethynyl)magnesium (6.64 mL, 3.32 mmol, 3.00 eq., 0.5 M in tetrahydrofuran) dropwise at 0° C. under a nitrogen atmosphere. The mixture was stirred for 2 h at 0° C. and then concentrated under reduced pressure. The residue was purified by silica gel column chromatography, eluted with dichloromethane:methanol (12:1) to afford tert-butyl 3-(1-hydroxyprop-2-yn-1-yl)-4-(4-(methylcarbamoyl)phenyl)-5-oxo-5,6,7,9-tetrahydropyrazolo[1,5-a]pyrido[4,3-e]pyrimidine-8(4H)-carboxylate (240 mg, 45% yield) as a yellow solid. LCMS (ESI, m/z): 478 [M+H]⁺.

A 100 mL round-bottom flask was charged with tert-butyl 3-(1-hydroxyprop-2-yn-1-yl)-4-(4-(methylcarbamoyl)phenyl)-5-oxo-5,6,7,9-tetrahydropyrazolo[1,5-a]pyrido[4,3-e]pyrimidine-8(4H)-carboxylate (200 mg, 0.419 mmol, 1.00 eq.), triethylsilane (974 mg, 8.38 mmol, 20.0 eq.), trifluoroacetic acid (1.91 g, 16.8 mmol, 40.0 eq.) and dichloromethane (20 mL) at rt. The mixture was stirred for overnight at rt and then concentrated under reduced pressure. The crude product was purified by prep-HPLC with the following conditions: Column: XBridge Prep OBD C₁₈ Column, 30×150 mm, 5 μm; Mobile Phase A: Water (10 mmol/L NH₄HCO₃+0.1% NH₃·H₂O), Mobile Phase B: ACN; Flow rate: 60 mL/min; Gradient: 32% B to 58% B in 7 min to afford tert-butyl 4-(4-(methylcarbamoyl)phenyl)-5-oxo-3-(prop-2-yn-1-yl)-5,6,7,9-tetrahydropyrazolo[1,5-a]pyrido[4,3-e]pyrimidine-8(4H)-carboxylate (35.0 mg, 18% yield) as a white solid. LCMS (ESI, m/z): 462 [M+H]⁺.

A 50 mL round-bottom flask was charged with tert-butyl 4-(4-(methylcarbamoyl)phenyl)-5-oxo-3-(prop-2-yn-1-yl)-5,6,7,9-tetrahydropyrazolo[1,5-a]pyrido[4,3-e]pyrimidine-8(4H)-carboxylate (35.0 mg, 0.0760 mmol, 1.00 eq.), dichloromethane (5 mL) and trifluoroacetic acid (1 mL) at rt. The mixture was stirred for 2 h at rt and then concentrated under reduced pressure to afford N-methyl-4-(5-oxo-3-(prop-2-yn-1-yl)-6,7,8,9-tetrahydropyrazolo[1,5-a]pyrido[4,3-e]pyrimidin-4(5H)-yl)benzamide trifluoroacetic acid salt (35.6 mg, crude) as a yellow oil. LCMS (ESI, m/z): 362 [M+H-TFA]±.

A 40 mL vial was charged with N-methyl-4-(5-oxo-3-(prop-2-yn-1-yl)-6,7,8,9-tetrahydropyrazolo[1,5-a]pyrido[4,3-e]pyrimidin-4(5H)-yl)benzamide trifluoroacetic acid salt (35.6 mg, 0.075 mmol, 1.00 eq.), 4-bromo-3-(trifluoromethyl)benzoic acid (20.1 mg, 0.075 mmol, 1.00 eq.), 1-hydroxybenzotrizole (10.1 mg, 0.075 mmol, 1.00 eq.), N-(3-dimethylaminopropyl)-N'-ethylcarbodiimide hydrochloride (14.3 mg, 0.075 mmol, 1.00 eq.), N,N-diisopropylethylamine (29.0 mg, 0.225 mmol, 3.00 eq.) and DMF (2 mL) at rt. The mixture was stirred for overnight at rt. The reaction was quenched with water (10 mL) at rt. The mixture was extracted with ethyl acetate (3×30 mL). The organic layers were combined, washed with water (3×30 mL), dried over anhydrous sodium sulfate, filtered and concentrated under reduced pressure. The crude product was purified by prep-HPLC with the following conditions: Column: YMC-Actus Triart $C_{18}$, 30×150 mm, 5 um; Mobile Phase A: Water (10 mmol/L $NH_4HCO_3$+0.1% $NH_3 \cdot H_2O$), Mobile Phase B: ACN; Flow rate: 60 mL/min; Gradient: 48% B to 68% B in 7 min to afford 4-(8-(4-bromo-3-(trifluoromethyl)benzoyl)-5-oxo-3-(prop-2-yn-1-yl)-6,7,8,9-tetrahydropyrazolo[1,5-a]pyrido[4,3-e]pyrimidin-4(5H)-yl)-N-methylbenzamide (42) (11.8 mg, 26% yield) as a white solid. LCMS (ESI, m/z): 612 [M+H]+. $^1$H NMR (300 MHz, CDCl$_3$) δ 7.96 (d, J=8.4 Hz, 2H), 7.90-7.70 (m, 3H), 7.60-7.40 (m, 3H), 6.22 (d, J=4.5 Hz, 1H), 5.15 (s, 2H), 3.73 (d, J=6.3 Hz, 2H), 3.07 (d, J=4.8 Hz, 3H), 2.74 (s, 2H), 2.48 (s, 2H), 2.01 (d, J=3.3 Hz, 1H).

Example 42 rac-(11R)-5-benzyl-12-[4-bromo-3-(trifluoromethyl)benzoyl]-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one (47a) and rac-(11S)-5-benzyl-12-[4-bromo-3-(trifluoromethyl)benzoyl]-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one (47b)

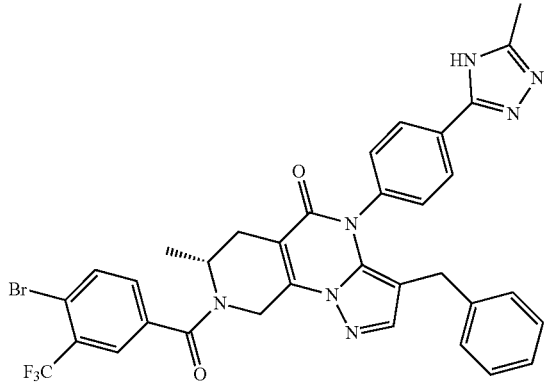

47a

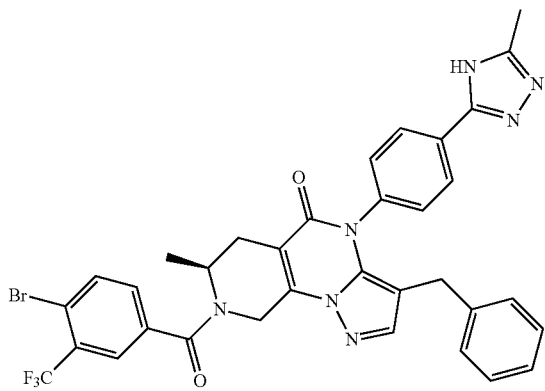

47b

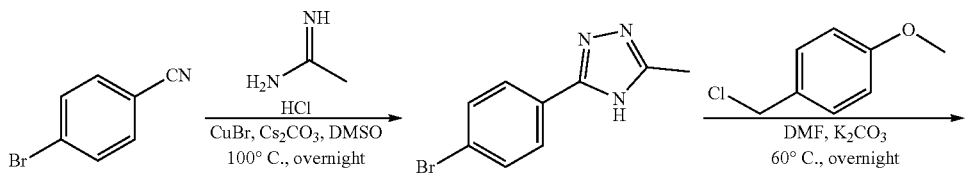

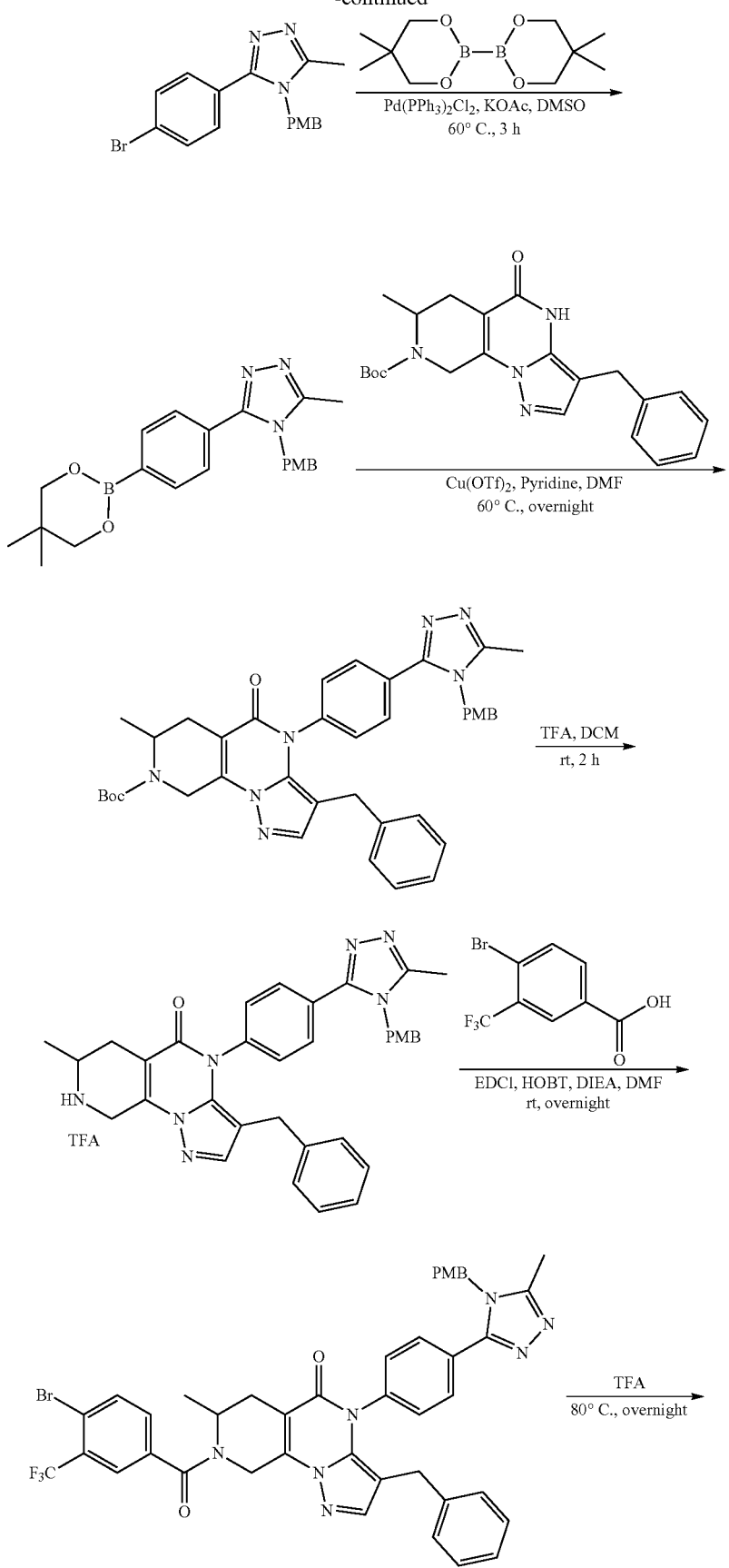

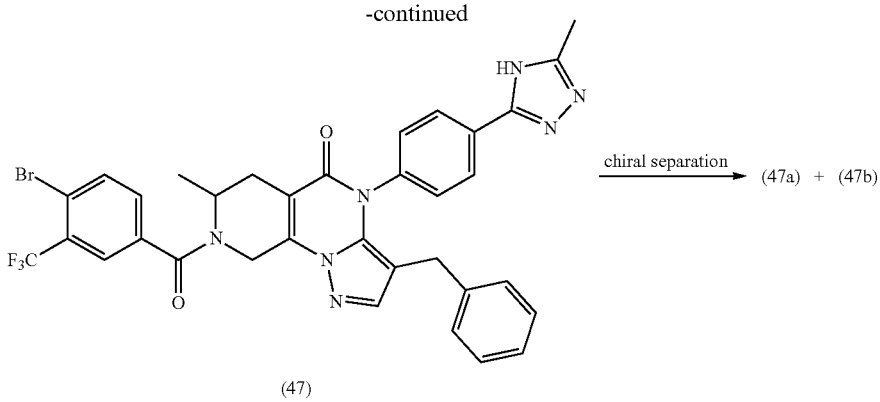

(47)

A 250 mL round-bottom flask was charged with 4-bromobenzonitrile (5.00 g, 27.5 mmol, 1.00 eq.), acetamidine hydrochloride (3.90 g, 41.2 mmol, 1.50 eq.), cuprous bromide (0.390 g, 2.74 mmol, 0.10 eq.), cesium carbonate (26.8 g, 82.4 mmol, 3.00 eq.) and DMSO (50 mL). The mixture was stirred for overnight at 100° C. The reaction was quenched with water (50 mL). The mixture was acidified to pH 4 with hydrochloric acid (1M aq.) and extracted with ethyl acetate (3×150 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (3:1) to afford 3-(4-bromophenyl)-5-methyl-4H-1,2,4-triazole (2.50 g, 38% yield) as a light yellow solid. LCMS (ESI, m/z): 238 [M+H]+.

A 100 mL round-bottom flask was charged with 3-(4-bromophenyl)-5-methyl-4H-1,2,4-triazole (3.00 g, 12.6 mmol, 1.00 eq.) and 4-methoxybenzyl chloride (2.17 g, 13.8 mmol, 1.10 eq.), potassium carbonate (5.22 g, 37.8 mmol, 3.00 eq.) and DMF (10 mL). The mixture was stirred for overnight at 60° C. under a nitrogen atmosphere. The reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with dichloromethane:methanol (10:1) to afford 3-(4-bromophenyl)-4-[(4-methoxyphenyl)methyl]-5-methyl-1,2,4-triazole (2.00 g, 44% yield) as a white solid. LCMS (ESI, m/z): 358 [M+H]+.

A 50 mL round-bottom flask was charged with 3-(4-bromophenyl)-4-[(4-methoxyphenyl)methyl]-5-methyl-1,2,4-triazole (1.50 g, 4.18 mmol, 1.00 eq.), 2-(5,5-dimethyl-1,3,2-dioxaborinan-2-yl)-5,5-dimethyl-1,3,2-dioxaborinane (4.73 g, 20.9 mmol, 5.00 eq.), bis (triphenylphosphorus) palladium chloride (0.590 g, 0.830 mmol, 0.20 eq.), AcOK (2.05 g, 20.9 mmol, 5.00 eq.) and DMSO (30 mL). The mixture was stirred for 3 h at 60° C. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with dichloromethane:methanol (10:1) to afford 3-(4-(5,5-dimethyl-1,3,2-dioxaborinan-2-yl)phenyl)-4-(4-methoxybenzyl)-5-methyl-4H-1,2,4-triazole (1.00 g, 61% yield) as an off-white solid. LCMS (ESI, m/z): 392 [M+H]+.

A 100 mL round-bottom flask was charged with 3-(4-(5,5-dimethyl-1,3,2-dioxaborinan-2-yl)phenyl)-4-(4-methoxybenzyl)-5-methyl-4H-1,2,4-triazole (446 mg, 1.14 mmol, 1.50 eq.) and tert-butyl 5-benzyl-11-methyl-8-oxo-2,3,7,12-tetraazatricyclo[7.4.0.0^{2,6}]trideca-1(9),3,5-triene-12-carboxylate (300 mg, 0.760 mmol, 1.00 eq.), Cu(OTf)$_2$ (275 mg, 0.760 mmol, 1.00 eq.), pyridine (180 mg, 2.28 mmol, 3.00 eq.) and DMF (10 mL). The mixture was stirred for overnight at 60° C. under an oxygen atmosphere. The reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with dichloromethane:methanol (10:1) to afford tert-butyl 5-benzyl-7-(4-{4-[(4-methoxyphenyl)methyl]-5-methyl-1,2,4-triazol-3-yl}phenyl)-11-methyl-8-oxo-2,3,7,12-tetraazatricyclo[7.4.0.0^{2,6}]trideca-1(9),3,5-triene-12-carboxylate (200 mg, 39% yield) as a white solid. LCMS (ESI, m/z): 672 [M+H]+.

A 100 mL round-bottom flask was charged with tert-butyl 5-benzyl-7-(4-{4-[(4-methoxyphenyl)methyl]-5-methyl-1,2,4-triazol-3-yl}phenyl)-11-methyl-8-oxo-2,3,7,12-tetraazatricyclo[7.4.0.0^{2,6}]trideca-1(9),3,5-triene-12-carboxylate (400 mg, 0.590 mmol, 1.00 eq.), trifluoroacetic acid (4 mL) and dichloromethane (20 mL). The mixture was stirred for 2 h at rt and then concentrated under reduced pressure to afford 5-benzyl-7-(4-{4-[(4-methoxyphenyl)methyl]-5-methyl-1,2,4-triazol-3-yl}phenyl)-11-methyl-2,3,7,12-tetraazatricyclo[7.4.0.0^{2,6}]trideca-1(9),3,5-trien-8-one trifluoroacetic acid salt (400 mg, crude). LCMS (ESI, m/z): 572 [M+H-TFA]+.

A 100 mL round-bottom flask was charged with 5-benzyl-7-(4-{4-[(4-methoxyphenyl)methyl]-5-methyl-1,2,4-triazol-3-yl}phenyl)-11-methyl-2,3,7,12-tetraazatricyclo[7.4.0.0^{2,6}]trideca-1(9),3,5-trien-8-one trifluoroacetic acid salt (400 mg, 0.583 mmol, 1.00 eq.), 4-bromo-3-(trifluoromethyl)benzoic acid (282 mg, 1.05 mmol, 1.80 eq., 3-(3-dimethylaminopropyl)-1-ethylcarbodiimide hydrochloride (201 mg, 1.05 mmol, 1.80 eq.), 1-hydroxybenzotriazole (141 mg, 1.05 mmol, 1.80 eq.), DIEA (452 mg, 3.50 mmol, 6.00 eq.) and DMF (5 mL). The mixture was stirred for overnight at rt. The reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by prep-TLC with THF:ethyl acetate (1:1) to afford 5-benzyl-12-[4-bromo-3-(trifluoromethyl)benzoyl]-7-(4-{14-[(4-methoxyphenyl)methyl]-5-methyl-1,2,4-triazol-3-yl}phenyl)-11-methyl-2,3,7,12-tetraazatricyclo[7.4.0.0^{2,6}]trideca-1(9),3,5-trien-8-one (250 mg, 42% yield) as a white solid. LCMS (ESI, m/z): 822 [M+H]⁺.

A 40 mL vial were charged with 5-benzyl-12-[4-bromo-3-(trifluoromethyl)benzoyl]-7-(4-{4-[(4-methoxyphenyl)methyl]-5-methyl-1,2,4-triazol-3-yl}phenyl)-11-methyl-2,3,7,12-tetraazatricyclo[7.4.0.0^{2,6}]trideca-1(9),3,5-trien-8-one (340 mg, 0.413 mmol, 1.00 eq.) and trifluoroacetic acid (10 mL). The mixture was stirred for overnight at 80° C. and then concentrated under reduced pressure. The residue was purified by prep-TLC with THF:ethyl acetate (1:1) to afford the crude product. The crude product was purified by prep-Chiral-HPLC with the following conditions: Column: CHIRAL ART Amylose-SA, 2×25 cm, 5 μm; Mobile Phase A: MtBE (0.5% 2M NH₃-MeOH)-HPLC, Mobile Phase B: EtOH-HPLC; Flow rate: 20 mL/min; Gradient: 30% B to 30% B in 14 min to afford (11R)-5-benzyl-12-[4-bromo-3-(trifluoromethyl)benzoyl]-11-methyl-7-[4-(5-methyl-4H-1,2,4-triazol-3-yl)phenyl]-2,3,7,12-tetraazatricyclo[7.4.0.0^{2,6}]trideca-1(9),3,5-trien-8-one (47a) (the first eluting enantiomer, 41.4 mg, 14% yield) as a white solid, and (47b) (the second eluting enantiomer, 35 mg, 12% yield) as a white solid. LCMS (ESI, m/z): 702 [M+H]⁺. ¹H NMR (400 MHz, CDCl₃) δ 8.10-8.00 (m, 2H), 7.95-7.70 (m, 2H), 7.60-7.38 (m, 2H), 7.25-7.18 (m, 2H), 7.20-7.00 (m, 3H), 6.72 (s, 2H), 5.80 (s, 1H), 4.50 (d, J=9.6 Hz 2H), 3.10 (s, 2H), 2.90-2.60 (m, 2H), 2.51 (s, 3H), 1.37 (d, J=3.2 Hz 3H).

Example 43

N-methyl-4-[rac-(11R)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]benzamide (50a) and N-methyl-4-[rac-(11S)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]benzamide (50b)

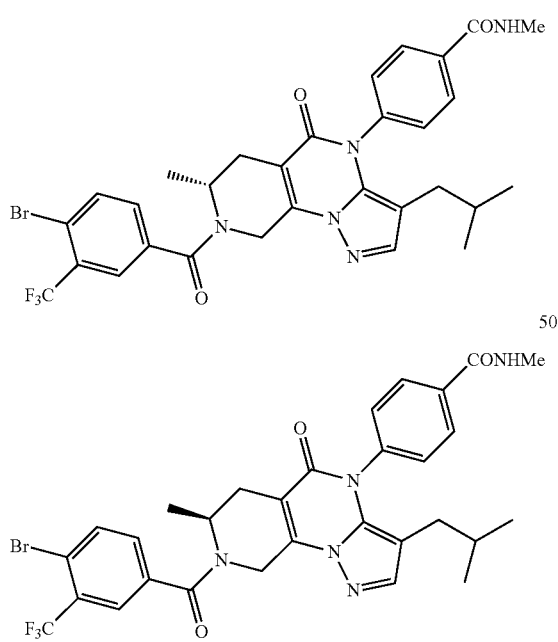

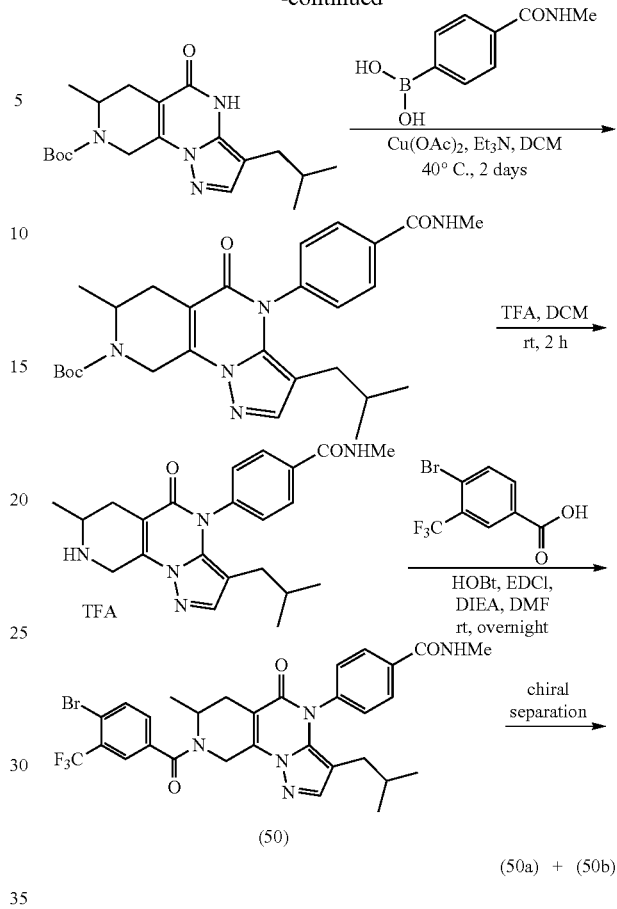

A 100 mL round-bottom flask was charged with tert-butyl 11-methyl-5-(2-methylpropyl)-8-oxo-2,3,7,12-tetraazatricyclo[7.4.0.0^{2,6}]trideca-1(9),3,5-triene-12-carboxylate (100 mg, 0.277 mmol, 1.00 eq.), 4-(methylcarbamoyl)phenylboronic acid (74.5 mg, 0.416 mmol, 1.50 eq.), Cu(OAc)₂ (151 mg, 0.831 mmol, 3.00 eq.), Et₃N (84.2 mg, 0.831 mmol, 3.00 eq.) and dichloromethane (50 mL). The mixture was stirred 2 days at 40° C. under an oxygen atmosphere. The reaction was quenched by water (100 mL). The mixture was extracted with dichloromethane (3×100 mL). The organic layers were combined, washed with water (3×1000 mL), dried over anhydrous sodium sulfate, filtered and concentrated under reduced pressure. The residue was purified by silica gel column chromatography, eluted with ethyl acetate/petroleum (1/3) to afford tert-butyl 11-methyl-7-[4-(methylcarbamoyl)phenyl]-5-(2-methylpropyl)-8-oxo-2,3,7,12-tetraazatricyclo[7.4.0.0^{2,6}]trideca-1(9),3,5-triene-12-carboxylate (73.2 mg, 53% yield) as a white solid. LCMS (ESI, m/z): 494 [M+H]⁺.

A 100 mL round bottom flask was charged with tert-butyl 11-methyl-7-[4-(methylcarbamoyl)phenyl]-5-(2-methylpropyl)-8-oxo-2,3,7,12-tetraazatricyclo[7.4.0.0^{2,6}]trideca-1(9),3,5-triene-12-carboxylate (150 mg, 0.304 mmol, 1.00 eq.), dichloromethane (40 mL) and trifluoroacetic acid (8 mL). The solution was stirred for 2 h at rt and then concentrated under reduced pressure to afford 4-(3-isobutyl-7-methyl-5-oxo-6,7,8,9-tetrahydropyrazolo[1,5-a]pyrido[4,3-e]pyrimidin-4(5H)-yl)-N-methylbenzamide (155 mg, crude) as a yellow solid. LCMS (ESI, m/z): 394 [M+H]⁺.

A 100 mL round bottom flask was charged with N-methyl-4-[11-methyl-5-(2-methylpropyl)-8-oxo-2,3,7, 12-tetraazatricyclo[7.4.0.0^{2,6}]trideca-1 (9),3,5-trien-7-yl]benzamide (240 mg, 0.610 mmol, 1.00 eq.), 4-bromo-3-(trifluoromethyl)benzoic acid (197 mg, 0.732 mmol, 1.20 eq.), HOBt (124 mg, 0.915 mmol, 1.50 eq.), EDCI (175 mg, 0.915 mmol, 1.50 eq.), DIEA (394 mg, 3.05 mmol, 5.00 eq.) and DMF (20 mL). The solution was stirred for overnight at rt. The reaction was quenched with water (100 mL). The mixture was extracted with ethyl acetate (3×100 mL). The organic layers were combined, washed with saturated sodium chloride solution (3×50 mL), dried over anhydrous sodium sulfate, filtered and concentrated under reduced pressure. The residue was purified by silica gel column chromatography, eluted with ethyl acetate:petroleum (1:3) to afford the crude product. The crude was separated by prep-HPLC: Column: CHIRAL ART Amylose-SA, 2×25 cm, 5 um; Mobile Phase A: MtBE (0.5% 2M $NH_3$-MeOH)-HPLC, Mobile Phase B: EtOH-HPLC; Flow rate: 20 mL/min; Gradient: 30% B to 30% B in 12 min to afford 4-[(11R)-12-[4-bromo-3-(trifluoromethyl)benzoyl]-11-methyl-5-(2-methylpropyl)-8-oxo-2,3,7,12-tetraazatricyclo[7.4.0.0^{2,6}]trideca-1(9),3,5-trien-7-yl]-N-methylbenzamide (50a) (the first eluting enantiomer, 69.7 mg, 17% yield) as an off-white solid, and 4-[(11S)-12-[4-bromo-3-(trifluoromethyl)benzoyl]-11-methyl-5-(2-methylpropyl)-8-oxo-2,3,7,12-tetraazatricyclo[7.4.0.0^{2,6}]trideca-1(9),3,5-trien-7-yl]-N-methylbenzamide (50b) (the second eluting enantiomer, 70 mg, 17% yield) as an off-white solid. LCMS (ESI, m/z): 644 [M+H]$^+$. $^1$H NMR (400 MHz, CDCl$_3$) δ 8.02-7.89 (m, 2H), 7.88-7.77 (m, 2H), 7.63-7.33 (m, 4H), 6.29 (d, J=5.0 Hz, 1H), 5.82 (s, 1H), 4.46 (d, J=16.2 Hz, 2H), 3.05 (d, J=4.7 Hz, 3H), 2.93-2.58 (m, 2H), 1.49 (d, J=7.1 Hz, 2H), 1.34 (d, J=6.8 Hz, 3H), 1.25-1.18 (m, 1H), 0.58 (d, J=6.5 Hz, 6H).

Example 44

N-methyl-2-[rac-(11R)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]pyrimidine-5-carboxamide (69a) and N-methyl-2-[rac-(11S)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]pyrimidine-5-carboxamide (69b)

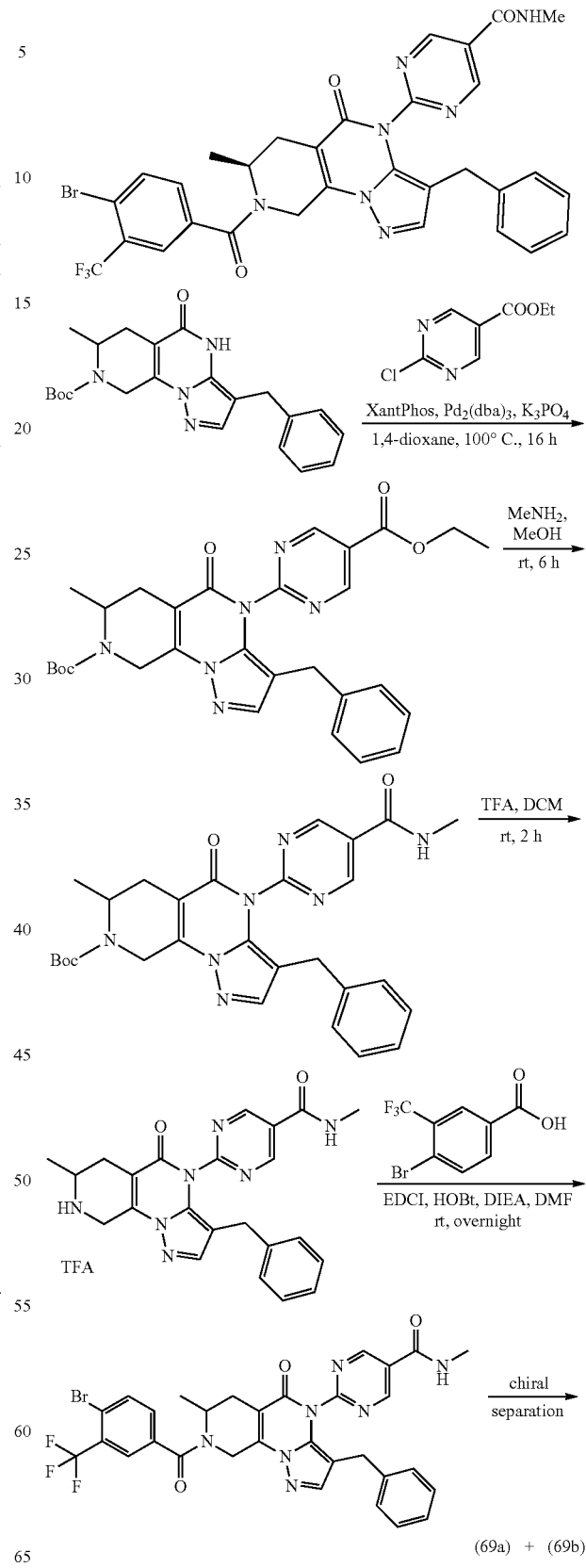

A 100 mL round-bottom flask was charged with tert-butyl 5-benzyl-11-methyl-8-oxo-2,3,7,12-tetraazatricyclo[7.4.0.0^{2,6}]trideca-1(9),3,5-triene-12-carboxylate (600 mg, 1.52 mmol, 1.00 eq.), ethyl 2-chloropyrimidine-5-carboxylate (340 mg, 1.83 mmol, 1.20 eq.), XantPhos (176 mg, 0.304 mmol, 0.20 eq.), Pd$_2$(dba)$_3$ (139 mg, 0.152 mmol, 0.10 eq.), potassium phosphate (969 mg, 4.56 mmol, 3.00 eq.) and 1,4-dioxane (40 mL). The mixture was stirred for 16 h at 100° C. under a nitrogen atmosphere. The reaction was quenched with water (80 mL). The mixture was extracted with ethyl acetate (3×100 mL). The organic layers were combined, washed with saturated sodium chloride solution (3×50 mL), dried over anhydrous sodium sulfate, filtered and concentrated under reduced pressure. The residue was purified by silica gel column chromatography, eluted with ethyl acetate:petroleum ether (1:1) to afford tert-butyl 5-benzyl-7-[5-(ethoxycarbonyl)pyrimidin-2-yl]-11-methyl-8-oxo-2,3,7,12-tetraazatricyclo[7.4.0.0^{2,6}]trideca-1(9),3,5-triene-12-carboxylate (332 mg, 40% yield) as a yellow solid. LCMS (ESI, m/z): 545 [M+H]$^+$.

A 100 mL round-bottom flask was charged with tert-butyl 5-benzyl-7-[5-(ethoxycarbonyl)pyrimidin-2-yl]-11-methyl-8-oxo-2,3,7,12-tetraazatricyclo[7.4.0.0^{2,6}]trideca-1(9),3,5-triene-12-carboxylate (100 mg, 0.184 mmol, 1.00 eq.) and methyl alcohol (30 mL). Then Methylamine (30-33 wt % in absolute ethanol, 1.00 mL) was added dropwise. The solution was stirred for 6 h at rt and then concentrated under reduced pressure to afford tert-butyl 3-benzyl-7-methyl-4-(5-(methylcarbamoyl)pyrimidin-2-yl)-5-oxo-5,6,7,9-tetrahydropyrazolo[1,5-a]pyrido[4,3-e]pyrimidine-8(4H)-carboxylate (70.0 mg, crude) as a yellow solid. LCMS (ESI, m/z): 530 [M+H]$^+$.

A 100 mL round bottom flask was charged with tert-butyl 5-benzyl-11-methyl-7-[5-(methylcarbamoyl)pyrimidin-2-yl]-8-oxo-2,3,7,12-tetraazatricyclo[7.4.0.0^{2,6}]trideca-1(9),3,5-triene-12-carboxylate (70.0 mg, 0.132 mmol, 1.00 eq.), dichloromethane (30 mL) and trifluoroacetic acid (6 mL). The solution was stirred for 2 h at rt and then concentrated under reduced pressure to afford 2-(3-benzyl-7-methyl-5-oxo-6,7,8,9-tetrahydropyrazolo[1,5-a]pyrido[4,3-e]pyrimidin-4(5H)-yl)-N-methylpyrimidine-5-carboxamide trifluoroacetic acid salt (70.0 mg, crude) as a yellow oil. LCMS (ESI, m/z): 430 [M+H-TFA]$^+$.

A 100 mL round bottom flask was charged with 2-{15-benzyl-11-methyl-8-oxo-2,3,7,12-tetraazatricyclo[7.4.0.0^{2,6}]trideca-1(9),3,5-trien-7-yl}-N-methylpyrimidine-5-carboxamide trifluoroacetic acid salt (165 mg, 0.303 mmol, 1.00 eq.), 4-bromo-3-(trifluoromethyl)benzoic acid (97.7 mg, 0.364 mmol, 1.20 eq.), EDCI (87.0 mg, 0.455 mmol, 1.50 eq.), HOBt (61.3 mg, 0.455 mmol, 1.50 eq.), DIEA (196 mg, 1.52 mmol, 5.00 eq.) and DMF (10 mL). The mixture was stirred for overnight at rt. The reaction was quenched with water (50 mL). The mixture was extracted with ethyl acetate (3×100 mL). The combined organic layers were washed with saturated sodium chloride solution (3×50 mL) and dried over anhydrous sodium sulfate. After filtration, the filtrate was concentrated under reduced pressure. The residue was purified by silica gel column chromatography, eluted with ethyl acetate:petroleum ether (1:2) to afford the crude product. The product was separated by prep-chiral-HPLC: Column: CHIRAL ART Cellulose-SB, 2×25 cm, 5 um; Mobile Phase A: Hex:DCM=3:1 (0.5% 2M NH$_3$-MeOH)-HPLC, Mobile Phase B: EtOH-HPLC; Flow rate: 20 mL/min; Gradient: 20% B to 20% B in 14 min to afford 2-[(11R)-5-benzyl-12-[4-bromo-3-(trifluoromethyl)benzoyl]-11-methyl-8-oxo-2,3,7,12-tetraazatricyclo[7.4.0.0^{2,6}]trideca-1(9),3,5-trien-7-yl]-N-methylpyrimidine-5-carboxamide (69a) (the first eluting enantiomer, 53.7 mg, 18% yield) as a light yellow solid, and 2-[(11S)-5-benzyl-12-[4-bromo-3-(trifluoromethyl)benzoyl]-11-methyl-8-oxo-2,3,7,12-tetraazatricyclo[7.4.0.0^{2,6}]trideca-1(9),3,5-trien-7-yl]-N-methylpyrimidine-5-carboxamide (69b) (the second eluting enantiomer, 53 mg, 18% yield) as a light yellow solid. LCMS (ESI, m/z): 680 [M+H]$^+$. $^1$H NMR (300 MHz, CDCl$_3$) δ 8.92 (s, 2H), 7.81 (d, J=8.1 Hz, 2H), 7.64-7.37 (m, 2H), 7.22-7.00 (m, 3H), 6.73-6.69 (m, 3H), 5.79 (s, 1H), 4.47 (m, 2H), 3.26-3.13 (m, 2H), 3.02 (d, J=4.7 Hz, 3H), 2.95-2.48 (m, 2H), 1.32 (d, J=6.8 Hz, 3H).

Example 45

N,2-dimethyl-5-[rac-(11R)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyrazole-3-carboxamide (77a) and N,2-dimethyl-5-[rac-(11S)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyrazole-3-carboxamide (77b)

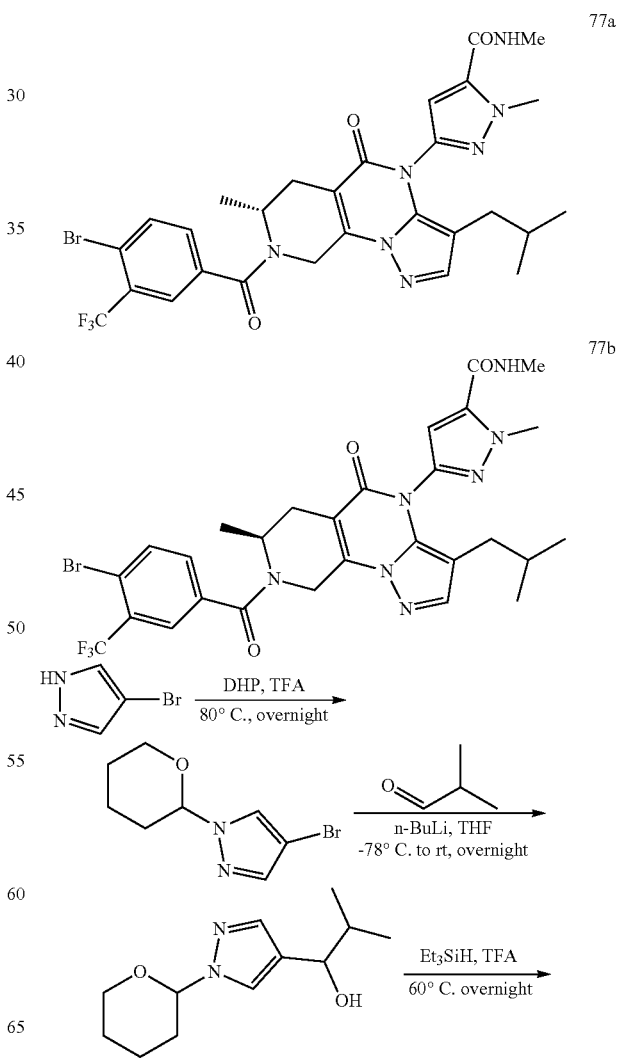

205
-continued

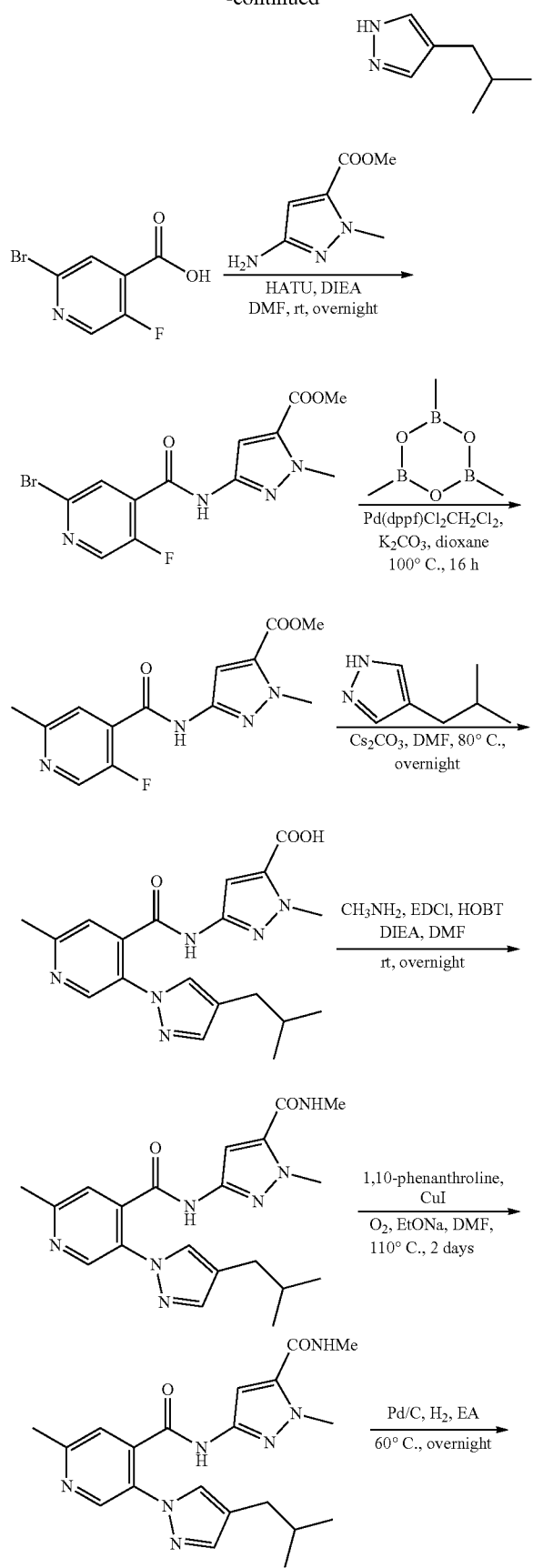

206
-continued

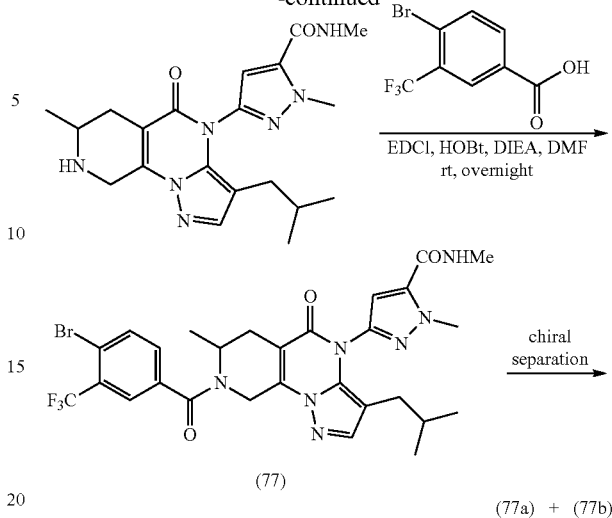

A 250 mL round-bottom flask was charged with 4-bromopyrazole (20.0 g, 136 mmol, 1.00 eq.), dihydropyran (22.9 g, 272 mmol, 2.00 eq.) and trifluoroacetic acid (0.5 mL). The mixture was stirred for overnight at 80° C. The mixture was diluted with ethyl acetate (200 mL) and washed with saturated sodium bicarbonate (3×50 mL) and saturated sodium chloride (1×50 mL) and dried over anhydrous sodium sulfate. After filtration, the filtrate was concentrated under reduced pressure. The residue was purified by silica gel column chromatography, eluted with dichloromethane: petroleum ether (9:1) to afford 4-bromo-1-(oxan-2-yl)pyrazole (24.6 g, 78% yield) as a light yellow oil. LCMS (ESI, m/z): 231 [M+H]⁺.

A 250 mL three neck round bottom flask was charged with 4-bromo-1-(oxan-2-yl)pyrazole (10.0 g, 21.6 mmol, 1.00 eq.) and tetrahydrofuran (50 mL). n-BuLi (51.6 ml, 130 mmol, 3.00 eq., 2.50 M in n-hexane) was added at −78° C. under a nitrogen atmosphere. The mixture was stirred for 30 min at −78° C. Isobutyraldehyde (3.74 g, 51.9 mmol, 1.20 eq.) in tetrahydrofuran (10 mL) was added dropwise at −78° C. The mixture was allowed to warm to rt. The mixture was stirred for overnight at rt. The reaction was quenched with water (100 mL). The mixture was extracted with ethyl acetate (3×80 mL). The combined organic layers were washed with saturated sodium chloride solution (3×40 mL) and dried over anhydrous sodium sulfate. After filtration, the filtrate was concentrated under reduced pressure. The residue was purified by silica gel column chromatography, eluted with petroleum ether:ethyl acetate (1:5) to afford 2-methyl-1-[1-(oxan-2-yl)pyrazol-4-yl]propan-1-ol (3.36 g, 34% yield) as a brown oil. LCMS (ESI, m/z): 225 [M+H]⁺.

A 100 mL round bottom flask was charged with 2-methyl-1-[1-(oxan-2-yl)pyrazol-4-yl]propan-1-ol (1.00 g, 4.46 mmol, 1.00 eq.), triethylsilane (1.56 g, 13.4 mmol, 3.00 eq.) and trifluoroacetic acid (60 mL). The mixture was stirred for overnight at 60° C. The reaction was quenched with water (150 mL). The mixture was extracted with ethyl acetate (3×60 mL). The combined organic layers were washed with saturated sodium chloride solution (3×50 mL) and dried over anhydrous sodium sulfate. After filtration, the filtrate was concentrated under reduced pressure. The residue was purified by silica gel column chromatography, eluted with ethyl acetate:petroleum ether (1:1) to afford 4-(2-methylpropyl)-1H-pyrazole (331 mg, 60% yield) as a light yellow solid. LCMS (ESI, m/z): 125 [M+H]$^+$.

A 100 mL round bottom flask was charged with methyl 5-amino-2-methylpyrazole-3-carboxylate (1.50 g, 9.67 mmol, 1.00 eq.), 2-bromo-5-fluoropyridine-4-carboxylic acid (2.55 g, 11.6 mmol, 1.20 eq.), HATU (7.35 g, 19.3 mmol, 2.00 eq.), DIEA (6.25 g, 48.3 mmol, 5.00 eq.) and DMF (35 mL). The solution was stirred overnight at rt. The reaction was quenched with water (100 mL). The mixture was extracted with ethyl acetate (3×100 mL). The organic layers were combined, washed with saturated sodium chloride solution (3×50 mL), dried over anhydrous sodium sulfate, filtered and concentrated under reduced pressure. The residue was purified by silica gel column chromatography, eluted with dichloromethane:methyl alcohol (9:1) to afford methyl 5-(2-bromo-5-fluoropyridine-4-amido)-2-methylpyrazole-3-carboxylate (2.36 g, 68% yield) as a pink solid. LCMS (ESI, m/z): 357 [M+H]$^+$.

A 250 mL round bottom flask was charged with methyl 5-(2-bromo-5-fluoropyridine-4-amido)-2-methylpyrazole-3-carboxylate (4.00 g, 11.2 mmol, 1.00 eq.), trimethyl-1,3,5,2,4,6-trioxatriborinane (16.9 g, 67.2 mmol, 6.00 eq., 50% wt in THF), Pd(dppf)Cl$_2$·CH$_2$Cl$_2$ (0.91 g, 1.12 mmol, 0.10 eq.), potassium carbonate (4.64 g, 33.6 mmol, 3.00 eq.) and 1,4-dioxane (30 mL). The mixture was stirred for 16 h at 110° C. under a nitrogen atmosphere. The reaction was quenched with water (100 mL). The mixture was extracted with ethyl acetate (3×200 mL). The organic layers were combined, washed with saturated sodium chloride solution (3×50 mL), dried over anhydrous sodium sulfate, filtered and concentrated under reduced pressure. The residue was purified by silica gel column chromatography, eluted with dichloromethane:methyl alcohol (12:1) to afford methyl 5-(5-fluoro-2-methylpyridine-4-amido)-2-methylpyrazole-3-carboxylate (2.91 g, 89% yield) as a yellow solid. LCMS (ESI, m/z): 293 [M+H]$^+$.

A 100 mL round bottom flask was charged with methyl 5-(5-fluoro-2-methylpyridine-4-amido)-2-methylpyrazole-3-carboxylate (700 mg, 2.34 mmol, 1.00 eq.), 4-(2-methylpropyl)-1H-pyrazole (357 mg, 2.88 mmol, 1.20 eq.), cesium carbonate (1.56 g, 4.79 mmol, 2.00 eq.) and DMF (40 mL). The mixture was stirred for overnight at 120° C. The reaction was quenched with water (100 mL). The pH value of the mixture was acidified to 6 with HCl (aq. 1 mol/L). The mixture was extracted with ethyl acetate (3×80 mL). The combined organic layers were washed with saturated sodium chloride solution (3×40 mL) and dried over anhydrous sodium sulfate. After filtration, the filtrate was concentrated under reduced pressure. The residue was purified by silica gel column chromatography, eluted with dichloromethane:methanol (6:1) to afford 2-methyl-5-{2-methyl-5-[4-(2-methylpropyl)pyrazol-1-yl]pyridine-4-amido}pyrazole-3-carboxylic acid (372 mg, 41% yield) as a tan solid. LCMS (ESI, m/z): 383 [M+H]$^+$.

A 100 mL round bottom flask was charged with 2-methyl-5-{12-methyl-5-[4-(2-methylpropyl)pyrazol-1-yl]pyridine-4-amido}pyrazole-3-carboxylic acid (500 mg, 1.31 mmol, 1.00 eq.), EDCI (376 mg, 1.96 mmol, 1.50 eq.), HOBt (265 mg, 1.96 mmol, 1.50 eq.), DIEA (845 mg, 6.54 mmol, 5.00 eq.), DMF (20 mL) and methylamine (30-33 wt % in absolute ethanol, 1.0 mL). The mixture was stirred for overnight at rt. The reaction was quenched with water (100 mL). The mixture was extracted with ethyl acetate (3×80 mL). The combined organic layers were washed with saturated sodium chloride solution (3×40 mL) and dried over anhydrous sodium sulfate. After filtration, the filtrate was concentrated under reduced pressure. The residue was purified by silica gel column chromatography, eluted with dichloromethane:methanol (13:1) to afford 2-methyl-N-[1-methyl-5-(methylcarbamoyl)pyrazol-3-yl]-5-[4-(2-methylpropyl)pyrazol-1-yl]pyridine-4-carboxamide (253 mg, 49% yield) as a brown yellow solid. LCMS (ESI, m/z): 396 [M+H]$^+$.

A 100 mL round bottom flask was charged with 2-methyl-N-[1-methyl-5-(methylcarbamoyl)pyrazol-3-yl]-5-[4-(2-methylpropyl)pyrazol-1-yl]pyridine-4-carboxamide (710 mg, 1.76 mmol, 1.00 eq.), 1,10-phenanthroline (129 mg, 0.718 mmol, 0.40 eq.), CuI (68.4 mg, 0.359 mmol, 0.20 eq.), EtONa (367 mg, 5.39 mmol, 3.00 eq.) and DMF (20 mL). The mixture was stirred for 2 days at 110° C. under an oxygen atmosphere. The reaction was quenched by water (100 mL). The mixture was extracted with ethyl acetate (3×80 mL). The combined organic layers were washed with saturated sodium chloride solution (3×40 mL) and dried over anhydrous sodium sulfate. After filtration, the filtrate was concentrated under reduced pressure. The residue was purified by prep-TLC (ethyl acetate:methyl alcohol (15:1) to afford N,2-dimethyl-5-[11-methyl-5-(2-methylpropyl)-8-oxo-2,3,7,12-tetraazatricyclo[7.4.0.0^{2,6}]trideca-1(9),3,5,10,12-pentaen-7-yl]pyrazole-3-carboxamide (211 mg, 30% yield) as a brown yellow solid. LCMS (ESI, m/z): 394 [M+H]$^+$ A 100 mL round-bottom flask was charged with 4-[5-(cyclopropylmethyl)-11-methyl-8-oxo-2,3,7,12-tetraazatricyclo[7.4.0.0^{2,6}]trideca-1(9),3,5,10,12-pentaen-7-yl]-N-methylbenzamide (300 mg, 0.763 mmol, 1.00 eq.), 10% Pd/C (20 mg), glacial acetic acid (20 mL) and ethyl acetate (20 mL). The mixture was stirred overnight at 60° C. under a hydrogen atmosphere (2-3 atm). The solids were filtered off, and the filter cake was washed with ethyl acetate (3×50 mL). The filtrate was concentrated under reduced pressure to afford 3-(3-isobutyl-7-methyl-5-oxo-6,7,8,9-tetrahydropyrazolo[1,5-a]pyrido[4,3-e]pyrimidin-4(5H)-yl)-N,1-dimethyl-1H-pyrazole-5-carboxamide (280 mg, crude) as a pink oil. LCMS (ESI, m/z): 398 [M+H]$^+$ A 100 mL round-bottom flask charged with 4 N,2-dimethyl-5-[11-methyl-5-(2-methylpropyl)-8-oxo-2,3,7,12-tetraazatricyclo[7.4.0.0^{2,6}]trideca-1 (9),3,5-trien-7-yl] pyrazole-3-carboxamide (100 mg, 0.252 mmol, 1.00 eq.), 4-bromo-3-(trifluoromethyl)benzoic acid (81.2 mg, 0.302 mmol, 1.20 eq.), EDCI (72.3 mg, 0.378 mmol, 1.50 eq.), HOBt (51.0 mg, 0.378 mmol, 1.50 eq.), DIEA (162 mg, 1.26 mmol, 5.00 eq.) and DMF (20 mL). The mixture was stirred for overnight at rt. The reaction was quenched with water (100 mL). The mixture was extracted with ethyl acetate (3×50 mL). The combined organic layers were washed with saturated sodium chloride solution (3×30 mL) and dried over anhydrous sodium sulfate. After filtration, the filtrate was concentrated under reduced pressure. The residue was purified by prep-TLC with ethyl acetate:MeOH (12:1) to afford the crude product. The crude product was separated by prep-chiral-HPLC: Column: CHIRALPAK IF, 2×25 cm, 5 um; Mobile Phase A: MtBE (0.5% 2M NH$_3$-MeOH)-HPLC, Mobile Phase B: EtOH-HPLC; Flow rate: 15 mL/min; Gradient: 50% B to 50% B in 12 min to afford 5-[(11S)-12-[4-bromo-3-(trifluoromethyl)benzoyl]-11-methyl-5-(2-methylpropyl)-8-oxo-2,3,7,12-tetraazatricyclo[7.4.0.0^{2,6}]trideca-1 (9),3,5-trien-7-yl]-N,2-dimethylpyrazole-3-carboxamide (77a) (the first eluting enantiomer, 11 mg, 7% yield) and 5-[(11R)-12-[4-bromo-3-(trifluoromethyl)benzoyl]-11-methyl-5-(2-methylpropyl)-8-oxo-2,3,7,12-tetraazatricyclo[7.4.0.0^{2,6}]trideca-1(9),3,5-trien-7-yl]-N,2-dimethylpyrazole-3-carboxamide (77b) (the second eluting enantiomer, 6.6 mg, 4% yield). $^1$H NMR (300 MHz, CDCl$_3$) δ 7.92-7.74 (m, 2H), 7.63-7.37 (m, 2H), 6.62-6.54 (m, 2H), 5.57 (s, 1H), 4.47 (s, 1H), 4.41 (s, 1H), 4.22 (s, 3H), 2.91 (d, J=4.8 Hz, 3H), 2.83-2.58 (m, 2H), 1.63 (d, J=4.1 Hz, 2H), 1.44-1.28 (m, 4H), 0.70 (d, J=6.6 Hz, 6H). LCMS (ESI, m/z): 648 [M+H]$^+$.
Example 46
N-methyl-4-[rac-(11R)-12-[4-bromo-3-(trifluoromethyl)benzoyl]-11-methyl-8-oxo-5-prop-2-ynyl-2,3,7,12-tetrazatricyclo[7.4.0.0^2,6]trideca-1(9),3,5-trien-7-yl]benzamide (78a) and N-methyl-4-[rac-(11S)-12-[4-bromo-3-(trifluoromethyl)benzoyl]-11-methyl-8-oxo-5-prop-2-ynyl-2,3,7,12-tetrazatricyclo[7.4.0.0^2,6]trideca-1(9),3,5-trien-7-yl]benzamide (78b)
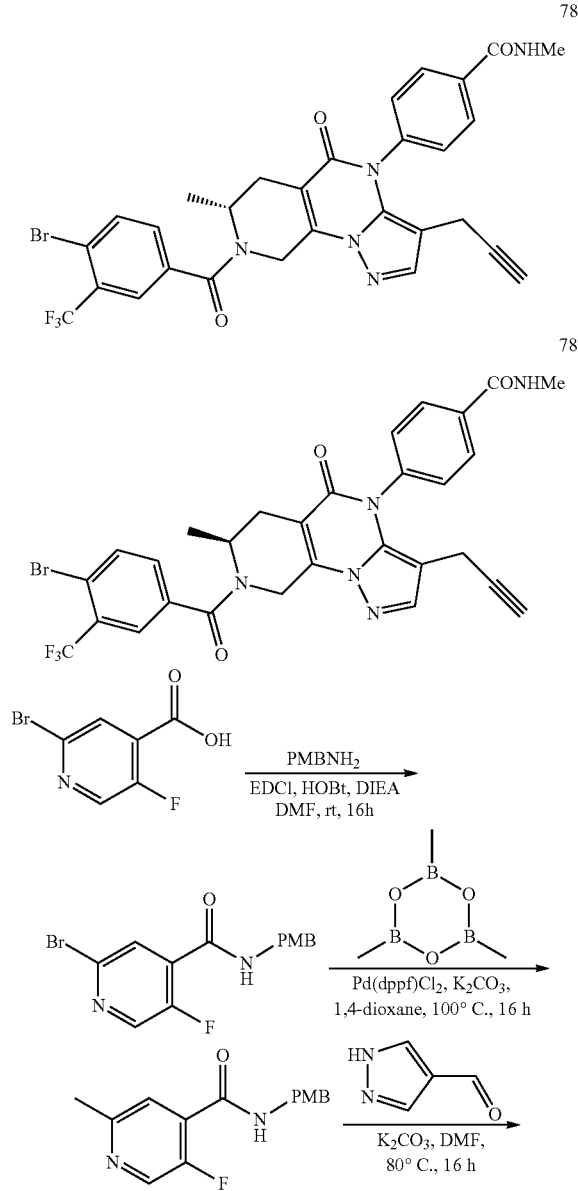
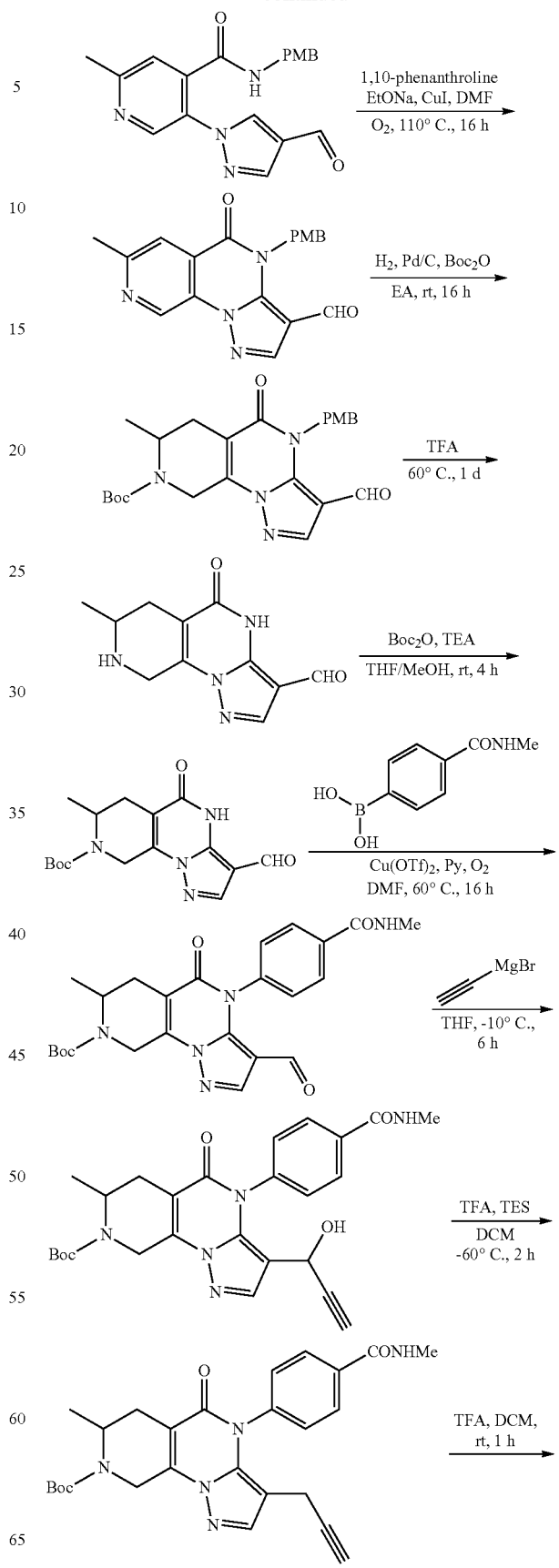

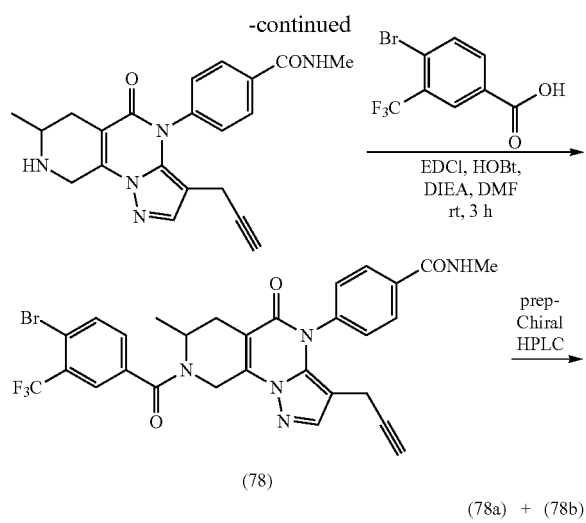

(78a) + (78b)

A mixture of 2-bromo-5-fluoroisonicotinic acid (5.00 g, 22.7 mmol, 1.00 eq.), (4-methoxyphenyl)methanamine (4.68 g, 34.1 mmol, 1.50 eq.), EDCI (10.9 g, 56.8 mmol, 2.50 eq.), HOBt (9.21 g, 68.2 mmol, 3.00 eq.) and DIEA (14.7 g, 114 mmol, 5.00 eq.) in DMF (115 mL) was stirred for 16 h at rt and quenched with water (600 mL). The mixture was extracted with ethyl acetate (3×500 mL) and the organic layers were combined, washed with water (3×500 mL), dried over anhydrous sodium sulfate, filtered and concentrated under reduced pressure. The residue was purified by silica gel column chromatography, eluted with 0-100% ethyl acetate in petroleum ether to afford 2-bromo-5-fluoro-N-(4-methoxybenzyl)isonicotinamide (7.20 g, 93% yield) as a light yellow solid. LCMS (ESI, m/z): 339 [M+H]⁺.

To a mixture of 2-bromo-5-fluoro-N-(4-methoxybenzyl) isonicotinamide (7.20 g, 21.2 mmol, 1.00 eq.), 2,4,6-trimethyl-1,3,5,2,4,6-trioxatriborinane (26.6 g, 106 mmol, 5.00 eq., 50% wt in THF) and potassium carbonate (5.87 g, 42.5 mmol, 2.00 eq.) in 1,4-dioxane (105 mL) was added Pd(dppf)Cl$_2$·CH$_2$Cl$_2$ (1.72 g, 2.12 mmol, 0.10 eq.). The resulting mixture was stirred for 16 hours at 100° C. under nitrogen. The solids were filtered out and the filtrate was concentrated under reduced pressure. The residue was purified by silica gel column chromatography, eluted with 0-100% ethyl acetate in petroleum ether to afford 5-fluoro-N-(4-methoxybenzyl)-2-methylisonicotinamide (5.49 g, 94% yield) as a light brown solid. LCMS (ESI, m/z): 275 [M+H]⁺.

A mixture of 5-fluoro-N-(4-methoxybenzyl)-2-methylisonicotinamide (5.21 g, 19.0 mmol, 1.00 eq.), 1H-pyrazole-4-carbaldehyde (2.74 g, 28.5 mmol, 1.50 eq.) and K$_2$CO$_3$ (13.1 g, 95.0 mmol, 5.00 eq.) in DMF (95 mL) was stirred for 16 hours at 80° C. and quenched with water (400 mL). The mixture was extracted with ethyl acetate (3×300 mL) and the organic layers were combined, washed with water (3×500 mL), dried over anhydrous sodium sulfate, filtered and concentrated under reduced pressure. The residue was purified by silica gel column chromatography, eluted with 0-100% ethyl acetate in dichloromethane to afford 5-(4-formyl-1H-pyrazol-1-yl)-N-(4-methoxybenzyl)-2-methylisonicotinamide (6.40 g, 96% yield) as a light yellow solid. LCMS (ESI, m/z): 351 [M+H]⁺.

A mixture of 5-(4-formyl-1H-pyrazol-1-yl)-N-(4-methoxybenzyl)-2-methylisonicotinamide (5.50 g, 15.7 mmol, 1.00 eq.), cuprous iodide (1.20 g, 6.28 mmol, 0.40 eq.), 1,10-phenanthroline (1.13 g, 6.28 mmol, 0.40 eq.) and EtONa (3.2 g, 47.1 mmol, 3.00 eq.) in DMF (160 mL) was stirred for 16 hours at 110° C. under oxygen. The solids were filtered out and the filtrate was concentrated under reduced pressure. The residue was purified by silica gel column chromatography, eluted with 0-10% methanol in dichloromethane to afford 4-(4-methoxybenzyl)-7-methyl-5-oxo-4,5-dihydropyrazolo[1,5-c]pyrido[4,3-e]pyrimidine-3-carbaldehyde (3.99 g, 73% yield) as an off-white solid. LCMS (ESI, m/z): 349 [M+H]⁺.

To a suspension of 4-(4-methoxybenzyl)-7-methyl-5-oxo-4,5-dihydropyrazolo[1,5-a]pyrido[4,3-e]pyrimidine-3-carbaldehyde (1.50 g, 4.31 mmol, 1.00 eq.) in ethyl acetate (220 mL) were added 10% Pd/C (0.20 g) and di-tert-butyl dicarbonate (9.40, 43.1 mmol, 10.0 eq.). The resulting mixture was stirred for 16 h at rt under hydrogen (2-3 atm). The solids were filtered out and washed with dichloromethane (2×100 mL). The combined filtrate was concentrated under reduced pressure. The residue was purified by silica gel column chromatography, eluted with 0-48% ethyl acetate in dichloromethane to afford tert-butyl 3-formyl-4-(4-methoxybenzyl)-7-methyl-5-oxo-5,6,7,9-tetrahydropyrazolo[1,5-a]pyrido[4,3-e]pyrimidine-8(4H)-carboxylate (1.03 g, 53% yield) as a white solid. LCMS (ESI, m/z): 453 [M+H]⁺.

A suspension of tert-butyl 3-formyl-4-(4-methoxybenzyl)-7-methyl-5-oxo-5,6,7,9-tetrahydropyrazolo[1,5-a]pyrido[4,3-e]pyrimidine-8(4H)-carboxylate (3.06 g, 6.76 mmol, 1.00 eq.) in TFA (75 mL) was stirred for 1 day at 60° C. and concentrated under reduced pressure. The residue was triturated with diethyl ether/dichloromethane (280 mL, v/v=3/1). The solids were collected by filtration, washed with n-hexane (300 mL) and dried to afford 7-methyl-5-oxo-4,5,6,7,8,9-hexahydropyrazolo[1,5-a]pyrido[4,3-e]pyrimidine-3-carbaldehyde trifluoroacetic acid salt (2.57 g, crude) as a light purple solid, which was used in the next step directly without any further purification. LCMS (ESI, m/z): 233 [M+H-TFA]±.

To a mixture of 7-methyl-5-oxo-4,5,6,7,8,9-hexahydropyrazolo[1,5-a]pyrido[4,3-e]pyrimidine-3-carbaldehyde trifluoroacetic acid salt (2.57 g, 7.43 mmol, 1.00 eq.) in THF/MeOH (100 mL, v/v=4/1) were added trimethylamine (7.66 g, 59.4 mmol, 8.00 eq.) and Boc$_2$O (4.73 g, 21.7 mmol, 2.92 eq.) at rt. The resulting mixture was stirred for 4 hours at rt and concentrated under reduced pressure. The residue was purified by reverse phase chromatography with following condition: Column: Agela C$_{18}$ Column, 330 g; Mobile Phase A: Water (10 mM NH$_4$HCO$_3$), Mobile Phase B: ACN; Flow rate: 50 mL/min; Gradient: 0% B to 41% B in 20 min to afford tert-butyl 3-formyl-7-methyl-5-oxo-5,6,7,9-tetrahydropyrazolo[1,5-a]pyrido[4,3-e]pyrimidine-8(4H)-carboxylate (1.68 g, 68% yield) as a light yellow solid. LCMS (ESI, m/z): 333 [M+H]⁺.

To a mixture of tert-butyl 3-formyl-7-methyl-5-oxo-5,6,7,9-tetrahydropyrazolo[1,5-a]pyrido[4,3-e]pyrimidine-8(4H)-carboxylate (885 mg, 2.66 mmol, 1.00 eq.) and (4-(methylcarbamoyl)phenyl)boronic acid (2.70 g, 13.3 mmol, 5.00 eq.) in DMF (16 mL) were added copper(II) trifluoromethanesulfonate (2.19 g, 5.32 mmol, 2.00 eq.) and pyridine (1.05 g, 13.3 mmol, 5.00 eq.) at rt. The resulting mixture was stirred for 16 hours at 60° C. under oxygen and concentrated under reduced pressure. The residue was purified by reverse phase chromatography with following condition: Column: Agela C$_{18}$ Column, 330 g; Mobile Phase A: Water (10 mM NH$_4$HCO$_3$), Mobile Phase B: ACN; Flow rate: 50 mL/min; Gradient: 0% B to 55% B in 25 min to afford tert-butyl 3-formyl-7-methyl-4-(4-(methylcarbamoyl)phenyl)-5-oxo-5,6,7,9-tetrahydropyrazolo[1,5-a]pyrido[4,3-e]pyrimidine-8(4H)-carboxylate (828 mg, 67% yield) as a light yellow solid. LCMS (ESI, m/z): 466 [M+H]$^+$.

To a solution of tert-butyl 3-formyl-7-methyl-4-(4-(methylcarbamoyl)phenyl)-5-oxo-5,6,7,9-tetrahydropyrazolo[1,5-a]pyrido[4,3-e]pyrimidine-8(4H)-carboxylate (682 mg, 1.46 mmol, 1.00 eq.) in THF (30 mL) was added ethynylmagnesium bromide (29.3 mL, 14.6 mmol, 10.0 eq., 0.5 M solution in THF) at −78° C. under nitrogen, then stirred for 6 hours at −10° C. The reaction mixture was quenched with saturated aqueous ammonium chloride (100 mL) at 0° C. The mixture was extracted with ethyl acetate (3×300 mL) and the organic layers were combined, washed with water (3×500 mL), dried over anhydrous sodium sulfate, filtered and concentrated under reduced pressure. The residue was purified by silica gel column chromatography, eluted with 0-80% ethyl acetate in dichloromethane to afford tert-butyl 3-(1-hydroxyprop-2-yn-1-yl)-7-methyl-4-(4-(methylcarbamoyl)phenyl)-5-oxo-5,6,7,9-tetrahydropyrazolo[1,5-a]pyrido[4,3-e]pyrimidine-8(4H)-carboxylate (462 mg, 64% yield) as a light yellow solid. LCMS (ESI, m/z): 492 [M+H]$^+$.

To a solution of tert-butyl 3-(1-hydroxyprop-2-yn-1-yl)-7-methyl-4-(4-(methylcarbamoyl)phenyl)-5-oxo-5,6,7,9-tetrahydropyrazolo[1,5-a]pyrido[4,3-e]pyrimidine-8(4H)-carboxylate (462 mg, 0.940 mmol, 1.00 eq.) in DCM (45 mL) was added TFA (4.5 mL) and triethoxysilane (4.5 mL) at −78° C. under nitrogen. Then the mixture was stirred for 2 hours at −60° C. and concentrated under reduced pressure. The residue was purified by reverse phase chromatography with following condition: Column: Agela C$_{18}$ Column, 120 g; Mobile Phase A: Water (0.05% TFA), Mobile Phase B: ACN; Flow rate: 40 mL/min; Gradient: 0% B to 100% B in 40 min; Wave Length: 220 nm to afford tert-butyl 7-methyl-4-(4-(methylcarbamoyl)phenyl)-5-oxo-3-(prop-2-yn-1-yl)-5,6,7,9-tetrahydropyrazolo[1,5-a]pyrido[4,3-e]pyrimidine-8(4H)-carboxylate (172 mg, 38% yield) as a light yellow solid. LCMS (ESI, m/z): 476 [M+H]$^+$.

To a solution of tert-butyl 7-methyl-4-(4-(methylcarbamoyl)phenyl)-5-oxo-3-(prop-2-yn-1-yl)-5,6,7,9-tetrahydropyrazolo[1,5-a]pyrido[4,3-e]pyrimidine-8(4H)-carboxylate (172 mg, 0.360 mmol, 1.00 eq.) in DCM (12 mL) was added TFA (4 mL). The resulting mixture was stirred for 1 hour at rt and concentrated under reduced pressure. The residue was purified by reverse phase chromatography with following condition: Column: Agela C$_{18}$ Column, 120 g; Mobile Phase A: Water (0.05% TFA), Mobile Phase B: ACN; Flow rate: 40 mL/min; Gradient: 0% B to 100% B in 40 min to afford N-methyl-4-(7-methyl-5-oxo-3-(prop-2-yn-1-yl)-6,7,8,9-tetrahydropyrazolo[1,5-a]pyrido[4,3-e]pyrimidin-4(5H)-yl)benzamide trifluoroacetic acid salt (118 mg, 67% yield) as a light brown solid. LCMS (ESI, m/z): 376 [M+H-TFA]$^+$.

A mixture of N-methyl-4-(7-methyl-5-oxo-3-(prop-2-yn-1-yl)-6,7,8,9-tetrahydropyrazolo[1,5-a]pyrido[4,3-e]pyrimidin-4(5H)-yl)benzamide trifluoroacetic acid salt (208 mg, 0.425 mmol, 1.00 eq.), 4-bromo-3-(trifluoromethyl)benzoic acid (226 mg, 0.840 mmol, 1.97 eq.), EDCI (266 mg, 1.40 mmol, 3.29 eq.), HOBT (225 mg, 1.68 mmol, 3.95 eq.) and DIEA (0.548 g, 4.25 mmol, 10.0 eq.) in DMF (10 mL) was stirred for 3 hours at rt. The solids were filtered out and the filtrate was purified by reverse phase chromatography with following condition: Column: Agela C$_{18}$ Column, 120 g; Mobile Phase A: Water (10 mM NH$_4$HCO$_3$), Mobile Phase B: ACN; Flow rate: 50 mL/min; Gradient: 0% B to 100% B in 40 min; Wave Length: 220 nm to afford the crude product. Then the product was re-purified by prep-HPLC with following condition: Column: XBridge Prep OBD C$_{18}$ Column, 30×150 mm, 5 um; Mobile Phase A: Water (10 mmol/L NH$_4$HCO$_3$+0.1% NH$_3$·H$_2$O), Mobile Phase B: ACN; Flow rate: 60 mL/min; Gradient: 34% B to 64% B in 7 min to afford 4-(8-(4-bromo-3-(trifluoromethyl)benzoyl)-7-methyl-5-oxo-3-(prop-2-yn-1-yl)-6,7,8,9-tetrahydropyrazolo[1,5-a]pyrido[4,3-e]pyrimidin-4(5H)-yl)-N-methylbenzamide (166 mg, 62% yield) as a white solid. LCMS (ESI, m/z): 626 [M+H]$^+$.

The racemic product 4-(8-(4-bromo-3-(trifluoromethyl)benzoyl)-7-methyl-5-oxo-3-(prop-2-yn-1-yl)-6,7,8,9-tetrahydropyrazolo[1,5-a]pyrido[4,3-e]pyrimidin-4(5H)-yl)-N-methylbenzamide (78) (166 mg) was purified by prep-Chiral HPLC with following condition: Column: CHIRAL ART Amylose-SA, 2×25 cm, 5 um; Mobile Phase A: MtBE (0.5% 2M NH$_3$-MeOH)-HPLC, Mobile Phase B: EtOH-HPLC; Flow rate: 20 mL/min; Gradient: 50% B to 50% B in 11.5 min to afford (R)-4-(8-(4-bromo-3-(trifluoromethyl)benzoyl)-7-methyl-5-oxo-3-(prop-2-yn-1-yl)-6,7,8,9-tetrahydropyrazolo[1,5-a]pyrido[4,3-e]pyrimidin-4(5H)-yl)-N-methylbenzamide (78a) (the first eluting enantiomer, 44.0 mg) as a white solid and (S)-4-(8-(4-bromo-3-(trifluoromethyl)benzoyl)-7-methyl-5-oxo-3-(prop-2-yn-1-yl)-6,7,8,9-tetrahydropyrazolo[1,5-a]pyrido[4,3-e]pyrimidin-4(5H)-yl)-N-methylbenzamide (78b) (the second eluting enantiomer, 42.0 mg) as a white solid. LCMS (ESI, m/z): 626 [M+H]$^+$. $^1$H NMR (400 MHz, CDCl$_3$) δ 7.95-7.93 (m, 2H), 7.84-7.80 (m, 3H), 7.52-7.40 (m, 3H), 6.38-6.36 (m, 1H), 5.84-5.59 (br m, 1H), 4.69-4.30 (br m, 1H), 3.05 (d, J=4.8 Hz, 3H), 2.88-2.66 (m, 2H), 2.49 (d, J=2.7 Hz, 2H), 2.00 (d, J=2.8 Hz, 1H), 1.33 (d, J=6.8 Hz, 3H).

Example 47
[[4-[(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]-methylamino]methyl (2S)-2-amino-3-methyl-butanoate (90) and N-(hydroxymethyl)-N-methyl-4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1 (9),3,5-trien-7-yl]benzamide (91)
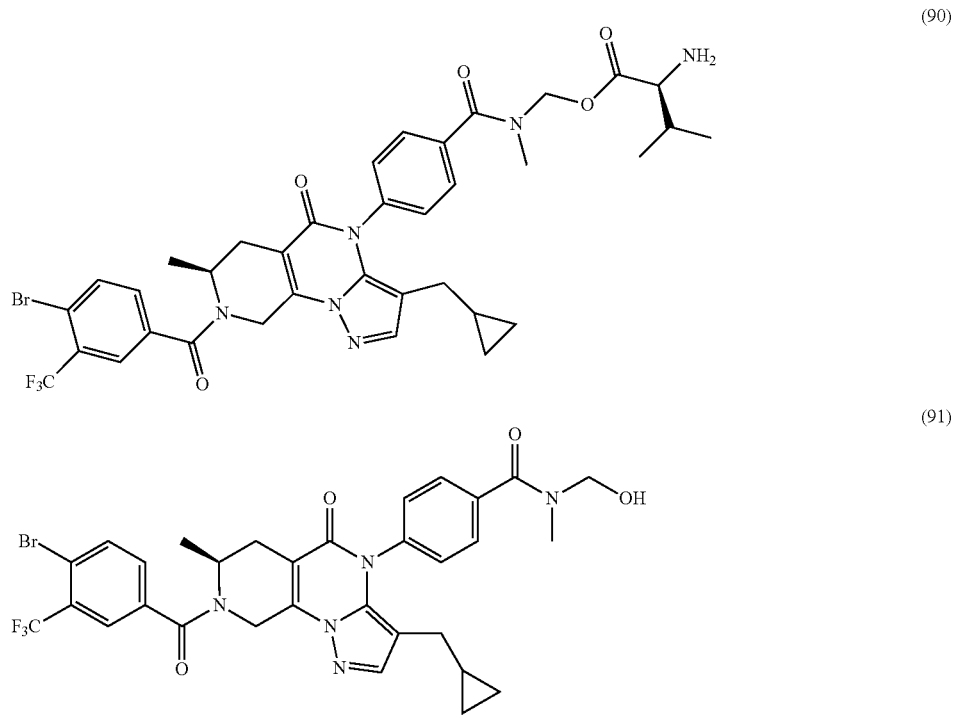
(90)
(91)
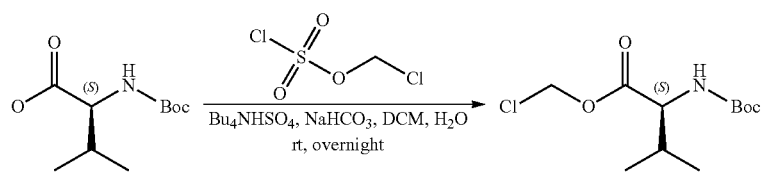
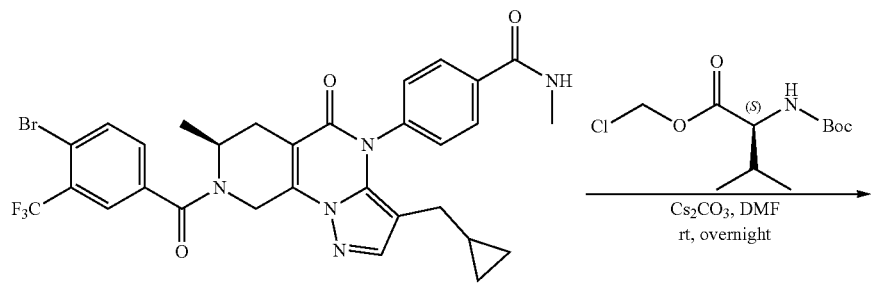

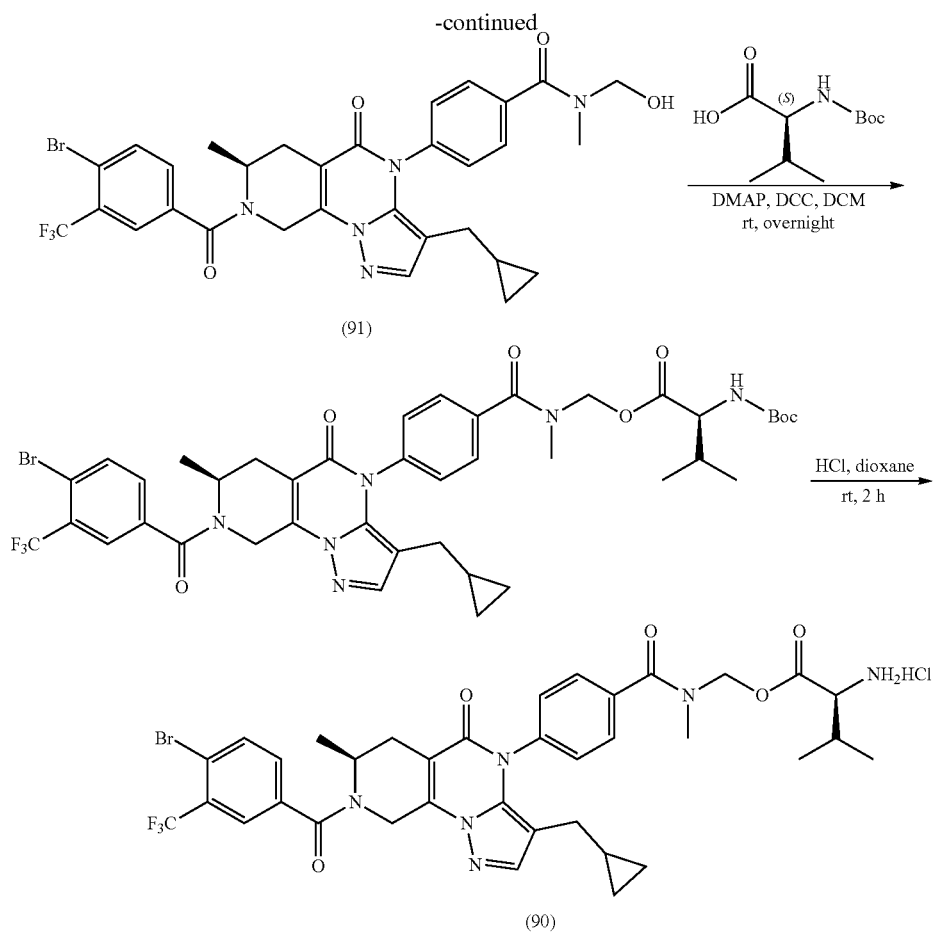

(91)

(90)

A 250 mL round-bottom flask was charged with (2S)-2-[(tert-butoxycarbonyl)amino]-3-methylbutanoic acid (2.00 g, 9.21 mmol, 1.00 eq.), chloromethyl sulfurochloridate (1.82 g, 11.0 mmol, 1.20 eq.), Bu$_4$NHSO$_4$ (1.56 g, 4.60 mmol, 0.50 eq.), sodium bicarbonate (2.32 g, 27.6 mmol, 3.00 eq.), water (50 mL) and dichloromethane (50 mL) at 0° C. The resulting solution was stirred for overnight at rt and diluted with dichloromethane (100 mL). The mixture was washed with water (3×80 mL). The organic layers were combined dried over anhydrous sodium sulfate, filtered and concentrated under reduced pressure. The residue was purified by silica gel column chromatography, eluted with ethyl acetate/petroleum (1/10) to afford chloromethyl (2S)-2-[(tert-butoxycarbonyl)amino]-3-methylbutanoate (566 mg, 23% yield) as a colorless oil. LCMS (ESI, m/z): 266 [M+H]$^+$ A 100 mL round-bottom flask was charged with 4-[(11S)-12-[4-bromo-3-(trifluoromethyl)benzoyl]-5-(cyclopropylmethyl)-11-methyl-8-oxo-2,3,7,12-tetraazatricyclo[7.4.0.0^{2,6}]trideca-1(9),3,5-trien-7-yl]-N-methylbenzamide (80.0 mg, 0.125 mmol, 1.00 eq.), chloromethyl (2S)-2-[(tert-butoxycarbonyl)amino]-3-methylbutanoate (66.2 mg, 0.250 mmol, 2.00 eq.), cesium carbonate (81.1 mg, 0.250 mmol, 2.00 eq.) and DMF (30 mL). The resulting solution was stirred overnight at rt and quenched with water (50 mL). The mixture was extracted with ethyl acetate (3×100 mL). The organic layers were combined, washed with saturated sodium chloride solution (3×50 mL), dried over anhydrous sodium sulfate, filtered and concentrated under reduced pressure. The residue was purified by Prep-TLC with ethyl acetate/petroleum (8/1) to afford 4-[(11S)-12-[4-bromo-3-(trifluoromethyl)benzoyl]-5-(cyclopropylmethyl)-11-methyl-8-oxo-2,3,7,12-tetraazatricyclo[7.4.0.0^{2,6}]trideca-1(9),3,5-trien-7-yl]-N-(hydroxymethyl)-N-methylbenzamide (91) (23.4 mg, 27% yield) as a white solid. LCMS (ESI, m/z): 672 [M+H]$^+$. $^1$H NMR (400 MHz, DMSO-d$_6$) δ 8.35 (s, 1H), 8.00-7.91 (m, 4H), 7.88 (d, J=2.0 Hz, 1H), 7.79-7.62 (m, 2H), 7.51-7.45 (m, 2H), 5.64-5.60 (m, 1H), 5.08-5.02 (m, 1H), 4.42-4.27 (m, 1H), 4.16-4.10 (m, 1H), 3.91-3.85 (m, 1H), 2.52-2.48 (m, 4H), 2.84-2.78 (m, 4H), 1.05 (d, J=6.5 Hz, 1H), 0.68-0.52 (m, 1H), 0.35-0.19 (m, 2H), −0.19--0.24 (m, 2H).

A 100 mL round bottom flask was charged with 4-[(11S)-12-[4-bromo-3-(trifluoromethyl)benzoyl]-5-(cyclopropylmethyl)-11-methyl-8-oxo-2,3,7,12-tetraazatricyclo[7.4.0.0^{2,6}]trideca-1(9),3,5-trien-7-yl]-N-(hydroxymethyl)-N-methylbenzamide (200 mg, 0.297 mmol, 1.00 eq.), (2S)-2-[(tert-butoxycarbonyl)amino]-3-methylbutanoic acid (77.5 mg, 0.356 mmol, 1.20 eq.), DMAP (54.5 mg, 0.446 mmol, 1.50 eq.), DCC (92.0 mg, 0.446 mmol, 1.50 eq.) and dichloromethane (50 mL). The resulting solution was stirred for overnight at rt and quenched with water (100 mL). The mixture was extracted with dichloromethane (3×100 mL). The organic layers were combined, dried over anhydrous sodium sulfate, filtered and concentrated under reduced pressure. The residue was purified by silica gel column chromatography, eluted with ethyl acetate/petroleum (1/2) to afford (1-{4-[(11S)-12-[4-bromo-3-(trifluoromethyl)benzoyl]-5-(cyclopropylmethyl)-11-methyl-8-oxo-2,3,7,12-tetraazatricyclo[7.4.0.0^{2,6}]trideca-1(9),3,5-trien-7-yl]phenyl}-N-methylformamido)methyl (2S)-2-[(tert-butoxycarbonyl)amino]-3-methylbutanoate (136.6 mg, 53% yield) as a yellow solid. LCMS (ESI, m/z): 871 [M+H]+.

A 100 mL round bottom flask was charged with (1-{4-[(11S)-12-[4-bromo-3-(trifluoromethyl)benzoyl]-5-(cyclopropylmethyl)-11-methyl-8-oxo-2,3,7,12-tetraazatricyclo[7.4.0.0^{2,6}]trideca-1(9),3,5-trien-7-yl]phenyl}-N-methylformamido)methyl (2S)-2-[(tert-butoxycarbonyl)amino]-3-methylbutanoate (180 mg, 0.206 mmol, 1.00 eq.) and hydrogen chloride (30 mL, 1 M in 1,4-dioxane). The resulting solution was stirred 2 h at rt and concentrated under reduced pressure. The crude product was purified by Prep-HPLC with following conditions: Column: XBridge Prep OBD C$_{18}$ Column, 30×150 mm, 5 um; Mobile Phase A: Water (0.05% TFA), Mobile Phase B: ACN; Flow rate: 60 mL/min; Gradient: 33% B to 63% B in 7 min to afford (1-{4-[(11S)-12-[4-bromo-3-(trifluoromethyl)benzoyl]-5-(cyclopropylmethyl)-11-methyl-8-oxo-2,3,7,12-tetraazatricyclo[7.4.0.0^{2,6}]trideca-1(9),3,5-trien-7-yl]phenyl}-N-methylformamido)methyl (2S)-2-amino-3-methylbutanoate hydrochloride (90) (40.9 mg, 25% yield) as a white solid. $^1$H NMR (400 MHz, DMSO-d$_6$) δ 8.67 (s, 1H), 8.39 (s, 2H), 8.13-7.97 (m, 3H), 7.96-7.85 (m, 2H), 7.82-7.72 (m, 1H), 7.63 (dd, J=8.6, 2.1 Hz, 1H), 7.51-7.39 (m, 1H), 7.31-6.99 (m, 2H), 5.95 (s, 1H), 4.86 (d, J=3.6 Hz, 2H), 4.38 (m, 1H), 3.92 (d, J=4.9 Hz, 1H), 2.85-2.83 (m, 4H), 2.78-2.63 (m, 1H), 2.19-1.98 (m, 1H), 1.47-1.33 (m, 2H), 1.03 (d, J=6.4 Hz, 3H), 0.93 (t, J=6.8 Hz, 6H), 0.62-0.57 (m, 1H), 0.39-0.22 (m, 2H), -0.11--0.13 (m, 2H). LCMS (ESI, m/z): 771 [M+H—HCl]+

Example 48

(11R)-12-[4-bromo-3-(trifluoromethyl)benzoyl]-5-isobutyl-11-methyl-7-[4-(4-methyl-1,2,4-triazol-3-yl)phenyl]-2,3,7,12-tetrazatricyclo[7.4.0.0^2,6]trideca-1(9),3,5-trien-8-one (60a) and (11S)-12-[4-bromo-3-(trifluoromethyl)benzoyl]-5-isobutyl-11-methyl-7-[4-(4-methyl-1,2,4-triazol-3-yl)phenyl]-2,3,7,12-tetrazatricyclo[7.4.0.0^2,6]trideca-1(9),3,5-trien-8-one (60b)

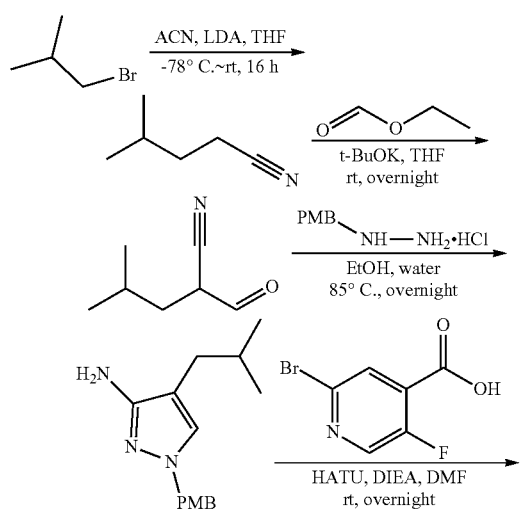
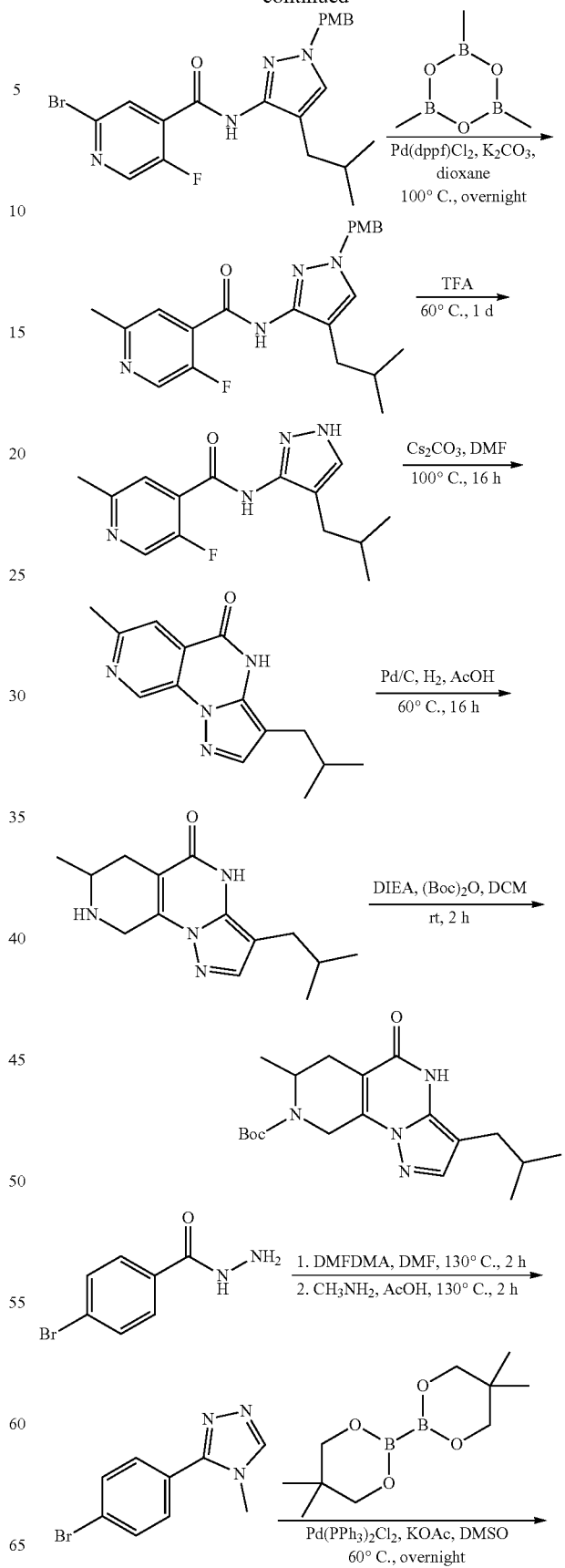

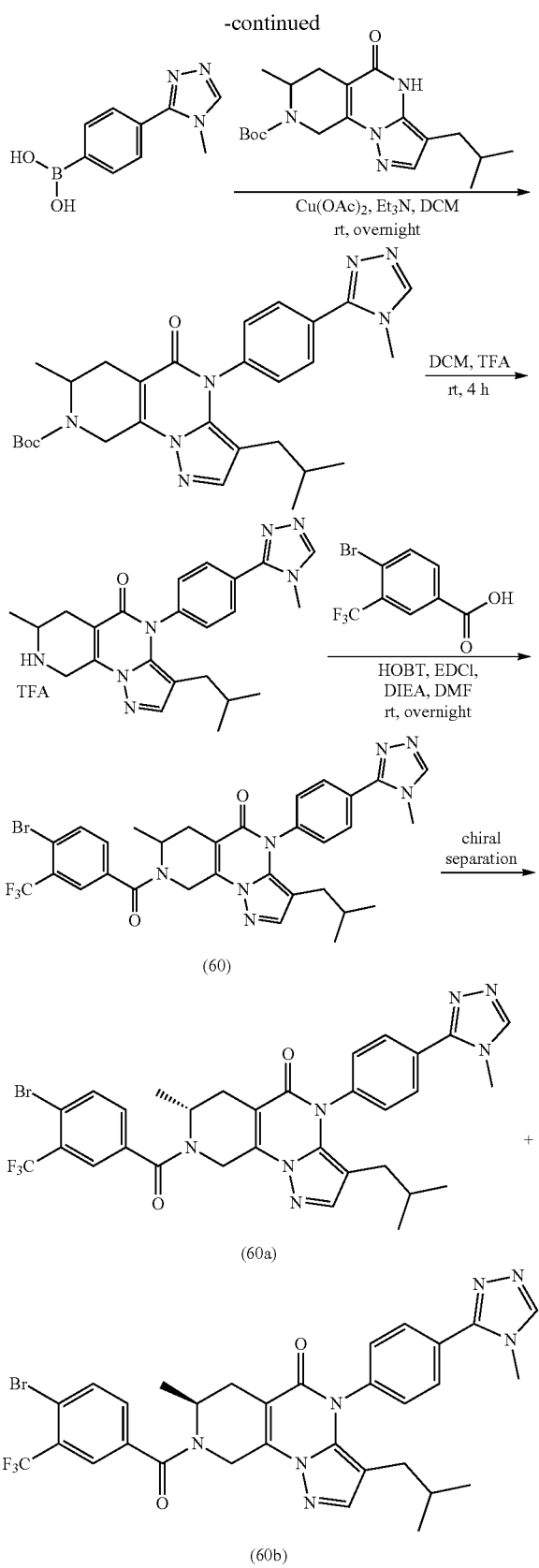

(60)

(60a)

(60b)

To a stirred solution of acetonitrile (3.00 g, 73.1 mmol, 1.00 eq.) in THF (100 mL) was added LDA (36.6 mL, 73.1 mmol, 1.00 eq., 2M in THF) dropwise over 2 h at −78° C. under a nitrogen atmosphere. The mixture was stirred for 1 h at −78° C. Isobutyl bromide (11.0 g, 80.4 mmol, 1.10 eq.) in THF (100 mL) was added dropwise. The mixture was stirred for 16 h at rt. The reaction was quenched with saturated NH$_4$Cl (200 mL) at rt. The mixture was extracted with dichloromethane (3×200 mL). The combined organic layers were washed with brine (3×200 mL) and dried over anhydrous sodium sulfate. After filtration, the filtrate was concentrated under reduced pressure to afford 4-methylpentanitrile (7.00 g, crude) as a dark yellow oil. GCMS (ESI, m/z): 97 [M]$^+$.

To a stirred mixture of 4-methylpentanitrile (7.00 g, 72.0 mmol, 1.00 eq.) in THF (200 mL) was added t-BuOK (24.2 g, 216 mmol, 3.00 eq.) at 0° C. under a nitrogen atmosphere. The mixture was stirred for 15 min at rt under nitrogen atmosphere. Ethyl formate (26.7 g, 360 mmol, 5.00 eq.) was added dropwise very slowly, and the mixture was stirred for overnight at rt under a nitrogen atmosphere. The reaction was quenched with 1.0 M HCl (500 mL) at 0° C. The mixture was extracted with ethyl acetate (3×500 mL). The combined organic layers were washed with brine (2×500 mL) and dried over anhydrous sodium sulfate. After filtration, the filtrate was concentrated under reduced pressure to afford 2-formyl-4-methylpentanenitrile (8.00 g, 89% yield) as a dark yellow oil. GCMS (ESI, m/z): 125 [M]$^+$.

A 500 mL round-bottom flask was charged with 2-formyl-4-methylpentanenitrile (16.0 g, 128 mmol, 1.00 eq.), [(4-methoxyphenyl)methyl]hydrazine hydrochloride (16.9 g, 89.5 mmol, 0.70 eq.), EtOH (300 mL) and H$_2$O (60 mL). The mixture was stirred overnight at 85° C. under a nitrogen atmosphere and then concentrated under reduced pressure. The mixture was basified to pH 8 with saturated NaHCO$_3$ (aq.). The mixture was extracted with ethyl acetate (3×500 mL). The combined organic layers were washed with brine (2×500 mL) and dried over anhydrous sodium sulfate. After filtration, the filtrate was concentrated under reduced pressure. The residue was purified by silica gel column chromatography, eluted with ethyl acetate:hexane (1:1) to afford 1-[(4-methoxyphenyl)methyl]-4-(2-methylpropyl)pyrazol-3-amine (12.0 g, 36% yield) as a dark yellow oil. LCMS (ESI, m/z): 260 [M+H]$^+$.

A 500 mL round-bottom flask was charged with 1-[(4-methoxyphenyl)methyl]-4-(2-methylpropyl)pyrazol-3-amine (6.02 g, 23.2 mmol, 1.00 eq.), 2-bromo-5-fluoropyridine-4-carboxylic acid (6.13 g, 27.8 mmol, 1.20 eq.), N,N,N',N'-tetramethyl-O-(7-azabenzotriazol-1-yl)uronium hexafluorophosphate (5.00 g, 46.4 mmol, 2.00 eq.)), N,N-diisopropylethylamine (15.0 g, 116 mmol, 5.00 eq.) and DMF (100 mL). The mixture was stirred for overnight at rt under nitrogen. The reaction was quenched with water (500 mL). The solution was extracted with ethyl acetate (3×500 mL). The organic layers were combined, washed with brine (3×500 mL), dried over anhydrous sodium sulfate, filtered and concentrated under reduced pressure. The residue was purified by silica gel column chromatography, eluted with ethyl acetate:petroleum ether (3:7) to afford 2-bromo-5-fluoro-N-{1-[(4-methoxyphenyl)methyl]-4-(2-methylpropyl)pyrazol-3-yl}pyridine-4-carboxamide (7.66 g, 72% yield) as a dark yellow oil. LCMS (ESI, m/z): 461 [M+H]$^+$.

A 500 mL round-bottom flask was charged with 2-bromo-5-fluoro-N-{1-[(4-methoxyphenyl)methyl]-4-(2-methylpropyl)pyrazol-3-yl}pyridine-4-carboxamide (2.00 g, 4.34 mmol, 1.00 eq.), trimethyl-1,3,5,2,4,6-trioxatriborinane (5.46 g, 21.7 mmol, 5.00 eq., 50% w/w in THF), 1,1'-bis(diphenylphosphino)ferrocenepalladiumdichloride (0.354 g, 0.433 mmol, 0.10 eq.), K$_2$CO$_3$ (1.80 g, 13.0 mmol, 3.00 eq.)

and 1,4-dioxane (200 mL). The mixture was stirred for overnight at 100° C. under nitrogen. The reaction was quenched with water (500 mL). The solution was extracted with ethyl acetate (3×500 mL). The organic layers were combined, washed with brine (2×500 mL), dried over anhydrous sodium sulfate, filtered and concentrated under reduced pressure. The residue was purified by silica gel column chromatography, eluted with ethyl acetate:petroleum ether (1:1) to afford 5-fluoro-N-{1-[(4-methoxyphenyl)methyl]-4-(2-methylpropyl)pyrazol-3-yl}-2-methylpyridine-4-carboxamide (1.32 g, 77% yield) as a dark yellow oil. LCMS (ESI, m/z): 397 [M+H]$^+$.

A 100 mL round-bottom flask was charged with 5-fluoro-N-{1-[(4-methoxyphenyl)methyl]-4-(2-methylpropyl)pyrazol-3-yl}-2-methylpyridine-4-carboxamide (1.30 g, 3.28 mmol, 1.00 eq.) and trifluoroacetic acid (30 mL). The reaction was stirred for 1 day at 60° C. and then concentrated under reduced pressure. The residue was purified by silica gel column chromatography, eluted with dichloromethane:methanol (92:8) to afford 5-fluoro-2-methyl-N-[4-(2-methylpropyl)-1H-pyrazol-3-yl]pyridine-4-carboxamide (0.816 g, 90% yield) as a yellow solid. LCMS (ESI, m/z): 277 [M+H]$^+$.

A 500 mL round-bottom flask was charged with 5-fluoro-2-methyl-N-[4-(2-methylpropyl)-1H-pyrazol-3-yl]pyridine-4-carboxamide (4.20 g, 15.2 mmol, 1.00 eq.), cesium carbonate (24.8 g, 76.0 mmol, 5.00 eq.) and DMF (50 mL). The mixture was stirred for 16 h at 100° C. The reaction was quenched with water (300 mL). The solution was extracted with ethyl acetate (3×500 mL). The organic layers were combined, washed with brine (3×500 mL), dried over anhydrous sodium sulfate, filtered and concentrated under reduced pressure to afford 3-isobutyl-7-methylpyrazolo[1,5-a]pyrido[4,3-e]pyrimidin-5(4H)-one (2.30 g, 59% yield) as a white solid. LCMS (ESI, m/z): 257 [M+H]$^+$.

A 500 mL round-bottom flask was charged with 3-isobutyl-7-methylpyrazolo[1,5-a]pyrido[4,3-e]pyrimidin-5(4H)-one (5.31 g, 20.7 mmol, 1.00 eq.)), acetic acid (100 mL) and 10% palladium carbon (0.5 g). The solution was stirred for 16 h at 60° C. under a hydrogen atmosphere (2-3 atm). The solid was filtered off. The filtrate was concentrated under reduced pressure to afford 3-isobutyl-7-methyl-6,7,8,9-tetrahydropyrazolo[1,5-a]pyrido[4,3-e]pyrimidin-5(4H)-one (4.50 g, crude) as a yellow solid. LCMS (ESI, m/z): 261 [M+H]$^+$.

A 500 mL round-bottom flask was charged with 3-isobutyl-7-methyl-6,7,8,9-tetrahydropyrazolo[1,5-a]pyrido[4,3-e]pyrimidin-5(4H)-one (4.50 g, 17.3 mmol, 1.00 eq.), N,N-diisopropylethylamine (11.2 g, 86.4 mmol, 5.00 eq.), Boc$_2$O (7.54 g, 34.5 mmol, 2.00 eq.) and DCM (200 mL). The mixture was stirred for 2 h at rt. The reaction was quenched with water (200 mL). The solution was extracted with DCM (3×200 mL). The organic layers were combined, washed with brine (3×200 mL), dried over anhydrous sodium sulfate, filtered and concentrated under reduced pressure. The residue was purified by silica gel column chromatography, eluted with ethyl acetate:petroleum ether (3:7) to afford tert-butyl 3-isobutyl-7-methyl-5-oxo-5,6,7,9-tetrahydropyrazolo[1,5-a]pyrido[4,3-e]pyrimidine-8(4H)-carboxylate (5.12 g, 82% yield) as an off-white solid. LCMS (ESI, m/z): 361 [M+H]$^+$.

A 250 mL round-bottom flask was charged with 4-bromobenzoylhydrazine (10.0 g, 46.5 mmol, 1.00 eq.), DMF-DMA (6.65 g, 55.8 mmol, 1.20 eq.) and DMF (60 mL). The mixture was stirred for 2 h at 130° C. The mixture was cooled to rt. CH$_3$NH$_2$ (17.5 g, 186 mmol, 4.00 eq., 33% in EtOH) and AcOH (16.8 g, 270 mmol, 6.00 eq.) were added. The mixture was stirred 2 h at 130° C. The reaction was quenched with water (100 mL). The pH value of the mixture was adjusted to 7 with NaOH (2 mol/L) and then extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with CH$_2$Cl$_2$:MeOH (10:1) to afford 3-(4-bromophenyl)-4-methyl-1,2,4-triazole (4.80 g, 43% yield) as a light yellow oil. LCMS (ESI, m/z): 238 [M+H]$^+$.

A 250 mL round-bottom flask was charged with 3-(4-bromophenyl)-4-methyl-1,2,4-triazole (4.80 g, 20.2 mmol, 1.00 eq.), 2-(5,5-dimethyl-1,3,2-dioxaborinan-2-yl)-5,5-dimethyl-1,3,2-dioxaborinane (5.69 g, 25.2 mmol, 1.50 eq.), Pd(PPh$_3$)$_2$Cl$_2$ (1.18 g, 1.68 mmol, 0.10 eq.), KOAc (5.94 g, 60.5 mmol, 3.00 eq.) and DMSO (40 mL). The solution was stirred for overnight at 60° C. under a nitrogen atmosphere. The mixture was extracted with ethyl acetate (3×300 mL). The combined organic layers were washed with water (3×300 mL), dried over anhydrous sodium sulfate, filtered and concentrated under reduced pressure. The residue was purified by reverse flash chromatography with the following conditions: column, C$_{18}$ column; mobile phase, ACN in water (0.05% TFA), 10% to 50% gradient in 23 min; detector, UV 254 nm to afford 4-(4-methyl-1,2,4-triazol-3-yl)phenylboronic acid (2.74 g, 67% yield) as a light yellow oil. LCMS (ESI, m/z): 204 [M+H]$^+$.

A 100 mL round-bottom flask was charged with tert-butyl 11-methyl-5-(2-methylpropyl)-8-oxo-2,3,7,12-tetraazatricyclo[7.4.0.0^{2,6}]trideca-1(9),3,5-triene-12-carboxylate (300 mg, 0.832 mmol, 1.00 eq.), 4-(4-methyl-1,2,4-triazol-3-yl)phenylboronic acid (253 mg, 1.25 mmol, 1.50 eq.), Cu(OAc)$_2$ (151 mg, 0.832 mmol, 1.00 eq.), Et$_3$N (253 mg, 2.47 mmol, 3.00 eq.) and DCM (10 mL). The mixture was stirred for 2 h at rt under an oxygen atmosphere. The reaction was quenched with water (100 mL). The mixture was extracted with DCM (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford tert-butyl 11-methyl-7-[4-(4-methyl-1,2,4-triazol-3-yl)phenyl]-5-(2-methylpropyl)-8-oxo-2,3,7,12-tetraazatricyclo[7.4.0.0^{2,6}]trideca-1(9),3,5-triene-12-carboxylate (100 mg, 23% yield) as a yellow solid. LCMS (ESI, m/z): 518 [M+H]$^+$.

A 100 mL round bottom flask was charged with tert-butyl 11-methyl-7-[4-(4-methyl-1,2,4-triazol-3-yl)phenyl]-5-(2-methylpropyl)-8-oxo-2,3,7,12-tetraazatricyclo[7.4.0.0^{2,6}]trideca-1(9),3,5-triene-12-carboxylate (100 mg, 0.193 mmol, 1.00 eq.), TFA (2.00 mL) and DCM (10 mL). The mixture was stirred for 4 h at rt and then concentrated under reduced pressure to afford 11-methyl-7-[4-(4-methyl-1,2,4-triazol-3-yl)phenyl]-5-(2-methylpropyl)-2,3,7,12-tetraazatricyclo[7.4.0.0^{2,6}]trideca-1(9),3,5-trien-8-one trifluoroacetic acid salt (90 mg, crude) as a yellow oil. LCMS (ESI, m/z): 418 [M-TFA+H]±.

A 40 mL vial was charged with 11-methyl-7-[4-(4-methyl-1,2,4-triazol-3-yl)phenyl]-5-(2-methylpropyl)-2,3,7,12-tetraazatricyclo[7.4.0.0^{2,6}]trideca-1(9),3,5-trien-8-one trifluoroacetic acid salt (90.0 mg, 0.169 mmol, 1.00 eq.), 4-bromo-3-(trifluoromethyl)benzoic acid (69.7 mg, 0.259 mmol, 1.50 eq.), EDCI (62.0 mg, 0324 mmol, 1.90 eq.), HOBT (43.7 mg, 0.324 mmol, 1.90 eq.), DIEA (83.6 mg, 0.648 mmol, 3.80 eq.) and DMF (10 mL). The mixture was stirred for overnight at rt. The reaction was quenched with water (50 mL). The mixture was extracted with EtOAc (3×100 mL). The combined organic layers were washed with water (3×80 mL), dried over anhydrous sodium sulfate, filtered and concentrated under reduced pressure. The residue was purified by prep-TLC with $CH_2Cl_2$:MeOH (10:1) to afford the crude product. The crude product was purified by prep-chiral-HPLC with the following conditions: Column: CHIRAL ART Amylose-SA, 2×25 cm, 5 μm; Mobile Phase A: MtBE (0.5% 2M $NH_3$-MeOH)-HPLC, Mobile Phase B: EtOH-HPLC; Flow rate: 20 mL/min; Gradient: 50% B to 50% B in 12 min to afford (11R)-12-(4-bromo-3-chlorobenzoyl)-11-methyl-7-[4-(4-methyl-1,2,4-triazol-3-yl)phenyl]-5-(2-methylpropyl)-2,3,7,12-tetraazatricyclo[7.4.0.0ˆ{2,6}]trideca-1(9),3,5-trien-8-one (60a) (the first eluting enantiomer, Rt=1.9 min, 17.8 mg, 16% yield) as a white solid, and (11S)-12-(4-bromo-3-chlorobenzoyl)-11-methyl-7-[4-(4-methyl-1,2,4-triazol-3-yl)phenyl]-5-(2-methylpropyl)-2,3,7,12-tetraazatricyclo[7.4.0.0ˆ{2,6}]trideca-1(9),3,5-trien-8-one (60b) (the second eluting enantiomer, Rt=2.63 min, 35 mg, 32% yield) as a white solid. LCMS (ESI, m/z): 668 [M+H]$^+$. $^1$H NMR (400 MHz, CDCl$_3$) δ 8.40 (br s, 1H), 7.93 (m, 2H), 7.86-7.78 (m, 2H), 7.66-7.43 (m, 4H), 5.86 (br m, 1H), 4.48 (br m, 2H), 3.87 (s, 3H), 2.88-2.60 (m, 2H), 1.57 (d, J=7.0 Hz, 2H), 1.39-1.19 (m, 4H), 0.61 (d, J=6.5 Hz, 6H).

Example 49

Dimethyl [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0ˆ2,6]trideca-1(9),3,5-trien-7-yl]benzoyl]amino]methyl Phosphate (103)

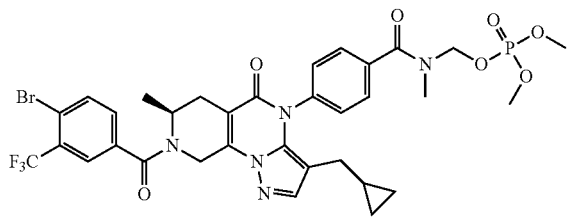 [SMILES: COP(=O)(OC)OCN(C)C(=O)c1ccc(-n2c(=O)c3c(n4ncc(CC5CC5)c24)CN(C(=O)c2ccc(Br)c(C(F)(F)F)c2)[C@@H](C)C3)cc1]

To a solution of rac-(S)-4-(8-(4-bromo-3-(trifluoromethyl)benzoyl)-3-(cyclopropylmethyl)-7-methyl-5-oxo-6,7,8,9-tetrahydropyrazolo[1,5-a]pyrido[4,3-e]pyrimidin-4(5H)-yl)-N-(hydroxymethyl)-N-methylbenzamide (410 mg, 0.610 mmol, 1.00 eq.) in anhydrous dichloromethane (20 mL) were added N-methylimidazole (206 mg, 2.51 mmol, 4.10 eq.) and dimethyl phosphorochloridate (144 mg, 1.00 mmol, 1.60 eq.) at −20° C. The mixture was warmed to rt naturally and stirred for 16 h at rt. The mixture was concentrated under reduced pressure. The residue was purified by silica gel column chromatography, eluted with 0-16% methanol in dichloromethane to afford the crude product. The crude product was re-purified by prep-HPLC with the following condition: Column: Xselect CSH C$_{18}$ OBD Column 30×150 mm 5 μm; Mobile Phase A: Water (0.05% TFA), Mobile Phase B: ACN; Flow rate: 60 mL/min; Gradient: 36% B to 65% B in 7 min; Wave Length: 254 nm to afford dimethyl [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0ˆ2,6]trideca-1(9),3,5-trien-7-yl]benzoyl]amino]methyl phosphate (103) (87.5 mg, 18% yield) as a white solid. LCMS (ESI, m/z): 780 [M+H]$^+$. $^1$H NMR (300 MHz, Chloroform-d) δ 7.96-7.94 (m, 3H), 7.84 (d, J=8.1 Hz, 1H), 7.77 (s, 1H), 7.67 (dd, J=8.1, 2.0 Hz, 1H), 7.46 (d, J=8.7 Hz, 2H), 6.31 (d, J=4.2 Hz, 1H), 6.01 (s, 1H), 5.05-4.98 (m, 1H), 4.74-4.67 (m, 1H), 4.45-4.42 (m, 1H), 3.73 (d, J=11.4 Hz, 6H), 3.07 (d, J=4.8 Hz, 3H), 2.94-2.81 (m, 2H), 1.48 (d, J=6.9 Hz, 2H), 1.07 (d, J=6.6 Hz, 3H), 0.66-0.61 (m, 1H), 0.45-0.39 (m, 2H), −0.06--0.11 (m, 2H).

Example 50

Methyl [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0ˆ2,6]trideca-1(9),3,5-trien-7-yl]benzoyl]amino]methyl Hydrogen Phosphate (107)

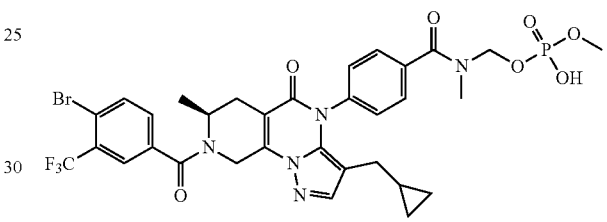

To a solution of rac-(S)-(4-(8-(4-bromo-3-(trifluoromethyl)benzoyl)-3-(cyclopropylmethyl)-7-methyl-5-oxo-6,7,8,9-tetrahydropyrazolo[1,5-a]pyrido[4,3-e]pyrimidin-4(5H)-yl)-N-methylbenzamido)methyl dimethyl phosphate (103) (219 mg, 0.280 mmol, 1.00 eq.) in acetonitrile (12 mL) was added bromotrimethylsilane (0.320 mL, 2.42 mmol, 8.60 eq.) at −20° C. The mixture was stirred for 2 h at rt and then concentrated under reduced pressure. The residue was dissolved in methanol (20 mL) and water (1.25 mL). The mixture was stirred for 1 h at rt and then concentrated under reduced pressure. The residue was purified by reverse phase chromatography with following condition: Column: Agela C$_{18}$ Column, 120 g; Mobile Phase A: Water (0.05% TFA), Mobile Phase B: ACN; Flow rate: 40 mL/min; Gradient: 0% B to 45% B in 30 min; Wave Length: 220 nm to afford the crude product. The crude product was re-purified by prep-HPLC with the following condition: Column: XBridge Shield RP18 OBD Column, 19×250 mm, 10 μm; Mobile Phase A: Water (0.05% TFA), Mobile Phase B: ACN; Flow rate: 25 mL/min; Gradient: 40% B to 65% B in 7 min; Wave Length: 254 nm to afford methyl [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0ˆ2,6]trideca-1(9),3,5-trien-7-yl]benzoyl]amino]methyl hydrogen phosphate (107) (28.0 mg, 13% yield) as a white solid. LCMS (ESI, m/z): 766 [M+H]$^+$. $^1$H NMR (400 MHz, Methanol-d$_4$) δ 8.03-7.94 (m, 4H), 7.79-7.68 (m, 2H), 7.53 (d, J=8.4 Hz, 2H), 6.48 (brs, 1H), 4.94-4.92 (m, 1H), 4.82-4.81 (m, 1H), 4.36 (brs, 1H), 3.65 (d, J=11.2 Hz, 3H), 2.99 (s, 3H), 2.79-2.63 (m, 2H), 1.51-1.49 (m, 6H), 0.65 (s, 1H), 0.40-0.30 (m, 2H), −0.05--0.20 (m, 2H).

Example 51

[methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]amino]methyl Dihydrogen Phosphate (110)

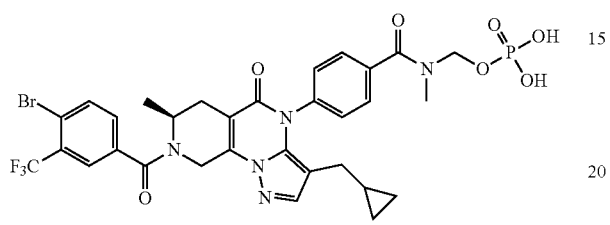

To a solution of rac-(S)-(4-(8-(4-bromo-3-(trifluoromethyl)benzoyl)-3-(cyclopropylmethyl)-7-methyl-5-oxo-6,7,8,9-tetrahydropyrazolo[1,5-a]pyrido[4,3-e]pyrimidin-4(5H)-yl)-N-methylbenzamido)methyl dimethyl phosphate (103) (181 mg, 0.230 mmol, 1.00 eq.) in anhydrous dichloromethane (10 mL) was added N,O-bis(trimethylsilyl)acetamide (0.630 mL, 2.55 mmol, 11.0 eq.) at rt. The mixture was stirred for 1 h at rt under nitrogen. Iodotrimethylsilane (0.270 mL, 1.86 mmol, 8.00 eq.) was added at −78° C. The mixture was stirred for 3 h at rt and then concentrated under reduced pressure. The residue was dissolved in acetonitrile (7 mL) and water (3 mL), stirred for 5 minutes at rt and concentrated under reduced pressure. The residue was purified by reverse phase chromatography with following condition: Column: Agela $C_{18}$ Column, 120 g; Mobile Phase A: Water (0.05% TFA), Mobile Phase B: ACN; Flow rate: 40 mL/min; Gradient: 0% B to 50% B in 30 min; Wave Length: 220 nm to afford the crude product. The crude product was re-purified by prep-HPLC with the following condition: Column: Xselect CSH $C_{18}$ OBD Column 30×150 mm 5 μm, n; Mobile Phase A: Water (0.05% TFA), Mobile Phase B: ACN; Flow rate: 60 mL/min; Gradient: 47% B to 67% B in 7 min, 67% B; Wave Length: 254 nm; RT (min): 5.68 to afford [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]amino]methyl dihydrogen phosphate (110) (60.0 mg, 34% yield) as a white solid. LCMS (ESI, m/z): 752 [M+H]$^+$. $^1$H NMR (400 MHz, Methanol-$d_4$) δ 8.03-7.96 (m, 4H), 7.83-7.70 (m, 2H), 7.63-7.54 (m, 2H), 5.98 (s, 1H), 4.86-4.80 (m, 2H), 4.54-4.46 (m, 2H), 3.05-3.02 (m, 1H), 2.96 (s, 3H), 2.82-2.79 (m, 1H), 1.51 (d, J=6.8 Hz, 2H), 1.09 (d, J=6.4 Hz, 3H), 0.68-0.67 (m, 1H), 0.42-0.33 (m, 2H), −0.11--0.15 (m, 2H).

Example 52

N-methyl-4-[rac-(11R)-5-benzyl-12-[4-bromo-3-(trifluoromethyl)benzoyl]-11-cyclopropyl-8-oxo-2,3,7,12-tetrazatricyclo[7.4.0.0^2,6]trideca-1(9),3,5-trien-7-yl]benzamide (104a) and N-methyl-4-[rac-(11S)-5-benzyl-12-[4-bromo-3-(trifluoromethyl)benzoyl]-11-cyclopropyl-8-oxo-2,3,7,12-tetrazatricyclo[7.4.0.0^2,6]trideca-1(9),3,5-trien-7-yl]benzamide (104b)

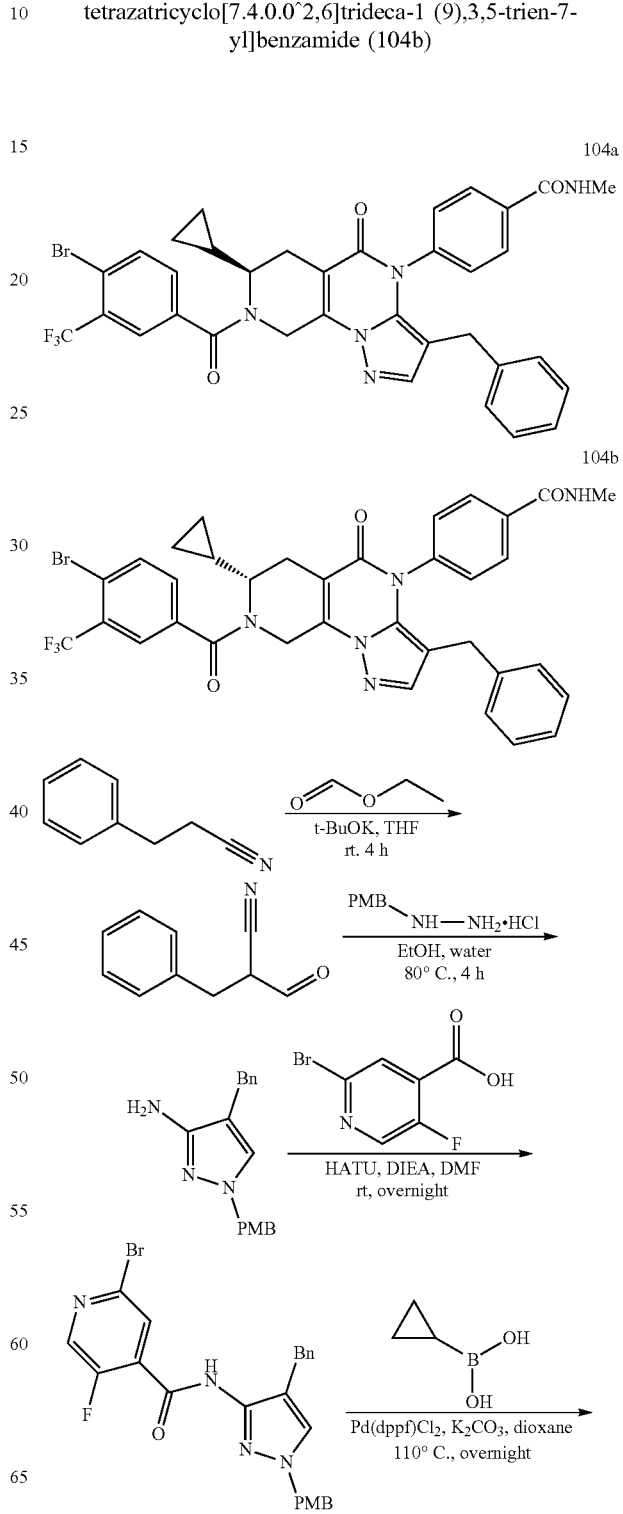

-continued

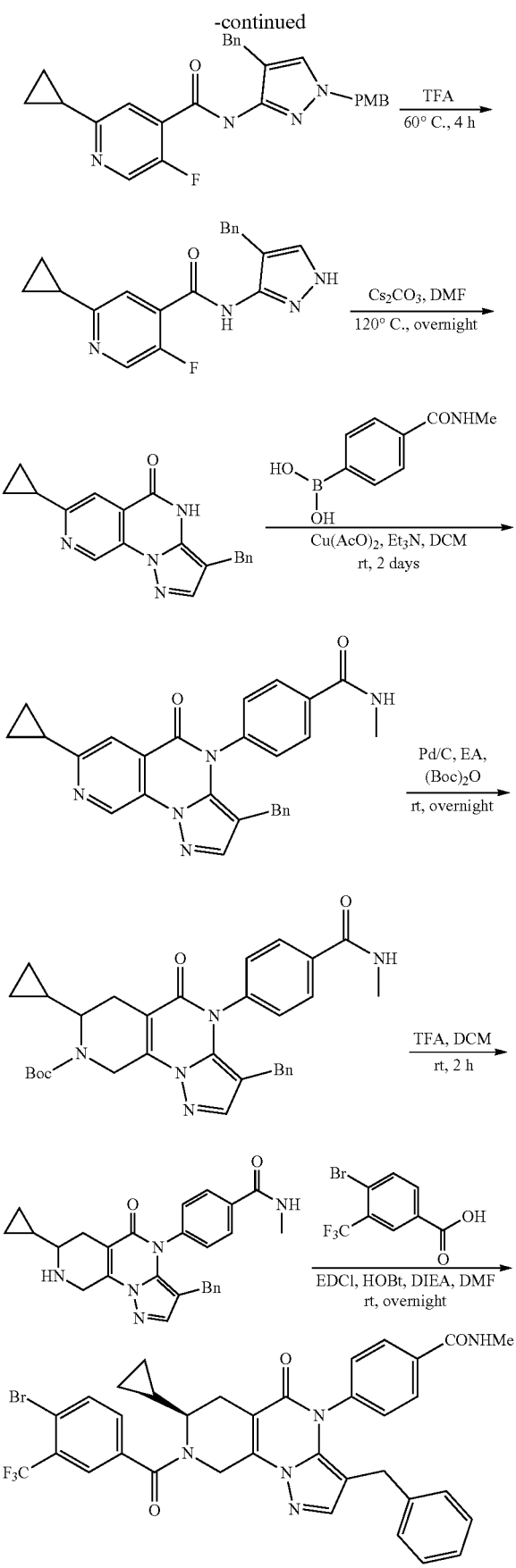

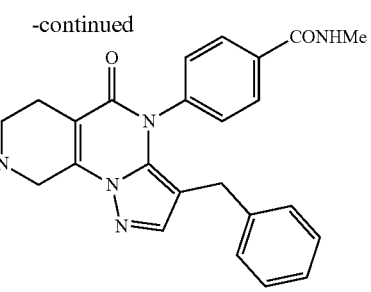

A 1 L round bottom flask was charged with benzylacetonitrile (25.0 g, 0.190 mol, 1.00 eq.) and anhydrous tetrahydrofuran (500 mL). t-BuOK (64.1 g, 0.571 mol, 3.00 eq.) was added at 0° C. The mixture was stirred for 10 mins at rt. Ethyl formate (70.6 g, 0.954 mol, 5.00 eq.) was added dropwise at 0° C. The solution was stirred for 4 h at rt. The reaction was quenched with water (1 L). The mixture was extracted with ethyl acetate (3×500 mL). The combined organic layers were washed with brine (2×500 mL) and water (500 mL), dried over anhydrous sodium sulfate, filtered and concentrated under reduced pressure to afford 2-formyl-3-phenylpropanenitrile (30.0 g, crude) as a brown yellow oil.

A 1 L round bottom flask was charged with 2-formyl-3-phenylpropanenitrile (30.0 g, 188 mmol, 1.00 eq.), [(4-methoxyphenyl)methyl]hydrazine hydrochloride (35.5 g, 188 mmol, 1.00 eq.), EtOH (300 mL) and water (100 mL). The solution was stirred for 4 h at 80° C. and then concentrated under reduced pressure. The residue was diluted with ethyl acetate (1 L), washed with water (3×300 mL), dried over anhydrous sodium, filtered and concentrated under reduced pressure. The residue was purified by trituration with ethyl acetate (80 mL). The light yellow solid was collected by filtration and dried under reduced pressure to afford 4-benzyl-1-[(4-methoxyphenyl)methyl]pyrazol-3-amine (21.0 g, 38% yield) as a light yellow solid. LCMS (ESI, m/z): 294 [M+H]+.

A 250 mL round bottom flask was charged with 4-benzyl-1-[(4-methoxyphenyl)methyl]pyrazol-3-amine (10.0 g, 34.1 mmol, 1.00 eq.), 2-bromo-5-fluoroisonicotinic acid (9.00 g, 40.9 mmol, 1.20 eq.), HATU (19.4 g, 51.1 mmol, 1.50 eq.), DIEA (13.2 g, 102 mmol, 3.00 eq.) and DMF (100 mL). The mixture was stirred for overnight at rt. The reaction was quenched with water (500 mL). The solids were collected by filtration and dried under reduced pressure to afford N-{4-benzyl-1-[(4-methoxyphenyl)methyl]pyrazol-3-yl}-2-bromo-5-fluoropyridine-4-carboxamide (14.5 g, 85% yield) as a light yellow solid. LCMS (ESI, m/z): 495 [M+H]+.

A 100 mL round bottom flask was charged with N-{4-benzyl-1-[(4-methoxyphenyl)methyl]pyrazol-3-yl}-2-bromo-5-fluoropyridine-4-carboxamide (1.00 g, 2.02 mmol, 1.00 eq.), cyclopropylboronic acid (0.220 mg, 2.42 mmol, 1.20 eq.), K2CO3 (0.843 g, 6.06 mmol, 3.00 eq.), Pd(dppf)Cl2 (0.148 g, 0.200 mmol, 0.100 eq.) and 1,4-dioxane (20 mL) at rt. The mixture was stirred for overnight at 100° C. under nitrogen atmosphere. The reaction was quenched with water (100 mL). The mixture was extracted with ethyl acetate (3×100 mL). The organic layers were combined, washed with brine (3×100 mL), dried over anhydrous sodium sulfate, filtered and concentrated under reduced pressure. The residue was purified by silica gel column chromatography, eluted with EA:PE (2:1) to afford N-{4-benzyl-1-[(4-methoxyphenyl)methyl]pyrazol-3-yl}-2-cyclopropyl-5-fluoropyridine-4-carboxamide (0.50 g, 54% yield) as a yellow solid. LCMS (ESI, m/z): 457 [M+H]$^+$.

A 250 mL round-bottom flask was charged with N-{4-benzyl-1-[(4-methoxyphenyl)methyl]pyrazol-3-yl}-2-cyclopropyl-5-fluoropyridine-4-carboxamide (1.00 g, 2.19 mmol, 1.00 eq.) and trifluoroacetic acid (20 mL) at rt. The mixture was stirred for 4 h at 60° C. and then concentrated under reduced pressure. The mixture was diluted with ethyl acetate (50 mL). The mixture was washed with of saturated sodium bicarbonate solution (3×50 mL), dried over anhydrous sodium sulfate, filtered and concentrated under reduced pressure. The residue was purified by silica gel column chromatography, eluted with EA:PE (1:1) to afford N-(4-benzyl-1H-pyrazol-3-yl)-2-cyclopropyl-5-fluoropyridine-4-carboxamide (720 mg, 98% yield) as a light yellow solid. LCMS (ESI, m/z): 337 [M+H]$^+$.

A 250 mL round-bottom flask was charged with added N-(4-benzyl-1H-pyrazol-3-yl)-2-cyclopropyl-5-fluoropyridine-4-carboxamide (1.00 g, 2.97 mmol, 1.00 eq.), $Cs_2CO_3$ (2.91 g, 8.92 mmol, 3.00 eq.) and DMF (25 mL) at rt. The mixture was stirred for overnight at 120° C. The reaction was quenched with water (100 mL). The mixture was extracted with dichloromethane (3×100 mL). The organic layers were combined, washed with brine (3×100 mL), dried over anhydrous sodium sulfate, filtered and concentrated under reduced pressure. The residue was recrystallized with EA (20 mL). The solid was collected by filtration and dried to afford 5-benzyl-11-cyclopropyl-2,3,7,12-tetraazatricyclo[7.4.0.0^{2,6}]trideca-1(9),3,5,10,12-pentaen-8-one (880 mg, 94% yield) as a light yellow solid. LCMS (ESI, m/z): 317 [M+H]$^+$.

A 100 mL round-bottom flask was charged with 5-benzyl-11-cyclopropyl-2,3,7,12-tetraazatricyclo[7.4.0.0^{2,6}]trideca-1(9),3,5,10,12-pentaen-8-one (400 mg, 1.26 mmol, 1.00 eq.), 4-(methylcarbamoyl)phenylboronic acid (271 mg, 1.52 mmol, 1.20 eq.), $Cu(OAc)_2$ (230 mg, 1.26 mmol, 1.00 eq.), $Et_3N$ (384 mg, 3.79 mmol, 3.00 eq.) and DCM (30 mL) at rt. The mixture was stirred for 2 days at rt under O2 atmosphere. The reaction was quenched with water (100 mL). The mixture was extracted with dichloromethane (3×100 mL). The organic layers were combined, washed with brine (3×100 mL), dried over anhydrous sodium sulfate, filtered and concentrated under reduced pressure. The residue was purified by silica gel column chromatography, eluted with EA:PE (1:1) to afford 4-{15-benzyl-11-cyclopropyl-8-oxo-2,3,7,12-tetraazatricyclo[7.4.0.0^{2,6}]trideca-1(9),3,5,10,12-pentaen-7-yl}-N-methylbenzamide (200 mg, 35% yield) as a greenish solid. LCMS (ESI, m/z): 450 [M+H]$^+$.

A 100 mL round-bottom flask was charged with 4-{15-benzyl-11-cyclopropyl-8-oxo-2,3,7,12-tetraazatricyclo[7.4.0.0^{2,6}]trideca-1(9),3,5,10,12-pentaen-7-yl}-N-methylbenzamide (200 mg, 0.445 mmol, 1.00 eq.), 10% Pd/C (20 mg), $Boc_2O$ (194 mg, 0.890 mmol, 2.00 eq.) and EA (100 mL). The mixture was stirred for overnight at rt under hydrogen (2-3 atm) atmosphere. The solid was filtered off and washed with EA (3×20 mL). The filtrate was concentrated under reduced pressure. The residue was purified by silica gel column chromatography, eluted with EA:PE (2:1) to afford tert-butyl 5-benzyl-11-cyclopropyl-7-[4-(methylcarbamoyl)phenyl]-8-oxo-2,3,7,12-tetraazatricyclo[7.4.0.0^{2,6}]trideca-1(9),3,5-triene-12-carboxylate (110 mg, 44% yield) as an off-white solid. LCMS (ESI, m/z): 554 [M+H]$^+$.

A 100 mL round-bottom flask was charged with tert-butyl 5-benzyl-11-cyclopropyl-7-[4-(methylcarbamoyl)phenyl]-8-oxo-2,3,7,12-tetraazatricyclo[7.4.0.0^{2,6}]trideca-1(9),3,5-triene-12-carboxylate (100 mg, 0.181 mmol, 1.00 eq.), TFA (2 mL) and DCM (10 mL). The mixture was stirred for 2 h at rt and then concentrated under reduced pressure to afford 4-{5-benzyl-11-cyclopropyl-8-oxo-2,3,7,12-tetraazatricyclo[7.4.0.0^{2,6}]trideca-1(9),3,5-trien-7-yl}-N-methylbenzamide trifluoroacetic acid salt (100 mg, crude) as a yellow oil. LCMS (ESI, m/z): 454 [M-TFA+H]$^+$.

A 40 mL vial was charged with 4-{15-benzyl-11-cyclopropyl-8-oxo-2,3,7,12-tetraazatricyclo[7.4.0.0^{2,6}]trideca-1(9),3,5-trien-7-yl}-N-methylbenzamide trifluoroacetic acid salt (100 mg, 0.176 mmol, 1.00 eq.), 4-bromo-3-(trifluoromethyl)benzoic acid (71.2 mg, 0.264 mmol, 1.50 eq.), EDCI (50.7 mg, 0.264 mmol, 1.50 eq.), HOBT (35.8 mg, 0.264 mmol, 1.50 eq.), DIEA (142 mg, 1.10 mmol, 6.25 eq.) and DMF (20 mL). The mixture was stirred for overnight at rt. The reaction was quenched with water (100 mL). The mixture was extracted with ethyl acetate (3×100 mL). The organic layers were combined, washed with brine (3×100 mL), dried over anhydrous sodium sulfate, filtered and concentrated under reduced pressure. The residue was purified by Prep-TLC (PE:EA=1:1) to afford the crude product. The crude product was purified by Chiral-Prep-HPLC with the following conditions: Column: CHIRAL ART Cellulose-SA, 2×25 cm, 5 µm; Mobile Phase A: MtBE (0.5% 2M $NH_3$-MeOH)-HPLC, Mobile Phase B: EtOH-HPLC; Flow rate: 20 mL/min; Gradient: 50% B to 50% B in 16 min; Wave Length: 220/254 nm to afford 4-[rac-(11R)-5-benzyl-12-[4-bromo-3-(trifluoromethyl)benzoyl]-11-cyclopropyl-8-oxo-2,3,7,12-tetraazatricyclo[7.4.0.0^{2,6}]trideca-1(9),3,5-trien-7-yl]-N-methylbenzamide (the first elution, 6.0 mg, 4% yield) as a white solid. LCMS (ESI, m/z): 704 [M+H]$^+$. $^1$H NMR (400 MHz, Chloroform-d) δ 7.92-7.67 (m, 4H), 7.47 (s, 2H), 7.28 (d, J=2.2 Hz, 1H), 7.22 (d, J=8.3 Hz, 1H), 7.17-7.07 (m, 3H), 6.69 (s, 2H), 6.14 (d, J=5.1 Hz, 1H), 5.98-4.69 (m, 2H), 3.40-2.97 (m, 6H), 2.97-2.78 (m, 2H), 1.32-1.17 (m, 1H), 0.67-0.10 (m, 4H); and 4-[rac-(11S)-5-benzyl-12-[4-bromo-3-(trifluoromethyl)benzoyl]-11-cyclopropyl-8-oxo-2,3,7,12-tetraazatricyclo[7.4.0.0^{2,6}]trideca-1(9),3,5-trien-7-yl]-N-methylbenzamide (the second elution, 8.5 mg, 5% yield) as a white solid. LCMS (ESI, m/z): 704 [M+H]$^+$. $^1$H NMR (400 MHz, Chloroform-d) δ 7.92-7.67 (m, 4H), 7.47 (s, 2H), 7.28 (d, J=2.1 Hz, 1H), 7.22 (d, J=8.3 Hz, 1H), 7.16-7.10 (m, 3H), 6.68 (s, 2H), 6.15 (d, J=5.1 Hz, 1H), 5.98-4.69 (m, 2H), 3.33-2.99 (m, 6H), 2.97-2.76 (m, 2H), 1.30-1.13 (m, 1H), 0.74-0.11 (m, 4H).

Example 53 rac-(11R)-12-[4-bromo-3-(trifluoromethyl)benzoyl]-7-[1-(2-hydroxyethyl)benzotriazol-5-yl]-5-isobutyl-11-methyl-2,3,7,12-tetrazatricyclo[7.4.0.0^2,6]trideca-1(9),3,5-trien-8-one (108a) and rac-(11S)-12-[4-bromo-3-(trifluoromethyl)benzoyl]-7-[1-(2-hydroxyethyl)benzotriazol-5-yl]-5-isobutyl-11-methyl-2,3,7,12-tetrazatricyclo[7.4.0.0^2,6]trideca-1(9),3,5-trien-8-one (108b)

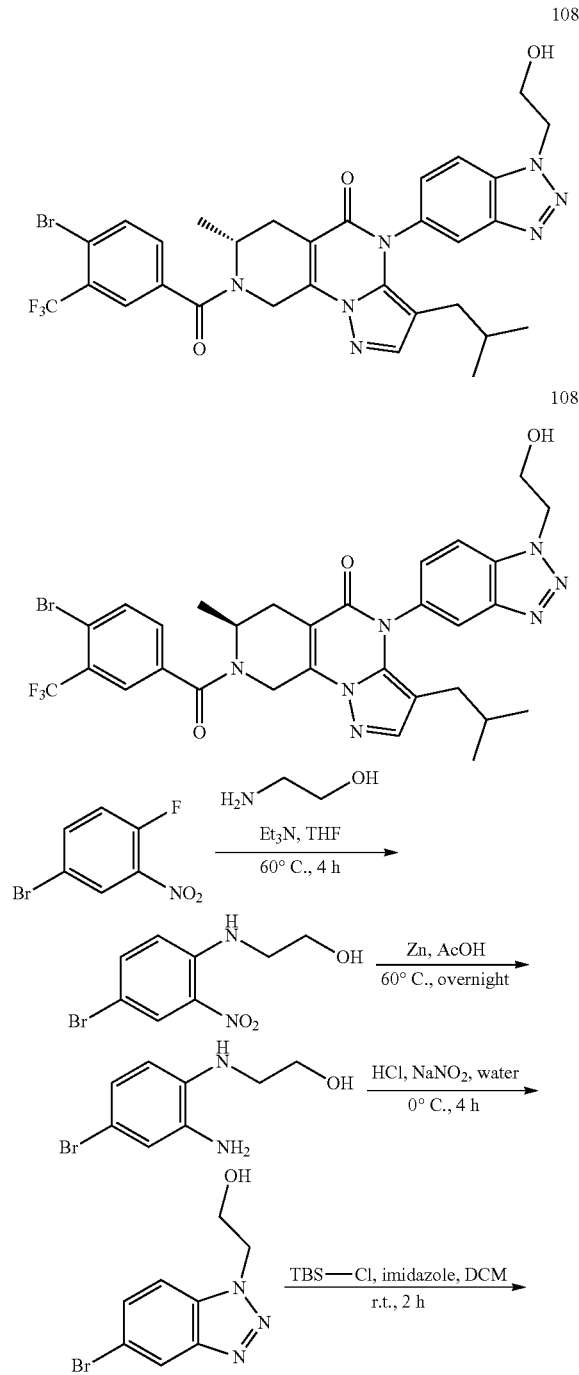

A 250 mL round bottom flask was charged with 4-bromo-1-fluoro-2-nitrobenzene (10.0 g, 45.5 mmol, 1.00 eq.), tetrahydrofuran (100 mL), ethanolamine (3.33 g, 54.5 mmol, 1.20 eq.) and triethylamine (13.8 g, 136 mmol, 3.00 eq.). The resulting solution was stirred for 4 h at 60° C. The mixture was allowed to cool down to room temperature, quenched with water (200 mL) and extracted with ethyl acetate (3×100 mL). The organic layers were combined, washed with saturated brine (3×30 mL), dried over anhydrous sodium sulfate, filtered and concentrated under reduced pressure to afford 2-[(4-bromo-2-nitrophenyl)amino]ethanol (12.1 g, crude) as a yellow solid. LCMS (ESI, m/z): 261 [M+H]⁺.

A 100 mL round bottom flask was charged with 2-[(4-bromo-2-nitrophenyl)amino]ethanol (12.1 g, 46.3 mmol, 1.00 eq.), acetic acid (40 mL) and zinc (9.09 g, 139 mmol, 3.00 eq.). The resulting solution was stirred for overnight at 60° C. The mixture was allowed cool down to room temperature and the solid was filtered off. The filter cake was washed with ethyl acetate (3×10 mL). The filtrate was concentrated under reduced pressure. Then the mixture was diluted with water (100 mL). The mixture was extracted with ethyl acetate (3×100 mL) and the organic layers were combined, washed with brine (3×100 mL), dried over anhydrous sodium sulfate, filtered and concentrated under reduced pressure. The residue was purified by silica gel column chromatography, eluted with ethyl acetate/petroleum ether (1/10) to afford 2-[(2-amino-4-bromophenyl)amino]ethanol (5.60 g, 52% yield) as a brown solid. LCMS (ESI, m/z): 231 [M+H]⁺.

A 100 mL round bottom flask was charged with 2-[(2-amino-4-bromophenyl)amino]ethanol (5.60 g, 24.2 mmol, 1.00 eq.), concentrated hydrogen chloride (4.1 mL) and water (20 mL). Sodium nitrite (3.01 g, 43.6 mmol, 1.80 eq.) in water (10 mL) was added dropwise at 0° C. The mixture was stirred for 4 h at 0° C. The pH value of the mixture was adjusted to 7-8 with 10% Na₂CO₃ and then extracted with ethyl acetate (3×50 mL). The combined organic layers were washed with saturated brine (3×50 mL), dried over anhydrous sodium sulfate and concentrated under reduced pressure. The residue was purified by silica gel column chromatography, eluted with EA:PE (1:10) to afford 2-(5-bromo-1,2,3-benzotriazol-1-yl)ethanol (1.60 g, 27% yield) as a yellow solid. LCMS (ESI, m/z): 242 [M+H]⁺.

A 100 mL round bottom flask was charged with 2-(5-bromo-1,2,3-benzotriazol-1-yl)ethanol (1.60 g, 6.61 mmol, 1.00 eq.), dichloromethane (30 mL), imidazole (2.70 g, 39.7 mmol, 6.00 eq.) and t-butyldimethyl chlorosilane (3.98 g, 26.4 mmol, 4.00 eq.). The solution was stirred for 2 h at rt. The reaction was quenched with water (100 mL). The mixture was extracted with dichloromethane (3×100 mL). The organic layers were combined, washed with brine (3×100 mL), dried over anhydrous sodium sulfate, filtered and concentrated under reduced pressure. The residue was purified by silica gel column chromatography, eluted with EA:PE (1:20) to afford 5-bromo-1-{2-[(tert-butyldimethylsilyl)oxy]ethyl}-1,2,3-benzotriazole (2.30 g, 97% yield) as a yellow solid. LCMS (ESI, m/z): 356 [M+H]⁺.

A 100 mL round bottom flask charged with 5-bromo-1-{2-[(tert-butyldimethylsilyl)oxy]ethyl}-1,2,3-benzotriazole (2.30 g, 6.46 mmol, 1.00 eq.), 2-(5,5-dimethyl-1,3,2-dioxaborinan-2-yl)-5,5-dimethyl-1,3,2-dioxaborinane (2.92 g, 12.9 mmol, 2.00 eq.), potassium acetate (1.27 g, 12.9 mmol, 2.00 eq.) and Pd(PPh₃)₂Cl₂ (0.23 g, 0.323 mmol, 0.05 eq.) and DMSO (20 mL). The solution was stirred for overnight at 60° C. under nitrogen atmosphere. The reaction was quenched with water (100 mL). The mixture was extracted with EA (3×100 mL). The organic layers were combined, washed with brine (3×100 mL), dried over anhydrous sodium sulfate, filtered and concentrated under reduced pressure. The residue was purified by silica gel column chromatography, eluted with EA:PE (1:20) to afford 1-{2-[(tert-butyldimethylsilyl)oxy]ethyl}-1,2,3-benzotriazol-5-ylboronic acid (1.10 g, 44% yield) as a yellow solid. LCMS (ESI, m/z): 390 [M+H]⁺.

A 25 mL round bottom flask was charged with 1-{2-[(tert-butyldimethylsilyl)oxy]ethyl}-1,2,3-benzotriazol-5-ylboronic acid (376 mg, 1.17 mmol, 1.50 eq.), dichloromethane (10 mL), tert-butyl 11-methyl-5-(2-methylpropyl)-8-oxo-2,3,7,12-tetraazatricyclo[7.4.0.0ˆ{2,6}]trideca-1(9),3,5-triene-12-carboxylate (281 mg, 0.780 mmol, 1.00 eq.), cupric acetate (141 mg, 0.780 mmol, 1.00 eq.) and triethylamine (158 mg, 1.56 mmol, 2.00 eq.) at rt under oxygen atmosphere. The solution was stirred for overnight at rt. The reaction was quenched with water (50 mL). The mixture was extracted with dichloromethane (3×50 mL). The organic layers were combined, washed with brine (3×50 mL), dried over anhydrous sodium sulfate, filtered and concentrated under reduced pressure. The residue was purified by Prep-TLC (ethyl acetate/petroleum ether=1/10) to afford tert-butyl 7-[1-(2-hydroxyethyl)-1,2,3-benzotriazol-5-yl]-11-methyl-8-oxo-5-propyl-2,3,7,12-tetraazatricyclo[7.4.0.0ˆ{2,6}]trideca-1(9),3,5-triene-12-carboxylate (140 mg, 28% yield) as a brown solid. LCMS (ESI, m/z): 636 [M+H]⁺.

A 250 mL round bottom flask was charged with tert-butyl 7-(1-{2-[(tert-butyldimethylsilyl)oxy]ethyl}-1,2,3-benzotriazol-5-yl)-11-methyl-5-(2-methylpropyl)-8-oxo-2,3,7,12-tetraazatricyclo[7.4.0.0ˆ{2,6}]trideca-1(9),3,5-triene-12-carboxylate (140 mg, 0.283 mmol, 1.00 eq.), DCM (6 mL) and TFA (1 mL). The mixture was stirred for 2 h at rt and then concentrated under reduced pressure to afford 7-[1-(2-hydroxyethyl)-1,2,3-benzotriazol-5-yl]-11-methyl-5-(2-methylpropyl)-2,3,7,12-tetraazatricyclo[7.4.0.0ˆ{2,6}]trideca-1(9),3,5-trien-8-one trifluoro acetic salt (150 mg, crude) as a brown solid. LCMS (ESI, m/z): 422[M-TFA+H]±.

A 50 mL round bottom flask was charged with 7-[1-(2-hydroxyethyl)-1,2,3-benzotriazol-5-yl]-11-methyl-5-(2-methylpropyl)-2,3,7,12-tetraazatricyclo[7.4.0.0ˆ{2,6}]trideca-1(9),3,5-trien-8-one trifluoro acetic salt (149 mg, 0.278 mmol, 1.00 eq.), DMF (15 mL), 4-bromo-3-(trifluoromethyl)benzoic acid (112 mg, 0.417 mmol, 1.50 eq.), HOBT (75.0 mg, 0.556 mmol, 2.00 eq.), EDCI (106.4 mg, 0.556 mmol, 2.00 eq.) and DIEA (179 mg, 1.390 mmol, 5.00 eq.). The mixture was stirred for overnight at rt under nitrogen atmosphere. The reaction was quenched with water (50 mL). The mixture was extracted with EA (3×30 mL). The organic layers were combined, washed with brine (3×30 mL), dried over anhydrous sodium sulfate, filtered and concentrated under reduced pressure. The residue was purified by Prep-TLC (dichloromethane:methanol=50:1) to afford the crude product. The crude product was purified by Prep-CHIRAL-HPLC with the following conditions: Column: CHIRAL ART Cellulose-SA, 2×5 cm, 5 μm; Mobile Phase A: MtBE (0.5% 2M NH₃-MeOH)-HPLC, Mobile Phase B: EtOH-HPLC; Flow rate: 20 mL/min; Gradient: 50% B to 50% B in 9 min; Wave Length: 220/254 nm to afford rac-(11R)-[4-bromo-3-(trifluoromethyl)benzoyl]-7-[1-(2-hydroxyethyl)-1,2,3-benzotriazol-5-yl]-11-methyl-5-(2-methylpropyl)-2,3,7,12-tetraazatricyclo[7.4.0.0ˆ{2,6}]trideca-1(9),3,5-trien-8-one) (108a) (the first elution, 5.60 mg, 3% yield) as a white solid; and rac-(11S)-[4-bromo-3-(trifluoromethyl)benzoyl]-7-[1-(2-hydroxyethyl)-1,2,3-benzotriazol-5-yl]-11-methyl-5-(2-methylpropyl)-2,3,7,12-tetraazatricyclo[7.4.0.0ˆ{2,6}]trideca-1(9),3,5-trien-8-one) (108b) (the second elution, 5.0 mg, 3% yield) as a white solid. LCMS (ESI, m/z): 672 [M+H]⁺. ¹H NMR (400 MHz, Chloroform-d) δ 8.10 (d, J=11.7 Hz, 1H), 7.85 (t, J=9.1 Hz, 3H), 7.57-7.43 (m, 3H), 4.87 (q, J=5.2 Hz, 2H), 4.50 (s, 1H), 4.29 (t, J=4.9 Hz, 2H), 2.84 (s, 1H), 2.71 (d, J=16.3 Hz, 1H), 1.50-1.31 (m, 6H), 1.20 (s, 2H), 0.48 (d, J=6.6 Hz, 3H), 0.44 (d, J=6.6 Hz, 3H).

Example 54

Synthesis of Intermediates I-1 to I-25

4-(oxolan-3-ylmethyl)-1H-pyrazole (I-1)

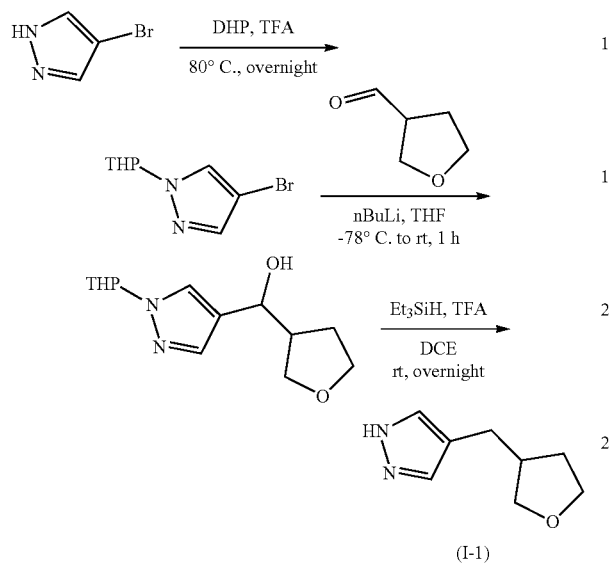

(I-1)

A mixture of 4-bromopyrazole (7.00 g, 47.6 mmol, 1.00 eq.), dihydropyran (6.01 g, 71.4 mmol, 1.50 eq.) and trifluoroacetic acid (0.271 g, 2.38 mmol, 0.05 eq.) was stirred for overnight at 80° C. The mixture was diluted with ethyl acetate (200 mL) and washed with saturated sodium bicarbonate (3×20 mL) and saturated sodium chloride (1×20 mL) and dried over anhydrous sodium sulfate. After filtration, the filtrate was concentrated under reduced pressure. The residue was purified by silica gel column chromatography, eluted with dichloromethane:petroleum ether (9:1) to afford 4-bromo-1-(oxan-2-yl)pyrazole (9.30 g, 84% yield) as a light yellow oil. LCMS (ESI, m/z): 231 [M+H]+.

A mixture of 4-bromo-1-(oxan-2-yl)pyrazole (3.00 g, 13.0 mmol, 1.00 eq.) and tetrahydrofuran (50 mL) under nitrogen was added n-butyllithium (7.8 mL, 19.5 mmol, 1.50 eq. 2.5 M in hexane) at −78° C. The mixture was stirred for 0.5 h at −78° C., then oxolane-3-carbaldehyde (1.95 g, 19.5 mmol, 1.50 eq.) was added. The mixture was stirred for 1 h at rt. The reaction was quenched with saturated ammonium chloride (50 mL aq.) at 0° C. The mixture was extracted with ethyl acetate (3×50 mL). The organic layers were combined, washed with water (3×20 mL), dried over anhydrous sodium sulfate, filtered and concentrated under reduced pressure. The residue was purified by silica gel column chromatography, eluted with ethyl acetate:petroleum ether (1:3) to afford [1-(oxan-2-yl)pyrazol-4-yl](oxolan-3-yl)methanol (1.80 g, 55% yield) as a yellow oil. LCMS (ESI, m/z): 253 [M+H]+.

A 250 mL round-bottom flask was charged with [1-(oxan-2-yl)pyrazol-4-yl](oxolan-3-yl)methanol (1.80 g, 7.13 mmol, 1.00 eq.), triethylsilane (12.4 g, 107 mmol, 15.0 eq.), trifluoroacetic acid (24.4 g, 214 mmol, 30.0 eq.) and 1,2-dichloroethane (20 mL) at rt. The mixture was stirred for overnight at rt and then concentrated under reduced pressure. The mixture was basified to pH 8-9 with saturated sodium bicarbonate (aq.) and extracted with dichloromethane (3×50 mL). The organic layers were combined, washed with water (3×50 mL), dried over anhydrous sodium sulfate, filtered and concentrated under reduced pressure. The residue was purified by silica gel column chromatography, eluted with THF:ethyl acetate (1:4) to afford 4-(oxolan-3-ylmethyl)-1H-pyrazole (800 mg, 74% yield) as a light yellow oil. LCMS (ESI, m/z): 153 [M+H]+.

4-[(3,3-difluorocyclobutyl)methyl]-1H-pyrazole (I-2)

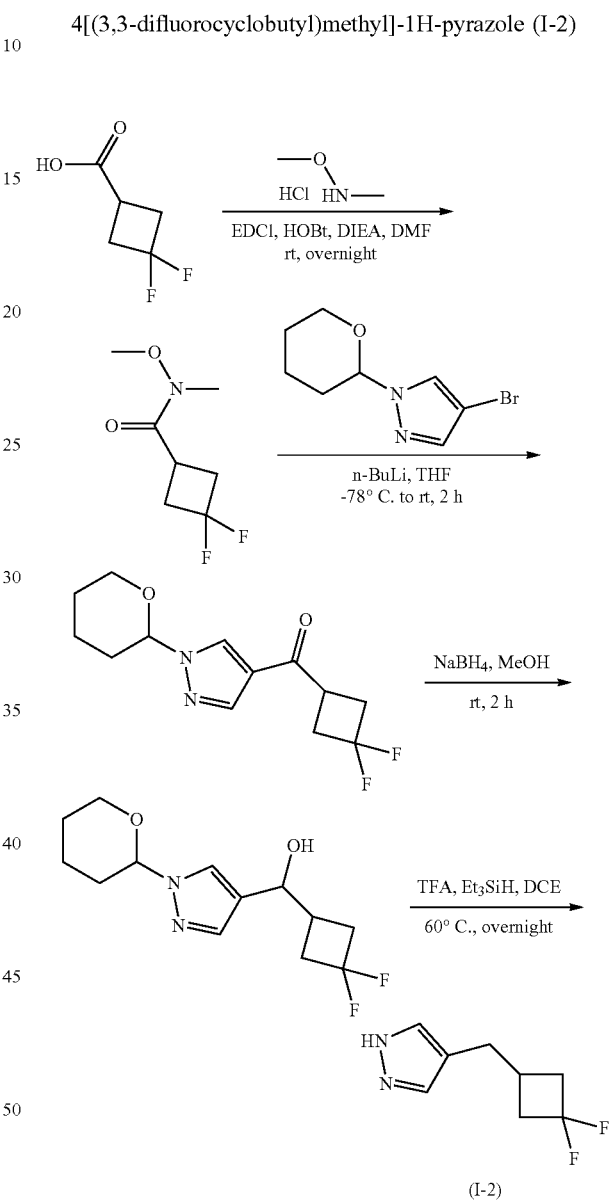

(I-2)

A 250 mL round bottom flask was charged with 3,3-difluorocyclobutane-1-carboxylic acid (5.00 g, 36.7 mmol, 1.00 eq.), methoxy(methyl)amine hydrochloride (3.94 g, 40.4 mmol, 1.10 eq.), HOBt (7.45 g, 55.2 mmol, 1.50 eq.), EDCI (10.5 g, 55.1 mmol, 1.50 eq.), DIEA (19.0 g, 147 mmol, 4.00 eq.) and DMF (100 mL). The solution was stirred for overnight at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:5) to afford 3,3-difluoro-N-methoxycyclobutane-1-carboxamide (4.00 g, 61% yield) as a white solid. LCMS (ESI, m/z): 180 [M+H]$^+$.

A 250 mL round bottom flask was charged with 4-bromo-1-(oxan-2-yl)pyrazole (2.00 g, 8.66 mmol, 1.00 eq.) and THF (30 mL). n-BuLi (5.2 mL, 13.0 mmol, 1.50 eq., 2.5 M in hexane) was added dropwise at −78° C. under a nitrogen atmosphere. The solution was stirred for 30 min at −78° C., and then 3,3-difluoro-N-methoxy-N-methylcyclobutane-1-carboxamide (1.86 g, 10.4 mmol, 1.20 eq.) was added at −78° C. The mixture was stirred for 2 h at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:5) to afford 4-(3,3-difluorocyclobutanecarbonyl)-1-(oxan-2-yl)pyrazole (1.85 g, 79% yield) as a white solid. LCMS (ESI, m/z): 271 [M+H]$^+$.

A 250 mL round bottom flask was charged with 4-(3,3-difluorocyclobutanecarbonyl)-1-(oxan-2-yl)pyrazole (1.80 g, 6.66 mmol, 1.00 eq.) and MeOH (50 mL), and then NaBH$_4$ (0.755 g, 20.0 mmol, 3.00 eq.) was added at 0° C. The solution was stirred for 2 h at rt. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure to afford (3,3-difluorocyclobutyl)[1-(oxan-2-yl)pyrazol-4-yl]methanol (1.85 g, crude) as a light yellow oil. LCMS (ESI, m/z): 273 [M+H]$^+$.

A 250 mL round bottom flask were charged with (3,3-difluorocyclobutyl)[1-(oxan-2-yl)pyrazol-4-yl]methanol (1.80 g, 6.61 mmol, 1.00 eq.), TFA (22.6 g, 198 mmol, 30.0 eq.), Et$_3$SiH (11.5 g, 99.1 mmol, 15.0 eq.) and DCE (30 mL). The mixture was stirred for overnight at 60° C. and then concentrated under reduced pressure. The reaction was quenched with saturated NaHCO$_3$ (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with dichloromethane:methanol (20:1) to afford 4-[(3,3-difluorocyclobutyl)methyl]-1H-pyrazole (990 mg, 87% yield) as a white solid. LCMS (ESI, m/z): 173 [M+H]$^+$.

7-bromo-N-[(4-methoxyphenyl)methyl]-N-methyl-[1,2,4]triazolo[4,3-a]pyridin-3-amine (I-3)

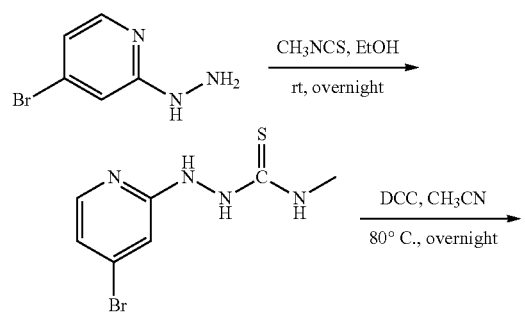

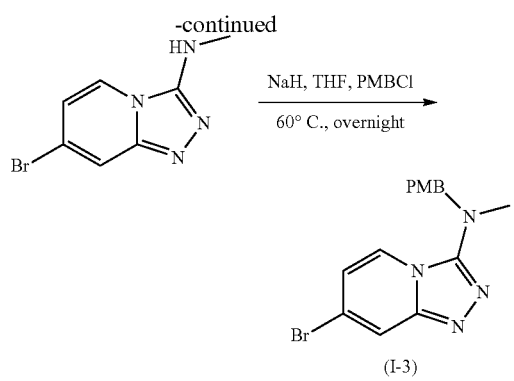

A 100 mL round-bottom flask was charged with 4-bromo-2-hydrazinylpyridine (7.60 g, 40.4 mmol, 1.00 eq.), methyl isothiocyanate (4.36 g, 60.6 mmol, 1.20 eq.) and EtOH (100 mL). The mixture was stirred for overnight at rt and then concentrated under reduced pressure. Petroleum ether (50 mL) was added to the mixture. The solids were collected by filtration, washed with petroleum ether (3×10 mL) and dried to afford 2-(4-bromopyridin-2-yl)-N-methylhydrazine-1-carbothioamide (9.70 g, 92% yield) as a yellow solid. LCMS (ESI, m/z): 262 [M+H]$^+$.

A 250 mL round-bottom flask was charged with 1-[(4-bromopyridin-2-yl)amino]-3-methylthiourea (9.70 g, 37.1 mmol, 1.00 eq.), DCC (11.5 g, 55.7 mmol, 1.50 eq.) and acetonitrile (100 mL). The mixture was stirred for overnight at 80° C. under a nitrogen atmosphere. The precipitated solids were collected by filtration and washed with ethyl acetate (3×100 mL). The residue was purified by silica gel column chromatography, eluted with dichloromethane:methanol (10:1) to afford 7-bromo-N-methyl-[1,2,4]triazolo[4,3-a]pyridin-3-amine (7.70 g, 91% yield) as a light yellow solid. LCMS (ESI, m/z): 227 [M+H]$^+$.

A 100 mL round-bottom flask was charged with 7-bromo-N-methyl-[1,2,4]triazolo[4,3-a]pyridin-3-amine (4.00 g, 17.6 mmol, 1.00 eq.), 4-methoxybenzyl chloride (4.14 g, 26.4 mmol, 1.50 eq.), NaH (0.85 g, 21.2 mmol, 1.20 eq., 60% dispersion in mineral oil) and THF (35 mL). The mixture was stirred for overnight at 60° C. The reaction was quenched with ice/water (50 mL). The mixture was extracted with ethyl acetate (3×200 mL). The organic layers were combined, washed with water (3×100 mL), dried over anhydrous sodium sulfate, filtered and concentrated under reduced pressure. The residue was purified by silica gel column chromatography, eluted with dichloromethane:methanol (10:1) to afford 7-bromo-N-[(4-methoxyphenyl)methyl]-N-methyl-[1,2,4]triazolo[4,3-a]pyridin-3-amine (1.90 g, 31% yield) as a brown solid. LCMS (ESI, m/z): 347 [M+H]$^+$.

4-(4,5-dimethyl-1,2,4-triazol-3-yl)phenylboronic Acid (I-4)

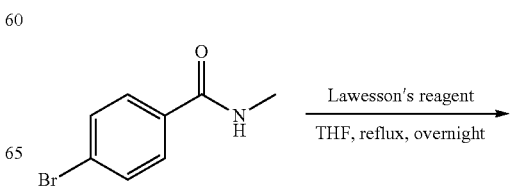

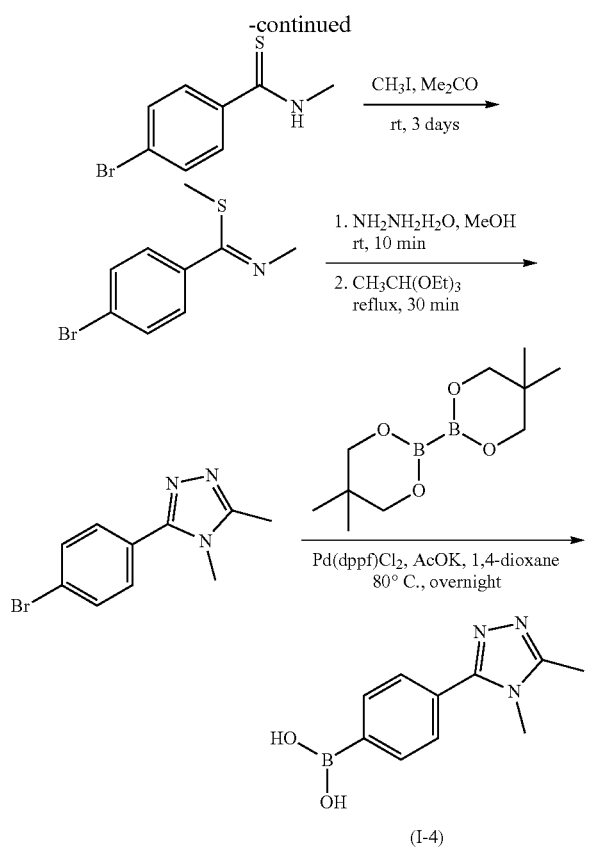

(I-4)

A 250 mL round-bottom flask was charged with 4-bromo-N-methylbenzamide (5.00 g, 23.4 mmol, 1.00 eq.), Lawesson's Reagent (18.9 g, 46.7 mmol, 2.00 eq.) and tetrahydrofuran (100 mL). The solution was refluxed for overnight and then concentrated under reduced pressure. The mixture was diluted with water (200 mL) and extracted with ethyl acetate (3×200 mL). The organic layers were combined, washed with saturated sodium chloride solution (3×50 mL), dried over anhydrous sodium sulfate, filtered and concentrated under reduced pressure. The residue was purified by silica gel column chromatography, eluted with ethyl acetate: petroleum ether (3:1) to afford 4-bromo-N-methylbenzenecarbothioamide (4.63 g, 86% yield) as a yellow solid. LCMS (ESI, m/z): 230 [M+H]$^+$.

A 100 mL round-bottom flask was charged with 4-bromo-N-methylbenzenecarbothioamide (1.00 g, 4.35 mmol, 1.00 eq.), methyl iodide (1.85 g, 13.0 mmol, 3.00 eq.) and acetone (30 mL). The mixture was stirred for 3 days at rt. The precipitated solids were collected by filtration and washed with tetrahydrofuran (3×30 mL). The solid was dried to afford (Z)-[(4-bromophenyl)(methylsulfanyl)methylidene](methyl)amine (856 mg, 81% yield) as a yellow solid. LCMS (ESI, m/z): 244 [M+H]$^+$.

A 100 mL round-bottom flask was charged with (Z)-[(4-bromophenyl)(methylsulfanyl)methylidene](methyl)amine (1.00 g, 4.10 mmol, 1.00 eq.) and methanol (10 mL). Hydrazine hydrate (0.307 g, 6.14 mmol, 1.50 eq.) was added dropwise at 0° C. The solution was stirred for 10 min at rt and then concentrated under reduced pressure to afford the crude intermediate. $CH_3CH(OEt)_3$ (1.33 g, 8.19 mmol, 2.00 eq.) and ethyl alcohol (20 mL) were added. The solution was refluxed for 30 min. The reaction was quenched with water (100 mL). The mixture was extracted with ethyl acetate (3×100 mL). The organic layers were combined, washed with water (3×50 mL), dried over anhydrous sodium sulfate, filtered and concentrated under reduced pressure. The residue was purified by silica gel column chromatography, eluted with methanol:dichloromethane (1:12) to afford methyl 5-hydroxy-2-methylpyrazole-3-carboxylate (0.599 g, 58% yield) as a light brown semi-solid. LCMS (ESI, m/z): 252 [M+H]$^+$.

A 100 mL round-bottom flask was charged with 3-(4-bromophenyl)-4,5-dimethyl-1,2,4-triazole (500 mg, 1.98 mmol, 1.00 eq.), 2-(5,5-dimethyl-1,3,2-dioxaborinan-2-yl)-5,5-dimethyl-1,3,2-dioxaborinane (1.34 g, 5.95 mmol, 3.00 eq.), Pd(dppf)Cl$_2$ (72.6 mg, 0.10 mmol, 0.05 eq.), AcOK (584 mg, 5.95 mmol, 3.00 eq.) and 1,4-dioxane (50 mL). The solution was stirred for overnight at 80° C. The reaction was quenched with water (100 mL). The mixture was extracted with ethyl acetate (3×100 mL). The organic layers were combined, washed with water (3×50 mL), dried over anhydrous sodium sulfate, filtered and concentrated under reduced pressure. The residue was purified by reverse flash chromatography with the following conditions: Column: Agela C$_{18}$ Column, 120 g; Mobile Phase A: Water (0.05% TFA), Mobile Phase B: ACN; Flow rate: 60 mL/min; Gradient: 5% B to 55% B in 40 min to afford 4-(4,5-dimethyl-1,2,4-triazol-3-yl)phenylboronic acid (144 mg, 33% yield) as a white solid. LCMS (ESI, m/z): 218 [M+H]$^+$.

4-(3-methylimidazol-4-yl)phenylboronic Acid (I-5)

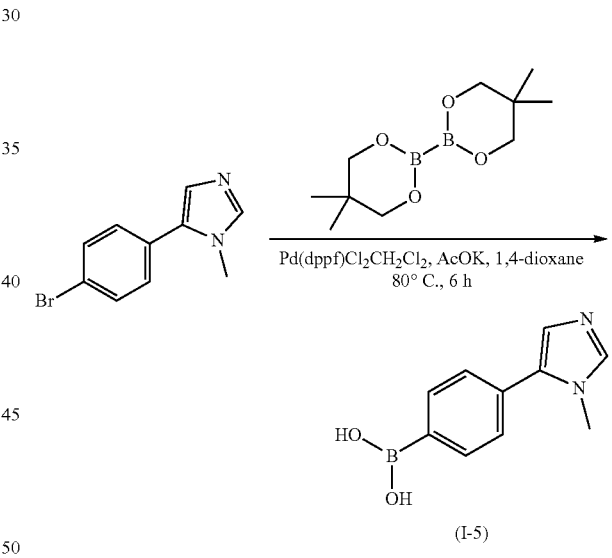

(I-5)

A 250 mL round-bottom flask was charged with 5-(4-bromophenyl)-1-methylimidazole (2.00 g, 8.44 mmol, 1.00 eq.), 2-(5,5-dimethyl-1,3,2-dioxaborinan-2-yl)-5,5-dimethyl-1,3,2-dioxaborinane (5.72 g, 25.3 mmol, 3.00 eq.), Pd(dppf)Cl$_2$·CH$_2$Cl$_2$ (0.34 g, 0.422 mmol, 0.05 eq.), AcOK (2.48 g, 25.3 mmol, 3.00 eq.) and 1,4-dioxane (100 mL). The solution was stirred for 6 h at 80° C. and then concentrated under reduced pressure. The reaction was quenched with water (100 mL), and the mixture was extracted with ethyl acetate (3×100 mL). The organic layers were combined, washed with water (3×50 mL), dried over anhydrous sodium sulfate, filtered and concentrated under reduced pressure. The residue was purified by reverse flash chromatography with the following conditions: Column: Agela C$_{18}$ Column, 120 g; Mobile Phase A: Water (0.05% TFA), Mobile Phase B: ACN; Flow rate: 60 mL/min; Gradient: 15% B to 75% B in 40 min to afford 4-(3-methylimidazol-4-yl)phenylboronic acid (1.23 g, 72% yield) as an off-white solid. LCMS (ESI, m/z): 203 [M+H]⁺.

4-(5-methyl-1,2,3-triazol-1-yl)phenylboronic Acid
(I-6)

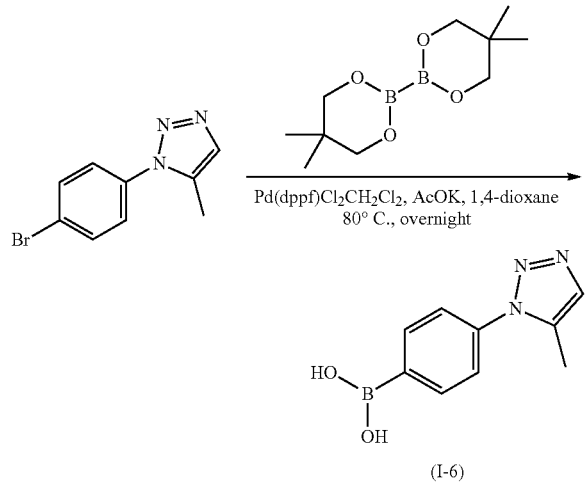

(I-6)

A 250 mL round-bottom flask was charged with 1-(4-bromophenyl)-5-methyl-1,2,3-triazole (2.00 g, 8.40 mmol, 1.00 eq.), 2-(5,5-dimethyl-1,3,2-dioxaborinan-2-yl)-5,5-dimethyl-1,3,2-dioxaborinane (5.69 g, 25.2 mmol, 3.00 eq.), Pd(dppf)Cl$_2$·CH$_2$Cl$_2$ (0.34 g, 0.420 mmol, 0.05 eq.), AcOK (2.47 g, 25.2 mmol, 3.00 eq.) and 1,4-dioxane (100 mL). The solution was stirred for overnight at 80° C. and then concentrated under reduced pressure. The mixture was diluted with water (100 mL) and extracted with ethyl acetate (3×100 mL). The organic layers were combined, washed with water (3×50 mL), dried over anhydrous sodium sulfate, filtered and concentrated under reduced pressure. The residue was purified by reverse flash chromatography with the following conditions: Column: Agela C$_{18}$ Column, 120 g; Mobile Phase A: Water (0.05% TFA), Mobile Phase B: ACN; Flow rate: 60 mL/min; Gradient: 5% B to 65% B in 35 min to afford 4-(5-methyl-1,2,3-triazol-1-yl)phenylboronic acid (1.13 g, 66% yield) as an off-white solid. LCMS (ESI, m/z): 204 [M+H]⁺.

4-(5-methyl-1,2,4-triazol-1-yl)phenylboronic Acid
(I-7)

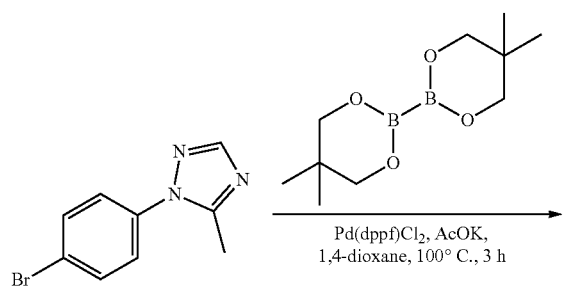

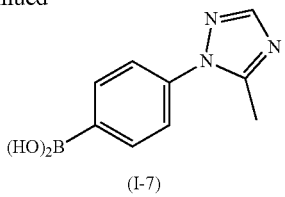

(I-7)

A mixture of 1-(4-bromophenyl)-5-methyl-1,2,4-triazole (1.40 g, 5.88 mmol, 1.00 eq.), 2-(5,5-dimethyl-1,3,2-dioxaborinan-2-yl)-5,5-dimethyl-1,3,2-dioxaborinane (1.46 g, 6.47 mmol, 1.10 eq.), Pd(dppf)Cl$_2$·CH$_2$Cl$_2$ (0.480 g, 0.590 mmol, 0.10 eq.) and AcOK (1.15 g, 11.8 mmol, 2.00 eq.) in 1,4-dioxane (30 mL) was stirred for 3 hours at 100° C. under a nitrogen atmosphere. The mixture was cooled to rt, and the solids were filtered off. The filtrate was concentrated under reduced pressure. The residue was purified by reverse phase chromatography with the following condition: Column: Agela C$_{18}$ Column, 120 g; Mobile Phase A: Water (0.05% TFA), Mobile Phase B: ACN; Flow rate: 60 mL/min; Gradient: 5% B to 55% B in 40 min to afford 4-(5-methyl-1,2,4-triazol-1-yl)phenylboronic acid (1.10 g, 92% yield) as a yellow solid. LCMS (ESI, m/z): 204 [M+H]⁺.

4-(4-methyl-5-oxo-1,2,4-oxadiazol-3-yl)phenylboronic Acid (I-8)

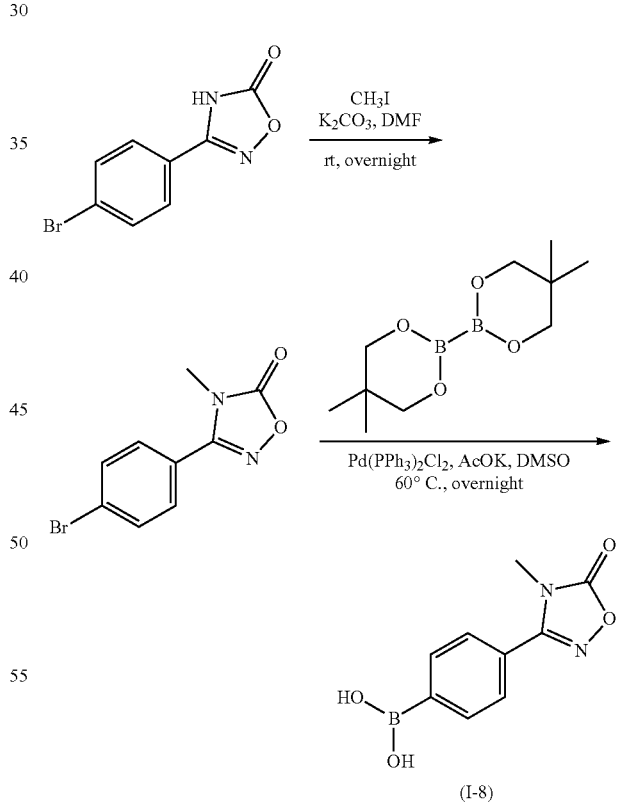

A 40 mL vial was charged with 3-(4-bromophenyl)-4H-1,2,4-oxadiazol-5-one (2.00 g, 8.30 mmol, 1.00 eq.), methyl iodide (1.77 g, 12.4 mmol, 1.50 eq.), potassium carbonate (3.44 g, 24.9 mmol, 3.00 eq.) and DMF (20 mL). The mixture was stirred for overnight at rt. The reaction was quenched with water (50 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford 3-(4-bromophenyl)-4-methyl-1,2,4-oxadiazol-5-one (1.58 g, 75% yield) as a white solid. LCMS (ESI, m/z): 255 [M+H]⁺.

A 40 mL vial was charged with 3-(4-bromophenyl)-4-methyl-1,2,4-oxadiazol-5-one (1.50 g, 5.88 mmol, 1.00 eq.), Pd(PPh$_3$)$_2$Cl$_2$ (0.413 g, 0.588 mmol, 0.10 eq.), AcOK (1.73 g, 17.6 mmol, 3.00 eq.) and DMSO (20 mL). The mixture was stirred for overnight at 60° C. under a nitrogen atmosphere. The reaction was quenched with water (100 mL). The mixture was extracted with ethyl acetate (3×150 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford the crude product. The residue was purified by reverse flash chromatography with the following conditions: column, C$_{18}$ column; mobile phase, acetonitrile in water (0.05% TFA), 0% to 50% gradient in 50 min to afford 4-(4-methyl-5-oxo-1,2,4-oxadiazol-3-yl)phenylboronic acid (0.560 g, 43% yield) as a yellow solid. LCMS (ESI, m/z): 221 [M+H]⁺.

4-(2-methyl-5-oxo-1,2,4-oxadiazol-3-yl)phenylboronic Acid (I-9)

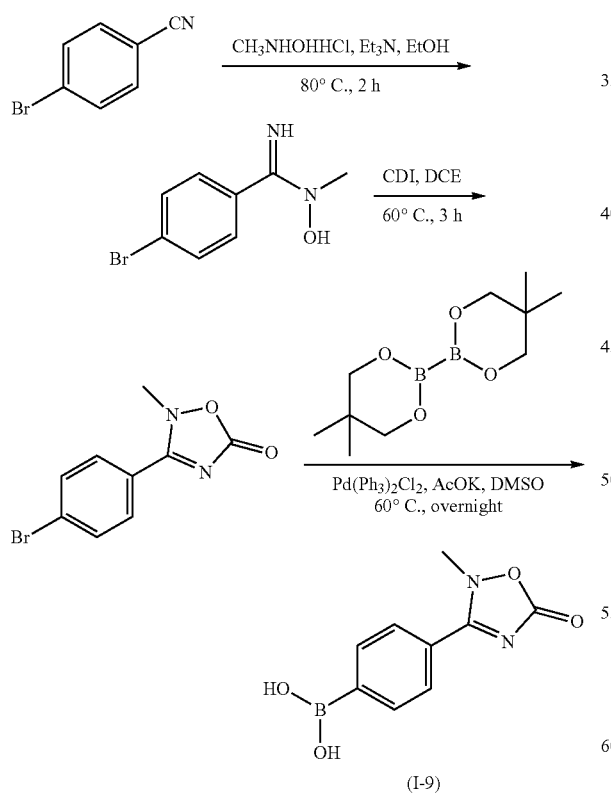

A 250 mL round-bottom flask was charged with 4-bromobenzonitrile (1.00 g, 5.49 mmol, 1.00 eq.), N-methylhydroxylamine (646 mg, 13.7 mmol, 2.50 eq.), Et$_3$N (2.50 g, 24.7 mmol, 4.50 eq.), and ethanol (20 mL). The mixture was stirred for 2 h at 80° C. and then concentrated under reduced pressure to afford 4-bromo-N-hydroxy-N-methylbenzenecarboximidamide (630 mg, crude) as a white solid. LCMS (ESI, m/z): 229 [M+H]⁺.

A 250 mL round-bottom flask was charged with the crude 4-bromo-N-hydroxy-N-methyl benzenecarboximidamide (630 mg, 2.75 mmol, 1.00 eq.), CDI (1.45 g, 8.99 mmol, 3.27 eq.) and DCE (100 mL). The solution was stirred 3 h at 60° C. The reaction was quenched with water (100 mL). The mixture was extracted with dichloromethane (3×100 mL). The organic layers were combined, washed with water (3×100 mL), dried over anhydrous sodium sulfate, filtered and concentrated under reduced pressure. The residue was purified by silica gel column chromatography, eluted with methanol:dichloromethane (1:10) to afford 3-(4-bromophenyl)-2-methyl-1,2,4-oxadiazol-5-one (420 mg, 60% yield) as a white solid. LCMS (ESI, m/z): 255 [M+H]⁺.

A 100 mL round-bottom flask was added 3-(4-bromophenyl)-2-methyl-1,2,4-oxadiazol-5-one (1.00 g, 3.92 mmol, 1.00 eq.), 2-(5,5-dimethyl-1,3,2-dioxaborinan-2-yl)-5,5-dimethyl-1,3,2-dioxaborinane (0.973 g, 4.31 mmol, 1.10 eq.), Pd(PPh$_3$)$_2$Cl$_2$ (1.38 g, 1.96 mmol, 0.50 eq.), KOAc (1.15 g, 11.7 mmol, 3.00 eq.) and DMSO (30 mL) at rt. The mixture was stirred for overnight at 60° C. under a nitrogen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The mixture was concentrated under reduced pressure. The crude product was purified by prep-HPLC with the following conditions: Column: XBridge Prep OBD C$_{18}$ Column, 30×150 mm, 5 um; Mobile Phase A: Water (0.1% TFA), Mobile Phase B: ACN; Flow rate: 60 mL/min; Gradient: 47% B to 73% B in 7 min to afford 4-(2-methyl-5-oxo-1,2,4-oxadiazol-3-yl)phenylboronic acid (450 mg, 52% yield) as a white solid. LCMS (ESI, m/z): 221 [M+H]⁺.

5-[4-(5,5-dimethyl-1,3,2-dioxaborinan-2-yl)phenyl]-1-methyl-1,2,4-triazole (I-10)

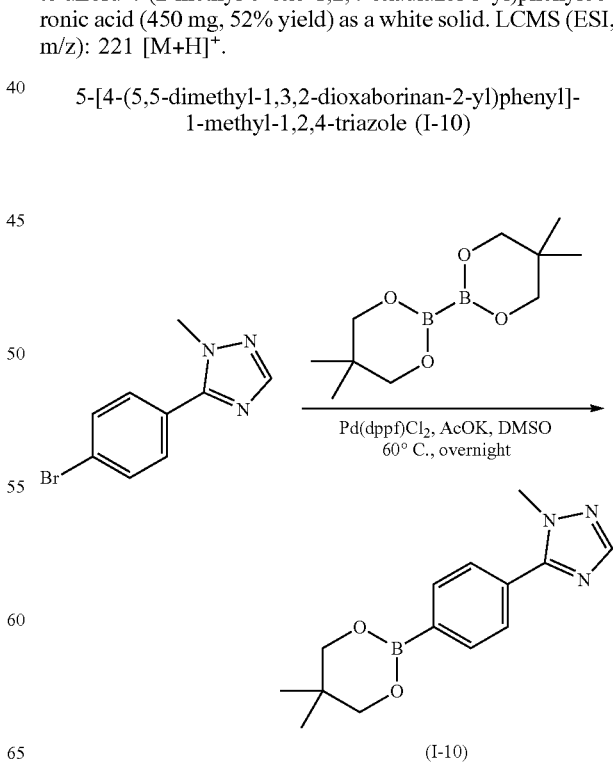

A 40 mL vial were charged with 5-(4-bromophenyl)-1-methyl-1,2,4-triazole (0.300 g, 1.26 mmol, 1.00 eq.), 2-(5,5-dimethyl-1,3,2-dioxaborinan-2-yl)-5,5-dimethyl-1,3,2-dioxaborinane (1.42 g, 6.30 mmol, 5.00 eq.), Pd(PPh$_3$)$_2$Cl$_2$ (88.4 mg, 0.126 mmol, 0.10 eq.), AcOK (247 mg, 2.52 mmol, 2.00 eq.) and DMSO (5 mL). The mixture was stirred for overnight at 60° C. under a nitrogen atmosphere. The reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with ethyl acetate/petroleum ether (2/1) to afford 5-[4-(5,5-dimethyl-1,3,2-dioxaborinan-2-yl)phenyl]-1-methyl-1,2,4-triazole (320 mg, 94% yield) as a yellow solid. LCMS (ESI, m/z): 272 [M+H]$^+$.

(4-(1-(4-methoxybenzyl)-4-methyl-1H-1,2,3-triazol-5-yl)phenyl)boronic Acid (I-11)

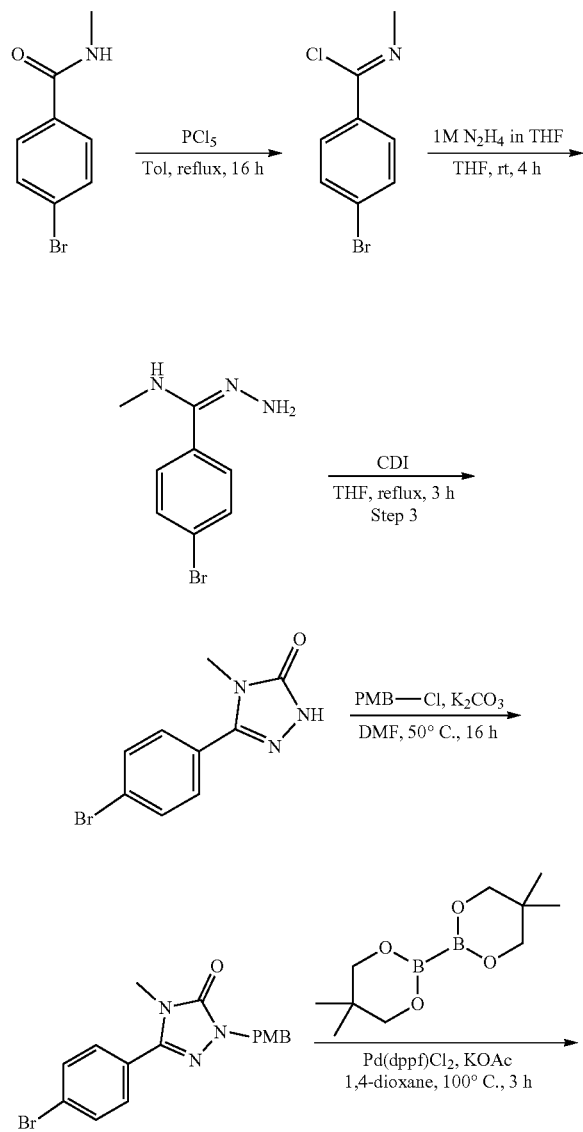

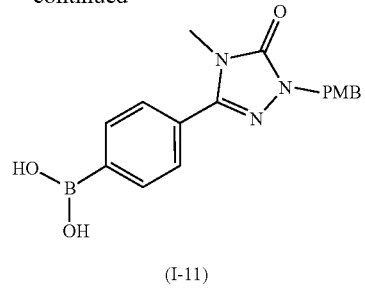

(I-11)

To a suspension of 4-bromo-N-methylbenzamide (2.14 g, 10.0 mmol, 1.00 eq.) in toluene (50 mL) was added phosphorous pentachloride (3.13 g, 15.0 mmol, 1.5 eq.). The mixture was refluxed for 16 under a nitrogen atmosphere. The mixture was cooled and concentrated under reduced pressure to afford (Z)-4-bromo-N-methylbenzimidoyl chloride (2.33 g, crude) as a light yellow solid, which was used in the next step directly and immediately without any further purification.

A suspension of (Z)-4-bromo-N-methylbenzimidoyl chloride (2.33 g, 10.0 mmol, 1.00 eq.) in THF (100 mL) was added dropwise to an anhydrous hydrazine solution (50 mL, 1 M in THF) at 0° C. under nitrogen. The mixture was stirred for 4 h at rt under nitrogen. The mixture was cooled and used in the next step directly and immediately without any further purification. LCMS (ESI, m/z): 228 [M+H]$^+$.

To a mixture of (E)-4-bromo-N-methylbenzohydrazonamide in THF (10.00 mmol assumed, from reaction mixture of last step) was added CDI (8.11 g, 50.00 mmol, 5.0 eq.) batchwise at 0° C. under nitrogen. The mixture was refluxed for 3 h under nitrogen and then concentrated under reduced pressure. The residue was purified by silica gel column chromatography, eluted with 0-70% dichloromethane in ethyl acetate to afford 5-(4-bromophenyl)-4-methyl-2,4-dihydro-3H-1,2,4-triazol-3-one (634 mg, 25% yield) as a yellow solid. LCMS (ESI, m/z): 254 [M+H]$^+$.

A mixture of 5-(4-bromophenyl)-4-methyl-2,4-dihydro-3H-1,2,4-triazol-3-one (634 mg, 2.50 mmol, 1.00 eq.), potassium carbonate (1.73 g, 12.50 mmol, 5.00 eq.) and 4-methoxybenzylchloride (1.17 g, 7.50 mmol, 3.00 eq.) in DMF (20 mL) was stirred for 16 h at 50 C. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with 0-60% ethyl acetate in petroleum the to afford 5-(4-bromophenyl)-2-(4-methoxybenzyl)-4-methyl-2,4-dihydro-3H-1,2,4-triazol-3-one (821 mg, 89% yield) as an off-white solid. LCMS (ESI, m/z): 374 [M+H]$^+$.

To a mixture of 5-(4-bromophenyl)-2-(4-methoxybenzyl)-4-methyl-2,4-dihydro-3H-1,2,4-triazol-3-one (821 mg, 2.20 mmol, 1.00 eq.) and 5,5,5',5'-tetramethyl-2,2'-bi(1,3,2-dioxaborinane) (994 mg, 4.40 mmol, 2.00 eq.) and potassium acetate (1.08 g, 11.0 mmol, 5.00 eq.) in 1,4-dioxane (11 mL) was added Pd(dppf)Cl$_2$·CH$_2$Cl$_2$ (179 mg, 0.22 mmol, 0.10 eq.). The mixture was stirred for 3 h at 100° C. The solids were filtered off, and the filtrate was concentrated under reduced pressure. The residue was purified by reverse phase chromatography with following condition: Column: Agela C$_{18}$ Column, 120 g; Mobile Phase A: Water (0.05% TFA), Mobile Phase B: ACN; Flow rate: 60 mL/min;

Gradient: 0% B to 70% B in 40 min; to afford (4-(1-(4-methoxybenzyl)-4-methyl-1H-1,2,3-triazol-5-yl)phenyl)boronic acid (670 mg, 90% yield) as an off-white solid. LCMS (ESI, m/z): 340 [M+H]⁺.

1-[4-(5,5-dimethyl-1,3,2-ioxaborinan-2-yl)phenyl]-3-(trifluoromethyl)pyrazole (I-12)

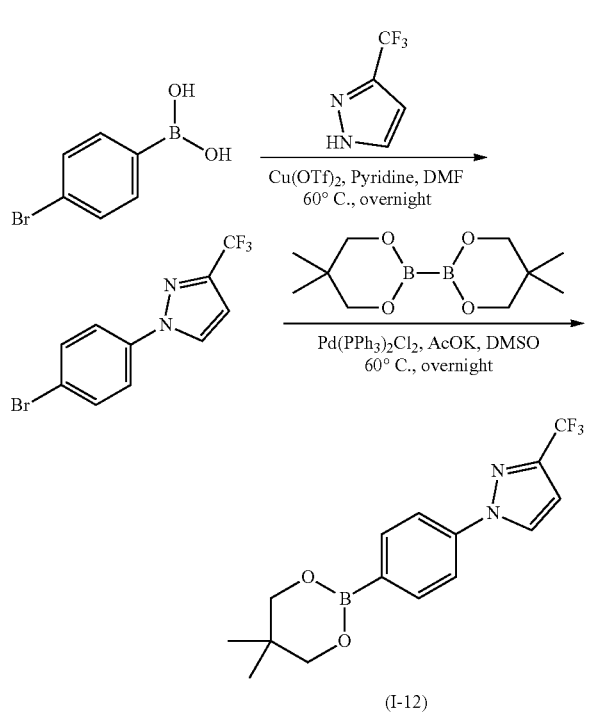

(I-12)

A 250 mL round-bottom flask was charged with 4-bromophenylboric acid (500 mg, 2.49 mmol, 1.00 eq.), 3-(trifluoromethyl)-1H-pyrazole (406 mg, 2.98 mmol, 1.20 eq.), Cu(OTf)₂ (900 mg, 2.49 mmol, 1.00 eq.), pyridine (590 mg, 7.47 mmol, 3.00 eq.) and DMF (20 mL). The mixture was stirred for overnight at 60° C. under an oxygen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:5) to afford 1-(4-bromophenyl)-3-(trifluoromethyl)pyrazole (510 mg, 70% yield) as a white solid. LCMS (ESI, m/z): 291 [M+H]⁺.

A 250 mL round-bottom flask was charged with 1-(4-bromophenyl)-3-(trifluoromethyl)pyrazole (100 mg, 0.344 mmol, 1.00 eq.), 2-(5,5-dimethyl-1,3,2-dioxaborinan-2-yl)-5,5-dimethyl-1,3,2-dioxaborinane (232 mg, 1.03 mmol, 3.00 eq.), Pd(PPh₃)₂Cl₂ (121 mg, 0.172 mmol, 0.50 eq.), AcOK (67.4 mg, 0.688 mmol, 2.00 eq.) and DMSO (20 mL) at rt. The mixture was stirred for overnight at 60° C. under N₂ atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:3) to afford 1-[4-(5,5-dimethyl-1,3,2-ioxaborinan-2-yl)phenyl]-3-(trifluoromethyl)pyrazole (89.0 mg, 80% yield) as a yellow oil. LCMS (ESI, m/z): 325 [M+H]⁺.

3-[4-(5,5-dimethyl-1,3,2-dioxaborinan-2-yl)phenyl]-4-[(4-methoxyphenyl)methyl]-5-(trifluoromethyl)-1,2,4-triazole (I-13)

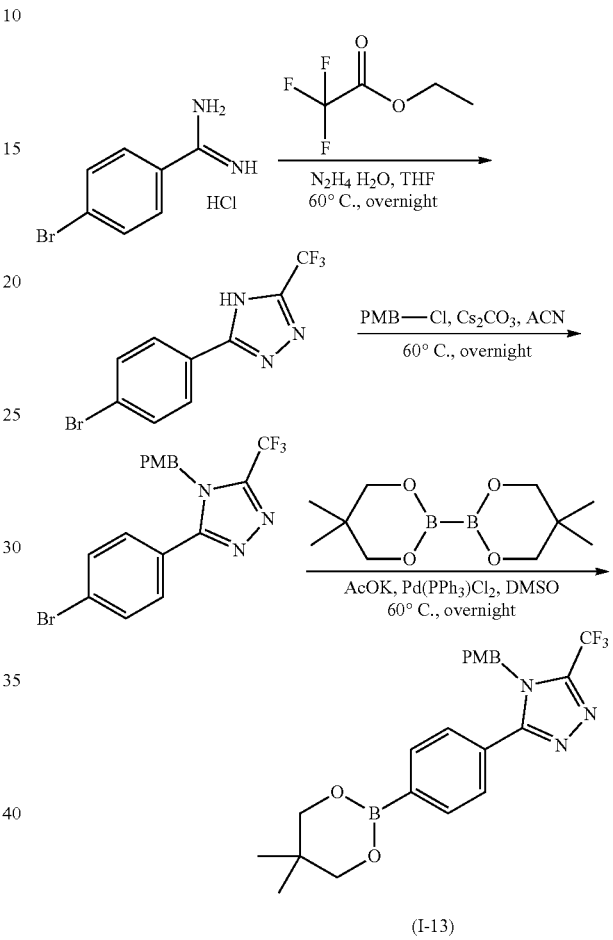

(I-13)

A 250 mL round-bottom flask was charged with 4-bromobenzenecarboximidamide hydrochloride (3.56 g, 15.1 mmol, 1.00 eq.), ethyl 2,2,2-trifluoroacetate (2.14 g, 15.1 mmol, 1.00 eq.), NaOH (0.60 g, 15.1 mmol, 1.00 eq.), hydrazine hydrate (0.751 g, 15.1 mmol, 1.00 eq.) and THF (60 mL). The mixture was stirred for overnight at 60° C. The reaction was quenched with water (200 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford 3-(4-bromophenyl)-5-(trifluoromethyl)-4H-1,2,4-triazole (3.10 g, 70% yield) as a light yellow oil. LCMS (ESI, m/z): 292 [M+H]⁺.

A 250 mL round-bottom flask was charged with 3-(4-bromophenyl)-5-(trifluoromethyl)-4H-1,2,4-triazole (3.10 g, 10.6 mmol, 1.00 eq.), PMB-Cl (4.99 g, 31.8 mmol, 3.00 eq.), Cs₂CO₃ (10.4 g, 31.8 mmol, 3.00 eq.) and acetonitrile (50 mL). The mixture was stirred for overnight at 60° C. and then concentrated under reduced pressure. The mixture was diluted with water (100 mL), extracted with ethyl acetate (3×100 mL), dried over anhydrous sodium sulfate, filtered and concentrated under reduced pressure. The residue was purified by silica gel column chromatography, eluted with ethyl acetate:petroleum ether (1:1) to afford 3-(4-bromophenyl)-4-[(4-methoxyphenyl)methyl]-5-(trifluoromethyl)-1,2,4-triazole (2.70 g, 62% yield) as a light yellow oil. LCMS (ESI, m/z): 412 [M+H]$^+$.

A 100 mL round-bottom flask was charged with 3-(4-bromophenyl)-4-[(4-methoxyphenyl)methyl]-5-(trifluoromethyl)-1,2,4-triazole (2.70 g, 6.55 mmol, 1.00 eq.), 2-(5,5-dimethyl-1,3,2-dioxaborinan-2-yl)-5,5-dimethyl-1,3,2-dioxaborinane (4.44 g, 19.7 mmol, 3.00 eq.), AcOK (1.29 g, 13.1 mmol, 2.00 eq.), Pd(PPh$_3$)$_2$Cl$_2$ (0.460 g, 0.655 mmol, 0.10 eq.) and DMSO (30 mL). The mixture was stirred for overnight at 60° C. under a nitrogen atmosphere. The reaction was quenched with water (100 mL). The mixture was diluted with water (100 mL), extracted with ethyl acetate (3×100 mL), dried over anhydrous sodium sulfate, filtered and concentrated under reduced pressure. The residue was purified by silica gel column chromatography, eluted with ethyl acetate:petroleum ether (1:1) to afford 3-[4-(5,5-dimethyl-1,3,2-dioxaborinan-2-yl)phenyl]-4-[(4-methoxyphenyl)methyl]-5-(trifluoromethyl)-1,2,4-triazole (2.40 g, 82% yield) as a yellow solid. LCMS (ESI, m/z): 446 [M+H]$^+$.

2-(4-(5,5-dimethyl-1,3,2-dioxaborinan-2-yl)phenyl)-4-methyl-2H-1,2,3-triazole (I-14)

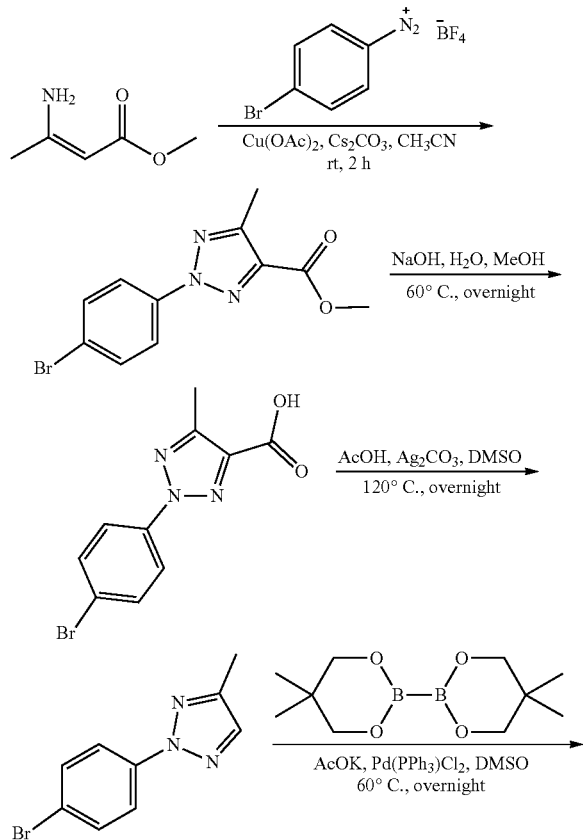

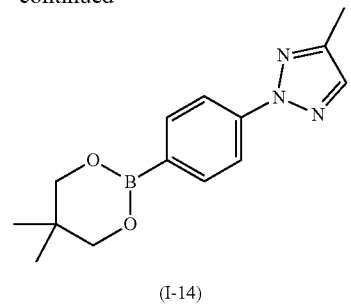

(I-14)

A 250 mL round-bottom flask was charged with methyl (2Z)-3-aminobut-2-enoate (2.50 g, 21.7 mmol, 1.00 eq.), 4-bromobenzenediazonium tetrafluoroborate (8.84 g, 32.6 mmol, 1.50 eq.), Cu(OAc)$_2$ (3.94 g, 21.7 mmol, 1.00 eq.), Cs$_2$CO$_3$ (14.15 g, 43.4 mmol, 2.00 eq.) and CH$_3$CN (100 mL) at rt. The mixture was stirred for 2 h at rt and then concentrated under reduced pressure. The mixture was diluted with water (200 mL) and extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford methyl 2-(4-bromophenyl)-5-methyl-1,2,3-triazole-4-carboxylate (3.40 g, 53% yield) as a light yellow oil. LCMS (ESI, m/z): 296 [M+H]$^+$.

A 250 mL round-bottom flask was charged with methyl 2-(4-bromophenyl)-5-methyl-1,2,3-triazole-4-carboxylate (3.40 g, 11.5 mmol, 1.00 eq.), NaOH (0.920 g, 22.9 mmol, 2.00 eq.), H$_2$O (5 mL) and MeOH (20 mL). The mixture was stirred for overnight at 60° C. The pH value of the mixture was adjusted to 4 with 1N HCl (aq.). The mixture was concentrated under reduced pressure to afford 2-(4-bromophenyl)-5-methyl-1,2,3-triazole-4-carboxylic acid (3.92 g, crude) as a yellow solid. LCMS (ESI, m/z): 282 [M+H]$^+$.

A 100 mL round-bottom flask was charged with 2-(4-bromophenyl)-5-methyl-1,2,3-triazole-4-carboxylic acid (2.70 g, 9.57 mmol, 1.00 eq.), Ag$_2$CO$_3$ (264 mg, 0.957 mmol, 0.10 eq.) and DMSO (30 mL). The mixture was stirred for overnight at 120 C. The reaction as quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford 2-(4-bromophenyl)-4-methyl-1,2,3-triazole (750 mg, 33% yield) as a yellow solid. LCMS (ESI, m/z): 238 [M+H]$^+$.

A 100 mL round bottom flask was charged with 2-(4-bromophenyl)-4-methyl-1,2,3-triazole (1.00 g, 4.20 mmol, 1.00 eq.), 2-(5,5-dimethyl-1,3,2-dioxaborinan-2-yl)-5,5-dimethyl-1,3,2-dioxaborinane (1.42 g, 6.30 mmol, 1.50 eq.), AcOK (1.24 mg, 12.6 mmol, 3.00 eq.), Pd(PPh$_3$)$_2$Cl$_2$ (294 mg, 0.420 mmol, 0.10 eq.) and DMSO (10 mL) at rt. The mixture was stirred for overnight at 60° C. under a nitrogen atmosphere. The reaction was quenched with water (100 mL). The mixture was extracted with ethyl acetate (3×300 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (2:1) to afford 2-(4-(5,5-dimethyl-1,3,2-dioxaborinan-2-yl)phenyl)-4-methyl-2H-1,2,3-triazole (800 mg, 70% yield) as a yellow solid. LCMS (ESI, m/z): 272 [M+H]⁺. 5-(4-(5,5-dimethyl-1,3,2-dioxaborinan-2-yl)phenyl)-4-(4-methoxybenzyl)-2-methyl-2,4-dihydro-3H-1,2,4-triazol-3-one (I-15)

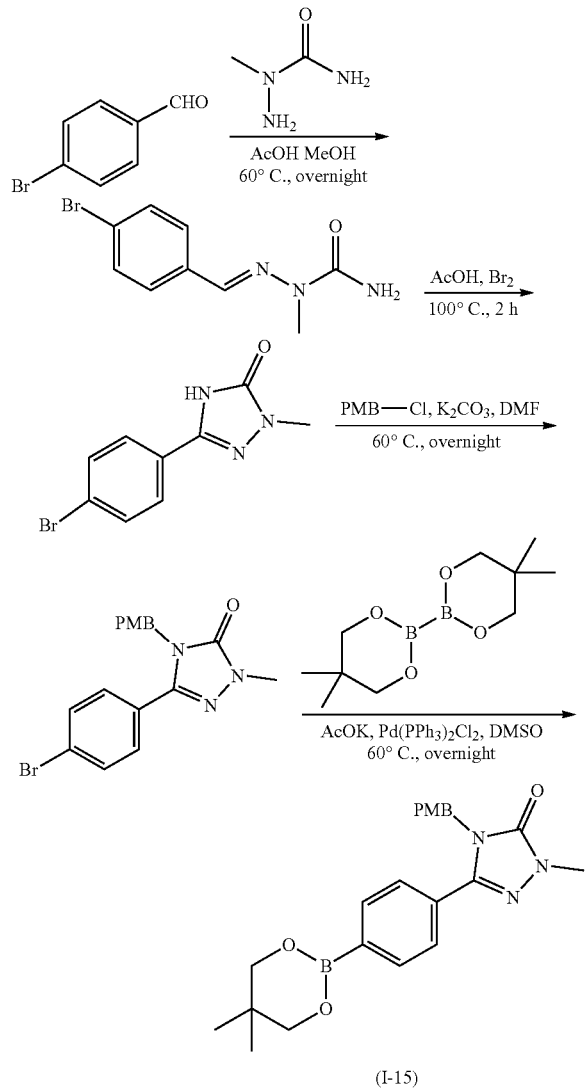

(I-15)

A 100 mL round-bottom flask was charged with 4-bromobenzaldehyde (5.00 g, 27.0 mmol, 1.00 eq.), 3-amino-3-methylurea (2.40 g, 27.0 mmol, 1.00 eq.), methanol (50 mL) and acetic acid (2.5 mL). The mixture was stirred for overnight at 60° C. and then concentrated under reduced pressure. The mixture was diluted with ethyl acetate (50 mL) and washed with water (3×10 mL). The combined organic layers dried over anhydrous sodium sulfate, filtered and concentrated under reduced pressure. The residue was purified by silica gel column chromatography, eluted with ethyl acetate:petroleum ether (1:7) to afford 1-[(E)-[(4-bromophenyl)methylidene]amino]-1-methylurea (5.00 g, 72% yield) as a white solid. LCMS (ESI, m/z): 256 [M+H]⁺.

A 100 mL round-bottom flask was charged with 1-[(E)-[(4-bromophenyl)methylidene]amino]-1-methylurea (4.00 g, 15.6 mmol, 1.00 eq.) and acetic acid (15 mL). Br₂ (5.00 g, 31.2 mmol, 2.00 eq.) was added to the mixture at rt. The mixture was stirred for 2 h at 100° C. The reaction was quenched with water (100 mL). The mixture was extracted with ethyl acetate (3×50 mL). The organic layers were combined, washed with water (3×20 mL), dried over anhydrous sodium sulfate, filtered and concentrated under reduced pressure. The residue was purified by silica gel column chromatography, eluted with ethyl acetate:petroleum ether (1:5) to afford 5-(4-bromophenyl)-2-methyl-4H-1,2,4-triazol-3-one (1.30 g, 26% yield) as a yellow solid. LCMS (ESI, m/z): 254 [M+H]⁺.

A 100 mL round-bottom flask was charged with 5-(4-bromophenyl)-2-methyl-4H-1,2,4-triazol-3-one (1.30 g, 5.12 mmol, 1.00 eq.), 1-(chloromethyl)-4-methoxybenzene (1.20 g, 7.67 mmol, 1.50 eq.), K₂CO₃ (2.12 mg, 15.3 mmol, 3.00 eq.) and DMF (15 mL). The mixture was stirred for overnight at 60° C. The reaction was quenched with water (50 mL). The mixture was extracted with ethyl acetate (3×50 mL). The organic layers were combined, washed with water (3×20 mL), dried over anhydrous sodium sulfate, filtered and concentrated under reduced pressure. The residue was purified by silica gel column chromatography, eluted with ethyl acetate:petroleum ether (1:6) to afford 5-(4-bromophenyl)-4-[(4-methoxyphenyl)methyl]-2-methyl-1,2,4-triazol-3-one (800 mg, 42% yield) as a light yellow solid. LCMS (ESI, m/z): 374 [M+H]⁺.

A 100 mL round-bottom flask was charged with 5-(4-bromophenyl)-4-[(4-methoxyphenyl)methyl]-2-methyl-1,2,4-triazol-3-one (800 mg, 2.14 mmol, 1.00 eq.), 2-(5,5-dimethyl-1,3,2-dioxaborinan-2-yl)-5,5-dimethyl-1,3,2-dioxaborinane (725 mg, 3.21 mmol, 1.50 eq.), KOAc (420 mg, 4.28 mmol, 2.00 eq.), Pd(PPh₃)₂Cl₂ (75.0 mg, 0.107 mmol, 0.05 eq.) and DMSO (10 mL). The mixture was stirred for overnight at 60° C. The reaction was quenched with water (50 mL). The mixture was extracted with ethyl acetate (3×50 mL). The organic layers were combined, washed with water (3×20 mL), dried over anhydrous sodium sulfate, filtered and concentrated under reduced pressure. The residue was purified by silica gel column chromatography, eluted with ethyl acetate:petroleum ether (1:6) to afford 5-(4-(5,5-dimethyl-1,3,2-dioxaborinan-2-yl)phenyl)-4-(4-methoxybenzyl)-2-methyl-2,4-dihydro-3H-1,2,4-triazol-3-one (700 mg, 80% yield) as yellow oil. LCMS (ESI, m/z): 408 [M+H]⁺.

5-[5-(5,5-dimethyl-1,3,2-dioxaborinan-2-yl)-2-methylpyrazol-3-yl]-1-[(4-methoxyphenyl)methyl]-4-methyl-1,2,3-triazole (I-16)

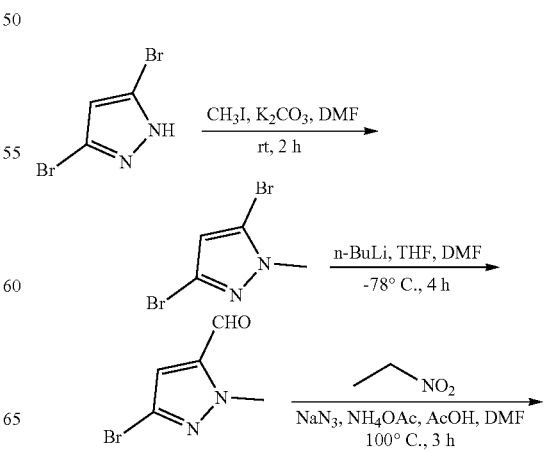

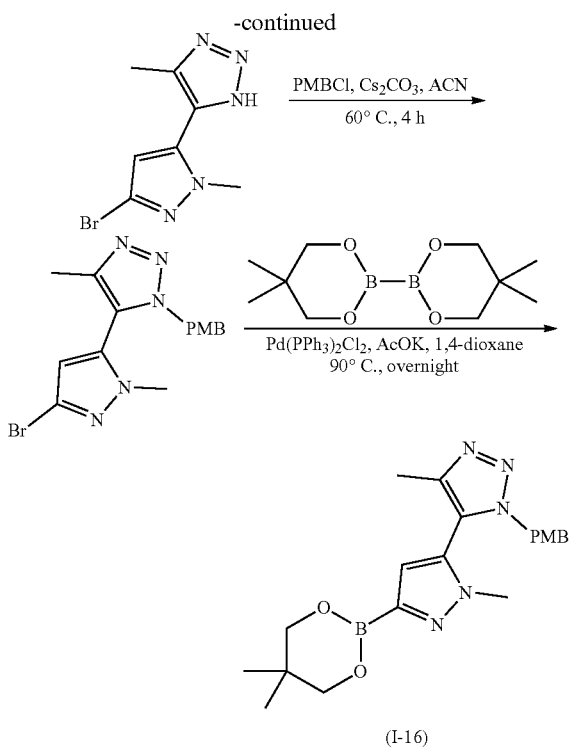

(I-16)

A 250 mL round bottom flask was charged with 3,5-dibromo-1H-pyrazole (10.0 g, 44.3 mmol, 1.00 eq.), CH$_3$I (7.54 g, 53.1 mmol, 1.20 eq.), K$_2$CO$_3$ (12.3 g, 88.5 mmol, 2.00 eq.) and DMF (50 mL). The solution was stirred for 2 h at rt. The reaction was quenched with water (200 mL). The mixture was extracted with ethyl acetate (3×100 mL). The organic layers were combined, washed with water (3×100 mL), dried over anhydrous sodium sulfate, filtered and concentrated under reduced pressure to provide 3,5-dibromo-1-methylpyrazole (8.00 g, 75% yield) as a colorless oil. LCMS (ESI, m/z): 239 [M+H]$^+$.

A 250 mL round bottom flask was charged with 3,5-dibromo-1-methylpyrazole (8.00 g, 33.3 mmol, 1.00 eq.) and tetrahydrofuran (100 mL). n-butyllithium (20.0 mL, 50.0 mmol, 1.50 eq., 2.5 M in hexane) was added dropwise at −78° C. under a nitrogen atmosphere. The solution was stirred for 1 h at −78° C. Dimethylformamide (4.88 g, 66.7 mmol, 2.00 eq.) was added at −78° C. The solution was stirred for 2 h at −78° C. The reaction was quenched with water (200 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:8) to afford 5-bromo-2-methylpyrazole-3-carbaldehyde (3.10 g, 49% yield) as a white solid. LCMS (ESI, m/z): 189 [M+H]$^+$.

A 250 mL round bottom was charged with 5-bromo-2-methylpyrazole-3-carbaldehyde (4.50 g, 23.8 mmol, 1.00 eq.), azido sodium (4.64 g, 71.4 mmol, 3.00 eq.), nitroethane (8.94 g, 119 mmol, 5.00 eq.), acetic acid (0.710 g, 11.9 mmol, 0.50 eq.) and NH$_4$OAc (1.84 g, 23.8 mmol, 1.00 eq.). The solution was stirred for 3 h at 100° C. The reaction was quenched with saturated sodium bicarbonate solution (200 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:5) to afford 4-(5-bromo-2-methylpyrazol-3-yl)-5-methyl-3H-1,2,3-triazole (2.50 g, 43% yield) as a white solid. LCMS (ESI, m/z): 242 [M+H]$^+$.

A 250 mL round bottom flask was charged with 4-(5-bromo-2-methylpyrazol-3-yl)-5-methyl-3H-1,2,3-triazole (2.50 g, 10.3 mmol, 1.00 eq.), cesium carbonate (6.75 g, 20.7 mmol, 2.00 eq.), 4-methoxybenzyl chloride (2.43 g, 15.5 mmol, 1.50 eq.) and acetonitrile (50 mL). The solution was stirred for 4 h at 60° C. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:8) to afford 5-(5-bromo-2-methylpyrazol-3-yl)-1-[(4-methoxyphenyl)methyl]-4-methyl-1,2,3-triazole (2.90 g, 77% yield) as a white solid. LCMS (ESI, m/z): 362 [M+H]$^+$.

A 100 mL round bottom was charged with 5-(5-bromo-2-methylpyrazol-3-yl)-1-[(4-methoxyphenyl)methyl]-4-methyl-1,2,3-triazole (2.40 g, 6.63 mmol, 1.00 eq.), Pd(PPh$_3$)$_2$Cl$_2$ (0.230 g, 0.331 mmol, 0.05 eq.), 2-(5,5-dimethyl-1,3,2-dioxaborinan-2-yl)-5,5-dimethyl-1,3,2-dioxaborinane (2.99 g, 13.2 mmol, 2.00 eq.), AcOK (1.63 g, 16.5 mmol, 2.50 eq.) and 1,4-dioxane (50 mL). The solution was stirred for overnight at 90° C. under nitrogen. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate to afford 5-[5-(5,5-dimethyl-1,3,2-dioxaborinan-2-yl)-2-methylpyrazol-3-yl]-1-[(4-methoxyphenyl)methyl]-4-methyl-1,2,3-triazole (2.00 g, 76% yield) as a white solid. LCMS (ESI, m/z): 396 [M+H]$^+$.

Tert-butyl 5-benzyl-11-ethyl-8-oxo-2,3,7,12-tetraazatricyclo[7.4.0.0^{2,6}]trideca-1(9),3,5-triene-12-carboxylate (I-17)

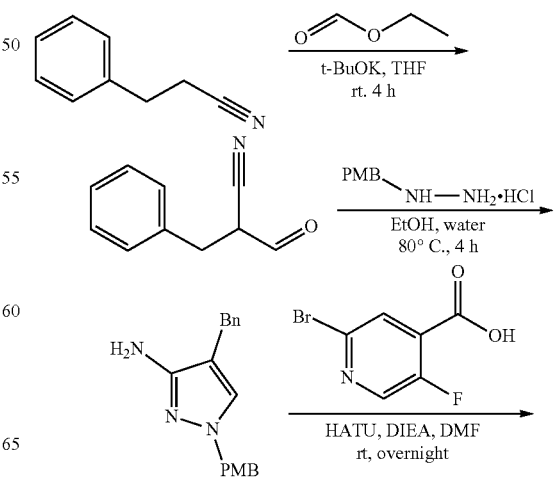

-continued

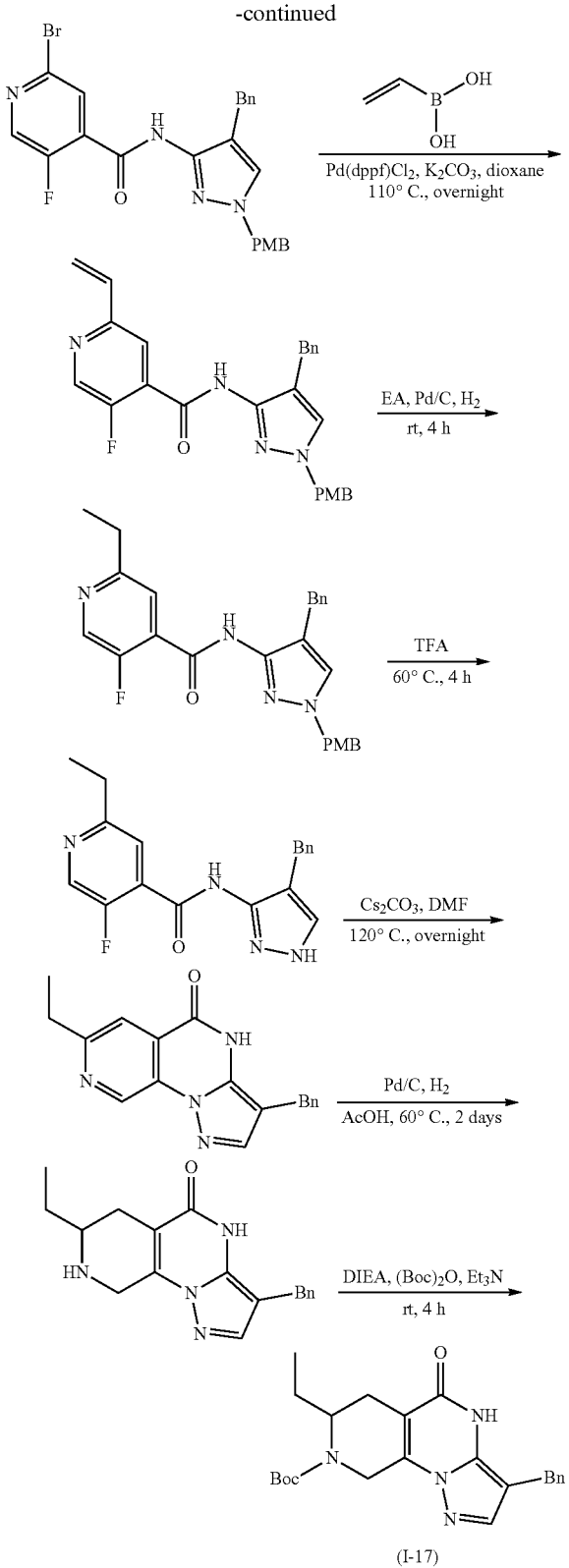

A 500 mL round-bottom flask was charged with benzylacetonitrile (5.00 g, 38.1 mmol, 1.00 eq.), t-BuOK (12.8 g, 114 mmol, 3.00 eq.), ethyl formate (14.1 g, 190 mmol, 5.00 eq.) and THF (200 mL) at 0° C. The mixture was stirred for 4 h at rt. The reaction was quenched with water (200 mL). The mixture was extracted with ethyl acetate (3×100 mL). The organic layers were combined, washed with water (3×100 mL), dried over anhydrous sodium sulfate, filtered and concentrated under reduced pressure to afford 2-formyl-3-phenylpropanenitrile (5.22 g, crude) as a yellow oil.

A 1 L round bottom flask was charged with 2-formyl-3-phenylpropanenitrile (5.00 g, 31.4 mmol, 1.00 eq.), [(4-methoxyphenyl)methyl]hydrazine hydrochloride (7.11 g, 37.6 mmol, 1.20 eq.), EtOH (300 mL) and H$_2$O (100 mL). The solution was stirred 4 h at 80° C. and then concentrated under reduced pressure. The residue was diluted with ethyl acetate (1 L), washed with water (3×300 mL), dried over anhydrous sodium, filtered and concentrated under reduced pressure. The residue was purified by trituration with ethyl acetate (30 mL). The light yellow solid was collected by filtration and dried to provide 4-benzyl-1-[(4-methoxyphenyl)methyl]pyrazol-3-amine (5.11 g, 55% yield) as a light yellow solid. LCMS (ESI, m/z): 294 [M+H]$^+$.

A 500 mL round bottom flask was charged with 4-benzyl-1-[(4-methoxyphenyl)methyl]pyrazol-3-amine (10.0 g, 34.1 mmol, 1.00 eq.), 2-bromo-5-fluoropyridine-4-carboxylic acid (9.00 g, 40.9 mmol, 1.20 eq.), HATU (19.4 g, 51.2 mmol, 1.50 eq.), DIEA (13.2 g, 102 mmol, 3.00 eq.) and DMF (50 mL). The mixture was stirred for overnight at rt. The reaction was quenched with water (200 mL). The solid was collected by filtration, washed with water (3×20 mL) and dried to afford N-{4-benzyl-1-[(4-methoxyphenyl)methyl]pyrazol-3-yl}-2-bromo-5-fluoropyridine-4-carboxamide (12.0 g, 71% yield) as a yellow solid. LCMS (ESI, m/z): 495 [M+H]$^+$.

A 40 mL vial was charged with N-{4-benzyl-1-[(4-methoxyphenyl)methyl]pyrazol-3-yl}-2-bromo-5-fluoropyridine-4-carboxamide (1.00 g, 2.02 mmol, 1.00 eq.), ethenylboronic acid (0.174 g, 2.42 mmol, 1.20 eq.), potassium carbonate (0.843 g, 6.06 mmol, 3.00 eq.), Pd(dppf)Cl$_2$ (0.147 mg, 0.200 mmol, 0.10 eq.) and 1,4-dioxane (10 mL) at rt. The mixture was stirred for overnight at 110° C. under a nitrogen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (2:1) to afford N-{4-benzyl-1-[(4-methoxyphenyl)methyl]pyrazol-3-yl}-2-ethenyl-5-fluoropyridine-4-carboxamide (510 mg, 57% yield) as a yellow solid. LCMS (ESI, m/z): 443 [M+H]$^+$.

A 100 mL round-bottom flask was charged with N-{4-benzyl-1-[(4-methoxyphenyl)methyl]pyrazol-3-yl}-2-ethenyl-5-fluoropyridine-4-carboxamide (1.80 g, 4.07 mmol, 1.00 eq.), ethyl acetate (50 mL) and 10% Pd/C (0.45 g) at rt. The mixture was stirred for 4 h at rt under a hydrogen atmosphere (2-3 atm). The solids were filtered off, and washed with ethyl acetate (3×10 mL). The filtrate was concentrated under reduced pressure to afford N-{4-benzyl-1-[(4-methoxyphenyl)methyl]pyrazol-3-yl}-2-ethyl-5-fluoropyridine-4-carboxamide (1.74 g, 96% yield) as a light yellow solid. LCMS (ESI, m/z): 445 [M+H]$^+$.

A 100 mL round-bottom flask was charged with N-{4-benzyl-1-[(4-methoxyphenyl)methyl]pyrazol-3-yl}-2-ethyl-5-fluoropyridine-4-carboxamide (1.50 g, 3.38 mmol, 1.00 eq.) and TFA (10 mL). The mixture was stirred for 4 h at 60° C. and then concentrated under reduced pressure to afford N-(4-benzyl-1H-pyrazol-3-yl)-2-ethyl-5-fluoropyridine-4-carboxamide (1.02 g, crude) as a light yellow solid. LCMS (ESI, m/z): 325 [M+H]$^+$.

A 250 mL round-bottom flask was charged with N-(4-benzyl-1H-pyrazol-3-yl)-2-ethyl-5-fluoropyridine-4-carboxamide (1.00 g, 3.08 mmol, 1.00 eq.), DMF (50 mL) and Cs$_2$CO$_3$ (3.01 g, 9.24 mmol, 3.00 eq.) at rt. The mixture was stirred for overnight at 120° C. The reaction was quenched with water (200 mL). The mixture was extracted with dichloromethane (3×100 mL). The organic layers were combined, washed with water (3×100 mL), dried over anhydrous sodium sulfate, filtered and concentrated under reduced pressure to provide 5-benzyl-11-ethyl-2,3,7,12-tetraazatricyclo[7.4.0.0ˆ{2,6}]trideca-1(9),3,5,10,12-pentaen-8-one (700 mg, crude) as a light yellow solid. LCMS (ESI, m/z): 305 [M+H]$^+$.

A 100 mL round-bottom flask were charged with 5-benzyl-11-ethyl-2,3,7,12-tetraazatricyclo[7.4.0.0ˆ{2,6}]trideca-1(9),3,5,10,12-pentaen-8-one (1.87 g, 6.14 mmol, 1.00 eq.), 10% Pd/C (0.330 g) and AcOH (50 mL) at rt. The mixture was stirred for 2 days at 60° C. under a hydrogen atmosphere (2-3 atm). The solids were filtered off and washed with ethyl acetate (3×10 mL). The filtrate was concentrated under reduced pressure to afford 5-benzyl-11-ethyl-2,3,7,12-tetraazatricyclo[7.4.0.0ˆ{2,6}]trideca-1(9),3,5-trien-8-one (1.50 g, 79% yield) as an off-white solid. LCMS (ESI, m/z): 309 [M+H]$^+$.

A 100 mL round-bottom flask were charged with 5-benzyl-11-ethyl-2,3,7,12-tetraazatricyclo[7.4.0.0ˆ{2,6}]trideca-1(9),3,5-trien-8-one (920 mg, 2.98 mmol, 1.00 eq.), Et$_3$N (0.600 g, 5.97 mmol, 2.00 eq.), (Boc)$_2$O (0.780 g, 3.58 mmol, 1.20 eq.) and dichloromethane (50 mL). The mixture was stirred for 4 h at rt. The reaction was quenched with water (200 mL). The mixture was extracted with dichloromethane (3×100 mL). The organic layers were combined, washed with water (3×100 mL), dried over anhydrous sodium sulfate, filtered and concentrated under reduced pressure. The residue was purified by silica gel column chromatography, eluted with ethyl acetate:petroleum ether (1:1) to afford tert-butyl 5-benzyl-11-ethyl-8-oxo-2,3,7,12-tetraazatricyclo[7.4.0.0ˆ{2,6}]trideca-1(9),3,5-triene-12-carboxylate (1.05 g, 86% yield) as an off-white solid. LCMS (ESI, m/z): 409 [M+H]$^+$.

(4-(5-(trifluoromethyl)-1H-tetrazol-1-yl)phenyl)boronic Acid (I-18)

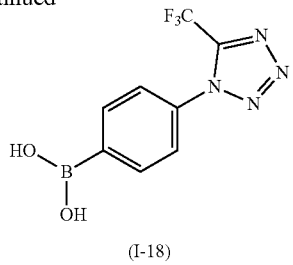

(I-18)

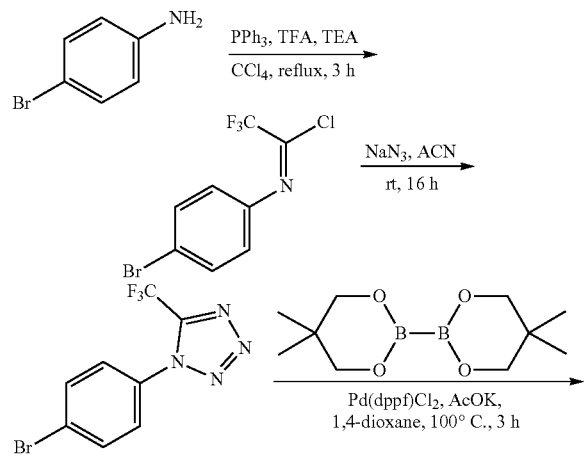

To a mixture of triphenylphosphine (34.50 g, 132 mmol, 2.50 eq.) and triethylamine (5.35 g, 53.0 mmol, 1.00 eq.) in CCl$_4$ (25 mL) was added TFA (5.02 g, 44.0 mmol, 0.80 eq.) at 0° C. The mixture was stirred for 15 mins at 0° C. A solution of 4-bromoaniline (9.12 g, 53.0 mmol, 1.00 eq.) in CCl$_4$ (30 mL) was added at 0° C. The mixture was refluxed for 3 h. The solids were filtered off and washed with hexane (3×100 mL). The combined filtrate was concentrated under reduced pressure. The residue was purified by silica gel column chromatography, eluted with 0-20% ethyl acetate in petroleum ether to afford (E)-N-(4-bromophenyl)-2,2,2-trifluoroacetimidoyl chloride (9.93 g, 65% yield) as a light yellow liquid.

To a solution of (E)-N-(4-bromophenyl)-2,2,2-trifluoroacetimidoyl chloride (2.80 g, 9.77 mmol, 1.00 eq.) in acetonitrile (16 mL) was added NaN$_3$ (0.636 g, 9.77 mmol, 1.00 eq.) at rt. The mixture was stirred for 16 h at rt and then concentrated under reduced pressure. The residue was purified by silica gel column chromatography, eluted with 0-50% ethyl acetate in petroleum ether to afford 1-(4-bromophenyl)-5-(trifluoromethyl)-1H-tetrazole (926 mg, 32% yield) as a pale yellow oil. LCMS (ESI, m/z): 293 [M+H]$^+$.

To a mixture of 1-(4-bromophenyl)-5-(trifluoromethyl)-1H-tetrazole (0.926 g, 3.16 mmol, 1.00 eq.) and 5,5,5',5'-tetramethyl-2,2'-bi(1,3,2-dioxaborinane) (1.43 g, 6.32 mmol, 2.00 eq.) and potassium acetate (1.55 g, 15.8 mmol, 5.00 eq.) in 1,4-dioxane (24 mL) was added Pd(dppf)Cl$_2$·CH$_2$Cl$_2$ (257 mg, 0.320 mmol, 0.10 eq.). The mixture was stirred for 3 h at 100° C. The solids were filtered off, and the filtrate was concentrated under reduced pressure. The residue was purified by reverse phase chromatography with following condition: Column: Agela C$_{18}$ Column, 330 g; Mobile Phase A: Water (0.05% TFA), Mobile Phase B: ACN; Flow rate: 60 mL/min; Gradient: 0% B to 60% B in 40 min to afford (4-(5-(trifluoromethyl)-1H-tetrazol-1-yl)phenyl)boronic acid (704 mg, 86% yield) as a light yellow solid. LCMS (ESI, m/z): 259 [M+H]$^+$.

5-[4-(5,5-dimethyl-1,3,2-dioxaborinan-2-yl)phenyl]-1-methyl-1,2,3-triazole (I-19)

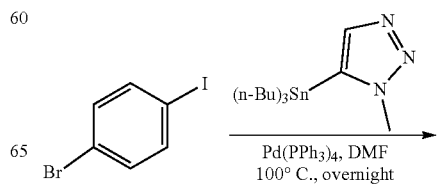

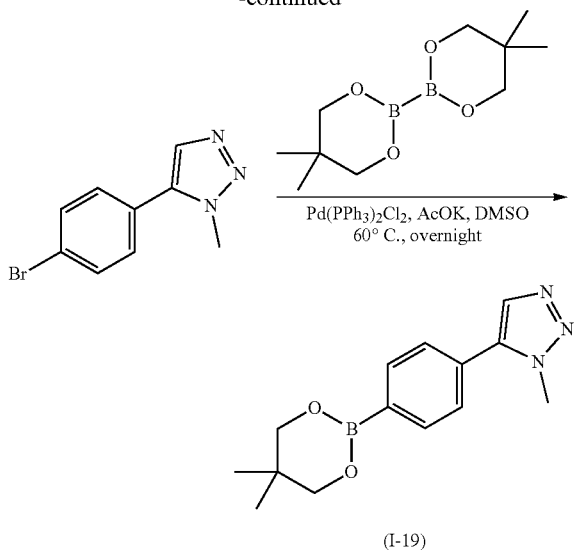

(I-19)

A 100 mL vial was charged with 4-bromoiodobenzene (1.50 g, 5.30 mmol, 1.00 eq.), tetrakis(triphenylphosphine) palladium (0.310 g, 0.265 mmol, 0.05 eq.), DMF (20 mL) and 1-methyl-5-(tributylstannyl)-1,2,3-triazole (3.95 g, 10.6 mmol, 2.00 eq.). The solution was stirred for overnight at 100° C. under nitrogen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with EA:PE (1:5) to afford 5-(4-bromophenyl)-1-methyl-1,2,3-triazole (400 mg, 31% yield) as a white solid. LCMS (ESI, m/z): 238 [M+H]+.

A 40 mL vial was charged with 5-(4-bromophenyl)-1-methyl-1,2,3-triazole (400 mg, 1.68 mmol, 1.00 eq.), 2-(5,5-dimethyl-1,3,2-dioxaborinan-2-yl)-5,5-dimethyl-1,3,2-dioxaborinane (759 mg, 3.36 mmol, 2.00 eq.), Pd(PPh$_3$)$_2$Cl$_2$ (59.0 mg, 0.084 mmol, 0.05 eq.), AcOK (330 mg, 3.36 mmol, 2.00 eq.) and DMSO (20 mL). The solution was stirred for overnight at 60° C. under nitrogen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with EA:PE (1:5) to afford 5-[4-(5,5-dimethyl-1,3,2-dioxaborinan-2-yl)phenyl]-1-methyl-1,2,3-triazole (I-19) (350 mg, 76% yield) as a white solid. LCMS (ESI, m/z): 272 [M+H]+.

tert-butyl 5-benzyl-11-methyl-7-[5-(methylcarbamoyl)pyridin-2-yl]-8-oxo-2,3,7,12-tetraazatricyclo[7.4.0.0^{2,6}]trideca-1(9),3,5-triene-12-carboxylate (I-20)

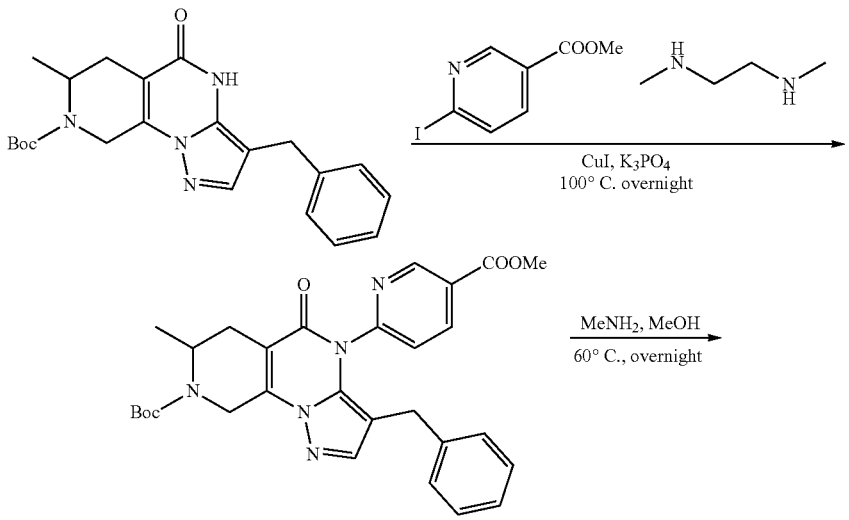

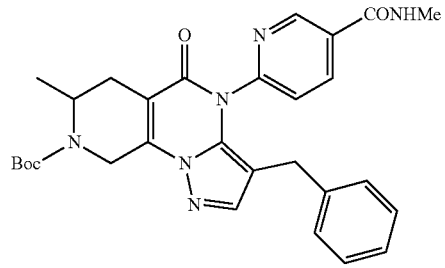

(I-20)

A 100 mL round-bottom flask was charged with tert-butyl 5-benzyl-11-methyl-8-oxo-2,3,7,12-tetraazatricyclo[7.4.0.0^{2,6}]trideca-1(9),3,5-triene-12-carboxylate (500 mg, 1.27 mmol, 1.00 eq.), methyl 6-iodopyridine-3-carboxylate (500 mg, 1.90 mmol, 1.50 eq.), methyl[2-(methylamino)ethyl]amine (22.4 mg, 0.254 mmol, 0.20 eq.), CuI (24.1 mg, 0.127 mmol, 0.10 eq.), $K_3PO_4$ (538 mg, 2.54 mmol, 2.00 eq.) and toluene (10 mL). The mixture was stirred for overnight at 100° C. under nitrogen atmosphere. The reaction was quenched with water (100 mL). The mixture was extracted with ethyl acetate (3×100 mL). The organic layers were combined, washed with brine (3×100 mL), dried over anhydrous sodium sulfate, filtered and concentrated under reduced pressure. The residue was purified by Prep-HPL with the following conditions: Column: YMC-Actus Triart $C_{18}$ ExRS, 30×150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 55% B to 75% B in 8 min; Wave Length: 254 nm to afford tert-butyl 5-benzyl-7-[5-(methoxycarbonyl)pyridin-2-yl]-11-methyl-8-oxo-2,3,7,12-tetraazatricyclo[7.4.0.0^{2,6}]trideca-1(9),3,5-triene-12-carboxylate (220 mg, 33% yield) as a white solid. LCMS (ESI, m/z): 530 $[M+H]^+$.

A 100 mL round-bottom flask was charged with tert-butyl 5-benzyl-7-[5-(methoxycarbonyl)pyridin-2-yl]-11-methyl-8-oxo-2,3,7,12-tetraazatricyclo[7.4.0.0^{2,6}]trideca-1(9),3,5-triene-12-carboxylate (220 mg, 0.415 mmol, 1.00 eq.), $CH_3NH_2$ (0.5 mL, 30% w/w in ethanol) and $CH_3OH$ (10 mL) at rt. The mixture was stirred for overnight at 60° C. and then concentrated under reduced pressure. The residue was purified by prep-TLC ($CH_2Cl_2$/MeOH=10/1) to afford tert-butyl 5-benzyl-11-methyl-7-[5-(methylcarbamoyl)pyridin-2-yl]-8-oxo-2,3,7,12-tetraazatricyclo[7.4.0.0^{2,6}]trideca-1(9),3,5-triene-12-carboxylate (I-20) (150 mg, 68% yield) as a yellow solid. LCMS (ESI, m/z): 529 $[M+H]^+$.

1-(2-((tert-butyldimethylsilyl)oxy)ethyl)-5-(5,5-dimethyl-1,3,2-dioxaborinan-2-yl)-1H-benzo[d][1,2,3]triazole (I-21)

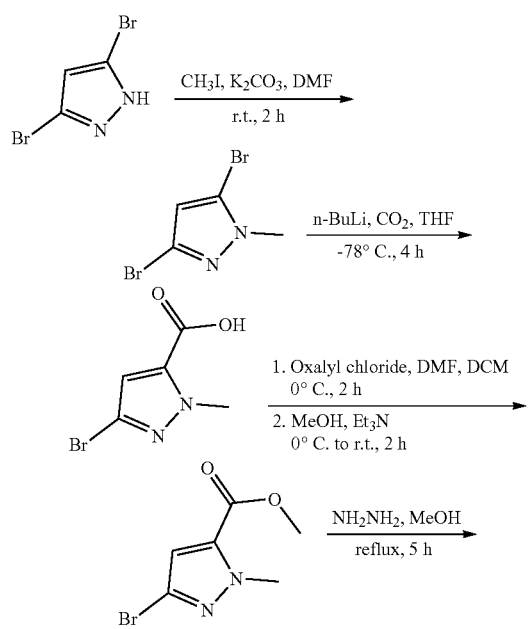

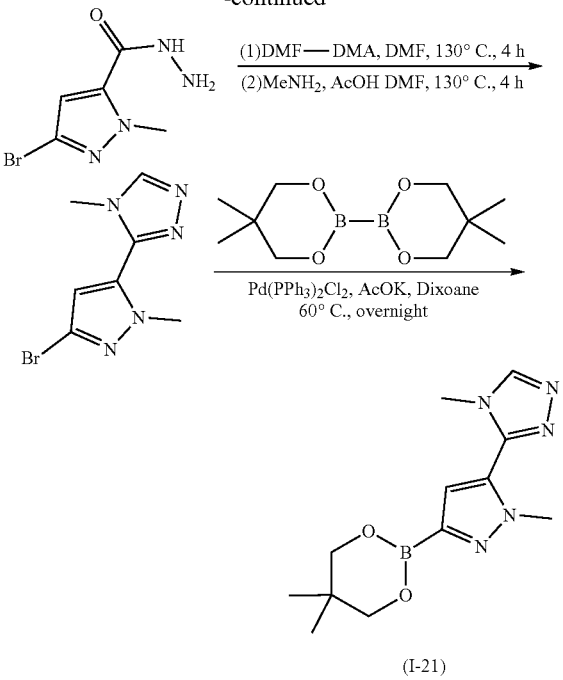

(I-21)

A 250 mL round bottom flask was charged with 3,5-dibromo-1H-pyrazole (10.0 g, 44.3 mmol, 1.00 eq.), DMF (50 mL, 684 mmol, 15.0 eq.), methyl iodide (6.60 g, 46.5 mmol, 1.05 eq.) and $K_2CO_3$ (12.2 g, 88.5 mmol, 2.00 eq.). The solution was stirred for 2 h at rt and then diluted with water (100 mL). The mixture was extracted with ethyl acetate (3×100 mL). The combined organic layers were washed with water (3×100 mL), dried over anhydrous sodium sulfate, filtered and concentrated under reduced pressure. The residue was purified by silica gel column chromatography, eluted with EA:PE (1:10) to afford 3,5-dibromo-1-methylpyrazole (10.3 g, 97% yield) as a colorless oil. LCMS (ESI, m/z): 239 $[M+H]^+$.

A 500 mL round bottom flask was charged with 3,5-dibromo-1-methylpyrazole (9.40 g, 39.2 mmol, 1 eq.) and tetrahydrofuran (100 mL). Butyllithium (23.5 mL, 58.8 mmol, 1.50 eq., 2.5 mol/L in n-hexane) was added dropwise to above mixture at −78° C. under nitrogen atmosphere. The solution was stirred 2 h at −78° C. and then stirred other 2 h at −78° C. under $CO_2$ atmosphere. The reaction was quenched with water (10 mL) at −78° C. and then concentrated under reduced pressure to afford 5-bromo-2-methylpyrazole-3-carboxylic acid (9.23 g, crude). LCMS (ESI, m/z): 205 $[M+H]^+$.

A 250 mL round bottom flask was charged with 5-bromo-2-methylpyrazole-3-carboxylic acid (7.81 g, 38.1 mmol, 1.00 eq.), DCM (100 mL) and DMF (0.03 g, cat.). The oxalyl chloride (24.2 g, 190 mmol, 5.00 eq.) was added dropwise at 0° C. under nitrogen atmosphere. The solution was stirred for 2 h at 0° C. A mixture solution of methanol (12.2 g, 380 mmol, 10.0 eq.) and $Et_3N$ (19.3 g, 190 mmol, 5.00 eq.) was added dropwise at 0° C. under nitrogen atmosphere. The solution was stirred for other 2 h at rt. The reaction was quenched with water (100 mL). The mixture was extracted with ethyl acetate (3×50 mL). The combined organic layers were washed with brine (3×50 mL), dried over anhydrous sodium sulfate, filtered and concentrated under reduced pressure. The residue was purified by silica gel column chromatography, eluted with EA:PE (1:5) to afford methyl 5-bromo-2-methylpyrazole-3-carboxylate (6.02 g, 72% yield) as a yellow solid. LCMS (ESI, m/z): 219 [M+H]+.

A 250 mL round bottom flask was charged with methyl 5-bromo-2-methylpyrazole-3-carboxylate (4.50 g, 20.5 mmol, 1.00 eq.), methanol (100 mL) and hydrazine hydrate (1.32 g, 21.1 mmol, 1.03 eq., 80% in water). The mixture was stirred for 5 h at 70° C. and then concentrated under reduced pressure to afford 5-bromo-2-methylpyrazole-3-carbohydrazide (4.40 g, crude) as a yellow solid. LCMS (ESI, m/z): 219 [M+H]+.

A 100 mL round bottom flask was charged with 5-bromo-2-methylpyrazole-3-carbohydrazide (1.00 g, 4.57 mmol, 1.00 eq.), DMF (20 mL) and DMF-DMA (0.63 g, 27.4 mmol, 6.00 eq.). The solution was stirred for 4 h at 130° C. The mixture was allowed to cool to rt. Methylamine (3.78 g, 36.5 mmol, 8.00 eq., 30% w/w in EtOH) and acetic acid (1.37 g, 22.8 mmol, 5.00 eq.) were added. The solution was stirred for other 4 h at 130° C. The mixture was allowed to cool to rt. The reaction was quenched with water (100 mL). resulting mixture was extracted with EA (3×50 mL). The organic layers were combined, washed with water (3×50 mL), dried over anhydrous sodium sulfate, filtered and concentrated under reduced pressure. The residue was purified by silica gel column chromatography, eluted with MeOH:CH$_2$Cl$_2$ (1:10) to afford 3-(5-bromo-2-methylpyrazol-3-yl)-4-methyl-1,2,4-triazole (260 mg, 24% yield) as a light yellow solid. LCMS (ESI, m/z): 242 [M+H]+.

A 100 mL round bottom flask was charged with 3-(5-bromo-2-methylpyrazol-3-yl)-4-methyl-1,2,4-triazole (443 mg, 1.83 mmol, 1.00 eq.), 2-(5,5-dimethyl-1,3,2-dioxaborinan-2-yl)-5,5-dimethyl-1,3,2-dioxaborinane (1.24 g, 5.49 mmol, 3.00 eq.), 1,4-dioxane (20 mL), potassium acetate (539 mg, 5.49 mmol, 3.00 eq.) and bis(triphenylphosphine) palladium dichloride (128 mg, 0.183 mmol, 0.10 eq.). The mixture was stirred for 2 h at 60° C. under nitrogen atmosphere. The mixture was allowed to cool to rt. The solid was filtered off, and the filter cake was washed with 1,4-dioxane (3×5 mL). The filtrate was concentrated under reduced pressure. The residue was purified by reverse flash chromatography with the following conditions: column, Agela C$_{18}$ Column, 120 g; mobile phase, MeCN in Water, 5% to 15% gradient in 20 min; detector, UV 254 nm. The eluent was concentrated under reduced pressure to afford 3-[5-(5,5-dimethyl-1,3,2-dioxaborinan-2-yl)-2-methylpyrazol-3-yl]-4-methyl-1,2,4-triazole (50 mg, 10% yield) as a yellow solid. LCMS (ESI, m/z): 276 [M+H]+.

tert-butyl 3-benzyl-7-methyl-4-(5-(4-methyl-4H-1,2, 4-triazol-3-yl)pyridin-2-yl)-5-oxo-5,6,7,9-tetrahydropyrazolo[1,5-a]pyrido[4,3-e]pyrimidine-8(4H)-carboxylate (I-22)

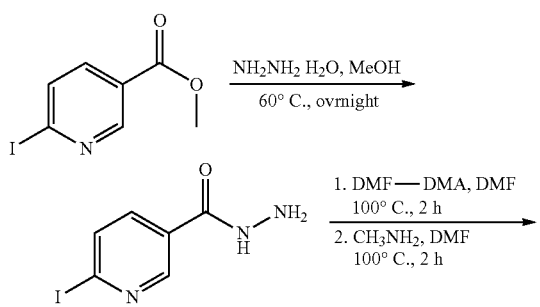

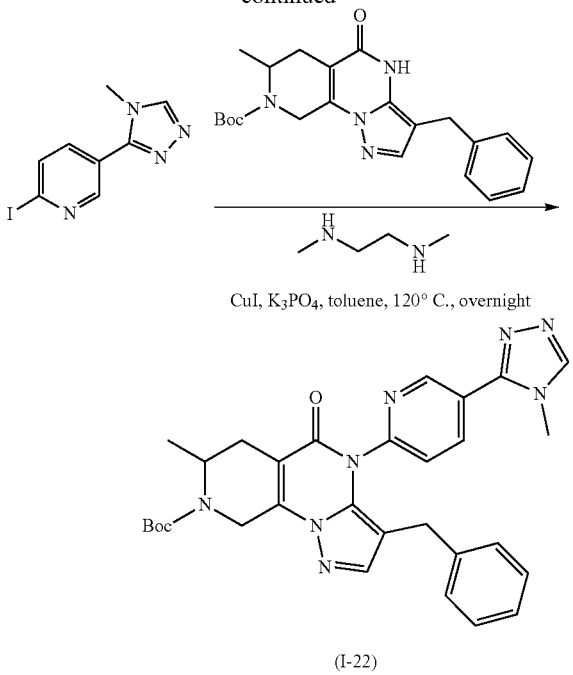

(I-22)

A 100 mL round bottom flask was charged with methyl 6-iodopyridine-3-carboxylate (1.00 g, 3.80 mmol, 1.00 eq.), hydrazine monohydrate (1.19 g, 19.0 mmol, 5.00 eq., 80% in water) and MeOH (50 mL). The mixture was stirred for overnight at 60° C. and concentrated under reduced pressure. The residue was dissolved with ethyl acetate (100 mL), washed with water (3×50 mL), dried over anhydrous sodium sulfate, filtered and concentrated under reduced pressure to afford 6-iodonicotinohydrazide (980 mg, crude) as a white solid. LCMS (ESI, m/z): 264 [M+H]+.

A 100 mL round bottom flask was charged with 6-iodopyridine-3-carbohydrazide (980 mg, 3.72 mmol, 1.00 eq.), DMF-DMA (543 mg, 4.56 mmol, 1.22 eq.) and DMF (20 mL). The mixture was stirred for 2 h at 100° C., and then cooled to rt. CH$_3$NH$_2$ (0.70 mL, 30% w/w in methanol) and AcOH (1.37 g, 22.8 mmol, 6.00 eq.) were added. The solution was stirred for 2 h at 100° C. The mixture was diluted with water (100 mL) and the pH of the mixture was adjusted to 9 using NaOH (1 mmol/L). The mixture was extracted with EtOAc (3×100 mL). The organic layers were combined, washed with water (3×100 mL), dried over anhydrous sodium sulfate, filtered and concentrated under reduced pressure. The residue was purified by silica gel column chromatography, eluted with CH$_2$Cl$_2$:MeOH (10:1) to afford 2-iodo-5-(4-methyl-1,2,4-triazol-3-yl)pyridine (90.0 mg, 8% yield) as light yellow solid. LCMS (ESI, m/z): 287 [M+H]+.

A 40 mL vial was charged with tert-butyl 11-methyl-5-(2-methylpropyl)-8-oxo-2,3,7,12-tetraazatricyclo [7.4.0.0ˆ{2,6}]trideca-1 (9),3,5-triene-12-carboxylate (200 mg, 0.506 mmol, 1.00 eq.), 6-bromo-3-methylimidazo[4,5-c]pyridine (90 mg, 0.313 mmol, 0.6 eq.), copper(I) iodide (40 mg, 0.210 mmol, 0.20 eq.), methyl[2-(methylamino) ethyl]amine (10.0 mg, 0.114 mmol, 0.22 eq.), K$_3$PO$_4$ (430 mg, 2.02 mmol, 4.00 eq.) and toluene (10 mL). The mixture was stirred for overnight at 120° C. under nitrogen atmosphere. The reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with CH$_2$Cl$_2$:MeOH (10:1) to afford tert-butyl 3-benzyl-7-methyl-4-(5-(4-methyl-4H-1,2,4-triazol-3-yl)pyridin-2-yl)-5-oxo-5,6,7,9-tetrahydropyrazolo[1,5-a]pyrido[4,3-e]pyrimidine-8(4H)-carboxylate (40 mg, 14% yield) as a white solid. LCMS (ESI, m/z): 553 [M+H]$^+$.

4-(4-(5,5-dimethyl-1,3,2-dioxaborinan-2-yl)phenyl)-2-methyl-1-((2-(trimethylsilyl)ethoxy)methyl)-1H-imidazole (I-23)

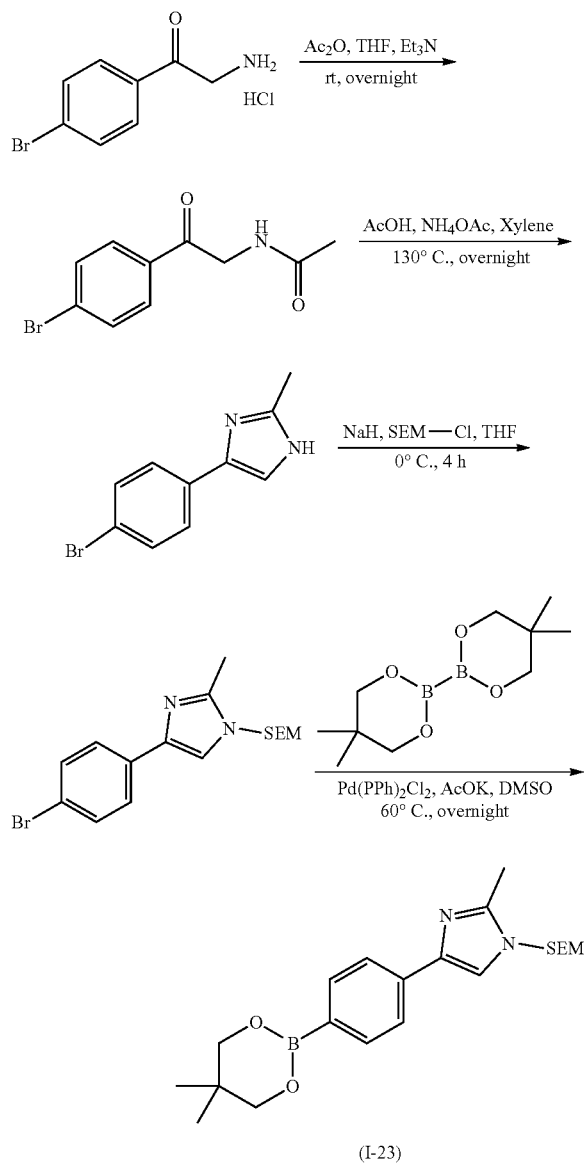

A 250 three-necked round bottom flask was charged with 2-amino-1-(4-bromophenyl)ethan-1-one hydrochloride (12.0 g, 47.9 mmol, 1.00 eq.), tetrahydrofuran (100 mL) and acetic anhydride (14.7 g, 143 mmol, 3.00 eq.). Triethylamine (14.5 g, 143 mmol, 3.00 eq.) was added dropwise at 0° C. The mixture was stirred for overnight at rt. The reaction was quenched with water (200 mL). The mixture was extracted with EA (3×100 mL). The organic layers were combined, washed with brine (3×100 mL), dried over anhydrous sodium sulfate, filtered and concentrated under reduced pressure to afford N-[2-(4-bromophenyl)-2-oxoethyl]acetamide (11.6 g, 95% yield) as a yellow solid. LCMS (ESI, m/z): 256 [M+H]$^+$.

A 250 mL three-necked round bottom flask was charged with N-[2-(4-bromophenyl)-2-oxoethyl]acetamide (11.6 g, 45.3 mmol, 1.00 eq.), xylene (100 mL), NH$_4$OAc (17.4 g, 226 mmol, 5.00 eq.) and acetic acid (13.6 g, 226 mmol, 5.00 eq.). The solution was stirred for overnight at 130° C. and then concentrated under reduced pressure. The residue was dissolved with EA (500 mL), washed with saturated sodium bicarbonate solution (200 mL) and water (3×200 mL), dried over anhydrous sodium sulfate and concentrated under reduced pressure. The residue was purified by silica gel column chromatography, eluted with PE:EA (1:5) to afford 4-(4-bromophenyl)-2-methyl-1H-imidazole (7.86 g, 73% yield) as a yellow solid. LCMS (ESI, m/z): 237 [M+H]$^+$.

A 250 mL round-bottom flask was charged with 4-(4-bromophenyl)-2-methyl-1H-imidazole (4.00 g, 16.9 mmol, 1.00 eq.) and tetrahydrofuran (100 mL). Sodium hydride (0.808 g, 20.2 mmol, 1.20 eq., 60% in mineral oil) was added in portion at 0° C. under N$_2$ atmosphere. The solution was stirred for 1.5 h at rt under N$_2$ atmosphere. [2-(chloromethoxy)ethyl]trimethylsilane (3.66 g, 21.9 mmol, 1.30 eq., in 10 mL THF) was added dropwise at 0° C. The solution was stirred for 1.5 h at rt under N$_2$ atmosphere. The reaction was quenched with water (100 mL) at 0° C. The mixture was extracted with EA (3×100 mL). The organic layers were combined, washed with brine (3×100 mL), dried over anhydrous sodium sulfate, filtered and concentrated under reduced pressure. The residue was purified by silica gel column chromatography, eluted with EA:PE (1:3) to afford 4-(4-bromophenyl)-2-methyl-1-{[2-(trimethylsilyl)ethoxy]methyl}imidazole (4.00 g, 64% yield) as a yellow solid. LCMS (ESI, m/z): 367 [M+H]$^+$.

A 100 mL round bottom flask was charged with 4-(4-bromophenyl)-2-methyl-1-{[2-(trimethylsilyl)ethoxy]methyl}imidazole (4.10 g, 10.9 mmol, 1.00 eq.), DMSO (20 mL), 2-(5,5-dimethyl-1,3,2-dioxaborinan-2-yl)-5,5-dimethyl-1,3,2-dioxaborinane (7.38 g, 32.7 mmol, 3.00 eq.), potassium acetate (3.21 g, 32.7 mmol, 3.00 eq.) and bis(triphenylphosphine)palladium dichloride (0.760 g, 1.09 mmol, 0.10 eq.). The mixture was stirred for overnight at 60° C. under N$_2$ atmosphere. The reaction was quenched with water (100 mL). The mixture was extracted with EA (3×30 mL). The organic layers were combined, washed with water (3×100 mL), dried over anhydrous sodium sulfate and concentrated under reduced pressure. The residue was purified by silica gel column chromatography, eluted with EA:PE (1:3) to afford 4-[4-(5,5-dimethyl-1,3,2-dioxaborinan-2-yl)phenyl]-2-methyl-1-{[2-(trimethylsilyl)ethoxy]methyl}imidazole (3.90 g, 89% yield) as a yellow solid. LCMS (ESI, m/z): 401 [M+H]$^+$.

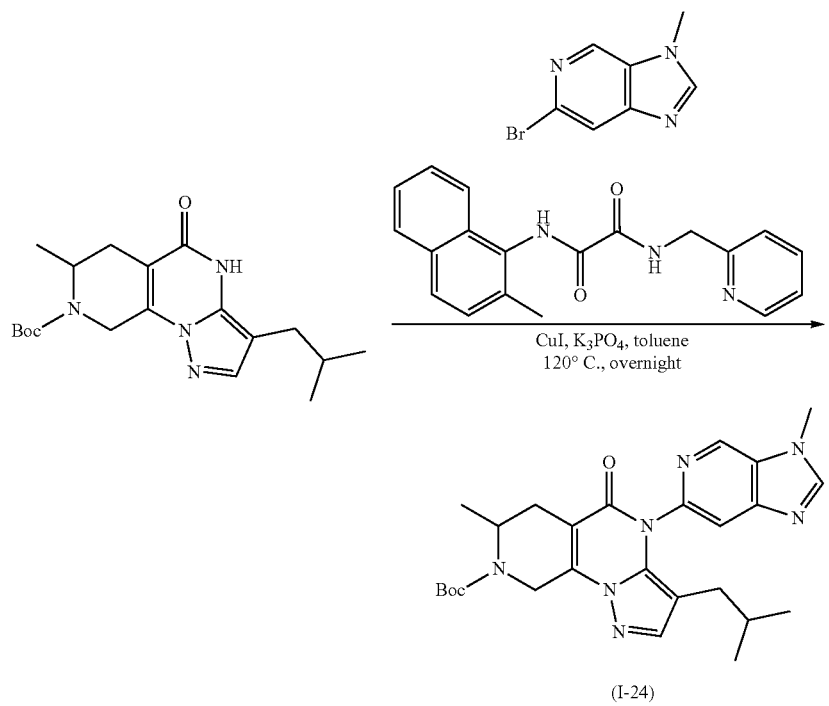

(I-24)

A 40 mL vial was charged with tert-butyl 11-methyl-5-(2-methylpropyl)-8-oxo-2,3,7,12-tetraazatricyclo[7.4.0.0^{2,6}]trideca-1(9),3,5-triene-12-carboxylate (500 mg, 1.39 mmol, 1.00 eq.), 6-bromo-3-methylimidazo[4,5-c]pyridine (294 mg, 1.39 mmol, 1.00 eq.), copper(I) iodide (52.8 mg, 0.277 mmol, 0.200 eq.), N-(2-methylnaphthalen-1-yl)-N'-[(pyridin-2-yl)methyl]ethanediamide (177.6 mg, 0.556 mmol, 0.40 eq.), $K_3PO_4$ (589 mg, 2.77 mmol, 2.00 eq.) and toluene (20 mL). The mixture was stirred for overnight at 120° C. under nitrogen atmosphere. The reaction was quenched with water (50 mL). The mixture was extracted with EA (3×100 mL). The organic layers were combined, washed with brine (3×100 mL), dried over anhydrous sodium sulfate, filtered and concentrated under reduced pressure. The residue was purified by prep-TLC ($CH_2Cl_2$: MeOH=10:1) to afford tert-butyl 11-methyl-7-{3-methyl-imidazo[4,5-c]pyridin-6-yl}-5-(2-methylpropyl)-8-oxo-2,3,7,12-tetraazatricyclo[7.4.0.0^{2,6}]trideca-1(9),3,5-triene-12-carboxylate (250 mg, 37% yield) as a white solid. LCMS (ESI, m/z): 492 [M+H]$^+$.

4-isobutyl-1-(4-methoxybenzyl)-5-methyl-1H-pyrazol-3-amine (I-25)

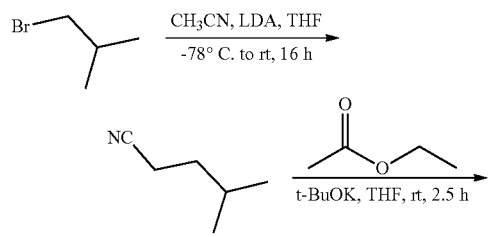

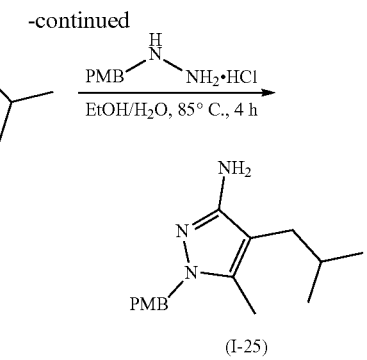

(I-25)

To a solution of acetonitrile (8.20 g, 200 mmol, 1.00 eq.) in anhydrous THF (500 mL) was added LDA (100 mL, 200 mmol, 1.00 eq., 2M solution in n-hexane) at −78° C. under nitrogen atmosphere. The mixture was stirred for 1 h at −78° C. A solution of 1-bromo-2-methylpropane (30.2 g, 220 mmol, 1.10 eq.) in THF (100 mL) was added dropwise at −78° C. The mixture was warmed to rt naturally and then stirred for 16 h at rt. The mixture was poured to saturated $NH_4Cl$ (aq.) (1 L), extracted with dichloromethane (3×1 L). The combined organic layers were washed with brine (2×500 mL), dried over sodium sulfate and filtered. The filtrate was concentrated under reduced pressure to afford 4-methylpentanenitrile (12.2 g, crude) as orange red oil, which was used for next step without further purification. GCMS: M=97.

To a solution of 4-methylpentanenitrile (12.2 g, 126 mmol, 1.00 eq.) in anhydrous THF (500 mL) was added potassium tert-butoxide (42.3 g, 377 mmol, 3.00 eq.) at 0° C. under nitrogen atmosphere. The mixture was stirred for 30 mins at rt. Ethyl acetate (61.3 mL, 629 mmol, 5.00 eq.) was added dropwise very slowly at 0° C. The mixture was stirred for 2.5 h at rt. The mixture was poured to a mixture of water (1 L), concentrated HCl (aq.) (100 mL) and ice (100 g). The mixture was extracted with EA (3×1 L). The combined organic layers were washed with brine (2×500 mL), dried over sodium sulfate and filtered. The filtrate was concentrated under reduced pressure to afford 2-acetyl-4-methylpentanenitrile (17.5 g, crude) as orange red oil, which was used without further purification. LCMS (ESI, m/z): 140 [M+H]$^+$.

A mixture of 2-acetyl-4-methylpentanenitrile (17.5 g, 126 mmol, 1.00 eq.) and (4-methoxybenzyl)hydrazine hydrochloride (23.7 g, 126 mmol, 1.00 eq.) in ethanol (600 mL) and water (100 mL) was stirred for 4 h at 85° C. The mixture was cooled to ambient temperature and then concentrated under reduced pressure. The residue was diluted with water (1 L) and concentrated NH$_3$ (aq.) (200 mL), and extracted with EA (3×1 L). The combined organic layers were washed with brine (2×500 mL), dried over sodium sulfate and filtered. The filtrate was concentrated under reduced pressure. The residue was purified by silica gel column chromatography, eluted with 0-30% EA in dichloromethane to afford 4-isobutyl-1-(4-methoxybenzyl)-5-methyl-1H-pyrazol-3-amine (6.30 g, 18% yield) as a light yellow solid. LCMS (ESI, m/z): 274 [M+H]$^+$.

Example 55

Synthesis of Compounds 39-115 and 119

Compounds 39-115 and 119 were synthetized following the pathways and using the intermediates described herein and/or known in the art. The chiral centers referred to as rac-(R) or rac-(S) in the compound name have been chosen arbitrarily. Tables A1 and A2 depict the structures of Compounds 39-115 and 119, their analytical details and the chiral HPLC methods used to assess enantiomers, when applicable.

TABLE A1

| Cmpd. # | Name | Structure: | chiral HPLC retention time (min) | method chiral HPLC |
|---|---|---|---|---|
| 39a | rac-(11R)-5-benzyl-12-[4-bromo-3-(trifluoromethyl)benzoyl]-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 2.40 min | chiralpak IA-3 4.6*50 mm 3 µm, MtBE (0.1% DEA): EtOH 70:30 |
| 39b | rac-(11S)-5-benzyl-12-[4-bromo-3-(trifluoromethyl)benzoyl]-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 4.29 min | |
| 40a | rac-(11R)-12-[4-bromo-3-(trifluoromethyl)benzoyl]-5-(cyclopropylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 1.96 min | chiralpak IA-3 4.6*50 mm 3 µm, (Hex: DCM 3:1) (0.1% DEA): EtOH 70:30 |

TABLE A1-continued

| Cmpd. # | Name | Structure: | chiral HPLC retention time (min) | method chiral HPLC |
|---|---|---|---|---|
| 40b | rac-(11S)-12-[4-bromo-3-(trifluoromethyl)benzoyl]-5-(cyclopropylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 3.57 min | |
| 41a | 4-methyl-3-[4-[rac-(11R)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]phenyl]-1,2,4-oxadiazol-5-one | | 2.4 min | chiralpak IA-3 4.6*50 mm 3 µm, (Hex: DCM 3:1) (0.1% DEA): EtOH 50:50 |
| 41b | 4-methyl-3-[4-[rac-(11S)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]phenyl]-1,2,4-oxadiazol-5-one | | 3.36 min | |
| 43a | rac-(11R)-5-benzyl-12-[4-bromo-3-(trifluoromethyl)benzoyl]-11-methyl-7-[3-(methylamino)-1H-indazol-6-yl]-2,3,7,12-tetrazatricyclo[7.4.0.0^2,6]trideca-1(9),3,5-trien-8-one | | 1.68 min | chiralpak IA-3 4.6*50 mm 3 µm, MtBE (0.1% DEA): EtOH 85:15 |
| 43b | rac-(11S)-5-benzyl-12-[4-bromo-3-(trifluoromethyl)benzoyl]-11-methyl-7-[3-(methylamino)-1H-indazol-6-yl]-2,3,7,12-tetrazatricyclo[7.4.0.0^2,6]trideca-1(9),3,5-trien-8-one | | 3.39 min | |

TABLE A1-continued

| Cmpd. # | Name | Structure: | chiral HPLC retention time (min) | method chiral HPLC |
|---|---|---|---|---|
| 44a | 2-methyl-3-[4-[rac-(11R)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]phenyl]-1,2,4-oxadiazol-5-one | | 2.75 | chiralpak IF-3 4.6*50 mm 3 μm, MtBE (0.1% DEA): EtOH 80:20 |
| 44b | 2-methyl-3-[4-[rac-(11S)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]phenyl]-1,2,4-oxadiazol-5-one | | 3.37 | |
| 45a | rac-(11R)-12-[4-bromo-3-(trifluoromethyl)benzoyl]-5-(cyclobutylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 1.65 min | chiralpak IA-3 4.6*50 mm 3 μm, MtBE (0.1% DEA): EtOH 50:50 |
| 45b | rac-(11S)-12-[4-bromo-3-(trifluoromethyl)benzoyl]-5-(cyclobutylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 3.15 min | |
| 46a | rac-(11R)-5-benzyl-12-[4-bromo-3-(trifluoromethyl)benzoyl]-11-methyl-7-[4-(5-methyltetrazol-1-yl)phenyl]-2,3,7,12-tetrazatricyclo[7.4.0.0^2,6]trideca-1(9),3,5-trien-8-one | | 2.04 min | chiralpak IA-3 4.6*50 mm 3 μm, (Hex: DCM 3:1) (0.1% DEA): EtOH 70:30 |

TABLE A1-continued

| Cmpd. # | Name | Structure: | chiral HPLC retention time (min) | method chiral HPLC |
|---|---|---|---|---|
| 46b | rac-(11S)-5-benzyl-12-[4-bromo-3-(trifluoromethyl)benzoyl]-11-methyl-7-[4-(5-methyltetrazol-1-yl)phenyl]-2,3,7,12-tetrazatricyclo[7.4.0.0^2,6]trideca-1(9),3,5-trien-8-one | | 3.14 min | |
| 48a | rac-(11R)-12-(4-bromo-3-chloro-benzoyl)-5-(cyclobutylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 3.38 min | chiralpak IA-3 4.6*50 mm 3 μm, MtBE (0.1% DEA): EtOH 70:30 |
| 48b | rac-(11S)-12-(4-bromo-3-chloro-benzoyl)-5-(cyclobutylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 7.16 | |
| 49a | rac-(11R)-5-benzyl-12-[4-bromo-3-(trifluoromethyl)benzoyl]-11-methyl-7-[4-(2-methyl-1,2,4-triazol-3-yl)phenyl]-2,3,7,12-tetrazatricyclo[7.4.0.0^2,6]trideca-1(9),3,5-trien-8-one | | 2.39 min | chiralpak IA-3 4.6*50 mm 3 μm, MtBE (0.1% DEA): EtOH 70:30 |
| 49b | rac-(11S)-5-benzyl-12-[4-bromo-3-(trifluoromethyl)benzoyl]-11-methyl-7-[4-(2-methyl-1,2,4-triazol-3-yl)phenyl]-2,3,7,12-tetrazatricyclo[7.4.0.0^2,6]trideca-1(9),3,5-trien-8-one | | 5.28 min | |

TABLE A1-continued

| Cmpd. # | Name | Structure: | chiral HPLC retention time (min) | method chiral HPLC |
|---|---|---|---|---|
| 51a | rac-(11R)-12-[4-chloro-3-(trifluoromethyl)benzoyl]-5-(cyclobutylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 2.67 min | chiralpak IA-3 4.6*50 mm 3 µm, MtBE (0.1% DEA): EtOH 70:30 |
| 51b | rac-(11S)-12-[4-chloro-3-(trifluoromethyl)benzoyl]-5-(cyclobutylmethyl)-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 6.22 min | |
| 52a | rac-(11R)-5-benzyl-12-[4-chloro-3-(trifluoromethyl)benzoyl]-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.48 min | chiralpak IA-3 4.6*50 mm 3 µm, MtBE (0.1% DEA): EtOH 70:30 |
| 52b | rac-(11S)-5-benzyl-12-[4-chloro-3-(trifluoromethyl)benzoyl]-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 3.16 min | |
| 53a | rac-(11R)-5-benzyl-12-(4-bromo-3-chloro-benzoyl)-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.82 min | chiralpak IA-3 4.6*50 mm 3 µm, MtBE (0.1% DEA): EtOH 70:30 |

TABLE A1-continued

| Cmpd. # | Name | Structure: | chiral HPLC retention time (min) | method chiral HPLC |
|---|---|---|---|---|
| 53b | rac-(11S)-5-benzyl-12-(4-bromo-3-chloro-benzoyl)-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 4.01 min | |
| 54a | N-methyl-4-[rac-(11R)-12-[4-chloro-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]benzamide | | 1.05 min | chiralpak IA-3 4.6*50 mm 3 μm, MtBE (0.1% DEA): EtOH 70:30 |
| 54b | N-methyl-4-[rac-(11S)-12-[4-chloro-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]benzamide | | 1.98 min | |
| 55a | N-methyl-4-[rac-(11R)-12-(4-bromo-3-chloro-benzoyl)-5-isobutyl-11-methyl-8-oxo-2,3,7,12-tetrazatricyclo[7.4.0.0^2,6]trideca-1(9),3,5-trien-7-yl]benzamide | | 1.84 | chiralpak IA-3 4.6*50 mm 3 μm, MtBE (0.1% DEA): EtOH 70:30 |
| 55b | N-methyl-4-[rac-(11S)-12-(4-bromo-3-chloro-benzoyl)-5-isobutyl-11-methyl-8-oxo-2,3,7,12-tetrazatricyclo[7.4.0.0^2,6]trideca-1(9),3,5-trien-7-yl]benzamide | | 2.99 | |

TABLE A1-continued

| Cmpd. # | Name | Structure: | chiral HPLC retention time (min) | method chiral HPLC |
|---|---|---|---|---|
| 56a | rac-(11R)-12-[4-chloro-3-(trifluoromethyl)benzoyl]-5-isobutyl-11-methyl-7-[3-(methylamino)-1H-indazol-6-yl]-2,3,7,12-tetrazatricyclo[7.4.0.0^2,6]trideca-1(9),3,5-trien-8-one | | 1.49 | chiralpak IA-3 4.6*50 mm 3 μm, (Hex: DCM 3:1) (0.1% DEA): EtOH 50:50 |
| 56b | rac-(11S)-12-[4-chloro-3-(trifluoromethyl)benzoyl]-5-isobutyl-11-methyl-7-[3-(methylamino)-1H-indazol-6-yl]-2,3,7,12-tetrazatricyclo[7.4.0.0^2,6]trideca-1(9),3,5-trien-8-one | | 2.19 | |
| 57a | rac-(11R)-12-(4-bromo-3-chloro-benzoyl)-5-isobutyl-11-methyl-7-[3-(methylamino)-1H-indazol-6-yl]-2,3,7,12-tetrazatricyclo[7.4.0.0^2,6]trideca-1(9),3,5-trien-8-one | | 1.91 | chiralpak IA-3 4.6*50 mm 3 μm, (Hex: DCM 3:1) (0.1% DEA): EtOH 50:50 |
| 57b | rac-(11S)-12-(4-bromo-3-chloro-benzoyl)-5-isobutyl-11-methyl-7-[3-(methylamino)-1H-indazol-6-yl]-2,3,7,12-tetrazatricyclo[7.4.0.0^2,6]trideca-1(9),3,5-trien-8-one | | 2.75 | |
| 58a | rac-(11R)-5-benzyl-12-[4-bromo-3-(trifluoromethyl)benzoyl]-11-methyl-7-[4-(4-methyl-5-oxo-1H-1,2,4-triazol-3-yl)phenyl]-2,3,7,12-tetrazatricyclo[7.4.0.0^2,6]trideca-1(9),3,5-trien-8-one | | 2.41 | chiralpak IA-3 4.6*50 mm 3 μm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 58b | rac-(11S)-5-benzyl-12-[4-bromo-3-(trifluoromethyl)benzoyl]-11-methyl-7-[4-(4-methyl-5-oxo-1H-1,2,4-triazol-3-yl)phenyl]-2,3,7,12-tetrazatricyclo[7.4.0.0^2,6]trideca-1(9),3,5-trien-8-one | | 3.8 | |
| 59a | rac-(11R)-12-[4-bromo-3-(trifluoromethyl)benzoyl]-5-isobutyl-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.19 | chiralpak IA-3 4.6*50 mm 3 μm, (Hex: DCM 3:1) (0.1% DEA): EtOH 70:30 |
| 59b | rac-(11S)-12-[4-bromo-3-(trifluoromethyl)benzoyl]-5-isobutyl-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.53 | |
| 61a | rac-(11R)-12-[4-bromo-3-(trifluoromethyl)benzoyl]-5-isobutyl-11-methyl-7-[3-(methylamino)-1H-indazol-6-yl]-2,3,7,12-tetrazatricyclo[7.4.0.0^2,6]trideca-1(9),3,5-trien-8-one | | 1.1 | chiralpak IA-3 4.6*50 mm 3 μm, MtBE (0.1% DEA): EtOH 50:50 |
| 61b | rac-(11S)-12-[4-bromo-3-(trifluoromethyl)benzoyl]-5-isobutyl-11-methyl-7-[3-(methylamino)-1H-indazol-6-yl]-2,3,7,12-tetrazatricyclo[7.4.0.0^2,6]trideca-1(9),3,5-trien-8-one | | 1.67 | |

TABLE A1-continued

| Cmpd. # | Name | Structure: | chiral HPLC retention time (min) | method chiral HPLC |
|---|---|---|---|---|
| 62a | rac-(11R)-12-[4-bromo-3-(trifluoromethyl)benzoyl]-5-isobutyl-11-methyl-7-[4-(4-methyl-1H-triazol-5-yl)phenyl]-2,3,7,12-tetrazatricyclo[7.4.0.0^2,6]trideca-1(9),3,5-trien-8-one | | 1.47 | chiralpak IA-3 4.6*50 mm 3 μm, MtBE (0.1% DEA): EtOH 50:50 |
| 62b | rac-(11S)-12-[4-bromo-3-(trifluoromethyl)benzoyl]-5-isobutyl-11-methyl-7-[4-(4-methyl-1H-triazol-5-yl)phenyl]-2,3,7,12-tetrazatricyclo[7.4.0.0^2,6]trideca-1(9),3,5-trien-8-one | | 2.37 | |
| 63a | rac-(11R)-12-[4-chloro-3-(trifluoromethyl)benzoyl]-5-isobutyl-11-methyl-7-[4-(4-methyl-1H-triazol-5-yl)phenyl]-2,3,7,12-tetrazatricyclo[7.4.0.0^2,6]trideca-1(9),3,5-trien-8-one | | 1.48 | chiralpak IA-3 4.6*50 mm 3 μm, MtBE (0.1% DEA): EtOH 50:50 |
| 63b | rac-(11S)-12-[4-chloro-3-(trifluoromethyl)benzoyl]-5-isobutyl-11-methyl-7-[4-(4-methyl-1H-triazol-5-yl)phenyl]-2,3,7,12-tetrazatricyclo[7.4.0.0^2,6]trideca-1(9),3,5-trien-8-one | | 2.45 | |
| 64a | rac-(11R)-12-(4-bromo-3-chloro-benzoyl)-5-isobutyl-11-methyl-7-[4-(4-methyl-1H-triazol-5-yl)phenyl]-2,3,7,12-tetrazatricyclo[7.4.0.0^2,6]trideca-1(9),3,5-trien-8-one | | 1.99 | chiralpak IA-3 4.6*50 mm 3 μm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 64b | rac-(11S)-12-(4-bromo-3-chloro-benzoyl)-5-isobutyl-11-methyl-7-[4-(4-methyl-1H-triazol-5-yl)phenyl]-2,3,7,12-tetrazatricyclo[7.4.0.0^2,6]trideca-1(9),3,5-trien-8-one | | 3.23 | |
| 65a | rac-(11R)-12-[4-chloro-3-(trifluoromethyl)benzoyl]-5-isobutyl-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.14 | chiralpak IA-3 4.6*50 mm 3 µm, (Hex: DCM 3:1) (0.1% DEA): EtOH 70:30 |
| 65b | rac-(11S)-12-[4-chloro-3-(trifluoromethyl)benzoyl]-5-isobutyl-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.5 | |
| 66a | rac-(11R)-12-(4-bromo-3-chloro-benzoyl)-5-isobutyl-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.25 | chiralpak IA-3 4.6*50 mm 3 µm, (Hex: DCM 3:1) (0.1% DEA): EtOH 70:30 |
| 66b | rac-(11S)-12-(4-bromo-3-chloro-benzoyl)-5-isobutyl-11-methyl-7-[4-(5-methyl-4H-1,2,4-triazol-3-yl)phenyl]-2,3,7,12-tetrazatricyclo[7.4.0.0^2,6]trideca-1(9),3,5-trien-8-one | | 1.62 | |

TABLE A1-continued

| Cmpd. # | Name | Structure: | chiral HPLC retention time (min) | method chiral HPLC |
|---|---|---|---|---|
| 67a | rac-(11R)-12-[4-chloro-3-(trifluoromethyl)benzoyl]-5-isobutyl-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 1.43 | chiralpak IA-3 4.6*50 mm 3 μm, MtBE (0.1% DEA): EtOH 50:50 |
| 67b | rac-(11S)-12-[4-chloro-3-(trifluoromethyl)benzoyl]-5-isobutyl-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 2.33 | |
| 68a | rac-(11R)-12-(4-bromo-3-chloro-benzoyl)-5-isobutyl-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 2.31 | chiralpak IA-3 4.6*50 mm 3 μm, (Hex: DCM 3:1) (0.1% DEA): EtOH 80:20 |
| 68b | rac-(11S)-12-(4-bromo-3-chloro-benzoyl)-5-isobutyl-11-methyl-7-[4-(4-methyl-1,2,4-triazol-3-yl)phenyl]-2,3,7,12-tetrazatricyclo[7.4.0.0^2,6]trideca-1(9),3,5-trien-8-one | | 2.93 | |
| 70a | rac-(11R)-5-benzyl-12-[4-bromo-3-(trifluoromethyl)benzoyl]-11-methyl-7-[4-[3-(trifluoromethyl)pyrazol-1-yl]phenyl]-2,3,7,12-tetrazatricyclo[7.4.0.0^2,6]trideca-1(9),3,5-trien-8-one | | 1.11 | chiralpak IA-3 4.6*50 mm 3 μm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 70b | rac-(11S)-5-benzyl-12-[4-bromo-3-(trifluoromethyl)benzoyl]-11-methyl-7-[4-[3-(trifluoromethyl)pyrazol-1-yl]phenyl]-2,3,7,12-tetrazatricyclo[7.4.0.0^2,6]trideca-1(9),3,5-trien-8-one | | 2.82 | |
| 71a | rac-(11R)-5-benzyl-12-[4-bromo-3-(trifluoromethyl)benzoyl]-11-methyl-7-[4-(1H-tetrazol-5-yl)phenyl]-2,3,7,12-tetrazatricyclo[7.4.0.0^2,6]trideca-1(9),3,5-trien-8-one | | 1.14 | chiralpak IA-3 4.6*50 mm 3 µm, (Hex: DCM 3:1) (0.1% DEA): EtOH 50:50 |
| 71b | rac-(11S)-5-benzyl-12-[4-bromo-3-(trifluoromethyl)benzoyl]-11-methyl-7-[4-(1H-tetrazol-5-yl)phenyl]-2,3,7,12-tetrazatricyclo[7.4.0.0^2,6]trideca-1(9),3,5-trien-8-one | | 1.66 | |
| 72b | rac-(11S)-5-benzyl-12-[4-bromo-3-(trifluoromethyl)benzoyl]-11-methyl-7-(1-methylbenzotriazol-5-yl)-2,3,7,12-tetrazatricyclo[7.4.0.0^2,6]trideca-1(9),3,5-trien-8-one | | 2.83 | chiralpak IA-3 4.6*50 mm 3 µm, MtBE (0.1% DEA): EtOH 50:50 |
| 72a | rac-(11R)-5-benzyl-12-[4-bromo-3-(trifluoromethyl)benzoyl]-11-methyl-7-(1-methylbenzotriazol-5-yl)-2,3,7,12-tetrazatricyclo[7.4.0.0^2,6]trideca-1(9),3,5-trien-8-one | | 1.59 | |

TABLE A1-continued

| Cmpd. # | Name | Structure: | chiral HPLC retention time (min) | method chiral HPLC |
|---|---|---|---|---|
| 73b | N-methyl-5-[rac-(11S)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]pyrazine-2-carboxamide | | 3.05 | chiralpak IA-3 4.6*50 mm 3 μm, MtBE (0.1% DEA): EtOH 50:50 |
| 73a | N-methyl-5-[rac-(11R)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]pyrazine-2-carboxamide | | 1.65 | |
| 74a | rac-(11R)-5-benzyl-12-[4-bromo-3-(trifluoromethyl)benzoyl]-11-methyl-7-[4-[5-(trifluoromethyl)-4H-1,2,4-triazol-3-yl]phenyl]-2,3,7,12-tetrazatricyclo[7.4.0.0^2,6]trideca-1(9),3,5-trien-8-one | | 1.49 | chiralpak IA-3 4.6*50 mm 3 μm, Hex (0.1% FA): EtOH 50:50 |
| 74b | rac-(11S)-5-benzyl-12-[4-bromo-3-(trifluoromethyl)benzoyl]-11-methyl-7-[4-[5-(trifluoromethyl)-4H-1,2,4-triazol-3-yl]phenyl]-2,3,7,12-tetrazatricyclo[7.4.0.0^2,6]trideca-1(9),3,5-trien-8-one | | 3.07 | |
| 75a | rac-(11R)-12-[4-bromo-3-(trifluoromethyl)benzoyl]-5-(cyclopropylmethyl)-11-methyl-7-[4-(4-methyl-1H-triazol-5-yl)phenyl]-2,3,7,12-tetrazatricyclo[7.4.0.0^2,6]trideca-1(9),3,5-trien-8-one | | 1.09 | chiralpak IA-3 4.6*50 mm 3 μm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 75b | rac-(11S)-12-[4-bromo-3-(trifluoromethyl)benzoyl]-5-(cyclopropylmethyl)-11-methyl-7-[4-(4-methyl-1H-triazol-5-yl)phenyl]-2,3,7,12-tetrazatricyclo[7.4.0.0^2,6]trideca-1(9),3,5-trien-8-one | | 3 | |
| 76a | rac-(11R)-12-[4-bromo-3-(trifluoromethyl)benzoyl]-5-(cyclobutylmethyl)-11-methyl-7-[4-(4-methyl-1H-triazol-5-yl)phenyl]-2,3,7,12-tetrazatricyclo[7.4.0.0^2,6]trideca-1(9),3,5-trien-8-one | | 1.11 | chiralpak IA-3 4.6*50 mm 3 μm, MtBE (0.1% DEA): EtOH 60:40 |
| 76b | rac-(11S)-12-[4-bromo-3-(trifluoromethyl)benzoyl]-5-(cyclobutylmethyl)-11-methyl-7-[4-(4-methyl-1H-triazol-5-yl)phenyl]-2,3,7,12-tetrazatricyclo[7.4.0.0^2,6]trideca-1(9),3,5-trien-8-one | | 2.58 | |
| 79a | rac-(11R)-5-benzyl-12-[4-bromo-3-(trifluoromethyl)benzoyl]-11-methyl-7-[4-(4-methyltriazol-2-yl)phenyl]-2,3,7,12-tetrazatricyclo[7.4.0.0^2,6]trideca-1(9),3,5-trien-8-one | | 1.23 | chiralpak IA-3 4.6*50 mm 3 μm, MtBE (0.1% DEA): EtOH 60:40 |
| 79b | rac-(11S)-5-benzyl-12-[4-bromo-3-(trifluoromethyl)benzoyl]-11-methyl-7-[4-(4-methyltriazol-2-yl)phenyl]-2,3,7,12-tetrazatricyclo[7.4.0.0^2,6]trideca-1(9),3,5-trien-8-one | | 2.95 | |

TABLE A1-continued

| Cmpd. # | Name | Structure: | chiral HPLC retention time (min) | method chiral HPLC |
|---|---|---|---|---|
| 80a | rac-(11R)-5-benzyl-12-[4-bromo-3-(trifluoromethyl)benzoyl]-11-methyl-7-[4-(4-methyl-1H-triazol-5-yl)phenyl]-2,3,7,12-tetrazatricyclo[7.4.0.0^2,6]trideca-1(9),3,5-trien-8-one | | 1.11 | chiralpak IA-3 4.6*50 mm 3 μm, MtBE (0.1% DEA): EtOH 50:50 |
| 80b | rac-(11S)-5-benzyl-12-[4-bromo-3-(trifluoromethyl)benzoyl]-11-methyl-7-[4-(4-methyl-1H-triazol-5-yl)phenyl]-2,3,7,12 tetrazatricyclo[7.4.0.0^2,6]trideca-1(9),3,5-trien-8-one | | 2.39 | |
| 81a | rac-(11R)-12-[4-bromo-3-(trifluoromethyl)benzoyl]-5-isobutyl-11-methyl-7-[4-(4-methyl-5-oxo-1H-1,2,4-triazol-3-yl)phenyl]-2,3,7,12-tetrazatricyclo[7.4.0.0^2,6]trideca-1(9),3,5-trien-8-one | | 1.53 | chiralpak IA-3 4.6*50 mm 3 μm, MtBE (0.1% DEA): EtOH 50:50 |
| 81b | rac-(11S)-12-[4-bromo-3-(trifluoromethyl)benzoyl]-5-isobutyl-11-methyl-7-[4-(4-methyl-5-oxo-1H-1,2,4-triazol-3-yl)phenyl]-2,3,7,12-tetrazatricyclo[7.4.0.0^2,6]trideca-1(9),3,5-trien-8-one | | 2.52 | |
| 82a | rac-(11R)-5-benzyl-12-[4-bromo-3-(trifluoromethyl)benzoyl]-11-methyl-7-[4-(1-methyl-5-oxo-4H-1,2,4-triazol-3-yl)phenyl]-2,3,7,12-tetrazatricyclo[7.4.0.0^2,6]trideca-1(9),3,5-trien-8-one | | 1.68 | chiralpak IA-3 4.6*50 mm 3 μm, (Hex: DCM 3:1) (0.1% DEA): EtOH 70:30 |

TABLE A1-continued

| Cmpd. # | Name | Structure: | chiral HPLC retention time (min) | method chiral HPLC |
|---|---|---|---|---|
| 82b | rac-(11S)-5-benzyl-12-[4-bromo-3-(trifluoromethyl)benzoyl]-11-methyl-7-[4-(1-methyl-5-oxo-4H-1,2,4-triazol-3-yl)phenyl]-2,3,7,12-tetrazatricyclo[7.4.0.0^2,6]trideca-1(9),3,5-trien-8-one | | 3.35 | |
| 83a | rac-(11R)-5-benzyl-12-[4-bromo-3-(trifluoromethyl)benzoyl]-11-methyl-7-[1-methyl-5-(4-methyl-1H-triazol-5-yl)pyrazol-3-yl]-2,3,7,12-tetrazatricyclo[7.4.0.0^2,6]trideca-1(9),3,5-trien-8-one | | 2.36 | chiralpak IA-3 4.6*50 mm 3 µm, MtBE (0.1% IPA-mine): EtOH 85:15 |
| 83b | rac-(11S)-5-benzyl-12-[4-bromo-3-(trifluoromethyl)benzoyl]-11-methyl-7-[1-methyl-5-(4-methyl-1H-triazol-5-yl)pyrazol-3-yl]-2,3,7,12-tetrazatricyclo[7.4.0.0^2,6]trideca-1(9),3,5-trien-8-one | | 4.71 | |
| 84a | rac-(11R)-5-benzyl-12-[4-bromo-3-(trifluoromethyl)benzoyl]-11-ethyl-7-[3-(methylamino)-1H-indazol-6-yl]-2,3,7,12-tetrazatricyclo[7.4.0.0^2,6]trideca-1(9),3,5-trien-8-one | | 1.7 | chiralpak IA-3 4.6*50 mm 3 µm, (Hex: DCM 3:1) (0.1% DEA): EtOH 50:50 |
| 84b | rac-(11S)-5-benzyl-12-[4-bromo-3-(trifluoromethyl)benzoyl]-11-ethyl-7-[3-(methylamino)-1H-indazol-6-yl]-2,3,7,12-tetrazatricyclo[7.4.0.0^2,6]trideca-1(9),3,5-trien-8-one | | 3.04 | |

TABLE A1-continued

| Cmpd. # | Name | Structure: | chiral HPLC retention time (min) | method chiral HPLC |
|---|---|---|---|---|
| 85a | N-methyl-2-[rac-(11R)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyrimidine-5-carboxamide | | 1.66 | chiralpak IA-3 4.6*50 mm 3 µm, MtBE (0.1% DEA): EtOH 50:50 |
| 85b | N-methyl-2-[rac-(11S)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyrimidine-5-carboxamide | | 4.97 | |
| 86a | rac-(11R)-12-[4-bromo-3-(trifluoromethyl)benzoyl]-5-isobutyl-11-methyl-7-(1-methylbenzimidazol-5-yl)-2,3,7,12-tetrazatricyclo[7.4.0.0^2,6]trideca-1(9),3,5-trien-8-one | | 1.53 | chiralpak IA-3 4.6*50 mm 3 µm, MtBE (0.1% DEA): EtOH 50:50 |
| 86b | rac-(11S)-12-[4-bromo-3-(trifluoromethyl)benzoyl]-5-isobutyl-11-methyl-7-(1-methylbenzimidazol-5-yl)-2,3,7,12-tetrazatricyclo[7.4.0.0^2,6]trideca-1(9),3,5-trien-8-one | | 2.52 | |
| 87 | 5-benzyl-12-[4-bromo-3-(trifluoromethyl)benzoyl]-11-methyl-7-[4-[5-(trifluoromethyl)tetrazol-1-yl]phenyl]-2,3,7,12-tetrazatricyclo[7.4.0.0^2,6]trideca-1(9),3,5-trien-8-one | | | |

TABLE A1-continued

| Cmpd. # | Name | Structure: | chiral HPLC retention time (min) | method chiral HPLC |
|---|---|---|---|---|
| 88a | rac-(11R)-5-benzyl-12-[4-bromo-3-(trifluoromethyl)benzoyl]-7-[3-(methylamino)-1H-indazol-6-yl]-11-propyl-2,3,7,12-tetrazatricyclo[7.4.0.0^2,6]trideca-1(9),3,5-trien-8-one | | 1.23 | chiralpak IA-3 4.6*50 mm 3 µm, MtBE (0.1% DEA): EtOH 50:50 |
| 88b | rac-(11S)-5-benzyl-12-[4-bromo-3-(trifluoromethyl)benzoyl]-7-[3-(methylamino)-1H-indazol-6-yl]-11-propyl-2,3,7,12-tetrazatricyclo[7.4.0.0^2,6]trideca-1(9),3,5-trien-8-one | | 2.54 | |
| 89a | N-methyl-5-[rac-(11R)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyrazine-2-carboxamide | | 1.46 | chiralpak IA-3 4.6*50 mm 3 µm, MtBE (0.1% DEA): EtOH 50:50 |
| 89b | [rac-(11S)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyrazine-2-carboxamide | | 3.6 | |
| 92a | rac-(11R)-5-benzyl-12-[4-bromo-3-(trifluoromethyl)benzoyl]-11-methyl-7-[4-[5-(trifluoromethyl)tetrazol-1-yl]phenyl]-2,3,7,12-tetrazatricyclo[7.4.0.0^2,6]trideca-1(9),3,5-trien-8-one | | 1.47 | chiralpak IA-3 4.6*50 mm 3 µm, (Hex: DCM 3:1) (0.1% DEA): EtOH 50:50 |

TABLE A1-continued

| Cmpd. # | Name | Structure: | chiral HPLC retention time (min) | method chiral HPLC |
|---|---|---|---|---|
| 92b | rac-(11S)-5-benzyl-12-[4-bromo-3-(trifluoromethyl)benzoyl]-11-methyl-7-[4-[5-(trifluoromethyl)tetrazol-1-yl]phenyl]-2,3,7,12-tetrazatricyclo[7.4.0.0^2,6]trideca-1(9),3,5-trien-8-one | | 2.32 | |
| 93a | 2-methyl-3-[4-[rac-(11R)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]phenyl]-1,2,4-oxadiazol-5-one | | 1.99 | chiralpak IA-3 4.6*50 mm 3 μm, (Hex: DCM 3:1) (0.1% DEA): EtOH 50:50 |
| 93b | 2-methyl-3-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]phenyl]-1,2,4-oxadiazol-5-one | | 3.84 | |
| 94a | 2-methyl-3-[4-[rac-(11R)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]phenyl]-1,2,4-oxadiazol-5-one | | 1.79 | chiralpak IA-3 4.6*50 mm 3 μm, MtBE (0.1% DEA): EtOH 50:50 |
| 94b | 2-methyl-3-[4-[rac-(11S)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]phenyl]-1,2,4-oxadiazol-5-one | | 2.77 | |

TABLE A1-continued

| Cmpd. # | Name | Structure: | chiral HPLC retention time (min) | method chiral HPLC |
|---|---|---|---|---|
| 95a | rac-(11R)-12-[4-bromo-3-(trifluoromethyl)benzoyl]-5-isobutyl-11-methyl-7-(1-methylbenzotriazol-5-yl)-2,3,7,12-tetrazatricyclo[7.4.0.0^2,6]trideca-1(9),3,5-trien-8-one | | 1.58 | chiralpak IA-3 4.6*50 mm 3 μm, (Hex: DCM 3:1) (0.1% DEA): EtOH 50:50 |
| 95b | rac-(11S)-12-[4-bromo-3-(trifluoromethyl)benzoyl]-5-isobutyl-11-methyl-7-(1-methylbenzotriazol-5-yl)-2,3,7,12-tetrazatricyclo[7.4.0.0^2,6]trideca-1(9),3,5-trien-8-one | | 2.02 | |
| 96 | [[4-[(11SR)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]-methyl-amino]methyl (2R)-2-amino-3-methyl-butanoate; hydrochloride | | NA | NA |
| 97 | [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]amino]methyl 2-aminoacetate | | NA | NA |
| 98a | rac-(11R)-12-[4-bromo-3-(trifluoromethyl)benzoyl]-5-isobutyl-11-methyl-7-[4-(4-methylpyrazol-1-yl)phenyl]-2,3,7,12-tetrazatricyclo[7.4.0.0^2,6]trideca-1(9),3,5-trien-8-one | | 1.27 | chiralpak IA-3 4.6*50 mm 3 μm, MtBE (0.1% DEA): EtOH 50:50 |
| 98b | rac-(11S)-12-[4-bromo-3-(trifluoromethyl)benzoyl]-5-isobutyl-11-methyl-7-[4-(4-methylpyrazol-1-yl)phenyl]-2,3,7,12-tetrazatricyclo[7.4.0.0^2,6]trideca-1(9),3,5-trien-8-one | | 2.5 | |

TABLE A1-continued

| Cmpd. # | Name | Structure: | chiral HPLC retention time (min) | method chiral HPLC |
|---|---|---|---|---|
| 99a | rac-(11R)-12-[4-bromo-3-(trifluoromethyl)benzoyl]-5-isobutyl-11-methyl-7-[4-(4-methyltriazol-2-yl)phenyl]-2,3,7,12-tetrazatricyclo[7.4.0.0^2,6]trideca-1(9),3,5-trien-8-one | | 1.08 | chiralpak IA-3 4.6*50 mm 3 µm, MtBE (0.1% DEA): EtOH 70:30 |
| 99b | rac-(11S)-12-[4-bromo-3-(trifluoromethyl)benzoyl]-5-isobutyl-11-methyl-7-[4-(4-methyltriazol-2-yl)phenyl]-2,3,7,12-tetrazatricyclo[7.4.0.0^2,6]trideca-1(9),3,5-trien-8-one | | 2.52 | |
| 100a | rac-(11R)-12-[4-bromo-3-(trifluoromethyl)benzoyl]-5-isobutyl-11-methyl-7-[4-(3-methylpyrazol-1-yl)phenyl]-2,3,7,12-tetrazatricyclo[7.4.0.0^2,6]trideca-1(9),3,5-trien-8-one | | 1.09 | chiralpak IA-3 4.6*50 mm 3 µm, MtBE (0.1% DEA): EtOH 50:50 |
| 100b | rac-(11S)-12-[4-bromo-3-(trifluoromethyl)benzoyl]-5-isobutyl-11-methyl-7-[4-(3-methylpyrazol-1-yl)phenyl]-2,3,7,12-tetrazatricyclo[7.4.0.0^2,6]trideca-1(9),3,5-trien-8-one | | 1.95 | |
| 101 | N-(hydroxymethyl)-N-methyl-4-[rac-(11R)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzamide | | NA | NA |
| 102a | rac-(11R)-12-[4-bromo-3-(trifluoromethyl)benzoyl]-5-isobutyl-11-methyl-7-[4-(3-methyltriazol-4-yl)phenyl]-2,3,7,12-tetrazatricyclo[7.4.0.0^2,6]trideca-1(9),3,5-trien-8-one | | 1.63 | chiralpak IA-3 4.6*50 mm 3 µm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 102b | rac-(11S)-12-[4-bromo-3-(trifluoromethyl)benzoyl]-5-isobutyl-11-methyl-7-[4-(3-methyltriazol-4-yl)phenyl]-2,3,7,12-tetrazatricyclo[7.4.0.0^2,6]trideca-1(9),3,5-trien-8-one | | 2.85 | |
| 103 | dimethyl [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]amino]methyl phosphate | | NA | NA |
| 104a | N-methyl-4-[rac-(11R)-5-benzyl-12-[4-bromo-3-(trifluoromethyl)benzoyl]-11-cyclopropyl-8-oxo-2,3,7,12-tetrazatricyclo[7.4.0.0^2,6]trideca-1(9),3,5-trien-7-yl]benzamide | | 1.04 | chiralpak IA-3 4.6*50 mm 3 μm, MtBE (0.1% DEA): EtOH 50:50 |
| 104b | N-methyl-4-[rac-(11S)-5-benzyl-12-[4-bromo-3-(trifluoromethyl)benzoyl]-11-cyclopropyl-8-oxo-2,3,7,12-tetrazatricyclo[7.4.0.0^2,6]trideca-1(9),3,5-trien-7-yl]benzamide | | 3.61 | |
| 105a | rac-(11R)-5-benzyl-12-[4-bromo-3-(trifluoromethyl)benzoyl]-11-methyl-7-[4-(3-methyltriazol-4-yl)phenyl]-2,3,7,12-tetrazatricyclo[7.4.0.0^2,6]trideca-1(9),3,5-trien-8-one | | 1.72 | chiralpak IA-3 4.6*50 mm 3 μm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 105b | rac-(11S)-5-benzyl-12-[4-bromo-3-(trifluoromethyl)benzoyl]-11-methyl-7-[4-(3-methyltriazol-4-yl)phenyl]-2,3,7,12-tetrazatricyclo[7.4.0.0^2,6]trideca-1(9),3,5-trien-8-one | | 3.61 | |
| 106 | [[4-[(11R)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]-methyl-amino]methyl (2S)-2-amino-3-methyl-butanoate | | NA | NA |
| 107 | methyl [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]amino]methyl hydrogen phosphate | | NA | NA |
| 108a | rac-(11R)-12-[4-bromo-3-(trifluoromethyl)benzoyl]-7-[1-(2-hydroxyethyl)benzotriazol-5-yl]-5-isobutyl-11-methyl-2,3,7,12-tetrazatricyclo[7.4.0.0^2,6]trideca-1(9),3,5-trien-8-one | | 1.27 | chiralpak IA-3 4.6*50 mm 3 μm, MtBE (0.1% DEA): EtOH 50:50 |
| 108b | rac-(11S)-12-[4-bromo-3-(trifluoromethyl)benzoyl]-7-[1-(2-hydroxyethyl)benzotriazol-5-yl]-5-isobutyl-11-methyl-2,3,7,12-tetrazatricyclo[7.4.0.0^2,6]trideca-1(9),3,5-trien-8-one | | 2.18 | |
| 109a | N-methyl-6-[rac-(11R)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]pyridine-3-carboxamide | | 1.36 | chiralpak IG-3 4.6*50 mm 3 μm, (Hex: DCM 1:1) (0.1% DEA): EtOH 50:50 |

TABLE A1-continued

| Cmpd. # | Name | Structure: | chiral HPLC retention time (min) | method chiral HPLC |
|---|---|---|---|---|
| 109b | N-methyl-6-[rac-(11S)-5-benzyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]pyridine-3-carboxamide | | 2.6 | |
| 110 | [methyl-[4-[rac-(11S)-12-[4-bromo-3-(trifluoromethyl)benzoyl]-5-(cyclopropylmethyl)-11-methyl-8-oxo-2,3,7,12-tetrazatricyclo[7.4.0.0^2,6]trideca-1(9),3,5-trien-7-yl]benzoyl]amino]methyl dihydrogen phosphate | | NA | NA |
| 111a | rac-(11R)-12-[4-bromo-3-(trifluoromethyl)benzoyl]-5-isobutyl-11-methyl-7-[4-(1-methyl-5-oxo-4H-1,2,4-triazol-3-yl)phenyl]-2,3,7,12-tetrazatricyclo[7.4.0.0^2,6]trideca-1(9),3,5-trien-8-one | | | chiralpak IA-3 4.6*50 mm 3 μm, (Hex: DCM 3:1) (0.1% DEA): EtOH 50:50 |
| 111b | rac-(11S)-12-[4-bromo-3-(trifluoromethyl)benzoyl]-5-isobutyl-11-methyl-7-[4-(1-methyl-5-oxo-4H-1,2,4-triazol-3-yl)phenyl]-2,3,7,12-tetrazatricyclo[7.4.0.0^2,6]trideca-1(9),3,5-trien-8-one | | | |
| 112a | rac-(11R)-5-benzyl-12-[4-bromo-3-(trifluoromethyl)benzoyl]-11-methyl-7-(1-methylbenzimidazol-5-yl)-2,3,7,12-tetrazatricyclo[7.4.0.0^2,6]trideca-1(9),3,5-trien-8-one | | 1.65 | chiralpak IA-3 4.6*50 mm 3 μm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 112b | rac-(11S)-5-benzyl-12-[4-bromo-3-(trifluoromethyl)benzoyl]-11-methyl-7-(1-methylbenzimidazol-5-yl)-2,3,7,12-tetrazatricyclo[7.4.0.0^2,6]trideca-1(9),3,5-trien-8-one | | 2.83 | |
| 113a | rac-(11S)-12-[4-bromo-3-(trifluoromethyl)benzoyl]-5-(cyclopropylmethyl)-11-methyl-7-(1-methylbenzimidazol-5-yl)-2,3,7,12-tetrazatricyclo[7.4.0.0^2,6]trideca-1(9),3,5-trien-8-one | | 3.26 | chiralpak IA-3 4.6*50 mm 3 μm, MtBE (0.1% DEA): EtOH 50:50 |
| 113b | rac-(11R)-12-[4-bromo-3-(trifluoromethyl)benzoyl]-5-(cyclopropylmethyl)-11-methyl-7-(1-methylbenzimidazol-5-yl)-2,3,7,12-tetrazatricyclo[7.4.0.0^2,6]trideca-1(9),3,5-trien-8-one | | 1.73 | |
| 114a | N-methyl-6-[rac-(11S)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyridazine-3-carboxamide | | 3.73 | chiralpak IA-3 4.6*50 mm 3 μm, MtBE (0.1% DEA): EtOH 50:50 |
| 114b | N-methyl-6-[rac-(11R)-12-[4-bromo-3-(trifluoromethyl)benzoyl]-5-isobutyl-11-methyl-8-oxo-2,3,7,12-tetrazatricyclo[7.4.0.0^2,6]trideca-1(9),3,5-trien-7-yl]pyridazine-3-carboxamide | | 2.24 | |
| 115a | N-methyl-4-[rac-(11S)-5-allyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]benzamide | | 2.02 | chiralpak IA-3 4.6*50 mm 3 μm, MtBE (0.1% DEA): EtOH 50:50 |

TABLE A1-continued

| Cmpd. # | Name | Structure: | chiral HPLC retention time (min) | method chiral HPLC |
|---|---|---|---|---|
| 115b | N-methyl-4-[rac-(11R)-5-allyl-12-[4-bromo-3-(trifluoromethyl)benzoyl]-11-methyl-8-oxo-2,3,7,12-tetrazatricyclo[7.4.0.0^2,6]trideca-1(9),3,5-trien-7-yl]benzamide | | 1.03 | |
| 119a | rac-(11R)-12-[4-bromo-3-(trifluoromethyl)benzoyl]-5-isobutyl-11-methyl-7-(3-methylimidazo[4,5-c]pyridin-6-yl)-2,3,7,12-tetrazatricyclo[7.4.0.0^2,6]trideca-1(9),3,5-trien-8-one | | 2.8 | chiralpak IA-3 4.6*50 mm 3 μm, MtBE (0.1% DEA): EtOH 50:50 |
| 119b | rac-(11S)-12-[4-bromo-3-(trifluoromethyl)benzoyl]-5-isobutyl-11-methyl-7-(3-methylimidazo[4,5-c]pyridin-6-yl)-2,3,7,12-tetrazatricyclo[7.4.0.0^2,6]trideca-1(9),3,5-trien-8-one | | 5.02 | |

TABLE A2

| Cmpd. # | $^1$H NMR | [M + H]+ |
|---|---|---|
| 39a 39b | (300 MHz, CDCl$_3$) δ 8.38 (s, 1H), 7.84 (d, J = 6.0 Hz, 2H), 7.76-7.69 (m, 2H), 7.51-7.48 (m, 2H), 7.38-7.30 (m, 2H), 7.17-7.12 (m, 3H), 6.74-6.71 (m, 2H), 5.33-6.21 (m, 1H), 4.60-4.24 (m, 2H), 3.81 (s, 3H), 3.18 (s, 2H), 2.85-2.64 (m, 2H), 1.37 (d, J = 4.0 Hz, 3H). | 704.1 |
| 40a 40b | (300 MHz, CDCl$_3$) δ 8.35 (s, 1H), 7.98-7.75 (m, 5H), 7.56-7.48 (m, 3H), 6.30-5.26 (m, 1H), 4.49 (m, 2H), 3.86 (s, 3H), 2.96-2.65 (m, 3H), 1.56 (d, J = 4.0 Hz, 2H), 1.35 (d, J = 4.0 Hz, 3H), 0.62-0.58 (m, 1H), 0.42-0.36 (m, 2H), −0.07--0.13 (m, 2H). | 668.05 |
| 41a 41b | (300 MHz, CDCl$_3$) δ 7.83 (t, J = 5.8 Hz, 2H), 7.75-7.40 (m, 4H), 7.40-7.30 (m, 2H), 7.20 (m, 3H), 6.66 (s, 2H), 6.10-5.60 (m, 1H), 4.65-4.30 (m, 2H), 3.33 (s, 3H), 3.20 (s, 2H), 2.90-2.50 (m, 2H), 1.36 (t, J = 18.8 Hz, 3H). | 721.05 |
| 43a 43b | (300 MHz, CDCl$_3$) δ 7.87-7.76 (m, 2H), 7.58-7.36 (m, 3H), 7.14-6.89 (m, 4H), 6.89-6.73 (m, 1H), 6.61 (m, 2H), 6.16-5.65 (m, 1H), 4.65-4.30 (m, 2H), 3.18-2.99 (m, 4H), 2.94-2.59 (m, 4H), 1.36 (d, J = 7.2 Hz, 3H). | 692.15 |
| 44a 44b | (400 MHz, CDCl$_3$) δ 7.88-7.78 (m, 2H), 7.77-7.65 (m, 2H), 7.61-7.46 (m, 2H), 7.40-7.28 (m, 2H), 7.18-7.08 (m, 3H), 6.66 (d, J = 4.2 Hz, 2H), 6.05-5.65 (m, 1H), 4.35-4.61 (m, 2H), 3.77 (s, 3H), 3.19 (s, 2H), 2.78 (m, 1H), 2.71-2.60 (m, 1H), 1.36 (d, J = 6.8 Hz, 3H). | 719.05 |
| 45a 45b | (300 MHz, CDCl$_3$) δ 8.47 (s, 1H), 8.02-7.90 (m, 2H), 7.89-7.75 (m, 2H), 7.60-7.40 (m, 4H), 6.02-5.57 (m, 1H), 4.67-4.37 (m, 2H), 3.88 (s, 3H), 2.88-2.55 (m, 2H), 2.35-2.05 (m, 2H), 1.90-1.60 (m, 6H), 1.45-1.28 (m, 5H). | 680.15 |
| 46a 46b | (300 MHz, CDCl$_3$) δ 7.95-7.75 (m, 2H), 7.58 (s, 1H), 7.52-7.27 (m, 5H), 7.16-7.12 (m, 3H), 6.83-6.43 (m, 2H), 5.95-5.52 (m, 1H), 4.38-4.71 (m, 2H), 3.26 (s, 2H), 2.82 (d, J = 18.1 Hz, 1H), 2.69-2.64 (m, 4H)), 1.37 (d, J = 6.9 Hz, 3H). | 705.1 |
| 48a 48b | (300 MHz, CDCl$_3$) δ 8.42 (s, 1H), 7.93 (t, J = 6.6 Hz 2H) 7.73 (d, J = 4.2 Hz 1H), 7.60-7.46 (m, 4H), 7.22-7.18 (m, 1H), 5.96-5.60 (m, 1H), 4.68-4.35 (m, 2H), 3.87 (s, 3H), 2.90-2.60 (m, 2H), 2.25-2.00 (m, 1H), 1.90-1.60 (m, 6H), 1.45-1.30 (m, 5H). | 648.1 |
| 49a 49b | (300 MHz, CDCl$_3$) δ 8.28-8.15 (m, 1H), 8.00-7.70 (m, 4H), 7.60-7.50 (m, 2H), 7.45-7.30 (m, 2H), 7.20-7.10 (m, 3H), 6.74 (d, J = 3.6 Hz 2H), 6.20-4.80 (m, 1H), 4.65-4.35 (m, 2H), 4.10 (s, 3H), 3.22 (s, 2H), 2.90-2.60 (m, 2H), 1.37 (d, J = 6.9 Hz, 3H). | 702.05 |
| 51a 51b | (300 MHz, CDCl$_3$) δ 9.36 (s, 1H), 8.02 (t, J = 6.2 Hz 2H) 7.82 (s, 1H), 7.70-7.50 (m, 5H), 5.90-5.51 (m, 1H), 4.62-4.20 (m, 2H), 4.04 (s, 3H), 2.89-2.60 (m, 2H), 2.22-2.00 (m, 1H), 1.90-1.80 (m, 2H), 1.80-1.60 (m, 4H), 1.42-1.30 (m, 5H). | 636.25 |

TABLE A2-continued

| Cmpd. # | ¹H NMR | [M + H]+ |
|---|---|---|
| 52a 52b | (300 MHz, CDCl₃) δ 8.13-7.93 (m, 2H), 7.84 (1, 1H), 7.68-7.54 (m, 2H), 7.44 (s, 1H), 7.30-7.28 (m, 1H), 7.24-7.21 (m, 1H), 7.12-7.09 (m, 3H), 6.74-6.71 (m, 2H), 5.96-5.55 (m, 1H), 4.68-4.35 (m, 2H), 3.09 (s, 2H), 2.94-2.57 (m, 2H), 2.44 (s, 3H), 1.37 (d, J = 6.8 Hz, 3H). | 658.15 |
| 53a 53b | (300 MHz, CDCl₃) δ 8.06-7.99 (m, 2H), 7.73 (d, J = 8.2 Hz, 1H), 7.58 (d, J = 1.9 Hz, 1H), 7.44 (s, 1H), 7.29-7.27 (m, 1H), 7.26-7.18 (m, 2H), 7.12-7.08 (m, 2H), 6.74-6.71 (m, 2H), 5.91-5.13 (m, 1H), 4.48 (m, 2H), 3.08 (s, 2H), 2.89-2.55 (m, 2H), 2.43 (s, 3H), 1.35 (d, J = 6.8 Hz, 3H). | 670 |
| 54a 54b | (400 MHz, CDCl₃) δ 8.06-7.88 (m, 2H), 7.81 (s, 1H), 7.65-7.55 (m, 2H), 7.52 (s, 1H), 7.44-7.39 (m, 2H), 6.27 (d, J = 4.9 Hz, 1H), 5.83-5.51 (m, 1H), 4.46 (d, J = 20.7 Hz, 2H), 3.06 (d, J = 4.8 Hz, 3H), 2.93-2.59 (m, 2H), 1.49 (d, J = 7.1 Hz, 2H), 1.35 (d, J = 6.8 Hz, 3H), 1.26-1.19 (m, 1H), 0.58 (d, J = 6.6 Hz, 6H). | 600.15 |
| 55a 55b | (400 MHz, CDCl₃) δ 7.95 (t, J = 8.3 Hz, 2H), 7.72 (d, J = 8.1 Hz, 1H), 7.60-7.47 (m, 2H), 7.44-7.39(m, 2H), 7.21 (d, J = 8.1, 1.9 Hz, 1H), 6.30 (d, J = 5.1 Hz, 1H), 5.82 (br m, 1H), 4.44 (br m, 2H), 3.05 (d, J = 4.7 Hz, 3H), 2.87-2.56 (m, 2H), 1.49 (d, J = 7.0 Hz, 2H), 1.33 (d, J = 6.9 Hz, 3H), 1.25-1.18 (m, 1H), 0.58 (d, J = 6.5 Hz, 6H). | 612.05 |
| 56a 56b | (400 MHz, CDCl₃) δ 7.84 (d, J = 1.9 Hz, 1H), 7.77-7.43 (m, 4H), 7.21 (s, 1H), 6.84 (m, 1H), 5.85 (br m, 1H), 4.49 (br m, 2H), 3.05 (s, 3H), 2.92-2.64 (m, 2H), 1.58-1.11 (m, 6H), 0.66-0.28 (m, 6H). | 612.15 |
| 57a 57b | (400 MHz, CDCl₃) δ 7.73 (dd, J = 8.2, 1.9 Hz, 1H), 7.66-7.41 (m, 3H), 7.23 (dd, J = 8.3, 2.0 Hz, 1H), 6.85 (m, 1H), 5.85 (br m, 1H), 4.49 (br m, 2H), 3.05 (s, 3H), 2.92-2.61 (m, 2H), 1.53-1.04 (m, 6H), 0.73-0.27 (m, 6H). | 622.1 |
| 58a 58b | (300 MHz, CDCl₃) δ 9.92 (br s, 1H), 7.90-7.75 (m, 2H), 7.62 (t, J = 7.3 Hz, 2H), 7.49 (d, J = 9.4 Hz, 2H), 7.37-7.27 (m, 2H), 7.13 (m, 3H), 6.79-6.50 (m, 2H), 5.29-6.21 (m, 1H), 4.49 (br m, 2H), 3.40 (s, 3H), 3.17 (s, 2H), 2.96-2.50 (m, 2H), 1.36 (d, J = 6.8 Hz, 3H). | 720.05 |
| 59a 59b | (300 MHz, CDCl₃) δ 8.30-8.09 (m, 2H), 7.84 (d, J = 8.2 Hz, 2H), 7.60-7.44 (m, 2H), 7.38 (dd, J = 11.5, 8.1 Hz, 2H), 5.1-6.0 (br m, 1H), 4.49 (br m, 2H), 2.91-2.58 (m, 2H), 2.49 (s, 3H), 1.54 (m, 1H), 1.36 (d, J = 6.8 Hz, 3H), 1.26 (dt, J = 13.4, 7.6 Hz, 1H), 0.56 (d, J = 6.5 Hz, 6H) | 670.1 |
| 61a 61b | (300 MHz, CDCl₃) δ 7.85-7.82 (m, 2H), 7.51-7.48 (m, 3H), 7.18 (s, 1H), 6.77 (t, J = 8.6 Hz, 1H), 5.83 (br m, 1H), 4.49 (br m, 2H), 3.01 (s, 3H), 2.92-2.63 (m, 2H), 1.37 (m, 4H), 1.27-1.19 (m, 2H), 0.61-0.32 (m, 6H). | 658.05 |
| 62a 62b | (400 MHz, CDCl₃) δ 7.85-7.79 (m, 4H), 7.54-7.50 (m, 2H), 7.41-7.37 (m, 2H), 5.92 (br m, 1H), 4.50 (br m, 2H), 2.88-2.72 (m, 2H), 2.44 (s, 3H), 1.56 (d, J = 4.0 Hz, 2H), 1.38 (d, J = 4.0 Hz, 3H), 1.23 (m, 1H), 0.58 (d, J = 4.0 Hz, 6H). | 668.2 |
| 63a 63b | (400 MHz, CDCl₃) δ 7.85-7.79 (m, 3H), 7.54-7.50 (m, 3H), 7.41-7.37 (m, 2H), 5.92 (br m, 1H), 4.50 (br m, 2H), 2.88-2.72 (m, 2H), 2.44 (s, 3H), 1.56 (d, J = 4.0 Hz, 2H), 1.38 (d, J = 4.0 Hz, 3H), 1.23 (m, 1H), 0.58 (d, J = 4.0 Hz, 6H). | 624.35 |
| 64a 64b | (400 MHz, CDCl₃) δ 7.84 (m, 2H), 7.73 (m, 1H), 7.54-7.50 (m, 2H), 7.41-7.37 (m, 2H), 7.23 (m, 1H), 5.92 (br m, 1H), 4.50 (br m, 2H), 2.88-2.72 (m, 2H), 2.44 (s, 3H), 1.56 (d, J = 4.0 Hz, 2H), 1.38 (d, J = 4.0 Hz, 3H), 1.23 (m, 1H), 0.58 (d, J = 4.0 Hz, 6H). | 636.2 |
| 65a 65b | (300 MHz, CDCl₃) δ 11.02 (br s, 1H), 8.30-8.12 (m, 2H), 7.84 (s, 1H), 7.67-7.46 (m, 3H), 7.46-7.30 (m, 2H), 6.00-5.55 (m, 1H), 4.74-4.07 (m, 2H), 2.94-2.63 (m, 2H), 2.51 (s, 3H), 1.55 (m, 1H), 1.41-1.20 (m, 4H), 0.57 (d, J = 6.5 Hz, 6H). | 624.15 |
| 66a 66b | (300 MHz, CDCl₃) δ 11.16 (br s, 1H), 8.20 (m, 2H), 7.73 (d, J = 8.2 Hz, 1H), 7.63-7.47 (m, 2H), 7.45-7.31 (m, 2H), 7.23 (dd, J = 8.2, 2.0 Hz, 1H), 5.76 (br m, 1H), 4.47 (br m, 2H), 2.97-2.56 (m, 2H), 2.50 (s, 3H), 1.55 (d, J = 7.0 Hz, 2H), 1.40-1.23 (m, 4H), 0.57 (d, J = 6.5 Hz, 6H). | 636.1 |
| 67a 67b | (400 MHz, CDCl₃) δ 8.37 (br s, 1H), 8.02-7.78 (m, 3H), 7.68-7.45 (m, 5H), 5.87 (br m, 1H), 4.47 (br m, 2H), 3.86 (s, 3H), 2.92-2.61 (m, 2H), 1.46 (m, 5H), 1.25 (m, 1H), 0.60 (d, J = 6.6 Hz, 6H). | 624.15 |
| 68a 68b | (400 MHz, CDCl₃) δ 8.39 (s, 1H), 7.92 (m, 2H), 7.73 (d, J = 8.2 Hz, 1H), 7.61-7.46 (m, 4H), 7.22 (m, 1H), 5.83 (br m, 1H), 4.46 (br m, 2H), 3.87 (s, 3H), 2.80 (d, J = 17.4 Hz, 1H), 2.66 (d, J = 17.2 Hz, 1H), 1.56 (d, J = 7.1 Hz, 2H), 1.34 (d, J = 6.8 Hz, 3H), 1.24 (m, 1H), 0.60 (d, J = 6.6 Hz, 6H). | 636.05 |
| 70a 70b | (400 MHz, CDCl₃) δ 7.97 (s, 1H), 7.87-7.78 (m, 2H), 7.78-7.68 (m, 2H), 7.53-7.43 (m, 2H), 7.35-7.27 (m, 2H), 7.20-7.10 (m, 3H), 6.82-6.67 (m, 3H), 5.90 (br m, 1H), 4.48 (br m, 2H), 3.17 (s, 2H), 2.90-2.75 (m, 1H), 2.75 C 2.60 (m, 1H), 1.35 (d, J = 6.9 Hz, 3H). | 757.05 |
| 71a 71b | (400 MHz, CDCl₃) δ 7.90-7.79 (m, 3H), 7.74 (m, 1H), 7.53 (d, J = 11.1 Hz, 2H), 7.25-7.12 (m, 2H), 7.12-7.01 (m, 3H), 6.62 (d, J = 6.5 Hz, 2H), 6.35-5.3 (br m, 1H), 4.65-4.4 (br m, 2H), 3.10 (s, 2H), 3.0-2.90 (m, 1H), 2.89-2.75 (m, 1H), 1.44 (d, J = 6.9 Hz, 3H). | 691.05 |
| 72a 72b | (400 MHz, CDCl₃) δ 7.99-7.94 (m, 1H), 7.89-7.82 (m, 2H), 7.60-7.38 (m, 3H), 7.32-7.22 (m, 1H), 7.12-7.04 (m, 3H), 6.58-6.54 (m, 2H), 5.91 (br m, 1H), 4.53-4.37 (br m, 2H), 4.34 (s, 3H), 3.15-3.09 (m, 1H), 2.98 (d, J = 16.9 Hz, 1H), 2.71 (m, 1H), 2.55 (d, J = 15.9Hz, 1H), 1.39 (t, J = 6.1 Hz, 3H). | 676.1 |
| 73a 73b | (400 MHz, CDCl₃) δ 9.31 (d, J = 1.4 Hz, 1H), 8.10 (d, J = 1.3 Hz, 1H), 7.95-7.79 (m, 2H), 7.67-7.63(m, 2H), 7.51 (dd, J = 8.1, 2.0 Hz, 1H), 7.16-7.08 (m, 1H), 7.07-7.02 (m, 2H), 6.56 (d, J = 7.4 Hz, 2H), 5.91 (br m, 1H), 4.53 (br m, 2H), 3.5-3.26 (m, 2H), 3.11 (d, J = 5.1 Hz, 3H), 2.82 (m, 1H), 2.65 (d, J = 17.2 Hz, 1H), 1.37 (d, J = 6.9 Hz, 3H). | 680.05 |
| 74a 74b | (300 MHz, CDCl₃) δ 7.87 (d, J = 6.0 Hz, 2H), 7.76 (d, J = 6.0 Hz, 1H), 7.66 (d, J = 6.0 Hz, 1H), 7.54-7.51 (m, 2H), 7.21 (d, J = 4.0 Hz, 1H), 7.15-7.05 (m, 4H), 6.64-6.62 (m, 2H), 5.22 (br m, 1H), 4.55 (br m, 2H), 3.05-2.91 (m, 2H), 2.84 (s, 1H), 2.78 (s, 1H), 1.43 (d, J = 4.0 Hz, 3H). | 756.3 |
| 75a 75b | (300 MHz, CDCl₃) δ 12.51 (br s, 1H), 8.00-7.71 (m, 5H), 7.50 (d, J = 8.1, 2.1 Hz, 1H), 7.39-7.18 (m, 2H), 5.80 (br m 1H), 4.50 (br m, 2H), 2.89 (d, J = 17.8 Hz, 1H), 2.68 (d, J = 17.2 Hz 1H), 2.46 (s, 3H), 1.56 (d, J = 6.9 Hz, 2H), 1.37 (d, J = 6.8 Hz, 3H), 0.61 (m, 1H), 0.45-0.27 (m, 2H), −0.11 (m, 2H). | 666 |
| 76a 76b | (300 MHz, CDCl₃) δ 7.92-7.72 (m, 4H), 7.62-7.44 (m, 2H), 7.44-7.31 (m, 2H), 5.84 (br m, 1H), 4.49 (br m, 2H), 2.94-2.63 (m, 2H), 2.47 (s, 3H), 2.17-2.09 (m, 1H), 1.87-1.76 (m, 2H), 1.75-1.59 (m, 4H), 1.41-1.32 (m, 5H) | 682 |
| 79a 79b | (300 MHz, CDCl₃) δ 8.11-8.02 (m, 2H), 7.86-7.77 (m, 2H), 7.61 (s, 1H), 7.53-7.40 (m, 2H), 7.36-7.27 (m, 2H), 7.18-7.05 (m, 3H), 6.80-6.68 (m, 2H), 5.83 (br m, 1H), 4.48 (br m, 2H), 3.15 (s, 2H), 2.90-2.61 (m, 2H), 2.44 (s, 3H), 1.35 (d, J = 6.8 Hz, 3H). | 704.2 |

TABLE A2-continued

| Cmpd. # | ¹H NMR | [M + H]+ |
|---|---|---|
| 80a 80b | (300 MHz, CDCl₃) δ 7.84 (d, J = 8.0 Hz, 2H), 7.66 (t, J = 6.2 Hz, 2H), 7.50 (d, J = 8.4 Hz, 2H), 7.26 (m, 1H), 7.24 (s, 1H), 7.13-7.07 (m, 3H), 6.72 (d, J = 5.7 Hz, 2H), 5.82 (br m, 1H), 4.51 (br m, 2H), 3.14 (s, 2H), 2.96-2.52 (m, 2H), 2.45 (s, 3H), 1.38 (d, J = 6.8 Hz, 3H). | 704.1 |
| 81a 81b | (300 MHz, CDCl₃) δ 9.62 (br s, 1H), 7.91-7.76 (m, 4H), 7.51 (m, 4H), 5.80 (br m, 1H), 4.47 (br m, 2H), 3.46 (s, 3H), 2.94-2.21 (m, 2H), 1.82-1.40 (m, 2H), 1.36 (d, J = 6.8 Hz, 3H), 1.21 (m, 1H), 0.60 (d, J = 6.5 Hz, 6H). | 684.05 |
| 82a 82b | (400 MHz, CDCl₃) δ 12.57 (s, 1H), 7.86 (m, 4H), 7.51 (d, J = 9.6 Hz, 2H), 7.33 (d, J = 9.6 Hz, 2H), 7.18-7.16 (m, 2H), 6.77-6.74 (m, 2H), 6.23-5.34 (br m, 1H), 4.50 (br m, 2H), 3.62 (s, 3H), 3.15 (s, 2H), 2.73 (m, 2H), 1.38 (d, J = 6.9 Hz, 3H). | 720 |
| 83a 83b | (400 MHz, CDCl₃) δ 7.88-7.72 (m, 2H), 7.49 (dd, J = 8.1, 2.1 Hz, 2H), 7.17-7.03 (m, 3H), 6.86 (d, J = 7.1 Hz, 2H), 6.24 (s, 1H), 6.00-5.52 (br m, 1H), 4.50 (br m, 2H), 3.99 (s, 3H), 3.32 (m, 3H), 2.95-2.62 (m, 2H), 2.17 (s, 3H), 1.34 (d, J = 6.9 Hz, 3H). | 706 |
| 84a 84b | (300 MHz, CDCl₃) δ 7.89-7.77 (m, 2H), 7.59-7.38 (m, 3H), 7.22-7.07 (m, 4H), 6.90-6.54 (m, 3H), 5.87 (br m, 1H), 4.50-3.99 (br m, 2H), 3.19-2.70 (m, 7H), 1.93-1.54 (m, 2H), 1.16-0.80 (m, 3H). | 706 |
| 85a 85b | (300 MHz, CDCl₃) δ 9.25 (s, 2H), 7.81 (d, J = 8.1 Hz, 2H), 7.53 (d, J = 7.7, 2.0 Hz, 1H), 7.45 (dd, J = 7.7, 2.0 Hz, 1H), 7.04 (m, 1H), 5.80 (br m, 1H), 4.46 (br m, 2H), 3.04 (d, J = 4.8 Hz, 3H), 2.91-2.82 (m, 1H), 2.62 (d, J = 17.2 Hz, 1H), 1.51-1.18 (m, 6H), 0.61 (d, J = 6.4 Hz, 6H). | 646 |
| 86a 86b | (300 MHz, CDCl₃) δ 8.03 (d, J = 3.7 Hz, 1H), 7.92-7.70 (m, 3H), 7.61-7.41 (m, 3H), 7.30 (dd, J = 8.7, 1.8 Hz, 1H), 5.83 (br m, 1H), 4.48 (br m, 2H), 3.94 (s, 3H), 2.88-2.68 (m, 2H), 1.47-1.36 (m, 5H), 1.26-1.56 (m, 1H), 0.42-0.51 (m, 6H). | 643 |
| 87 | (400 MHz, DMSO-d6) δ 8.04 (d, J = 8.0 Hz, 1H), 7.95 (s, 1H), 7.86-7.79 (m, 2H), 7.79-7.64 (m, 4H), 7.17-7.09 (m, 3H), 6.80-6.77 (m, 2H), 5.80-5.15 (m, 1H), 4.90-4.15 (m, 2H), 3.09 (s, 2H), 2.74-2.71 (m, 1H), 2.50-2.40 (m, 1H), 1.28 (d, J = 6.6 Hz, 3H). | 759.1 |
| 88a 88b | (300 MHz, CDCl₃) δ 7.86 (m, 2H), 7.53 (m, 3H), 7.10 (m, 4H), 6.92-6.74 (m, 1H), 5.85 (m, 1H), 4.5-4.12 (m, 4H), 3.02-2.63 (m, 3H), 1.83 (m, 1H), 1.66-1.15 (m, 3H), 0.98 (m, 3H). | 718.3 |
| 89a 89b | (300 MHz, CDCl₃) δ 9.47 (d, J = 1.4 Hz, 1H), 8.73 (d, J = 1.4 Hz, 1H), 7.96-7.75 (m, 3H), 7.68-7.42 (m, 2H), 5.81 (br m, 1H), 4.48 (br m, 2H), 3.11 (d, J = 5.1 Hz, 3H), 2.81 (d, J = 17.8 Hz, 1H), 2.65 (d, J = 17.2 Hz, 1H), 1.53 (d, J = 5.8 Hz, 2H), 1.34 (d, J = 6.9 Hz, 3H), 1.15 (m, 1H), 0.60 (dd, J = 6.6, 1.2 Hz, 6H). | 646 |
| 92a 92b | (400 MHz, DMSO-d6) δ 8.04 (d, J = 8.0 Hz, 1H), 7.95 (s, 1H), 7.86 C 7.79 (m, 2H), 7.79 C 7.64 (m, 4H), 7.17 C 7.09 (m, 3H), 6.80 C 6.77 (m, 2H), 5.80 C 5.15 (m, 1H), 4.90 C 4.15 (m, 2H), 3.09 (s, 2H), 2.74 C 2.71 (m, 1H), 2.50 C 2.40 (m, 1H), 1.28 (d, J = 6.6 Hz, 3H). | 757.1; 759.1 |
| 93a 93b | (300 MHz, Chloroform-d) δ 7.96 (s, 2H), 7.89-7.69 (m, 3H), 7.65-7.42 (m, 3H), 6.21-5.23 (m, 1H), 4.65-4.32 (m, 2H), 3.84 (s, 3H), 2.90-2.57 (m, 2H), 1.56-1.27 (m, 5H), 0.69-0.30 (m, 3H), −0.10 (d, J = 5.1 Hz, 2H). | 683.2; 685.2 |
| 94a 94b | (300 MHz, Chloroform-d) δ 8.07-7.91 (m, 2H), 7.90-7.77 (m, 2H), 7.66-7.44 (m, 4H), 6.11-4.85 (m, 4H), 4.47 (d, J = 20.0 Hz, 1H), 3.84 (s, 3H), 2.87-2.59 (m, 2H), 1.53 (d, J = 7.1 Hz, 2H), 1.44-0.96 (m, 5H), 0.59 (d, J = 6.6 Hz, 6H). | 685.25; 687.25 |
| 95a 95b | (400 MHz, Chloroform-d) δ 8.09 (dd, J = 11.1, 1.8 Hz, 1H), 7.89-7.80 (m, 2H), 7.73 (dd, J = 8.7, 0.7 Hz, 1H), 7.60-7.42 (m, 3H), 5.91 (s, 1H), 4.53-4.48 (m, 5H), 3.00-2.53 (m, 2H), 1.49-1.44 (m, 5H), 1.27-1.21 (m, 1H), 0.61-0.37 (m, 6H). | 642.0; 644.0 |
| 96 | (300 MHz, DMSO-d6) δ 8.65 (d, J = 4.6 Hz, 1H), 8.16-7.94 (m, 4H), 7.89 (s, 1H), 7.80 (dd, J = 8.2, 2.0 Hz, 1H), 7.62 (dd, J = 8.4, 2.2 Hz, 1H), 7.45 (dd, J = 8.5, 2.2 Hz, 1H), 5.89 (s, 1H), 4.98 (d, J = 11.6 Hz, 1H), 4.64 (dd, J = 11.6, 3.3 Hz, 1H), 4.33 (s, 1H), 3.44-3.35 (m, 4H), 2.91-2.65 (m, 5H), 1.82 (dt, J = 13.5, 6.7 Hz, 1H), 1.41 (d, J = 6.8 Hz, 2H), 1.02 (d, J = 6.4 Hz, 3H), 0.89-0.69 (m, 6H), 0.68-0.50 (m, 1H), 0.30 (dt, J = 8.7, 2.6 Hz, 2H), −0.13 (q, J = 4.8 Hz, 2H). | 771.1; 773.1 |
| 97 | (300 MHz, DMSO-d6) δ 8.68-8.64 (m, 1H), 8.10-7.81 (m, 5H), 7.75 (dd, J = 7.9, 2.0 Hz, 1H), 7.67-7.52 (m, 2H), 5.85 (s, 1H), 5.04 (d, J = 8.3 Hz, 1H), 4.48 (dd, J = 11.6, 3.2 Hz, 1H), 4.32-4.27 (m, 1H), 3.30 (d, J = 4.3 Hz, 2H), 2.81 (d, J = 4.4 Hz, 3H), 2.75-2.66 (m, 2H), 1.42-1.38 (m, 2H), 1.00 (d, J = 6.4 Hz, 3H), 0.71-0.47 (m, 1H), 0.32-0.26 (m, 2H), −0.13--0.18 (m, 2H) | |
| 98a 98b | (400 MHz, Chloroform-d) δ 7.92-7.74 (m, 5H), 7.63-7.36 (m, 5H), 5.83 (s, 1H), 4.69-4.10 (m, 2H), 2.95-2.51 (m, 2H), 2.19 (s, 3H), 1.58 (d, J = 7.0 Hz, 2H), 1.39-1.16 (m, 4H), 0.61 (d, J = 6.6 Hz, 6H) | 667.0; 669.0 |
| 99a 99b | (400 MHz, CDCl₃) δ 8.24-8.22 (m, 2H), 7.84-7.82 (m, 2H), 7.62 (s, 1H), 7.55-7.42 (m, 4H), 5.80 (s, 1H), 4.49-4.44 (m, 1H), 2.83-2.06 (m, 2H), 2.44 (s, 3H), 1.59-1.58 (m, 2H), 1.36-1.27 (m, 4H), 0.62 (d, J = 6.5 Hz, 6H). | 668.51 |
| 100a 100b | (400 MHz, Chloroform-d) δ 7.93-7.75 (m, 5H), 7.58-7.32 (m, 4H), 6.31 (d, J = 2.4 Hz, 1H), 5.83 (m, 1H), 4.46 (d, J = 20.0 Hz, 2H), 2.93-2.61 (m, 2H), 2.40 (s, 3H), 1.60 (s, 2H), 1.32 (m, 4H), 0.61 (d, J = 6.6 Hz, 6H). | 667.0; 669.0 |
| 101 | (400 MHz, Chloroform-d) δ 7.97-7.92 (m, 2H), 7.86-7.65 (m, 2H), 7.50-7.36 (m, 3H), 6.36-6.08 (m, 2H), 4.93 (s, 1H), 4.41 (d, J = 45.6 Hz, 2H), 4.06 (d, J = 11.7 Hz, 1H), 3.06 (d, J = 4.9 Hz, 3H), 2.87-2.49 (m, 2H), 1.47 (d, J = 7.1 Hz, 2H), 1.32 (m, 3H), 0.61 (s, 1H), 0.40 (d, J = 7.8 Hz, 2H),-0.10 (d, J = 5.3 Hz, 2H) | 672; 674 |
| 102a 102b | (300 MHz, Chloroform-d) δ 7.90-7.75 (m, 3H), 7.64 (d, J = 8.1 Hz, 2H), 7.59-7.43 (m, 4H), 6.00-5.50 (m, 1H), 4.47 (d, J = 19.8 Hz, 2H), 4.16 (s, 3H), 2.96-2.50 (m, 2H), 1.56 (d, J = 7.1 Hz, 2H), 1.36 (d, J = 6.9 Hz, 3H), 1.23 (dt, J = 13.2, 6.4 Hz, 1H), 0.61 (d, J = 6.5 Hz, 6H). | 668; 670 |
| 103 | (300 MHz, Chloroform-d) δ 7.96-7.94 (m, 3H), 7.84 (d, J = 8.1 Hz, 1H), 7.77 (s, 1H), 7.67 (dd, J = 8.1, 2.0 Hz, 1H), 7.46 (d, J = 8.7 Hz, 2H), 6.31 (d, J = 4.2 Hz, 1H), 6.01 (m, 1H), 5.05-4.98 (m, 1H), 4.74-4.67 (m, 1H), 4.45-4.42 (m, 1H), 3.74 (s, 3H), 3.70 (s, 3H), 3.07 (d, J = 4.8 Hz, 3H), 2.94-2.81 (m, 2H), 1.48 (d, J = 6.9 Hz, 2H), 1.07 (d, J = 6.6 Hz, 3H), 0.66-0.61 (m, 1H), 0.45-0.39 (m, 2H), −0.06--0.11 (m, 2H). | 780.15, 782.15 |
| 104a 104b | (400 MHz, Chloroform-d) δ 7.92-7.67 (m, 4H), 7.47 (s, 2H), 7.28 (d, J = 2.2 Hz, 1H), 7.22 (d, J = 8.3 Hz, 1H), 7.17-7.07 (m, 3H), 6.69 (s, 2H), 6.14 (d, J = 5.1 Hz, 2H), 4.69 (s, 2H), 3.40-2.97 (m, 6H), 2.97-2.78 (m, 1H), 1.32-1.17 (m, 1H), 0.67-0.10 (m, 4H). | 704.15; 706.15 |
| 105a 105b | (400 MHz, Chloroform-d) δ 7.95-7.81 (m, 2H), 7.80 (s, 1H), 7.60-7.47 (m, 2H), 7.47-7.38 (m, 2H), 7.38-7.29 (m, 2H), 7.24-7.03 (m, 3H), 6.73 (t, J = 4.6 Hz, 2H), 5.92 (s, 1H), | 702.05; 704.05 |

TABLE A2-continued

| Cmpd. # | ¹H NMR | [M + H]+ |
|---|---|---|
| | 4.52 (d, J = 20.8 Hz, 2H), 4.11 (s, 3H), 3.23 (s, 2H), 2.84 (d, J = 17.8 Hz, 1H), 2.70 (d, J = 17.2 Hz, 1H), 1.39 (d, J = 6.9 Hz, 3H) | |
| 106 | (400 MHz, DMSO-d6) δ 8.64 (q, J = 4.5 Hz, 1H), 8.10-7.95 (m, 4H), 7.89 (s, 1H), 7.81-7.77 (m, 1H), 7.63-7.59 (m, 1H), 7.49-7.46 (m, 1H), 5.89 (s, 1H), 4.98-4.91 (m, 1H), 4.64-4.57 (m, 1H), 4.39-4.25 (m, 1H), 3.12 (d, J = 5.6 Hz, 1H), 2.88-2.82 (m, 4H), 2.73-2.67 (m, 1H), 2.09 (s, 2H), 1.79-1.68 (m, 1H), 1.48-1.37 (m, 2H), 1.02 (d, J = 5.4 Hz, 3H), 0.80-0.73 (m, 6H), 0.65-0.55 (m, 1H), 0.33-0.29 (m, 2H), −0.11-−0.15 (m, 2H). | 771.2; 773.2 |
| 107 | (400 MHz, Methanol-d4) δ 8.03-7.94 (m, 4H), 7.79-7.68 (m, 2H), 7.53 (d, J = 8.4 Hz, 2H), 6.48 (brs, 1H), 4.94-4.92 (m, 1H), 4.82-4.81 (m, 1H), 4.36 (brs, 1H), 3.65 (d, J = 11.2 Hz, 3H), 2.99 (s, 3H), 2.79-2.63 (m, 2H), 1.51-1.49 (m, 6H), 0.65 (s, 1H), 0.40-0.30 (m, 2H), −0.05-−0.20 (m, 2H). | 766.1; 768.1 |
| 108a 108b | (400 MHz, Chloroform-d) δ 8.10 (d, J = 11.7 Hz, 1H), 7.85 (t, J = 9.1 Hz, 3H), 7.57-7.43 (m, 3H), 4.87 (q, J = 5.2 Hz, 2H), 4.50 (s, 1H), 4.29 (t, J = 4.9 Hz, 2H), 2.84 (s, 1H), 2.71 (d, J = 16.3 Hz, 1H), 1.50-1.31 (m, 6H), 1.20 (s, 2H), 0.48 (d, J = 6.6 Hz, 3H), 0.44 (d, J = 6.6 Hz, 3H). | 672.1; 674.1 |
| 109a 109b | (400 MHz, Methanol-d4) δ 8.89 (d, J = 2.5 Hz, 1H), 8.10-7.91 (m, 3H), 7.71-7.55 (m, 2H), 7.31 (d, J = 8.2 Hz, 1H), 7.11-7.01 (m, 3H), 6.66 (s, 2H), 5.78 (s, 1H), 4.7-4.3 (br m, 2H), 3.21 (s, 2H), 2.97 (s, 3H), 2.85-2.74 (m, 1H), 2.69-2.51 (m, 1H), 1.34 (s, 3H) | 679; 681 |
| 110 | (400 MHz, Methanol-d4) δ 8.03-7.96 (m, 4H), 7.82-7.79 (m, 2H), 7.57-7.54 (m, 2H), 5.98 (s, 1H), 4.86-4.80 (m, 2H), 4.52-4.46 (m, 2H), 3.07-3.03 (m, 1H), 2.96 (s, 3H), 2.82-2.78 (m, 1H), 1.51 (d, J = 7.2 Hz, 2H), 1.09 (d, J = 6.4 Hz, 3H), 0.70-0.65 (m, 1H), 0.39-0.35 (m, 2H), −0.11-−0.13 (m, 2H). | 752.15; 754.1 |
| 111a 111b | (400 MHz, Chloroform-d) δ 13.13 (s, 1H), 8.16-7.95 (m, 2H), 7.93-7.79 (m, 2H), 7.63-7.38 (m, 4H), 5.89 (s, 1H), 4.49 (d, J = 11.9 Hz, 2H), 3.63 (s, 3H), 2.94-2.63 (m, 2H), 1.58 (d, J = 7.0 Hz, 2H), 1.47-1.15 (m, 4H), 0.62 (d, J = 6.5 Hz, 6H). | 684.51 |
| 112a 112b | (400 MHz, Chloroform-d) δ 8.18 (d, J = 16.1 Hz, 1H), 7.90-7.74 (m, 3H), 7.51 (m, 1H), 7.42 (m, 2H), 7.26-7.07 (m, 4H), 6.69 (s, 2H), 5.99 (s, 1H), 4.52 (s, 2H), 3.95 (s, 3H), 3.02 (m, 1H), 2.87 (m, 2H), 2.72 (d, J = 17.2 Hz, 1H), 1.44-1.27 (m, 3H). | 675.05; 677.05 |
| 113a 113b | (400 MHz, Chloroform-d) δ 8.10 (d, J = 9.6 Hz, 1H), 7.86-7.65 (m, 4H), 7.59-7.43 (m, 2H), 7.35-7.28 (m, 1H), 6.02-5.57 (m, 1H), 4.48 (s, 2H), 3.96 (d, J = 1.4 Hz, 3H), 2.91-2.63 (m, 2H), 1.51-1.21 (m, 5H), 0.57 (s, 1H), 0.32 (d, J = 8.0 Hz, 2H), −0.19 (d, J = 4.9 Hz, 2H). | 639.1; 641.1 |
| 114a 114b | (300 MHz, Chloroform-d) δ 8.56 (d, J = 8.7 Hz, 1H), 8.15 (d, J = 5.2 Hz, 1H), 7.91-7.85 (m, 3H), 7.61-7.44(m, 2H), 4.49 (br d, J = 20.0 Hz, 1H), 3.21-3.08 (m, 3H), 2.81 (d, J = 16.2 Hz, 1H), 2.65 (d, J = 17.1 Hz, 1H), 1.51 (d, J = 7.1 Hz, 2H), 1.35 (d, J = 6.9 Hz, 3H), 1.13 (m, 1H), 0.58 (d, J = 6.4 Hz, 6H). | 646.05; 648.05 |
| 115a 115b | (400 MHz, Chloroform-d) δ 8.03-7.89 (m, 2H), 7.89-7.79 (m, 2H), 7.62-7.36 (m, 4H), 6.34 (d, J = 8.2 Hz, 1H), 5.89 (s, 1H), 5.65-5.45 (m, 1H), 4.99-4.87 (m, 1H), 4.72 (d, J = 11.0 Hz, 1H), 4.50 (d, J = 9.4 Hz, 2H), 3.08 (d, J = 4.7 Hz, 3H), 2.83 (d, J = 12.3 Hz, 1H), 2.69 (d, J = 11.2 Hz, 1H), 2.38 (d, J = 6.0 Hz, 2H), 1.36 (d, J = 6.8 Hz, 3H). | 628; 630 |
| 119a 119b | (300 MHz, Chloroform-d) δ 8.91 (s, 1H), 8.32 (s, 1H), 7.90-7.78 (m, 3H), 7.54-7.44 (m, 2H), 5.82 (s, 1H), 4.47 (d, J = 20.4 Hz, 1H), 4.09 (s, 3H), 2.94-2.50 (m, 3H), 1.45-1.14 (m, 6H), 0.48 (d, J = 5.7 Hz, 6H). | 642.0; 644.0 |

Additional compounds of Formula (I), such as Compounds 116-118 and 120-122 provided in Table B, can be prepared using similar materials and methods described herein, such as those described herein.

TABLE B

| Cmpd # | Name | Structure | MW |
|---|---|---|---|
| 116a | (R)-3-benzyl-8-(4-bromo-3-(trifluoromethyl)benzoyl)-7-methyl-4-(1-methyl-5-(4-methyl-4H-1,2,4-triazol-3-yl)-1H-pyrazol-3-yl)-6,7,8,9-tetrahydropyrazolo[1,5-a]pyrido[4,3-e]pyrimidin-5(4H)-one | 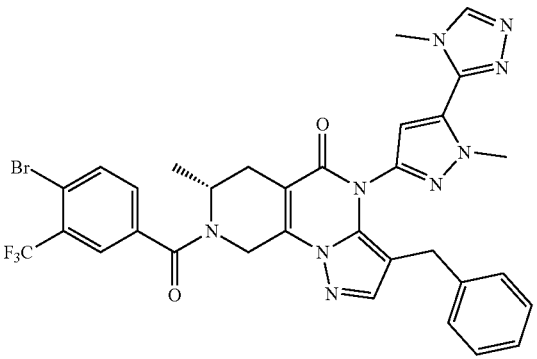 [SMILES: C[C@@H]1Cc2c(n3ncc(Cc4ccccc4)c3n(-c3cc(-c4nncn4C)n(C)n3)c2=O)CN1C(=O)c1ccc(Br)c(C(F)(F)F)c1] | 706.53 |

TABLE B-continued

| Cmpd # | Name | Structure | MW |
|---|---|---|---|
| 116b | (S)-3-benzyl-8-(4-bromo-3-(trifluoromethyl)benzoyl)-7-methyl-4-(1-methyl-5-(4-methyl-4H-1,2,4-triazol-3-yl)-1H-pyrazol-3-yl)-6,7,8,9-tetrahydropyrazolo[1,5-a]pyrido[4,3-e]pyrimidin-5(4H)-one | 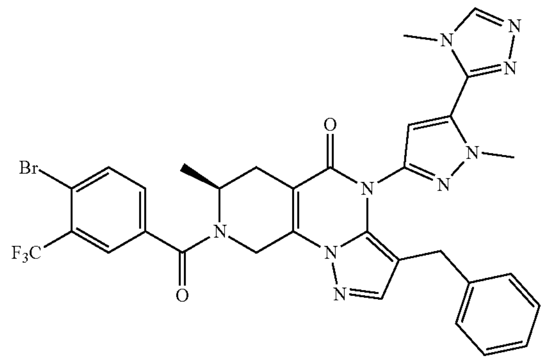 [SMILES: C[C@H]1Cc2c(n3ncc(Cc4ccccc4)c3n(-c3cc(-c4nncn4C)n(C)n3)c2=O)CN1C(=O)c1ccc(Br)c(C(F)(F)F)c1] | |
| 117a | (R)-3-benzyl-8-(4-bromo-3-(trifluoromethyl)benzoyl)-7-methyl-4-(5-(4-methyl-4H-1,2,4-triazol-3-yl)pyridin-2-yl)-6,7,8,9-tetrahydropyrazolo[1,5-a]pyrido[4,3-e]pyrimidin-5(4H)-one | 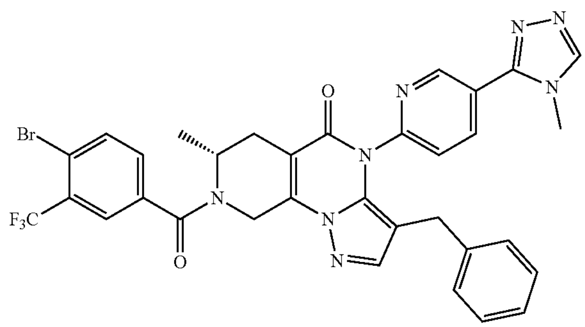 [SMILES: C[C@@H]1Cc2c(n3ncc(Cc4ccccc4)c3n(-c3ccc(-c4nncn4C)cn3)c2=O)CN1C(=O)c1ccc(Br)c(C(F)(F)F)c1] | 703.52 |
| 117b | (S)-3-benzyl-8-(4-bromo-3-(trifluoromethyl)benzoyl)-7-methyl-4-(5-(4-methyl-4H-1,2,4-triazol-3-yl)pyridin-2-yl)-6,7,8,9-tetrahydropyrazolo[1,5-a]pyrido[4,3-e]pyrimidin-5(4H)-one | 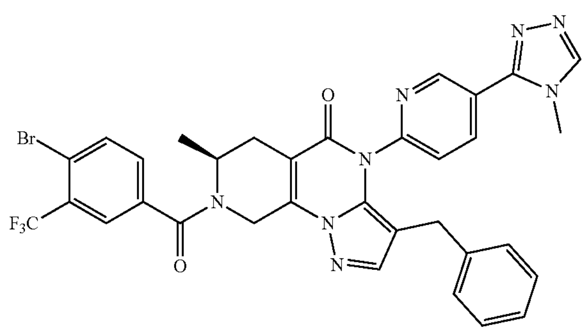 [SMILES: C[C@H]1Cc2c(n3ncc(Cc4ccccc4)c3n(-c3ccc(-c4nncn4C)cn3)c2=O)CN1C(=O)c1ccc(Br)c(C(F)(F)F)c1] | |
| 118a | (R)-8-(4-bromo-3-(trifluoromethyl)benzoyl)-3-isobutyl-7-methyl-4-(4-(2-methyl-1H-imidazol-4-yl)phenyl)-6,7,8,9-tetrahydropyrazolo[1,5-a]pyrido[4,3-e]pyrimidin-5(4H)-one | 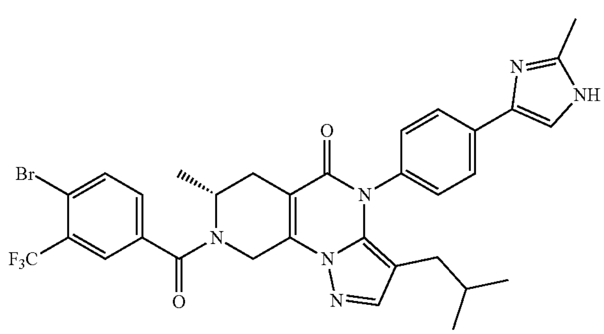 [SMILES: Cc1nc(-c2ccc(-n3c(=O)c4c(n5ncc(CC(C)C)c35)CN(C(=O)c3ccc(Br)c(C(F)(F)F)c3)[C@H](C)C4)cc2)c[nH]1] | 667.53 |

TABLE B-continued

| Cmpd # | Name | Structure | MW |
|---|---|---|---|
| 118b | (S)-8-(4-bromo-3-(trifluoromethyl)benzoyl)-3-isobutyl-7-methyl-4-(4-(2-methyl-1H-imidazol-4-yl)phenyl)-6,7,8,9-tetrahydropyrazolo[1,5-a]pyrido[4,3-e]pyrimidin-5(4H)-one | 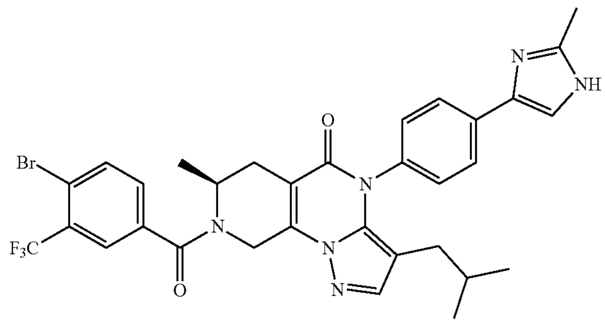 [SMILES: Cc1nc(-c2ccc(-n3c(=O)c4c(n5ncc(CC(C)C)c35)CN(C(=O)c3ccc(Br)c(C(F)(F)F)c3)[C@@H](C)C4)cc2)c[nH]1] | |
| 120a | (R)-4-(8-(4-bromo-3-(trifluoromethyl)benzoyl)-3-isobutyl-2,7-dimethyl-5-oxo-6,7,8,9-tetrahydropyrazolo[1,5-a]pyrido[4,3-e]pyrimidin-4(5H)-yl)-N-methylbenzamide | 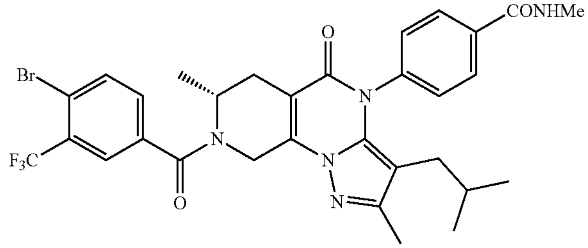 | 658.52 |
| 120b | (S)-4-(8-(4-bromo-3-(trifluoromethyl)benzoyl)-3-isobutyl-2,7-dimethyl-5-oxo-6,7,8,9-tetrahydropyrazolo[1,5-a]pyrido[4,3-e]pyrimidin-4(5H)-yl)-N-methylbenzamide | 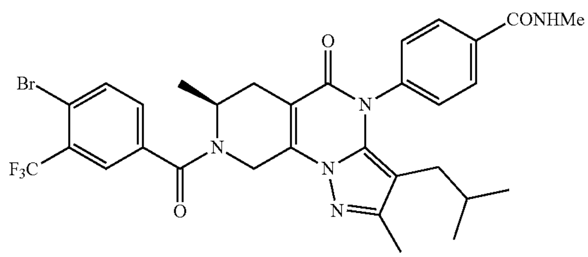 | |
| 121a | (R)-4-(8-(4-bromo-3-(trifluoromethyl)benzoyl)-3-isobutyl-7-methyl-5-oxo-6,7,8,9-tetrahydropyrazolo[1,5-a]pyrido[4,3-e]pyrimidin-4(5H)-yl-2-d)-N-methylbenzamide | 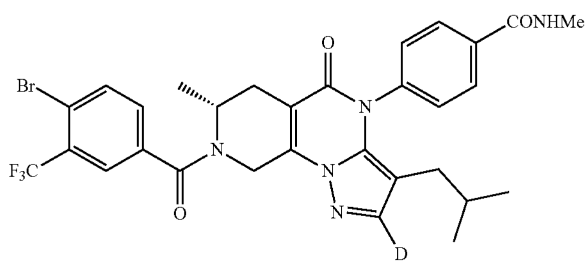 | 645.50 |
| 121b | (S)-4-(8-(4-bromo-3-(trifluoromethyl)benzoyl)-3-isobutyl-7-methyl-5-oxo-6,7,8,9-tetrahydropyrazolo[1,5-a]pyrido[4,3-e]pyrimidin-4(5H)-yl-2-d)-N-methylbenzamide | 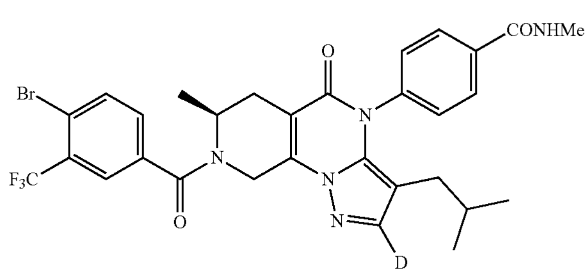 | |

TABLE B-continued

| Cmpd # | Name | Structure | MW |
|---|---|---|---|
| 122a | (R)-4-(8-(4-bromo-3-(trifluoromethyl)benzoyl)-2-fluoro-3-isobutyl-7-methyl-5-oxo-6,7,8,9-tetrahydropyrazolo[1,5-a]pyrido[4,3-e]pyrimidin-4(5H)-yl)-N-methylbenzamide | 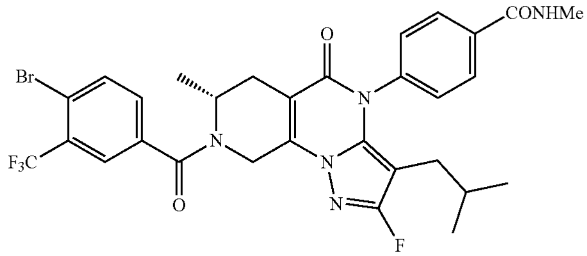 | 662.48 |
| 122b | (S)-4-(8-(4-bromo-3-(trifluoromethyl)benzoyl)-2-fluoro-3-isobutyl-7-methyl-5-oxo-6,7,8,9-tetrahydropyrazolo[1,5-a]pyrido[4,3-e]pyrimidin-4(5H)-yl)-N-methylbenzamide | 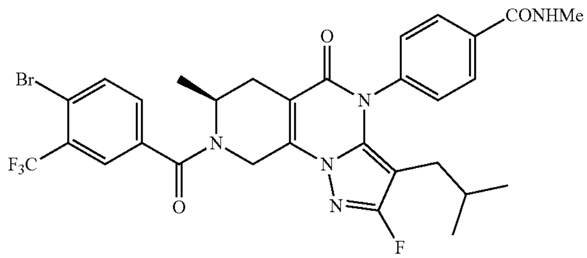 | |

Example A

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using CellTiter-Glo 2.0 (Promega).

On day 0, HepG2.117 cells (which are maintained in routine cell culture with doxycycline present in the medium at a final concentration of 1 μg/mL) were seeded in 96-well plates (white with clear bottom) at a density of $2.0 \times 10^4$ cells/well (0.1 mL/well) in medium without doxycycline to induce pgRNA transcription and subsequent formation of HBV particles. The cells were incubated at 37° C. and 5% $CO_2$.

On day 1, medium was removed from each well, the test articles were diluted in culture medium without doxycycline and 100 μL was added to cell culture wells (9 concentrations, 4-fold dilution). For each plate, 6 untreated (merely DMSO) wells were included. The final concentration of DMSO in the culture medium was 2%. Each plate was prepared in duplicate (one for HBV DNA extraction, one for CellTiter-Glo 2.0 measurement). The cells were incubated at 37° C. and 5% $CO_2$ for 3 days.

On day 4, cell viability was assessed using CellTiter-Glo 2.0 and cell lysates were prepared for HBV DNA extraction and subsequent quantification by qPCR.

HBV DNA Quantification by qPCR

Medium was removed from each well and 100 μL of 0.33% NP-40 in $H_2O$ was added to each well. Plates were sealed, incubated at 4° C. for 5 mins, vortexed extensively and centrifuged briefly. Next, 35 μL of lysate was added to 65 μL QuickExtract DNA Extraction Solution (Epicentre) in a PCR plate for each well. PCR plate was incubated at 65° C. for 6 mins, 98° C. for 2 mins and finally cooled to 4° C. HBV DNA was then quantified by qPCR with HBV-specific primers and probes as specified in Table 1 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 1

HBV DNA Primers and Probe for HepG2.117 assay

| Items | Name | Sequence (5'→3') |
|---|---|---|
| HBV Primer | HBV-forward | GTGTCTGCGGCGTT TTATCA (SEQ ID NO: 1) |
| | HBV-reverse | GACAAACGGGCAAC ATACCTT (SEQ ID NO: 2) |
| HBV Probe | HBV probe | FAM/CCTCTKCAT/ ZEN/CCTGCTGCTAT GCCTCATC/ 3IABkFQ/ (SEQ ID NO: 3) |

A DNA standard was prepared by dilution of an IDT gBlock corresponding to the amplicon with concentrations ranging from $10^2$ to $10^8$ copies/input (i.e. per 4 μL) and used to generate a standard curve by plotting Cq values vs. HBV DNA standard concentration. The quantity of HBV DNA in each sample was determined by interpolating from the standard curve.

Cell Viability

Using the other plates, the cell viability was quantified by CellTiter-Glo 2.0 according to the manufacturer's manual. In brief, 100 μL of reagent solution was added to the culture plates and shaken for 2'. The plates were incubated at room temperature for 10 min and luminescence signal was subsequently measured on a VarioSkan Lux (ThermoFisher) plate reader.

Data Analysis

Cell viability was calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir was required due to the excellent dynamic window of this assay. The $CC_{50}$, $EC_{50}$ and $EC_{90}$ values were determined by dose-response curves fitted by GraphPad Prism using "log (agonist) vs. response—Variable slope".

As shown in Table 2, compounds of Formula (I) are active against HBV, where 'A' indicates an $EC_{50} \leq 50$ nM, 'B' indicates an $EC_{50} > 50$ nM and $\leq 500$ nM, 'C' indicates an $EC_{50} > 500$ nM and $\leq 5000$ nM, and 'D' indicates an $EC_{50} > 5000$ nM. Cell viability assessments indicated a large window between effective antiviral concentrations and cytotoxic compound concentrations.

TABLE 2

| Compound | HepG2.117 $EC_{50}$ |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | B |
| 14 | A |
| 15 | A |
| 16 | A |
| 17 | A |
| 18 | A |
| 19 | B |
| 20 | A |
| 21a | A |
| 21b | B |
| 22a | A |
| 22b | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37a | A |
| 37b | B |
| 38a | A |
| 38b | A |
| 39a | A |
| 39b | B |
| 39a | A |
| 39b | B |
| 40a | A |
| 40b | B |
| 41a | A |
| 41b | B |
| 42 | A |
| 43a | A |
| 43b | A |
| 44a | A |
| 44b | A |
| 45a | A |
| 45b | B |
| 46a | A |
| 46b | B |
| 47a | A |
| 47b | A |
| 48a | A |
| 48b | B |
| 49a | A |
| 49b | B |
| 50a | A |
| 50b | B |
| 51a | A |
| 51b | C |
| 52a | A |
| 52b | B |
| 53a | A |
| 53b | B |
| 54a | A |
| 54b | B |
| 55a | A |
| 55b | B |
| 56a | A |
| 56b | B |
| 57a | A |
| 57b | B |
| 58a | A |
| 58b | A |
| 59a | A |
| 59b | B |
| 60a | A |
| 60b | B |
| 61a | A |
| 61b | B |
| 62a | A |
| 62b | B |
| 63a | A |
| 63b | C |
| 64a | A |
| 64b | B |
| 65a | A |
| 65b | C |
| 66a | A |
| 66b | B |
| 67a | A |
| 67b | B |
| 68a | A |
| 68b | B |
| 69a | A |
| 69b | A |
| 70a | B |
| 70b | C |
| 71a | C |
| 71b | D |
| 72b | A |
| 72a | A |
| 73b | A |
| 73a | A |
| 74a | A |
| 74b | B |
| 75a | A |
| 75b | B |
| 76a | A |
| 76b | B |
| 77a | A |
| 77b | A |
| 78a | A |
| 78b | B |
| 79a | A |
| 79b | B |
| 80a | A |
| 80b | B |
| 81a | A |
| 81b | B |
| 82a | A |

TABLE 2-continued

| Compound | HepG2.117 EC$_{50}$ |
|---|---|
| 82b | B |
| 83a | A |
| 83b | B |
| 84a | A |
| 84b | A |
| 85a | A |
| 85b | A |
| 86a | A |
| 86b | B |
| 87 | B |
| 88a | A |
| 88b | A |
| 89a | A |
| 89b | B |
| 90 | D |
| 91 | D |
| 92a | A |
| 92b | D |
| 93a | A |
| 93b | A |
| 94a | A |
| 94b | B |
| 95a | A |
| 95b | B |
| 96 | C |
| 97 | D |
| 98a | A |
| 98b | B |
| 99a | A |
| 99b | C |

TABLE 2-continued

| Compound | HepG2.117 EC$_{50}$ |
|---|---|
| 100a | A |
| 100b | C |
| 101 | B |
| 102a | A |
| 102b | B |
| 103 | D |
| 104a | A |
| 104b | A |
| 105a | A |
| 105b | B |
| 106 | A |
| 107 | D |
| 108a | A |
| 108b | B |
| 109a | B |
| 109b | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present application.

What is claimed is:

1. A compound of Formula (I), or a pharmaceutically acceptable salt thereof, having the structure:

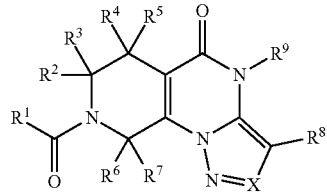

wherein:

X is CH, CD, CF, C(CH$_3$) or N;

$R^1$ is a 3,4-substituted phenyl substituted with two moieties independently selected from the group consisting of —Cl, —Br, —CHF$_2$, —CF$_3$, —CH$_3$ and —CN;

$R^2$ and $R^3$ are independently selected from the group consisting of hydrogen, an unsubstituted C$_{1-4}$ alkyl, an unsubstituted C$_{1-4}$ haloalkyl, an optionally substituted C$_{3-4}$ cycloalkyl, an optionally substituted aryl, an optionally substituted heteroaryl, an optionally substituted heterocyclyl, an optionally substituted aryl(C$_{1-4}$ alkyl), an optionally substituted heteroaryl(C$_{1-4}$ alkyl) and an optionally substituted heterocyclyl(C$_{1-4}$ alkyl);

$R^4$ and $R^5$ are independently selected from the group consisting of hydrogen, an unsubstituted C$_{1-4}$ alkyl, an unsubstituted C$_{1-4}$ haloalkyl, an optionally substituted aryl, an optionally substituted heteroaryl, an optionally substituted heterocyclyl, an optionally substituted aryl (C$_{1-4}$ alkyl), an optionally substituted heteroaryl(C$_{1-4}$ alkyl) and an optionally substituted heterocyclyl(C$_{1-4}$ alkyl);

$R^6$ and $R^7$ are independently selected from the group consisting of hydrogen, an unsubstituted C$_{1-4}$ alkyl and an unsubstituted C$_{1-4}$ haloalkyl;

$R^8$ is —CHR$^{8a}$R$^{8b}$;

$R^{8a}$ is hydrogen or —CH$_3$;

$R^{8b}$ is selected from the group consisting of an unsubstituted C$_{1-4}$ alkyl, an unsubstituted C$_{2-4}$ alkenyl, an unsubstituted C$_{2-4}$ alkynyl, an optionally substituted monocyclic C$_{3-6}$ cycloalkyl, an optionally substituted phenyl, an optionally substituted monocyclic heteroaryl and an optionally substituted monocyclic heterocyclyl; and $R^9$ is a substituted aryl, an optionally substituted heteroaryl or an optionally substituted heterocyclyl; and provided that be a compound of Formula (I), or a pharmaceutically acceptable salt thereof, cannot be selected from the group consisting of:

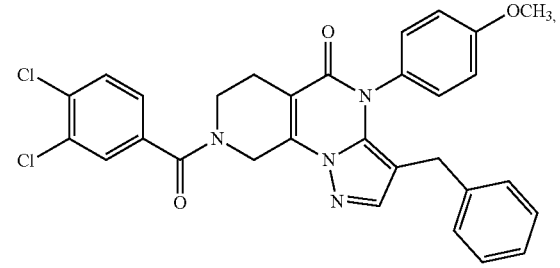

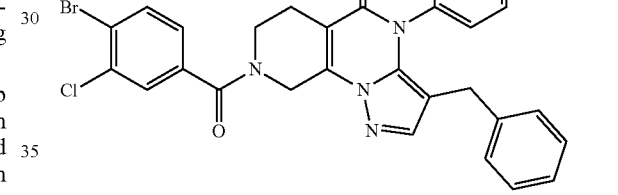

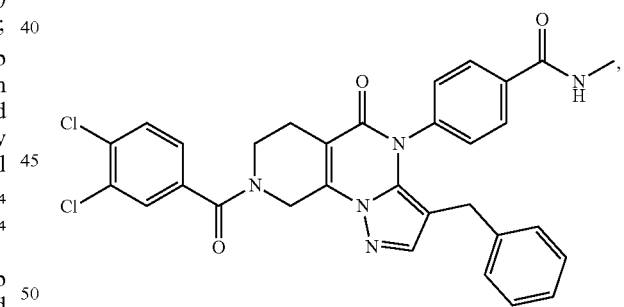

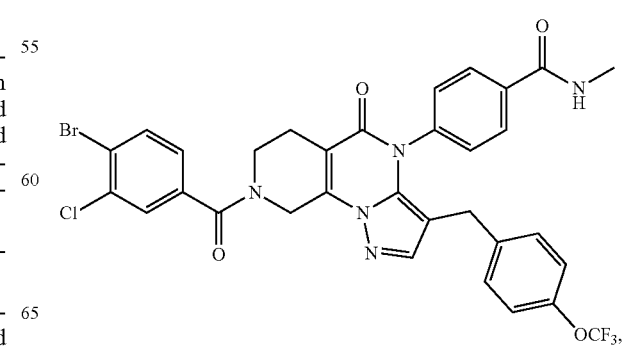

341
-continued
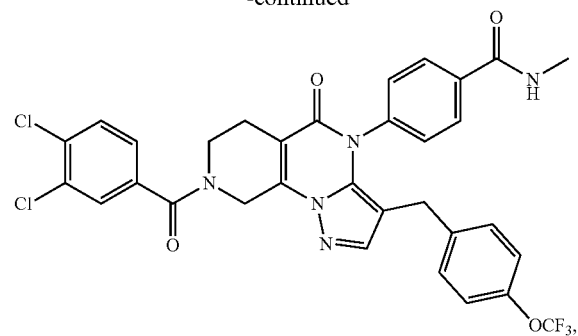
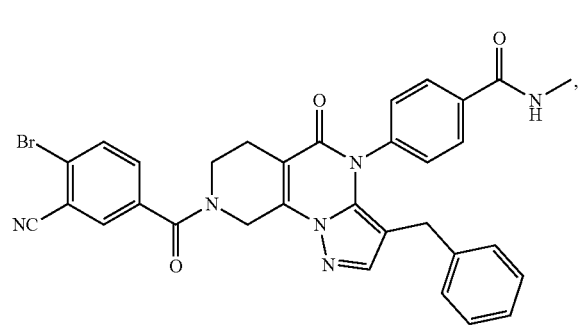
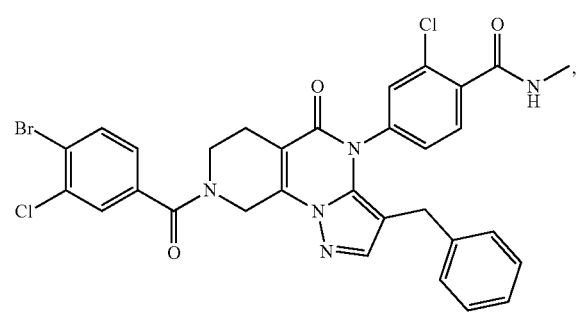
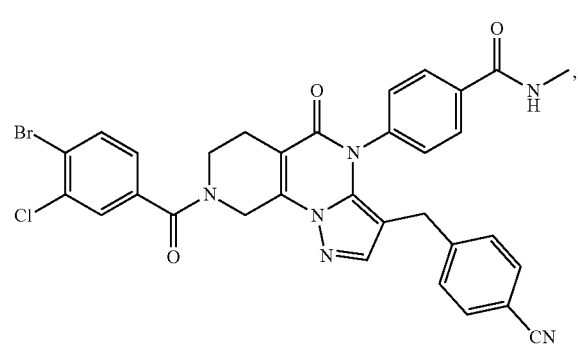
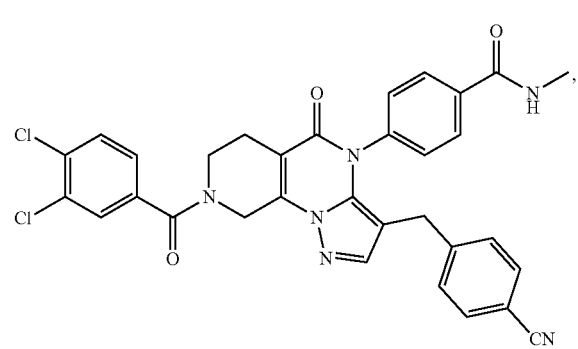
342
-continued
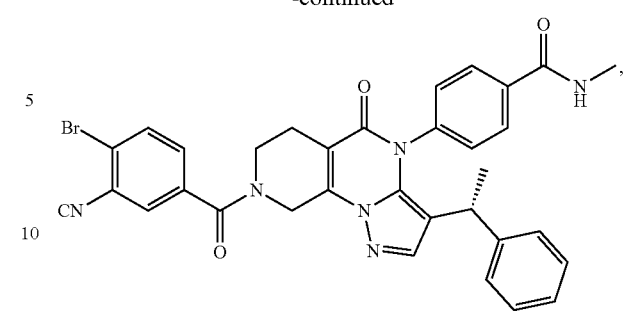
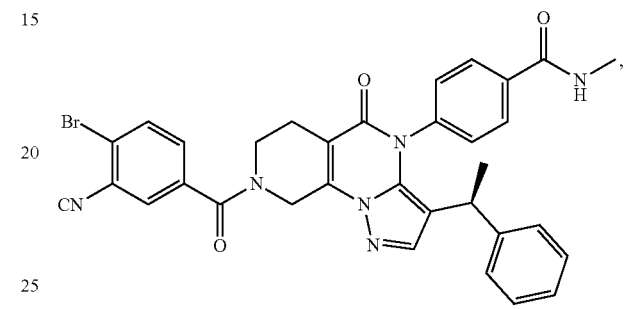
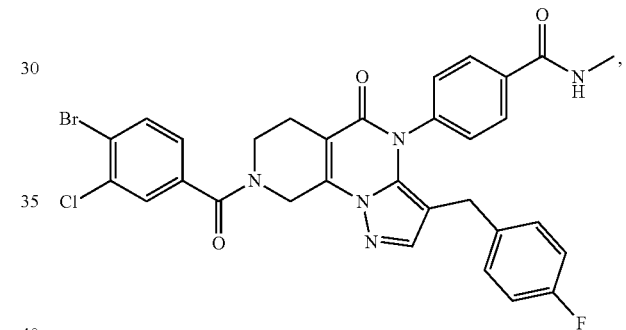
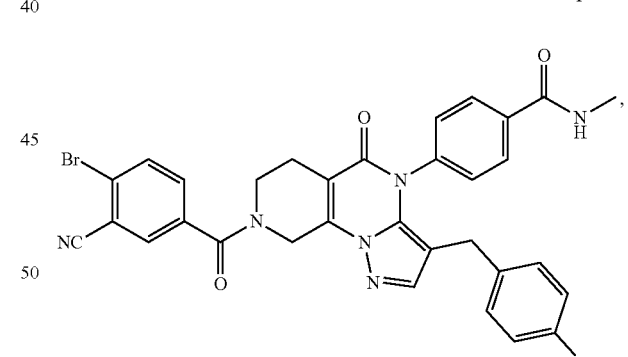
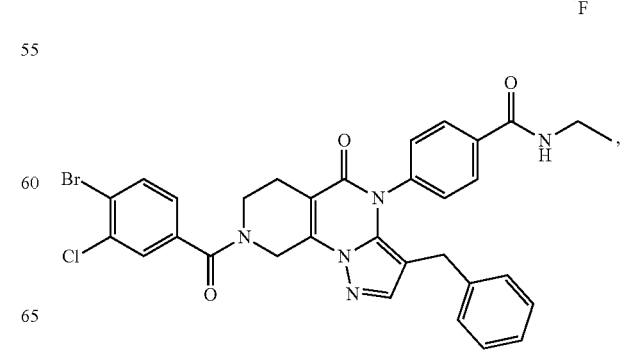

343
-continued
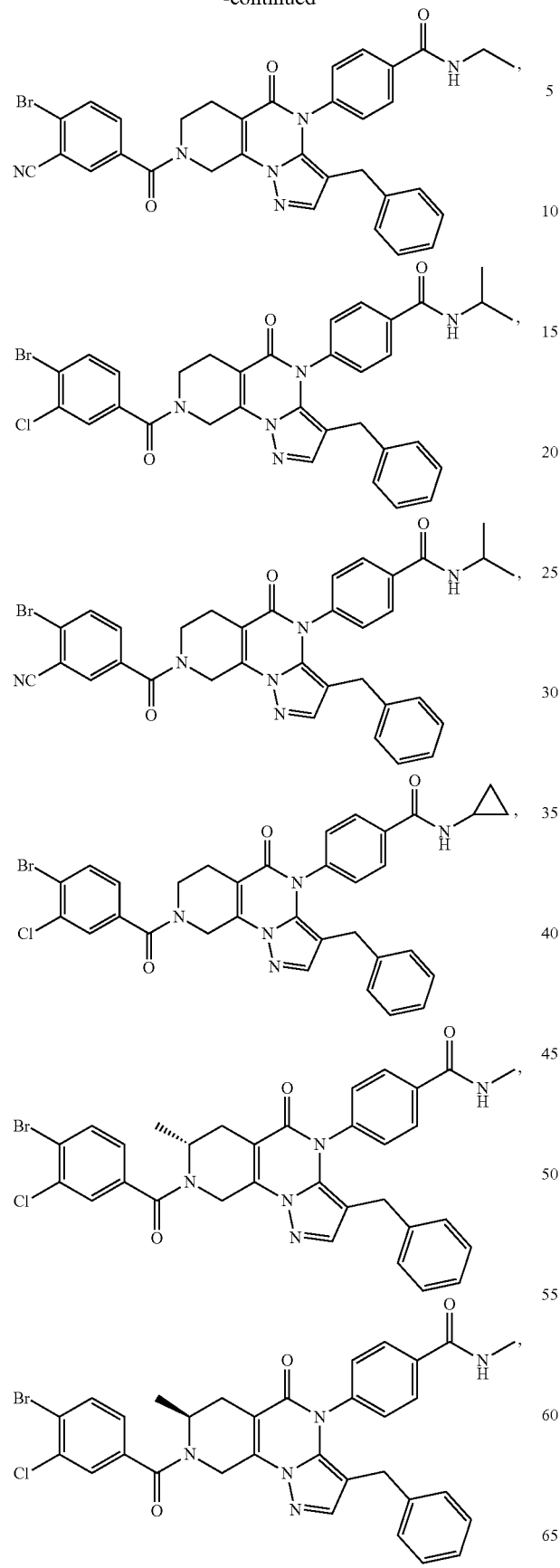
344
-continued
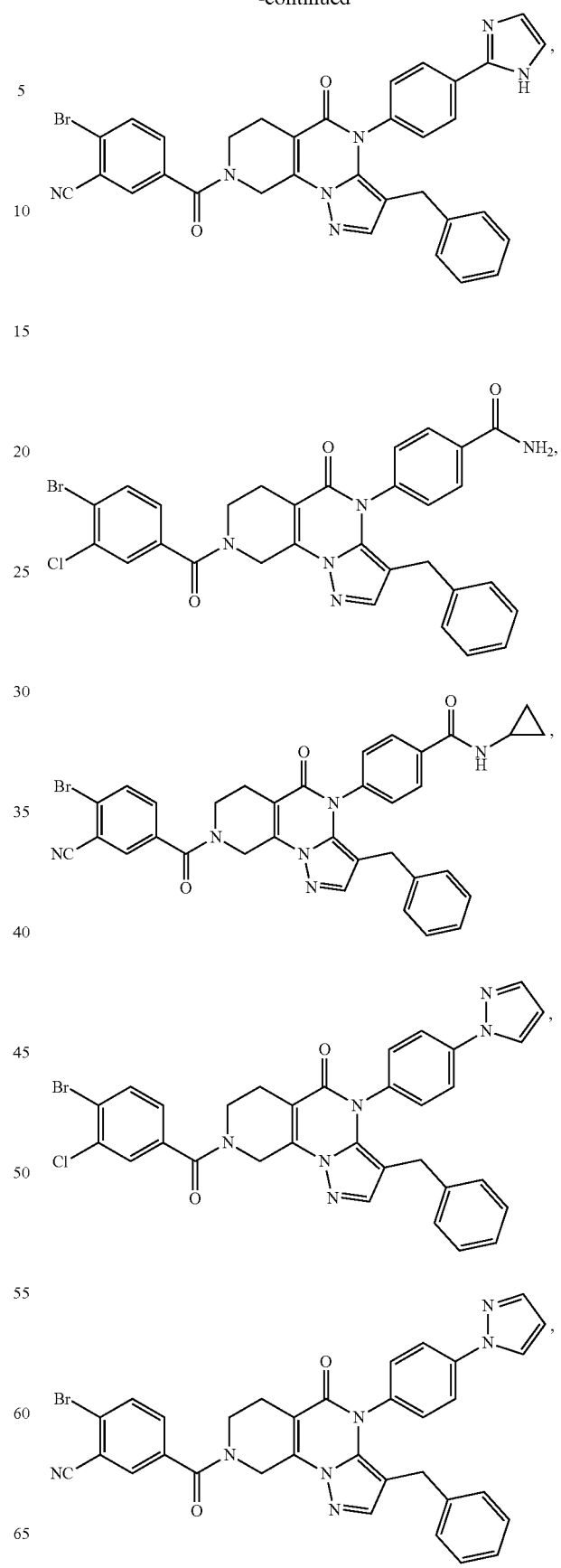

345
-continued
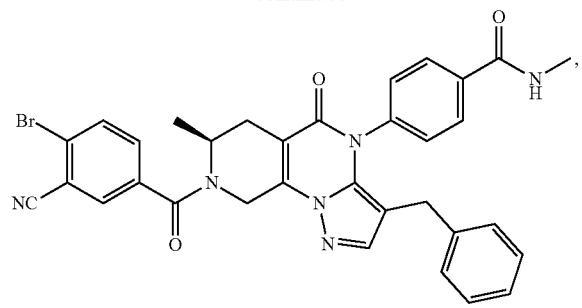
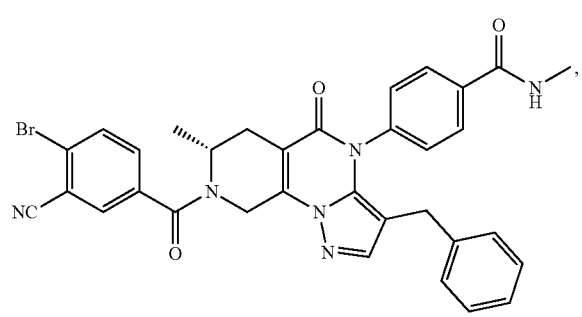
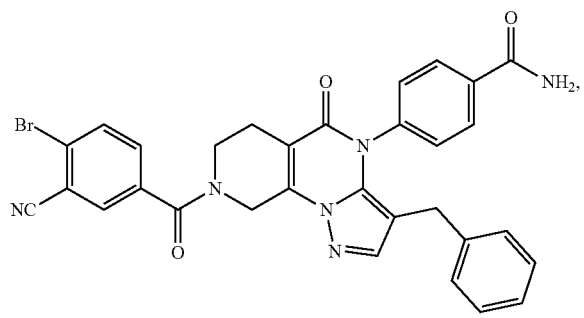
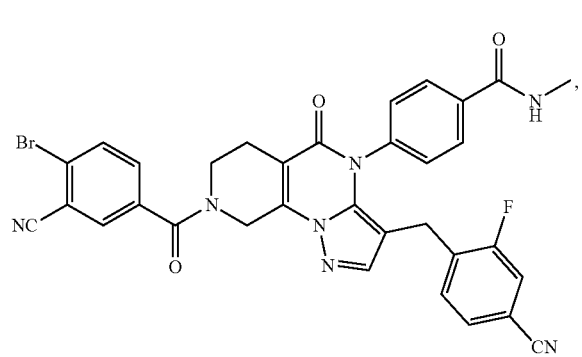
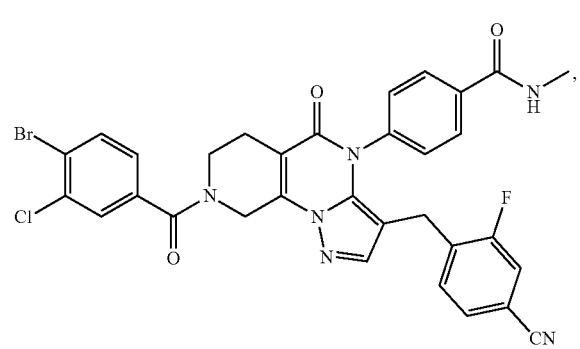
346
-continued
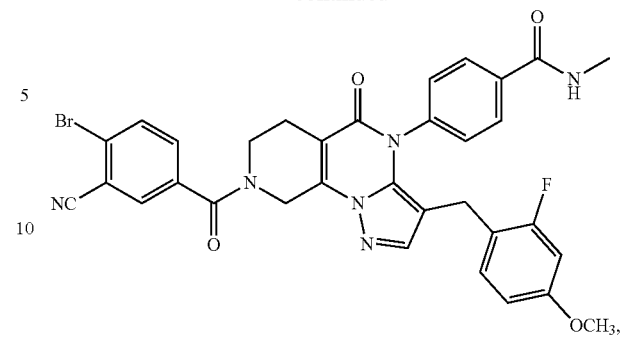
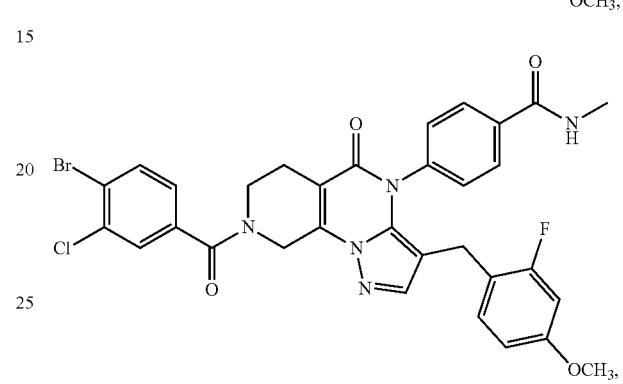
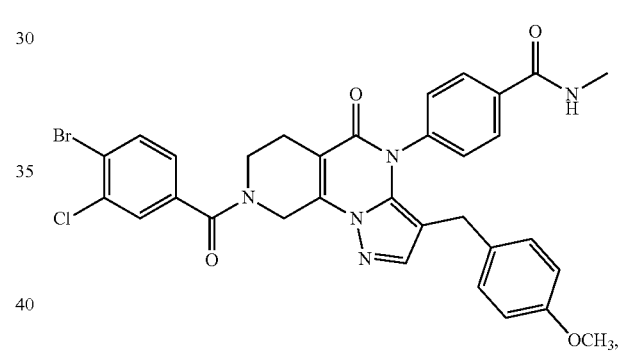
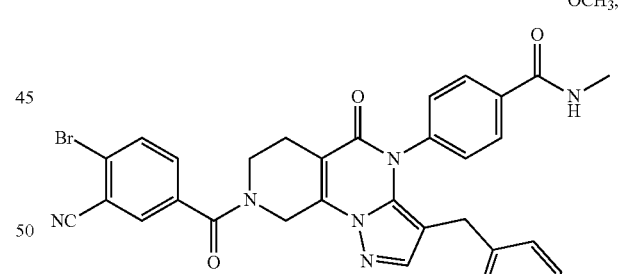
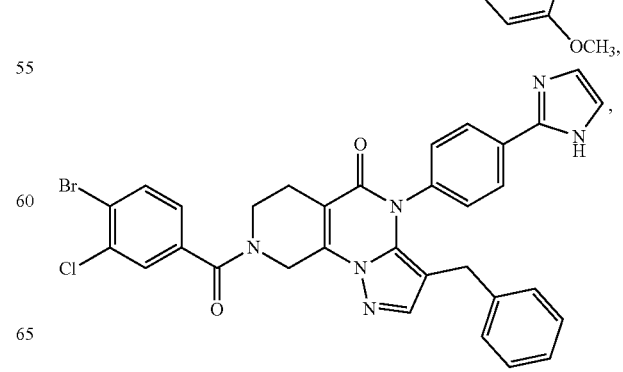

347
-continued
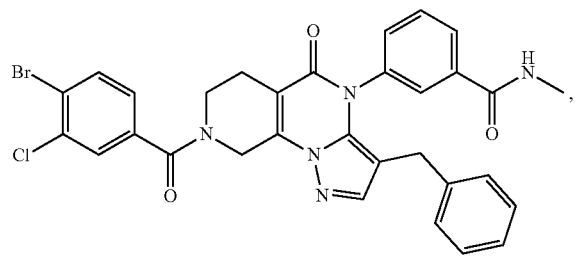
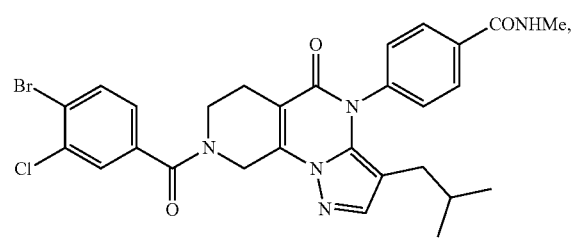
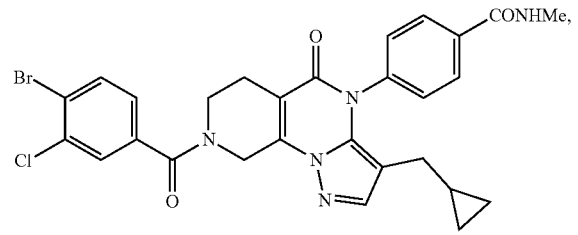
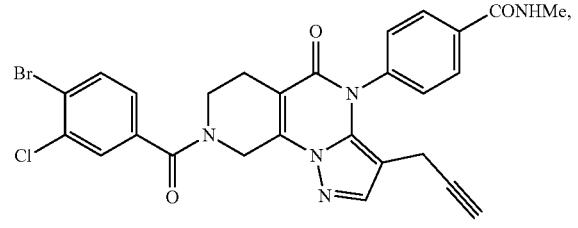
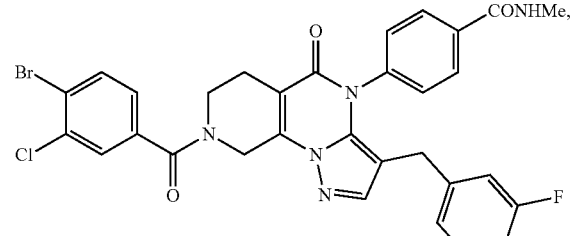
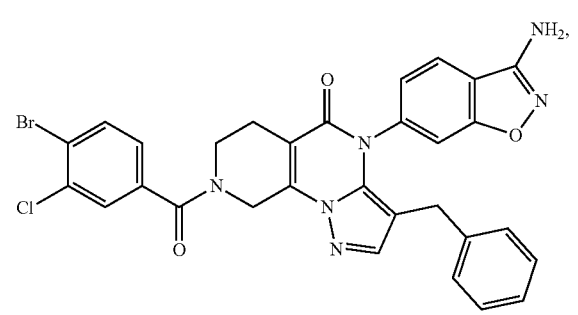
348
-continued
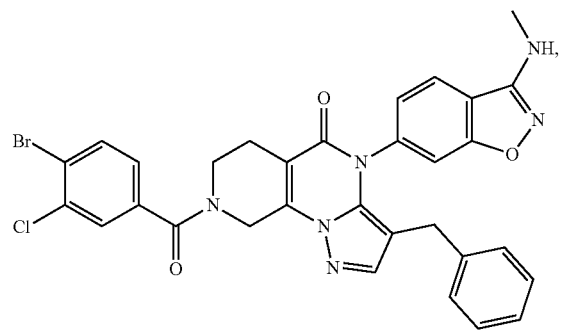
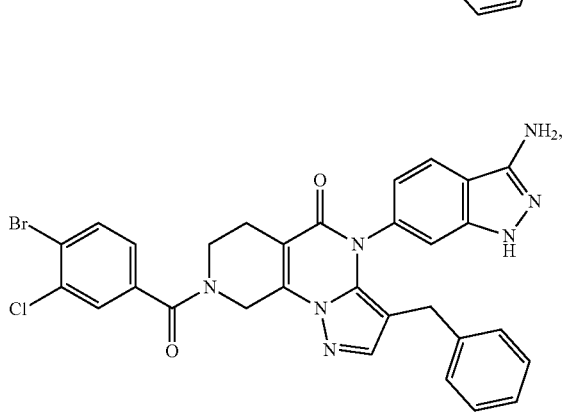
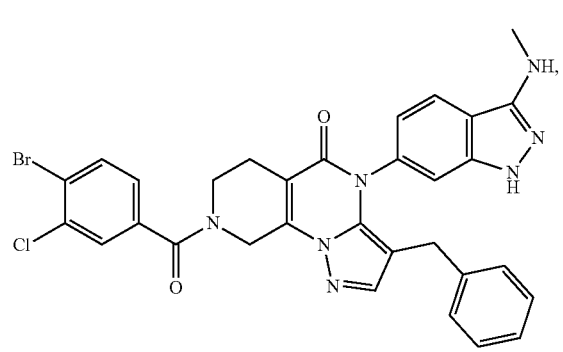
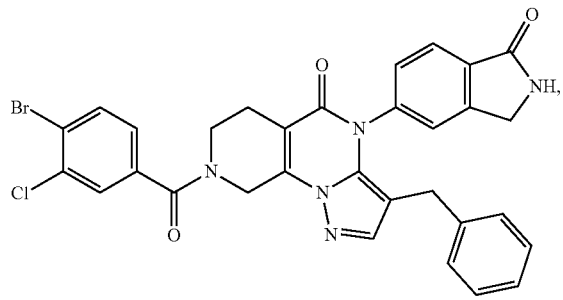
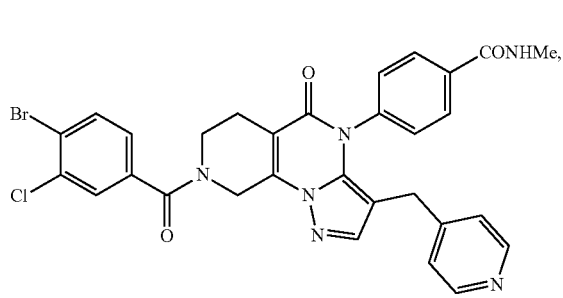

-continued

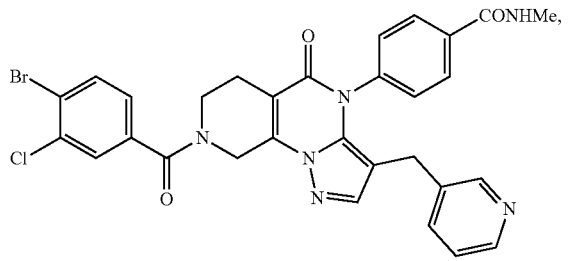

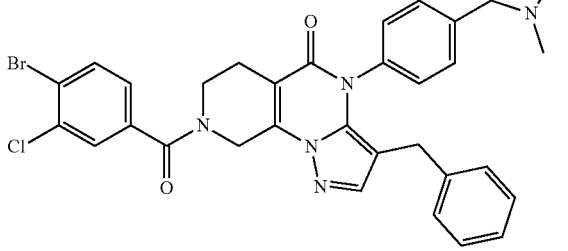

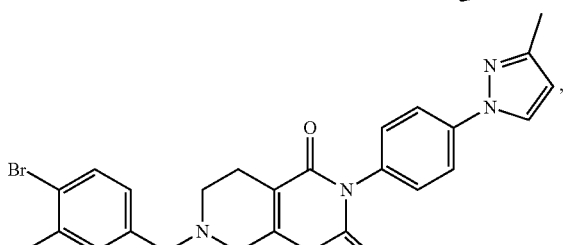

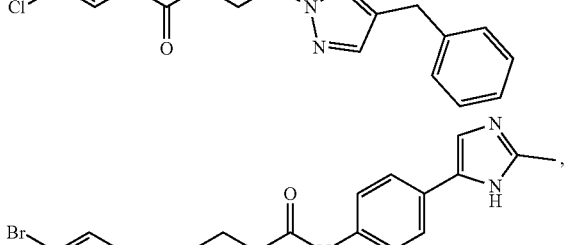

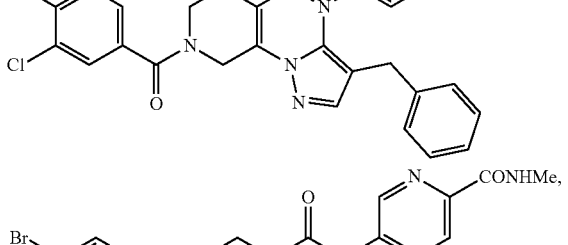

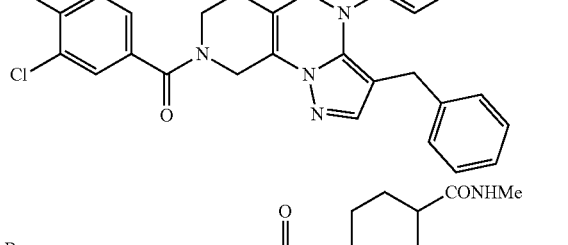

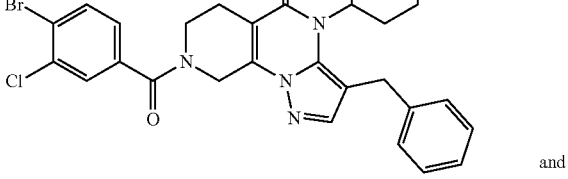

and

-continued

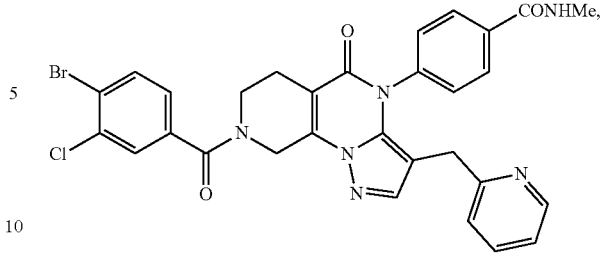

or a pharmaceutically acceptable salt of any of the foregoing.

2. The compound of claim 1, wherein $R^1$ is

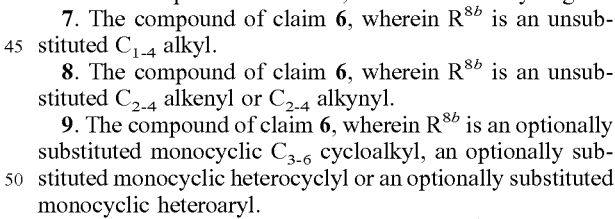

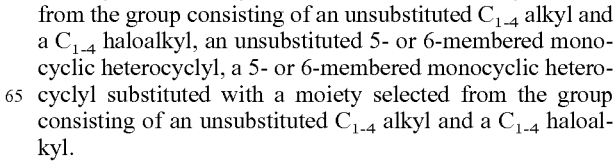

3. The compound of claim 2, wherein $R^2$ is an unsubstituted $C_{1-4}$ alkyl; $R^3$ is hydrogen; $R^4$ is hydrogen; $R^5$ is hydrogen; $R^6$ is hydrogen; and $R^7$ is hydrogen.

4. The compound of claim 2, wherein $R^2$ is hydrogen; $R^3$ is hydrogen; $R^4$ is hydrogen; $R^5$ is hydrogen; $R^6$ is hydrogen; and $R^7$ is hydrogen.

5. The compound of claim 3, wherein the unsubstituted $C_{1-4}$ alkyl is methyl.

6. The compound of claim 2, wherein $R^{8a}$ is hydrogen.

7. The compound of claim 6, wherein $R^{8b}$ is an unsubstituted $C_{1-4}$ alkyl.

8. The compound of claim 6, wherein $R^{8b}$ is an unsubstituted $C_{2-4}$ alkenyl or $C_{2-4}$ alkynyl.

9. The compound of claim 6, wherein $R^{8b}$ is an optionally substituted monocyclic $C_{3-6}$ cycloalkyl, an optionally substituted monocyclic heterocyclyl or an optionally substituted monocyclic heteroaryl.

10. The compound of claim 6, wherein $R^{8b}$ is an optionally substituted phenyl.

11. The compound of claim 2, wherein $R^9$ is a substituted phenyl.

12. The compound of claim 11, wherein $R^9$ is a substituted phenyl, wherein the phenyl is substituted with one or more substituents independently selected from the group consisting of —C(=O)NHCH$_3$, halogen, an unsubstituted 5- or 6-membered monocyclic heteroaryl, a 5- or 6-membered monocyclic heteroaryl substituted with a moiety selected from the group consisting of an unsubstituted $C_{1-4}$ alkyl and a $C_{1-4}$ haloalkyl, an unsubstituted 5- or 6-membered monocyclic heterocyclyl, a 5- or 6-membered monocyclic heterocyclyl substituted with a moiety selected from the group consisting of an unsubstituted $C_{1-4}$ alkyl and a $C_{1-4}$ haloalkyl.

13. The compound of claim 2, wherein $R^9$ is an optionally substituted heteroaryl.
14. The compound of claim 13, wherein $R^9$ is an optionally substituted bicyclic heteroaryl.
15. The compound of claim 2, wherein X is CH.
16. The compound of claim 1, wherein the compound of Formula (I), or a pharmaceutically acceptable salt thereof, is selected from the group consisting of:
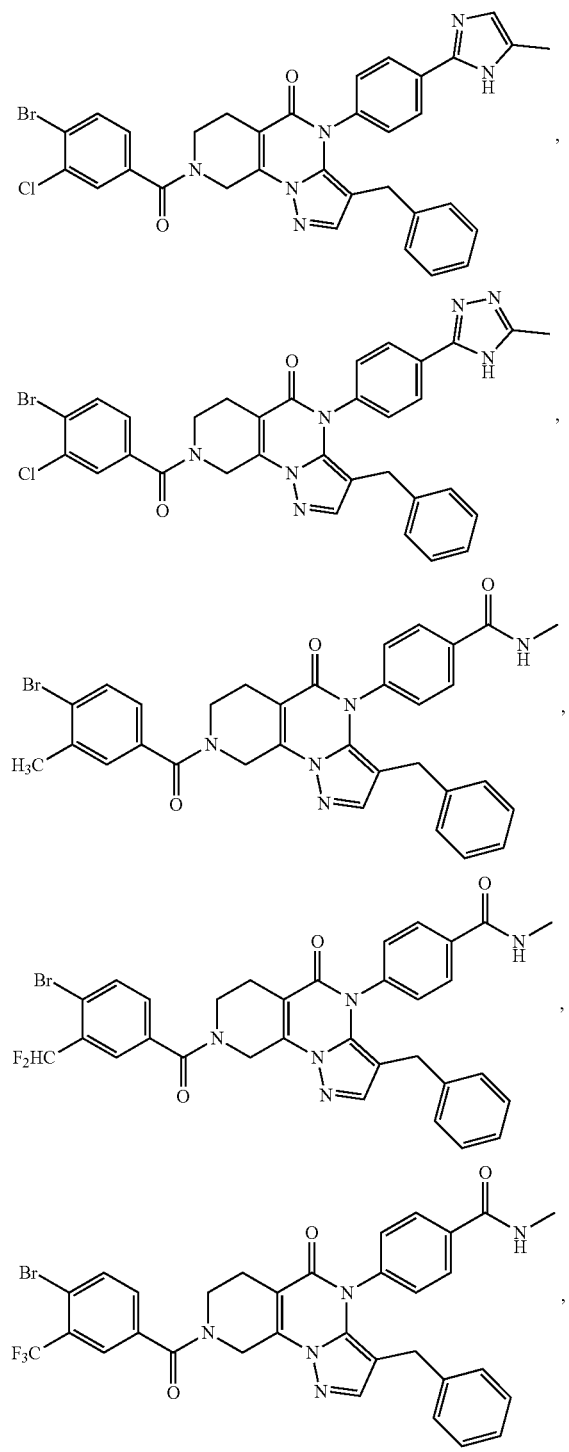
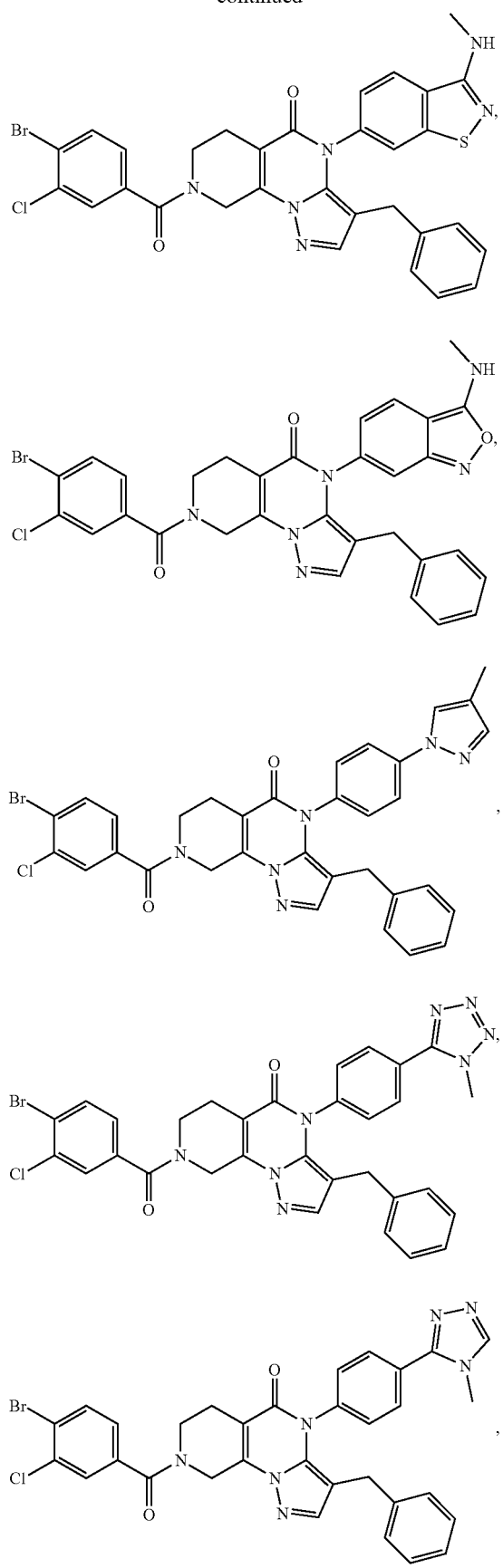

353
-continued
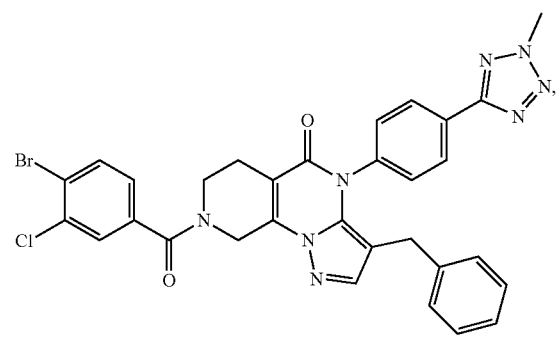
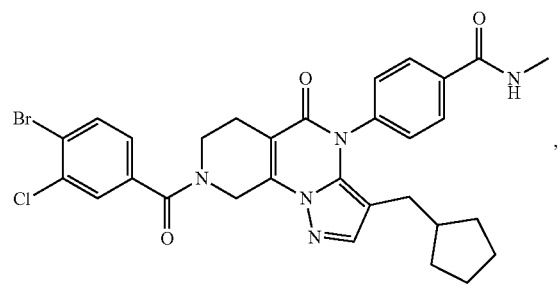
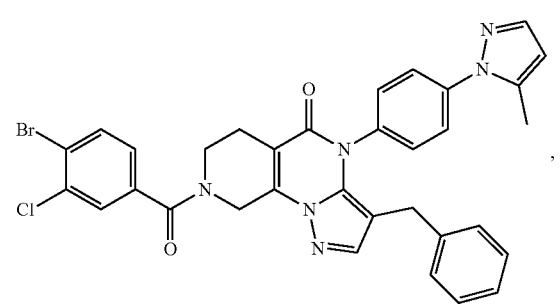
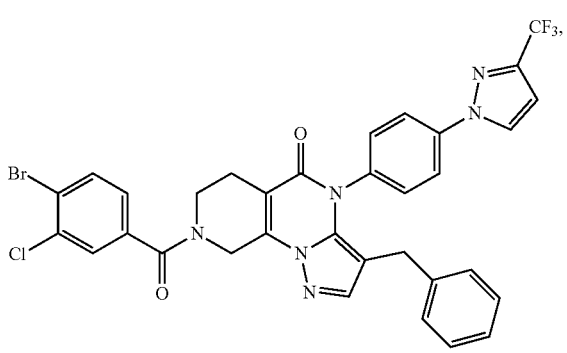
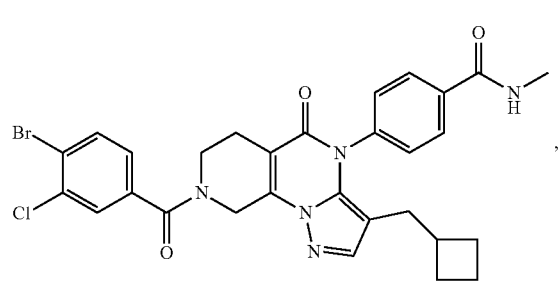
354
-continued
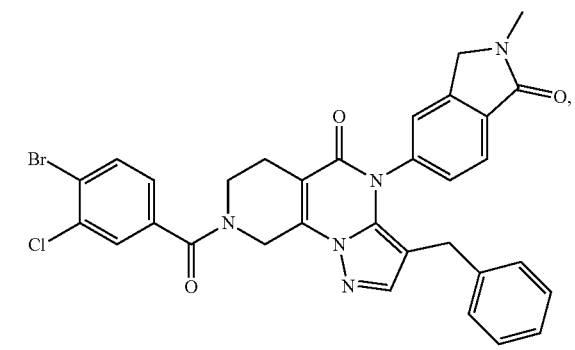
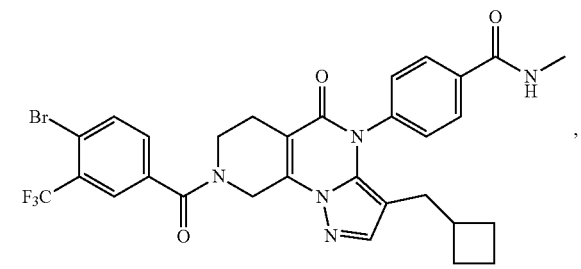
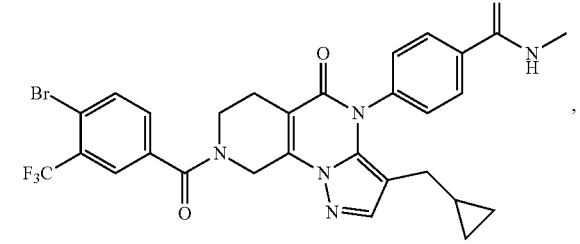
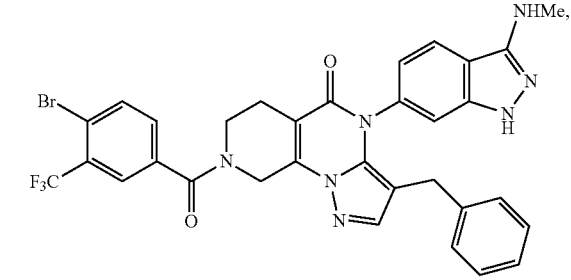
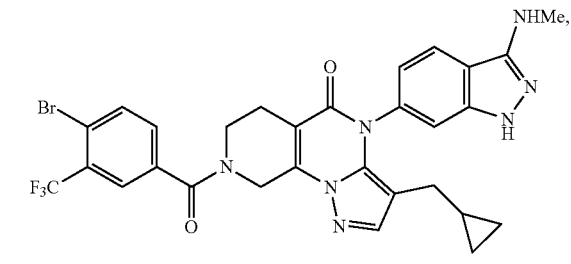
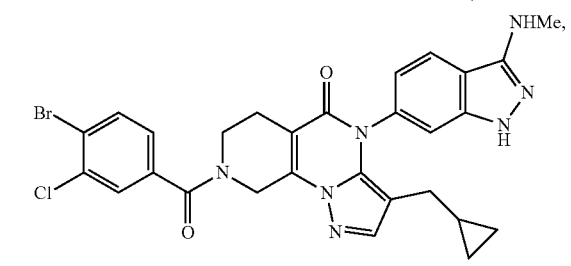

355
-continued
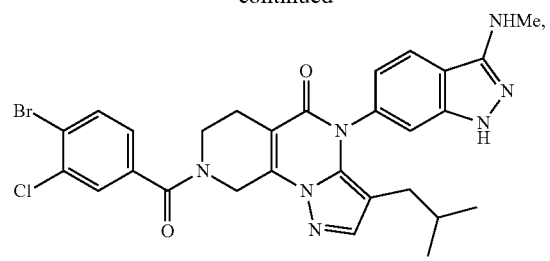
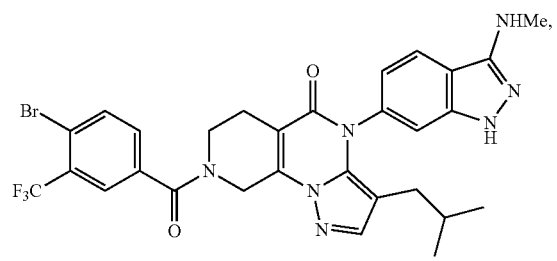
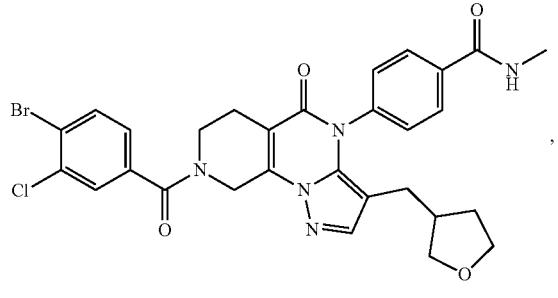
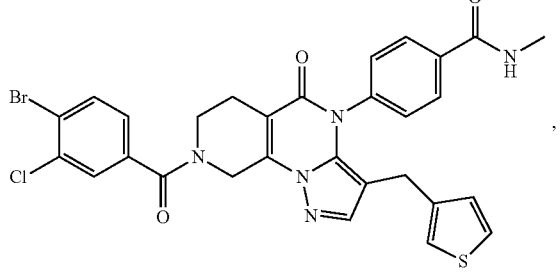
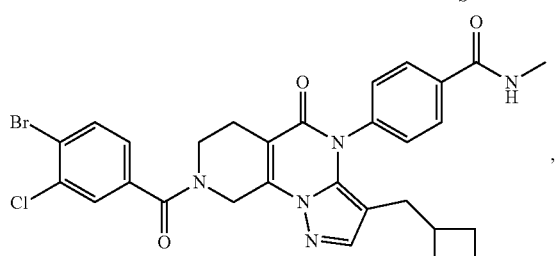
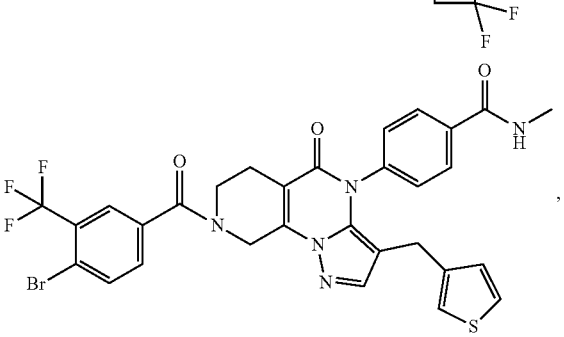
356
-continued
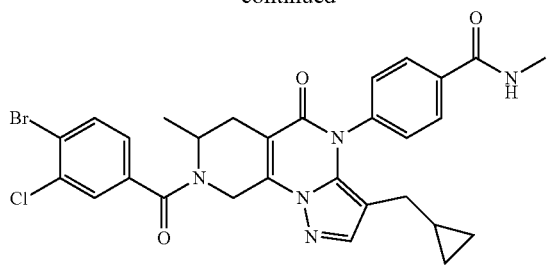
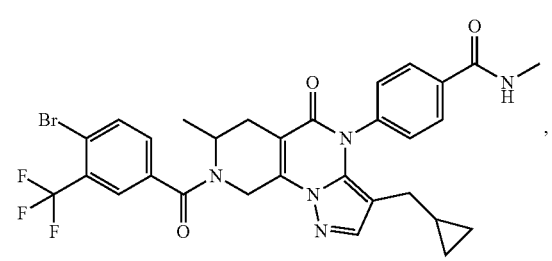
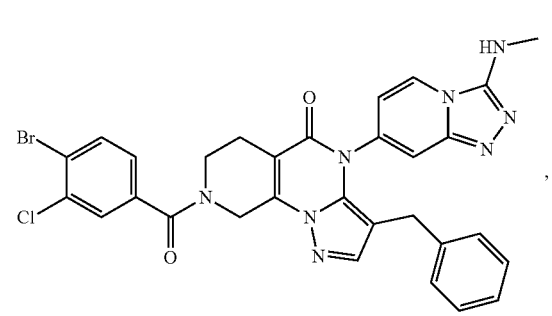
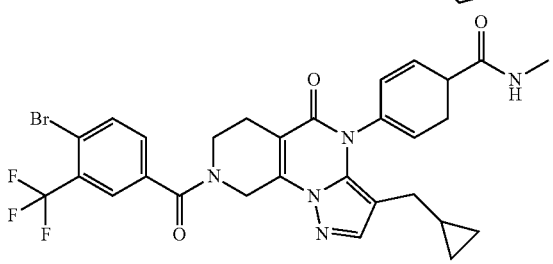
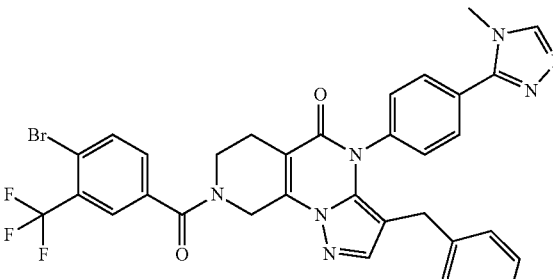
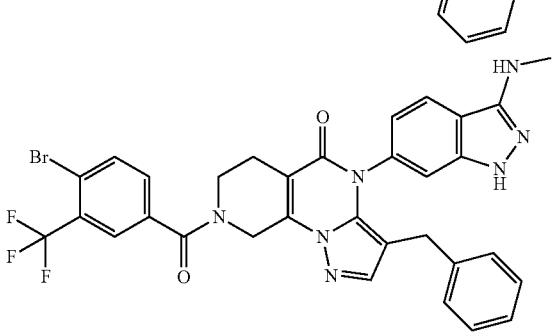

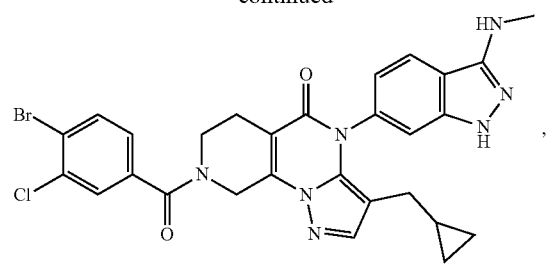
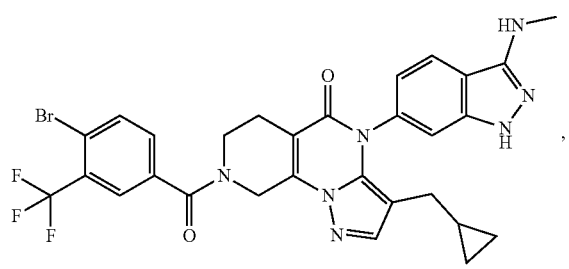
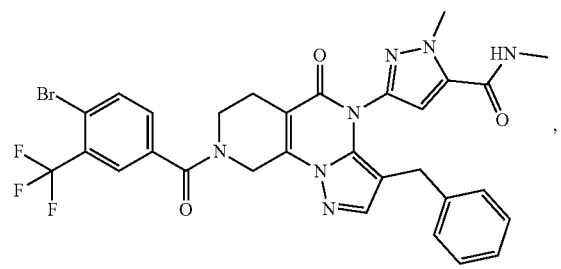
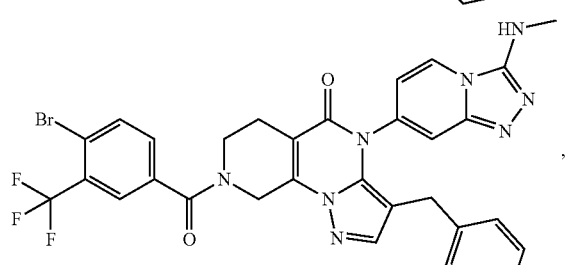
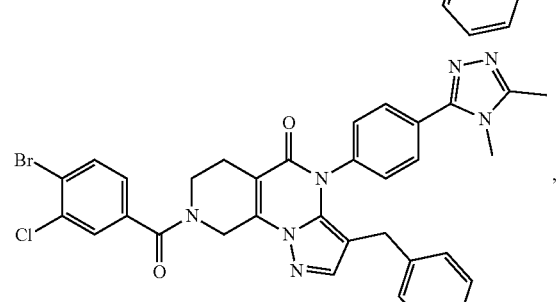
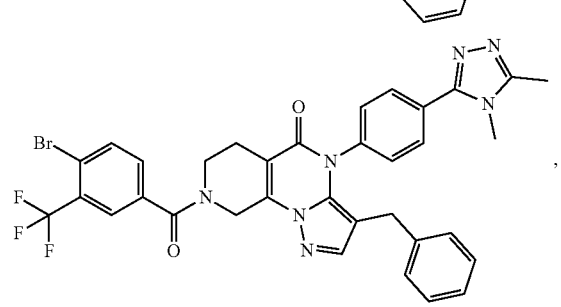
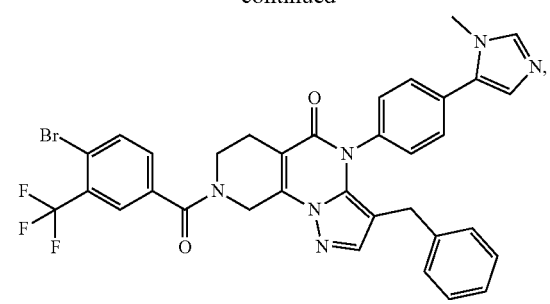
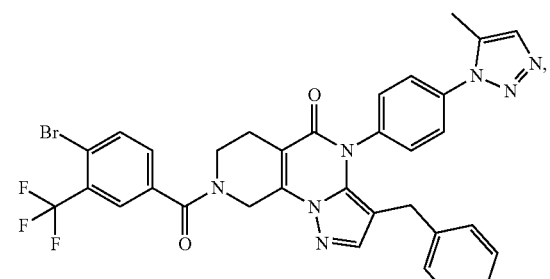
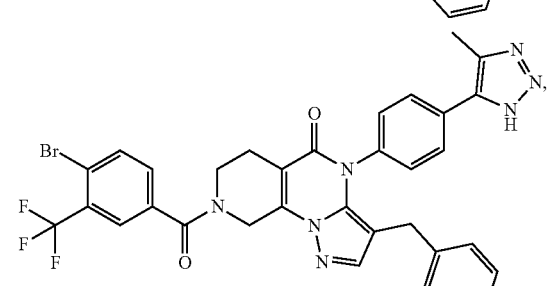
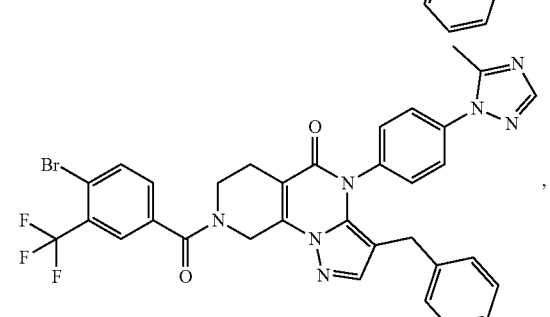
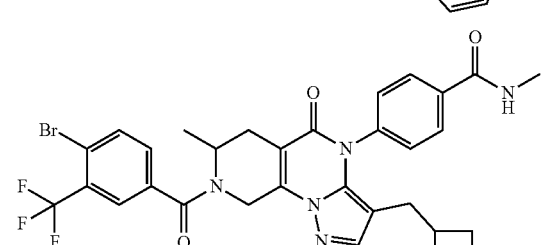
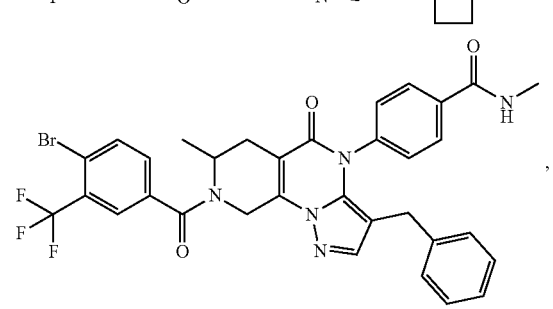

359
-continued
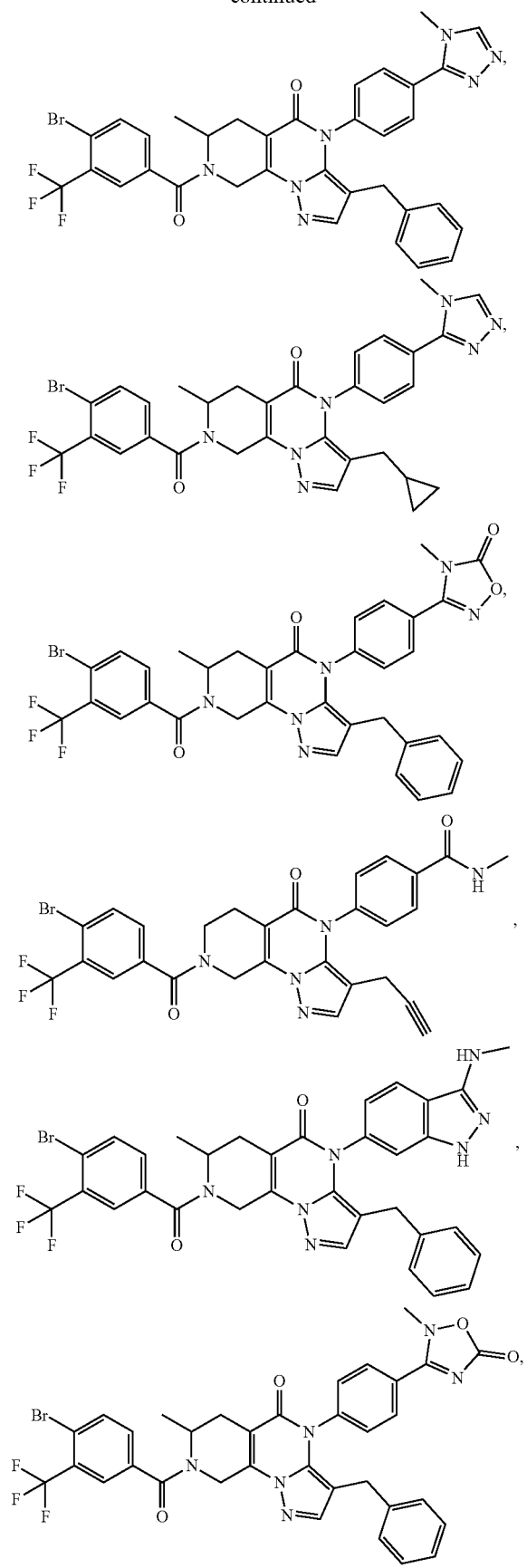
360
-continued
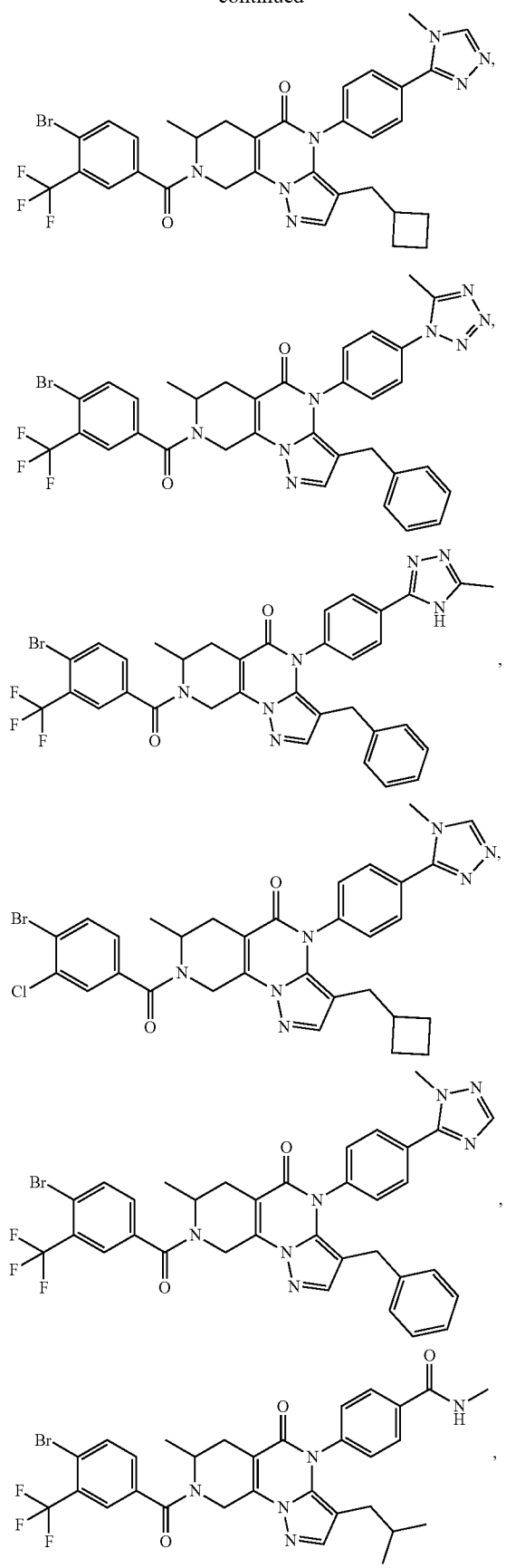

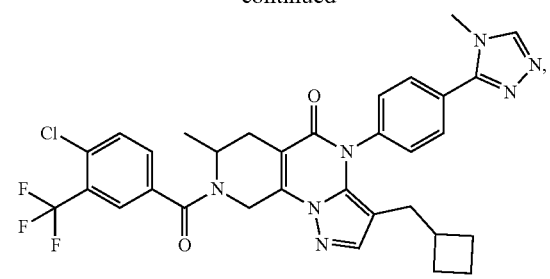
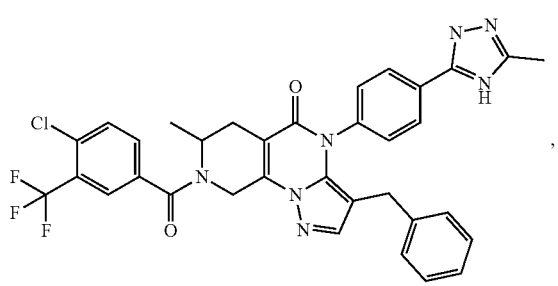
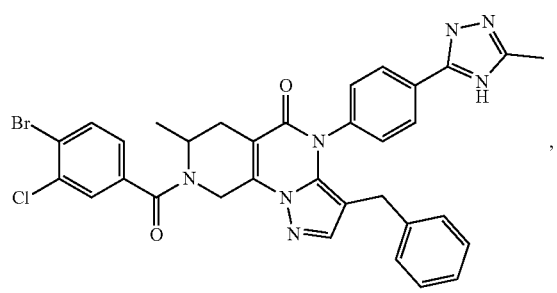
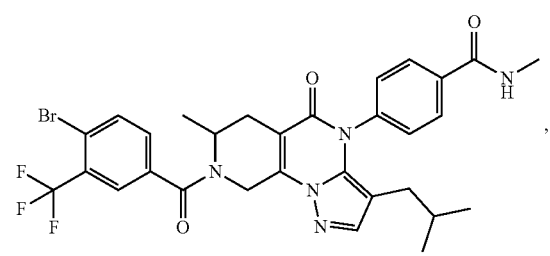
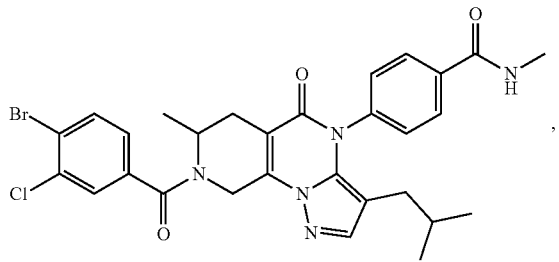
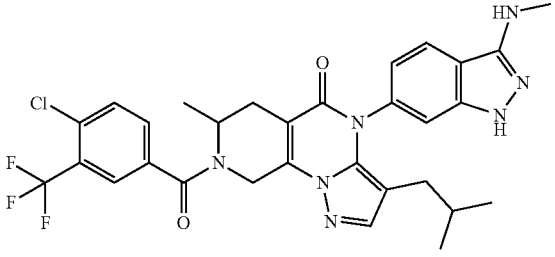
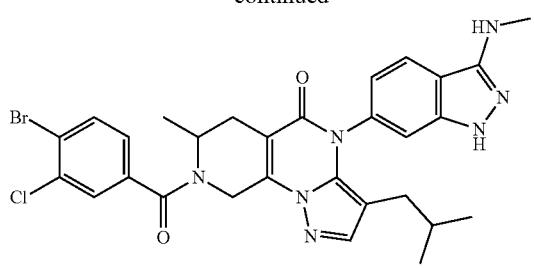
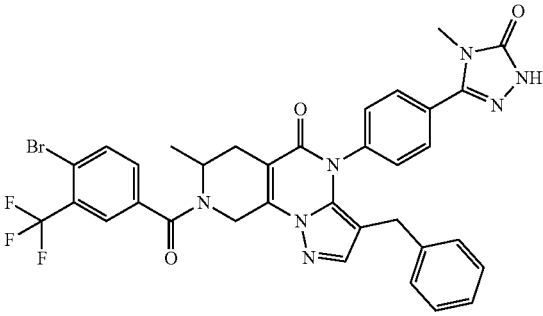
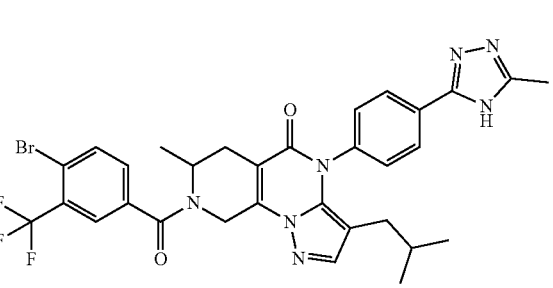
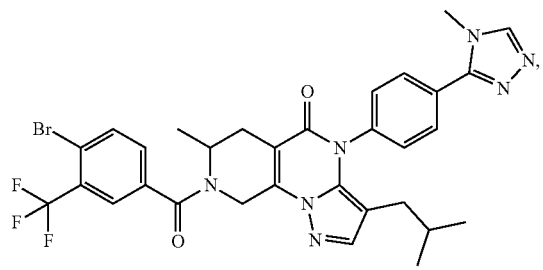
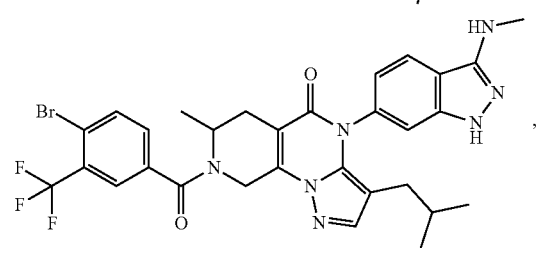
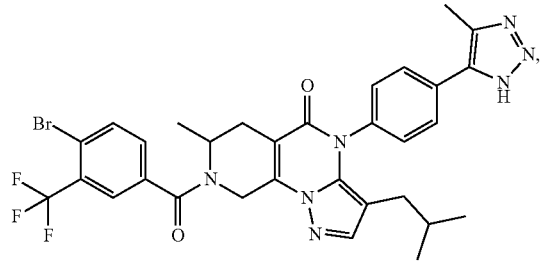

363
-continued
364
-continued
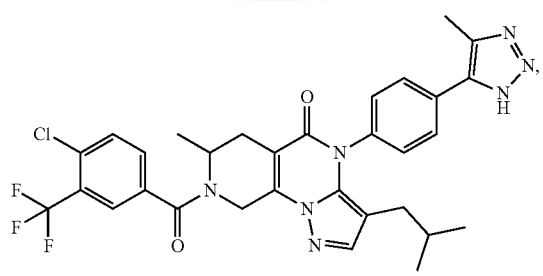
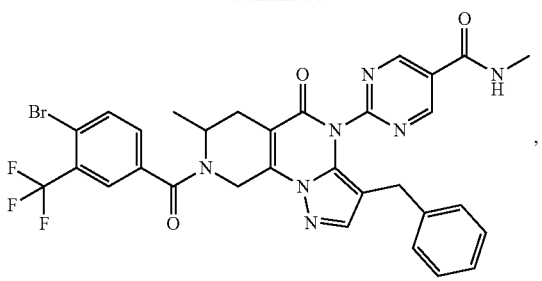

365
-continued
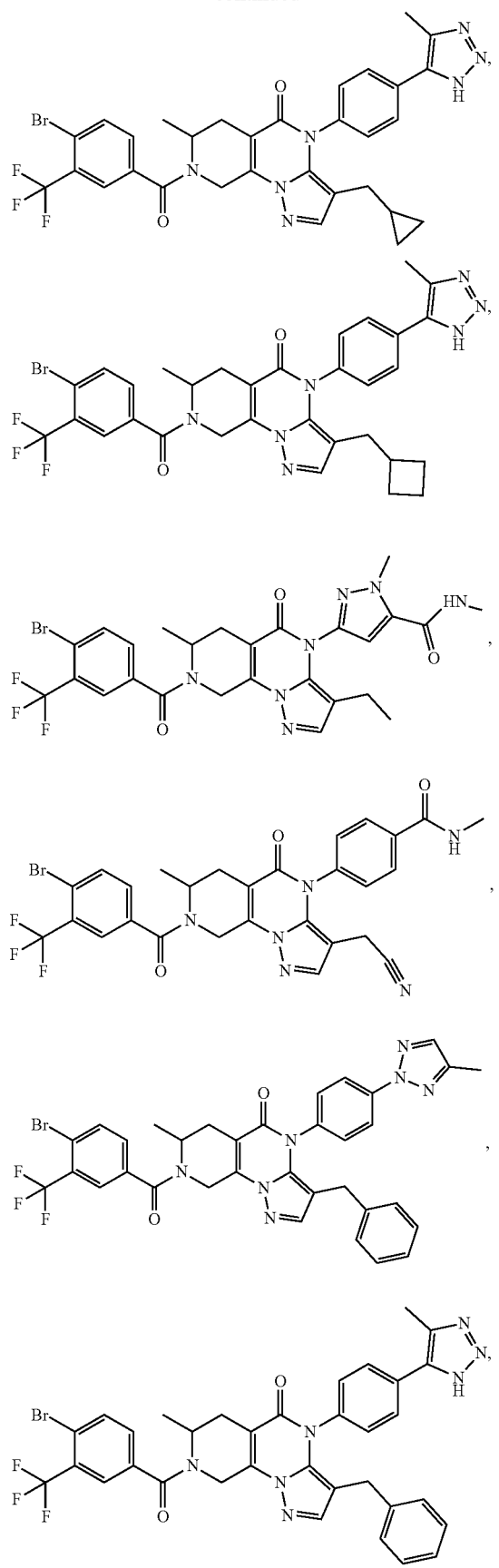
366
-continued
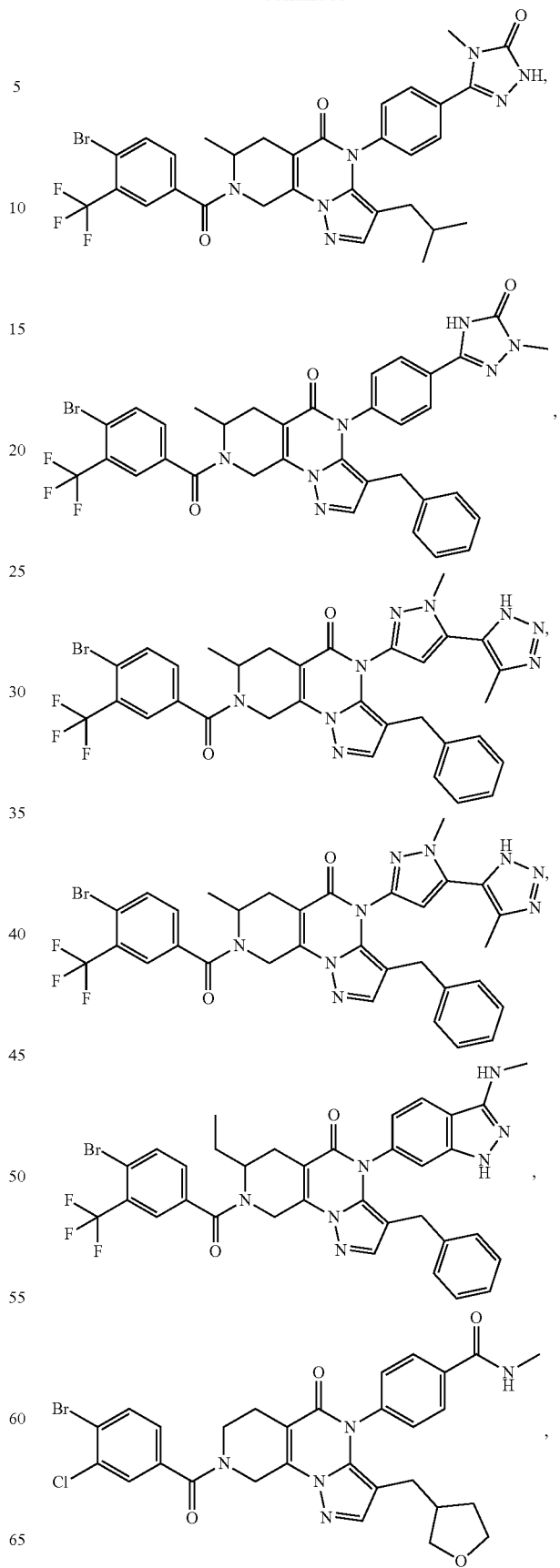

367
-continued
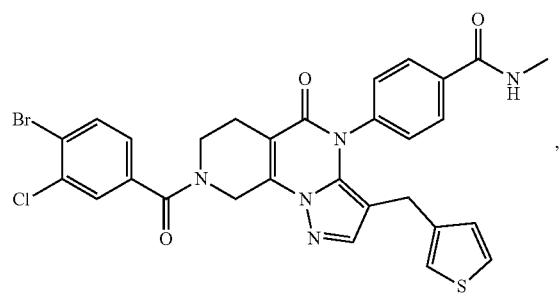,
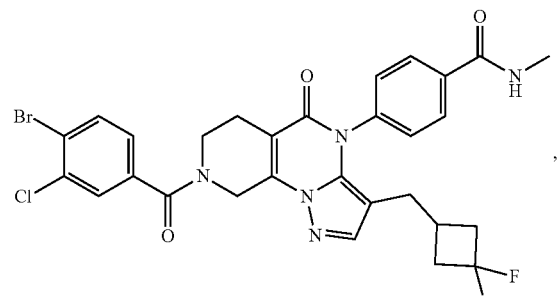,
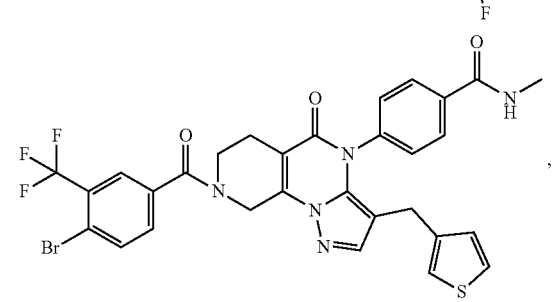,
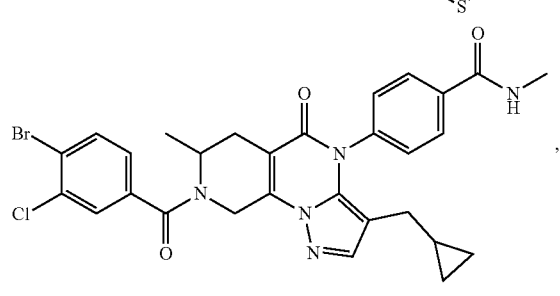,
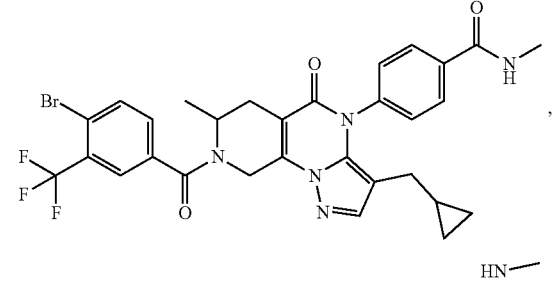,
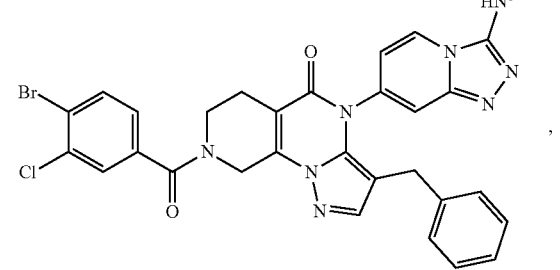,
368
-continued
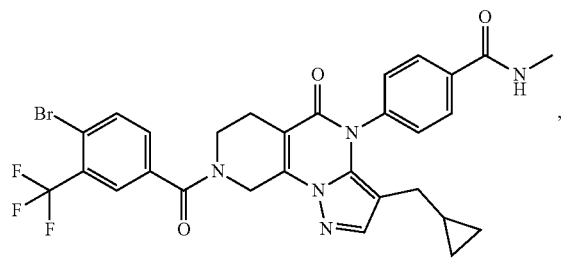,
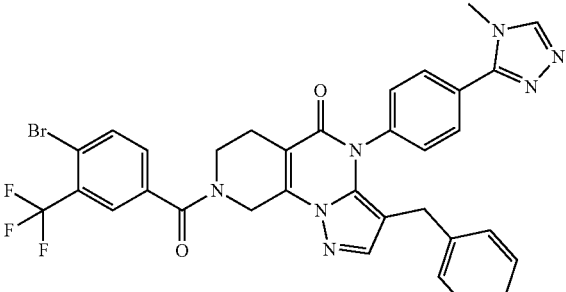,
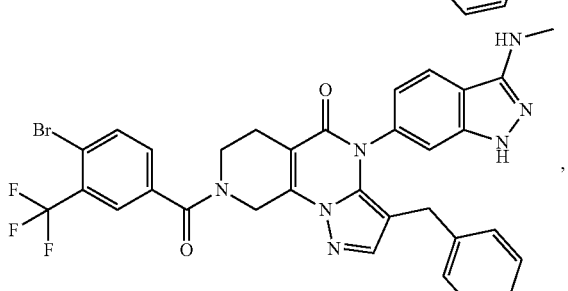,
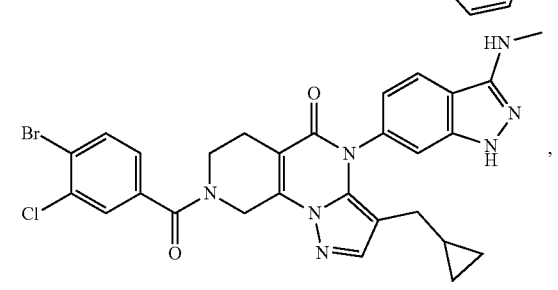,
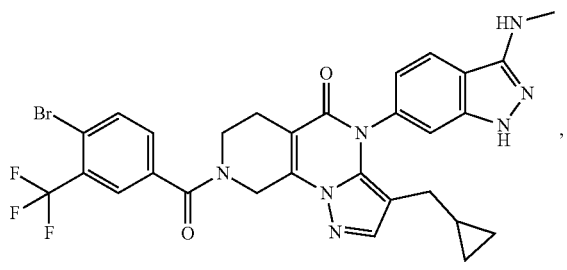,
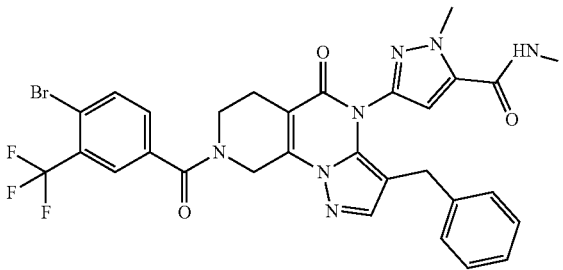, 369
-continued
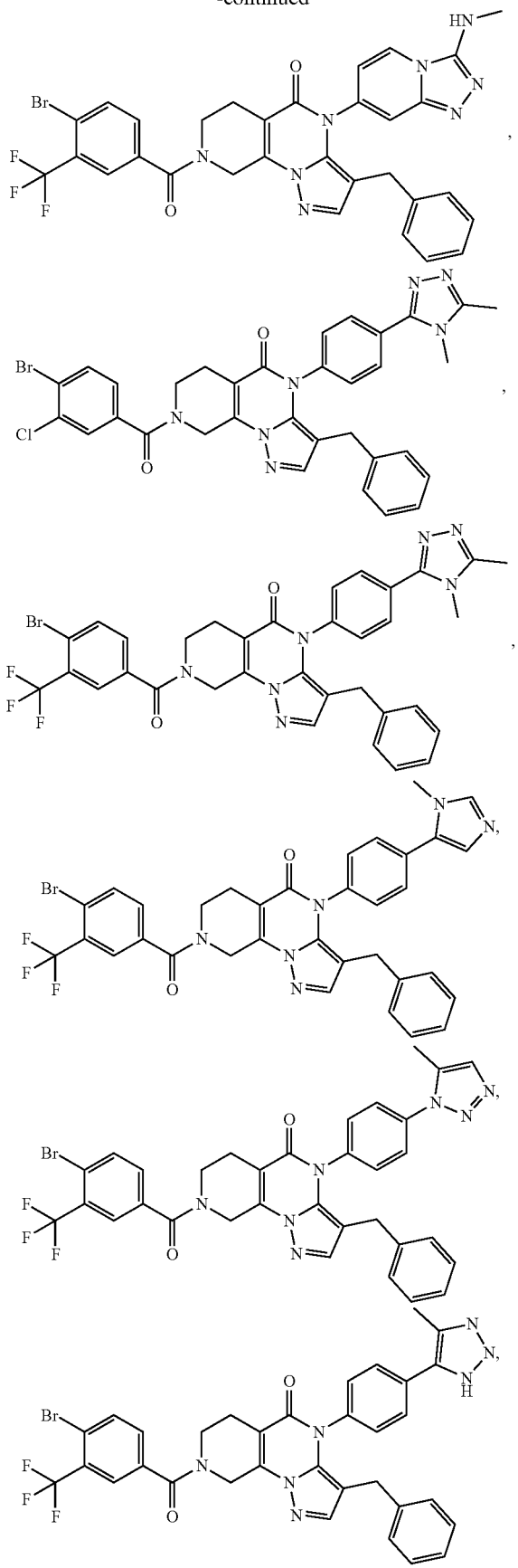
,
370
-continued
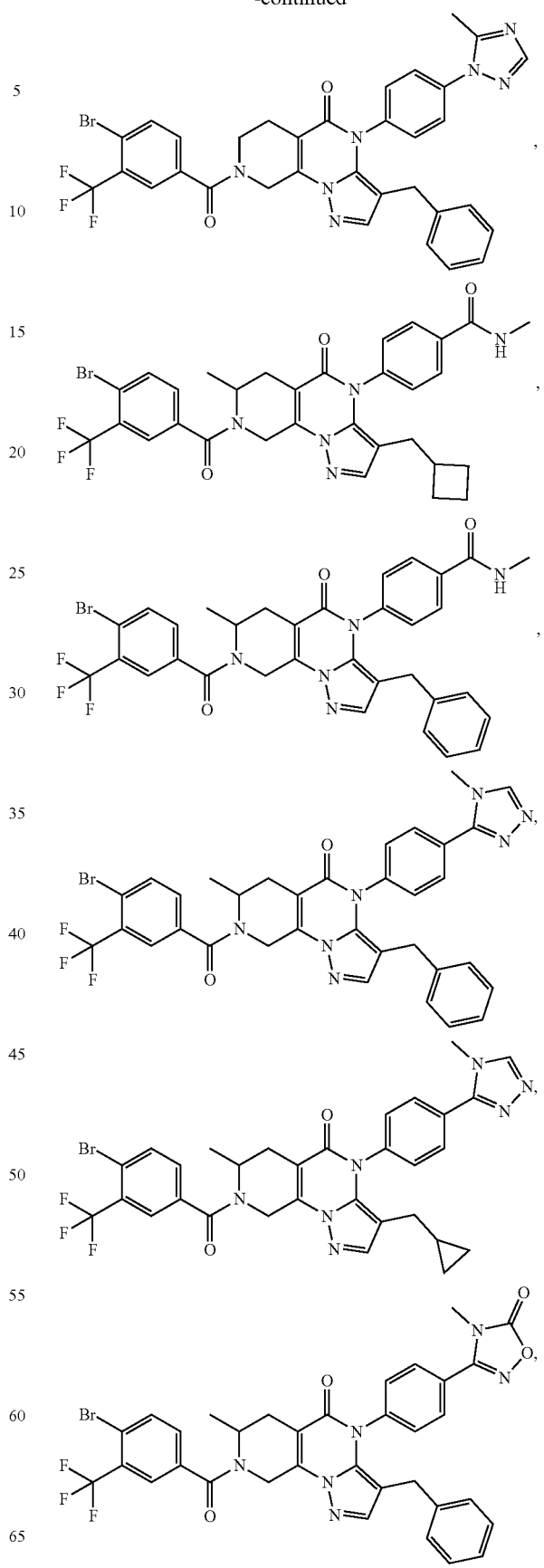
, 371
-continued
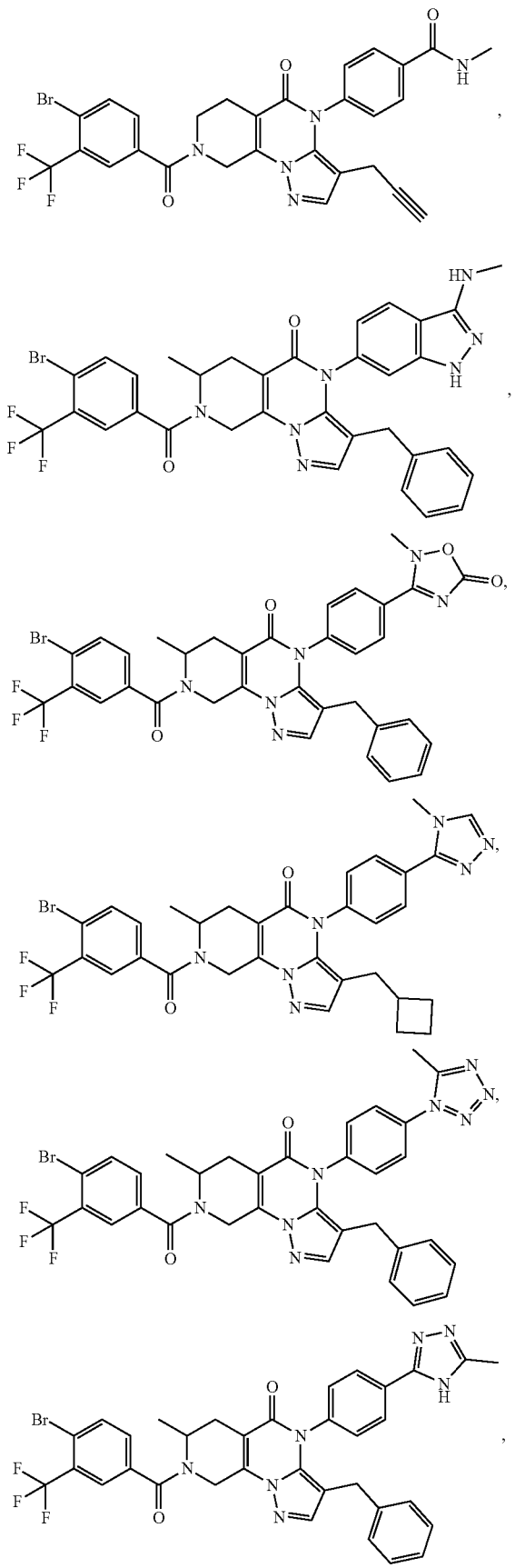
372
-continued
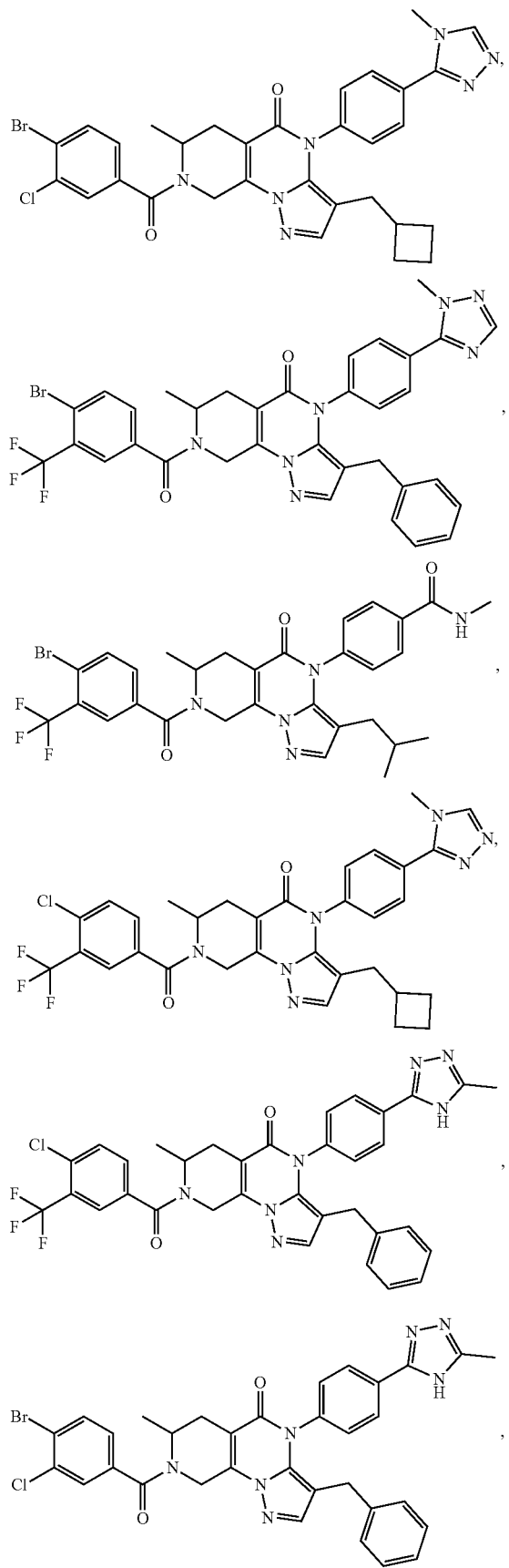

373
-continued
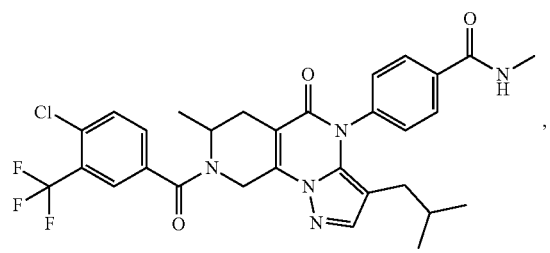,
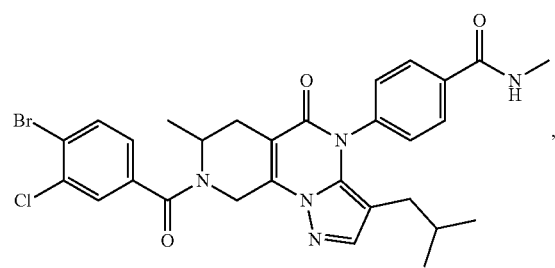,
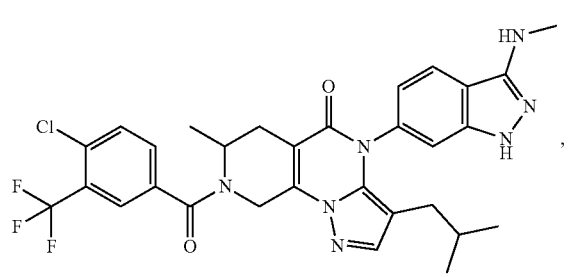,
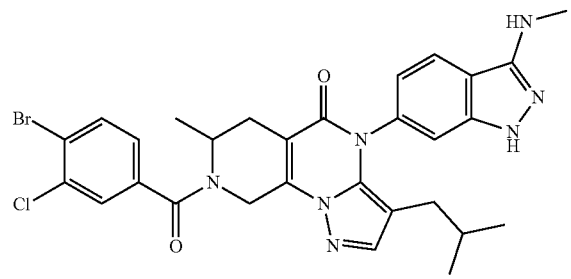,
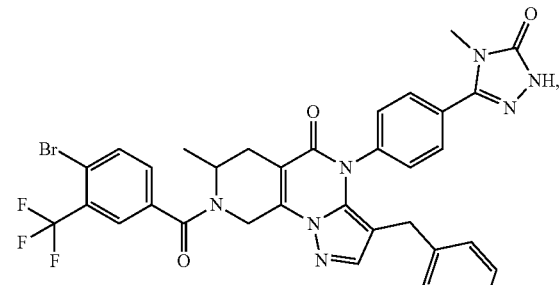,
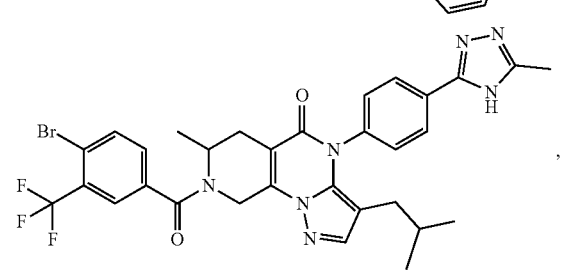,
374
-continued
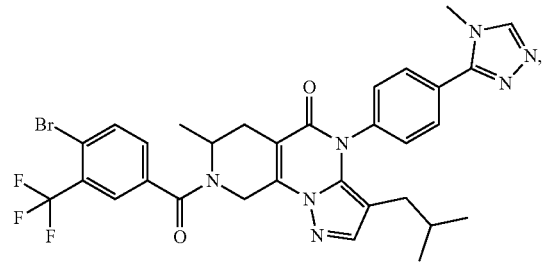,
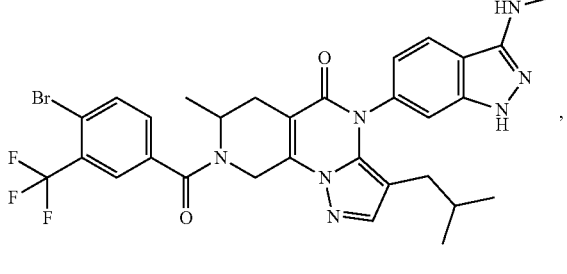,
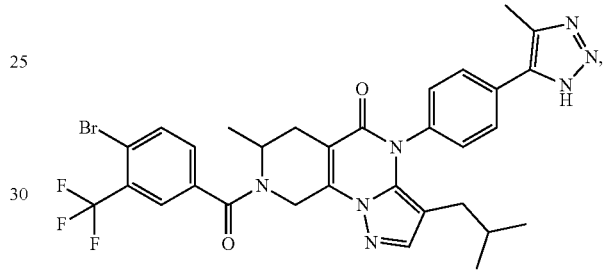,
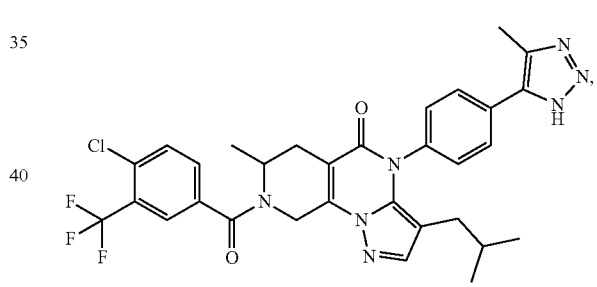,
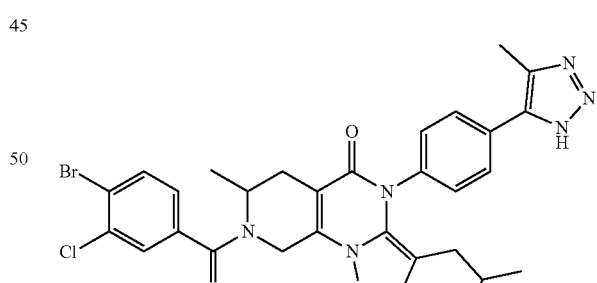,
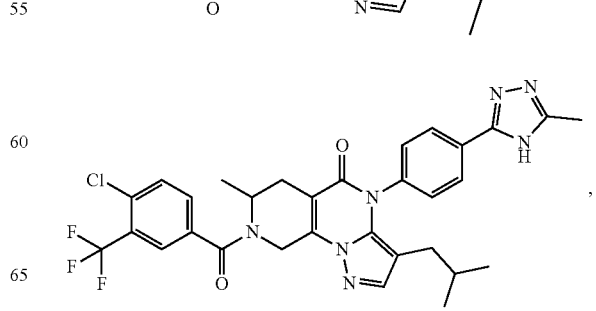, 375
-continued
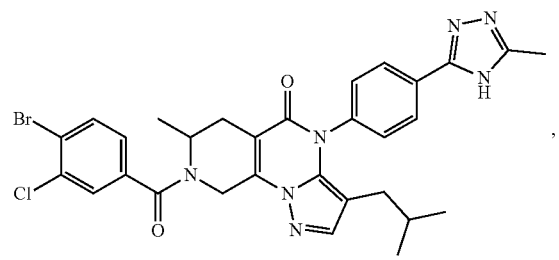
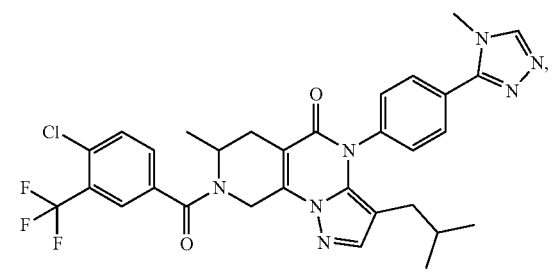
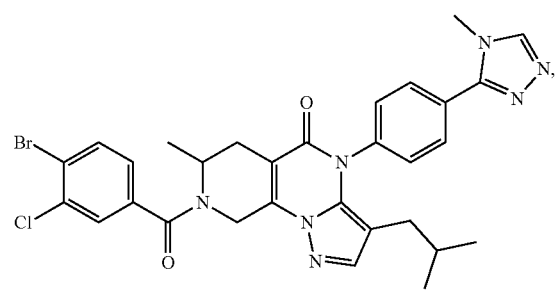
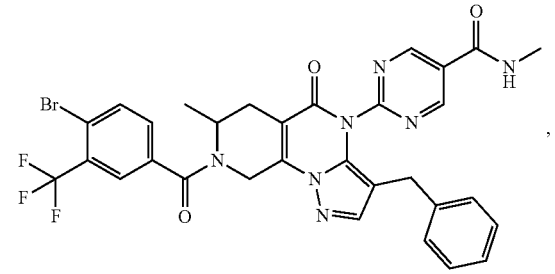
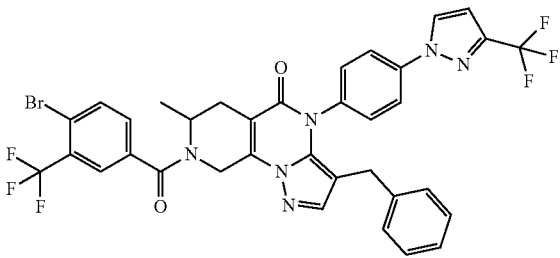
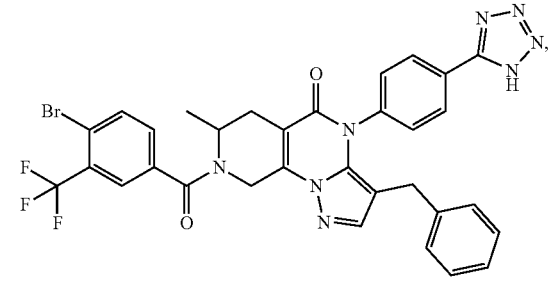
376
-continued
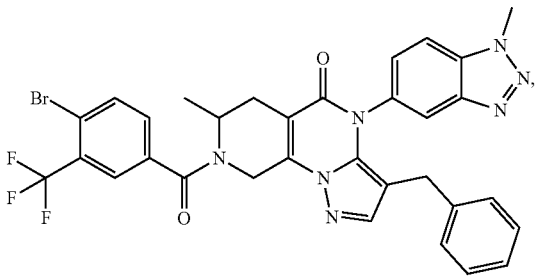
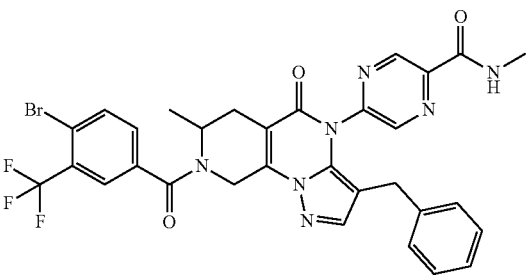
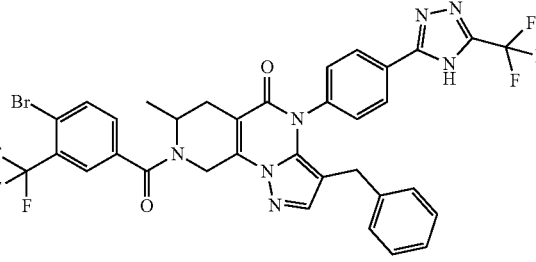
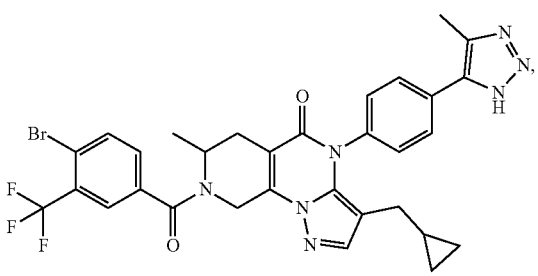
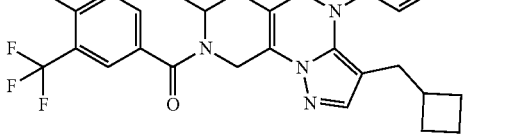
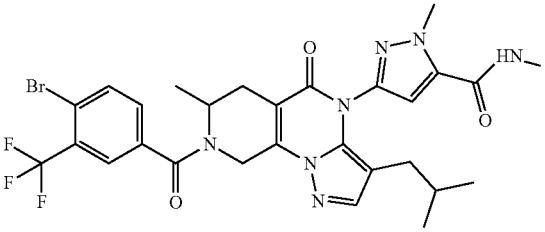

377
-continued
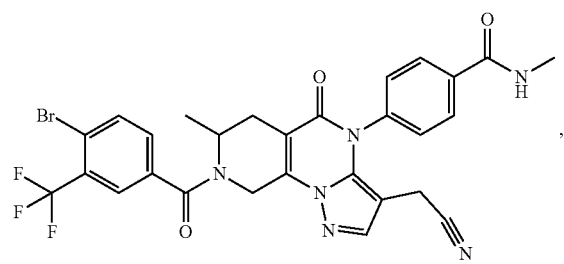,
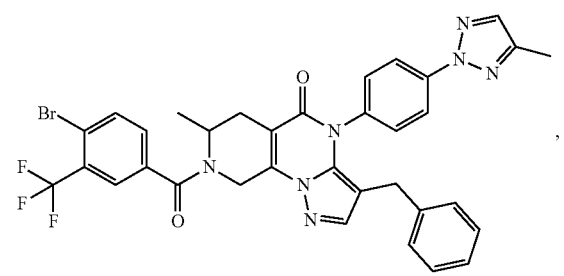,
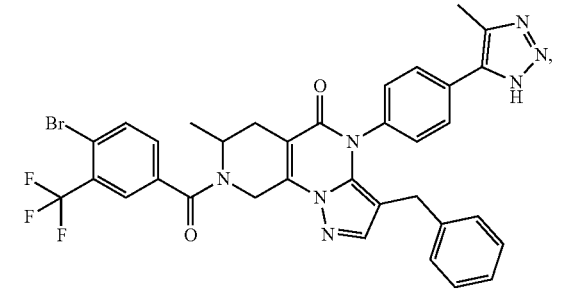,
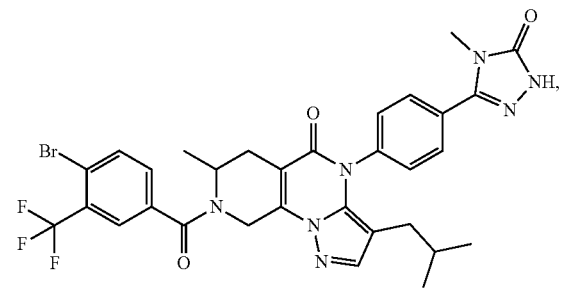,
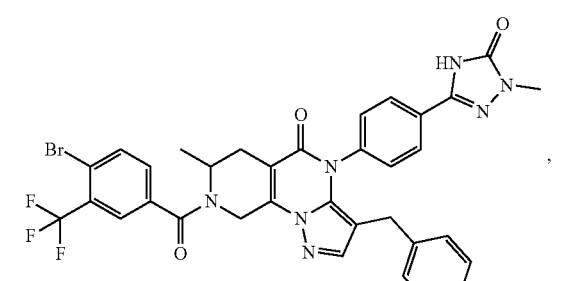,
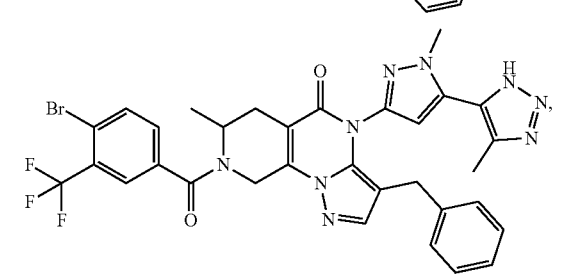
378
-continued
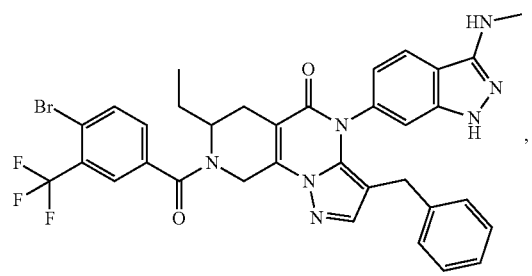,
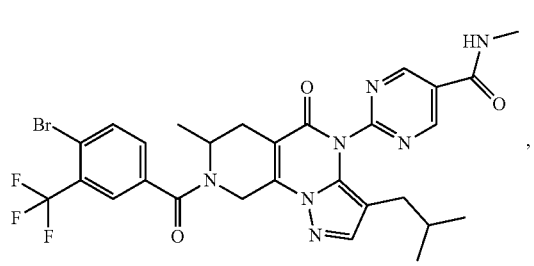,
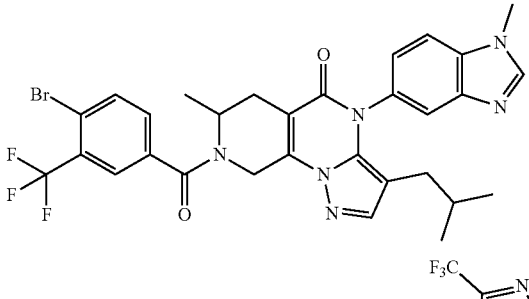,
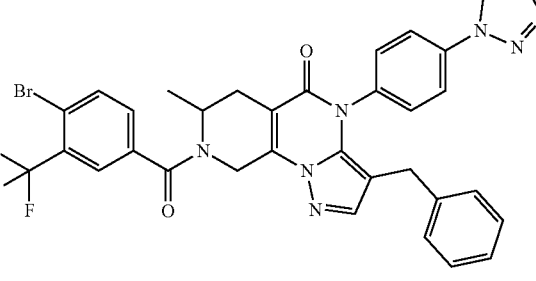,
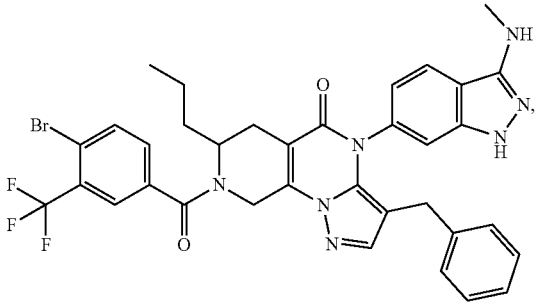,
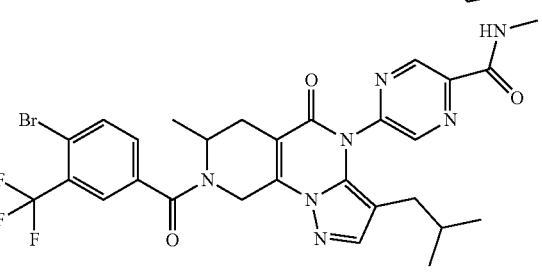, 379
-continued
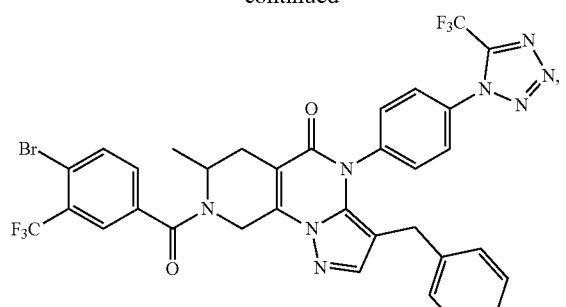,
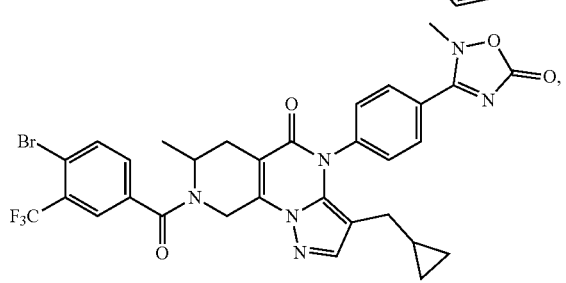,
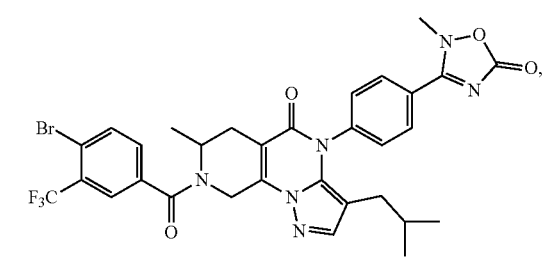,
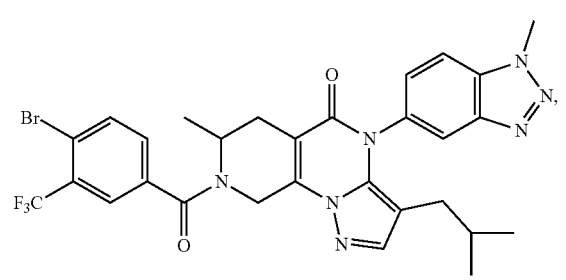,
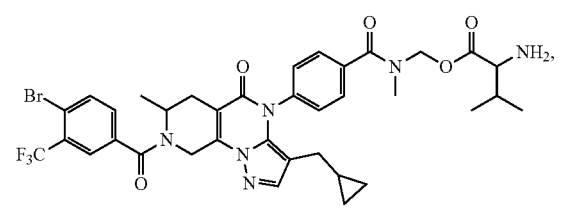,
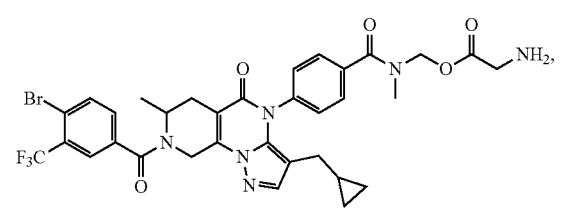,
380
-continued
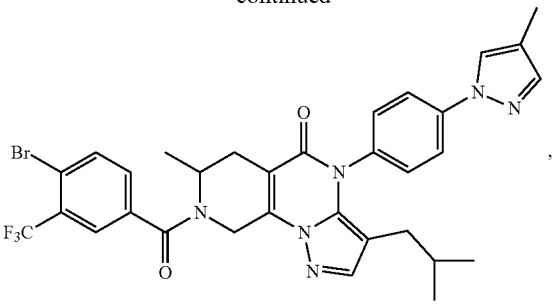,
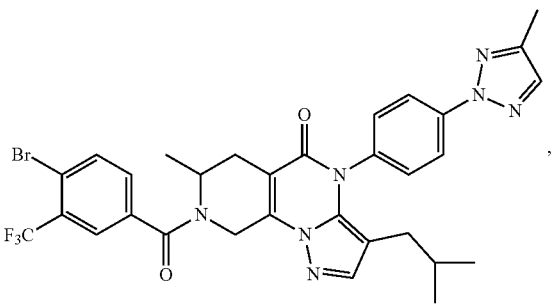,
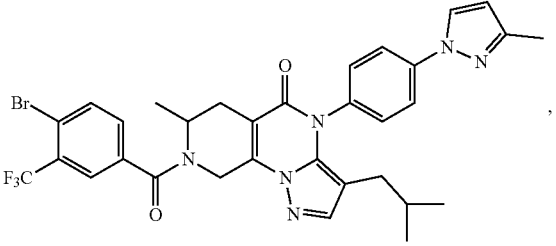,
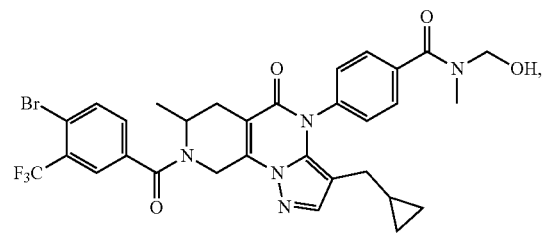,
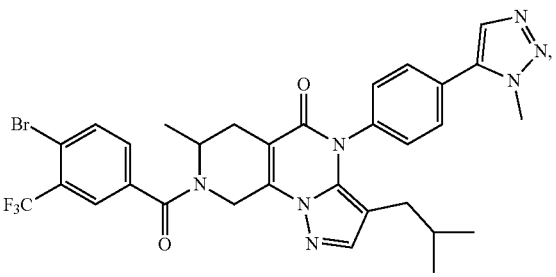,
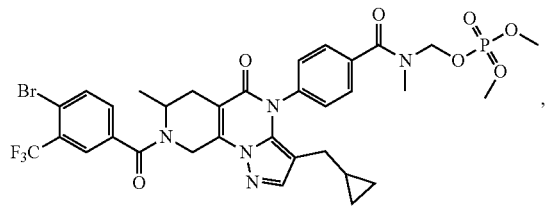, 381
-continued
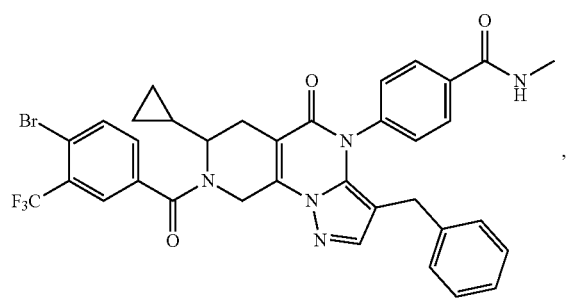
,
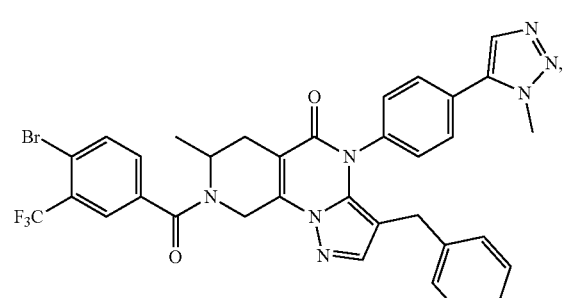
,
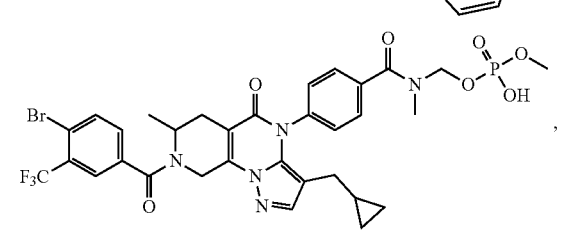
,
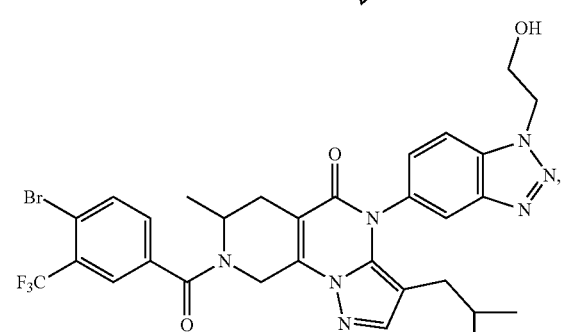
,
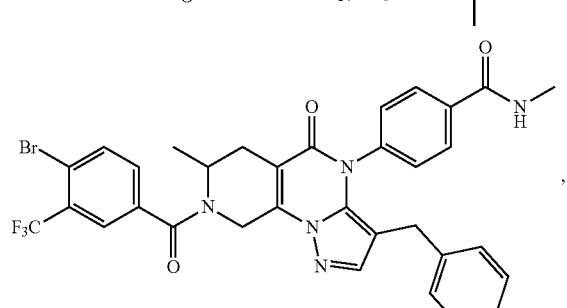
,
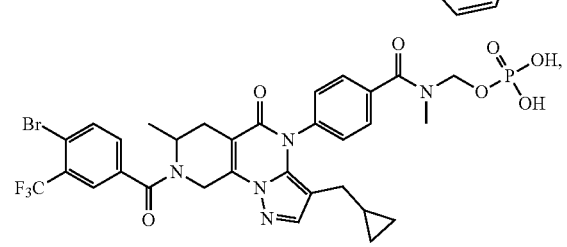
382
-continued
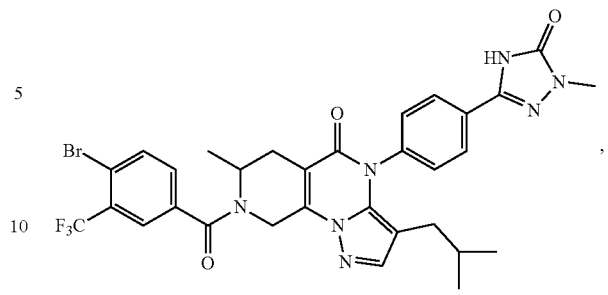
,
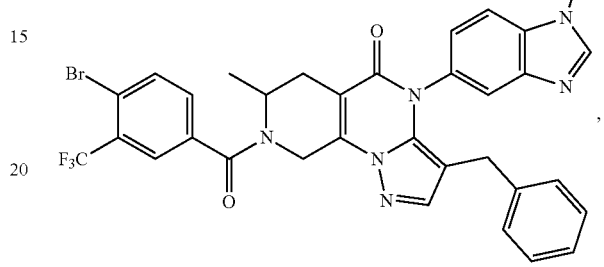
,
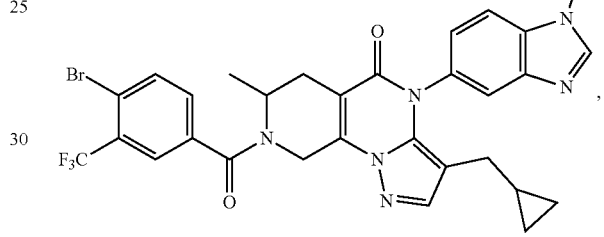
,
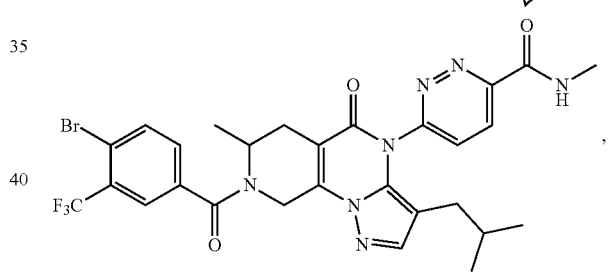
,
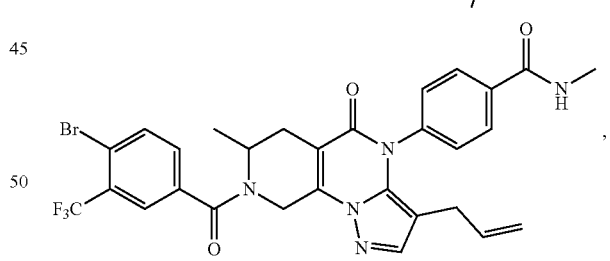
,
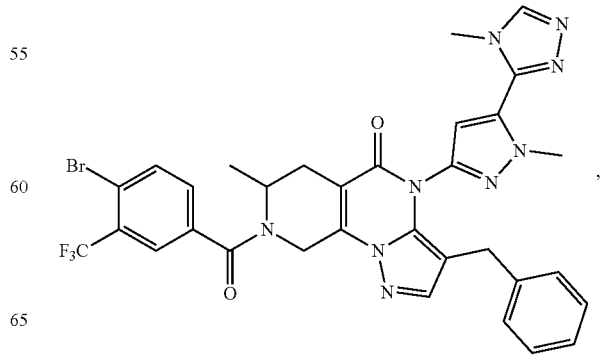
, 383
-continued
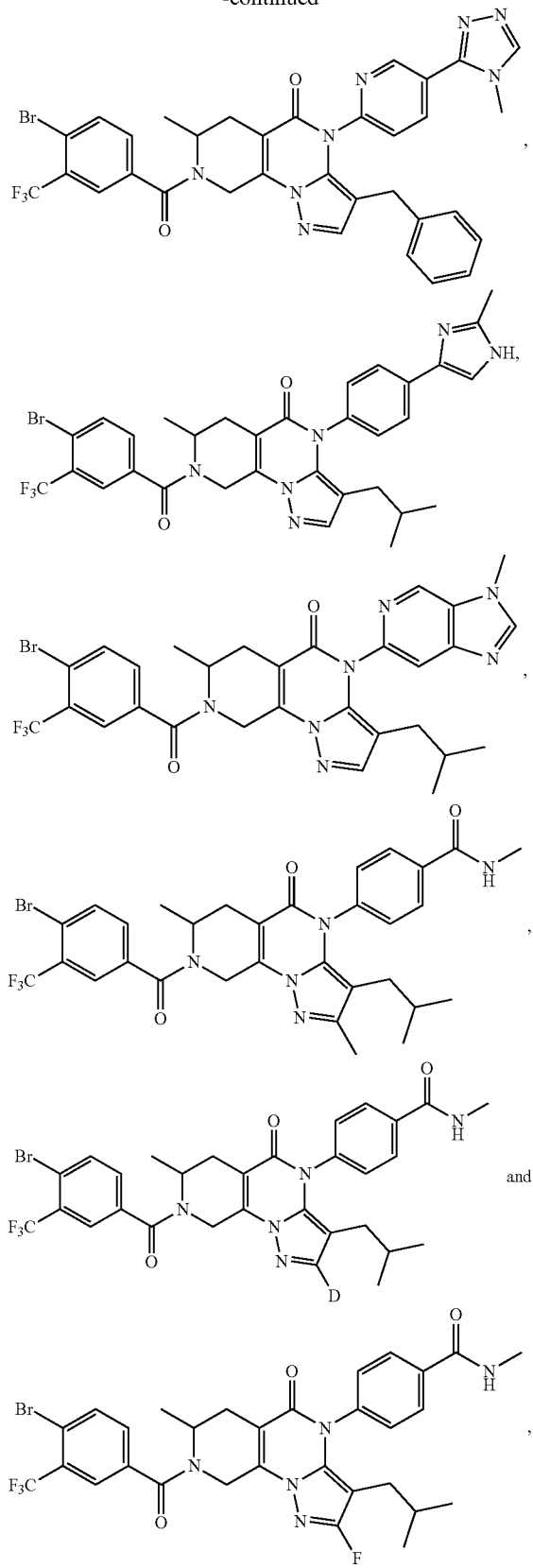
or a pharmaceutically acceptable salt of any of the foregoing.
384
17. The compound of claim 1, wherein the compound of Formula (I), or a pharmaceutically acceptable salt thereof, is selected from the group consisting of:
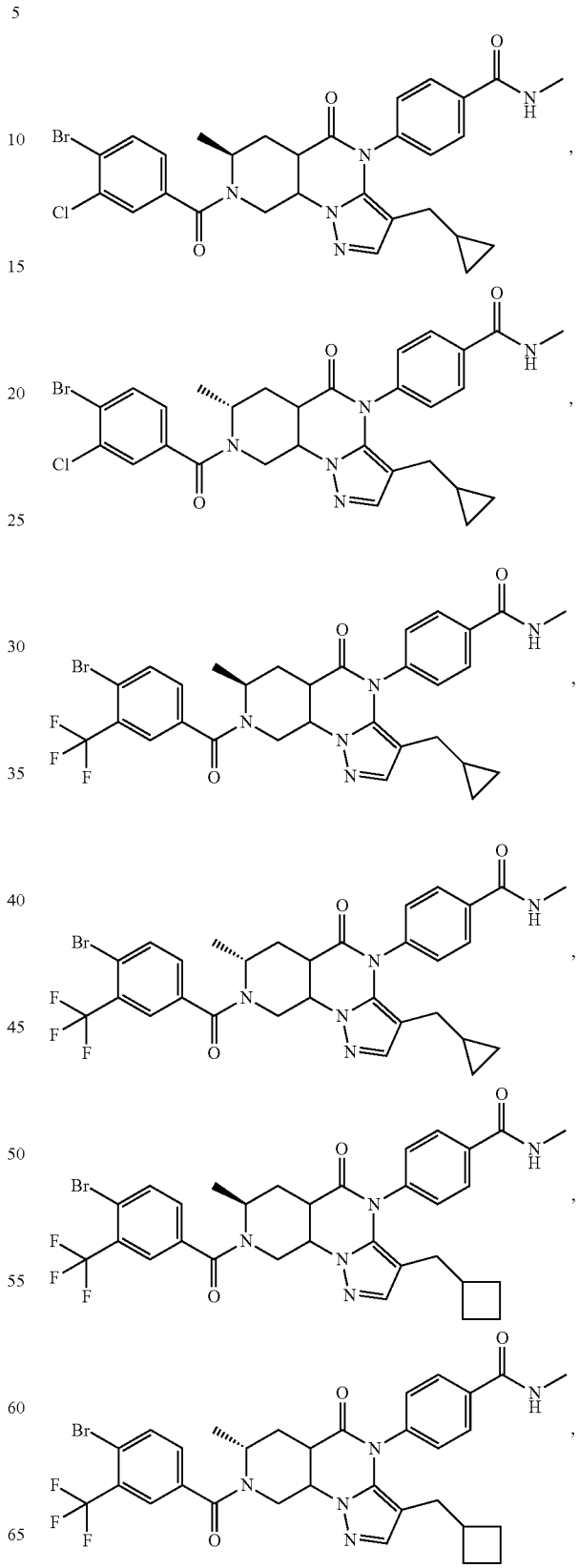
and

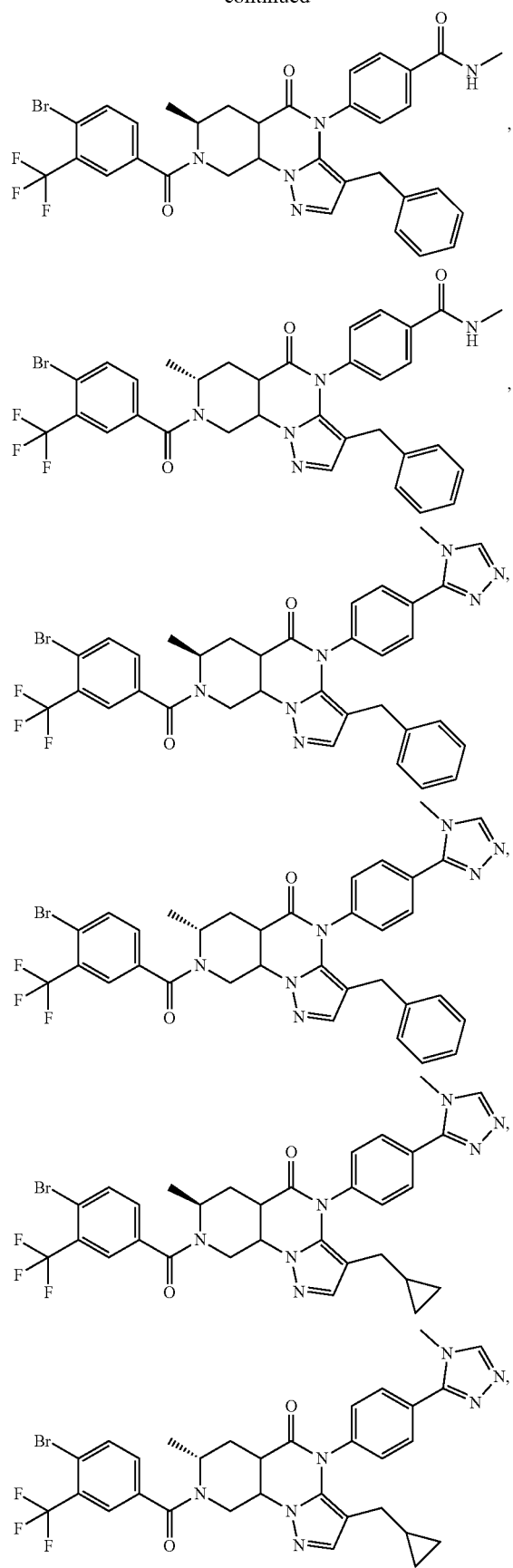
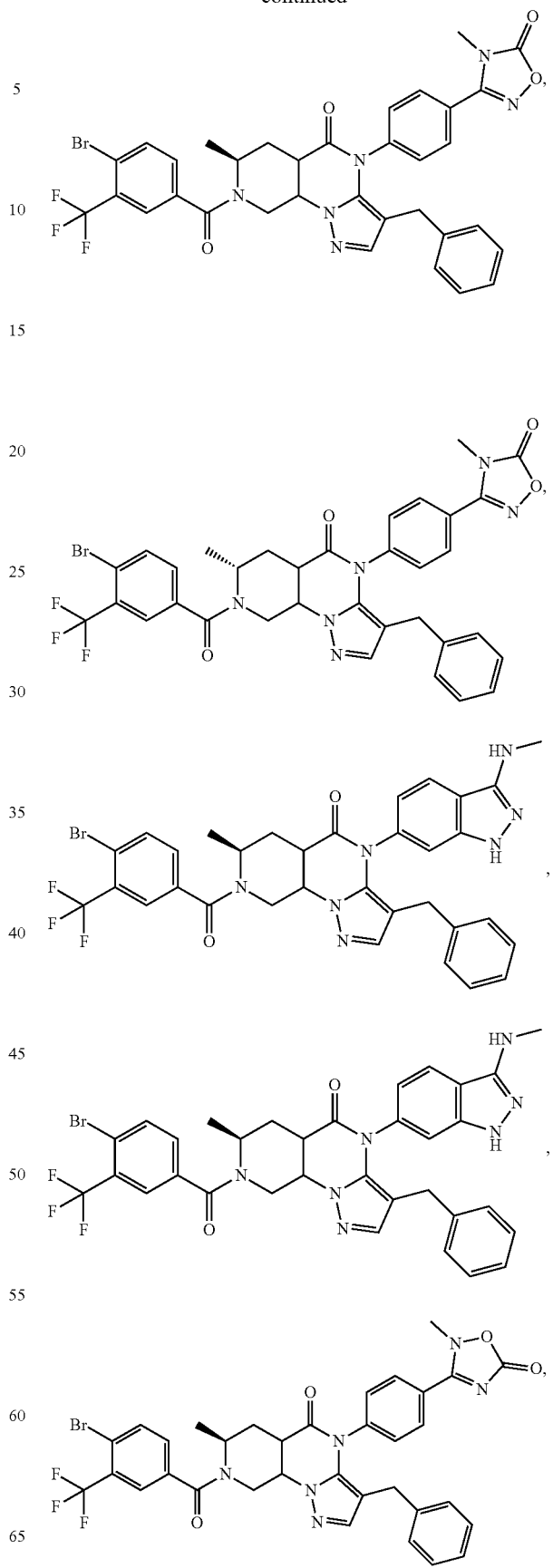

387
-continued
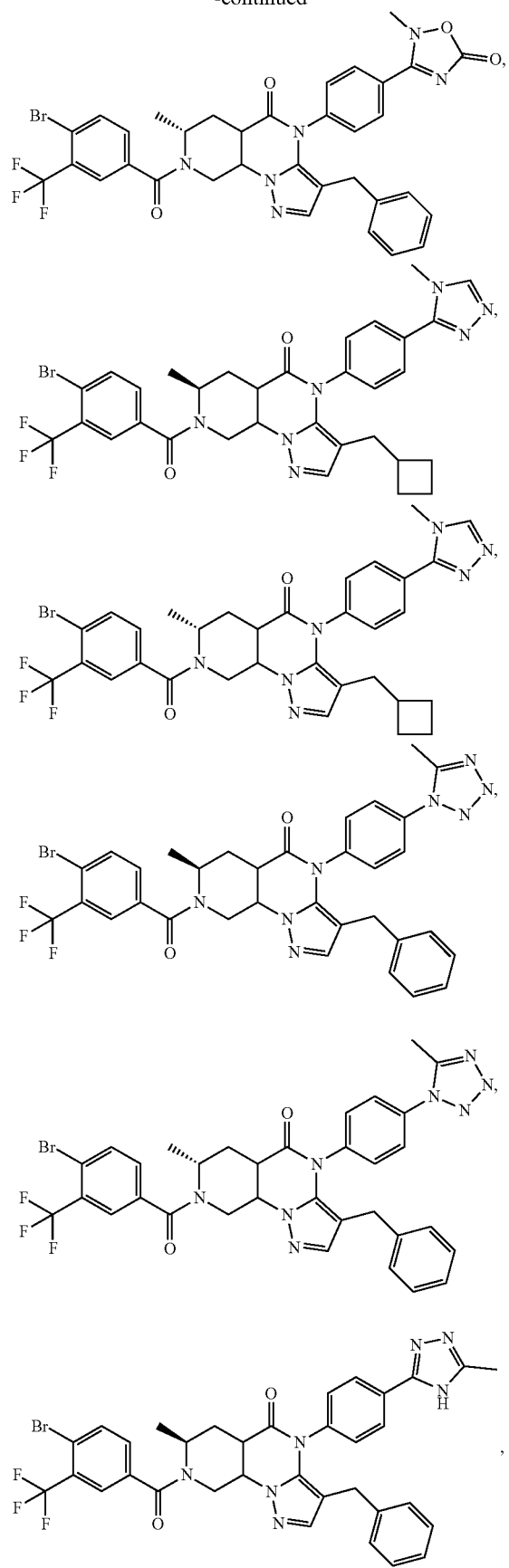
388
-continued
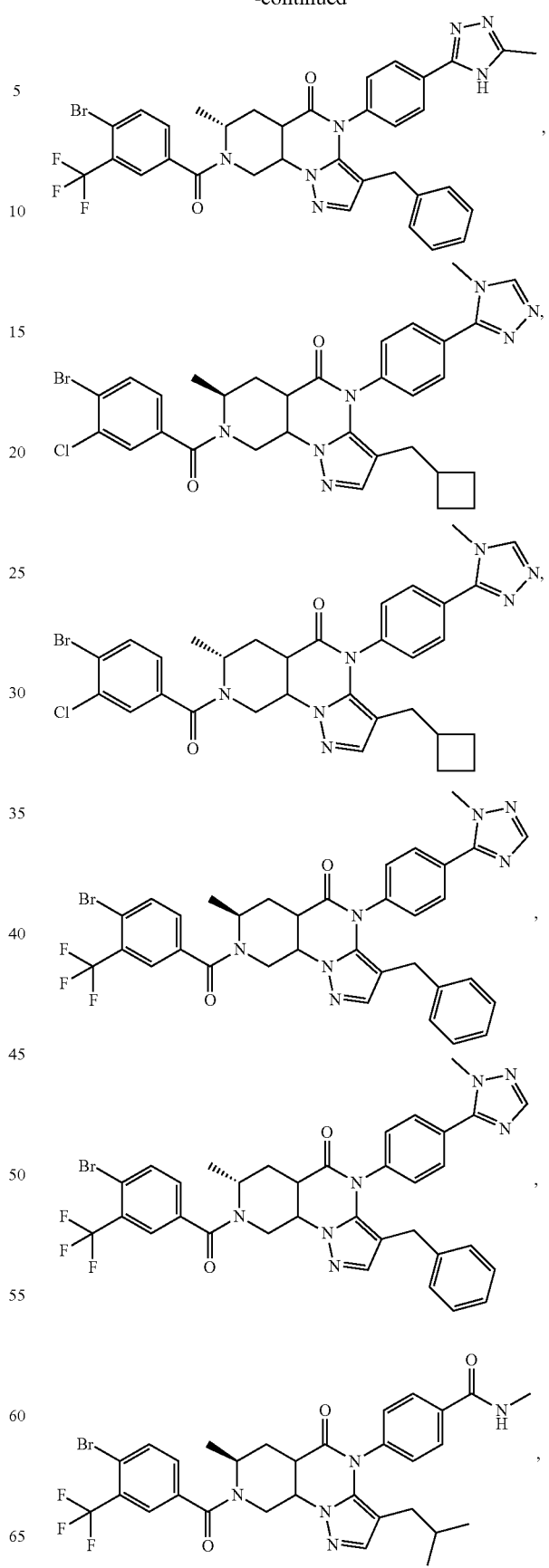

389
-continued
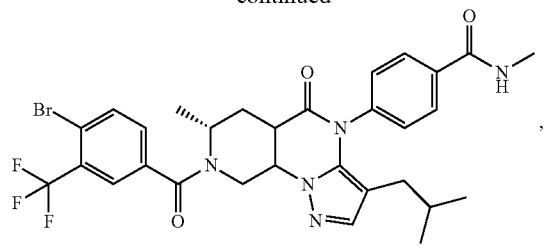,
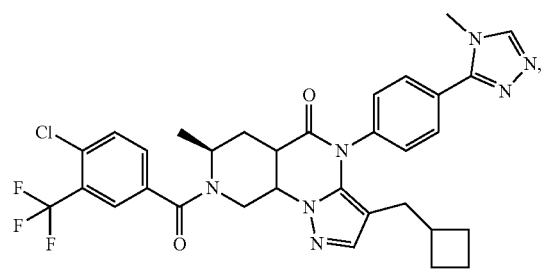,
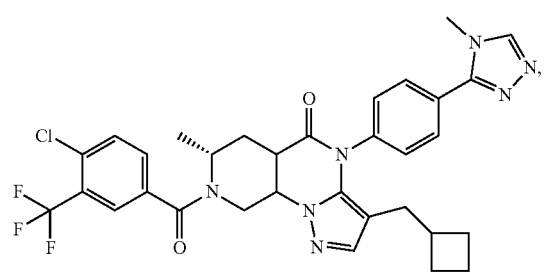,
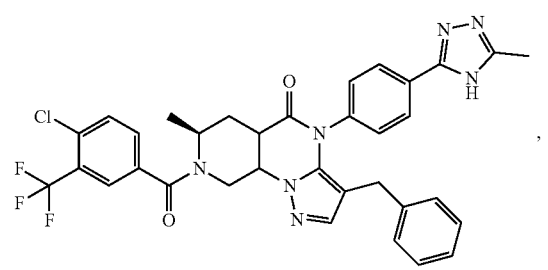,
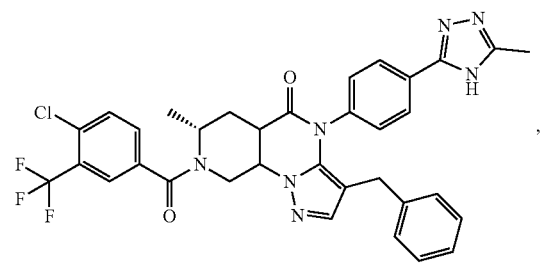,
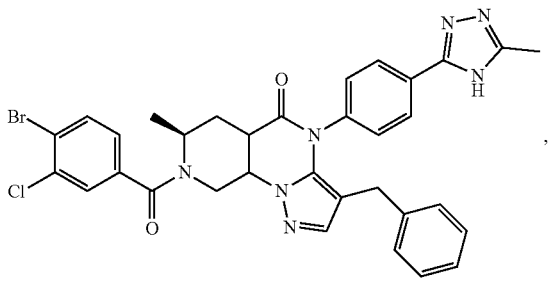,
390
-continued
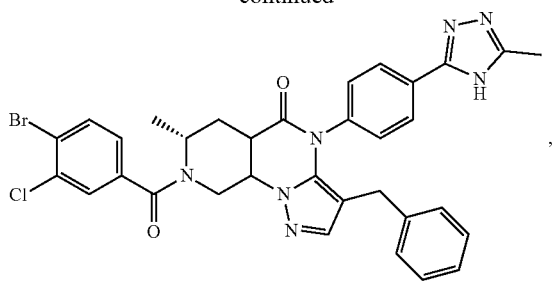,
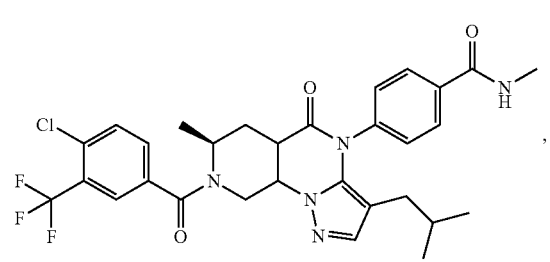,
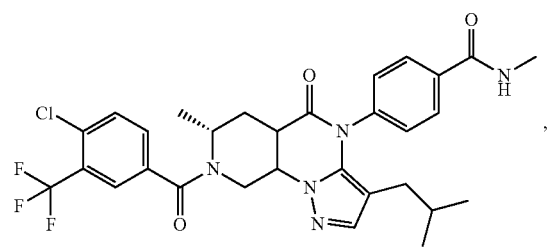,
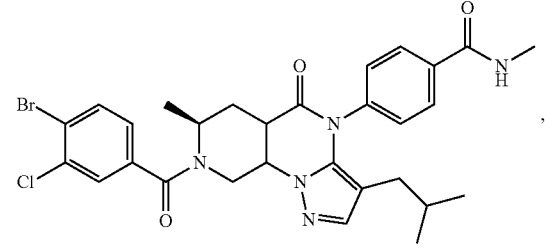,
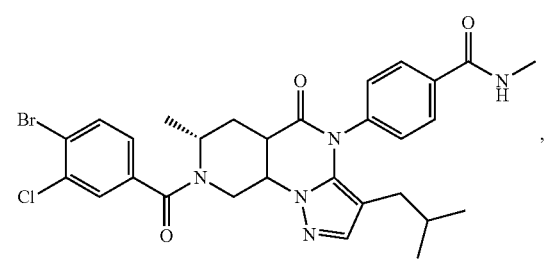,
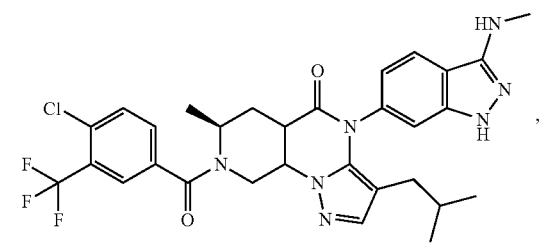,

391
-continued
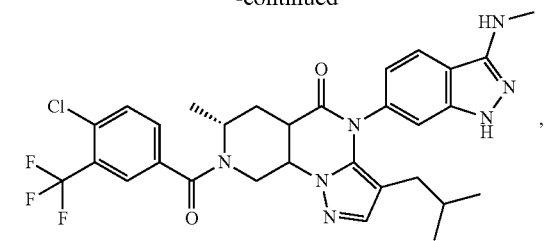
,
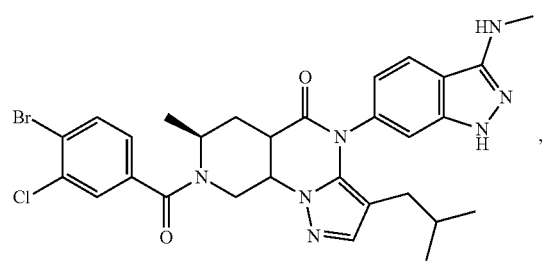
,
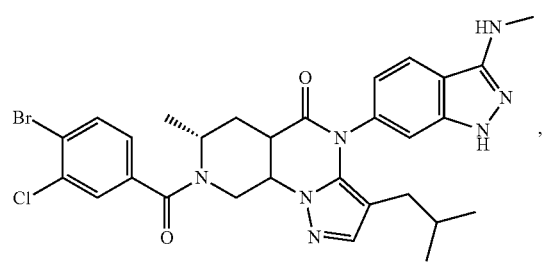
,
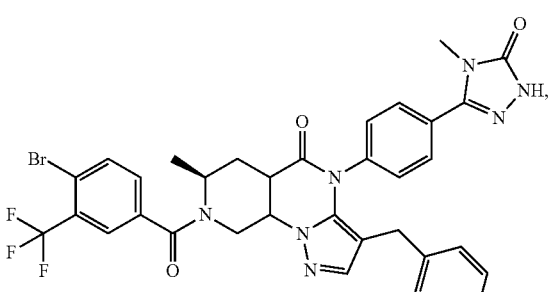
,
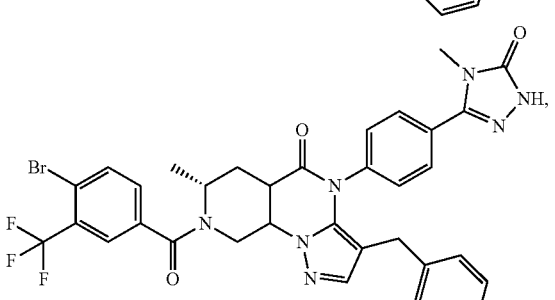
,
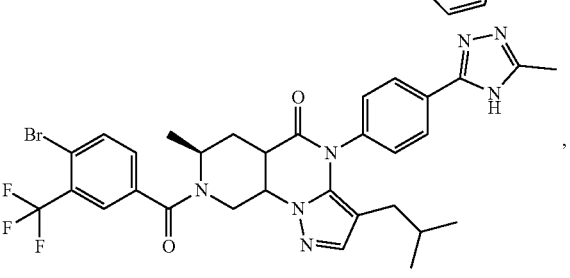
,
392
-continued
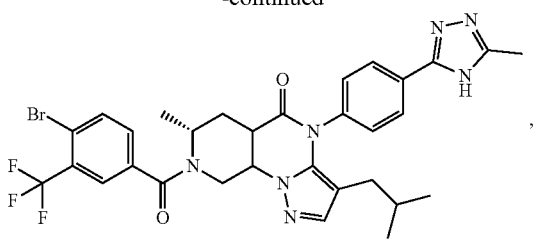
,
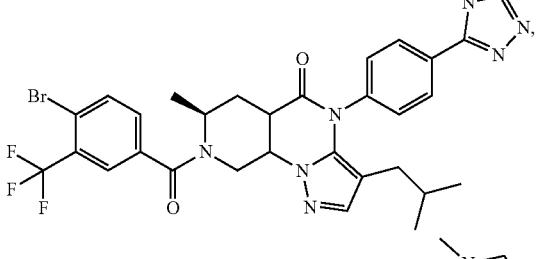
,
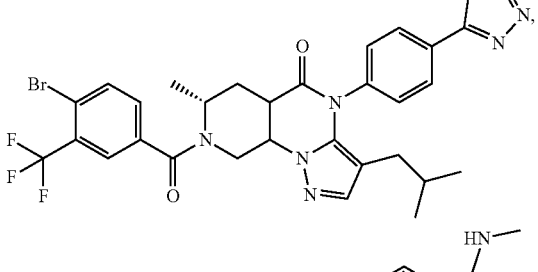
,
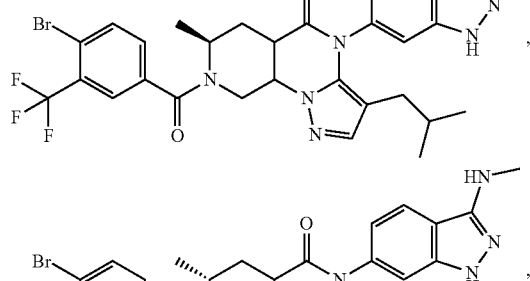
,
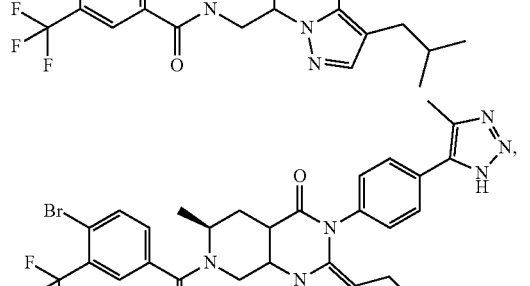
,
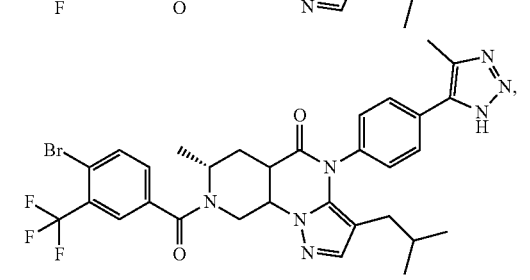
, 393
-continued
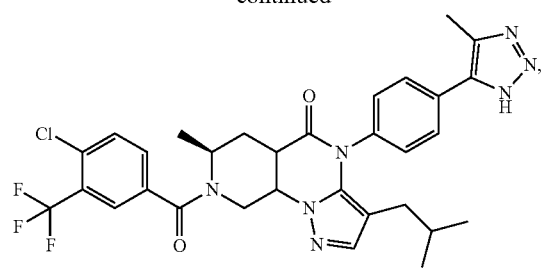
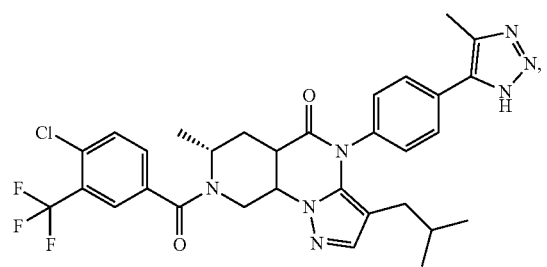
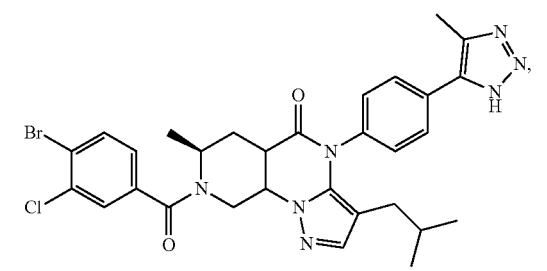
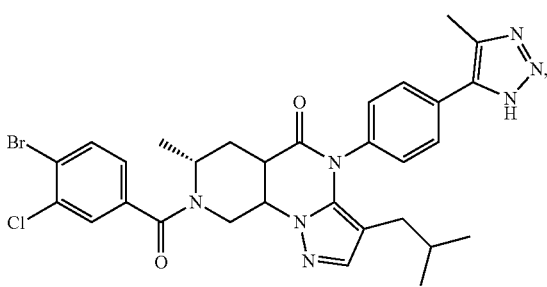
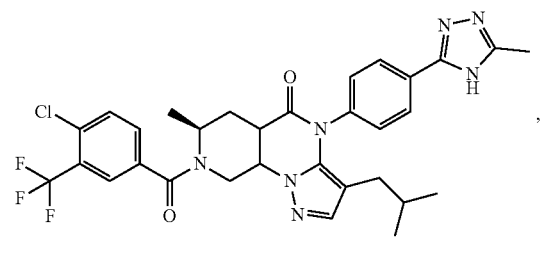
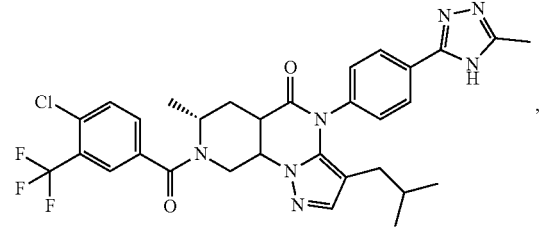
394
-continued
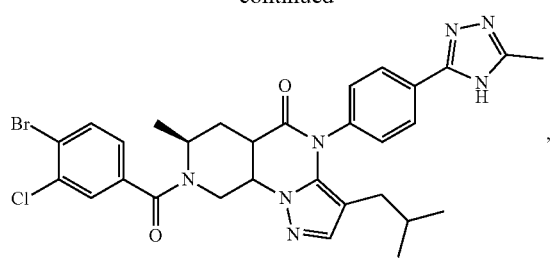
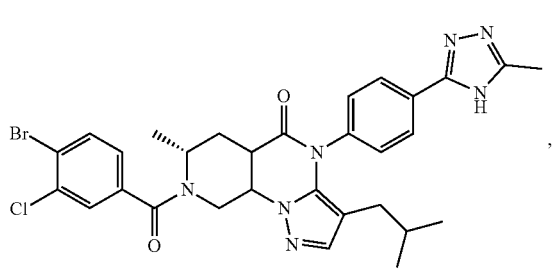
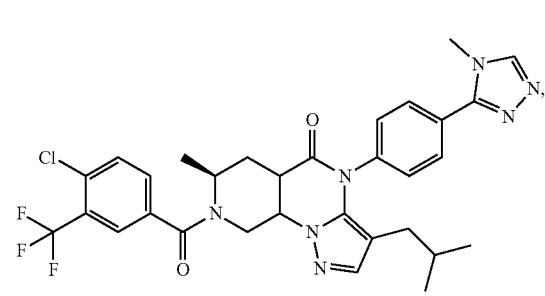
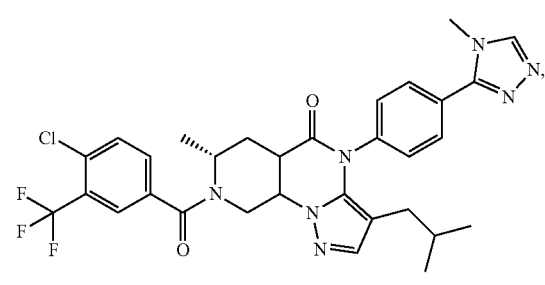
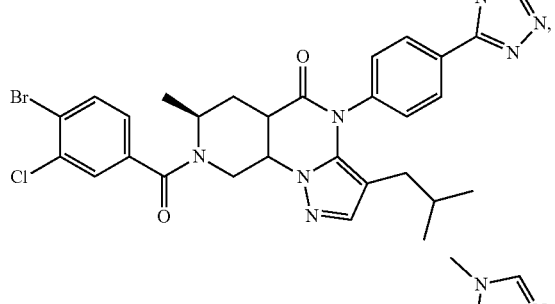
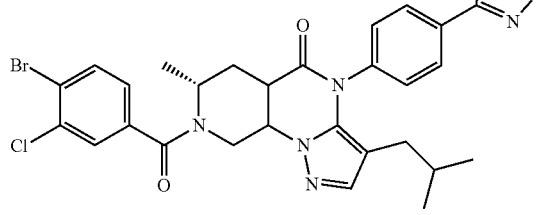

395
-continued
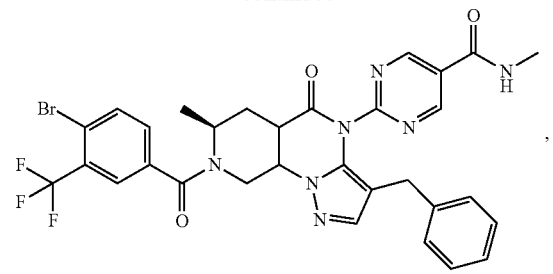
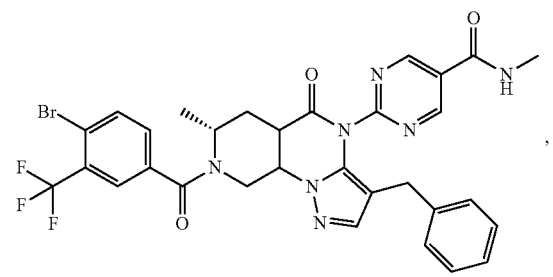
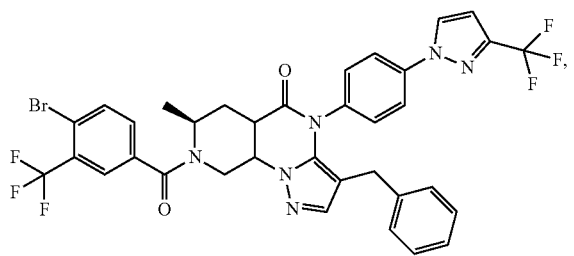
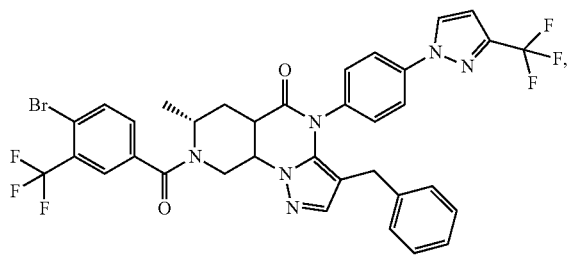
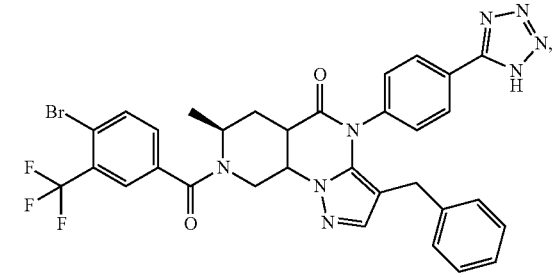
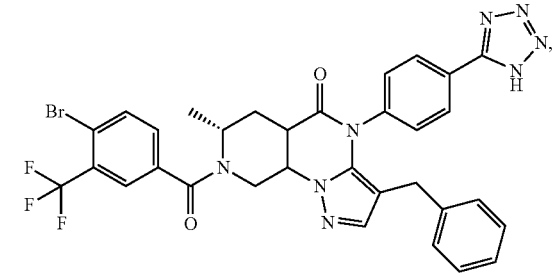
396
-continued
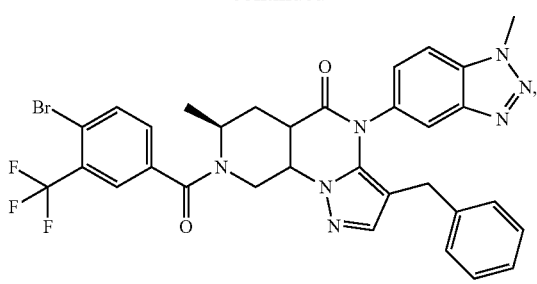
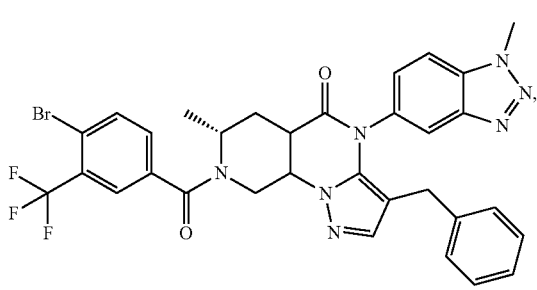
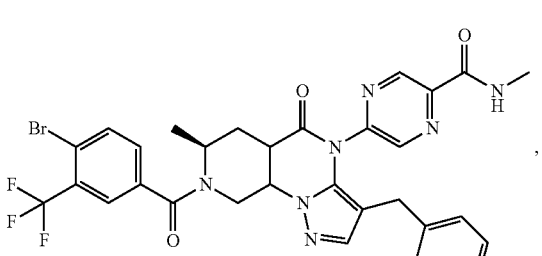
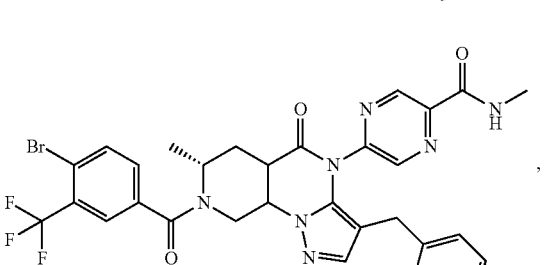
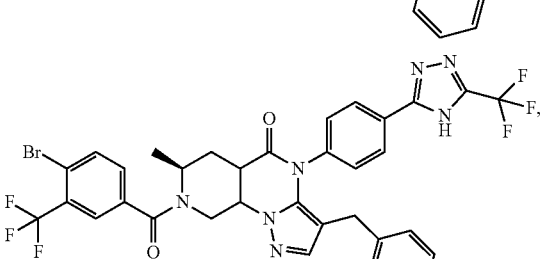
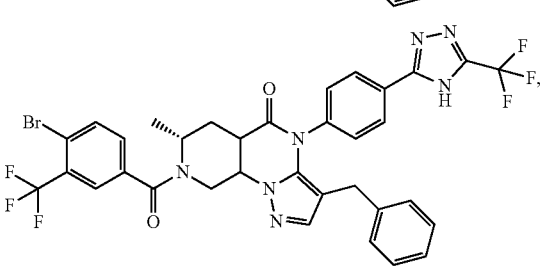

397
-continued
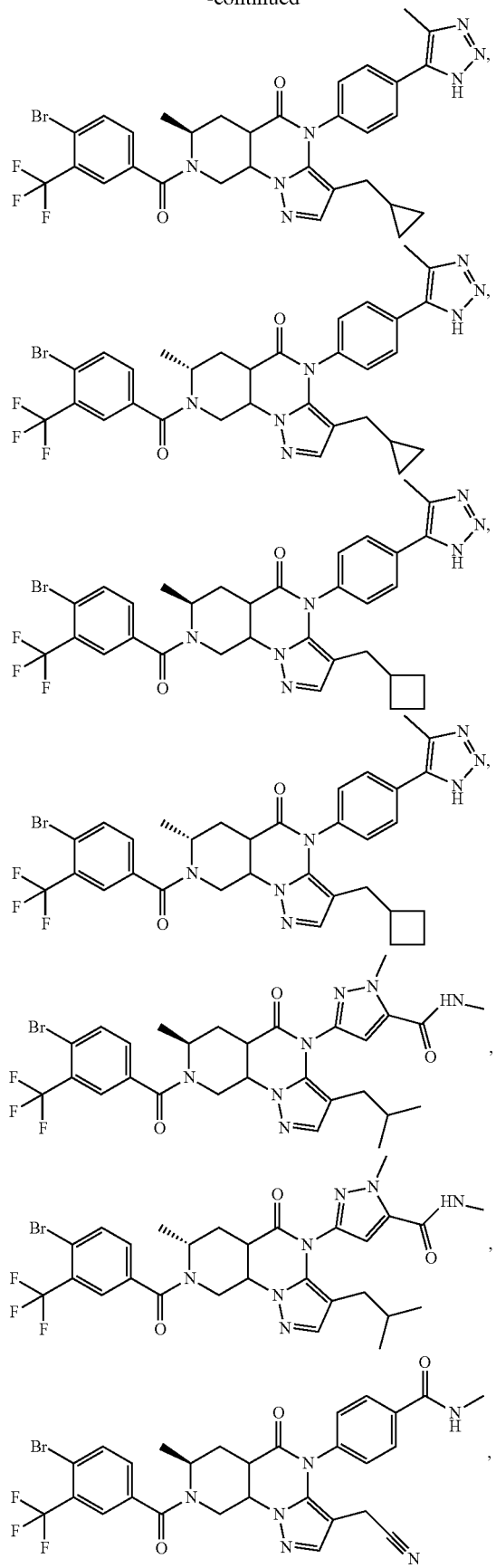
398
-continued
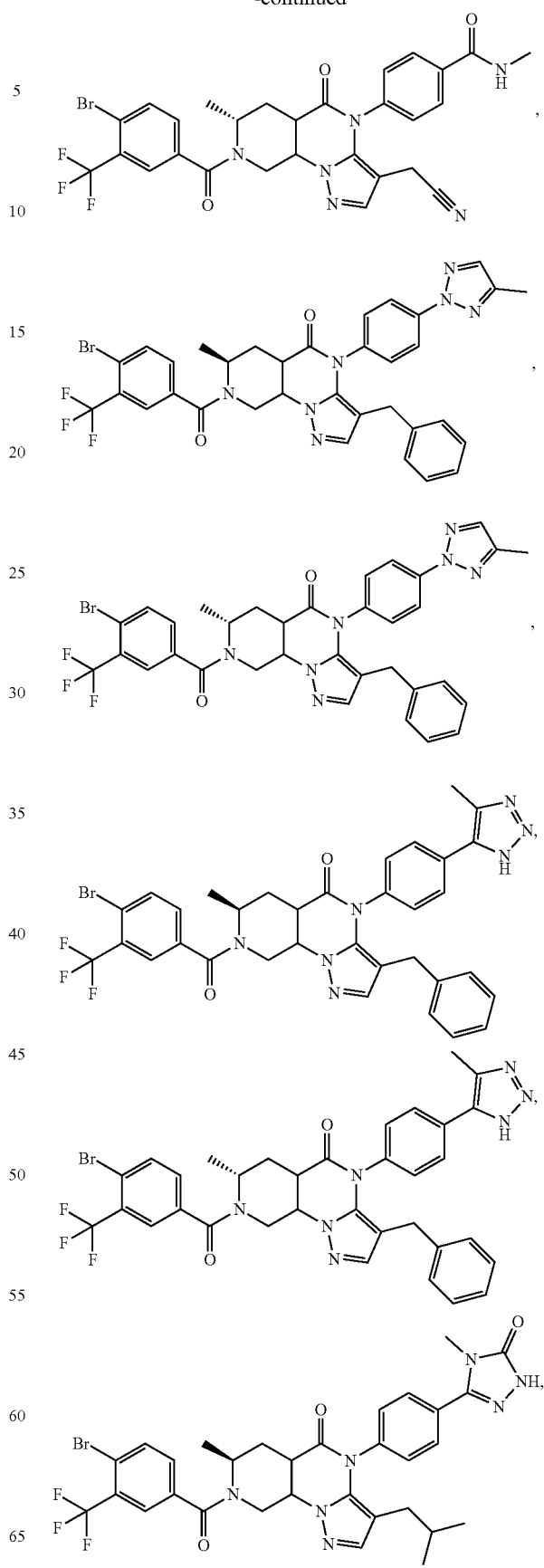

399
-continued
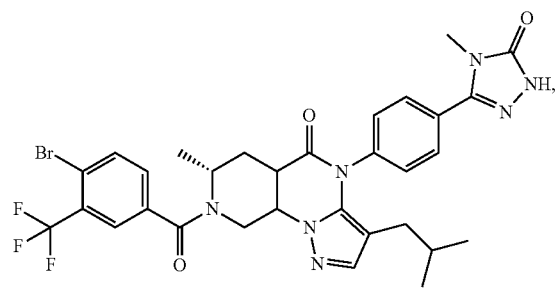
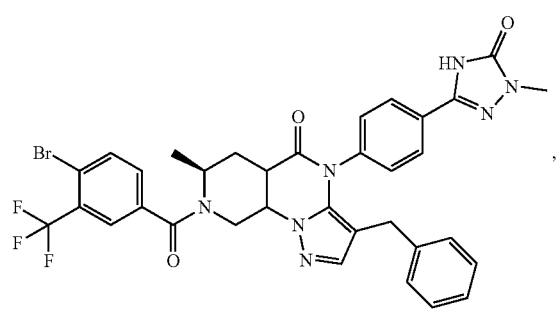
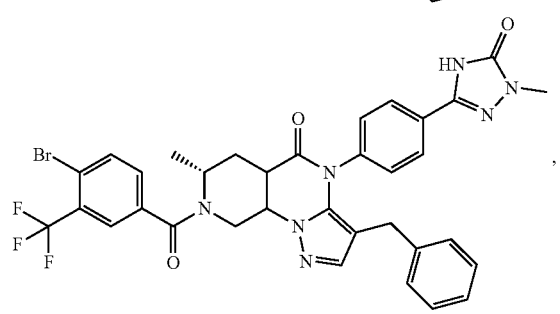
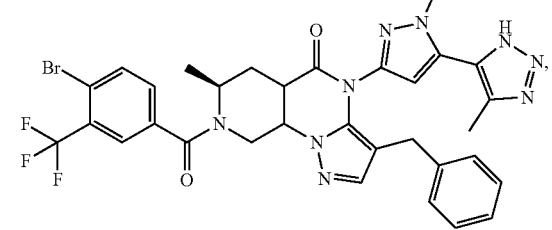
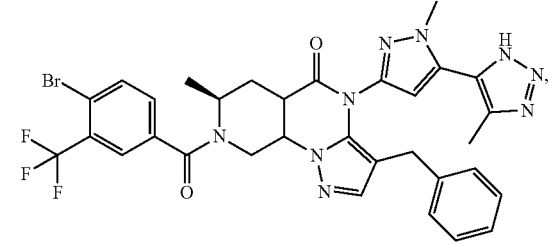
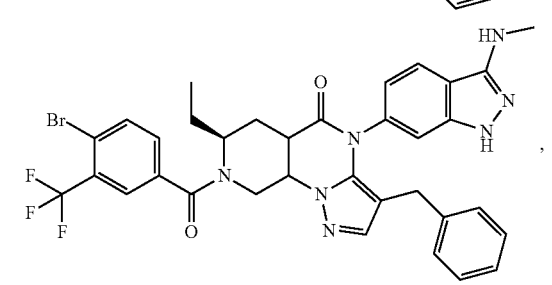
400
-continued
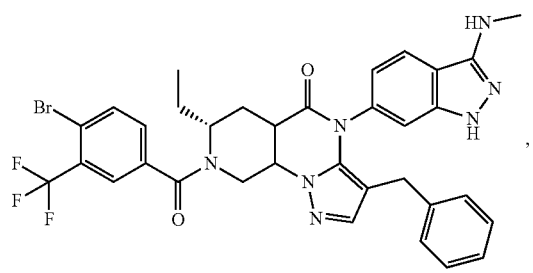
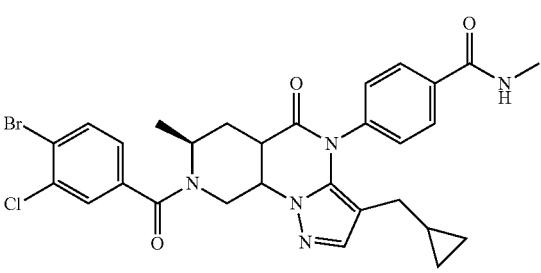
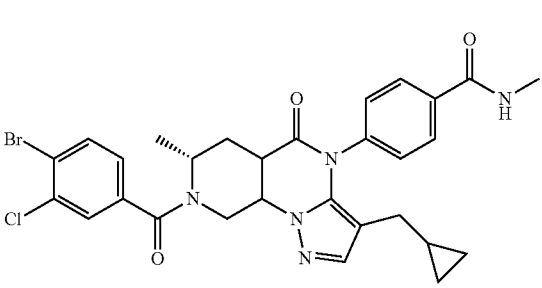
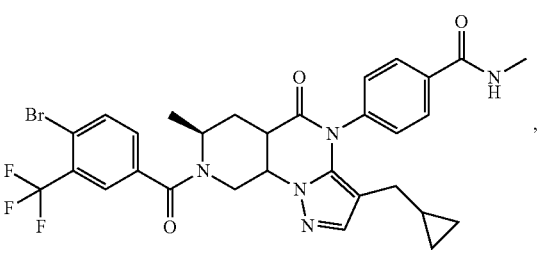
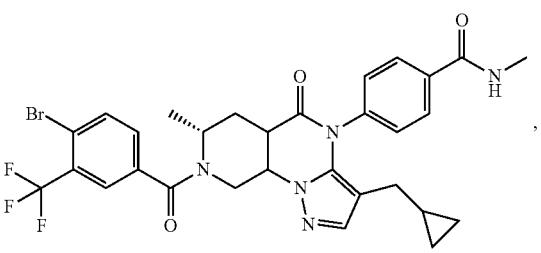
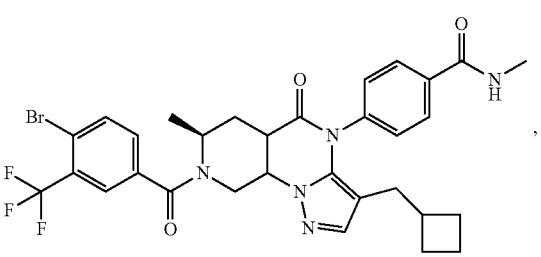

401
-continued
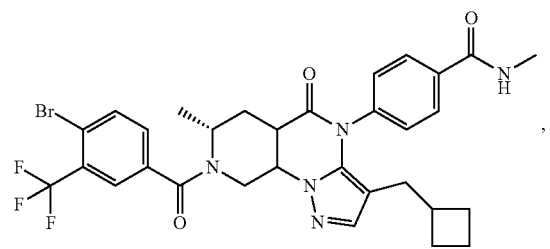
,
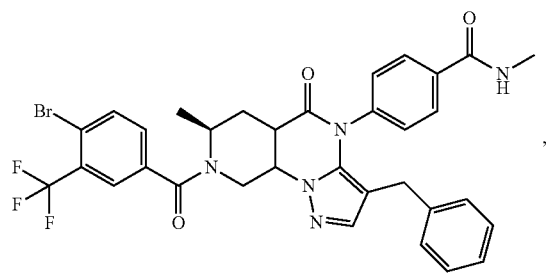
,
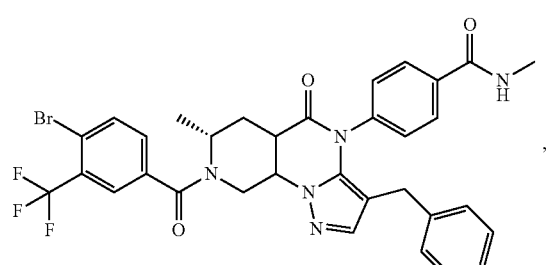
,
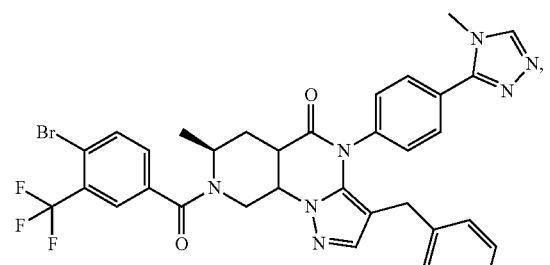
,
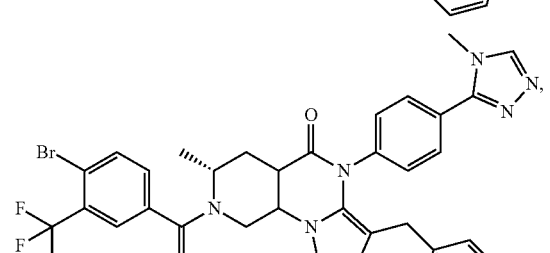
,
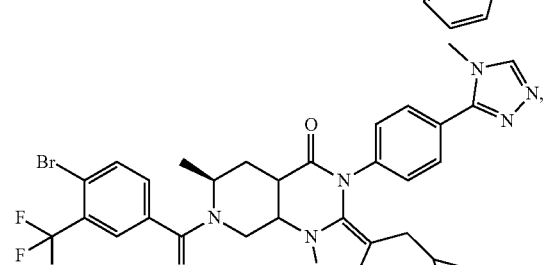
402
-continued
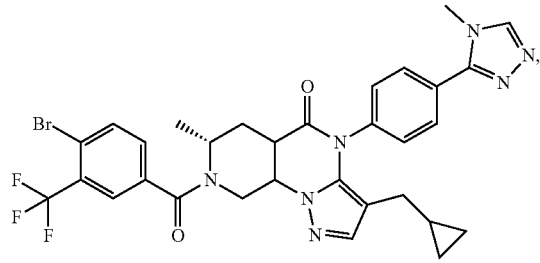
,
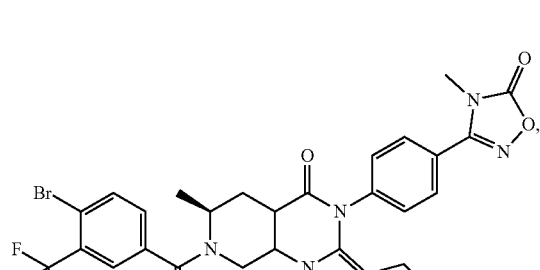
,
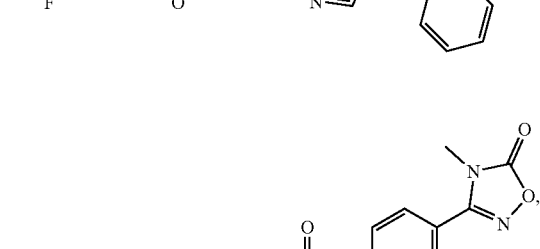
,
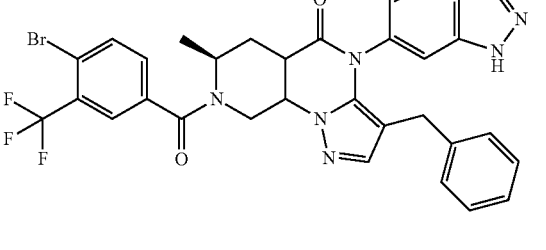
,
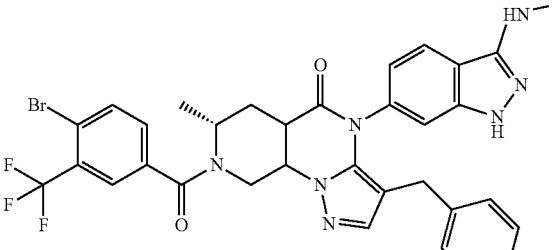
, 403
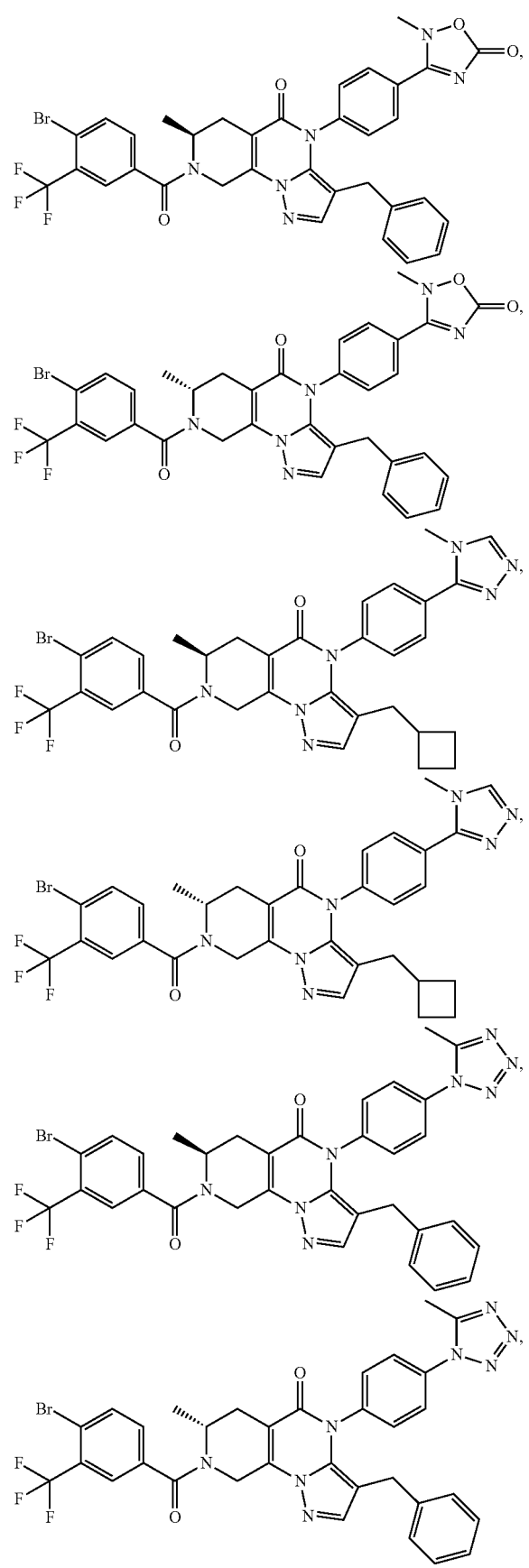
404
-continued
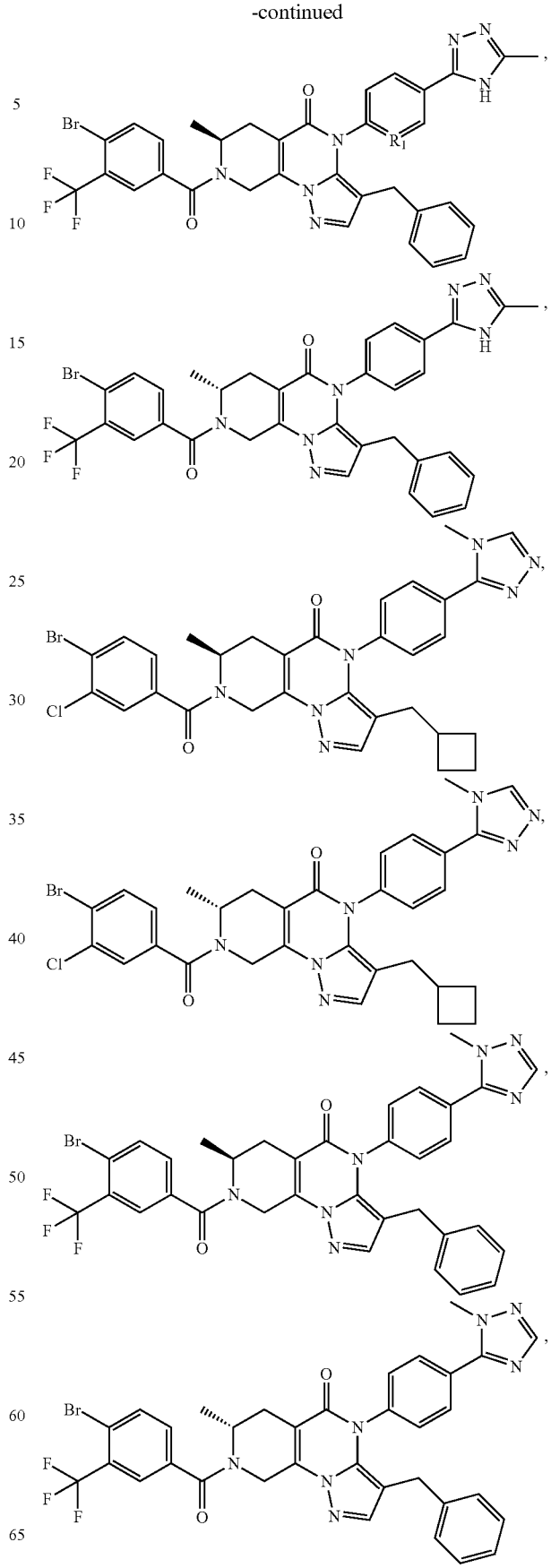

405
-continued
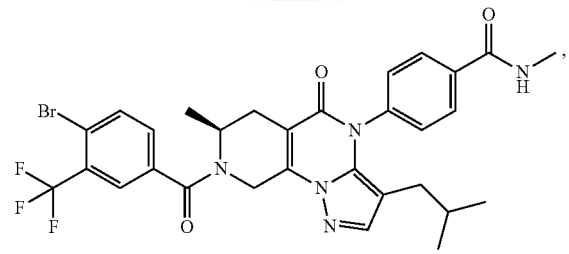
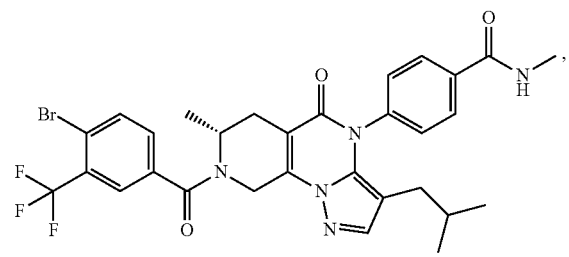
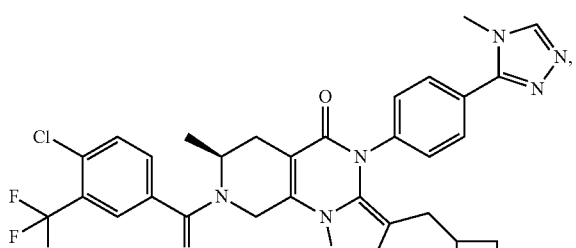
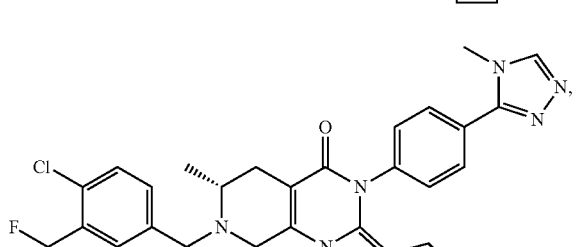
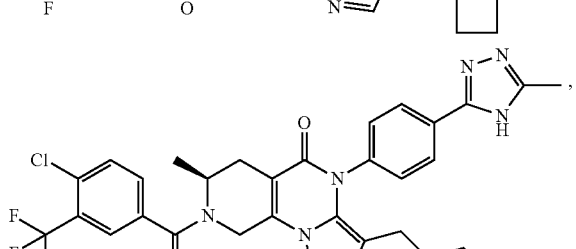
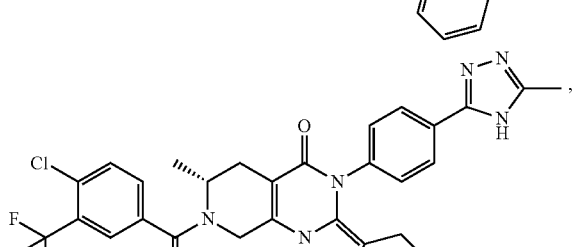
406
-continued
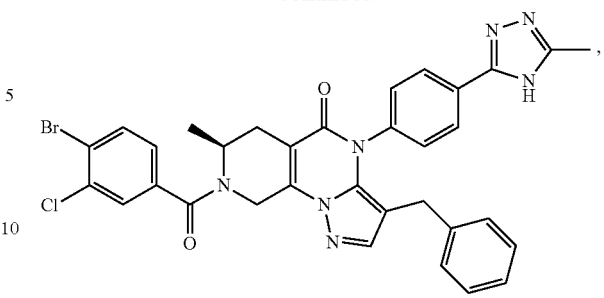
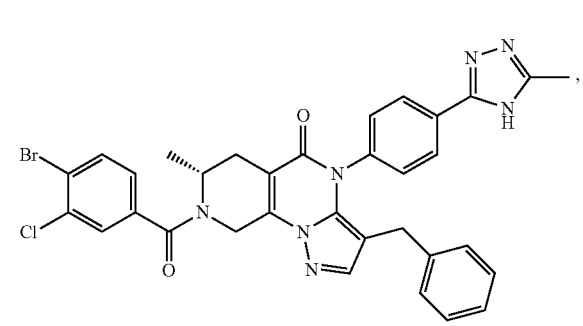
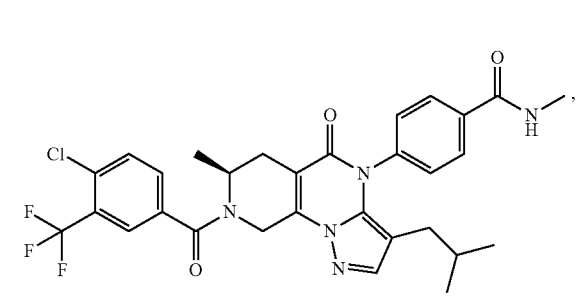
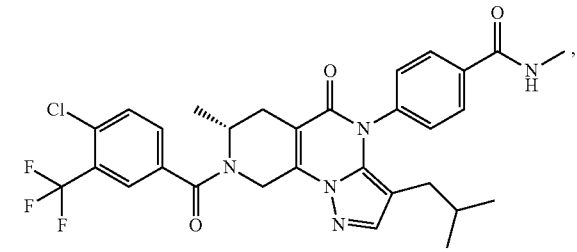
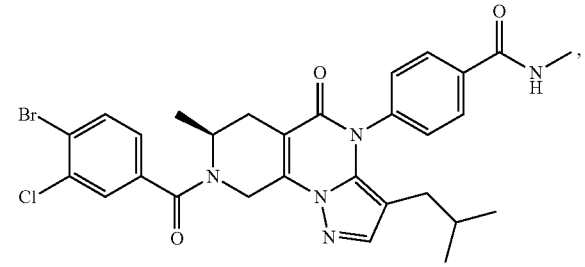
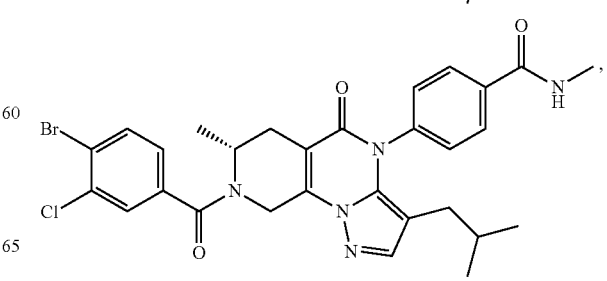

407
-continued
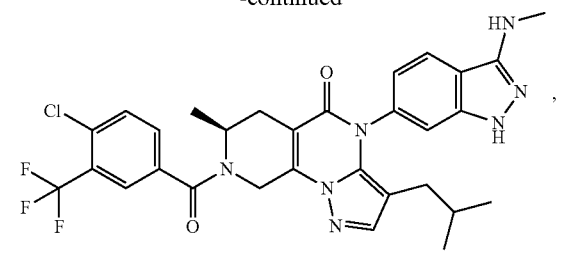
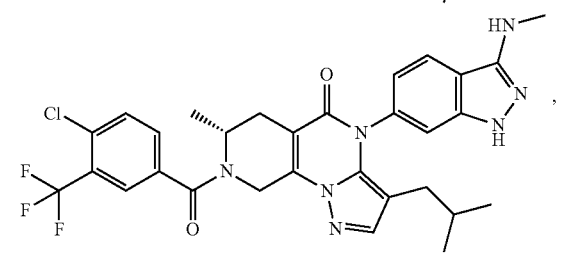
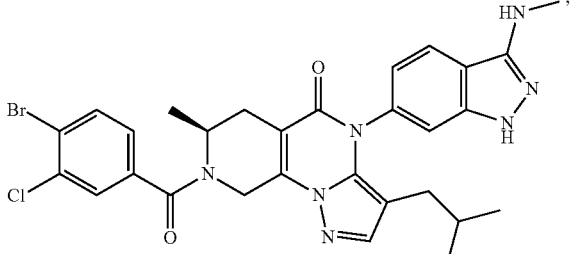
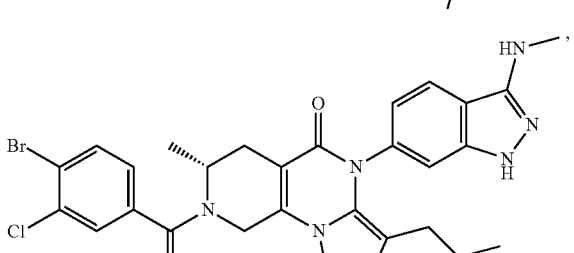
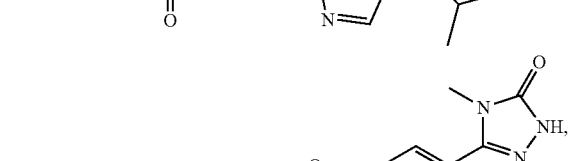
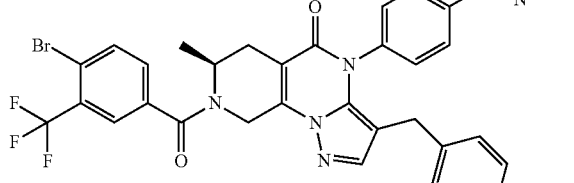
408
-continued
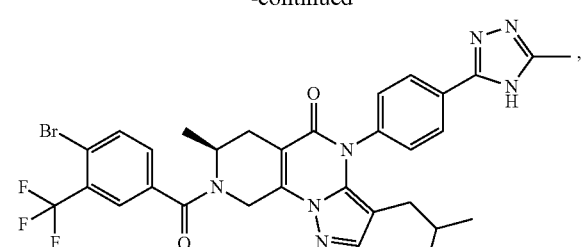
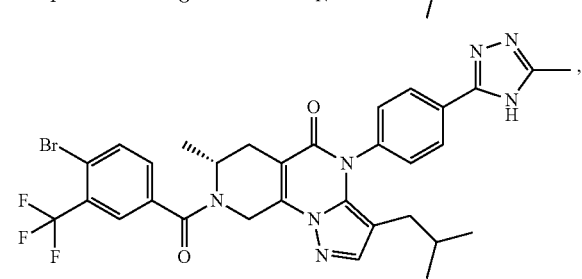
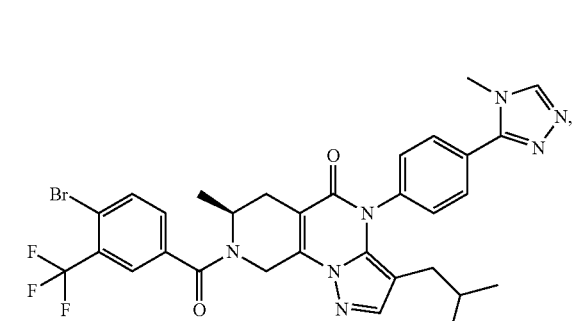
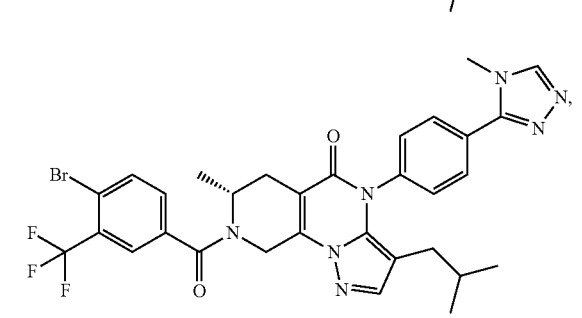
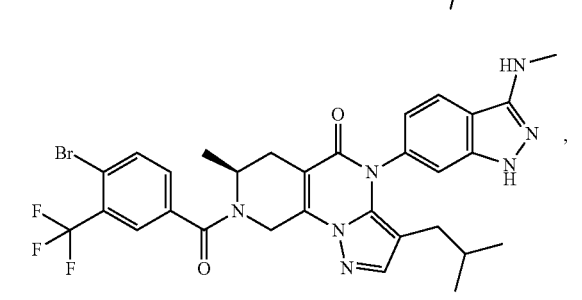
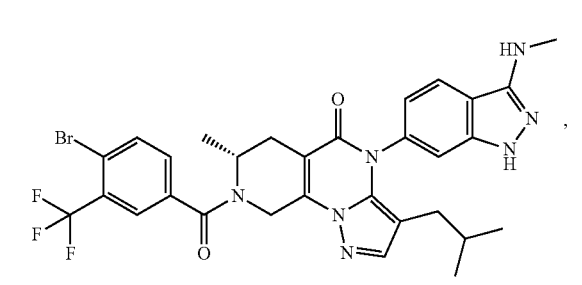

409
-continued
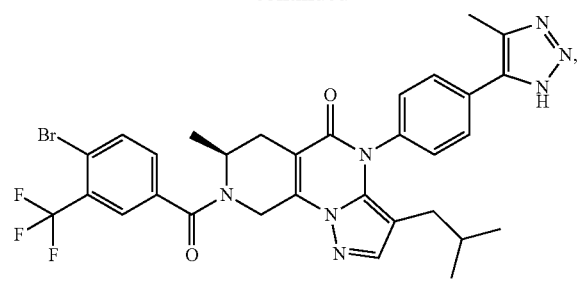
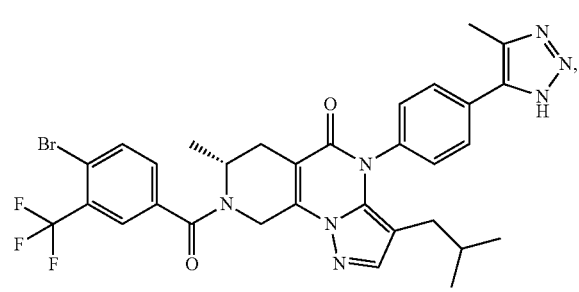
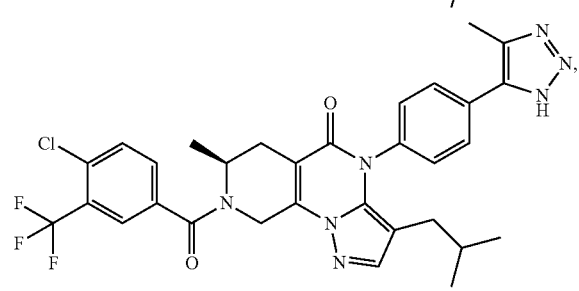
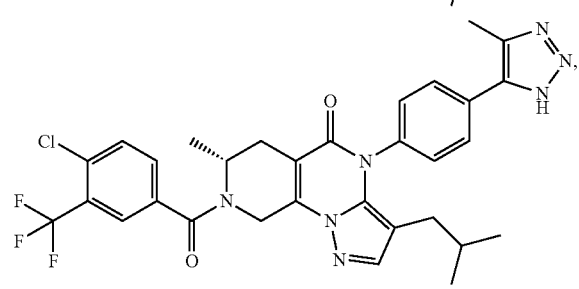
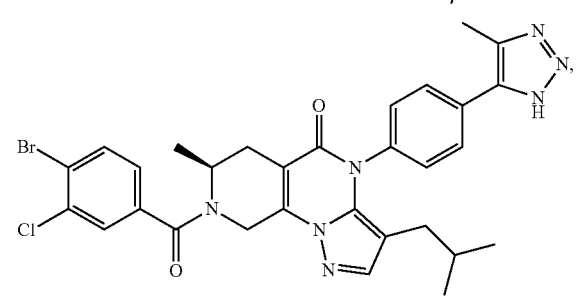
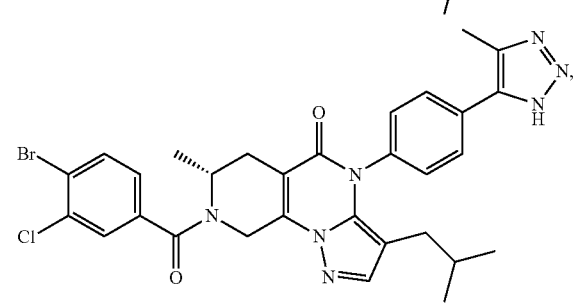
410
-continued
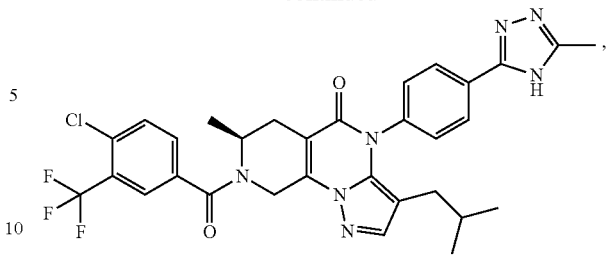
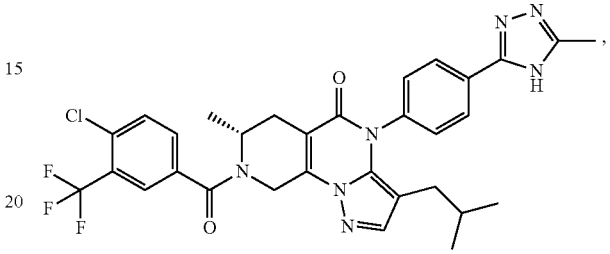
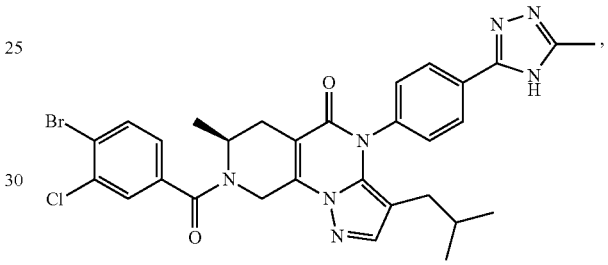
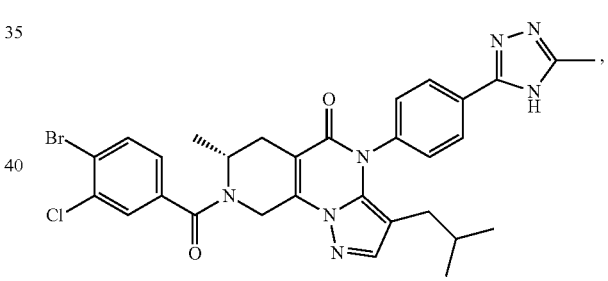
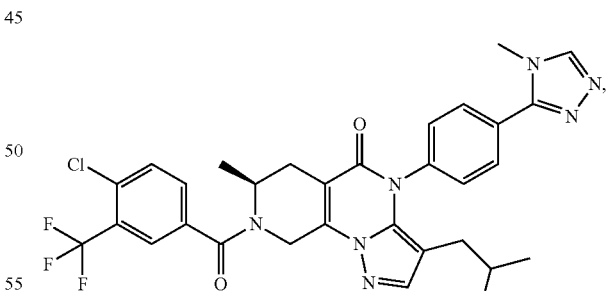
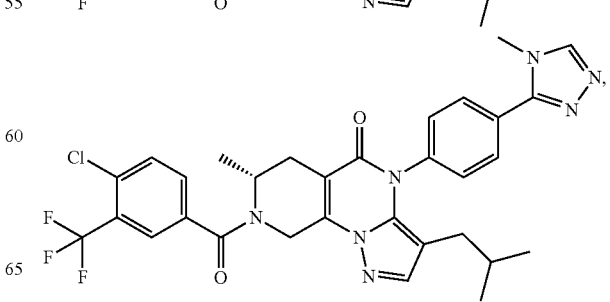

411
-continued
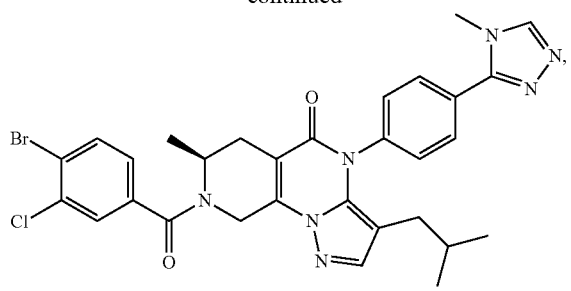
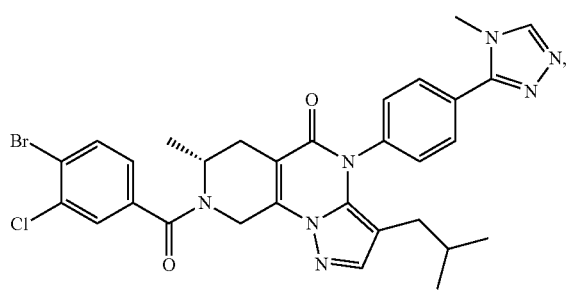
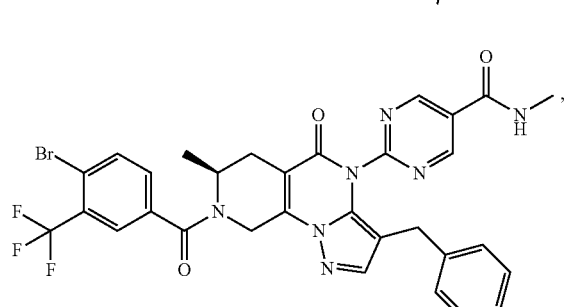
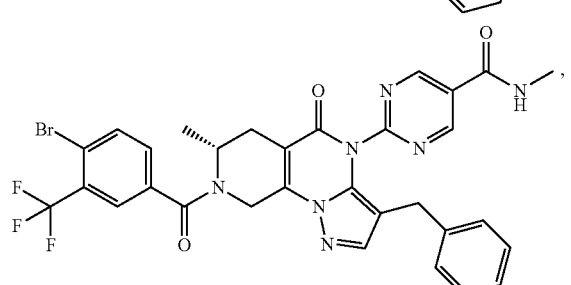
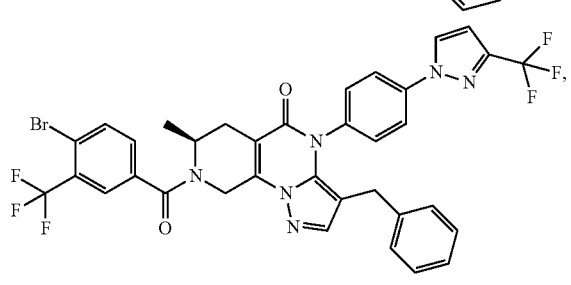
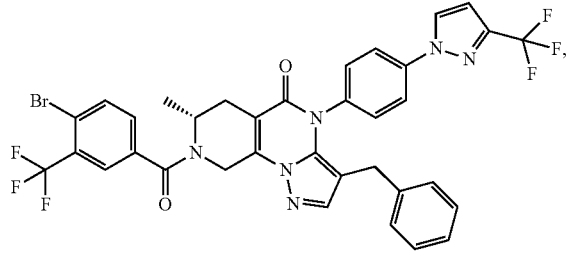
412
-continued
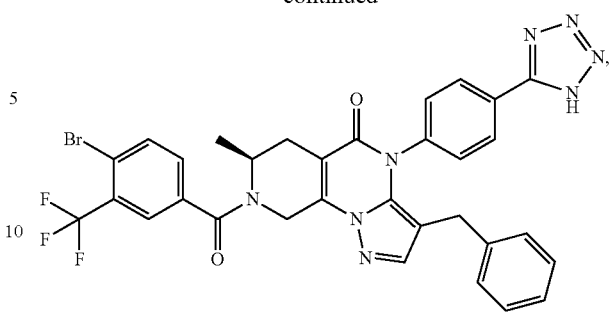
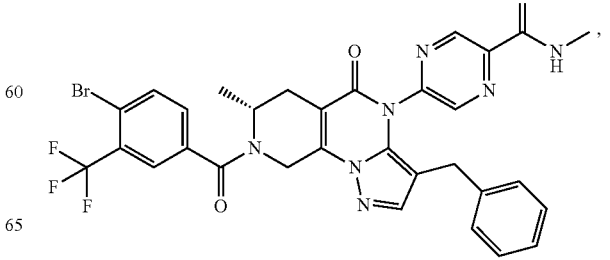

413
-continued
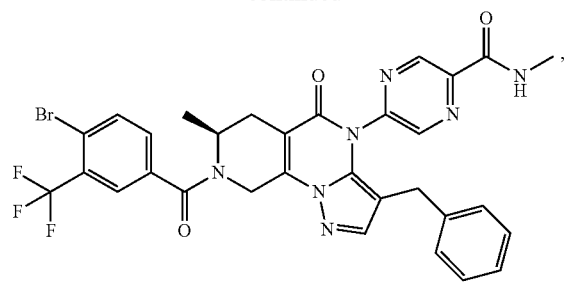
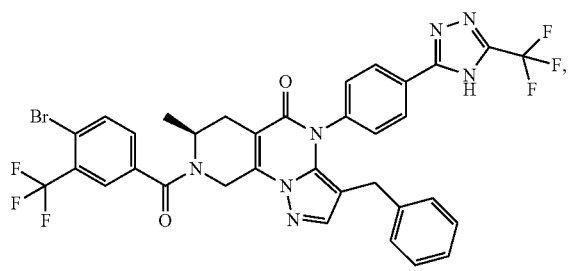
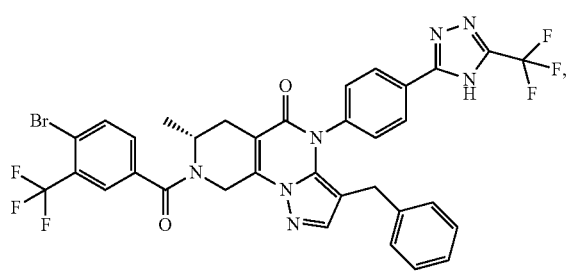
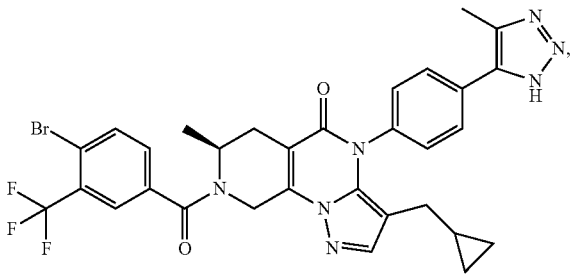
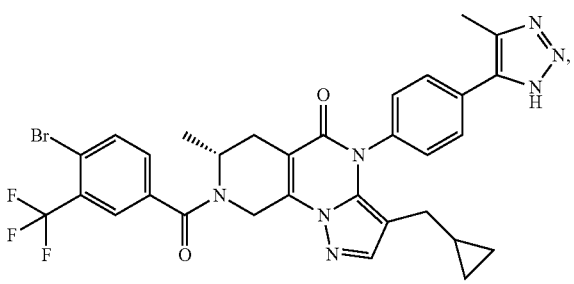
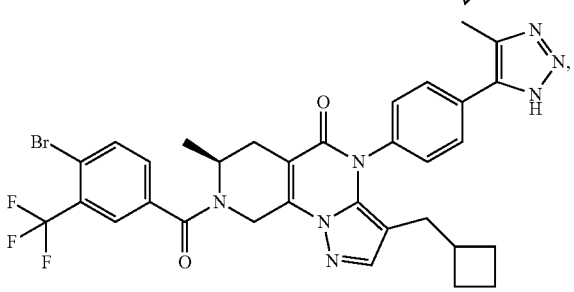
414
-continued
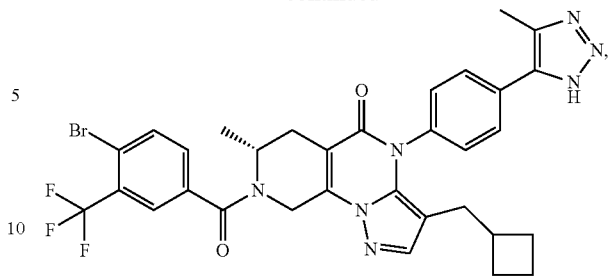
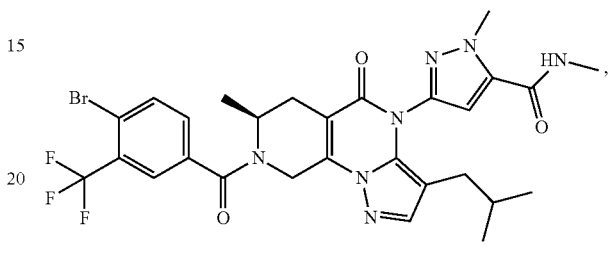
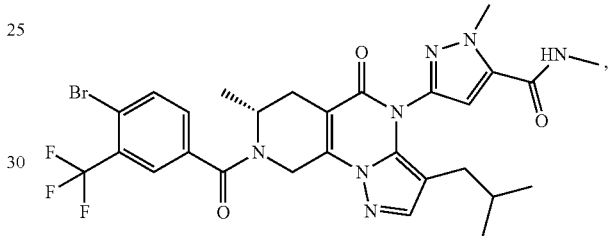
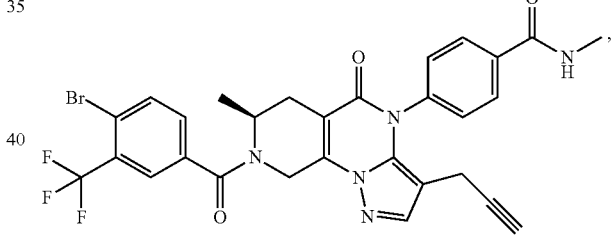
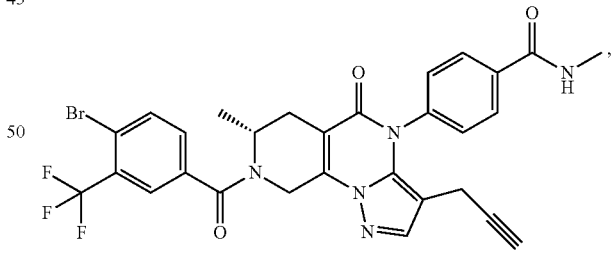
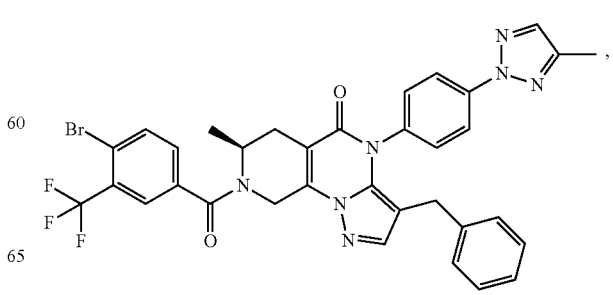

415
-continued
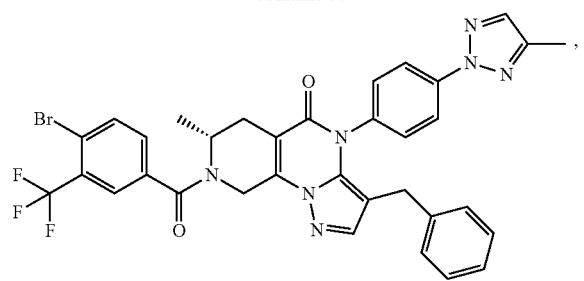
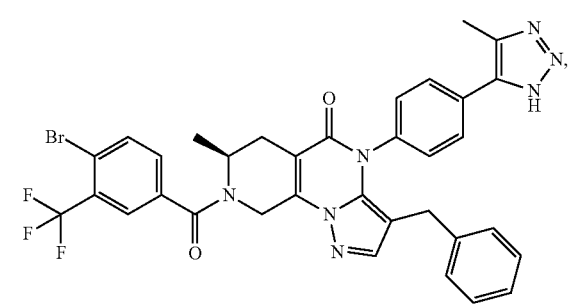
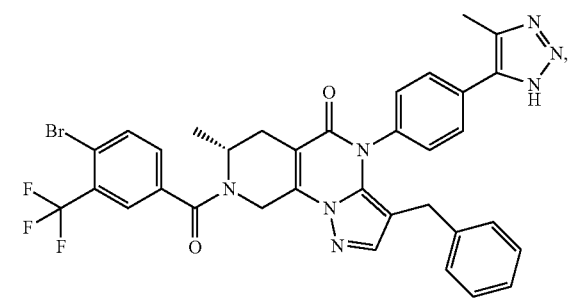
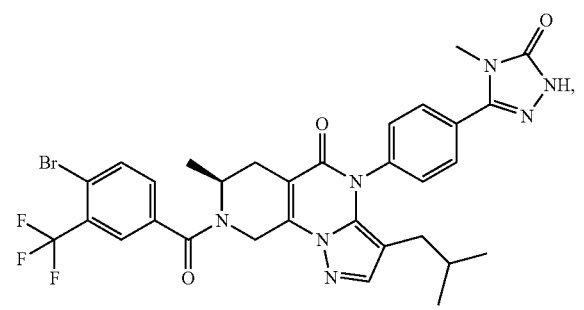
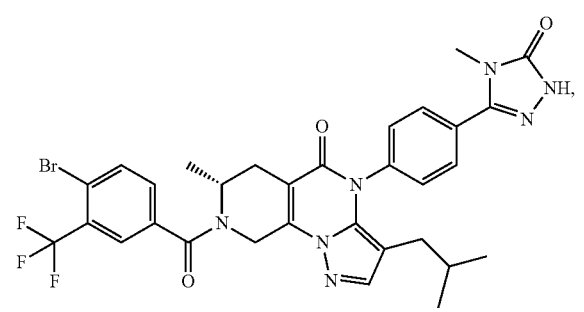
416
-continued
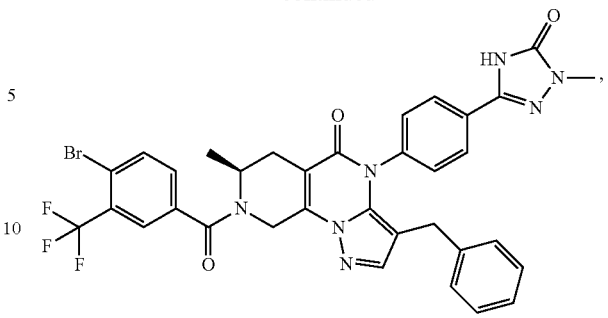
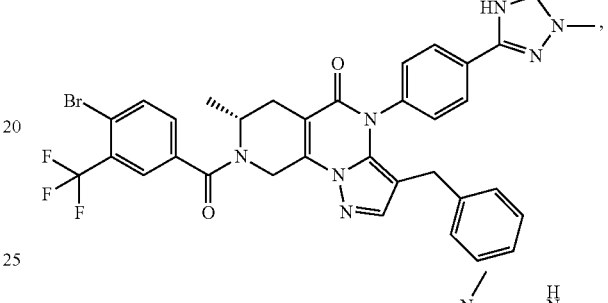
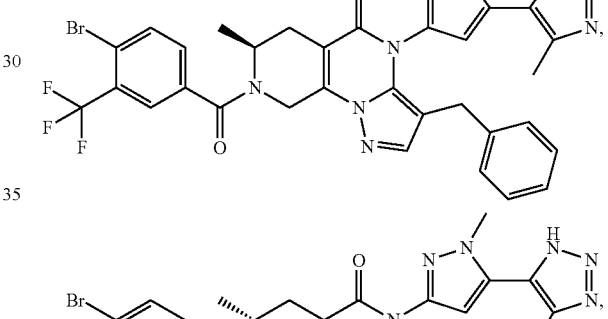
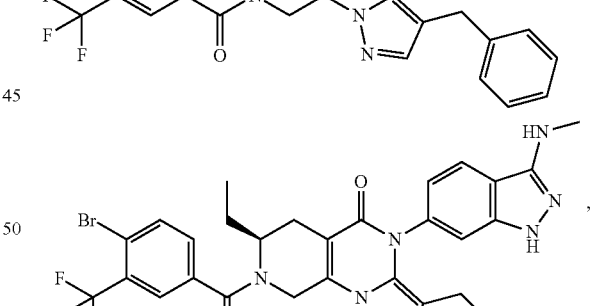
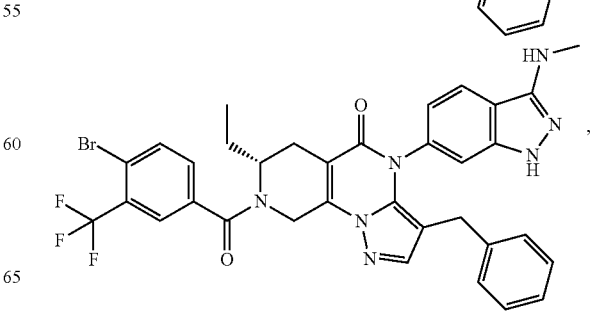

417
-continued
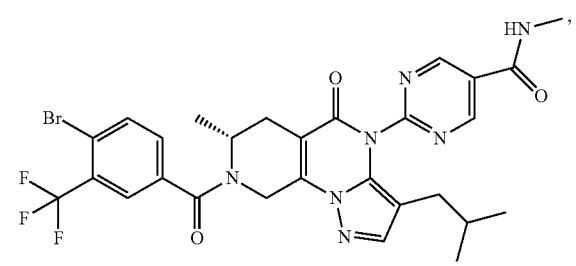
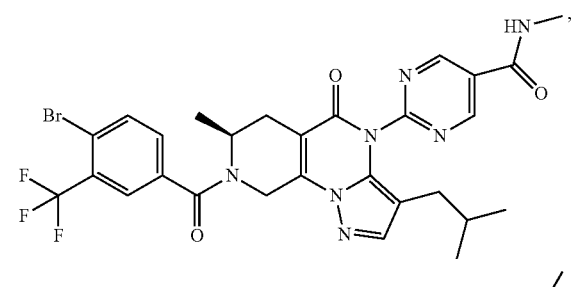
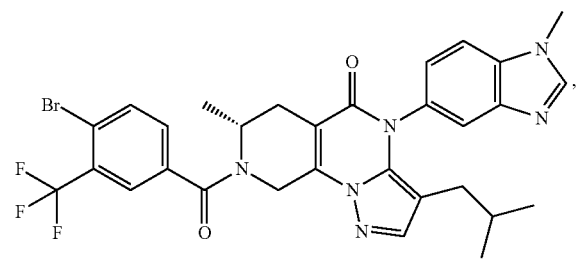
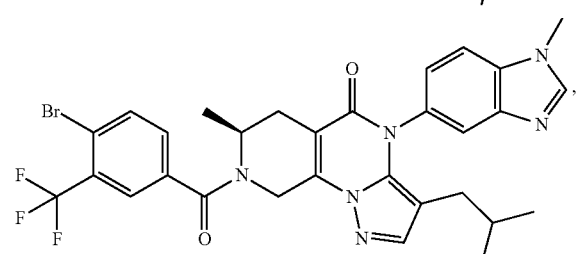
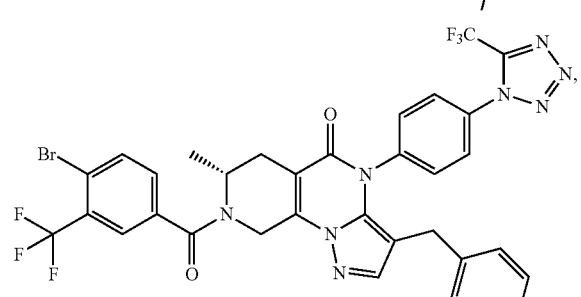
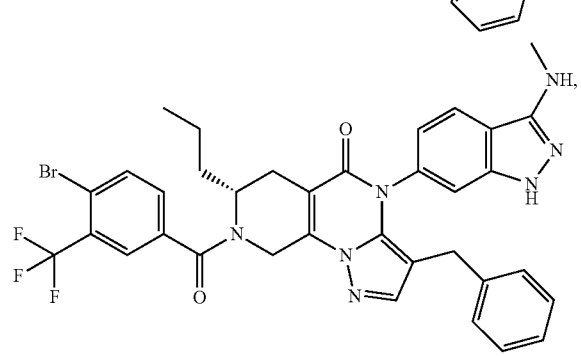
418
-continued
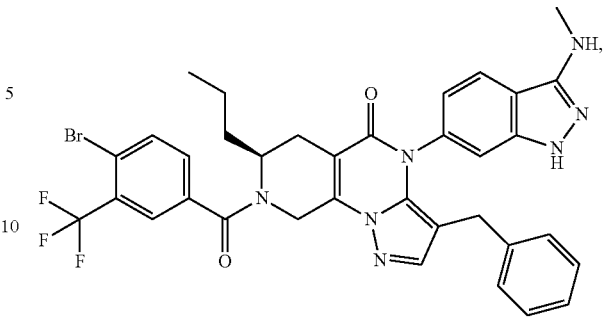
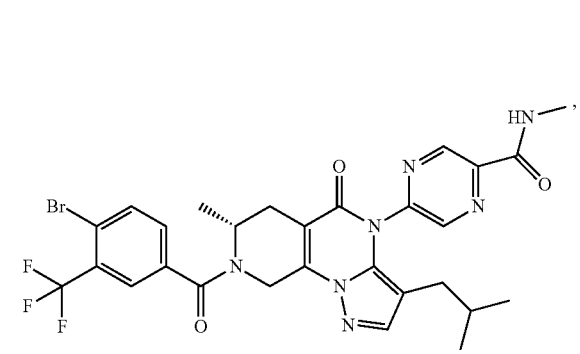
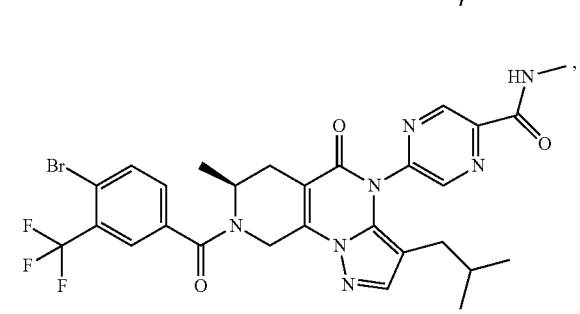
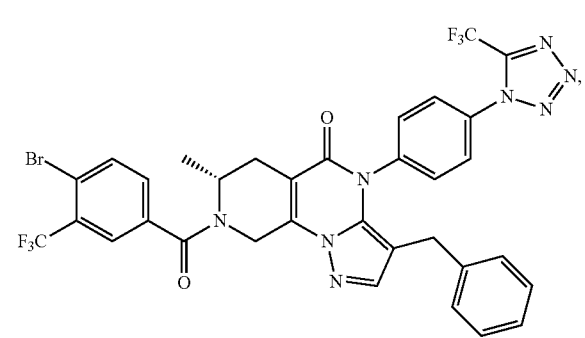
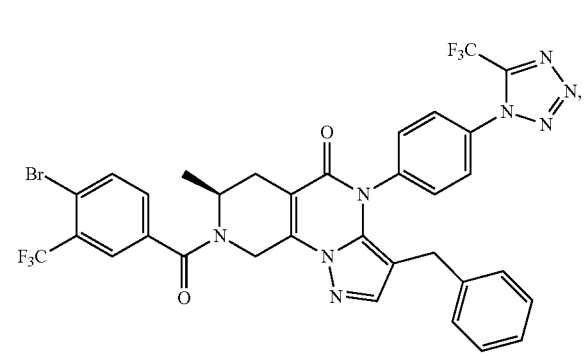

419
-continued
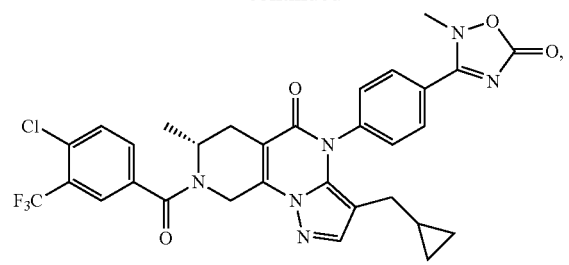
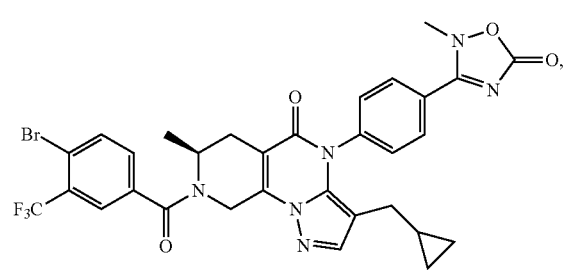
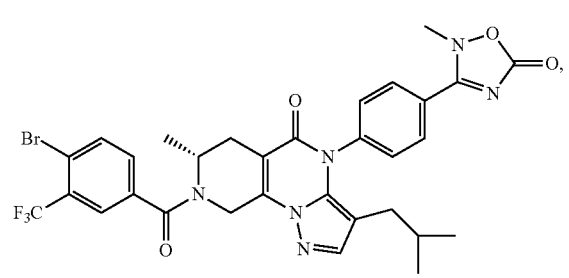
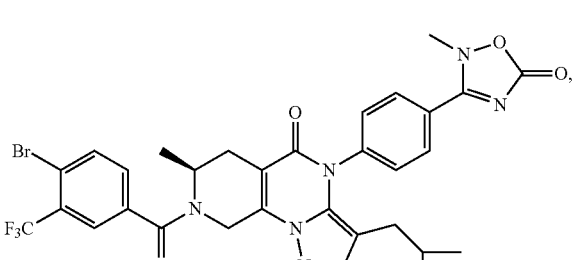
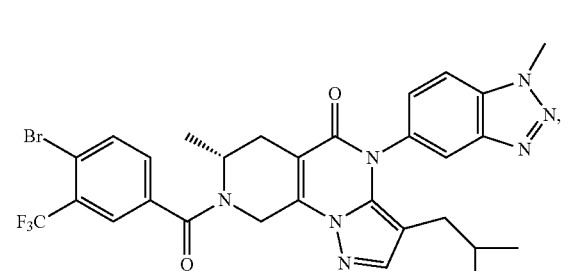
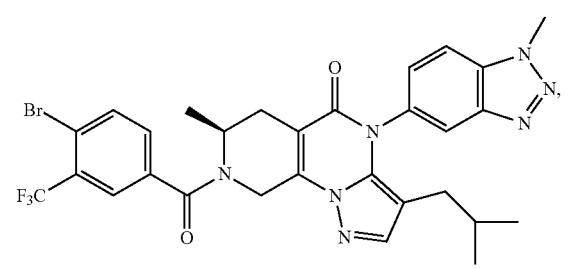
420
-continued
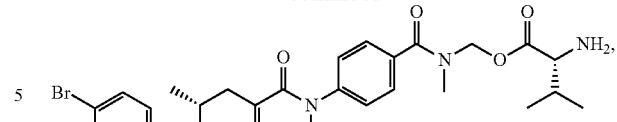
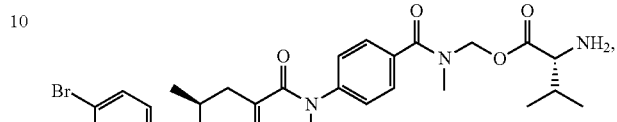
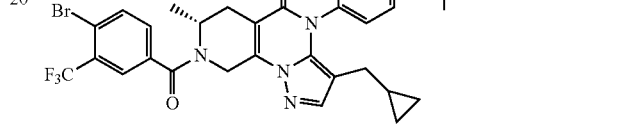
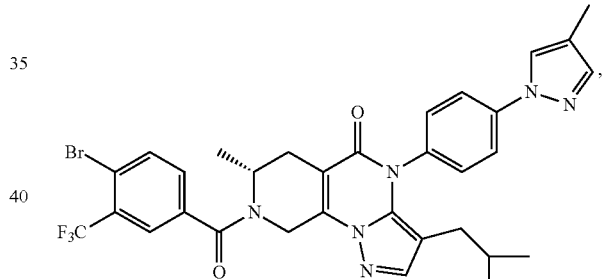
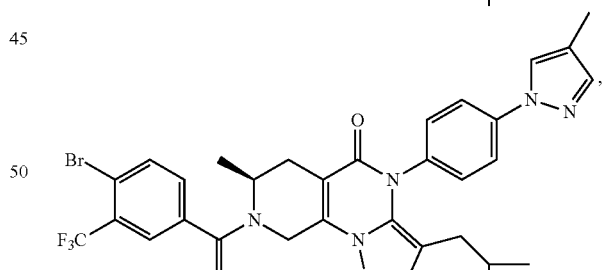
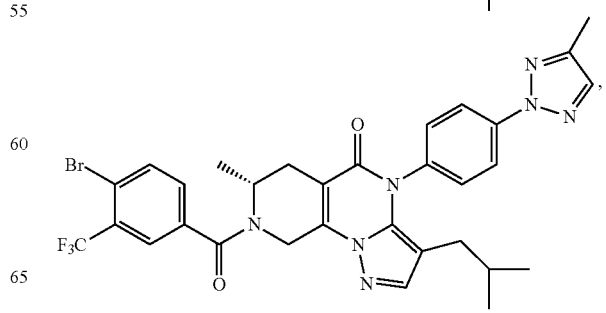

421
-continued
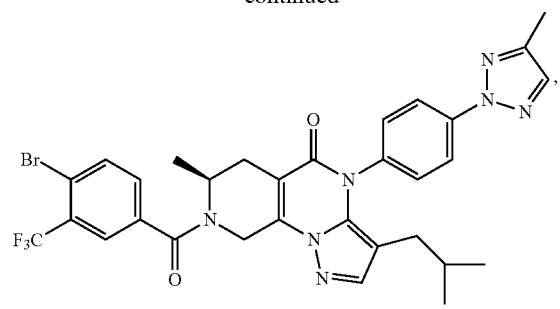
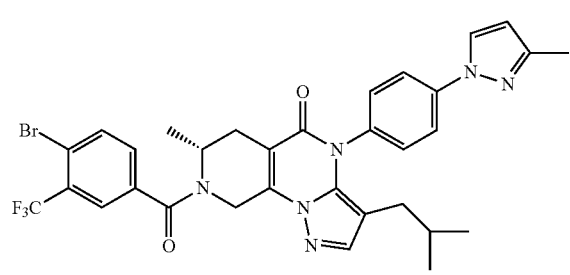
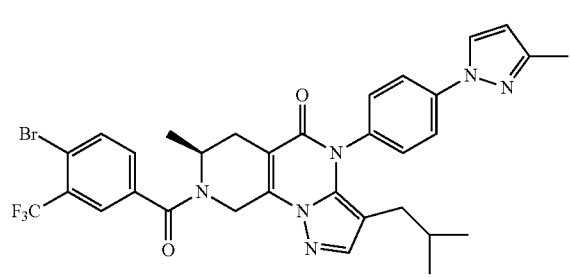
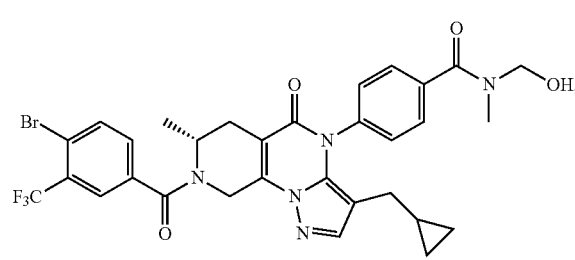
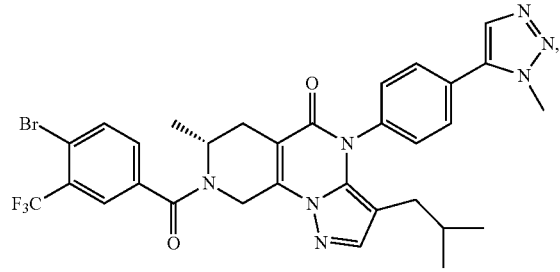
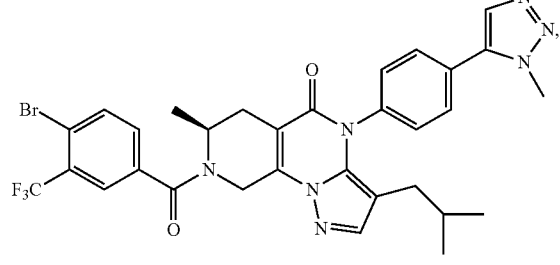
422
-continued
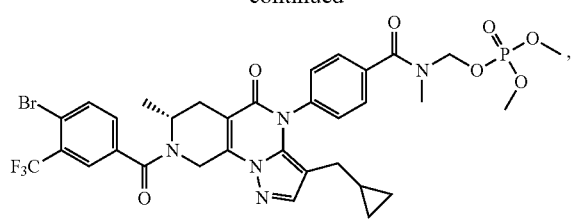
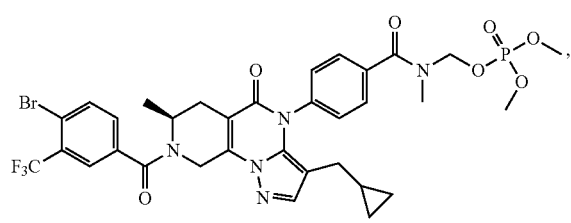
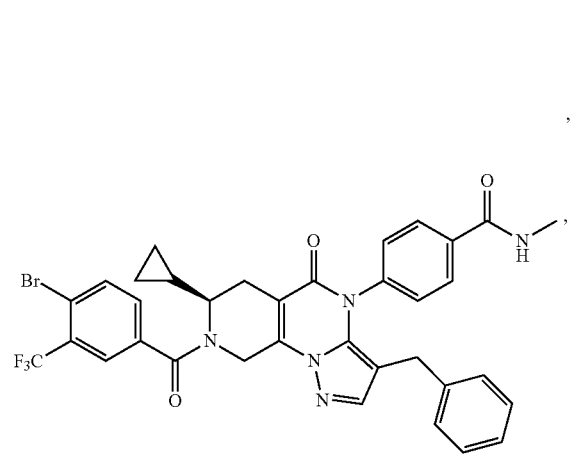
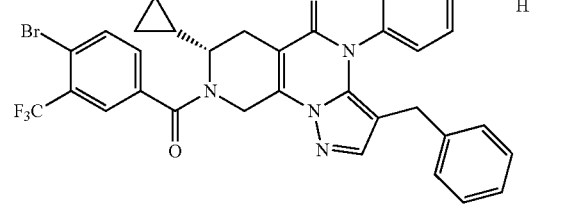
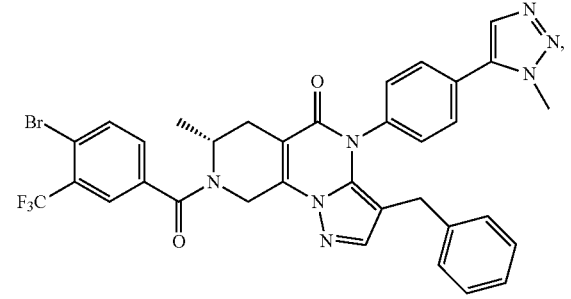

423
-continued
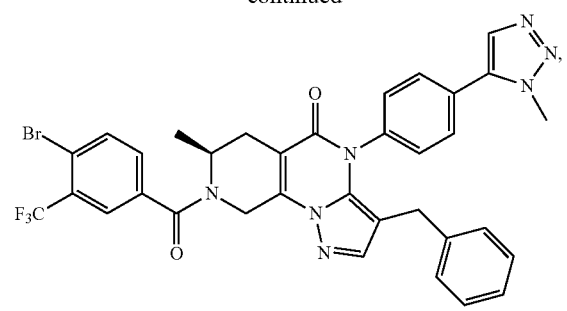
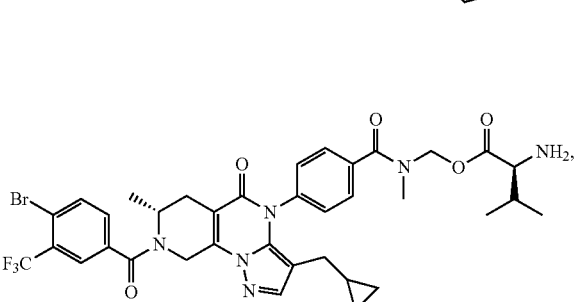
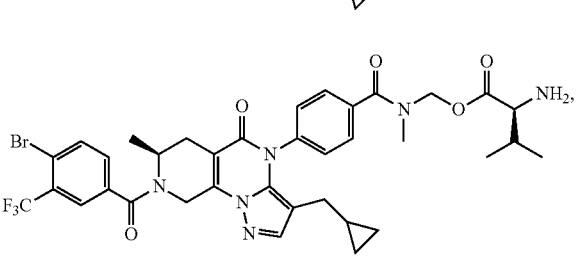
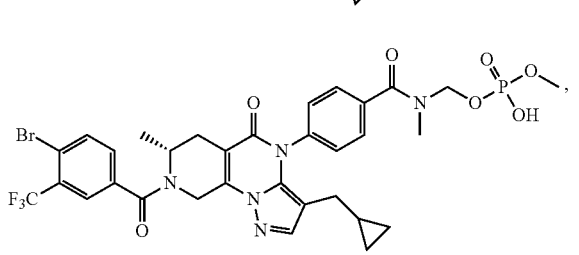
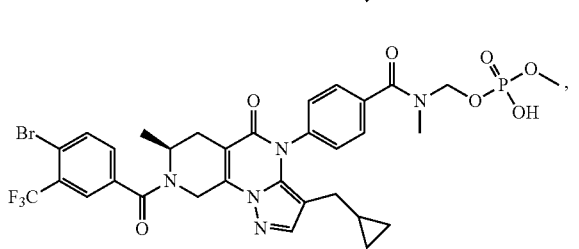
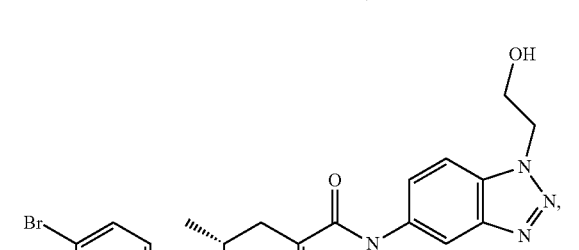
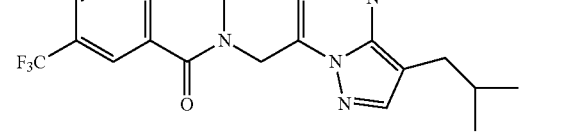
424
-continued
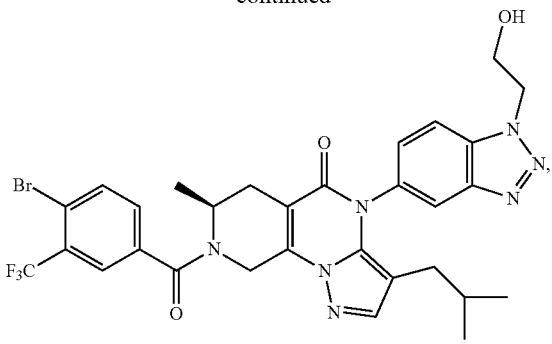
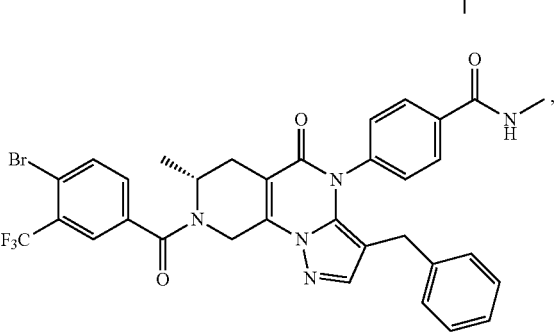
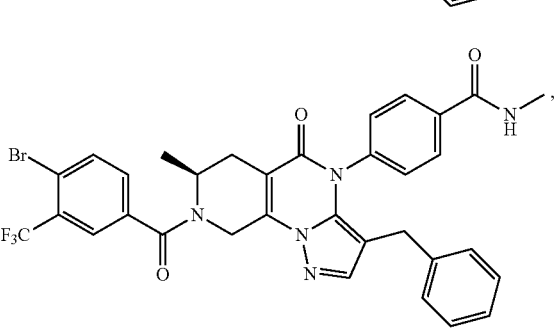
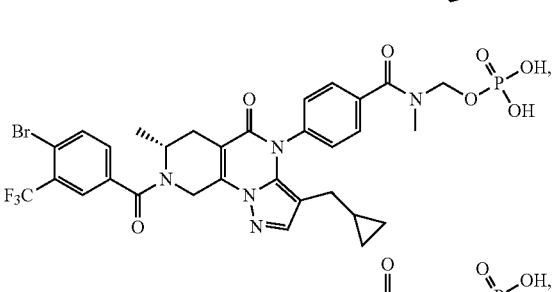
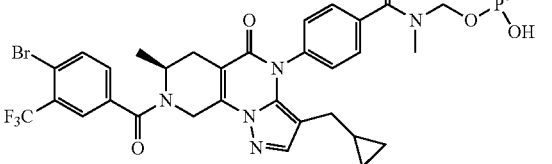
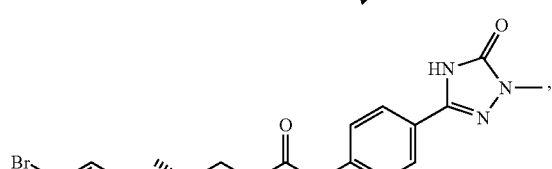
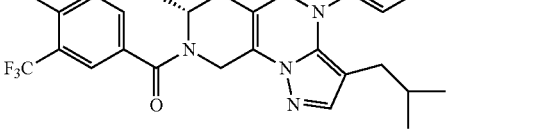

425
-continued
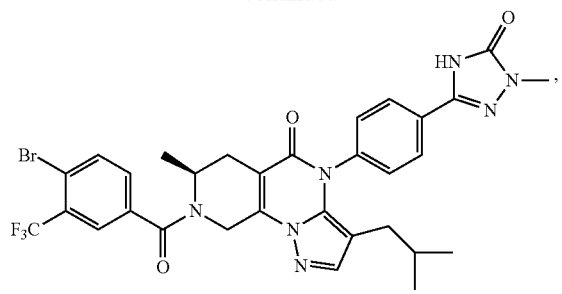
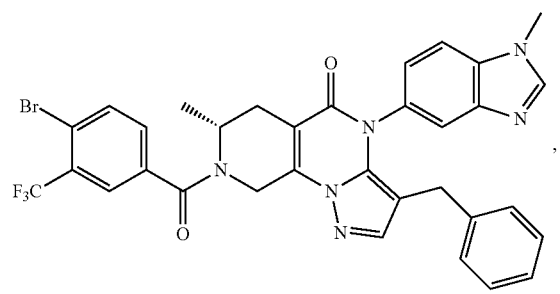
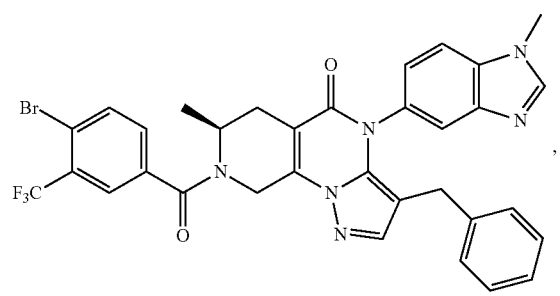
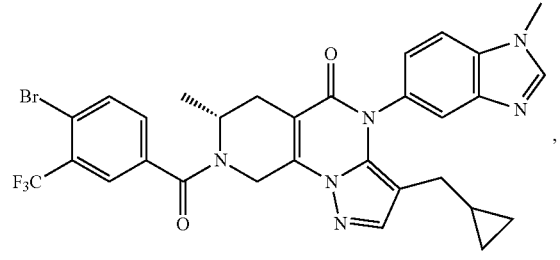
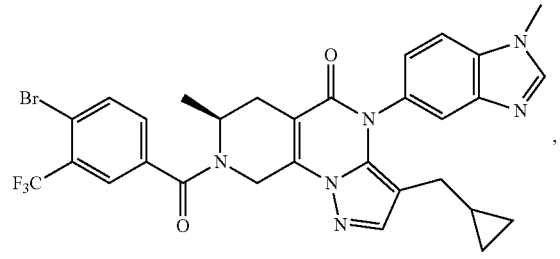
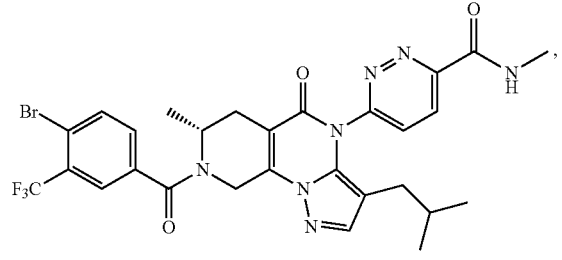
426
-continued
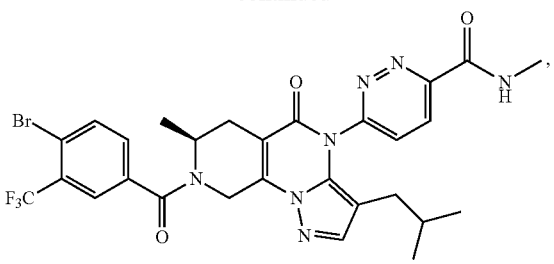
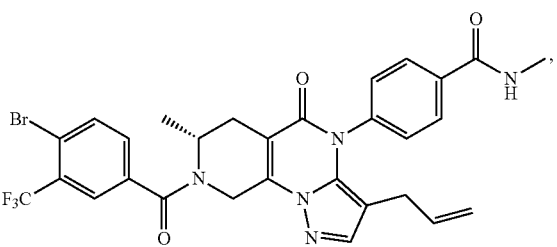
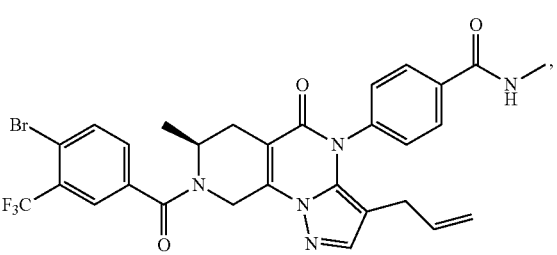
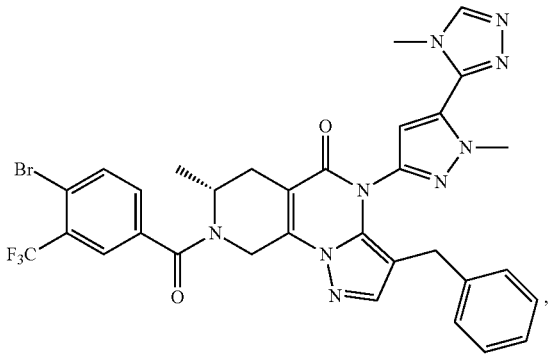
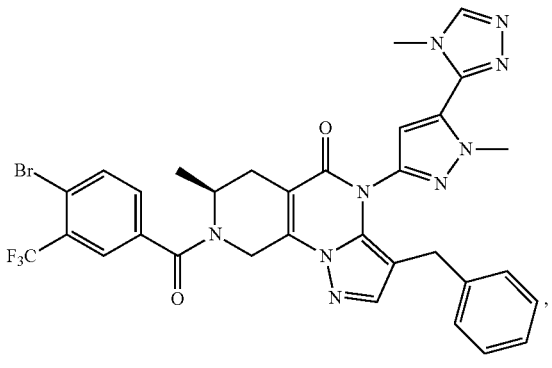

427
-continued
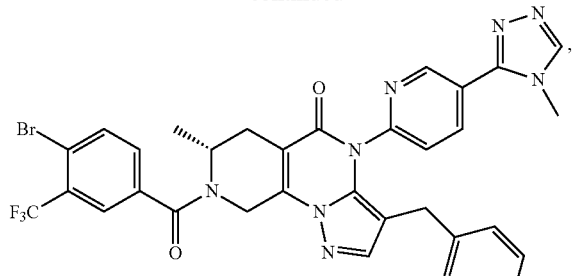
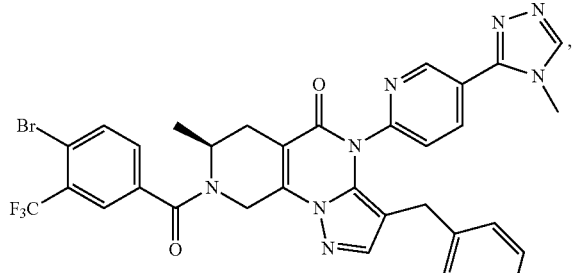
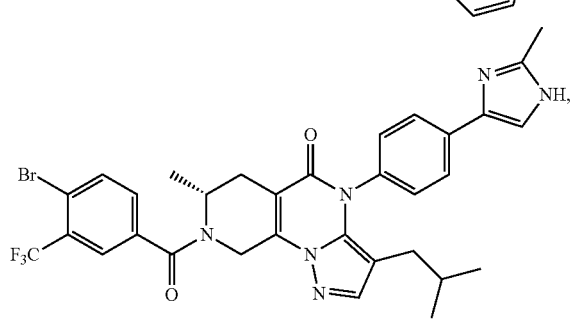
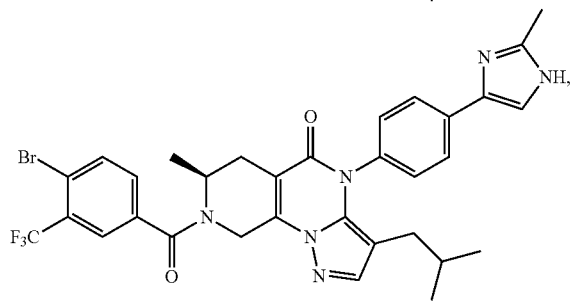
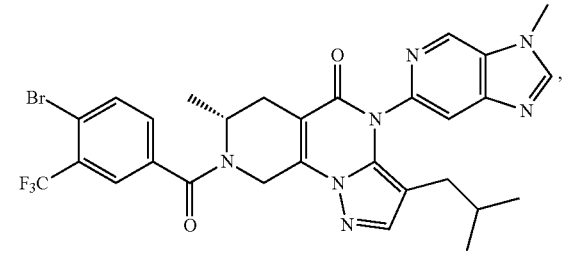
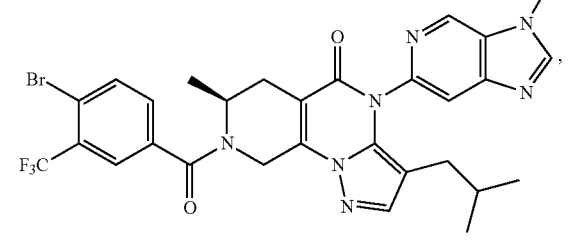
428
-continued
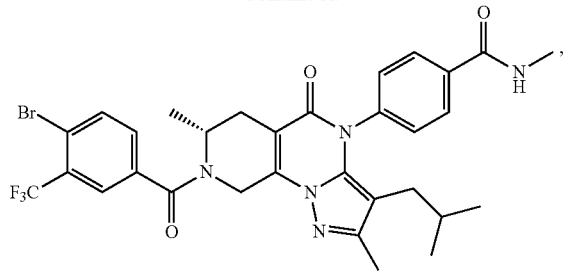
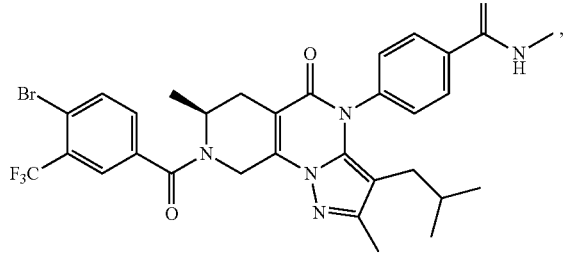
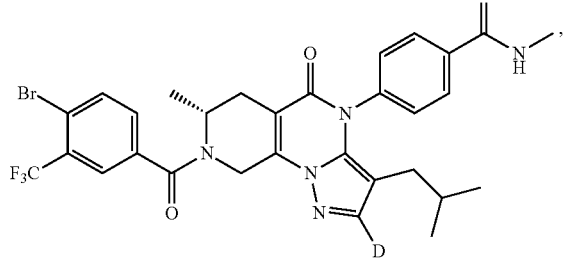
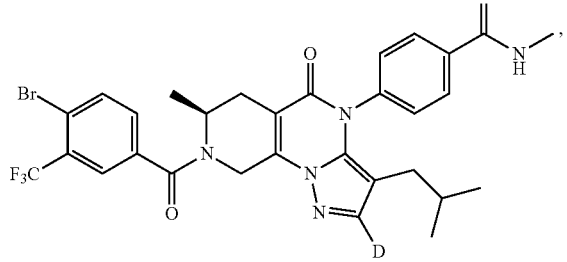
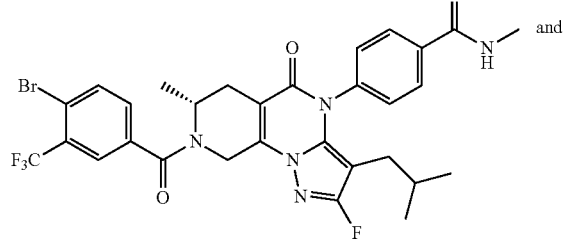
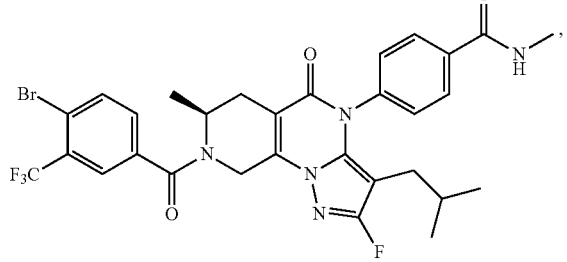
or a pharmaceutically acceptable salt of any of the foregoing.

18. A pharmaceutical composition comprising an effective amount of a compound of claim 1, or a pharmaceutically acceptable salt thereof, and excipient.

19. A method for treating hepatitis B in a subject comprising administering to the subject in need thereof an effective amount of a compound of claim 1, or a pharmaceutically acceptable salt thereof, suffering from hepatitis B.

20. A method for treating hepatitis D in a subject comprising administering to the subject in need thereof an effective amount of a compound of claim 1, or a pharmaceutically acceptable salt thereof, suffering from hepatitis D.

21. The method of claim 19, further comprising administering an additional agent selected from the group consisting of an interferon, a nucleoside analog, a nucleotide analog, a sequence specific oligonucleotide, a nucleic acid polymer, an entry inhibitor and a small molecule immunomodulator.

\* \* \* \* \*

UNITED STATES PATENT AND TRADEMARK OFFICE
CERTIFICATE OF CORRECTION

PATENT NO. : 11,820,773 B2
APPLICATION NO. : 17/456106
DATED : November 21, 2023
INVENTOR(S) : Sandrine Vendeville et al.

It is certified that error appears in the above-identified patent and that said Letters Patent is hereby corrected as shown below:

On the Title Page

Column 2 (Other Publications), Line 4, delete "7.Liang," and insert -- Liang, --.

In the Specification

Column 4, Line 59, delete "benzoisoxazole, benzoisothiazole," and insert -- benzisoxazole, benzisothiazole, --.

Column 5, Line 18 (Approx.), delete ""heterocyclyl" and insert -- heterocyclyl --.

Column 7, Line 21-22, delete ""$X_3CS(O)_2N(R^A)$—"" and insert -- "$X_3CS(O)_2N(R_A)$—" --.

Column 7, Line 22, delete "$R^A$" and insert -- $R_A$ --.

Column 7, Line 36, delete ""—$SO_2N(R^A R^B)$"" and insert -- "—$SO_2N(R_A R_B)$" --.

Column 7, Line 37, delete "$R^A$ and $R^B$" and insert -- $R_A$ and $R_B$ --.

Column 7, Line 42, delete ""$RSO_2N(R^A)$—"" and insert -- "$RSO_2N(R_A)$—" --.

Column 7, Line 43, delete "$R^A$" and insert -- $R_A$ --.

Column 7, Line 48-49, delete ""—$OC(=O)N(R^A R^B)$"" and insert -- "—$OC(=O)N(R_A R_B)$" --.

Column 7, Line 49, delete "$R^A$ and $R^B$" and insert -- $R_A$ and $R_B$ --.

Column 7, Line 54-55, delete ""$ROC(=O)N(R^A)$—"" and insert -- "$ROC(=O)N(R_A)$—" --.

Column 7, Line 55, delete "$R^A$" and insert -- $R_A$ --.

Signed and Sealed this
First Day of October, 2024

*Katherine Kelly Vidal*

Katherine Kelly Vidal
*Director of the United States Patent and Trademark Office*

Column 7, Line 60-61, delete ""—OC(=S)—N(R$^A$R$^B$)"" and insert -- "—OC(=S)—N(R$_A$R$_B$)" --.

Column 7, Line 61, delete "R$^A$ and R$^B$" and insert -- R$_A$ and R$_B$ --.

Column 7, Line 66-67, delete ""ROC(=S)N(R$^A$)—"" and insert -- "ROC(=S)N(R$_A$)—" --.

Column 7, Line 67, delete "R$^A$" and insert -- R$_A$ --.

Column 8, Line 5, delete ""—C(=O)N(R$^A$R$^B$)"" and insert -- "—C(=O)N(R$_A$R$_B$)" --.

Column 8, Line 6, delete "R$^A$ and R$^B$" and insert -- R$_A$ and R$_B$ --.

Column 8, Line 11, delete ""RC(=O)N(R$^A$)—"" and insert -- "RC(=O)N(R$_A$)—" --.

Column 8, Line 12, delete "R$^A$" and insert -- R$_A$ --.

Column 8, Line 17, delete ""—NHR$^A$"" and insert -- "—NHR$_A$" --.

Column 8, Line 18, delete "R$^A$" and insert -- R$_A$ --.

Column 8, Line 22, delete "—NHR$^A$," and insert -- —NHR$_A$, --.

Column 8, Line 23, delete "R$^A$" and insert -- R$_A$ --.

Column 8, Line 25, delete ""—NR$^A$R$^B$"" and insert -- "—NR$_A$R$_B$" --.

Column 8, Line 26, delete "R$^A$ and R$^B$" and insert -- R$_A$ and R$_B$ --.

Column 8, Line 31, delete "—NR$^A$R$^B$, wherein R$^A$ and R$^B$" and insert -- —NR$_A$R$_B$, wherein R$_A$ and R$_B$ --.

Column 21, Line 12-18, delete " 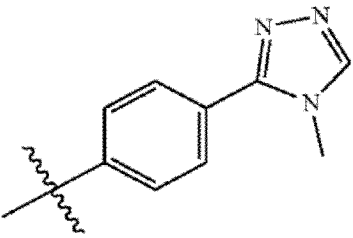 " and insert 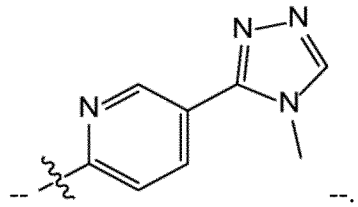 --.

Column 128, Line 5 (approx.), delete "tetrazacyclo" and insert -- tetrazatricyclo --.

Column 129, Line 30 (approx.), delete "3-phenylpropanitrile" and insert -- 3-phenylpropanenitrile --.

Column 142, Line 67, delete "6-7" and insert -- 6~7 --.

Column 144, Line 41 (approx.), delete "[7.4.0.0"2,6]" and insert -- [7.4.0.0^2,6] --.

Column 156, Line 26, delete "6.79-7.72" and insert -- δ 0.79-7.72 --.

Column 168, Line 17, delete "-{13-" and insert -- -{3- --.

Column 168, Line 22, delete "-{13-" and insert -- -{3- --.

Column 168, Line 28, delete "-{11-" and insert -- -{1- --.

Column 168, Line 54, delete "-{11-" and insert -- -{1- --.

Column 172, Line 62, delete "-{15-" and insert -- -{5- --.

Column 173, Line 20 (approx.), delete "-{15-" and insert -- -{5- --.

Column 178, Line 37, delete "TFA]±." and insert -- TFA]+. --.

Column 182, Line 17 (Approx.), delete "1, 1'-" and insert -- 1,1'- --.

Column 183, Line 46-47, delete "1-hydroxybenzotrizole" and insert -- 1-hydroxybenzotriazole --.

Column 188, Line 25 (approx.), delete "-{15-" and insert -- -{5- --.

Column 188, Line 30 (approx.), delete "-{15-" and insert -- -{5- --.

Column 193, Line 6 (approx.), delete "TFA]±." and insert -- TFA]+. --.

Column 193, Line 13 (approx.), delete "1-hydroxybenzotrizole" and insert -- 1-hydroxybenzotriazole --.

Column 199, Line 2, delete "-{14-" and insert -- -{4- --.

Column 203, Line 44, delete "-{15-" and insert -- -{5- --.

Column 207, Line 56, delete "-{12-" and insert -- -{2- --.

Column 212, Line 39, delete "TFA]±." and insert -- TFA]+. --.

Column 212, Line 41-42, delete "trifluroacetic" and insert -- trifluoroacetic --.

CERTIFICATE OF CORRECTION (continued)
U.S. Pat. No. 11,820,773 B2

Column 217, Line 53, delete "[M+H]+" and insert -- [M+H]$^+$. --.

Column 219, Line 32, delete "HCl]+" and insert -- HCl]$^+$. --.

Column 222, Line 10-11, delete "4-methylpentanitrile" and insert -- 4-methylpentanenitrile --.

Column 222, Line 13, delete "4-methylpentanitrile" and insert -- 4-methylpentanenitrile --.

Column 223, Line 40, delete "(2-3" and insert -- (2~3 --.

Column 224, Line 58, delete "TFA+H]±." and insert -- TFA+H]$^+$. --.

Column 230, Line 41 (Approx.), delete "[M+H]+" and insert -- [M+H]$^+$. --.

Column 231, Line 52 (Approx.), delete "-{15-" and insert -- -{5- --.

Column 231, Line 58 (Approx.), delete "-{15-" and insert -- -{5- --.

Column 232, Line 20 (Approx.), delete "-{15-" and insert -- -{5- --.

Column 236, Line 30 (Approx.), delete "H]±." and insert -- H]$^+$. --.

Column 246, Line 54 (Approx.), delete "Pd(dppf)Cl$_2$," and insert -- Pd(PPh$_3$)$_2$Cl$_2$, --.

Column 248, Line 52, delete "the" and insert -- ether --.

Column 249, Line 39-40, delete "4-bromophenylboric" and insert -- 4-bromophenylboronic --.

Column 333, Line 48, delete "doxcycyline" and insert -- doxycycline --.

In the Claims

Column 361, Line 37-46, Claim 16, delete

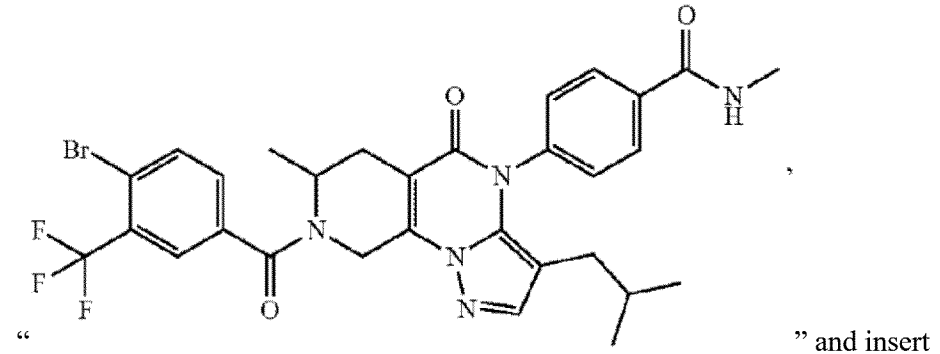

" and insert

CERTIFICATE OF CORRECTION (continued)
U.S. Pat. No. 11,820,773 B2

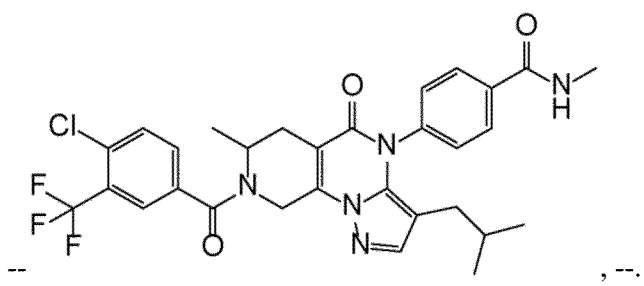

--    , --.

Column 365, Line 34-42, Claim 16, delete

"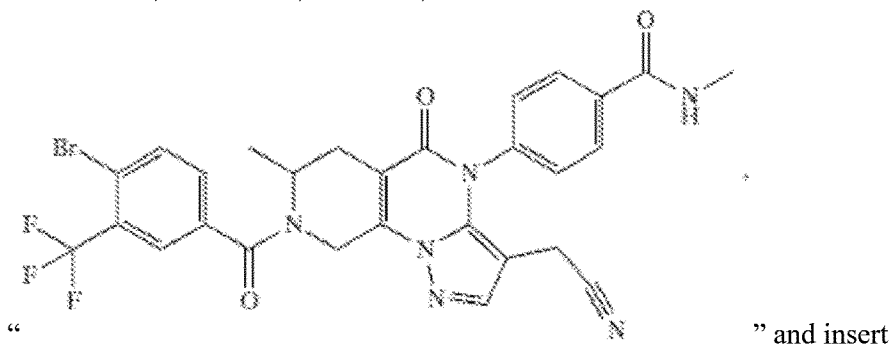" and insert

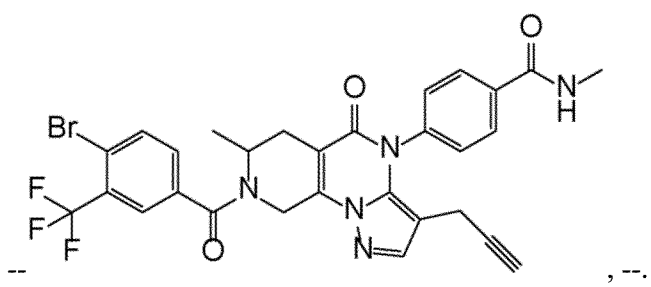

--    , --.

Column 377, Line 1-11, Claim 16, delete

"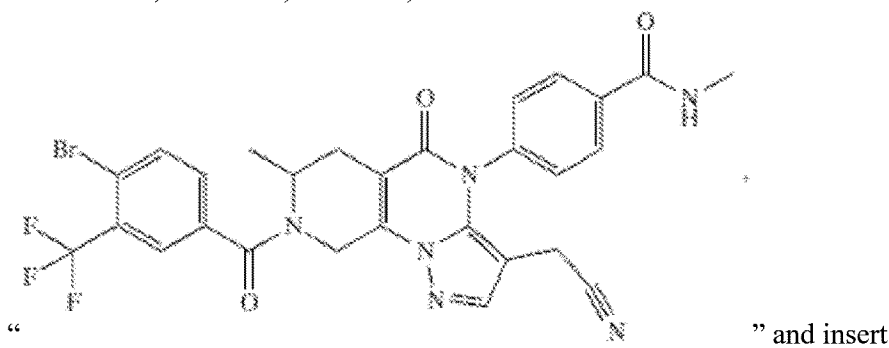" and insert

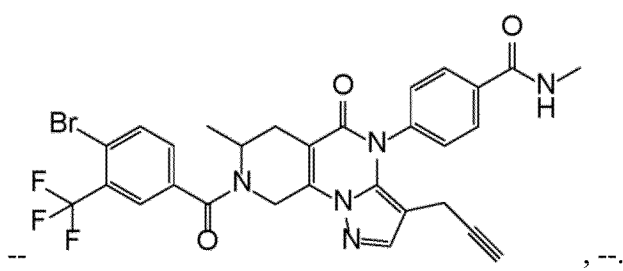

--    , --.

CERTIFICATE OF CORRECTION (continued)
U.S. Pat. No. 11,820,773 B2

Column 384, Line 6-16, Claim 17, delete "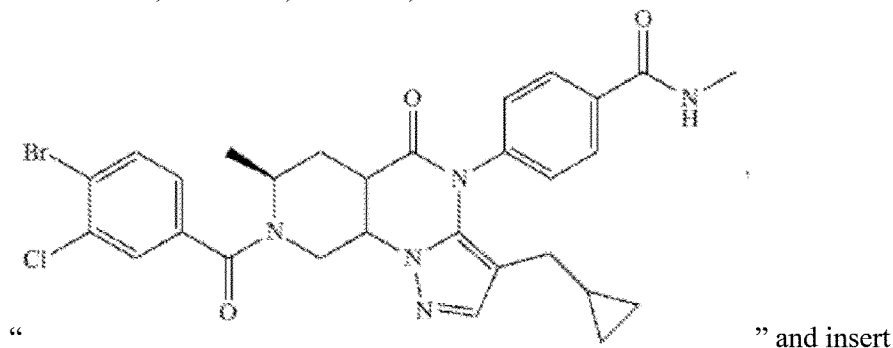" and insert

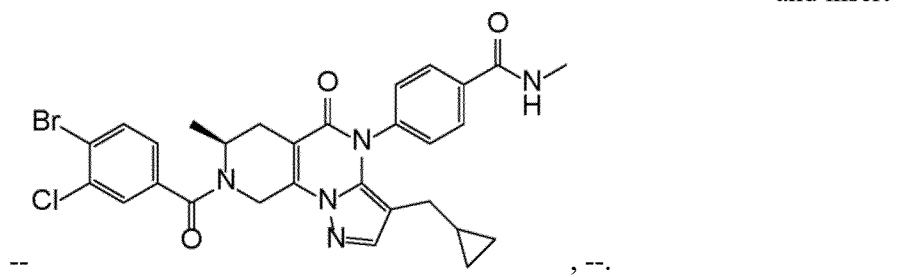 , --.

Column 384, Line 16-26, Claim 17, delete "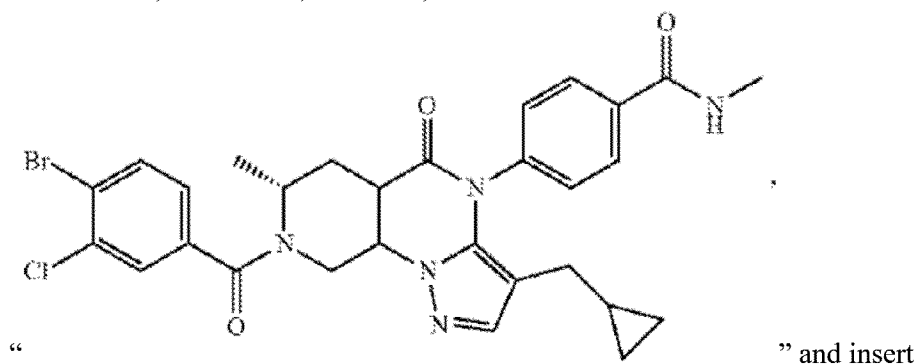" and insert

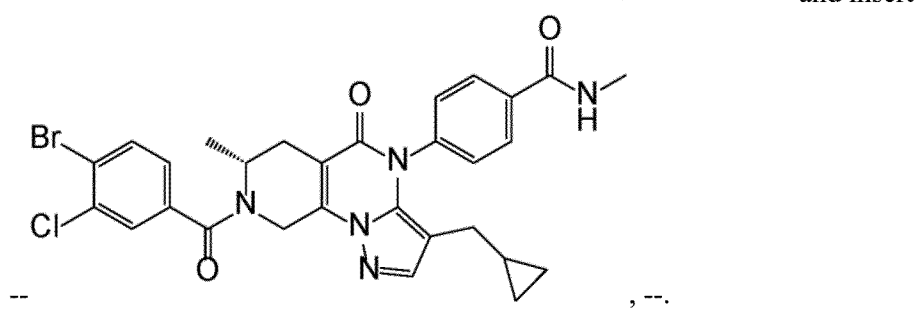 , --.

Column 384, Line 27-36, Claim 17, delete
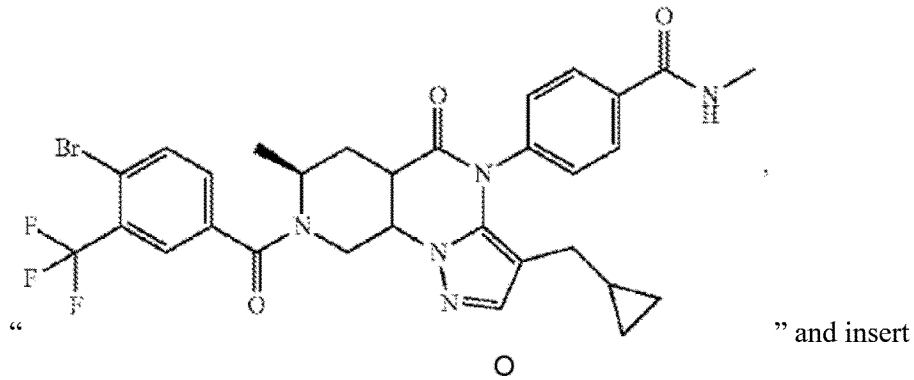 " and insert
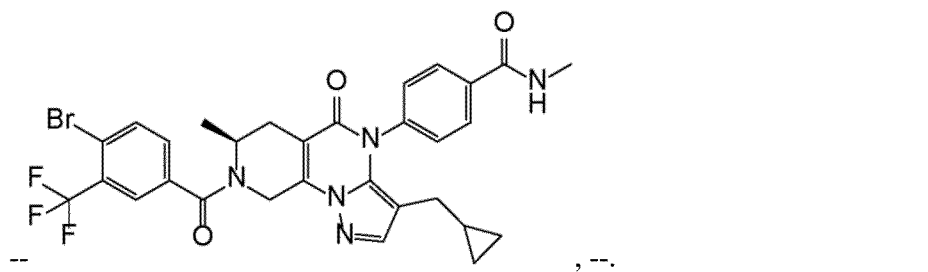 , --.
Column 384, Line 37-46, Claim 17, delete
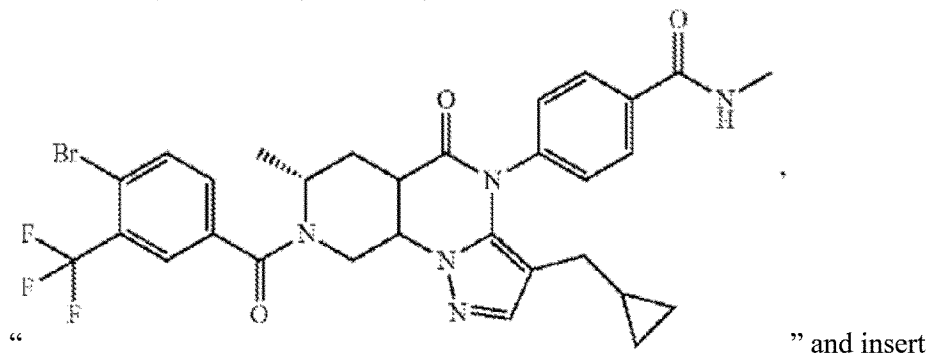 " and insert
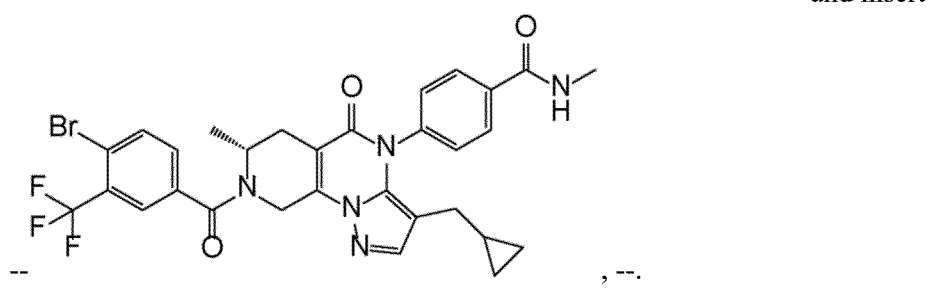 , --.

Column 384, Line 47-56, Claim 17, delete
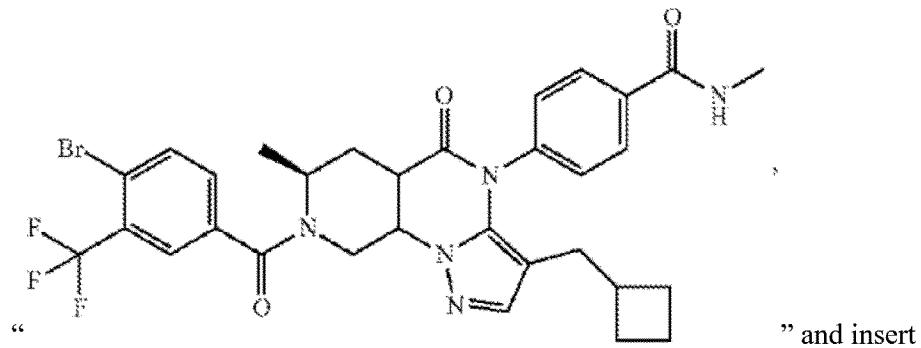 " and insert
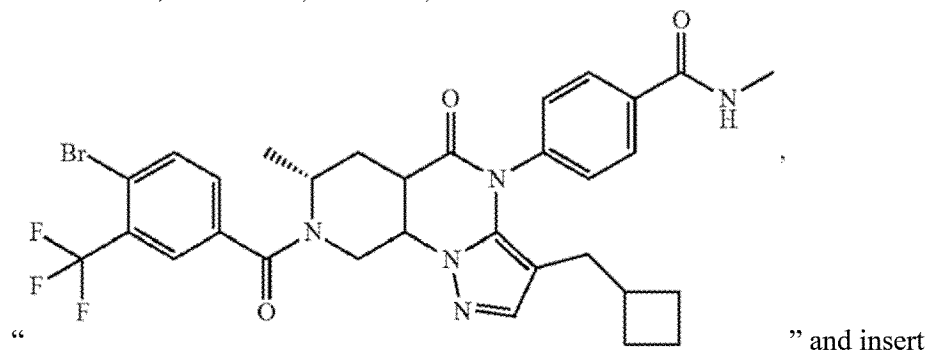 , --.
Column 384, Line 57-67, Claim 17, delete

CERTIFICATE OF CORRECTION (continued)
U.S. Pat. No. 11,820,773 B2

Column 385-386, Line 2-67, Claim 17, delete

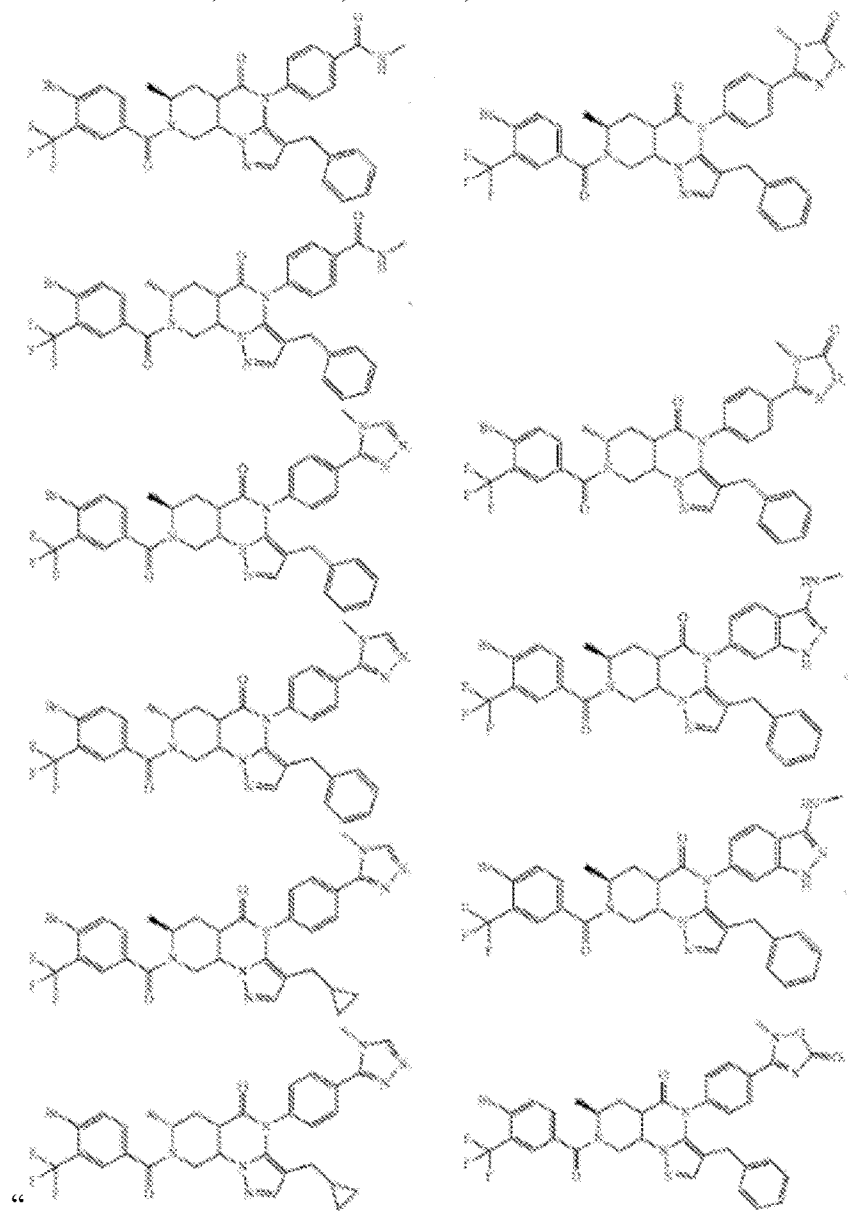

" and insert

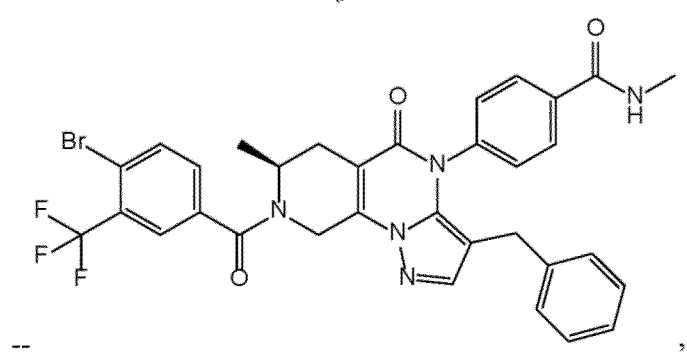

--

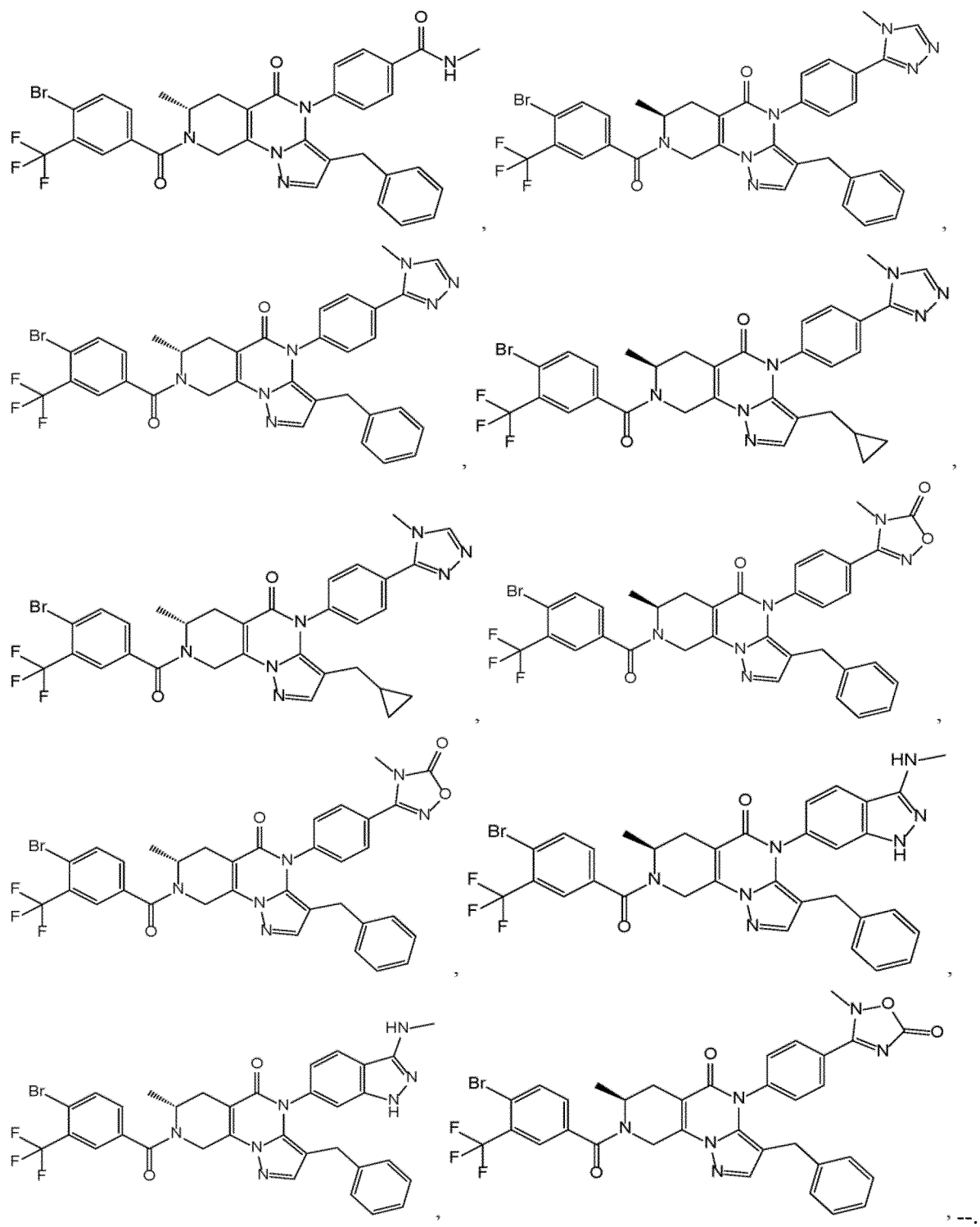

CERTIFICATE OF CORRECTION (continued)
U.S. Pat. No. 11,820,773 B2

Column 387-388, Line 2-67, Claim 17, delete

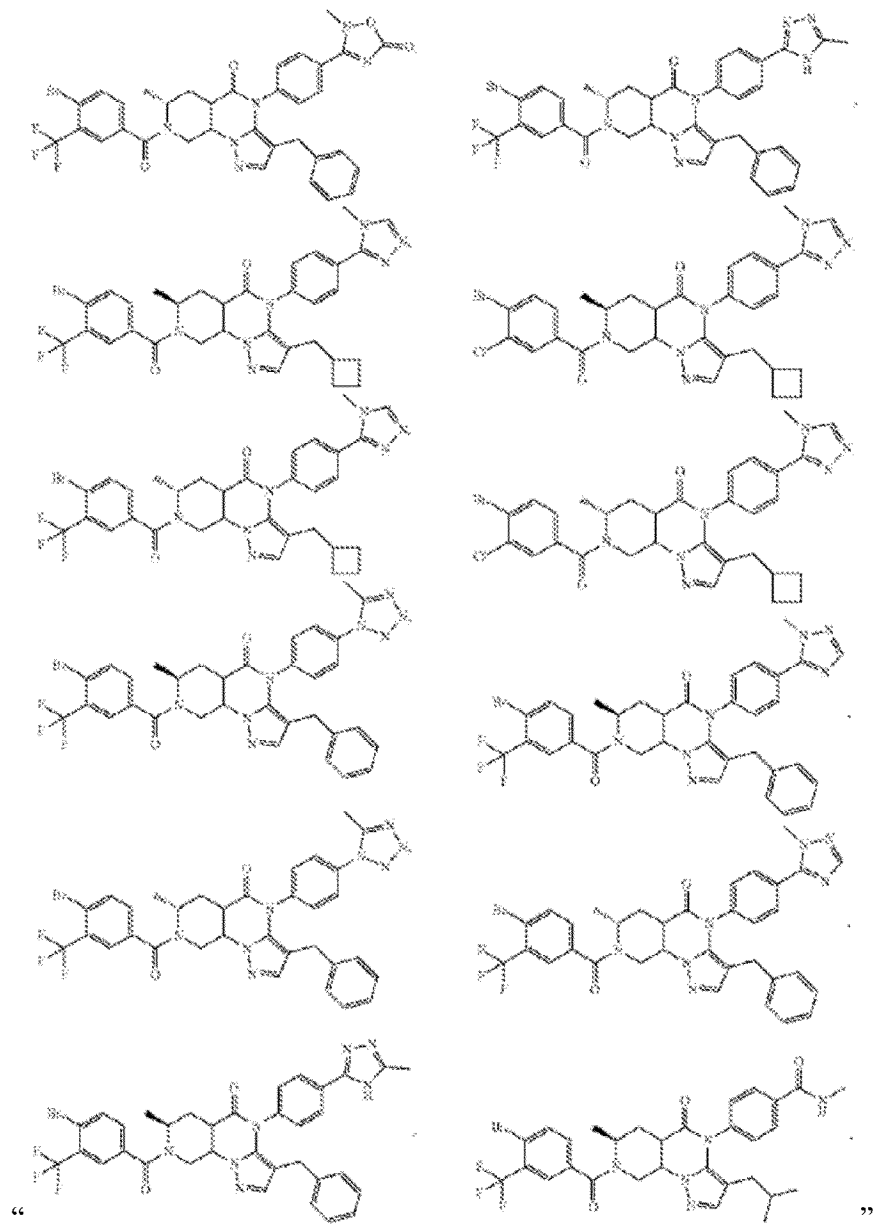

" and insert

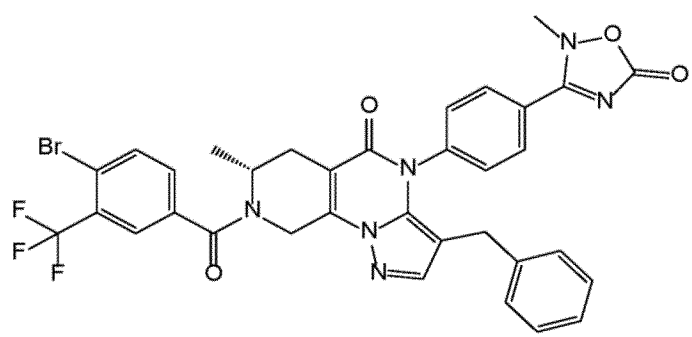

--

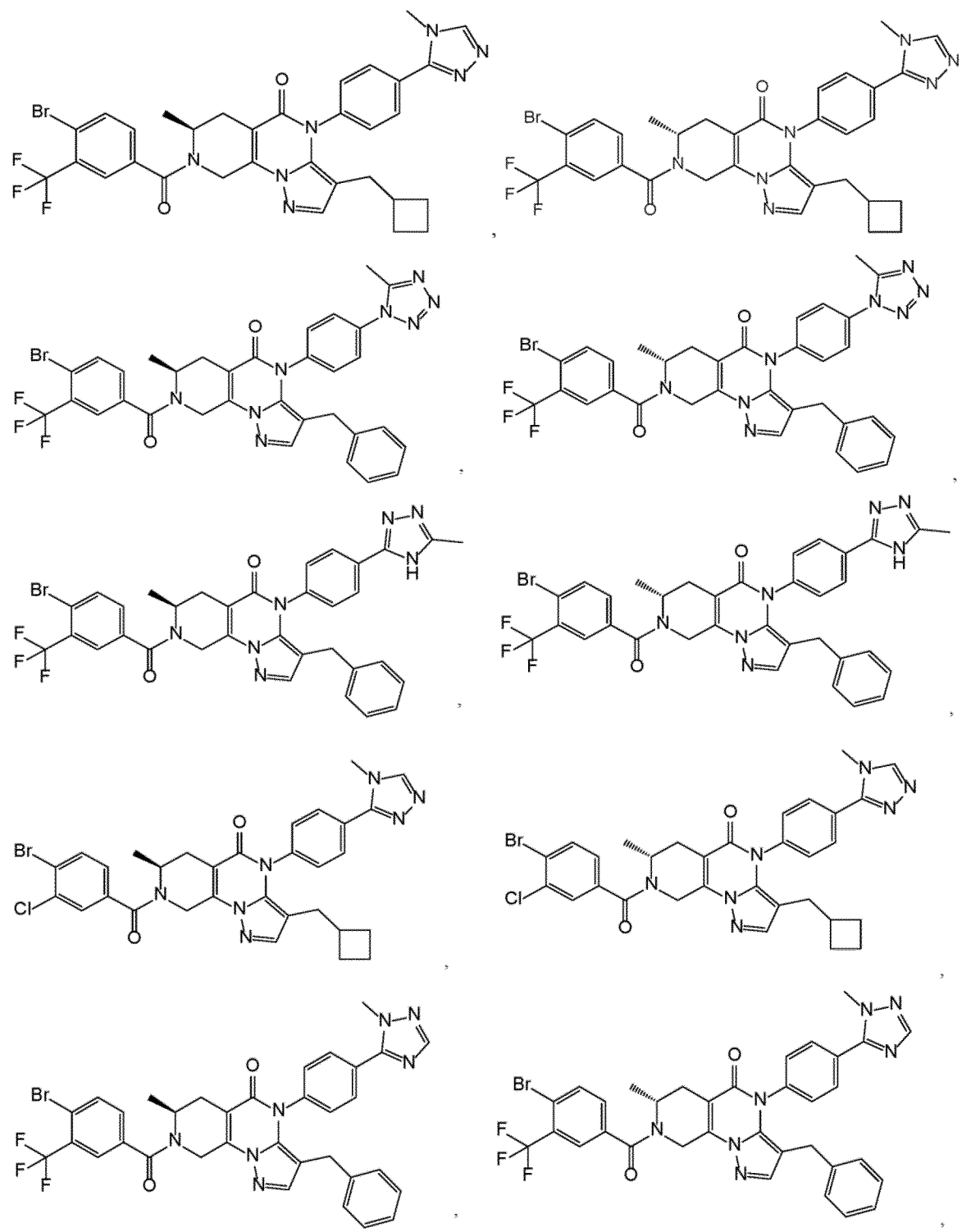

CERTIFICATE OF CORRECTION (continued)
U.S. Pat. No. 11,820,773 B2

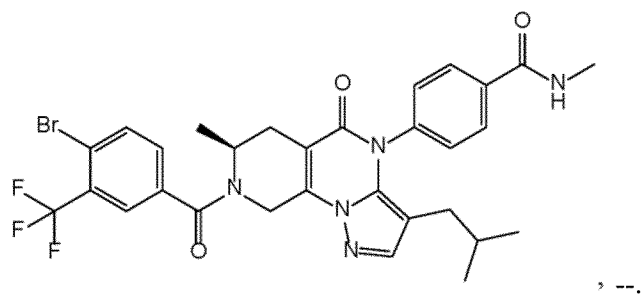

Column 389-390, Line 2-67, Claim 17, delete

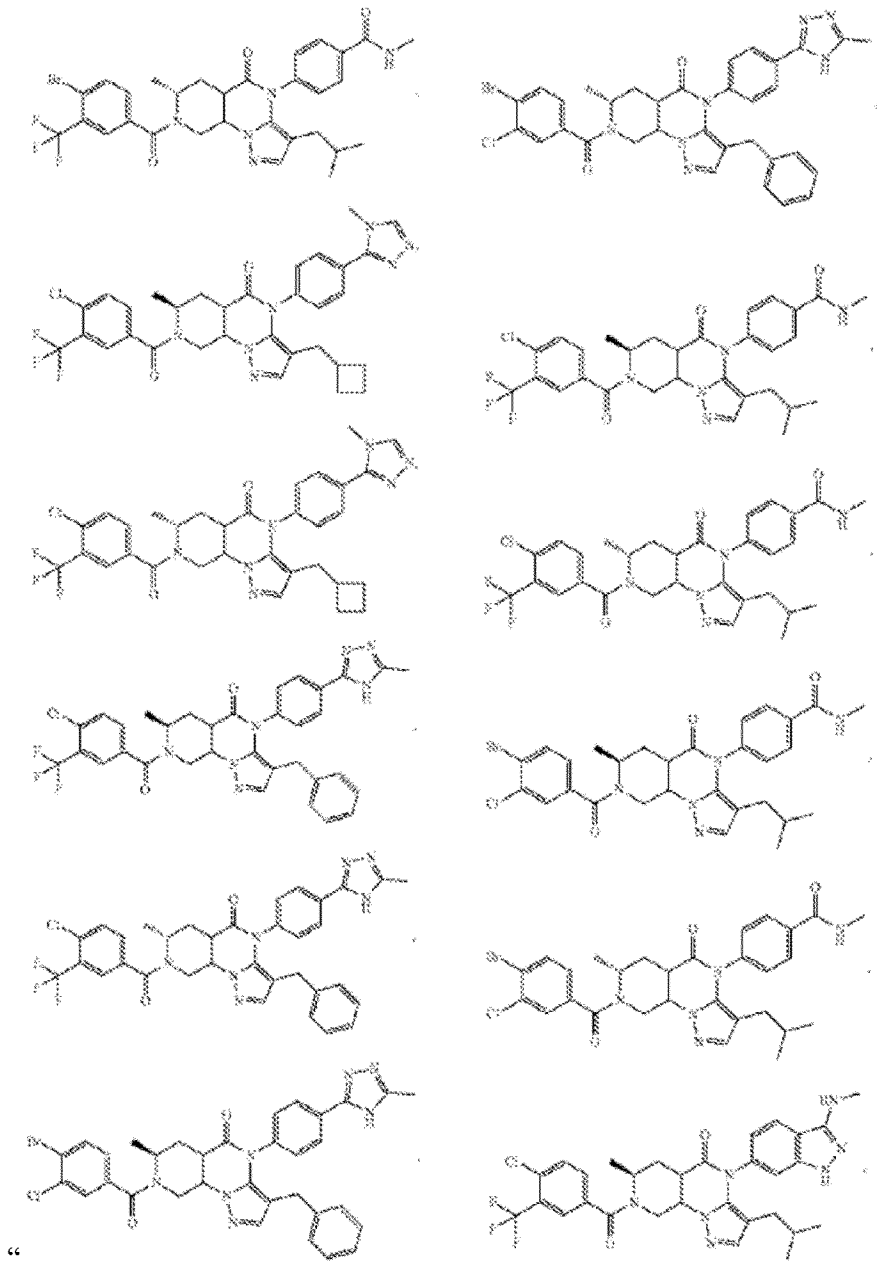

" and insert

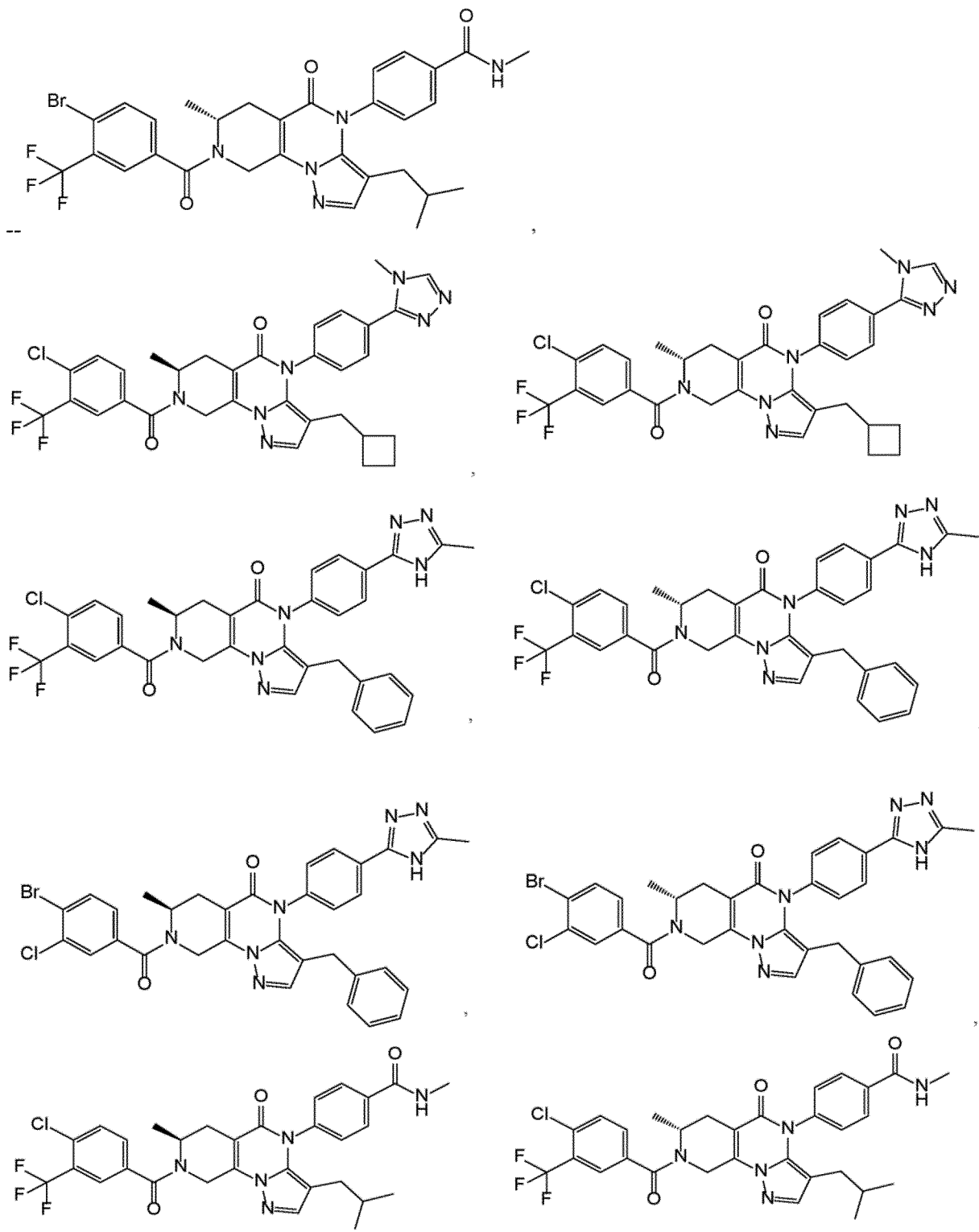

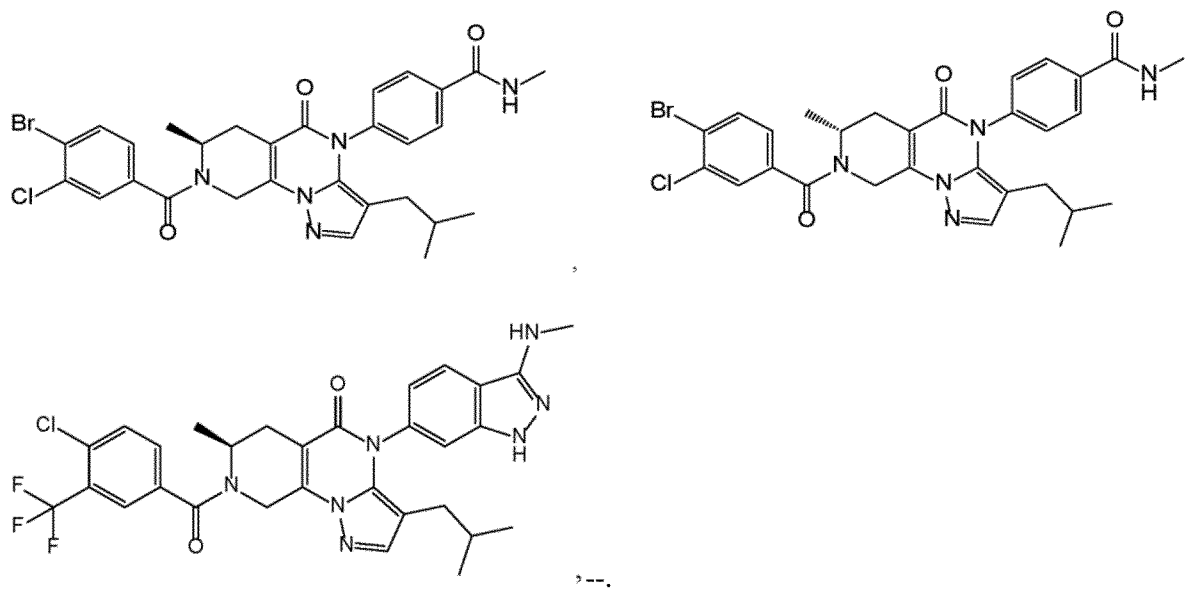
Column 391-392, Line 2-67, Claim 17, delete
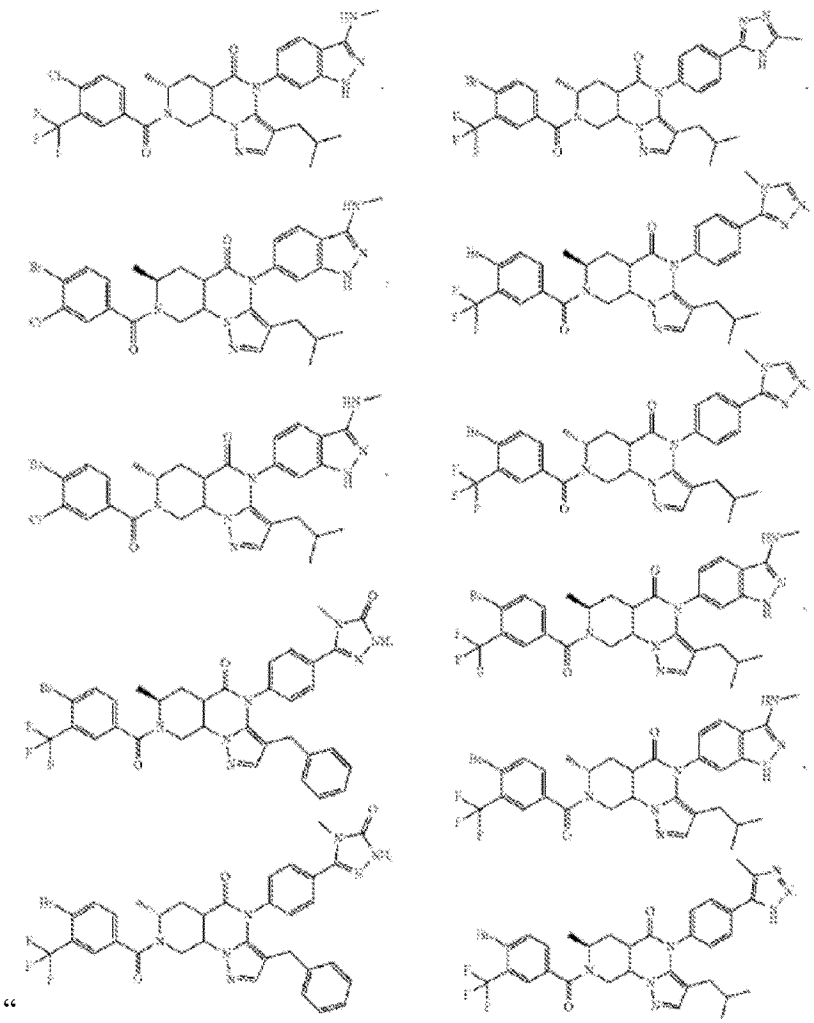
"

CERTIFICATE OF CORRECTION (continued)
U.S. Pat. No. 11,820,773 B2

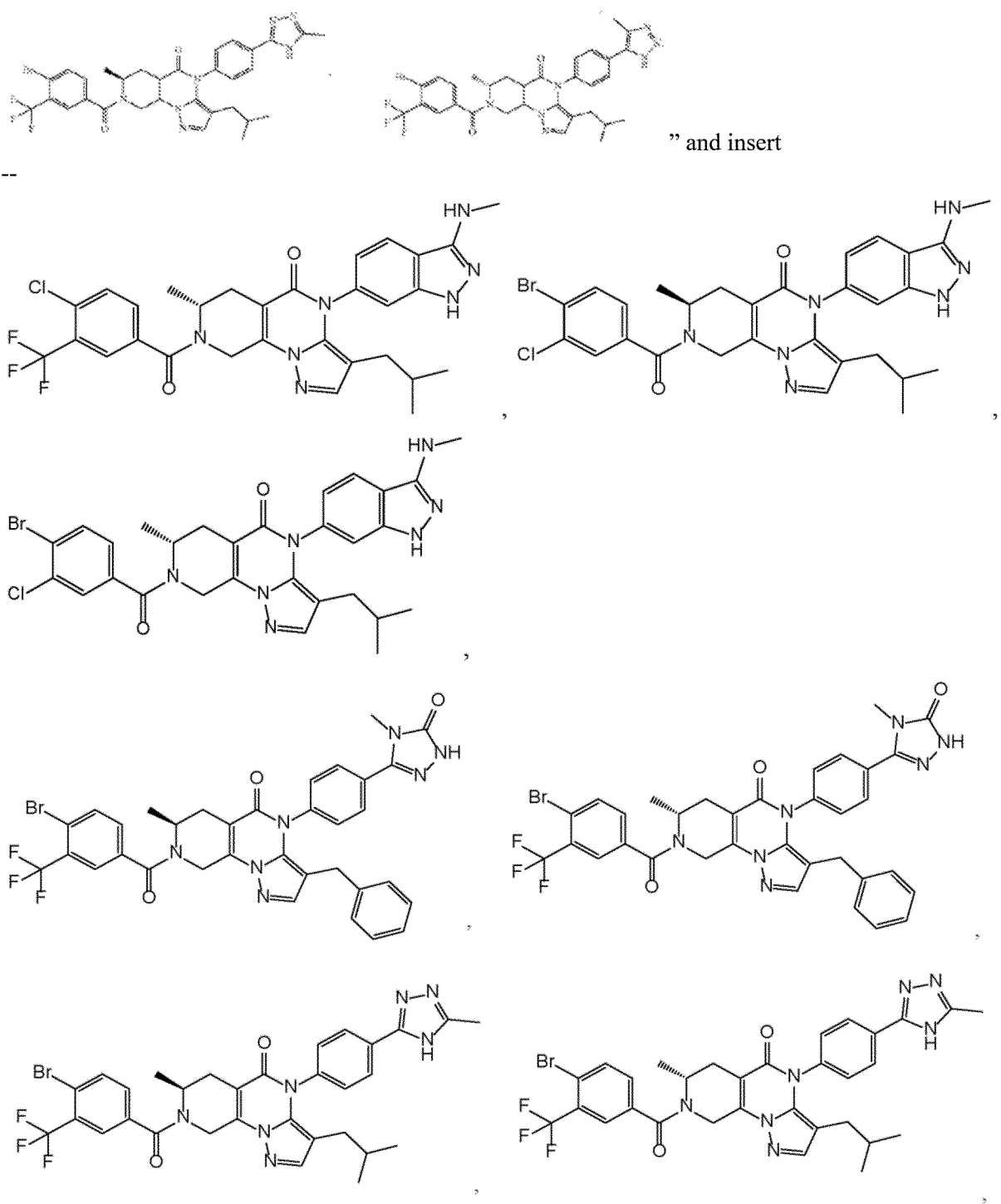

" and insert

--

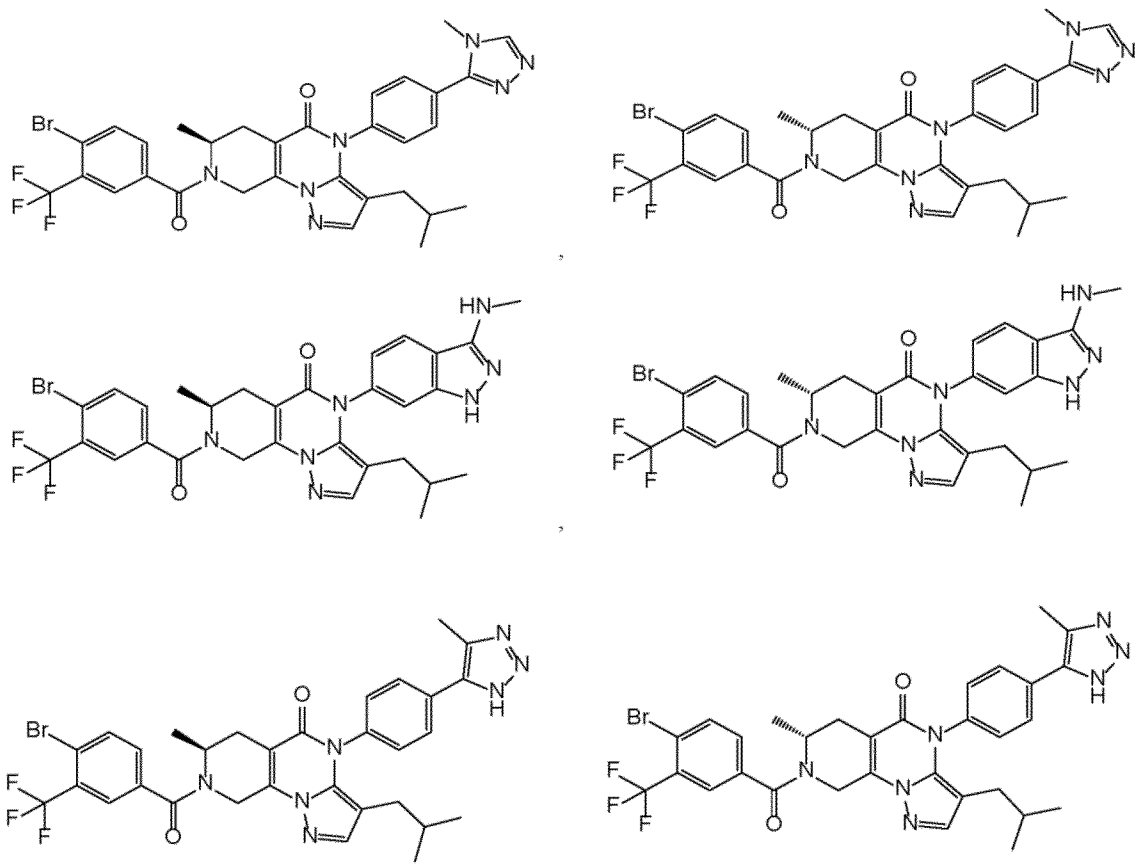
Column 393-394, Line 2-67, Claim 17, delete
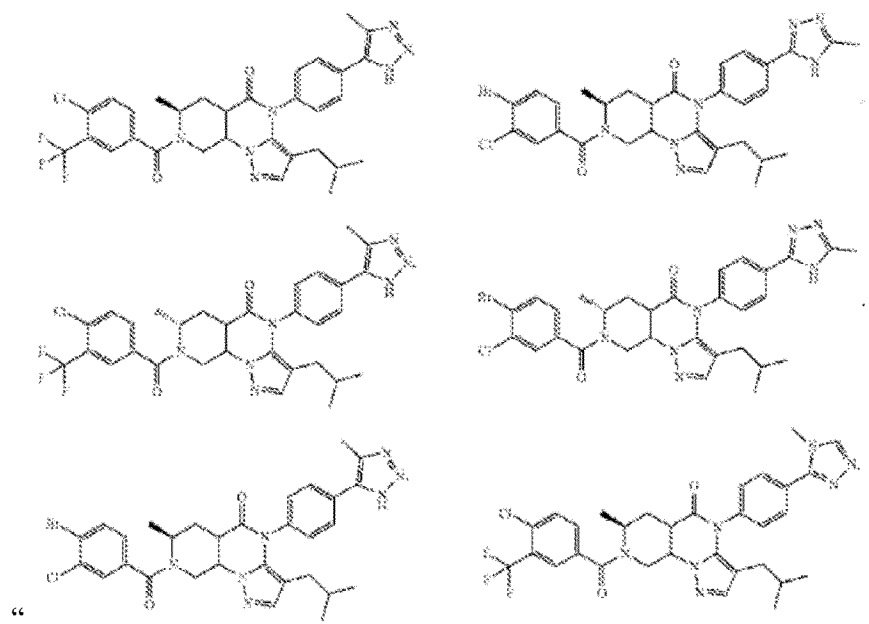
"

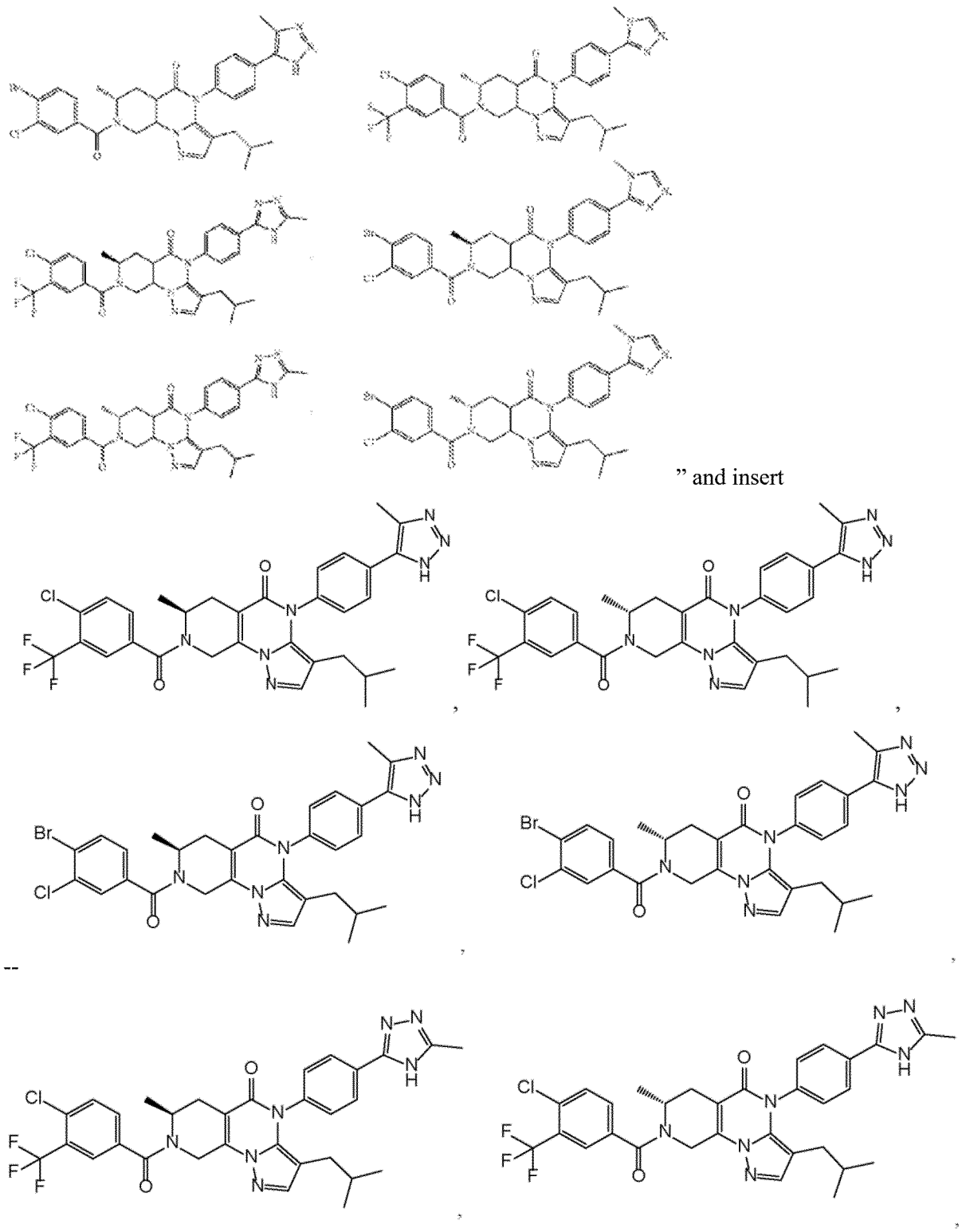

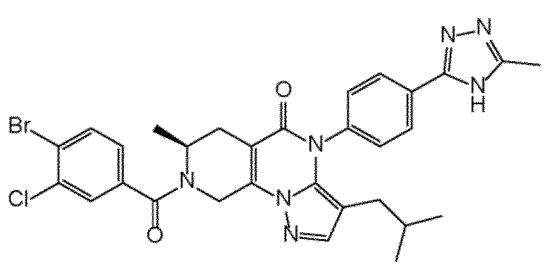 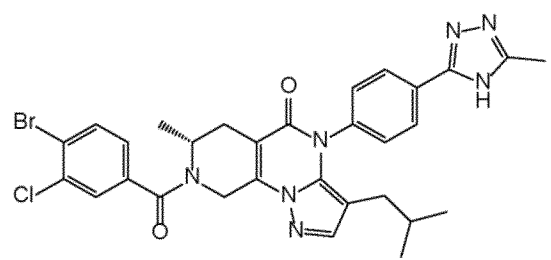
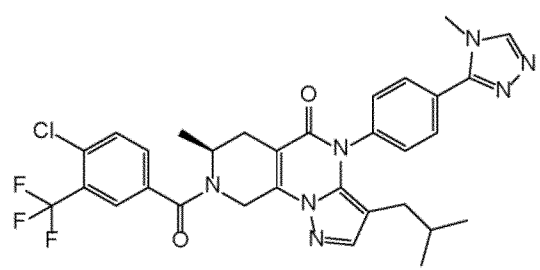 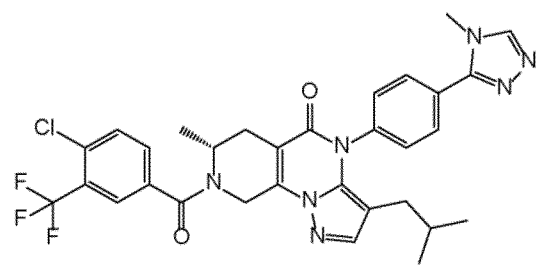
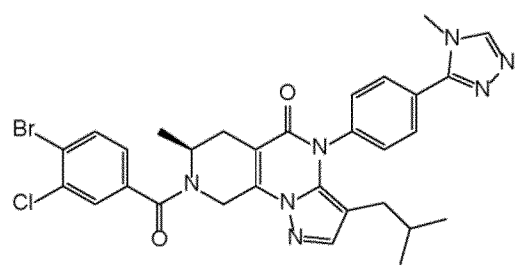 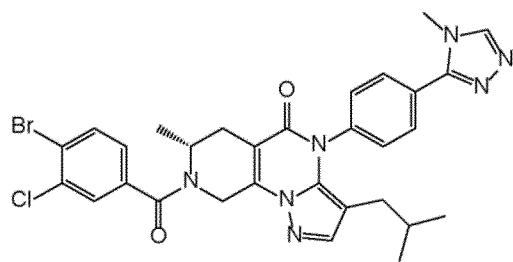
Column 395-396, Line 2-67, Claim 17, delete
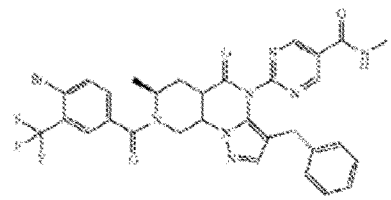 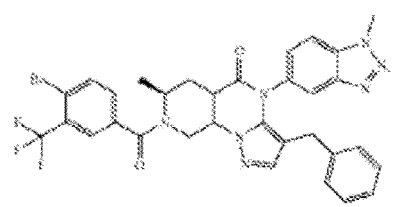
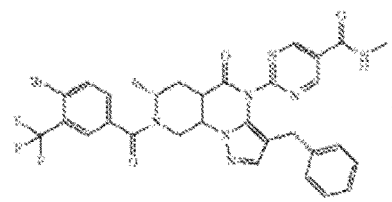 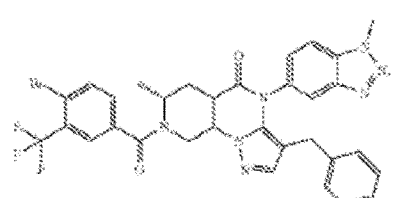
"

CERTIFICATE OF CORRECTION (continued)
U.S. Pat. No. 11,820,773 B2

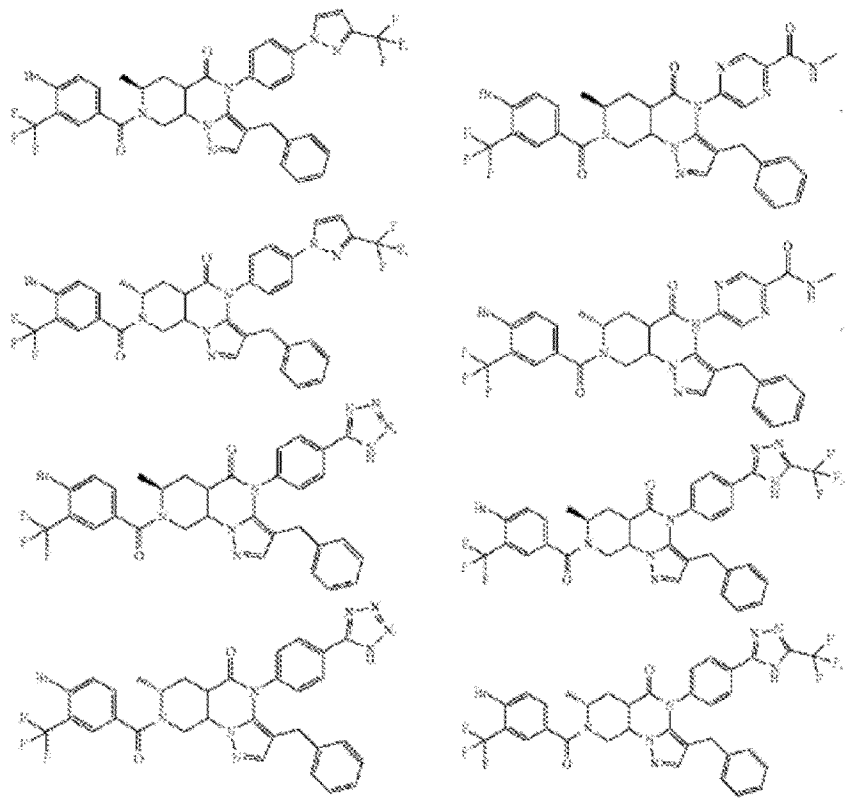

" and insert

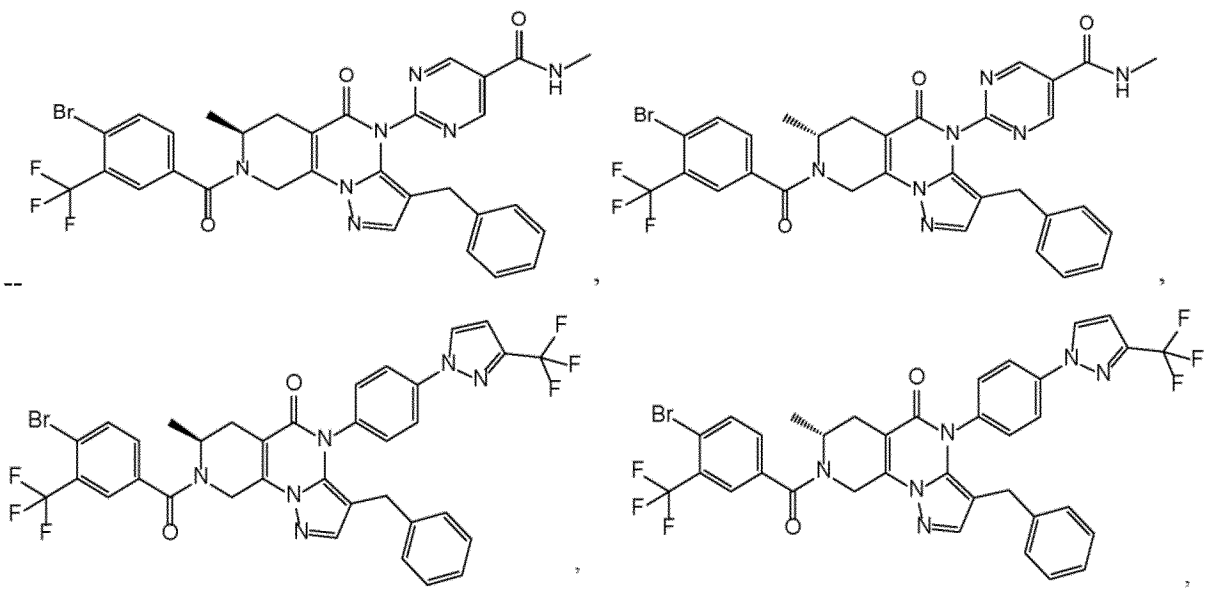

--

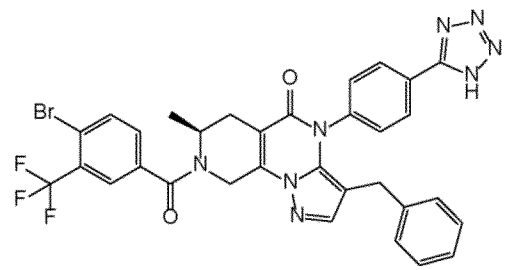
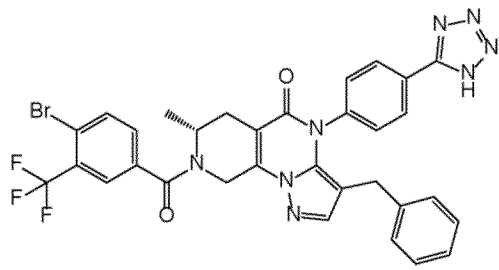
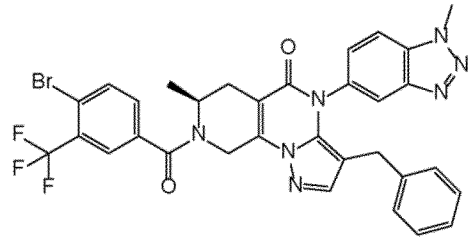
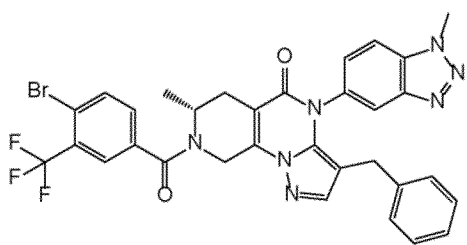
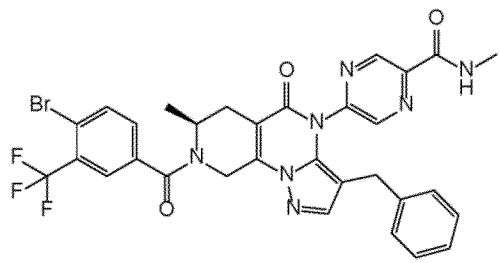
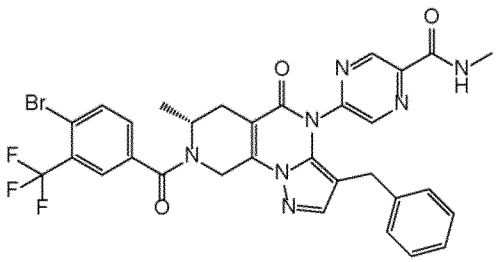
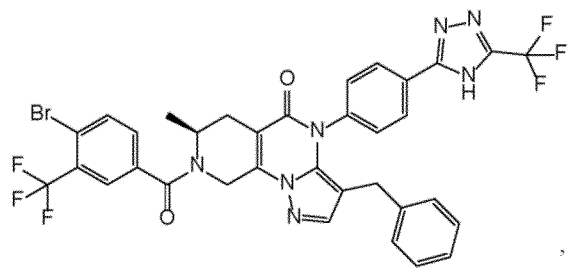
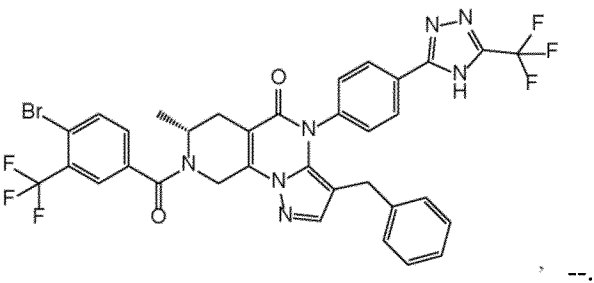

CERTIFICATE OF CORRECTION (continued)
U.S. Pat. No. 11,820,773 B2

Column 397-398, Line 2-67, Claim 17, delete

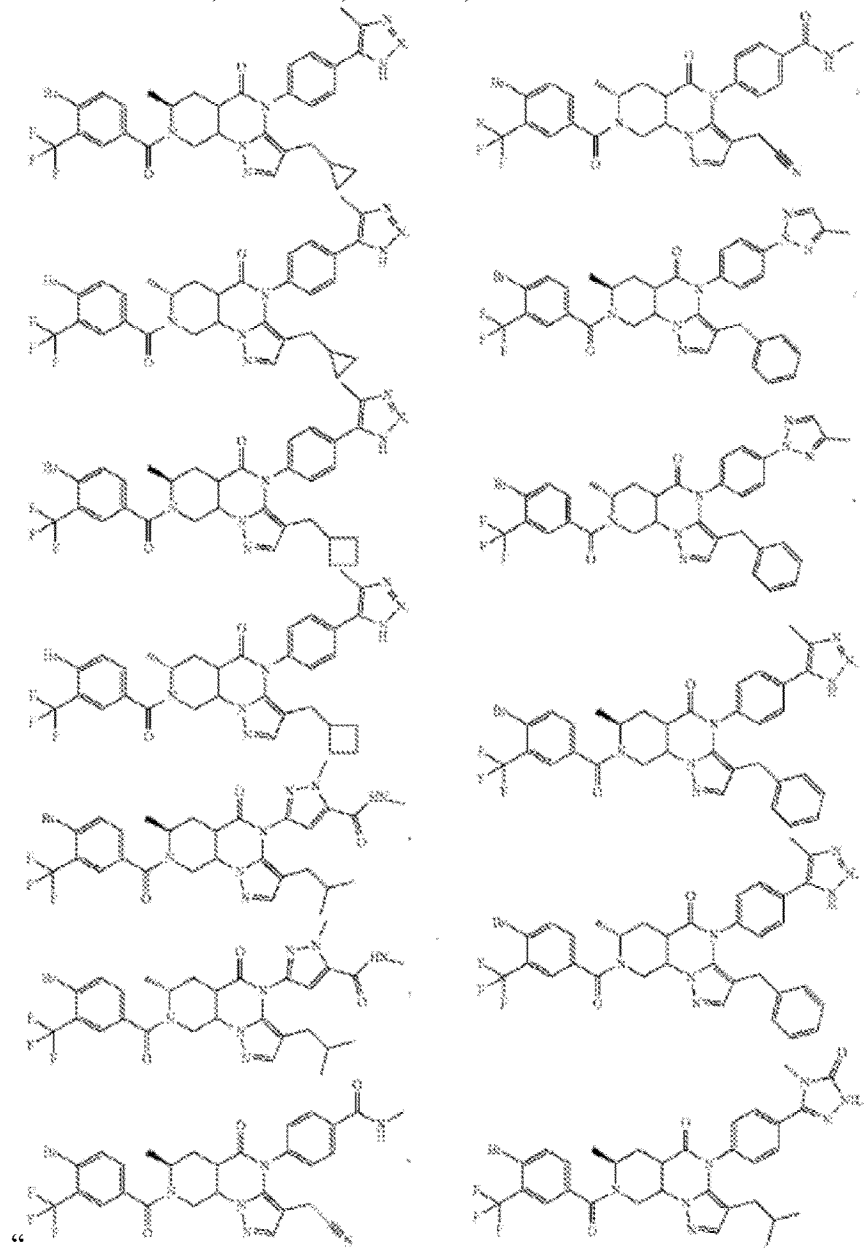

" and insert

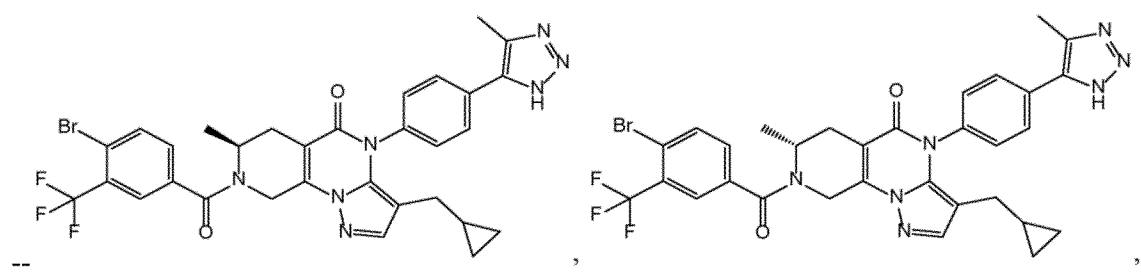

--

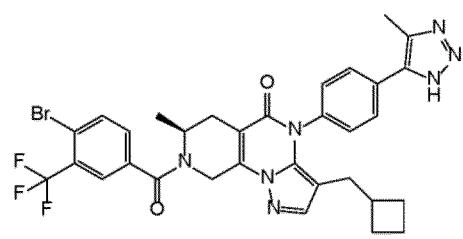 , 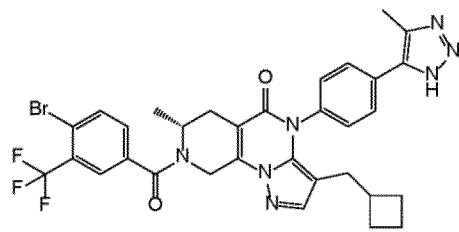 ,
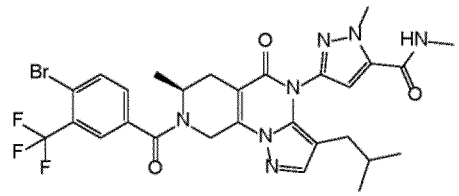 , 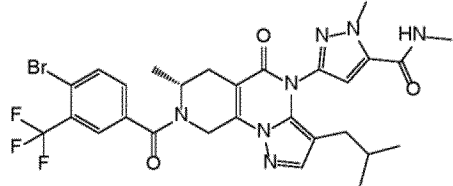 ,
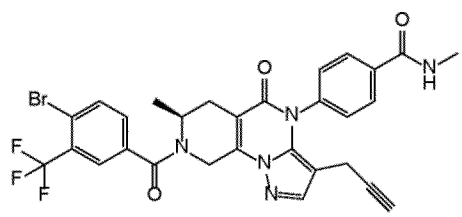 , 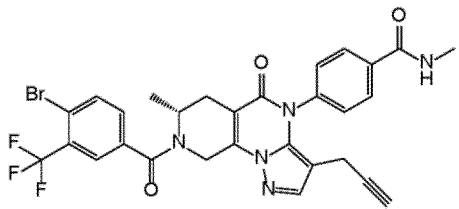 ,
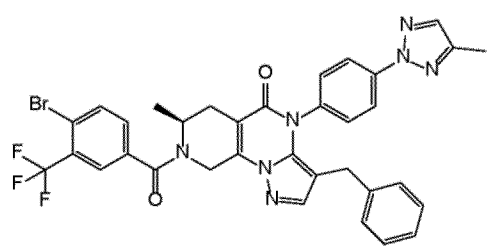 , 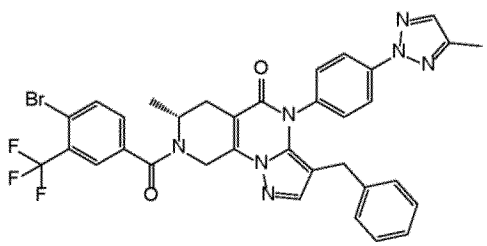 ,
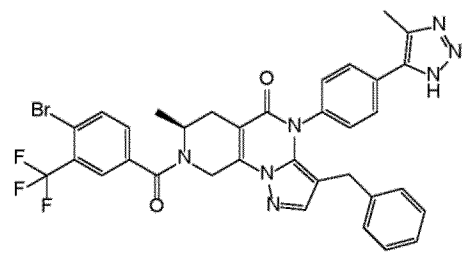 , 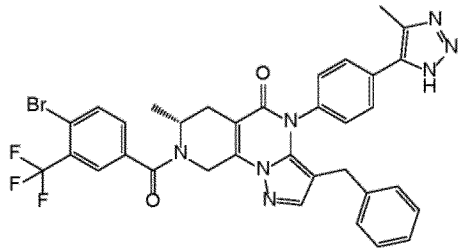 ,
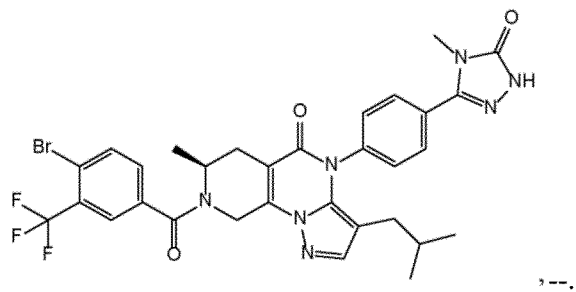 , --.

CERTIFICATE OF CORRECTION (continued)
U.S. Pat. No. 11,820,773 B2

Column 399-400, Line 2-67, Claim 17, delete

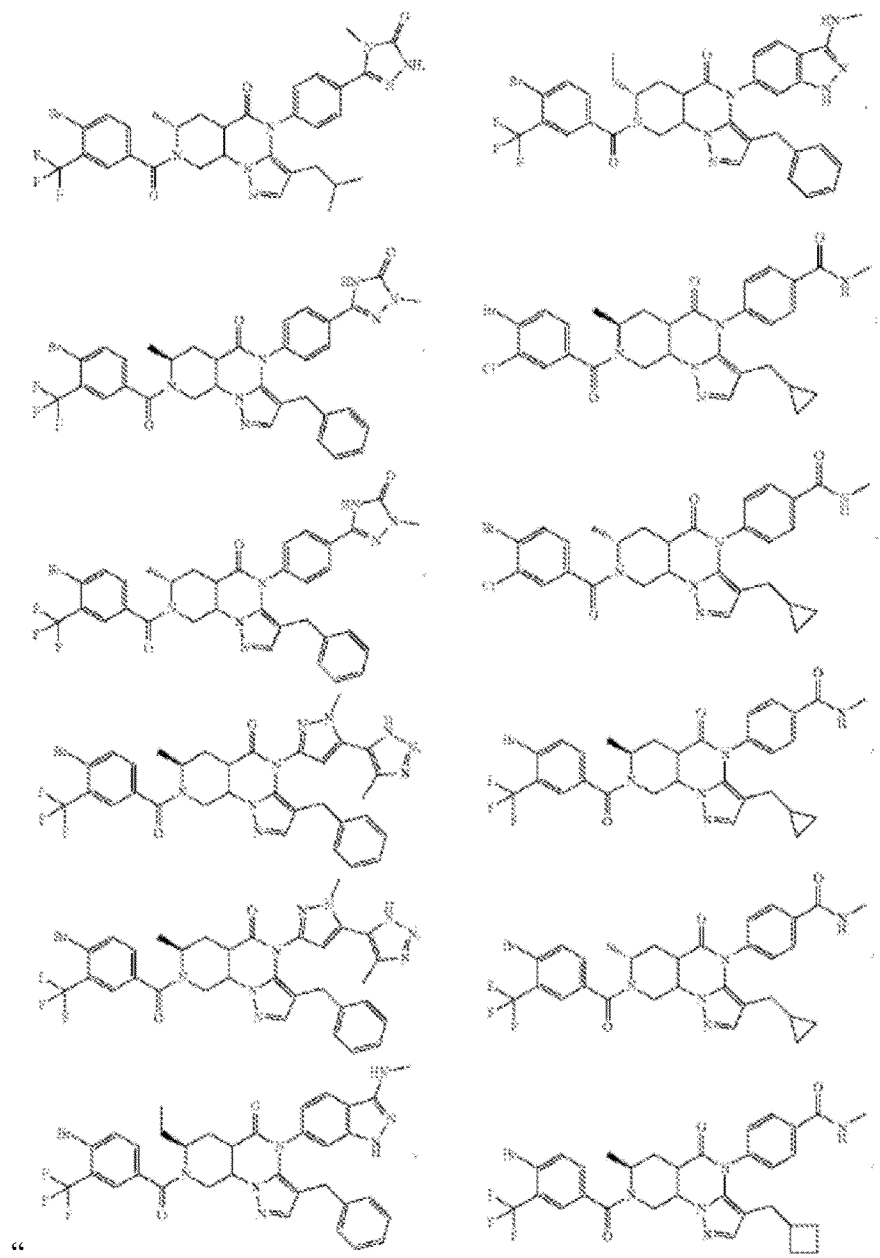

" and insert

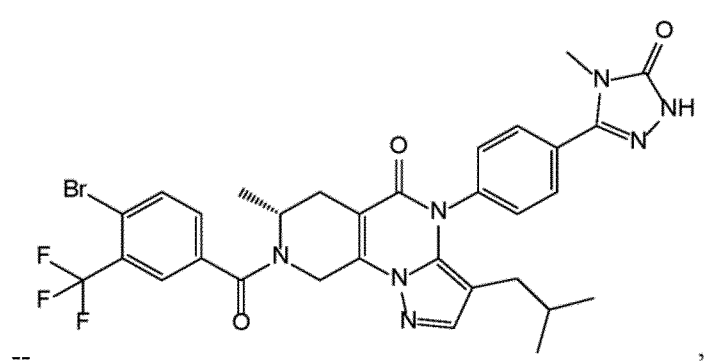

--

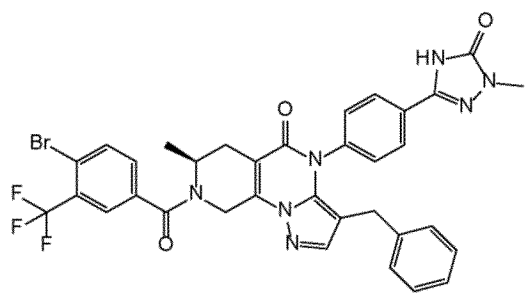
,
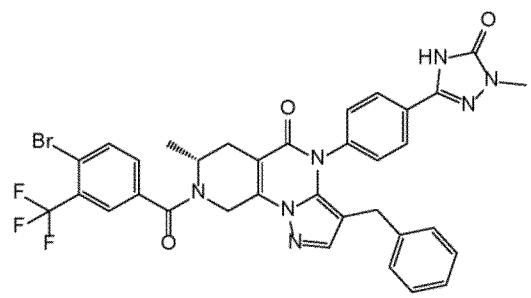
,
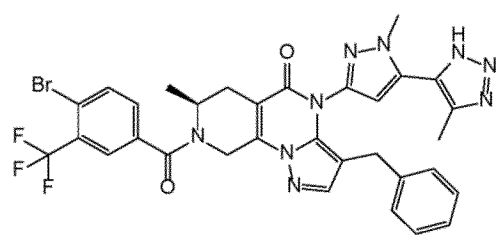
,
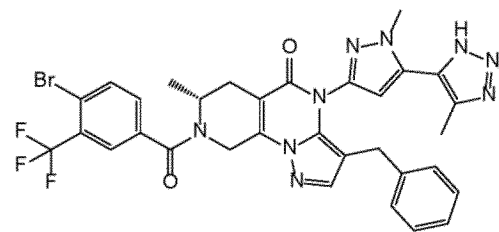
,
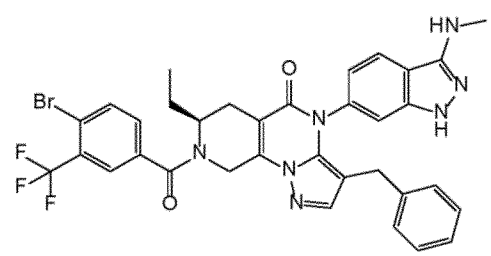
,
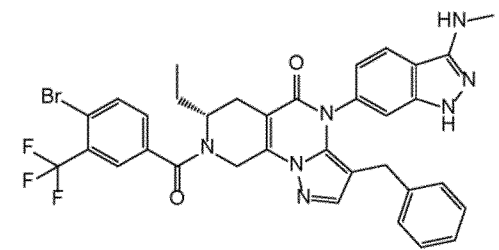
,
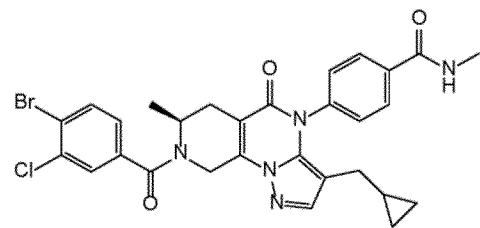
,
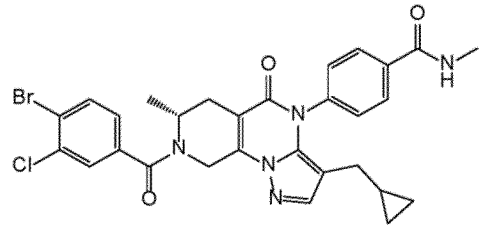
,
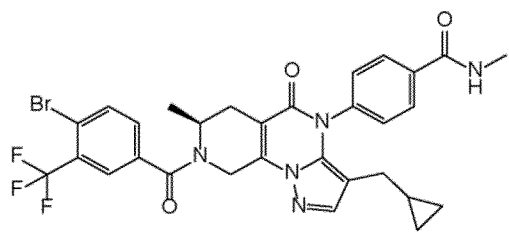
,
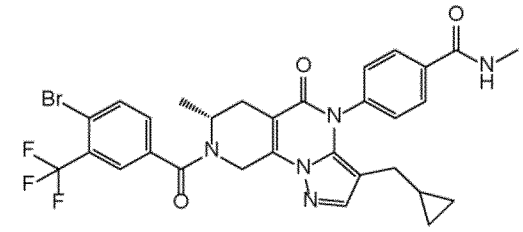
,

CERTIFICATE OF CORRECTION (continued)
U.S. Pat. No. 11,820,773 B2

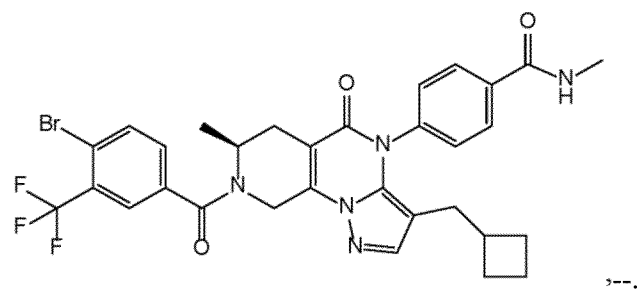

Column 401-402, Line 2-67, Claim 17, delete

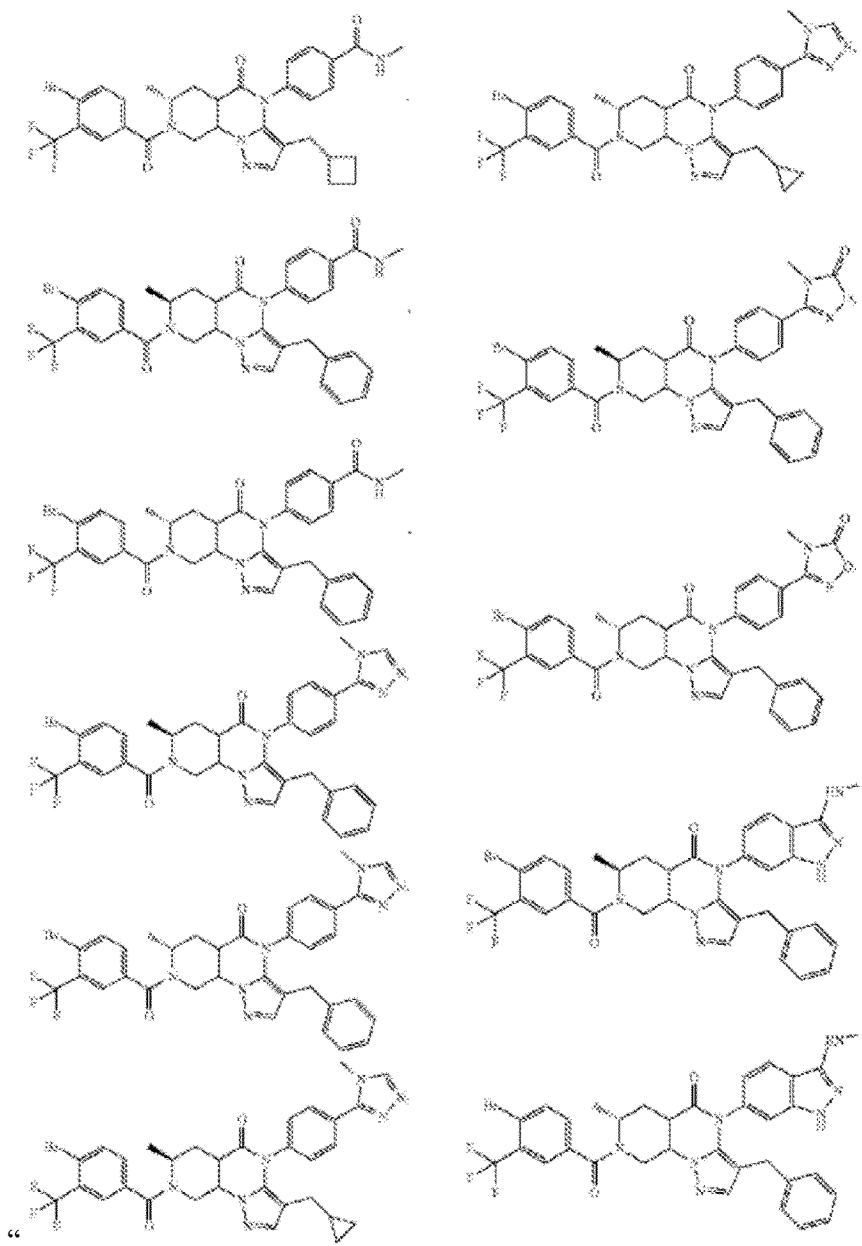

" and insert

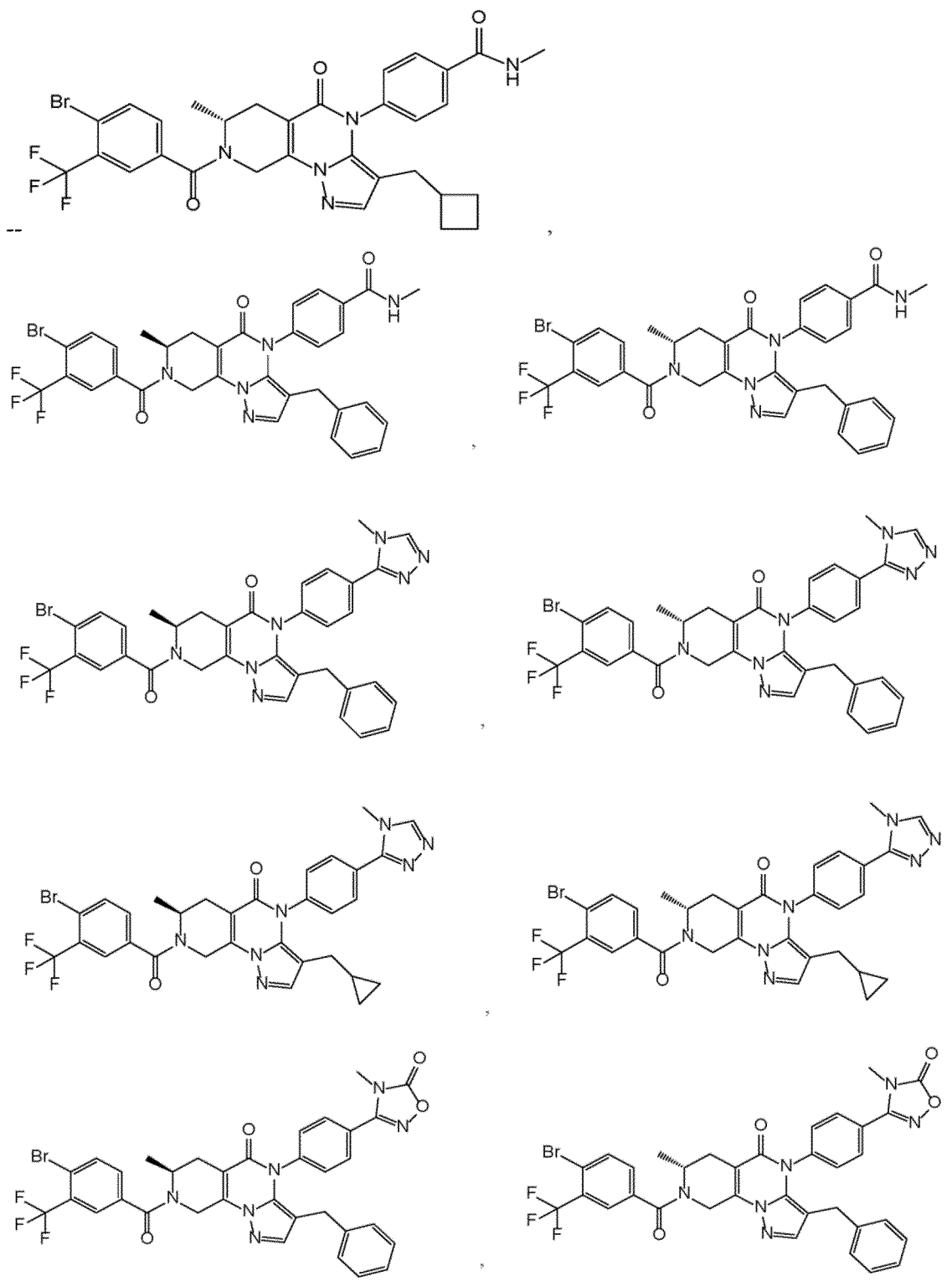

CERTIFICATE OF CORRECTION (continued)
U.S. Pat. No. 11,820,773 B2

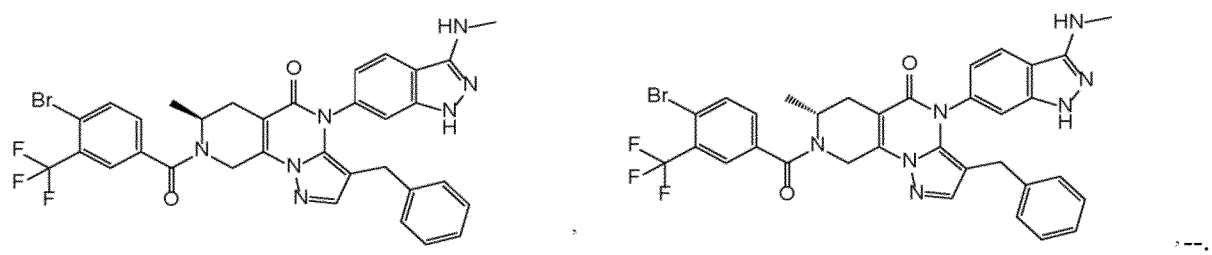

Column 419, Line 1-11, Claim 17, delete "

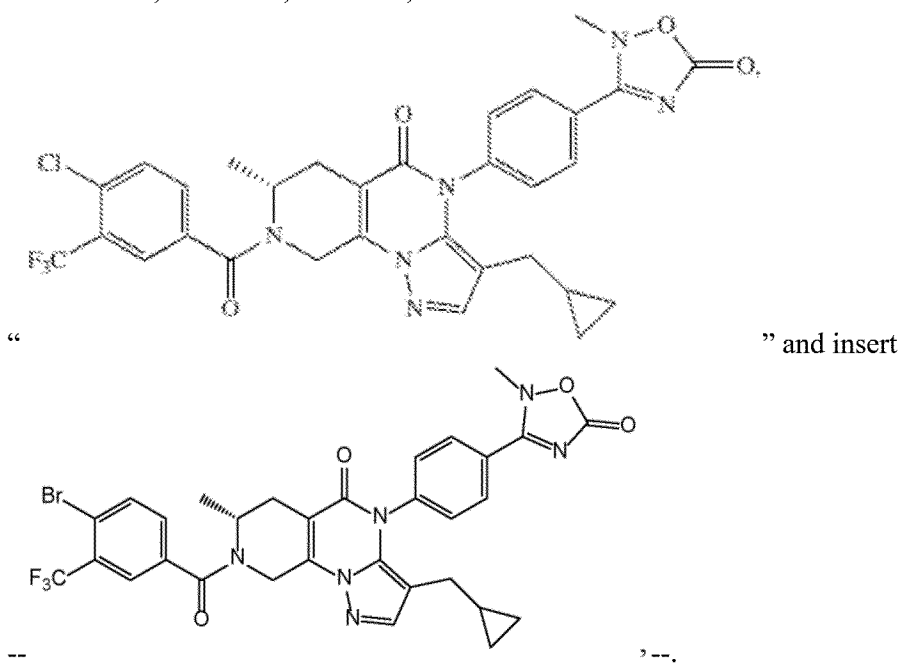

" and insert

-- ,--.